US012502423B2

(12) United States Patent
Hill et al.

(10) Patent No.: US 12,502,423 B2
(45) Date of Patent: Dec. 23, 2025

(54) VACCINE IMMUNOGENS

(71) Applicants: OXFORD UNIVERSITY INNOVATION LIMITED, Botley (GB); FUNDĀÇAO OSWALDO CRUZ, Rio de Janeiro (BR)

(72) Inventors: Adrian Vivian Sinton Hill, Headington (GB); Paulo Jorge Gonçalves de Bettencourt, Headington (GB); Alexandra Jane Spencer, Headington (GB); Nicola Maria Nathalie Ternette, Headington (GB); Ahmed Mahmoud Ahmed Ahmed Salman, Headington (GB); Caroline Furtado Junqueira, Belo Horizonte (BR); Ricardo Tostes Gazzinelli, Belo Horizonte (BR); Camila Raquel Rodrigues Barbosa, Belo Horizonte (BR)

(73) Assignees: OXFORD UNIVERSITY INNOVATION LIMITED, Botley (GB); FUNDĀÇAO OSWALDO CRUZ, Rio de Janeiro (BR)

( * ) Notice: Subject to any disclaimer, the term of this patent is extended or adjusted under 35 U.S.C. 154(b) by 387 days.

(21) Appl. No.: 17/610,380

(22) PCT Filed: May 11, 2020

(86) PCT No.: PCT/GB2020/051146
§ 371 (c)(1),
(2) Date: Nov. 10, 2021

(87) PCT Pub. No.: WO2020/229805
PCT Pub. Date: Nov. 19, 2020

(65) Prior Publication Data

US 2023/0173050 A1 Jun. 8, 2023

(30) Foreign Application Priority Data

May 10, 2019 (GB) ..................................... 1906641

(51) Int. Cl.

| | |
|---|---|
| *A61K 39/02* | (2006.01) |
| *A61K 39/015* | (2006.01) |
| *A61P 33/06* | (2006.01) |
| *C12N 15/861* | (2006.01) |

(52) U.S. Cl.
CPC ............ *A61K 39/015* (2013.01); *A61P 33/06* (2018.01); *C12N 15/861* (2013.01)

(58) Field of Classification Search
None
See application file for complete search history.

(56) References Cited

FOREIGN PATENT DOCUMENTS

| | | | |
|---|---|---|---|
| EP | 2409987 | A1 | 1/2012 |
| WO | 2017178809 | A1 | 10/2017 |
| WO | 2018193467 | A1 | 10/2018 |

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340,).*
Mikayama et al. (Nov. 1993. Proc. Natl.Acad.Sci. USA, vol. 90 : 10056-10060).*
Neafsey et al (Accession No. A0A024VRZ3 "The Genome Sequence of Plasmodium falciparum FCH/4."Submitted Feb. 2013 to the EMBL/GenBank/DDBJ databases).*
Sundararaman et al (Accession No. A0A151LKR9 Nat. Commun. 7:11078-11078. 2016).*
Otto et al (Accession No. A0A077Y1U9. BMC Biol. 12:86-86. 2014).*
Tachibana et al (Accession No. K6UTH7. Nat. Genet. 44: 1051-1055. 2012).*
Pathak et al (Journal of Biomedicine and Biotechnology (2012) 695843, pp. 1-11).*
Chatterjee et al, "Antibodies against ribosomal phosphoprotein PO of Plasmodium falciparum protect mice against challenge with Plasmodium yoelii", Infection and Immunity, American Society for Microbiology, US, vol. 68, No. 7, Jul. 1, 2000 (Jul. 1, 2000), p. 4312-4318.
Mcconkey, S. J. et al., Nature Medicine, vol. 9, 2003, pp. 729-735.
Anonymous, "PVX_094375-40S ribosomal protein S20e, putative—Plasmodium vivax (strain Salvador I)—PVX_094375 gene & protein", Jul. 10, 2007 (Jul. 10, 2007), URL:https://www.uniprot.org/uniprot/A5K757.
Dicks, M. D. et al., PLOS One, vol. 7, 2012.
UniProt: a hub for protein information, Nucleic Acids Res., vol. 43, 2015, pp. D204-D212.

(Continued)

*Primary Examiner* — Jennifer E Graser
(74) *Attorney, Agent, or Firm* — John J. Cunniff; Hahn Loeser & Parks LLP

(57) ABSTRACT

An immunogenic composition comprising: a) one or more *Plasmodium*-derived ribosomal or ribosomal associated protein or immunogenic fragment thereof which has a sequence which is at least about 80%, 85%, 90%, 95%, 98%, 99% or 100% identical to a ribosomal or ribosomal associated protein or an immunogenic fragment of a ribosomal or ribosomal associated protein recited in FIG. 1; or a ribosomal or ribosomal associated protein or peptide or immunogenic fragment thereof as recited in FIG. 2 or FIG. 3; and/or b) a polynucleotide encoding one or more protein, peptide or immunogenic fragment of a); wherein the immunogenic composition is for use in eliciting an immune response in a subject to treat or prevent malaria. Also provided are *Plasmodium*-derived ETRAMPs and/or histones, or immunogenic fragments thereof, for use in eliciting an immune response in a subject, preferably to treat or prevent malaria.

6 Claims, 46 Drawing Sheets

Figure 4:
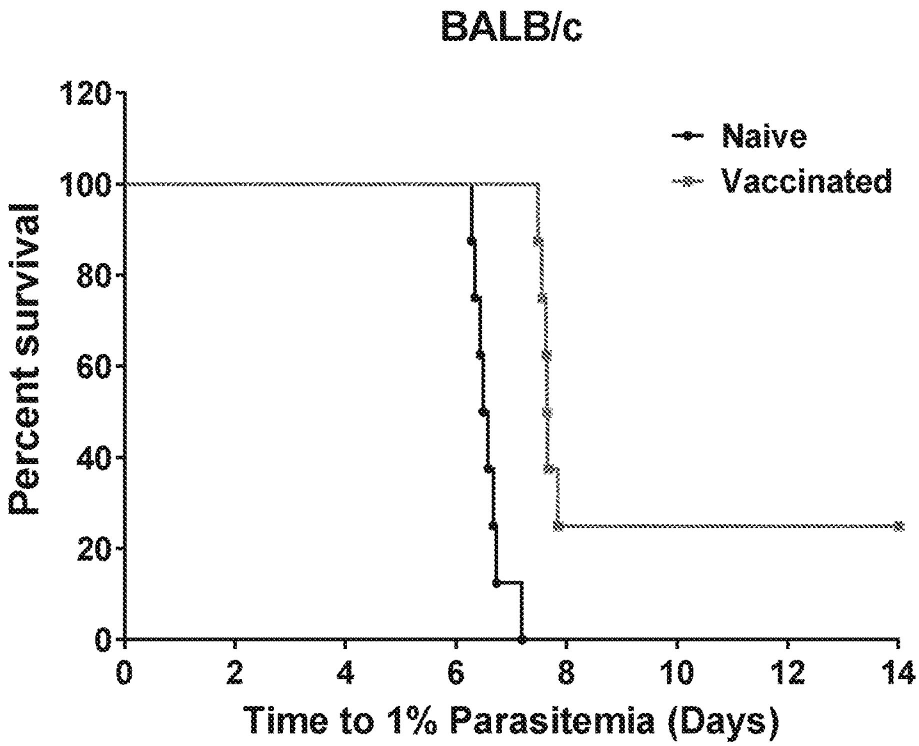

Specification includes a Sequence Listing.

(56) References Cited

OTHER PUBLICATIONS

Billman et al, "Defining rules of CD8+ T cell expansion against pre-erythrocytic Plasmodium antigens in sporozoite-immunized mice" , Malaria Journal, vol. 15, No. 1, Apr. 26, 2016 (Apr. 26, 2016).
Junqueira, C. et al., Nature Medicine, vol. 24, 2018, pp. 1330-1336.
Tran, N. H. et al., Nature Methods, vol. 16, 2019, pp. 63-66.
Uniprot, C. UniProt: a worldwide hub of protein knowledge, Nucleic Acids Research, vol. 47, 2019.
Bettencourt, P. et al. "Identification of antigens presented by MHC for vaccines against tuberculosis", NPJ Vaccines, vol. 5, 2020, pp. 2.
Rajeshwari, The P Domain of the P0 Protein of Plasmodium falciparum Protects against Challenge with Malaria Parasites ",Infection and Immunity, vol. 72, No. 9, Sep. 1, 200".
Soulard et al., Nature Communications, vol. 62015.

* cited by examiner

Figure 1

| SEQ IDNº | Entry | Entry Name | Protein names | Organism | Length |
|---|---|---|---|---|---|
| 475 | A5K757 | A5K757_PLAVS | 40S ribosomal protein S20e, putative | Plasmodium vivax (strain Salvador I) | 118 |
| 496 | A5KC76 | A5KC76_PLAVS | 40S ribosomal protein S10, putative | Plasmodium vivax (strain Salvador I) | 136 |
| 497 | A5K7Q0 | A5K7Q0_PLAVS | 40S ribosomal protein S11, putative | Plasmodium vivax (strain Salvador I) | 161 |
| 498 | A5KB87 | A5KB87_PLAVS | 40S ribosomal protein S12 | Plasmodium vivax (strain Salvador I) | 143 |
| 499 | A5K2J4 | A5K2J4_PLAVS | 40S ribosomal protein S13, putative | Plasmodium vivax (strain Salvador I) | 151 |
| 500 | A5K9J7 | A5K9J7_PLAVS | 40S ribosomal protein S14-2, putative | Plasmodium vivax (strain Salvador I) | 151 |
| 501 | A5JZG7 | A5JZG7_PLAVS | 40S ribosomal protein S15, putative | Plasmodium vivax (strain Salvador I) | 145 |
| 502 | A5K7Q8 | A5K7Q8_PLAVS | 40S ribosomal protein S15Aa, putative | Plasmodium vivax (strain Salvador I) | 130 |
| 503 | A5JZP0 | A5JZP0_PLAVS | 40S ribosomal protein S16, putative | Plasmodium vivax (strain Salvador I) | 144 |
| 504 | A5K8T0 | A5K8T0_PLAVS | 40S ribosomal protein S17, putative | Plasmodium vivax (strain Salvador I) | 137 |
| 505 | A5K4S2 | A5K4S2_PLAVS | 40S ribosomal protein S18, putative | Plasmodium vivax (strain Salvador I) | 156 |
| 506 | A5K662 | A5K662_PLAVS | 40S ribosomal protein S19s, putative | Plasmodium vivax (strain Salvador I) | 172 |
| 507 | A5K3U1 | A5K3U1_PLAVS | 40S ribosomal protein S2, putative | Plasmodium vivax (strain Salvador I) | 274 |
| 508 | A5K598 | A5K598_PLAVS | 40S ribosomal protein S21 | Plasmodium vivax (strain Salvador I) | 82 |
| 509 | A5KB86 | A5KB86_PLAVS | 40S ribosomal protein S23, putative | Plasmodium vivax (strain Salvador I) | 145 |
| 510 | A5K9G4 | A5K9G4_PLAVS | 40S ribosomal protein S24 | Plasmodium vivax (strain Salvador I) | 133 |
| 511 | A5K124 | A5K124_PLAVS | 40S ribosomal protein S25 | Plasmodium vivax (strain Salvador I) | 133 |
| 512 | A5KBU6 | A5KBU6_PLAVS | 40S ribosomal protein S26 | Plasmodium vivax (strain Salvador I) | 107 |
| 513 | A5JZ74 | A5JZ74_PLAVS | 40S ribosomal protein S27, putative | Plasmodium vivax (strain Salvador I) | 82 |
| 514 | A5KA63 | A5KA63_PLAVS | 40S ribosomal protein S29, putative | Plasmodium vivax (strain Salvador I) | 59 |
| 515 | A5K398 | A5K398_PLAVS | 40S ribosomal protein S3 | Plasmodium vivax (strain Salvador I) | 222 |
| 516 | A5KBT5 | A5KBT5_PLAVS | 40S ribosomal protein S30 | Plasmodium vivax (strain Salvador I) | 58 |
| 517 | A5K7J8 | RS3A_PLAVS | Small ribosomal subunit protein eS1 (40S ribosomal protein S3a) | Plasmodium vivax (strain Salvador I) | 262 |
| 518 | A5K478 | A5K478_PLAVS | 40S ribosomal protein S4 | Plasmodium vivax (strain Salvador I) | 261 |
| 519 | A5KC61 | A5KC61_PLAVS | 40S ribosomal protein S5, putative | Plasmodium vivax (strain Salvador I) | 195 |
| 520 | A5K858 | A5K858_PLAVS | 40S ribosomal protein S6, putative | Plasmodium vivax (strain Salvador I) | 391 |
| 521 | A5JZ21 | A5JZ21_PLAVS | 40S ribosomal protein S7 | Plasmodium vivax (strain Salvador I) | 194 |
| 522 | A5K1E3 | A5K1E3_PLAVS | 40S ribosomal protein S8 | Plasmodium vivax (strain Salvador I) | 221 |

Figure 1 continued

| | | | | | |
|---|---|---|---|---|---|
| 523 | A5K9F8 | A5K9F8_PLAVS | 40S ribosomal protein S9, putative | Plasmodium vivax (strain Salvador I) | 189 |
| 524 | A5KE24 | RSSA_PLAVS | Small ribosomal subunit protein uS2 (40S ribosomal protein SA) | Plasmodium vivax (strain Salvador I) | 263 |
| 525 | A5K0J8 | A5K0J8_PLAVS | 50S ribosomal protein L1, putative | Plasmodium vivax (strain Salvador I) | 359 |
| 526 | A5KAB4 | A5KAB4_PLAVS | 50S ribosomal protein L1, putative | Plasmodium vivax (strain Salvador I) | 296 |
| 527 | A5K4C2 | A5K4C2_PLAVS | Large ribosomal subunit protein uL11m | Plasmodium vivax (strain Salvador I) | 178 |
| 528 | A5KBY1 | A5KBY1_PLAVS | 50S ribosomal protein L13, putative | Plasmodium vivax (strain Salvador I) | 212 |
| 529 | A5K0W0 | A5K0W0_PLAVS | 50S ribosomal protein L15, putative | Plasmodium vivax (strain Salvador I) | 597 |
| 530 | A5K1I2 | A5K1I2_PLAVS | 50S ribosomal protein L16, putative | Plasmodium vivax (strain Salvador I) | 179 |
| 531 | A5K0U0 | A5K0U0_PLAVS | 50S ribosomal protein L17, putative | Plasmodium vivax (strain Salvador I) | 256 |
| 532 | A5K2Q6 | A5K2Q6_PLAVS | 50S ribosomal protein L17, putative | Plasmodium vivax (strain Salvador I) | 202 |
| 533 | A5K9D4 | A5K9D4_PLAVS | 50S ribosomal protein L17, putative | Plasmodium vivax (strain Salvador I) | 163 |
| 534 | A5K1X3 | A5K1X3_PLAVS | 50S ribosomal protein L18, putative | Plasmodium vivax (strain Salvador I) | 215 |
| 535 | A5K1U4 | A5K1U4_PLAVS | 50S ribosomal protein L19, chloroplastic | Plasmodium vivax (strain Salvador I) | 332 |
| 536 | A5K4Y6 | A5K4Y6_PLAVS | 50S ribosomal protein L2, putative | Plasmodium vivax (strain Salvador I) | 313 |
| 537 | A5K428 | A5K428_PLAVS | 50S ribosomal protein L20, putative | Plasmodium vivax (strain Salvador I) | 121 |
| 538 | A5K8Q4 | A5K8Q4_PLAVS | Large ribosomal subunit protein uL23m | Plasmodium vivax (strain Salvador I) | 270 |
| 539 | A5K039 | A5K039_PLAVS | Large ribosomal subunit protein uL24c | Plasmodium vivax (strain Salvador I) | 244 |
| 540 | A5KDV8 | A5KDV8_PLAVS | 50S ribosomal protein L27, putative | Plasmodium vivax (strain Salvador I) | 170 |
| 541 | A5K0I0 | A5K0I0_PLAVS | 50S ribosomal protein L29, putative | Plasmodium vivax (strain Salvador I) | 165 |
| 542 | A5K6T4 | A5K6T4_PLAVS | 50S ribosomal protein L29, putative | Plasmodium vivax (strain Salvador I) | 280 |
| 543 | A5K6P7 | A5K6P7_PLAVS | Large ribosomal subunit protein uL3c | Plasmodium vivax (strain Salvador I) | 316 |
| 544 | A5K8V6 | A5K8V6_PLAVS | 50S ribosomal protein L3, putative | Plasmodium vivax (strain Salvador I) | 336 |
| 545 | A5JZS8 | A5JZS8_PLAVS | 50S ribosomal protein L33, putative | Plasmodium vivax (strain Salvador I) | 111 |
| 546 | A5K6E8 | A5K6E8_PLAVS | 50S ribosomal protein L35 | Plasmodium vivax (strain Salvador I) | 162 |
| 547 | A5KC00 | A5KC00_PLAVS | 50S ribosomal protein L7/L12, putative | Plasmodium vivax (strain Salvador I) | 268 |
| 548 | A5K3E2 | A5K3E2_PLAVS | 50S ribosomal protein S28e, putative | Plasmodium vivax (strain Salvador I) | 67 |
| 549 | A5K1P8 | A5K1P8_PLAVS | Large ribosomal subunit protein uL24c | Plasmodium vivax (strain Salvador I) | 193 |
| 550 | A5K9B3 | A5K9B3_PLAVS | 50S ribosomal subunit protein L12, putative | Plasmodium vivax (strain Salvador I) | 246 |
| 551 | A5K9G7 | A5K9G7_PLAVS | 50S ribosomal subunit protein L14, putative | Plasmodium vivax (strain Salvador I) | 183 |

Figure 1 continued

| | | | | | |
|---|---|---|---|---|---|
| 552 | A5KAU7 | A5KAU7_PLAVS | Large ribosomal subunit protein bL28c | Plasmodium vivax (strain Salvador I) | 162 |
| 553 | A5K4W2 | A5K4W2_PLAVS | 60S acidic ribosomal protein P0 | Plasmodium vivax (strain Salvador I) | 315 |
| 554 | A5K457 | A5K457_PLAVS | 60S acidic ribosomal protein p1, putative | Plasmodium vivax (strain Salvador I) | 119 |
| 555 | A5K0Z7 | A5K0Z7_PLAVS | 60S ribosomal protein family L5, putative | Plasmodium vivax (strain Salvador I) | 295 |
| 556 | A5K186 | A5K186_PLAVS | 60S ribosomal protein L10, putative | Plasmodium vivax (strain Salvador I) | 219 |
| 557 | A5K3Z8 | A5K3Z8_PLAVS | 60S ribosomal protein L10a, putative | Plasmodium vivax (strain Salvador I) | 217 |
| 558 | A5KC77 | A5KC77_PLAVS | 60S ribosomal protein L11, putative | Plasmodium vivax (strain Salvador I) | 173 |
| 559 | A5K9I9 | A5K9I9_PLAVS | 60S ribosomal protein L12, putative | Plasmodium vivax (strain Salvador I) | 165 |
| 560 | A5JZN9 | A5JZN9_PLAVS | 60S ribosomal protein L13, putative | Plasmodium vivax (strain Salvador I) | 215 |
| 561 | A5K762 | A5K762_PLAVS | 60S ribosomal protein L13a, putative | Plasmodium vivax (strain Salvador I) | 202 |
| 562 | A5K0T3 | A5K0T3_PLAVS | 60S ribosomal protein L14, putative | Plasmodium vivax (strain Salvador I) | 170 |
| 563 | A5K8F1 | A5K8F1_PLAVS | 60S ribosomal protein L17, putative | Plasmodium vivax (strain Salvador I) | 199 |
| 564 | A5K852 | A5K852_PLAVS | 60S ribosomal protein L18, putative | Plasmodium vivax (strain Salvador I) | 187 |
| 565 | A5K851 | A5K851_PLAVS | 60S ribosomal protein L18a | Plasmodium vivax (strain Salvador I) | 184 |
| 566 | A5K1Y3 | A5K1Y3_PLAVS | 60S ribosomal protein L19, putative | Plasmodium vivax (strain Salvador I) | 182 |
| 567 | A5K5N3 | A5K5N3_PLAVS | Large ribosomal subunit protein eL22 (60S ribosomal protein L22) | Plasmodium vivax (strain Salvador I) | 136 |
| 568 | A5K7W5 | A5K7W5_PLAVS | 60S ribosomal protein L23, putative | Plasmodium vivax (strain Salvador I) | 139 |
| 569 | A5K303 | A5K303_PLAVS | 60S ribosomal protein L23a, putative | Plasmodium vivax (strain Salvador I) | 195 |
| 570 | A5JZ82 | A5JZ82_PLAVS | 60S ribosomal protein L24, putative | Plasmodium vivax (strain Salvador I) | 162 |
| 571 | A5KBD9 | A5KBD9_PLAVS | 60S ribosomal protein L26, putative | Plasmodium vivax (strain Salvador I) | 156 |
| 572 | A5K3E8 | A5K3E8_PLAVS | 60S ribosomal protein L27, putative | Plasmodium vivax (strain Salvador I) | 146 |
| 573 | A5K219 | A5K219_PLAVS | 60S ribosomal protein L27a, putative | Plasmodium vivax (strain Salvador I) | 148 |
| 574 | A5K583 | A5K583_PLAVS | 60S ribosomal protein L28, putative | Plasmodium vivax (strain Salvador I) | 127 |
| 575 | A5K3F2 | A5K3F2_PLAVS | 60S ribosomal protein L29 | Plasmodium vivax (strain Salvador I) | 67 |
| 576 | A5KCD7 | A5KCD7_PLAVS | 60S ribosomal protein L30, putative | Plasmodium vivax (strain Salvador I) | 108 |
| 577 | A5KAW8 | A5KAW8_PLAVS | 60S ribosomal protein L31, putative | Plasmodium vivax (strain Salvador I) | 119 |
| 578 | A5K6B0 | A5K6B0_PLAVS | 60S ribosomal protein L32, putative | Plasmodium vivax (strain Salvador I) | 131 |
| 579 | A5K584 | A5K584_PLAVS | 60S ribosomal protein L33-B, putative | Plasmodium vivax (strain Salvador I) | 146 |
| 580 | A5KAB1 | A5KAB1_PLAVS | 60S ribosomal protein L34-A, putative | Plasmodium vivax (strain Salvador I) | 150 |

Figure 1 continued

| | | | | | |
|---|---|---|---|---|---|
| 581 | A5K4R0 | A5K4R0_PLAVS | 60S ribosomal protein L35, putative | Plasmodium vivax (strain Salvador I) | 124 |
| 582 | A5K4B5 | A5K4B5_PLAVS | 60S ribosomal protein L36 | Plasmodium vivax (strain Salvador I) | 113 |
| 583 | A5KBQ3 | A5KBQ3_PLAVS | 60S ribosomal protein L37a, putative | Plasmodium vivax (strain Salvador I) | 96 |
| 584 | A5K4W1 | A5K4W1_PLAVS | 60S ribosomal protein L38-1, putative | Plasmodium vivax (strain Salvador I) | 93 |
| 585 | A5K5A1 | A5K5A1_PLAVS | 60S ribosomal protein L41 | Plasmodium vivax (strain Salvador I) | 39 |
| 586 | A5KB61 | A5KB61_PLAVS | 60S Ribosomal protein L44, putative | Plasmodium vivax (strain Salvador I) | 103 |
| 587 | A5K826 | A5K826_PLAVS | 60S ribosomal protein L6, putative | Plasmodium vivax (strain Salvador I) | 231 |
| 588 | A5K2F4 | A5K2F4_PLAVS | 60s ribosomal protein L7, putative | Plasmodium vivax (strain Salvador I) | 256 |
| 589 | A5KB88 | A5KB88_PLAVS | 60S ribosomal protein L7, putative | Plasmodium vivax (strain Salvador I) | 256 |
| 590 | A5K9J0 | A5K9J0_PLAVS | 60S ribosomal protein L8, putative | Plasmodium vivax (strain Salvador I) | 260 |
| 591 | A5K306 | A5K306_PLAVS | 60S ribosomal protein L9, putative | Plasmodium vivax (strain Salvador I) | 190 |
| 592 | A5K837 | A5K837_PLAVS | 60S ribosomal protein, mitochondrial, putative | Plasmodium vivax (strain Salvador I) | 109 |
| 593 | A5KAY8 | A5KAY8_PLAVS | 60S ribosomal subunit protein L24, putative | Plasmodium vivax (strain Salvador I) | 206 |
| 594 | A5KAZ9 | A5KAZ9_PLAVS | 60S ribosomal subunit protein L4/L1, putative | Plasmodium vivax (strain Salvador I) | 411 |
| 595 | A5K390 | A5K390_PLAVS | 60S ribosome subunit biogenesis protein NIP7 homolog | Plasmodium vivax (strain Salvador I) | 186 |
| 596 | A5K7X4 | A5K7X4_PLAVS | Eukaryotic translation initiation factor 6 (eIF-6) | Plasmodium vivax (strain Salvador I) | 247 |
| 597 | A5KBN4 | A5KBN4_PLAVS | KRR1 small subunit processome component (KRR-R motif-containing protein 1) | Plasmodium vivax (strain Salvador I) | 301 |
| 598 | A5K107 | A5K107_PLAVS | Nucleolar GTP-binding protein 2 | Plasmodium vivax (strain Salvador I) | 518 |
| 599 | A5K5H6 | A5K5H6_PLAVS | Large ribosomal subunit protein bL21m | Plasmodium vivax (strain Salvador I) | 323 |
| 600 | A5K2T1 | A5K2T1_PLAVS | Ribosome assembly factor mrt4 | Plasmodium vivax (strain Salvador I) | 221 |
| 601 | A5K592 | A5K592_PLAVS | Eukaryotic translation initiation factor 4C | Plasmodium vivax (strain Salvador I) | 155 |
| 602 | Q8IK02 | Q8IK02_PLAF7 | 40S ribosomal protein S20e, putative | Plasmodium falciparum (isolate 3D7) | 118 |
| 603 | Q8IBQ5 | Q8IBQ5_PLAF7 | 40S ribosomal protein S10, putative | Plasmodium falciparum (isolate 3D7) | 137 |
| 604 | O77381 | O77381_PLAF7 | 40S ribosomal protein S11, putative | Plasmodium falciparum (isolate 3D7) | 161 |

Figure 1 continued

| | | | | | |
|---|---|---|---|---|---|
| 606 | O97249 | RS12_PLAF7 | Small ribosomal subunit protein eS12 (40S ribosomal protein S12) | Plasmodium falciparum (isolate 3D7) | 141 |
| 607 | O77395 | O77395_PLAF7 | 40S ribosomal protein S15A, putative | Plasmodium falciparum (isolate 3D7) | 151 |
| 608 | Q8IAX5 | Q8IAX5_PLAF7 | 40S ribosomal protein S16, putative | Plasmodium falciparum (isolate 3D7) | 130 |
| 609 | Q8I502 | Q8I502_PLAF7 | 40S ribosomal protein S17, putative | Plasmodium falciparum (isolate 3D7) | 144 |
| 610 | Q8IIA2 | Q8IIA2_PLAF7 | 40S ribosomal protein S18, putative | Plasmodium falciparum (isolate 3D7) | 137 |
| 611 | C0H5C2 | C0H5C2_PLAF7 | 40S ribosomal protein S19 | Plasmodium falciparum (isolate 3D7) | 156 |
| 612 | Q8IFP2 | Q8IFP2_PLAF7 | 40S ribosomal protein S19 | Plasmodium falciparum (isolate 3D7) | 145 |
| 613 | Q8IHS5 | Q8IHS5_PLAF7 | 40S ribosomal protein S21 | Plasmodium falciparum (isolate 3D7) | 170 |
| 614 | O97248 | O97248_PLAF7 | 40S ribosomal protein S23, putative | Plasmodium falciparum (isolate 3D7) | 82 |
| 615 | Q8I3R6 | Q8I3R6_PLAF7 | 40S ribosomal protein S24 | Plasmodium falciparum (isolate 3D7) | 145 |
| 616 | Q8ILN8 | Q8ILN8_PLAF7 | 40S ribosomal protein S25 | Plasmodium falciparum (isolate 3D7) | 133 |
| 617 | O96258 | O96258_PLAF7 | 40S ribosomal protein S26 | Plasmodium falciparum (isolate 3D7) | 105 |
| 618 | Q8IEN2 | Q8IEN2_PLAF7 | 40S ribosomal protein S27 | Plasmodium falciparum (isolate 3D7) | 107 |
| 619 | Q8IKL9 | Q8IKL9_PLAF7 | 40S ribosomal protein S28e, putative | Plasmodium falciparum (isolate 3D7) | 82 |
| 620 | C0H4K8 | C0H4K8_PLAF7 | 40S ribosomal protein S29, putative | Plasmodium falciparum (isolate 3D7) | 67 |
| 621 | Q8IKH8 | Q8IKH8_PLAF7 | 40S ribosomal protein S3 | Plasmodium falciparum (isolate 3D7) | 54 |
| 622 | O96269 | RS30_PLAF7 | Small ribosomal subunit protein eS30 (40S ribosomal protein S30) | Plasmodium falciparum (isolate 3D7) | 221 |
| 623 | O96269 | RS30_PLAF7 | Small ribosomal subunit protein eS30 (40S ribosomal protein S30) | Plasmodium falciparum (isolate 3D7) | 58 |
| 624 | O97313 | RS3A_PLAF7 | Small ribosomal subunit protein eS1 (40S ribosomal protein S3a) | Plasmodium falciparum (isolate 3D7) | 58 |
| 625 | Q8IIU8 | Q8IIU8_PLAF7 | 40S ribosomal protein S4 | Plasmodium falciparum (isolate 3D7) | 262 |
| 626 | Q8IL02 | Q8IL02_PLAF7 | 40S ribosomal protein S5 | Plasmodium falciparum (isolate 3D7) | 261 |
| 627 | Q8IBN5 | Q8IBN5_PLAF7 | 40S ribosomal protein S5, putative | Plasmodium falciparum (isolate 3D7) | 272 |
| 628 | Q8IDR9 | Q8IDR9_PLAF7 | 40S ribosomal protein S6 | Plasmodium falciparum (isolate 3D7) | 195 |
| 629 | Q8IET7 | Q8IET7_PLAF7 | 40S ribosomal protein S7 | Plasmodium falciparum (isolate 3D7) | 306 |
| 630 | Q8IM10 | Q8IM10_PLAF7 | 40S ribosomal protein S8 | Plasmodium falciparum (isolate 3D7) | 194 |
| 631 | Q8I3R0 | Q8I3R0_PLAF7 | 40S ribosomal protein S9, putative | Plasmodium falciparum (isolate 3D7) | 218 |

Figure 1 continued

| | | | | | |
|---|---|---|---|---|---|
| 632 | Q8IJD4 | RSSA_PLAF7 | Small ribosomal subunit protein uS2 (40S ribosomal protein S2) (40S ribosomal protein SA) | Plasmodium falciparum (isolate 3D7) | 189 |
| 633 | Q8IJD4 | RSSA_PLAF7 | Small ribosomal subunit protein uS2 (40S ribosomal protein S2) (40S ribosomal protein SA) | Plasmodium falciparum (isolate 3D7) | 263 |
| 634 | Q8I5U9 | Q8I5U9_PLAF7 | 50S ribosomal protein L1, apicoplast, putative | Plasmodium falciparum (isolate 3D7) | 263 |
| 635 | Q8IBY1 | Q8IBY1_PLAF7 | 50S ribosomal protein L1, mitochondrial, putative | Plasmodium falciparum (isolate 3D7) | 339 |
| 636 | Q8I1U9 | Q8I1U9_PLAF7 | 50S ribosomal protein L10, putative | Plasmodium falciparum (isolate 3D7) | 399 |
| 637 | Q8I3L9 | Q8I3L9_PLAF7 | 50S ribosomal protein L12, apicoplast, putative | Plasmodium falciparum (isolate 3D7) | 280 |
| 638 | C0H4F9 | C0H4F9_PLAF7 | 50S ribosomal protein L17, apicoplast, putative | Plasmodium falciparum (isolate 3D7) | 257 |
| 639 | Q8IKG3 | Q8IKG3_PLAF7 | Large ribosomal subunit protein uL22c | Plasmodium falciparum (isolate 3D7) | 166 |
| 640 | Q8IJT7 | Q8IJT7_PLAF7 | Large ribosomal subunit protein uL22m | Plasmodium falciparum (isolate 3D7) | 294 |
| 641 | C6KSP8 | C6KSP8_PLAF7 | Large ribosomal subunit protein uL24c | Plasmodium falciparum (isolate 3D7) | 299 |
| 642 | Q8I5H8 | Q8I5H8_PLAF7 | Large ribosomal subunit protein uL24c | Plasmodium falciparum (isolate 3D7) | 194 |
| 643 | C0H4C3 | C0H4C3_PLAF7 | Large ribosomal subunit protein bL28c | Plasmodium falciparum (isolate 3D7) | 227 |
| 644 | C0H543 | C0H543_PLAF7 | Large ribosomal subunit protein uL3c | Plasmodium falciparum (isolate 3D7) | 262 |
| 645 | C6S3B5 | C6S3B5_PLAF7 | 50S ribosomal protein L33, putative | Plasmodium falciparum (isolate 3D7) | 317 |
| 646 | Q8I373 | Q8I373_PLAF7 | 50S ribosomal protein L35 | Plasmodium falciparum (isolate 3D7) | 119 |
| 647 | Q9NLA7 | Q9NLA7_PLAF7 | 50S ribosomal protein L9, apicoplast, putative | Plasmodium falciparum (isolate 3D7) | 191 |
| 648 | Q8II61 | Q8II61_PLAF7 | 60S acidic ribosomal protein P0 | Plasmodium falciparum (isolate 3D7) | 197 |
| 649 | Q8IIX0 | Q8IIX0_PLAF7 | 60S acidic ribosomal protein P1, putative | Plasmodium falciparum (isolate 3D7) | 316 |
| 650 | O00806 | RLA2_PLAF7 | Large ribosomal subunit protein P2 (60S acidic ribosomal protein P2) | Plasmodium falciparum (isolate 3D7) | 118 |
| 651 | Q8IBG6 | Q8IBG6_PLAF7 | 60S ribosomal export protein NMD3, putative | Plasmodium falciparum (isolate 3D7) | 112 |

Figure 1 continued

| | | | | | |
|---|---|---|---|---|---|
| 652 | Q8IL58 | Q8IL58_PLAF7 | 60S ribosomal protein L1, putative | Plasmodium falciparum (isolate 3D7) | 888 |
| 653 | Q8ILV2 | Q8ILV2_PLAF7 | 60S ribosomal protein L10, putative | Plasmodium falciparum (isolate 3D7) | 217 |
| 654 | Q8IBQ6 | Q8IBQ6_PLAF7 | 60S ribosomal protein L11a, putative | Plasmodium falciparum (isolate 3D7) | 219 |
| 655 | Q8I3T8 | Q8I3T8_PLAF7 | 60S ribosomal protein L12, putative | Plasmodium falciparum (isolate 3D7) | 173 |
| 656 | Q8IAX6 | Q8IAX6_PLAF7 | 60S ribosomal protein L13 | Plasmodium falciparum (isolate 3D7) | 165 |
| 657 | Q8IJZ7 | Q8IJZ7_PLAF7 | 60S ribosomal protein L13, putative | Plasmodium falciparum (isolate 3D7) | 215 |
| 658 | Q8ILE8 | Q8ILE8_PLAF7 | 60S ribosomal protein L14, putative | Plasmodium falciparum (isolate 3D7) | 202 |
| 659 | Q8IDI5 | Q8IDI5_PLAF7 | 60S ribosomal protein L17, putative | Plasmodium falciparum (isolate 3D7) | 165 |
| 660 | C0H5G3 | C0H5G3_PLAF7 | 60S ribosomal protein L18-2, putative | Plasmodium falciparum (isolate 3D7) | 203 |
| 661 | Q8IDS6 | Q8IDS6_PLAF7 | 60S ribosomal protein L18a | Plasmodium falciparum (isolate 3D7) | 187 |
| 662 | C6KSY6 | C6KSY6_PLAF7 | 60S ribosomal protein L19 | Plasmodium falciparum (isolate 3D7) | 184 |
| 663 | Q8I3T9 | Q8I3T9_PLAF7 | 60S ribosomal protein L2 | Plasmodium falciparum (isolate 3D7) | 182 |
| 664 | Q8ILK3 | Q8ILK3_PLAF7 | 60S ribosomal protein L21 | Plasmodium falciparum (isolate 3D7) | 260 |
| 665 | Q8IB51 | Q8IB51_PLAF7 | Large ribosomal subunit protein eL22 (60S ribosomal protein L22) | Plasmodium falciparum (isolate 3D7) | 161 |
| 666 | Q8IE82 | Q8IE82_PLAF7 | 60S ribosomal protein L23 | Plasmodium falciparum (isolate 3D7) | 139 |
| 667 | Q8IE09 | Q8IE09_PLAF7 | 60S ribosomal protein L23, putative | Plasmodium falciparum (isolate 3D7) | 190 |
| 668 | Q8IEM3 | Q8IEM3_PLAF7 | 60S ribosomal protein L24, putative | Plasmodium falciparum (isolate 3D7) | 139 |
| 669 | O77364 | O77364_PLAF7 | 60S ribosomal protein L26, putative | Plasmodium falciparum (isolate 3D7) | 162 |
| 670 | Q8IKM5 | Q8IKM5_PLAF7 | 60S ribosomal protein L27 | Plasmodium falciparum (isolate 3D7) | 126 |
| 671 | C6KT23 | C6KT23_PLAF7 | 60S ribosomal protein L27a, putative | Plasmodium falciparum (isolate 3D7) | 146 |
| 672 | Q8IHU0 | Q8IHU0_PLAF7 | 60S ribosomal protein L28 | Plasmodium falciparum (isolate 3D7) | 148 |
| 673 | C6S3J6 | C6S3J6_PLAF7 | 60S ribosomal protein L29 | Plasmodium falciparum (isolate 3D7) | 127 |
| 674 | Q8IJC6 | Q8IJC6_PLAF7 | 60S ribosomal protein L3 | Plasmodium falciparum (isolate 3D7) | 67 |
| 675 | Q8IJK8 | Q8IJK8_PLAF7 | 60S ribosomal protein L30e, putative | Plasmodium falciparum (isolate 3D7) | 386 |
| 676 | Q8I463 | Q8I463_PLAF7 | 60S ribosomal protein L31 | Plasmodium falciparum (isolate 3D7) | 108 |
| 677 | Q8I3B0 | Q8I3B0_PLAF7 | 60S ribosomal protein L32 | Plasmodium falciparum (isolate 3D7) | 120 |
| 678 | Q8IBY4 | Q8IBY4_PLAF7 | 60S ribosomal protein L34 | Plasmodium falciparum (isolate 3D7) | 131 |
| 679 | Q8IIB4 | Q8IIB4_PLAF7 | 60S ribosomal protein L35, putative | Plasmodium falciparum (isolate 3D7) | 150 |
| 680 | Q8IHT9 | Q8IHT9_PLAF7 | 60S ribosomal protein L35ae, putative | Plasmodium falciparum (isolate 3D7) | 124 |
| 681 | Q8I713 | Q8I713_PLAF7 | 60S ribosomal protein L36 | Plasmodium falciparum (isolate 3D7) | 140 |

Figure 1 continued

| | | | | | |
|---|---|---|---|---|---|
| 682 | O96184 | RL37A_PLAF7 | Large ribosomal subunit protein eL43 (60S ribosomal protein L37a) | Plasmodium falciparum (isolate 3D7) | 112 |
| 683 | O96184 | RL37A_PLAF7 | Large ribosomal subunit protein eL43 (60S ribosomal protein L37a) | Plasmodium falciparum (isolate 3D7) | 96 |
| 684 | Q8II62 | Q8II62_PLAF7 | 60S ribosomal protein L38 | Plasmodium falciparum (isolate 3D7) | 96 |
| 685 | C0H4H3 | C0H4H3_PLAF7 | 60S ribosomal protein L39 | Plasmodium falciparum (isolate 3D7) | 87 |
| 686 | Q8I431 | Q8I431_PLAF7 | 60S ribosomal protein L4 | Plasmodium falciparum (isolate 3D7) | 51 |
| 687 | C6S3G4 | C6S3G4_PLAF7 | 60S ribosomal protein L41 | Plasmodium falciparum (isolate 3D7) | 411 |
| 688 | O97231 | RL44_PLAF7 | Large ribosomal subunit protein eL42 (60S ribosomal protein L44) | Plasmodium falciparum (isolate 3D7) | 39 |
| 689 | Q8ILL3 | Q8ILL3_PLAF7 | 60S ribosomal protein L5, putative | Plasmodium falciparum (isolate 3D7) | 104 |
| 690 | Q8IE85 | Q8IE85_PLAF7 | 60S ribosomal protein L6, putative | Plasmodium falciparum (isolate 3D7) | 294 |
| 691 | O97250 | O97250_PLAF7 | 60S ribosomal protein L7, putative | Plasmodium falciparum (isolate 3D7) | 190 |
| 692 | C0H5I4 | C0H5I4_PLAF7 | 60S ribosomal protein L7-2, putative | Plasmodium falciparum (isolate 3D7) | 257 |
| 693 | Q8ILL2 | Q8ILL2_PLAF7 | 60S ribosomal protein L7a | Plasmodium falciparum (isolate 3D7) | 252 |
| 694 | Q8I1P0 | Q8I1P0_PLAF7 | 60S ribosomal protein L7ae/L30e, putative | Plasmodium falciparum (isolate 3D7) | 283 |
| 695 | Q8I441 | Q8I441_PLAF7 | 60S ribosomal subunit protein L24, putative | Plasmodium falciparum (isolate 3D7) | 236 |
| 696 | Q8IKH0 | Q8IKH0_PLAF7 | 60S ribosome subunit biogenesis protein NIP7 homolog | Plasmodium falciparum (isolate 3D7) | 204 |
| 697 | Q8IL87 | Q8IL87_PLAF7 | Eukaryotic translation initiation factor 2A (eIF-2A) | Plasmodium falciparum (isolate 3D7) | 179 |
| 698 | Q8I5S6 | Q8I5S6_PLAF7 | Eukaryotic translation initiation factor 3 subunit A (eIF3a) (Eukaryotic translation initiation factor 3 subunit 10) | Plasmodium falciparum (isolate 3D7) | 661 |
| 699 | Q8I3T1 | Q8I3T1_PLAF7 | Eukaryotic translation initiation factor 3 subunit B (eIF3b) (Eukaryotic translation initiation factor 3 subunit 9) | Plasmodium falciparum (isolate 3D7) | 1377 |
| 700 | Q8I5Y3 | Q8I5Y3_PLAF7 | Eukaryotic translation initiation factor 3 subunit C (eIF3c) (Eukaryotic translation initiation factor 3 subunit 8) | Plasmodium falciparum (isolate 3D7) | 716 |

Figure 1 continued

| | | | | | |
|---|---|---|---|---|---|
| 701 | Q8IJW4 | Q8IJW4_PLAF7 | Eukaryotic translation initiation factor 3 subunit D (eIF3d) (Eukaryotic translation initiation factor 3 subunit 7) | Plasmodium falciparum (isolate 3D7) | 984 |
| 702 | Q8I3I5 | Q8I3I5_PLAF7 | Eukaryotic translation initiation factor 3 subunit E (eIF3e) (Eukaryotic translation initiation factor 3 subunit 6) | Plasmodium falciparum (isolate 3D7) | 543 |
| 703 | Q8I2X0 | Q8I2X0_PLAF7 | Eukaryotic translation initiation factor 3 subunit F, putative | Plasmodium falciparum (isolate 3D7) | 517 |
| 704 | Q8IAZ3 | Q8IAZ3_PLAF7 | Eukaryotic translation initiation factor 3 subunit G (eIF3g) (Eukaryotic translation initiation factor 3 RNA-binding subunit) (eIF-3 RNA-binding subunit) (Eukaryotic translation initiation factor 3 subunit 4) | Plasmodium falciparum (isolate 3D7) | 320 |
| 705 | Q8IBT2 | Q8IBT2_PLAF7 | Eukaryotic translation initiation factor 3 subunit I (eIF3i) | Plasmodium falciparum (isolate 3D7) | 268 |
| 706 | C6KSW5 | C6KSW5_PLAF7 | Eukaryotic translation initiation factor 3 subunit L (eIF3l) | Plasmodium falciparum (isolate 3D7) | 327 |
| 707 | Q8I1Q5 | Q8I1Q5_PLAF7 | Eukaryotic translation initiation factor 3 subunit M (eIF3m) | Plasmodium falciparum (isolate 3D7) | 656 |
| 708 | Q8IE00 | Q8IE00_PLAF7 | Eukaryotic translation initiation factor 6 (eIF-6) | Plasmodium falciparum (isolate 3D7) | 429 |
| 709 | O96169 | O96169_PLAF7 | KRR1 small subunit processome component (KRR-R motif-containing protein 1) | Plasmodium falciparum (isolate 3D7) | 247 |
| 710 | C6KSX2 | C6KSX2_PLAF7 | Nucleolar GTP-binding protein 1 | Plasmodium falciparum (isolate 3D7) | 300 |
| 711 | Q8ILM2 | Q8ILM2_PLAF7 | Nucleolar GTP-binding protein 2 | Plasmodium falciparum (isolate 3D7) | 686 |
| 712 | Q6LFD5 | RK18_PLAF7 | Large ribosomal subunit protein uL18c (50S ribosomal protein L18, apicoplastic) | Plasmodium falciparum (isolate 3D7) | 487 |
| 713 | C0H4A6 | C0H4A6_PLAF7 | Ribosomal protein L15 | Plasmodium falciparum (isolate 3D7) | 213 |
| 714 | C0H4L5 | C0H4L5_PLAF7 | Ribosomal protein L37 | Plasmodium falciparum (isolate 3D7) | 205 |
| 715 | Q8IHT2 | Q8IHT2_PLAF7 | Eukaryotic translation initiation factor 4C | Plasmodium falciparum (isolate 3D7) | 92 |

Figure 1 continued

| | | | | | |
|---|---|---|---|---|---|
| 716 | C6KSR8 | C6KSR8_PLAF7 | Eukaryotic translation initiation factor 5B (Translation initiation factor IF-2) | Plasmodium falciparum (isolate 3D7) | 155 |
| 717 | Q8IM64 | Q8IM64_PLAF7 | Ribosomal protein S27a, putative | Plasmodium falciparum (isolate 3D7) | 149 |
| 718 | Q8ID50 | Q8ID50_PLAF7 | Ubiquitin-60S ribosomal protein L40 | Plasmodium falciparum (isolate 3D7) | 128 |
| 719 | A5K474 | A5K474_PLAVS | Histone H4 | Plasmodium vivax (strain Salvador I) | 103 |
| 720 | A5K1U7 | A5K1U7_PLAVS | Histone H3 | Plasmodium vivax (strain Salvador I) | 136 |
| 721 | A5K214 | A5K214_PLAVS | Histone H2A | Plasmodium vivax (strain Salvador I) | 133 |
| 722 | A5K7L8 | A5K7L8_PLAVS | Histone H2A | Plasmodium vivax (strain Salvador I) | 158 |

Figure 2

List of ribosomal protein antigens and peptides identified

| SEQ IDN° | Accession | Name | Peptide sequences |
|---|---|---|---|
| 454 | A5KC76 | 40S ribosomal protein S10, putative | TLSKKVVNRAPK |
| 363 | A5K7Q0 | 40S ribosomal protein S11, putative | SFFNSKKIKKGSK |
| 364 | | | SFFNSKKIKKGSKS |
| 275 | A5K2J4 | 40S ribosomal protein S13, putative | KYQSSTASALIA |
| 412 | A5JZP0 | 40S ribosomal protein S16, putative | TTKVKRVQT |
| 413 | | | TTKVKRVQTF |
| 455 | | | TTKVKRVQTFGKKK |
| 359 | A5K4S2 | 40S ribosomal protein S18, putative | RTVGVSKKKGA |
| 310 | A5K662 | 40S ribosomal protein S19s, putative | NKKVYKLDKE |
| 128 | A5K3U1 | 40S ribosomal protein S2, putative | GSAEDDLK |
| 279 | | | LETYQNMKIQKQTP |
| 456 | | | KDCFSSSCGKT |
| 385 | A5KB86 | 40S ribosomal protein S23, putative | SSHAKGIVV |
| 386 | | | SSHAKGIVVEKV |
| 375 | | | SLLALFKEKKEKPRS |
| 17 | | | ALFKEKKEKPRS |
| 264 | | | KSNPFRGSSHAK |
| 97 | A5K124 | 40S ribosomal protein S25, putative | GKGKNKEKL |
| 383 | | | SQKLYTKVA |
| 98 | | | GKGKNKEKLNHA |
| 99 | | | GKGKNKEKLNHAV |
| 100 | | | GKGKNKEKLNHAVF |
| 101 | | | GKGKNKEKLNHAVFI |
| 186 | | | KGKNKEKLNHAV |
| 187 | | | KGKNKEKLNHAVF |
| 241 | | | KNKEKLNHAVF |
| 307 | | | NKEKLNHAV |
| 308 | | | NKEKLNHAVF |
| 66 | | | EKLNHAVF |
| 172 | | | KEKLNHAVF |
| 330 | | | PPKERKTKEQIAAA |
| 2 | | | AAAAASGRSK(+27.99)KKKWG |
| 105 | | | GKNKEKLNHAVF |
| 457 | | | HAVFID(-18.01)KAL |
| 217 | | | KKKKW(+15.99)GKGKNKE |
| 458 | | | P(+71.04)PKERKTKEQIAAAA |
| 459 | A5K398 | 40S ribosomal protein S3, putative | NISVLEPKTETIEAL |
| 111 | A5KBT5 | 40S ribosomal protein S30 | GKVHGSLARAGKVK |
| 344 | | | RKKGPNSKL |
| 131 | | | GTGRKKGPNSKL |
| 361 | | | SDGTGRKKGPNSKL |
| 401 | | | TGRKKGPNSKL |
| 431 | | | VSKRKKLTGRAK |
| 432 | | | VSKRKKLTGRAKK |
| 340 | | | RAGKVKNQTPKVPK |
| 243 | | | KNQTPKVPKVSKRK |

*Continued in next page*

Figure 2 continued

List of ribosomal protein antigens and peptides identified - continued

| SEQ IDN° | Accession | Name | Peptide sequences |
|---|---|---|---|
| 133 | A5K858 | 40S ribosomal protein S6, putative | GVKKDVAK |
| 169 | | | KEDAKGGKKKK |
| 221 | | | KKNLKGAK |
| 222 | | | KKNLKGAKAEEGK |
| 253 | | | KPQKEDAKGGKK |
| 332 | | | PQKEDAKGGKKKK |
| 220 | | | KKKVIKEYKKVLNK |
| 120 | | | GPKRATKIRK |
| 119 | | | GPKRATKIR |
| 219 | | | KKKVIKEYKK |
| 165 | | | KDSQKKGGKKKD |
| 202 | | | KKDAGKKDAGKKD |
| 158 | | | KDAGKKDAGKKD |
| 161 | | | KDGVKKDVAKKD |
| 341 | | | RAISKNGKNRFIKPK |
| 370 | | | SKNGKNRFIKPK |
| 313 | | | NLKGAKAEEGKKD |
| 7 | | | AGKKDGAKKEVA |
| 271 | | | KVDKKAPAKPQKED |
| 392 | | | TDEDAGKKKKVKKSL |
| 371 | | | SKNGKNRFIKPKIQ |
| 167 | | | KDVAKKDAGKKD |
| 200 | | | KKAPAK(+226.08)PQ |
| 88 | A5K1E3 | 40S ribosomal protein S8 | GISRDGRHKL |
| 89 | | | GISRDGRHKLRLTG |
| 90 | | | GISRDGRHKLRLTGG |
| 211 | | | KKIGKSKQID |
| 130 | | | GSKQVHVV |
| 355 | | | RPPSNTKLGSKQV |
| 350 | | | RLTGGKKKIHK |
| 351 | | | RLTGGKKKIHKKK |
| 349 | | | RLTGGKKKIH |
| 75 | | | FYKRKM(+15.99)DKKKRN |
| 326 | A5K6T4 | 50S ribosomal protein L29, putative | PKIEPPKKKFIPSVL |
| 81 | A5K3E2 | 50S ribosomal protein S28e, putative | GDTELSGRF |
| 82 | | | GDTELSGRFL |
| 83 | | | GDTELSGRFLI |
| 190 | A5K0Z7 | 60S ribosomal protein family L5, putative | KHEKPKKLNAKLR |
| 191 | | | KHEKPKKLNAKLRK |
| 163 | A5K186 | 60S ribosomal protein L10, putative | KDINTIIES |
| 78 | | | GAFGKPNGV |
| 68 | A5JZN9 | 60S ribosomal protein L13, putative | EVSKIDKSYLAYK |
| 132 | | | GTPIEKLHPI |
| 240 | | | KNIKSKNGIGGIPAD |
| 440 | | | YESIEVSKID |
| 439 | | | YESIEVSKI |

*Continued in next page*

Figure 2 continued

List of ribosomal protein antigens and peptides identified - continued

| SEQ IDN° | Accession | Name | Peptide sequences |
|---|---|---|---|
| 460 | A5JZN9 | 60S ribosomal protein L13, putative | KERNTKPF |
| 239 | | | KNIKSKNGIG |
| 304 | | | NFSKNIKKKK |
| 293 | A5K762 | 60S ribosomal protein L13a, putative | MYKKVYVID |
| 301 | | | NEKKELKTEAL |
| 293 | | | M(+15.99)YKKVYVID |
| 372 | A5K8F1 | 60S ribosomal protein L17, putative | SKQNFAKNKKKAAN |
| 424 | | | VKYAKKLRD |
| 152 | | | ISKQNFAKNKKKAAN |
| 3 | A5K851 | 60S ribosomal protein L18a | AAKRPSTY |
| 461 | | | VRVADNSLKTNI(-.98) |
| 429 | | | VRVADNSLKTNIHQY |
| 414 | A5K5N3 | 60S ribosomal protein L22, putative | VAKKESKIIKKQK |
| 415 | | | VAKKESKIIKKQKK |
| 76 | A5K303 | 60S ribosomal protein L23a, putative | GADKEKKQLY |
| 462 | | | KEKKQLYKGKVKK |
| 171 | | | KEKKQLYKGKVK |
| 179 | | | KGADKEKKQLY |
| 215 | | | KKKGADKEKKQLY |
| 374 | | | SLGKQVGGKNQQVK |
| 5 | | | ADKEKKQLY |
| 102 | | | GKKKGADKEKK |
| 151 | | | ILKYPLTSEK |
| 214 | | | KKKGADKEKK |
| 103 | | | GKKKGADKEKKQLY |
| 189 | | | KGKVKKSLGKQVGGK |
| 87 | | | GILKYPLTSEKAM(+15.99)KK |
| 196 | | | KK(+31.99)GADKEKK |
| 463 | | | KKNAK(+31.99)NVK |
| 160 | A5JZ82 | 60S ribosomal protein L24, putative | KDFAKSKQV |
| 373 | | | SLALQKKKAA |
| 116 | | | GLTVEDIRNRKA |
| 6 | | | AGKEKDDKKKGKD |
| 69 | | | FAKSKQVNMAKTK |
| 464 | | | EAKNKSRM(+15.99)AGKEKD |
| 69 | | | FAKSKQVNM(+15.99)AKTK |
| 104 | A5K3E8 | 60S ribosomal protein L27, putative | GKLLKPGKVVI |
| 28 | A5K219 | 60S ribosomal protein L27a, putative | ATRFKKNRKKRG |
| 144 | A5K583 | 60S ribosomal protein L28, putative | IDEHAHLV |
| 325 | A5K3F2 | 60S ribosomal protein L29 | PKFFKNQRY |
| 15 | | | AKSKNHTNHNQNRKA |
| 343 | | | RKAHKNGIKKPK |
| 207 | | | KKELKLKQKQEKKN |
| 384 | | | SRKGLDPKFFK |
| 86 | | | GILKKKKELKLKQ |
| 213 | | | KKKELKLKQKQEKKN |

*Continued in next page*

Figure 2 continued

List of ribosomal protein antigens and peptides identified - continued

| SEQ IDN° | Accession | Name | Peptide sequences |
|---|---|---|---|
| 237 | A5K3F2 | 60S ribosomal protein L29 | KNGIKKPKKHKF |
| 324 | | | PKFFKNQR |
| 238 | | | KNGIKKPKKHKFM(+15.99)S |
| 422 | A5KCD7 | 60S ribosomal protein L30, putative | TDVGDSDIIKTNE |
| 362 | | | SDIIKTNE |
| 422 | | | VITDVGDSDIIKTNE |
| 420 | | | VGDSDIIKTNE |
| 29 | A5KAW8 | 60S ribosomal protein L31, putative | AVKKQKKTLKPVTK |
| 11 | | | AKAVKKQKKTLKPV |
| 33 | A5K6B0 | 60S ribosomal protein L32, putative | AVKKVGKIVKKRT |
| 34 | | | AVKKVGKIVKKRTK |
| 389 | | | SVINAKAKLQKTEE |
| 30 | | | AVKKVGKIV |
| 31 | | | AVKKVGKIVK |
| 32 | | | AVKKVGKIVKK |
| 80 | A5K584 | 60S ribosomal protein L33-B, putative | GDRVRILMYPSNI |
| 117 | | | GNAKGKKPAKKVI |
| 465 | | | KGKKPAKK(-.98) |
| 184 | | | KGKKPAKKVI |
| 297 | | | NAKGKKPAKKVI |
| 305 | | | NIPPKAFG |
| 358 | A5KAB1 | 60S ribosomal protein L34-A, putative | RTPGGKLTI |
| 49 | | | DNKKAKKVGDKRKGR |
| 312 | | | NKVRPIRTPGGKLTI |
| 230 | A5K4R0 | 60S ribosomal protein L35, putative | KKYKNKKFKPY |
| 348 | | | RLELTPKQKV |
| 231 | | | KKYKNKKFKPYNLRK |
| 126 | A5K4B5 | 60S ribosomal protein L36 | GRKSTIKPA |
| 256 | | | KRNLKKSIKKKPKSK |
| 353 | | | RNLKKSIKKKPKS |
| 354 | | | RNLKKSIKKKPKSK |
| 466 | | | GFNSGHVVTK |
| 127 | | | GRKSTIKPATGIAV |
| 398 | A5KBQ3 | 60S ribosomal protein L37a, putative | TGKYGTRYGSSL |
| 376 | | | SLTTPAAVAAK |
| 467 | A5K4W1 | 60S ribosomal protein L38-1, putative | KKSKTKKNTIITK |
| 135 | A5K5A1 | 60S ribosomal protein L41, putative | HGASRYKKSRA |
| 468 | A5KB61 | 60S Ribosomal protein L44, putative | EM(+15.99)GADKKKKGAVY |
| 72 | | | FGGQTKPV |
| 73 | | | FKKKAKTTKKIVLK |
| 77 | | | GADKKKKGAVY |
| 122 | | | GQTKPVFKKKAKTTK |
| 212 | | | KKKAKTTKKIVLK |
| 216 | | | KKKKGAVY |
| 426 | | | VNVPKTRKTY |
| 426 | | | VNVPKTRKTY(-.98) |

*Continued in next page*

Figure 2 continued

List of ribosomal protein antigens and peptides identified - continued

| SEQ IDN° | Accession | Name | Peptide sequences |
|---|---|---|---|
| 277 | A5K826 | 60S ribosomal protein L6, putative | KYYRVKGKKKILIPV |
| 113 | A5K9J0 | 60S ribosomal protein L8, putative | GLLRGAKKTK |
| 137 | | | HHKYRVKR |
| 400 | | | TGLLRGAKKTKLVG |
| 403 | | | TKLVGKTED |
| 430 | A5K306 | 60S ribosomal protein L9, putative | VSEVTTVEKDE |
| 18 | A5KAZ9 | 60S ribosomal subunit protein L4/L1, putative | ANKALLPTAGDD |
| 38 | | | DANKALLPTAGDD |
| 155 | | | KALLPTAGDD |
| 306 | | | NKALLPTAGDD |
| 469 | | | KKKITKKNYILPK |
| 444 | | | YGRIFKKKITKK |
| 445 | | | YGRIFKKKITKKN |
| 1 | | | A(+42.01)TVRPVANVYST |
| 84 | | | GGGM(+15.99)FNPTKV |
| 244 | | | KNSLTNFAVR(-.98) |
| 311 | | | NKNSLTNFAVR(-.98) |
| 318 | | | NSLTNFAVR(-.98) |
| 139 | A5K5X8 | Ribosomal protein L15 | HLSAKSRPS |
| 136 | | | HGKPKHQGV |
| 140 | | | HLSAKSRPSIR |
| 470 | A5K0Y7 | Ribosomal protein L21e, putative | GGKSKGKRSGTRY |
| 352 | A5KE14 | Ribosomal protein L3, putative | RNKKIYRIGLK |
| 443 | | | YGPLKKDLKA |
| 134 | A5KA70 | Ribosomal protein L37 | GYPSAKKRRF |
| 94 | | | GKAGKGTGSFGKR |
| 95 | | | GKAGKGTGSFGKRN |
| 96 | | | GKAGKGTGSFGKRNG |
| 93 | | | GKAGKGTGSFGK |
| 394 | | | TEGSTPKPKQR |
| 91 | | | GKAGKGTGSF |
| 92 | | | GKAGKGTGSFG |
| 471 | | | CAS(-2.02)CGYPSAKKRRF |
| 149 | A5K0Z6 | Ribosomal protein L7a, putative | IKKERKKGI |
| 205 | | | KKDIKKERKKGIRS |
| 162 | | | KDIKKERKKGIRS |
| 12 | | | AKDKKQLKKPS |
| 328 | | | PLSNKKTVK |

Figure 2 continued

List of ETRAMP protein antigens and peptides identified

| SEQ IDN° | Accession | Name | Peptide sequences |
|---|---|---|---|
| 114 | *A5KBH5 | Early transcribed membrane protein (ETRAMP) | GLNQKQPTKGSNIQ |
| 175 | | | K(+167.98)EPLLGGLNQKQPT |
| 175 | | | KEPLLGGLNQKQPT |
| 227 | | | KKVAAGYKKLTD |
| 282 | | | LGGLNQKQPT |
| 289 | | | LNQKQPTKGSNIQ |
| 309 | | | NKKGTPNTKKEPLL |
| 316 | | | NQKQPTKGSNIQ |
| 336 | | | Q(-17.03)KQPTKGSNIQ |
| 473 | *A5K676 | Early transcribed membrane protein (ETRAMP) | A(+27.99)GADSKSL |
| 258 | | | KSAGADSKSLKKLD |
| 369 | | | SKGPDTPIITN |
| 409 | | | TPIITNKPFG |
| 410 | | | TPIITNKPFGK |

List of Elongation factor 1-alpha peptides identified

| SEQ IDN° | Accession | Name | Peptide sequences |
|---|---|---|---|
| 395 | A5K2H7 | Elongation factor 1-alpha | TEYPPLGRF |
| 396 | | | TEYPPLGRFA |
| 474 | | | VSLEPKKPM(+15.99)VVETF |

List of Histone peptides identified

| SEQ IDN° | Accession | Name | Peptide sequences |
|---|---|---|---|
| 19 | *A5K1U7 | Histone H3 | APISAGIKKPHR |
| 360 | | | SAGIKKPHRYRPGTV |
| 157 | | | KAPRKQLASKAARK |
| 24 | *A5K214 | Histone H2A | ASGGVLPNIHNV |
| 124 | | | GRIGRYLKKGKYA |
| 125 | | | GRIGRYLKKGKYAK |
| 286 | | | LLPKKSQLK |
| 287 | | | LLPKKSQLKSG |
| 366 | | | SGGVLPNIHNV |
| 411 | | | TSNSAKAGLQFPV |
| 43 | *A5K474 | Histone H4 | DIVYSLKRQG |
| 273 | *A5K7L8 | Histone H2A | KVPVPPTQAKKPKKN |

Figure 3

| | All peptides identified by immunopeptidomics. | |
|---|---|---|
| SEQ IDNº | Peptide | Identifier |
| 1 | A(+42.01)TVRPVANVYST | tr\|A5KAZ9\|A5KAZ9_PLAVS 60S ribosomal subunit protein L4/L1 OX=126793 GN=PVX_097915 PE=4 SV=1 |
| 2 | AAAAASGRSK(+27.99)KKKWG | tr\|A5K124\|A5K124_PLAVS 40S ribosomal protein S25 OX=126793 GN=PVX_085420 PE=4 SV=1 |
| 3 | AAKRPSTY | tr\|A5K851\|A5K851_PLAVS 60S ribosomal protein L18a OX=126793 GN=PVX_082965 PE=3 SV=1 |
| 4 | AAQKKPAAPETSA | tr\|A5KC18\|A5KC18_PLAVS Uncharacterized protein OX=126793 GN=PVX_096030 PE=4 SV=1 |
| 5 | ADKEKKQLY | tr\|A5K303\|A5K303_PLAVS 60S ribosomal protein L23a OX=126793 GN=PVX_116700 PE=3 SV=1 |
| 6 | AGKEKDDKKKGKD | tr\|A5JZ82\|A5JZ82_PLAVS 60S ribosomal protein L24 OX=126793 GN=PVX_122285 PE=4 SV=1 |
| 7 | AGKKDGAKKEVA | tr\|A5K858\|A5K858_PLAVS 40S ribosomal protein S6 OX=126793 GN=PVX_083000 PE=4 SV=1 |
| 8 | AIEPSLAQLAQK | tr\|A5K2R4\|A5K2R4_PLAVS Ubiquitin/ribosomal OX=126793 GN=PVX_115255 PE=4 SV=1 |
| 9 | AIEPSLAQLAQKY | tr\|A5K2R4\|A5K2R4_PLAVS Ubiquitin/ribosomal OX=126793 GN=PVX_115255 PE=4 SV=1 |
| 10 | AIEPSLAQLAQKYN(-.98) | tr\|A5K2R4\|A5K2R4_PLAVS Ubiquitin/ribosomal OX=126793 GN=PVX_115255 PE=4 SV=1 |
| 11 | AKAVKKQKKTLKPV | tr\|A5KAW8\|A5KAW8_PLAVS 60S ribosomal protein L31 OX=126793 GN=PVX_097760 PE=4 SV=1 |
| 12 | AKDKKQLKKPS | tr\|A5K0Z6\|A5K0Z6_PLAVS Ribosomal protein L7a OX=126793 GN=PVX_085270 PE=4 SV=1 |
| 13 | AKKADAKKADAKK | tr\|A5K7E3\|A5K7E3_PLAVS QF122 antigen OX=126793 GN=PVX_094810 PE=4 SV=1 |
| 14 | AKKGEAKKGEAKK | tr\|A5K9P1\|A5K9P1_PLAVS MATH domain-containing protein OX=126793 GN=PVX_080660 PE=4 SV=1 |
| 15 | AKSKNHTNHNQNRKA | tr\|A5K3F2\|A5K3F2_PLAVS 60S ribosomal protein L29 OX=126793 GN=PVX_117440 PE=3 SV=1 |
| 16 | AKVVKEVK | tr\|A5K6T4\|A5K6T4_PLAVS 50S ribosomal protein L29 OX=126793 GN=PVX_099510 PE=4 SV=1 |
| 17 | ALFKEKKEKPRS | tr\|A5KB86\|A5KB86_PLAVS 40S ribosomal protein S23 OX=126793 GN=PVX_119470 PE=3 SV=1 |
| 18 | ANKALLPTAGDD | tr\|A5KAZ9\|A5KAZ9_PLAVS 60S ribosomal subunit protein L4/L1 |
| 19 | APISAGIKKPHR | tr\|A5K1U7\|A5K1U7_PLAVS Histone H3 OX=126793 GN=PVX_113665 PE=3 SV=1 |
| 20 | AQKIKKKKKLTPA | tr\|A5K197\|A5K197_PLAVS Sperm-specific protein Don juan |
| 21 | AQKIKKKKKLTPAKV | tr\|A5K197\|A5K197_PLAVS Sperm-specific protein Don juan OX=126793 GN=PVX_085790 PE=4 SV=1 |
| 22 | AQKKPAAPETSA | tr\|A5KC18\|A5KC18_PLAVS Uncharacterized protein OX=126793 GN=PVX_096030 PE=4 SV=1 |
| 23 | ARKKPATPKKQATPK | tr\|A5KC18\|A5KC18_PLAVS Uncharacterized protein OX=126793 GN=PVX_096030 PE=4 SV=1 |
| 24 | ASGGVLPNIHNV | tr\|A5K214\|A5K214_PLAVS Histone H2A OX=126793 GN=PVX_114015 PE=3 SV=1 |
| 25 | ASGNDKLGKKK | tr\|A5K303\|A5K303_PLAVS 60S ribosomal protein L23a OX=126793 GN=PVX_116700 PE=3 SV=1 |

Figure 3 continued

| | | |
|---|---|---|
| 26 | ASSEAQKL | tr\|A5K0Q2\|A5K0Q2_PLAVS Mitochondrial glycoprotein domain containing protein OX=126793 GN=PVX_084795 PE=4 SV=1 |
| 27 | ATEAATNMNA | tr\|A5KA75\|A5KA75_PLAVS Rhoptry associated membrane antigen OX=126793 GN=PVX_087885 PE=4 SV=1 |
| 28 | ATRFKKNRKKRG | tr\|A5K219\|A5K219_PLAVS 60S ribosomal protein L27a OX=126793 GN=PVX_114040 PE=3 SV=1 |
| 29 | AVKKQKKTLKPVTK | tr\|A5KAW8\|A5KAW8_PLAVS 60S ribosomal protein L31 OX=126793 GN=PVX_097760 PE=4 SV=1 |
| 30 | AVKKVGKIV | tr\|A5K6B0\|A5K6B0_PLAVS 60S ribosomal protein L32 OX=126793 GN=PVX_098640 PE=4 SV=1 |
| 31 | AVKKVGKIVK | tr\|A5K6B0\|A5K6B0_PLAVS 60S ribosomal protein L32 OX=126793 GN=PVX_098640 PE=4 SV=1 |
| 32 | AVKKVGKIVKK | tr\|A5K6B0\|A5K6B0_PLAVS 60S ribosomal protein L32 OX=126793 GN=PVX_098640 PE=4 SV=1 |
| 33 | AVKKVGKIVKKRT | tr\|A5K6B0\|A5K6B0_PLAVS 60S ribosomal protein L32 OX=126793 GN=PVX_098640 PE=4 SV=1 |
| 34 | AVKKVGKIVKKRTK | tr\|A5K6B0\|A5K6B0_PLAVS 60S ribosomal protein L32 OX=126793 GN=PVX_098640 PE=4 SV=1 |
| 35 | AVPSSVASHG | tr\|A5K1Y1\|A5K1Y1_PLAVS Transporter OX=126793 GN=PVX_113850 PE=4 SV=1 |
| 36 | AVSAKNPAKK | tr\|A5K2H7\|A5K2H7_PLAVS Elongation factor 1-alpha OX=126793 GN=PVX_114830 PE=3 SV=1 |
| 37 | C(+47.98)PTQRYNFRS | tr\|A5JZN9\|A5JZN9_PLAVS 60S ribosomal protein L13 OX=126793 GN=PVX_123070 PE=3 SV=1 |
| 38 | DANKALLPTAGDD | tr\|A5KAZ9\|A5KAZ9_PLAVS 60S ribosomal subunit protein L4/L1 OX=126793 GN=PVX_097915 PE=4 SV=1 |
| 39 | DEIERVAK | tr\|A5KC61\|A5KC61_PLAVS 40S ribosomal protein S5 OX=126793 GN=PVX_096265 PE=3 SV=1 |
| 40 | DGDHSDYNT | tr\|A5K1M4\|A5K1M4_PLAVS Uncharacterized protein OX=126793 GN=PVX_113295 PE=4 SV=1 |
| 41 | DGNGKKFNKKPF | tr\|A5K7V6\|A5K7V6_PLAVS RRM domain-containing protein OX=126793 GN=PVX_082480 PE=4 SV=1 |
| 42 | DGRFNILIVVKD | tr\|A5K4I3\|A5K4I3_PLAVS Ubiquitin C-terminal hydrolase family 1 OX=126793 GN=PVX_091485 PE=4 SV=1 |
| 43 | DIVYSLKRQG | tr\|A5K474\|A5K474_PLAVS Histone H4 OX=126793 GN=PVX_090930 PE=3 SV=1 |
| 44 | DKEKKQLY | tr\|A5K303\|A5K303_PLAVS 60S ribosomal protein L23a OX=126793 GN=PVX_116700 PE=3 SV=1 |
| 45 | DKIRYEAI | tr\|A5KA88\|A5KA88_PLAVS Heat shock protein 86 OX=126793 GN=PVX_087950 PE=3 SV=1 |
| 46 | DKKDDKKVKKNILK | tr\|A5K197\|A5K197_PLAVS Sperm-specific protein Don juan OX=126793 GN=PVX_085790 PE=4 SV=1 |
| 47 | DKKVKKNILK | tr\|A5K197\|A5K197_PLAVS Sperm-specific protein Don juan OX=126793 GN=PVX_085790 PE=4 SV=1 |
| 48 | DKSYLAYKTLR | tr\|A5JZN9\|A5JZN9_PLAVS 60S ribosomal protein L13 OX=126793 GN=PVX_123070 PE=3 SV=1 |
| 49 | DNKKAKKVGDKRKGR | tr\|A5KAB1\|A5KAB1_PLAVS 60S ribosomal protein L34-A OX=126793 GN=PVX_088065 PE=4 SV=1 |
| 50 | DNNEHVVQ(+.98)EKTVSF | tr\|A5JZN7\|A5JZN7_PLAVS Alba domain-containing protein OX=126793 GN=PVX_123060 PE=4 SV=1 |
| 51 | DNNEHVVQEKTV | tr\|A5JZN7\|A5JZN7_PLAVS Alba domain-containing protein OX=126793 GN=PVX_123060 PE=4 SV=1 |
| 50 | DNNEHVVQEKTVSF | tr\|A5JZN7\|A5JZN7_PLAVS Alba domain-containing protein OX=126793 GN=PVX_123060 PE=4 SV=1 |

Figure 3 continued

| | | |
|---|---|---|
| 53 | DSEEKEEQGQKPEKV | tr\|A5K8G8\|A5K8G8_PLAVS Uncharacterized protein OX=126793 GN=PVX_083555 PE=4 SV=1 |
| 54 | DSPGGEAN | tr\|A5KBE4\|A5KBE4_PLAVS Uncharacterized protein OX=126793 GN=PVX_119765 PE=4 SV=1 |
| 55 | DSRANAALDEPVL | tr\|A5K904\|A5K904_PLAVS Uncharacterized protein OX=126793 GN=PVX_101400 PE=4 SV=1 |
| 56 | EDYSPRKV | tr\|A5K8G9\|A5K8G9_PLAVS Uncharacterized protein OX=126793 GN=PVX_083560 PE=4 SV=1 |
| 57 | EDYSPRKVAF | tr\|A5K8G9\|A5K8G9_PLAVS Uncharacterized protein OX=126793 GN=PVX_083560 PE=4 SV=1 |
| 58 | EDYSPRKVAFR | tr\|A5K8G9\|A5K8G9_PLAVS Uncharacterized protein OX=126793 GN=PVX_083560 PE=4 SV=1 |
| 59 | EEDGYPEEGY | tr\|A5KCF9\|A5KCF9_PLAVS Uncharacterized protein OX=126793 GN=PVX_001950 PE=4 SV=1 |
| 60 | EEETFEEKKSEEKKD | tr\|A5K347\|A5K347_PLAVS Exported protein 2 OX=126793 GN=PVX_116915 PE=4 SV=1 |
| 61 | EETLQEESNLPVKGD | tr\|A5KE06\|A5KE06_PLAVS Uncharacterized protein OX=126793 GN=PVX_111290 PE=4 SV=1 |
| 62 | EFCFTDYE | tr\|A5K1L8\|A5K1L8_PLAVS C3H1-type domain-containing protein OX=126793 GN=PVX_113265 PE=4 SV=1 |
| 63 | EIKRLEEV | tr\|A5K0G3\|A5K0G3_PLAVS Uncharacterized protein OX=126793 GN=PVX_084350 PE=4 SV=1 |
| 64 | EKFEKIKIIDFN | tr\|A5K3Y0\|A5K3Y0_PLAVS Serine/threonine protein kinase OX=126793 GN=PVX_118340 PE=4 SV=1 |
| 65 | EKKKKKHTQ | tr\|A5K819\|A5K819_PLAVS zf-C2HC5 domain-containing protein OX=126793 GN=PVX_082800 PE=4 SV=1 |
| 66 | EKLNHAVF | tr\|A5K124\|A5K124_PLAVS 40S ribosomal protein S25 OX=126793 GN=PVX_085420 PE=4 SV=1 |
| 67 | EVASISEKH | tr\|A5KBH6\|A5KBH6_PLAVS Uncharacterized protein OX=126793 GN=PVX_003570 PE=4 SV=1 |
| 68 | EVSKIDKSYLAYK | tr\|A5JZN9\|A5JZN9_PLAVS 60S ribosomal protein L13 OX=126793 GN=PVX_123070 PE=3 SV=1 |
| 69 | FAKSKQVNM(+15.99)AKTK | tr\|A5JZ82\|A5JZ82_PLAVS 60S ribosomal protein L24 OX=126793 GN=PVX_122285 PE=4 SV=1 |
| 69 | FAKSKQVNMAKTK | tr\|A5JZ82\|A5JZ82_PLAVS 60S ribosomal protein L24 OX=126793 GN=PVX_122285 PE=4 SV=1 |
| 71 | FEGEDEDEGE | tr\|A5K0U8\|A5K0U8_PLAVS Aspartyl protease OX=126793 GN=PVX_085030 PE=3 SV=1 |
| 72 | FGGQTKPV | tr\|A5KB61\|A5KB61_PLAVS 60S Ribosomal protein L44 OX=126793 GN=PVX_119345 PE=3 SV=1 |
| 73 | FKKKAKTTKKIVLK | tr\|A5KB61\|A5KB61_PLAVS 60S Ribosomal protein L44 OX=126793 GN=PVX_119345 PE=3 SV=1 |
| 74 | FTHCTEHC | tr\|A5KB28\|A5KB28_PLAVS Uncharacterized protein OX=126793 GN=PVX_098060 PE=4 SV=1 |
| 75 | FYKRKM(+15.99)DKKKRN | tr\|A5K1E3\|A5K1E3_PLAVS 40S ribosomal protein S8 OX=126793 GN=PVX_086020 PE=3 SV=1 |
| 76 | GADKEKKQLY | tr\|A5K303\|A5K303_PLAVS 60S ribosomal protein L23a OX=126793 GN=PVX_116700 PE=3 SV=1 |
| 77 | GADKKKKGAVY | tr\|A5KB61\|A5KB61_PLAVS 60S Ribosomal protein L44 OX=126793 GN=PVX_119345 PE=3 SV=1 |
| 78 | GAFGKPNGV | tr\|A5K186\|A5K186_PLAVS 60S ribosomal protein L10 OX=126793 GN=PVX_085735 PE=4 SV=1 |
| 79 | GASCGESADQSGD | tr\|A5K103\|A5K103_PLAVS Uncharacterized protein OX=126793 GN=PVX_085310 PE=4 SV=1 |

Figure 3 continued

| | | |
|---|---|---|
| 80 | GDRVRILMYPSNI | tr\|A5K584\|A5K584_PLAVS 60S ribosomal protein L33-B OX=126793 GN=PVX_092735 PE=3 SV=1 |
| 81 | GDTELSGRF | tr\|A5K3E2\|A5K3E2_PLAVS 50S ribosomal protein S28e OX=126793 GN=PVX_117390 PE=3 SV=1 |
| 82 | GDTELSGRFL | tr\|A5K3E2\|A5K3E2_PLAVS 50S ribosomal protein S28e OX=126793 GN=PVX_117390 PE=3 SV=1 |
| 83 | GDTELSGRFLI | tr\|A5K3E2\|A5K3E2_PLAVS 50S ribosomal protein S28e OX=126793 GN=PVX_117390 PE=3 SV=1 |
| 84 | GGGM(+15.99)FNPTKV | tr\|A5KAZ9\|A5KAZ9_PLAVS 60S ribosomal subunit protein L4/L1 OX=126793 GN=PVX_097915 PE=4 SV=1 |
| 85 | GILHLLHKH | tr\|A5K9C7\|A5K9C7_PLAVS Uncharacterized protein OX=126793 GN=PVX_080090 PE=4 SV=1 |
| 86 | GILKKKKELKLKQ | tr\|A5K3F2\|A5K3F2_PLAVS 60S ribosomal protein L29 OX=126793 GN=PVX_117440 PE=3 SV=1 |
| 87 | GILKYPLTSEKAM(+15.99)KK | tr\|A5K303\|A5K303_PLAVS 60S ribosomal protein L23a OX=126793 GN=PVX_116700 PE=3 SV=1 |
| 88 | GISRDGRHKL | tr\|A5K1E3\|A5K1E3_PLAVS 40S ribosomal protein S8 OX=126793 GN=PVX_086020 PE=3 SV=1 |
| 89 | GISRDGRHKLRLTG | tr\|A5K1E3\|A5K1E3_PLAVS 40S ribosomal protein S8 OX=126793 GN=PVX_086020 PE=3 SV=1 |
| 90 | GISRDGRHKLRLTGG | tr\|A5K1E3\|A5K1E3_PLAVS 40S ribosomal protein S8 OX=126793 GN=PVX_086020 PE=3 SV=1 |
| 91 | GKAGKGTGSF | tr\|A5KA70\|A5KA70_PLAVS Ribosomal protein L37 OX=126793 GN=PVX_087860 PE=3 SV=1 |
| 92 | GKAGKGTGSFG | tr\|A5KA70\|A5KA70_PLAVS Ribosomal protein L37 OX=126793 GN=PVX_087860 PE=3 SV=1 |
| 93 | GKAGKGTGSFGK | tr\|A5KA70\|A5KA70_PLAVS Ribosomal protein L37 OX=126793 GN=PVX_087860 PE=3 SV=1 |
| 94 | GKAGKGTGSFGKR | tr\|A5KA70\|A5KA70_PLAVS Ribosomal protein L37 OX=126793 GN=PVX_087860 PE=3 SV=1 |
| 95 | GKAGKGTGSFGKRN | tr\|A5KA70\|A5KA70_PLAVS Ribosomal protein L37 OX=126793 GN=PVX_087860 PE=3 SV=1 |
| 96 | GKAGKGTGSFGKRNG | tr\|A5KA70\|A5KA70_PLAVS Ribosomal protein L37 OX=126793 GN=PVX_087860 PE=3 SV=1 |
| 97 | GKGKNKEKL | tr\|A5K124\|A5K124_PLAVS 40S ribosomal protein S25 |
| 98 | GKGKNKEKLNHA | tr\|A5K124\|A5K124_PLAVS 40S ribosomal protein S25 OX=126793 GN=PVX_085420 PE=4 SV=1 |
| 99 | GKGKNKEKLNHAV | tr\|A5K124\|A5K124_PLAVS 40S ribosomal protein S25 OX=126793 GN=PVX_085420 PE=4 SV=1 |
| 100 | GKGKNKEKLNHAVF | tr\|A5K124\|A5K124_PLAVS 40S ribosomal protein S25 OX=126793 GN=PVX_085420 PE=4 SV=1 |
| 101 | GKGKNKEKLNHAVFI | tr\|A5K124\|A5K124_PLAVS 40S ribosomal protein S25 OX=126793 GN=PVX_085420 PE=4 SV=1 |
| 102 | GKKKGADKEKK | tr\|A5K303\|A5K303_PLAVS 60S ribosomal protein L23a OX=126793 GN=PVX_116700 PE=3 SV=1 |
| 103 | GKKKGADKEKKQLY | tr\|A5K303\|A5K303_PLAVS 60S ribosomal protein L23a OX=126793 GN=PVX_116700 PE=3 SV=1 |
| 104 | GKLLKPGKVVI | tr\|A5K3E8\|A5K3E8_PLAVS 60S ribosomal protein L27 OX=126793 GN=PVX_117420 PE=4 SV=1 |
| 105 | GKNKEKLNHAVF | tr\|A5K124\|A5K124_PLAVS 40S ribosomal protein S25 OX=126793 GN=PVX_085420 PE=4 SV=1 |
| 106 | GKVHGSLA | tr\|A5KBT5\|A5KBT5_PLAVS 40S ribosomal protein S30 OX=126793 GN=PVX_002590 PE=3 SV=1 |
| 107 | GKVHGSLAR | tr\|A5KBT5\|A5KBT5_PLAVS 40S ribosomal protein S30 OX=126793 GN=PVX_002590 PE=3 SV=1 |

Figure 3 continued

| | | |
|---|---|---|
| 108 | GKVHGSLARA | tr\|A5KBT5\|A5KBT5_PLAVS 40S ribosomal protein S30 OX=126793 GN=PVX_002590 PE=3 SV=1 |
| 109 | GKVHGSLARAG | tr\|A5KBT5\|A5KBT5_PLAVS 40S ribosomal protein S30 OX=126793 GN=PVX_002590 PE=3 SV=1 |
| 110 | GKVHGSLARAGK | tr\|A5KBT5\|A5KBT5_PLAVS 40S ribosomal protein S30 OX=126793 GN=PVX_002590 PE=3 SV=1 |
| 111 | GKVHGSLARAGKVK | tr\|A5KBT5\|A5KBT5_PLAVS 40S ribosomal protein S30 OX=126793 GN=PVX_002590 PE=3 SV=1 |
| 112 | GLDPKFFK | tr\|A5K3F2\|A5K3F2_PLAVS 60S ribosomal protein L29 OX=126793 GN=PVX_117440 PE=3 SV=1 |
| 113 | GLLRGAKKTK | tr\|A5K9J0\|A5K9J0_PLAVS 60S ribosomal protein L8 OX=126793 GN=PVX_080405 PE=4 SV=1 |
| 114 | GLNQKQPTKGSNIQ | tr\|A5KBH5\|A5KBH5_PLAVS Early transcribed membrane protein (ETRAMP) |
| 115 | GLRLKEKD | tr\|A5KDT8\|A5KDT8_PLAVS Uncharacterized protein OX=126793 GN=PVX_110915 PE=4 SV=1 |
| 116 | GLTVEDIRNRKA | tr\|A5JZ82\|A5JZ82_PLAVS 60S ribosomal protein L24 OX=126793 GN=PVX_122285 PE=4 SV=1 |
| 117 | GNAKGKKPAKKVI | tr\|A5K584\|A5K584_PLAVS 60S ribosomal protein L33-B OX=126793 GN=PVX_092735 PE=3 SV=1 |
| 118 | GNGKKFNKKPF | tr\|A5K7V6\|A5K7V6_PLAVS RRM domain-containing protein OX=126793 GN=PVX_082480 PE=4 SV=1 |
| 119 | GPKRATKIR | tr\|A5K858\|A5K858_PLAVS 40S ribosomal protein S6 OX=126793 GN=PVX_083000 PE=4 SV=1 |
| 120 | GPKRATKIRK | tr\|A5K858\|A5K858_PLAVS 40S ribosomal protein S6 OX=126793 GN=PVX_083000 PE=4 SV=1 |
| 121 | GPVRGISL | tr\|A5K8T0\|A5K8T0_PLAVS 40S ribosomal protein S17 OX=126793 GN=PVX_101035 PE=3 SV=1 |
| 122 | GQTKPVFKKKAKTTK | tr\|A5KB61\|A5KB61_PLAVS 60S Ribosomal protein L44 OX=126793 GN=PVX_119345 PE=3 SV=1 |
| 123 | GRETPAKGGGHNVI | tr\|A5K035\|A5K035_PLAVS Uncharacterized protein OX=126793 GN=PVX_123805 PE=4 SV=1 |
| 124 | GRIGRYLKKGKYA | tr\|A5K214\|A5K214_PLAVS Histone H2A OX=126793 GN=PVX_114015 PE=3 SV=1 |
| 125 | GRIGRYLKKGKYAK | tr\|A5K214\|A5K214_PLAVS Histone H2A OX=126793 GN=PVX_114015 PE=3 SV=1 |
| 126 | GRKSTIKPA | tr\|A5K4B5\|A5K4B5_PLAVS 60S ribosomal protein L36 OX=126793 GN=PVX_091145 PE=3 SV=1 |
| 127 | GRKSTIKPATGIAV | tr\|A5K4B5\|A5K4B5_PLAVS 60S ribosomal protein L36 OX=126793 GN=PVX_091145 PE=3 SV=1 |
| 128 | GSAEDDLK | tr\|A5K3U1\|A5K3U1_PLAVS 40S ribosomal protein S2 OX=126793 GN=PVX_118145 PE=3 SV=1 |
| 129 | GSGKPSGL | tr\|A5KB86\|A5KB86_PLAVS 40S ribosomal protein S23 OX=126793 GN=PVX_119470 PE=3 SV=1 |
| 130 | GSKQVHVV | tr\|A5K1E3\|A5K1E3_PLAVS 40S ribosomal protein S8 OX=126793 GN=PVX_086020 PE=3 SV=1 |
| 131 | GTGRKKGPNSKL | tr\|A5KBT5\|A5KBT5_PLAVS 40S ribosomal protein S30 OX=126793 GN=PVX_002590 PE=3 SV=1 |
| 132 | GTPIEKLHPI | tr\|A5JZN9\|A5JZN9_PLAVS 60S ribosomal protein L13 OX=126793 GN=PVX_123070 PE=3 SV=1 |
| 133 | GVKKDVAK | tr\|A5K858\|A5K858_PLAVS 40S ribosomal protein S6 OX=126793 GN=PVX_083000 PE=4 SV=1 |
| 134 | GYPSAKKRRF | tr\|A5KA70\|A5KA70_PLAVS Ribosomal protein L37 OX=126793 GN=PVX_087860 PE=3 SV=1 |

Figure 3 continued

| | | |
|---|---|---|
| 135 | HGASRYKKSRA | tr\|A5K5A1\|A5K5A1_PLAVS 60S ribosomal protein L41 OX=126793 GN=PVX_092820 PE=4 SV=1 |
| 136 | HGKPKHQGV | tr\|A5K5X8\|A5K5X8_PLAVS Ribosomal protein L15 OX=126793 GN=PVX_089750 PE=3 SV=1 |
| 137 | HHKYRVKR | tr\|A5K9J0\|A5K9J0_PLAVS 60S ribosomal protein L8 OX=126793 GN=PVX_080405 PE=4 SV=1 |
| 138 | HLPTLKKEYRRKYAA | tr\|A5K851\|A5K851_PLAVS 60S ribosomal protein L18a OX=126793 GN=PVX_082965 PE=3 SV=1 |
| 139 | HLSAKSRPS | tr\|A5K5X8\|A5K5X8_PLAVS Ribosomal protein L15 OX=126793 GN=PVX_089750 PE=3 SV=1 |
| 140 | HLSAKSRPSIR | tr\|A5K5X8\|A5K5X8_PLAVS Ribosomal protein L15 OX=126793 GN=PVX_089750 PE=3 SV=1 |
| 141 | HPGHQYPNALG | tr\|A5K043\|A5K043_PLAVS Polyadenylate-binding protein OX=126793 GN=PVX_123845 PE=3 SV=1 |
| 142 | HQLVENADEV | tr\|A5K7A8\|A5K7A8_PLAVS Tubulin beta chain OX=126793 GN=PVX_094635 PE=3 SV=1 |
| 143 | HSNMHCSPYSGC | tr\|A5K2V5\|A5K2V5_PLAVS Uncharacterized protein OX=126793 GN=PVX_115460 PE=4 SV=1 |
| 144 | IDEHAHLV | tr\|A5K583\|A5K583_PLAVS 60S ribosomal protein L28 OX=126793 GN=PVX_092730 PE=4 SV=1 |
| 145 | IEKFEKESAEMGKG | tr\|A5K2H7\|A5K2H7_PLAVS Elongation factor 1-alpha OX=126793 GN=PVX_114830 PE=3 SV=1 |
| 146 | IGRFFSFLVR | tr\|A5K4L2\|A5K4L2_PLAVS Uncharacterized protein OX=126793 GN=PVX_091630 PE=4 SV=1 |
| 147 | IGYGSNKKTKF | tr\|A5K6B0\|A5K6B0_PLAVS 60S ribosomal protein L32 OX=126793 GN=PVX_098640 PE=4 SV=1 |
| 148 | IHKIKK(+119.04)VVR | tr\|A5K347\|A5K347_PLAVS Exported protein 2 OX=126793 GN=PVX_116915 PE=4 SV=1 |
| 149 | IKKERKKGI | tr\|A5K0Z6\|A5K0Z6_PLAVS Ribosomal protein L7a OX=126793 GN=PVX_085270 PE=4 SV=1 |
| 150 | IKSKTHSI | tr\|A5JZ18\|A5JZ18_PLAVS Uncharacterized protein OX=126793 GN=PVX_121965 PE=4 SV=1 |
| 151 | ILKYPLTSEK | tr\|A5K303\|A5K303_PLAVS 60S ribosomal protein L23a OX=126793 GN=PVX_116700 PE=3 SV=1 |
| 152 | ISKQNFAKNKKKAAN | tr\|A5K8F1\|A5K8F1_PLAVS 60S ribosomal protein L17 OX=126793 GN=PVX_083465 PE=3 SV=1 |
| 153 | KAFIPCLK | tr\|A5KB04\|A5KB04_PLAVS Cell differentiation protein rcd1 OX=126793 GN=PVX_097940 PE=4 SV=1 |
| 154 | KAKGAKNEMVK | tr\|A5K7A2\|A5K7A2_PLAVS Uncharacterized protein OX=126793 GN=PVX_094600 PE=4 SV=1 |
| 155 | KALLPTAGDD | tr\|A5KAZ9\|A5KAZ9_PLAVS 60S ribosomal subunit protein L4/L1 OX=126793 GN=PVX_097915 PE=4 SV=1 |
| 156 | KANGDSANK | tr\|A5JZ31\|A5JZ31_PLAVS PI3K/PI4K domain-containing protein OX=126793 GN=PVX_122030 PE=3 SV=1 |
| 157 | KAPRKQLASKAARK | tr\|A5K1U7\|A5K1U7_PLAVS Histone H3 OX=126793 GN=PVX_113665 PE=3 SV=1:tr\|A5K215\|A5K215_PLAVS Histone H3 OX=126793 GN=PVX_114020 PE=3 SV=1 |
| 158 | KDAGKKDAGKKD | tr\|A5K858\|A5K858_PLAVS 40S ribosomal protein S6 OX=126793 GN=PVX_083000 PE=4 SV=1 |
| 159 | KDAPPPYET | tr\|A5K0F8\|A5K0F8_PLAVS Uncharacterized protein OX=126793 GN=PVX_084325 PE=4 SV=1 |
| 160 | KDFAKSKQV | tr\|A5JZ82\|A5JZ82_PLAVS 60S ribosomal protein L24 OX=126793 GN=PVX_122285 PE=4 SV=1 |
| 161 | KDGVKKDVAKKD | tr\|A5K858\|A5K858_PLAVS 40S ribosomal protein S6 OX=126793 GN=PVX_083000 PE=4 SV=1 |

Figure 3 continued

| | | |
|---|---|---|
| 162 | KDIKKERKKGIRS | tr\|A5K0Z6\|A5K0Z6_PLAVS Ribosomal protein L7a OX=126793 GN=PVX_085270 PE=4 SV=1 |
| 163 | KDINTIIES | tr\|A5K186\|A5K186_PLAVS 60S ribosomal protein L10 OX=126793 GN=PVX_085735 PE=4 SV=1 |
| 164 | KDKAGCQNK | tr\|A5K2L2\|A5K2L2_PLAVS Guanylyl cyclase OX=126793 GN=PVX_114990 PE=4 SV=1 |
| 165 | KDSQKKGGKKKD | tr\|A5K858\|A5K858_PLAVS 40S ribosomal protein S6 OX=126793 GN=PVX_083000 PE=4 SV=1 |
| 166 | KDSQKKGGKKKDKK | tr\|A5K858\|A5K858_PLAVS 40S ribosomal protein S6 OX=126793 GN=PVX_083000 PE=4 SV=1 |
| 167 | KDVAKKDAGKKD | tr\|A5K858\|A5K858_PLAVS 40S ribosomal protein S6 OX=126793 GN=PVX_083000 PE=4 SV=1 |
| 168 | KDYSDNYCEK | tr\|A5KD88\|A5KD88_PLAVS Variable surface protein Vir12-like OX=126793 GN=PVX_077695 PE=4 SV=1 |
| 169 | KEDAKGGKKKK | tr\|A5K858\|A5K858_PLAVS 40S ribosomal protein S6 OX=126793 GN=PVX_083000 PE=4 SV=1 |
| 170 | KEGLILKKPQKV | tr\|A5K1Y3\|A5K1Y3_PLAVS 60S ribosomal protein L19 OX=126793 GN=PVX_113860 PE=3 SV=1 |
| 171 | KEKKQLYKGKVK | tr\|A5K303\|A5K303_PLAVS 60S ribosomal protein L23a OX=126793 GN=PVX_116700 PE=3 SV=1 |
| 172 | KEKLNHAVF | tr\|A5K124\|A5K124_PLAVS 40S ribosomal protein S25 OX=126793 GN=PVX_085420 PE=4 SV=1 |
| 173 | KEPIFSNT | tr\|A5K6T7\|A5K6T7_PLAVS S-adenosylmethionine synthase OX=126793 GN=PVX_099525 PE=3 SV=1 |
| 174 | KEPLLGGLN | tr\|A5KBH5\|A5KBH5_PLAVS Early transcribed membrane protein (ETRAMP) OX=126793 GN=PVX_003565 PE=4 SV=1 |
| 175 | KEPLLGGLNQKQPT | tr\|A5KBH5\|A5KBH5_PLAVS Early transcribed membrane protein (ETRAMP) OX=126793 GN=PVX_003565 PE=4 SV=1 |
| 176 | KEPLLGGLNQKQPTK | tr\|A5KBH5\|A5KBH5_PLAVS Early transcribed membrane protein (ETRAMP) OX=126793 GN=PVX_003565 PE=4 SV=1 |
| 177 | KFFRRRGEAT | tr\|A5K5I2\|A5K5I2_PLAVS ATP-dependent RNA helicase OX=126793 GN=PVX_089015 PE=3 SV=1 |
| 178 | KGAAPKKGA(+21.98) | tr\|A5KB38\|A5KB38_PLAVS PRESAN domain-containing protein OX=126793 GN=PVX_119225 PE=4 SV=1 |
| 179 | KGADKEKKQLY | tr\|A5K303\|A5K303_PLAVS 60S ribosomal protein L23a OX=126793 GN=PVX_116700 PE=3 SV=1 |
| 180 | KGAEQNGREPNG | tr\|A5K2Z4\|A5K2Z4_PLAVS Uncharacterized protein OX=126793 GN=PVX_116655 PE=4 SV=1 |
| 181 | KGGSGGGNIKK(-2.02) | tr\|A5KE19\|A5KE19_PLAVS Merozoite capping protein 1 OX=126793 GN=PVX_111355 PE=4 SV=1 |
| 182 | KGKDTCCC | tr\|A5K9Y3\|A5K9Y3_PLAVS Uncharacterized protein OX=126793 GN=PVX_081615 PE=4 SV=1 |
| 183 | KGKKNATT | tr\|A5K504\|A5K504_PLAVS Uncharacterized protein OX=126793 GN=PVX_092335 PE=4 SV=1 |
| 184 | KGKKPAKKVI | tr\|A5K584\|A5K584_PLAVS 60S ribosomal protein L33-B OX=126793 GN=PVX_092735 PE=3 SV=1 |
| 185 | KGKNKEKL | tr\|A5K124\|A5K124_PLAVS 40S ribosomal protein S25 OX=126793 GN=PVX_085420 PE=4 SV=1 |
| 186 | KGKNKEKLNHAV | tr\|A5K124\|A5K124_PLAVS 40S ribosomal protein S25 OX=126793 GN=PVX_085420 PE=4 SV=1 |
| 187 | KGKNKEKLNHAVF | tr\|A5K124\|A5K124_PLAVS 40S ribosomal protein S25 OX=126793 GN=PVX_085420 PE=4 SV=1 |

Figure 3 continued

| | | |
|---|---|---|
| 188 | KGKSSRSGRSARS | tr\|A5JZB7\|A5JZB7_PLAVS Uncharacterized protein OX=126793 GN=PVX_122465 PE=4 SV=1 |
| 189 | KGKVKKSLGKQVGGK | tr\|A5K303\|A5K303_PLAVS 60S ribosomal protein L23a OX=126793 GN=PVX_116700 PE=3 SV=1 |
| 190 | KHEKPKKLNAKLR | tr\|A5K0Z7\|A5K0Z7_PLAVS 60S ribosomal protein family L5 OX=126793 GN=PVX_085275 PE=3 SV=1 |
| 191 | KHEKPKKLNAKLRK | tr\|A5K0Z7\|A5K0Z7_PLAVS 60S ribosomal protein family L5 OX=126793 GN=PVX_085275 PE=3 SV=1 |
| 192 | KHIKKTKM | tr\|A5KBM4\|A5KBM4_PLAVS Serine-repeat antigen 5 (SERA) OX=126793 GN=PVX_003810 PE=3 SV=1 |
| 193 | KIFDEIIVNA | tr\|A5K0R4\|A5K0R4_PLAVS DNA topoisomerase 2 OX=126793 GN=PVX_084855 PE=3 SV=1 |
| 194 | KIRDEIKRTFCQR | tr\|A5KB28\|A5KB28_PLAVS Uncharacterized protein OX=126793 GN=PVX_098060 PE=4 SV=1 |
| 195 | KK(+28.03)AAPKKVAAP | tr\|A5K5D6\|A5K5D6_PLAVS Tryptophan-rich antigen (Pv-fam-a) OX=126793 GN=PVX_092995 PE=4 SV=1 |
| 196 | KK(+31.99)GADKEKK | tr\|A5K303\|A5K303_PLAVS 60S ribosomal protein L23a OX=126793 GN=PVX_116700 PE=3 SV=1 |
| 197 | KKAAARKKPATPK | tr\|A5KC18\|A5KC18_PLAVS Uncharacterized protein OX=126793 GN=PVX_096030 PE=4 SV=1 |
| 198 | KKAAQKKPAAPETSA | tr\|A5KC18\|A5KC18_PLAVS Uncharacterized protein OX=126793 GN=PVX_096030 PE=4 SV=1 |
| 199 | KKADK(+43.99)KDEKK | tr\|A5K197\|A5K197_PLAVS Sperm-specific protein Don juan OX=126793 GN=PVX_085790 PE=4 SV=1 |
| 200 | KKAPAK(+226.08)PQ | tr\|A5K858\|A5K858_PLAVS 40S ribosomal protein S6 OX=126793 GN=PVX_083000 PE=4 SV=1 |
| 201 | KKAPNTTKPKEDTK | tr\|A5K197\|A5K197_PLAVS Sperm-specific protein Don juan OX=126793 GN=PVX_085790 PE=4 SV=1 |
| 202 | KKDAGKKDAGKKD | tr\|A5K858\|A5K858_PLAVS 40S ribosomal protein S6 OX=126793 GN=PVX_083000 PE=4 SV=1 |
| 203 | KKDDK(+43.01)TKK | tr\|A5K197\|A5K197_PLAVS Sperm-specific protein Don juan OX=126793 GN=PVX_085790 PE=4 SV=1 |
| 204 | KKDDKKVKKNILK | tr\|A5K197\|A5K197_PLAVS Sperm-specific protein Don juan OX=126793 GN=PVX_085790 PE=4 SV=1 |
| 205 | KKDIKKERKKGIRS | tr\|A5K0Z6\|A5K0Z6_PLAVS Ribosomal protein L7a OX=126793 GN=PVX_085270 PE=4 SV=1 |
| 206 | KKEKAKSEKAVIKK | tr\|A5K197\|A5K197_PLAVS Sperm-specific protein Don juan OX=126793 GN=PVX_085790 PE=4 SV=1 |
| 207 | KKELKLKQKQEKKN | tr\|A5K3F2\|A5K3F2_PLAVS 60S ribosomal protein L29 OX=126793 GN=PVX_117440 PE=3 SV=1 |
| 208 | KKGIRSN(+.98)P | tr\|A5K0Z6\|A5K0Z6_PLAVS Ribosomal protein L7a OX=126793 GN=PVX_085270 PE=4 SV=1 |
| 209 | KKGPNSKL | tr\|A5KBT5\|A5KBT5_PLAVS 40S ribosomal protein S30 OX=126793 GN=PVX_002590 PE=3 SV=1 |
| 210 | KKIDKKKEQLSKK | tr\|A5KE19\|A5KE19_PLAVS Merozoite capping protein 1 OX=126793 GN=PVX_111355 PE=4 SV=1 |
| 211 | KKIGKSKQID | tr\|A5K1E3\|A5K1E3_PLAVS 40S ribosomal protein S8 OX=126793 GN=PVX_086020 PE=3 SV=1 |
| 212 | KKKAKTTKKIVLK | tr\|A5KB61\|A5KB61_PLAVS 60S Ribosomal protein L44 OX=126793 GN=PVX_119345 PE=3 SV=1 |
| 213 | KKKELKLKQKQEKKN | tr\|A5K3F2\|A5K3F2_PLAVS 60S ribosomal protein L29 OX=126793 GN=PVX_117440 PE=3 SV=1 |
| 214 | KKKGADKEKK | tr\|A5K303\|A5K303_PLAVS 60S ribosomal protein L23a OX=126793 GN=PVX_116700 PE=3 SV=1 |

Figure 3 continued

| | | |
|---|---|---|
| 215 | KKKGADKEKKQLY | tr\|A5K303\|A5K303_PLAVS 60S ribosomal protein L23a OX=126793 GN=PVX_116700 PE=3 SV=1 |
| 216 | KKKKGAVY | tr\|A5KB61\|A5KB61_PLAVS 60S Ribosomal protein L44 OX=126793 GN=PVX_119345 PE=3 SV=1 |
| 217 | KKKKW(+15.99)GKGKNKE | tr\|A5K124\|A5K124_PLAVS 40S ribosomal protein S25 OX=126793 GN=PVX_085420 PE=4 SV=1 |
| 218 | KKKLVKRST | tr\|A5K7A2\|A5K7A2_PLAVS Uncharacterized protein OX=126793 GN=PVX_094600 PE=4 SV=1 |
| 219 | KKKVIKEYKK | tr\|A5K858\|A5K858_PLAVS 40S ribosomal protein S6 OX=126793 GN=PVX_083000 PE=4 SV=1 |
| 220 | KKKVIKEYKKVLNK | tr\|A5K858\|A5K858_PLAVS 40S ribosomal protein S6 OX=126793 GN=PVX_083000 PE=4 SV=1 |
| 221 | KKNLKGAK | tr\|A5K858\|A5K858_PLAVS 40S ribosomal protein S6 OX=126793 GN=PVX_083000 PE=4 SV=1 |
| 222 | KKNLKGAKAEEGK | tr\|A5K858\|A5K858_PLAVS 40S ribosomal protein S6 OX=126793 GN=PVX_083000 PE=4 SV=1 |
| 223 | KKNSLHLEK | tr\|A5K034\|A5K034_PLAVS Phospholipid-transporting ATPase OX=126793 GN=PVX_123800 PE=4 SV=1 |
| 224 | KKPATPKKQATPK | tr\|A5KC18\|A5KC18_PLAVS Uncharacterized protein OX=126793 GN=PVX_096030 PE=4 SV=1;tr\|A5KC19\|A5KC19_PLAVS Uncharacterized protein OX=126793 GN=PVX_096035 PE=4 SV=1 |
| 225 | KKSDYDKLDK | tr\|A5K3H7\|A5K3H7_PLAVS Uncharacterized protein OX=126793 GN=PVX_117570 PE=4 SV=1 |
| 226 | KKSTAK(+226.08)DAKK | tr\|A5KAB1\|A5KAB1_PLAVS 60S ribosomal protein L34-A OX=126793 GN=PVX_088065 PE=4 SV=1 |
| 227 | KKVAAGYKKLTD | tr\|A5KBH5\|A5KBH5_PLAVS Early transcribed membrane protein (ETRAMP) |
| 228 | KKVKKNILK | tr\|A5K197\|A5K197_PLAVS Sperm-specific protein Don juan OX=126793 GN=PVX_085790 PE=4 SV=1 |
| 229 | KKVKKNILKTQKTKK | tr\|A5K197\|A5K197_PLAVS Sperm-specific protein Don juan OX=126793 GN=PVX_085790 PE=4 SV=1 |
| 230 | KKYKNKKFKPY | tr\|A5K4R0\|A5K4R0_PLAVS 60S ribosomal protein L35 OX=126793 GN=PVX_091865 PE=3 SV=1 |
| 231 | KKYKNKKFKPYNLRK | tr\|A5K4R0\|A5K4R0_PLAVS 60S ribosomal protein L35 OX=126793 GN=PVX_091865 PE=3 SV=1 |
| 232 | KLLLCVVL | tr\|A5K934\|A5K934_PLAVS Uncharacterized protein OX=126793 GN=PVX_101555 PE=4 SV=1 |
| 233 | KLMHGRDIE | tr\|A5K715\|A5K715_PLAVS High molecular weight rhoptry protein-2 OX=126793 GN=PVX_099930 PE=4 SV=1 |
| 234 | KM(+31.99)KKSIEAK | tr\|A5KAZ9\|A5KAZ9_PLAVS 60S ribosomal subunit protein L4/L1 OX=126793 GN=PVX_097915 PE=4 SV=1 |
| 235 | KMKEFSDAFST | tr\|A5K699\|A5K699_PLAVS Reticulocyte-binding protein 1 (RBP1) OX=126793 GN=PVX_098585 PE=4 SV=1 |
| 236 | KNFKKENQ | tr\|A5K7K0\|A5K7K0_PLAVS Uncharacterized protein OX=126793 GN=PVX_095095 PE=4 SV=1 |
| 237 | KNGIKKPKKHKF | tr\|A5K3F2\|A5K3F2_PLAVS 60S ribosomal protein L29 OX=126793 GN=PVX_117440 PE=3 SV=1 |
| 238 | KNGIKKPKKHKFM(+15.99)S | tr\|A5K3F2\|A5K3F2_PLAVS 60S ribosomal protein L29 OX=126793 GN=PVX_117440 PE=3 SV=1 |
| 239 | KNIKSKNGIG | tr\|A5JZN9\|A5JZN9_PLAVS 60S ribosomal protein L13 OX=126793 GN=PVX_123070 PE=3 SV=1 |
| 240 | KNIKSKNGIGGIPAD | tr\|A5JZN9\|A5JZN9_PLAVS 60S ribosomal protein L13 OX=126793 GN=PVX_123070 PE=3 SV=1 |
| 241 | KNKEKLNHAVF | tr\|A5K124\|A5K124_PLAVS 40S ribosomal protein S25 OX=126793 GN=PVX_085420 PE=4 SV=1 |

Figure 3 continued

| | | |
|---|---|---|
| 242 | KNPKCPKV(+21.98) | tr\|A5K303\|A5K303_PLAVS 60S ribosomal protein L23a OX=126793 GN=PVX_116700 PE=3 SV=1 |
| 243 | KNQTPKVPKVSKRK | tr\|A5KBT5\|A5KBT5_PLAVS 40S ribosomal protein S30 OX=126793 GN=PVX_002590 PE=3 SV=1 |
| 244 | KNSLTNFAVR(-.98) | tr\|A5KAZ9\|A5KAZ9_PLAVS 60S ribosomal subunit protein L4/L1 OX=126793 GN=PVX_097915 PE=4 SV=1 |
| 245 | KNSVKSNKKVKKM(+15.99)IK | tr\|A5KE19\|A5KE19_PLAVS Merozoite capping protein 1 OX=126793 GN=PVX_111355 PE=4 SV=1 |
| 246 | KNSYSAASK | tr\|A5K1B6\|A5K1B6_PLAVS Uncharacterized protein OX=126793 GN=PVX_085885 PE=4 SV=1 |
| 247 | KNYGLFSDNYFTTAY | tr\|A5K5J0\|A5K5J0_PLAVS HECT domain-containing protein OX=126793 GN=PVX_089055 PE=4 SV=1 |
| 248 | KPAAPETSA | tr\|A5KC18\|A5KC18_PLAVS Uncharacterized protein OX=126793 GN=PVX_096030 PE=4 SV=1 |
| 249 | KPAAPKKPA(+21.98) | tr\|A5KB38\|A5KB38_PLAVS PRESAN domain-containing protein OX=126793 GN=PVX_119225 PE=4 SV=1 |
| 250 | KPAHVTSK | tr\|A5K745\|A5K745_PLAVS Tryptophan-rich antigen OX=126793 GN=PVX_094305 PE=4 SV=1 |
| 251 | KPLIKFGT | tr\|A5KCC5\|A5KCC5_PLAVS Uncharacterized protein OX=126793 GN=PVX_001780 PE=4 SV=1 |
| 252 | KPNRHINL | tr\|A5K2R8\|A5K2R8_PLAVS Uncharacterized protein OX=126793 GN=PVX_115275 PE=4 SV=1 |
| 253 | KPQKEDAKGGKK | tr\|A5K858\|A5K858_PLAVS 40S ribosomal protein S6 OX=126793 GN=PVX_083000 PE=4 SV=1 |
| 254 | KPSRTTIT | tr\|A5K3K0\|A5K3K0_PLAVS Ferlin OX=126793 GN=PVX_117685 PE=4 SV=1 |
| 255 | KQVGGKNQQV | tr\|A5K303\|A5K303_PLAVS 60S ribosomal protein L23a OX=126793 GN=PVX_116700 PE=3 SV=1 |
| 256 | KRNLKKSIKKKPKSK | tr\|A5K4B5\|A5K4B5_PLAVS 60S ribosomal protein L36 OX=126793 GN=PVX_091145 PE=3 SV=1 |
| 257 | KS(+79.97)IEIDDEK | tr\|A5K858\|A5K858_PLAVS 40S ribosomal protein S6 OX=126793 GN=PVX_083000 PE=4 SV=1 |
| 258 | KSAGADSKSLKKLD | tr\|A5K676\|A5K676_PLAVS Early transcribed membrane protein (ETRAMP) |
| 259 | KSAYAISK | tr\|A5K9G3\|A5K9G3_PLAVS Endo/exonuclease/phosphatase domain-containing protein OX=126793 GN=PVX_080270 PE=4 SV=1 |
| 260 | KSDSSKIA | tr\|A5KAS9\|A5KAS9_PLAVS Tryptophan-rich antigen (Pv-fam-a) OX=126793 GN=PVX_097575 PE=4 SV=1 |
| 261 | KSIEAKKNNK | tr\|A5KAZ9\|A5KAZ9_PLAVS 60S ribosomal subunit protein L4/L1 OX=126793 GN=PVX_097915 PE=4 SV=1 |
| 262 | KSNDRSYYT | tr\|A5K3K0\|A5K3K0_PLAVS Ferlin OX=126793 GN=PVX_117685 PE=4 SV=1 |
| 263 | KSNGKRDPK | tr\|A5K3V9\|A5K3V9_PLAVS RNA helicase OX=126793 GN=PVX_118230 PE=4 SV=1 |
| 264 | KSNPFRGSSHAK | tr\|A5KB86\|A5KB86_PLAVS 40S ribosomal protein S23 OX=126793 GN=PVX_119470 PE=3 SV=1 |
| 265 | KSNSISLS | tr\|A5K1B7\|A5K1B7_PLAVS RHOMBOID-like protein OX=126793 GN=PVX_085890 PE=3 SV=1 |
| 266 | KSTNILGE | tr\|A5K0T3\|A5K0T3_PLAVS 60S ribosomal protein L14 OX=126793 GN=PVX_084955 PE=4 SV=1 |
| 267 | KSTTTGHIIYK | tr\|A5K2H7\|A5K2H7_PLAVS Elongation factor 1-alpha OX=126793 GN=PVX_114830 PE=3 SV=1 |
| 268 | KTINKTID | tr\|A5K197\|A5K197_PLAVS Sperm-specific protein Don juan OX=126793 GN=PVX_085790 PE=4 SV=1 |

Figure 3 continued

| | | |
|---|---|---|
| 269 | KTINKTIDKQKKAP(-.98) | tr\|A5K197\|A5K197_PLAVS Sperm-specific protein Don juan OX=126793 GN=PVX_085790 PE=4 SV=1 |
| 270 | KTIYNFLI | tr\|A5K9P1\|A5K9P1_PLAVS MATH domain-containing protein OX=126793 GN=PVX_080660 PE=4 SV=1 |
| 271 | KVDKKAPAKPQKED | tr\|A5K858\|A5K858_PLAVS 40S ribosomal protein S6 OX=126793 GN=PVX_083000 PE=4 SV=1 |
| 272 | KVINMK(+27.99)KAPN | tr\|A5K197\|A5K197_PLAVS Sperm-specific protein Don juan OX=126793 GN=PVX_085790 PE=4 SV=1 |
| 273 | KVPVPPTQAKKPKKN | tr\|A5K7L8\|A5K7L8_PLAVS Histone H2A OX=126793 GN=PVX_095190 PE=3 SV=1 |
| 274 | KYFLGLARE | tr\|A5K504\|A5K504_PLAVS Uncharacterized protein OX=126793 GN=PVX_092335 PE=4 SV=1 |
| 275 | KYQSSTASALIA | tr\|A5K2J4\|A5K2J4_PLAVS 40S ribosomal protein S13 OX=126793 GN=PVX_114910 PE=3 SV=1 |
| 276 | KYRQIREGLITKENK | tr\|A5K9G4\|A5K9G4_PLAVS 40S ribosomal protein S24 OX=126793 GN=PVX_080275 PE=3 SV=1 |
| 277 | KYYRVKGKKKILIPV | tr\|A5K826\|A5K826_PLAVS 60S ribosomal protein L6 OX=126793 GN=PVX_082840 PE=4 SV=1 |
| 278 | LETEREARRLR | tr\|A5K3E2\|A5K3E2_PLAVS 50S ribosomal protein S28e OX=126793 GN=PVX_117390 PE=3 SV=1 |
| 279 | LETYQN(+.98)M(+15.99)KIQKQTP | tr\|A5K3U1\|A5K3U1_PLAVS 40S ribosomal protein S2 OX=126793 GN=PVX_118145 PE=3 SV=1 |
| 279 | LETYQNM(+15.99)KIQKQTP | tr\|A5K3U1\|A5K3U1_PLAVS 40S ribosomal protein S2 |
| 279 | LETYQNMKIQKQTP | tr\|A5K3U1\|A5K3U1_PLAVS 40S ribosomal protein S2 OX=126793 GN=PVX_118145 PE=3 SV=1 |
| 282 | LGGLNQKQPT | tr\|A5KBH5\|A5KBH5_PLAVS Early transcribed membrane protein (ETRAMP) OX=126793 GN=PVX_003565 PE=4 SV=1 |
| 283 | LGSLVGFVF | tr\|A5K090\|A5K090_PLAVS Uncharacterized protein OX=126793 GN=PVX_124080 PE=4 SV=1 |
| 284 | LILRAAIKTK | tr\|A5K8J8\|A5K8J8_PLAVS PPR_long domain-containing protein OX=126793 GN=PVX_100625 PE=4 SV=1 |
| 285 | LLINVFLHH | tr\|A5K210\|A5K210_PLAVS Alpha adaptin OX=126793 GN=PVX_113995 PE=4 SV=1 |
| 286 | LLPKKSQLK | tr\|A5K214\|A5K214_PLAVS Histone H2A OX=126793 GN=PVX_114015 PE=3 SV=1 |
| 287 | LLPKKSQLKSG | tr\|A5K214\|A5K214_PLAVS Histone H2A OX=126793 GN=PVX_114015 PE=3 SV=1 |
| 288 | LNALENPPKPG | tr\|A5KC19\|A5KC19_PLAVS Uncharacterized protein OX=126793 GN=PVX_096035 PE=4 SV=1 |
| 289 | LNQKQPTKGSNIQ | tr\|A5KBH5\|A5KBH5_PLAVS Early transcribed membrane protein (ETRAMP) OX=126793 GN=PVX_003565 PE=4 SV=1 |
| 290 | LRPKKKLK | tr\|A5K2R4\|A5K2R4_PLAVS Ubiquitin/ribosomal OX=126793 GN=PVX_115255 PE=4 SV=1 |
| 291 | LSAAPAGV | tr\|A5K376\|A5K376_PLAVS Uncharacterized protein OX=126793 GN=PVX_117060 PE=4 SV=1 |
| 292 | M(+15.99)KQKGFGGQTKPV | tr\|A5KB61\|A5KB61_PLAVS 60S Ribosomal protein L44 OX=126793 GN=PVX_119345 PE=3 SV=1 |
| 293 | M(+15.99)YKKVYVID | tr\|A5K762\|A5K762_PLAVS 60S ribosomal protein L13a OX=126793 GN=PVX_094400 PE=3 SV=1 |
| 294 | MSCDTSASA | tr\|A5K6C3\|A5K6C3_PLAVS Mitochondrial carrier protein OX=126793 GN=PVX_098705 PE=3 SV=1 |
| 295 | MVSGTTGSTAN | tr\|A5K1W8\|A5K1W8_PLAVS Uncharacterized protein OX=126793 GN=PVX_113780 PE=4 SV=1 |

Figure 3 continued

| | | |
|---|---|---|
| 293 | MYKKVYVID | tr\|A5K762\|A5K762_PLAVS 60S ribosomal protein L13a OX=126793 GN=PVX_094400 PE=3 SV=1 |
| 297 | NAKGKKPAKKVI | tr\|A5K584\|A5K584_PLAVS 60S ribosomal protein L33-B OX=126793 GN=PVX_092735 PE=3 SV=1 |
| 298 | NAQLTKQKTKKVI | tr\|A5K197\|A5K197_PLAVS Sperm-specific protein Don juan OX=126793 GN=PVX_085790 PE=4 SV=1 |
| 299 | NCAQGHCSQ | tr\|A5K6H1\|A5K6H1_PLAVS Uncharacterized protein OX=126793 GN=PVX_098950 PE=4 SV=1 |
| 300 | NEGDPSKGEGAET | tr\|A5KDS2\|A5KDS2_PLAVS Erythrocyte binding protein OX=126793 GN=PVX_110835 PE=4 SV=1 |
| 301 | NEKKELKTEAL | tr\|A5K762\|A5K762_PLAVS 60S ribosomal protein L13a OX=126793 GN=PVX_094400 PE=3 SV=1 |
| 302 | NFDKYHPG | tr\|A5K219\|A5K219_PLAVS 60S ribosomal protein L27a OX=126793 GN=PVX_114040 PE=3 SV=1 |
| 303 | NFDVAAERF | tr\|A5K0F5\|A5K0F5_PLAVS SHNi-TPR domain-containing protein OX=126793 GN=PVX_084310 PE=4 SV=1 |
| 304 | NFSKNIKKKK | tr\|A5JZN9\|A5JZN9_PLAVS 60S ribosomal protein L13 OX=126793 GN=PVX_123070 PE=3 SV=1 |
| 305 | NIPPKAFG | tr\|A5K584\|A5K584_PLAVS 60S ribosomal protein L33-B OX=126793 GN=PVX_092735 PE=3 SV=1 |
| 306 | NKALLPTAGDD | tr\|A5KAZ9\|A5KAZ9_PLAVS 60S ribosomal subunit protein L4/L1 OX=126793 GN=PVX_097915 PE=4 SV=1 |
| 307 | NKEKLNHAV | tr\|A5K124\|A5K124_PLAVS 40S ribosomal protein S25 OX=126793 GN=PVX_085420 PE=4 SV=1 |
| 308 | NKEKLNHAVF | tr\|A5K124\|A5K124_PLAVS 40S ribosomal protein S25 OX=126793 GN=PVX_085420 PE=4 SV=1 |
| 309 | NKKGTPNTKKEPLL | tr\|A5KBH5\|A5KBH5_PLAVS Early transcribed membrane protein (ETRAMP) OX=126793 GN=PVX_003565 PE=4 SV=1 |
| 310 | NKKVYKLDKE | tr\|A5K662\|A5K662_PLAVS 40S ribosomal protein S19s OX=126793 GN=PVX_090160 PE=4 SV=1 |
| 311 | NKNSLTNFAVR(-.98) | tr\|A5KAZ9\|A5KAZ9_PLAVS 60S ribosomal subunit protein L4/L1 OX=126793 GN=PVX_097915 PE=4 SV=1 |
| 312 | NKVRPIRTPGGKLTI | tr\|A5KAB1\|A5KAB1_PLAVS 60S ribosomal protein L34-A OX=126793 GN=PVX_088065 PE=4 SV=1 |
| 313 | NLKGAKAEEGKKD | tr\|A5K858\|A5K858_PLAVS 40S ribosomal protein S6 OX=126793 GN=PVX_083000 PE=4 SV=1 |
| 314 | NNDFQKLESYD | tr\|A5KC18\|A5KC18_PLAVS Uncharacterized protein OX=126793 GN=PVX_096030 PE=4 SV=1;tr\|A5KC19\|A5KC19_PLAVS Uncharacterized protein OX=126793 GN=PVX_096035 PE=4 SV=1 |
| 315 | NPFNRYPAY | tr\|A5K436\|A5K436_PLAVS Uncharacterized protein OX=126793 GN=PVX_118625 PE=4 SV=1 |
| 316 | NQKQPTKGSNIQ | tr\|A5KBH5\|A5KBH5_PLAVS Early transcribed membrane protein (ETRAMP) OX=126793 GN=PVX_003565 PE=4 SV=1 |
| 317 | NQLRPKKKLK | tr\|A5K2R4\|A5K2R4_PLAVS Ubiquitin/ribosomal OX=126793 GN=PVX_115255 PE=4 SV=1 |
| 318 | NSLTNFAVR(-.98) | tr\|A5KAZ9\|A5KAZ9_PLAVS 60S ribosomal subunit protein L4/L1 OX=126793 GN=PVX_097915 PE=4 SV=1 |
| 319 | NSVKSNKKVKKM(+15.99)IK | tr\|A5KE19\|A5KE19_PLAVS Merozoite capping protein 1 OX=126793 GN=PVX_111355 PE=4 SV=1 |
| 320 | NTIAFVATEK | tr\|A5KBK1\|A5KBK1_PLAVS Uncharacterized protein OX=126793 GN=PVX_003695 PE=4 SV=1 |
| 321 | NVCYRVCC | tr\|A5JZ31\|A5JZ31_PLAVS PI3K/PI4K domain-containing protein OX=126793 GN=PVX_122030 PE=3 SV=1 |

Figure 3 continued

| | | |
|---|---|---|
| 322 | NVKGNPKAAA(-.98) | tr\|A5K303\|A5K303_PLAVS 60S ribosomal protein L23a OX=126793 GN=PVX_116700 PE=3 SV=1 |
| 323 | PGRGAPLAKI | tr\|A5K9J0\|A5K9J0_PLAVS 60S ribosomal protein L8 OX=126793 GN=PVX_080405 PE=4 SV=1 |
| 324 | PKFFKNQR | tr\|A5K3F2\|A5K3F2_PLAVS 60S ribosomal protein L29 OX=126793 GN=PVX_117440 PE=3 SV=1 |
| 325 | PKFFKNQRY | tr\|A5K3F2\|A5K3F2_PLAVS 60S ribosomal protein L29 |
| 326 | PKIEPPKKKFIPSVL | tr\|A5K6T4\|A5K6T4_PLAVS 50S ribosomal protein L29 OX=126793 GN=PVX_099510 PE=4 SV=1 |
| 327 | PLPDRNDVPL | tr\|A5K391\|A5K391_PLAVS Enkurin domain-containing protein OX=126793 GN=PVX_117135 PE=4 SV=1 |
| 328 | PLSNKKTVK | tr\|A5K0Z6\|A5K0Z6_PLAVS Ribosomal protein L7a OX=126793 GN=PVX_085270 PE=4 SV=1 |
| 329 | PPKDVVPS | tr\|A5KCE9\|A5KCE9_PLAVS RNA cytidine acetyltransferase OX=126793 GN=PVX_001895 PE=3 SV=1 |
| 330 | PPKERKTKEQIAAA | tr\|A5K124\|A5K124_PLAVS 40S ribosomal protein S25 OX=126793 GN=PVX_085420 PE=4 SV=1 |
| 331 | PPSGGSPNRSPP | tr\|A5K7B6\|A5K7B6_PLAVS Uncharacterized protein OX=126793 GN=PVX_094675 PE=4 SV=1 |
| 332 | PQKEDAKGGKKKK | tr\|A5K858\|A5K858_PLAVS 40S ribosomal protein S6 OX=126793 GN=PVX_083000 PE=4 SV=1 |
| 333 | PRNPNYRDQQYPD | tr\|A5K452\|A5K452_PLAVS Pv-fam-d protein OX=126793 GN=PVX_118695 PE=4 SV=1 |
| 334 | Q(-17.03)FTKQRSNI | tr\|A5K197\|A5K197_PLAVS Sperm-specific protein Don juan OX=126793 GN=PVX_085790 PE=4 SV=1 |
| 335 | Q(-17.03)KKPAAPETSA | tr\|A5KC18\|A5KC18_PLAVS Uncharacterized protein OX=126793 GN=PVX_096030 PE=4 SV=1 |
| 336 | Q(-17.03)KQPTKGSNIQ | tr\|A5KBH5\|A5KBH5_PLAVS Early transcribed membrane protein (ETRAMP) OX=126793 GN=PVX_003565 PE=4 SV=1 |
| 337 | QRSALVNNPL | tr\|A5K6C4\|A5K6C4_PLAVS Uncharacterized protein OX=126793 GN=PVX_098710 PE=4 SV=1 |
| 338 | R(+28.03)AAPEEHPVL | tr\|A5K8W3\|A5K8W3_PLAVS Actin OX=126793 GN=PVX_101200 PE=3 SV=1 |
| 339 | R(+28.03)GSAEDDLK | tr\|A5K3U1\|A5K3U1_PLAVS 40S ribosomal protein S2 OX=126793 GN=PVX_118145 PE=3 SV=1 |
| 340 | RAGKVKNQTPKVPK | tr\|A5KBT5\|A5KBT5_PLAVS 40S ribosomal protein S30 OX=126793 GN=PVX_002590 PE=3 SV=1 |
| 341 | RAISKNGKNRFIKPK | tr\|A5K858\|A5K858_PLAVS 40S ribosomal protein S6 OX=126793 GN=PVX_083000 PE=4 SV=1 |
| 342 | RGETDVETRQNNILL | tr\|A5KCS0\|A5KCS0_PLAVS Uncharacterized protein OX=126793 GN=PVX_000010 PE=4 SV=1 |
| 343 | RKAHKNGIKKPK | tr\|A5K3F2\|A5K3F2_PLAVS 60S ribosomal protein L29 OX=126793 GN=PVX_117440 PE=3 SV=1 |
| 344 | RKKGPNSKL | tr\|A5KBT5\|A5KBT5_PLAVS 40S ribosomal protein S30 OX=126793 GN=PVX_002590 PE=3 SV=1 |
| 345 | RKKPATPKKQATPK | tr\|A5KC18\|A5KC18_PLAVS Uncharacterized protein OX=126793 GN=PVX_096030 PE=4 SV=1 |
| 346 | RKKPATPKKQATPKK | tr\|A5KC18\|A5KC18_PLAVS Uncharacterized protein OX=126793 GN=PVX_096030 PE=4 SV=1 |
| 347 | RKYKIILAF | tr\|A5K729\|A5K729_PLAVS Uncharacterized protein OX=126793 GN=PVX_100005 PE=4 SV=1 |
| 348 | RLELTPKQKV | tr\|A5K4R0\|A5K4R0_PLAVS 60S ribosomal protein L35 OX=126793 GN=PVX_091865 PE=3 SV=1 |

Figure 3 continued

| | | |
|---|---|---|
| 349 | RLTGGKKKIH | tr\|A5K1E3\|A5K1E3_PLAVS 40S ribosomal protein S8 OX=126793 GN=PVX_086020 PE=3 SV=1 |
| 350 | RLTGGKKKIHK | tr\|A5K1E3\|A5K1E3_PLAVS 40S ribosomal protein S8 OX=126793 GN=PVX_086020 PE=3 SV=1 |
| 351 | RLTGGKKKIHKKK | tr\|A5K1E3\|A5K1E3_PLAVS 40S ribosomal protein S8 OX=126793 GN=PVX_086020 PE=3 SV=1 |
| 352 | RNKKIYRIGLK | tr\|A5KE14\|A5KE14_PLAVS Ribosomal protein L3 OX=126793 GN=PVX_111330 PE=3 SV=1 |
| 353 | RNLKKSIKKKPKS | tr\|A5K4B5\|A5K4B5_PLAVS 60S ribosomal protein L36 OX=126793 GN=PVX_091145 PE=3 SV=1 |
| 354 | RNLKKSIKKKPKSK | tr\|A5K4B5\|A5K4B5_PLAVS 60S ribosomal protein L36 OX=126793 GN=PVX_091145 PE=3 SV=1 |
| 355 | RPPSNTKLGSKQV | tr\|A5K1E3\|A5K1E3_PLAVS 40S ribosomal protein S8 OX=126793 GN=PVX_086020 PE=3 SV=1 |
| 356 | RSSGLTNSRQQKMK | tr\|A5K1G3\|A5K1G3_PLAVS Uncharacterized protein OX=126793 GN=PVX_086120 PE=4 SV=1 |
| 357 | RSYSFNSM | tr\|A5KB42\|A5KB42_PLAVS Protein kinase domain containing protein OX=126793 GN=PVX_119250 PE=4 SV=1 |
| 358 | RTPGGKLTI | tr\|A5KAB1\|A5KAB1_PLAVS 60S ribosomal protein L34-A OX=126793 GN=PVX_088065 PE=4 SV=1 |
| 359 | RTVGVSKKKGA | tr\|A5K4S2\|A5K4S2_PLAVS 40S ribosomal protein S18 OX=126793 GN=PVX_091925 PE=3 SV=1 |
| 360 | SAGIKKPHRYRPGTV | tr\|A5K1U7\|A5K1U7_PLAVS Histone H3 OX=126793 GN=PVX_113665 PE=3 SV=1 |
| 361 | SDGTGRKKGPNSKL | tr\|A5KBT5\|A5KBT5_PLAVS 40S ribosomal protein S30 OX=126793 GN=PVX_002590 PE=3 SV=1 |
| 362 | SDIIKTNE | tr\|A5KCD7\|A5KCD7_PLAVS 60S ribosomal protein L30 OX=126793 GN=PVX_001835 PE=4 SV=1 |
| 363 | SFFNSKKIKKGSK | tr\|A5K7Q0\|A5K7Q0_PLAVS 40S ribosomal protein S11 OX=126793 GN=PVX_095350 PE=3 SV=1 |
| 364 | SFFNSKKIKKGSKS | tr\|A5K7Q0\|A5K7Q0_PLAVS 40S ribosomal protein S11 |
| 365 | SGFLLHPSVTF | tr\|A5K2A7\|A5K2A7_PLAVS 4-methyl-5(B-hydroxyethyl)-thiazol monophosphate biosynthesis enzyme OX=126793 GN=PVX_114480 PE=4 SV=1 |
| 366 | SGGVLPNIHNV | tr\|A5K214\|A5K214_PLAVS Histone H2A OX=126793 GN=PVX_114015 PE=3 SV=1 |
| 367 | SGKSTTTGHIIYK | tr\|A5K2H7\|A5K2H7_PLAVS Elongation factor 1-alpha OX=126793 GN=PVX_114830 PE=3 SV=1 |
| 368 | SKDGKNEAAL | tr\|A5KDT8\|A5KDT8_PLAVS Uncharacterized protein OX=126793 GN=PVX_110915 PE=4 SV=1 |
| 369 | SKGPDTPIITN | tr\|A5K676\|A5K676_PLAVS Early transcribed membrane protein (ETRAMP) OX=126793 GN=PVX_090230 PE=4 SV=1 |
| 370 | SKNGKNRFIKPK | tr\|A5K858\|A5K858_PLAVS 40S ribosomal protein S6 OX=126793 GN=PVX_083000 PE=4 SV=1 |
| 371 | SKNGKNRFIKPKIQ | tr\|A5K858\|A5K858_PLAVS 40S ribosomal protein S6 OX=126793 GN=PVX_083000 PE=4 SV=1 |
| 372 | SKQNFAKNKKKAAN | tr\|A5K8F1\|A5K8F1_PLAVS 60S ribosomal protein L17 OX=126793 GN=PVX_083465 PE=3 SV=1 |
| 373 | SLALQKKKAA | tr\|A5JZ82\|A5JZ82_PLAVS 60S ribosomal protein L24 OX=126793 GN=PVX_122285 PE=4 SV=1 |
| 374 | SLGKQVGGKNQQVK | tr\|A5K303\|A5K303_PLAVS 60S ribosomal protein L23a OX=126793 GN=PVX_116700 PE=3 SV=1 |

Figure 3 continued

| | | |
|---|---|---|
| 375 | SLLALFKEKKEKPRS | tr\|A5KB86\|A5KB86_PLAVS 40S ribosomal protein S23 OX=126793 GN=PVX_119470 PE=3 SV=1 |
| 376 | SLTTPAAVAAK | tr\|A5KBQ3\|A5KBQ3_PLAVS 60S ribosomal protein L37a OX=126793 GN=PVX_003955 PE=3 SV=1 |
| 377 | SLVKQRSNI | tr\|A5K199\|A5K199_PLAVS Uncharacterized protein OX=126793 GN=PVX_085800 PE=4 SV=1 |
| 378 | SM(+15.99)KNKKDK TPPSK | tr\|A5K676\|A5K676_PLAVS Early transcribed membrane protein (ETRAMP) OX=126793 GN=PVX_090230 PE=4 SV=1 |
| 379 | SMCETTET | tr\|A5K739\|A5K739_PLAVS Uncharacterized protein OX=126793 GN=PVX_094275 PE=4 SV=1 |
| 380 | SNDDGNGKKFNKKP F | tr\|A5K7V6\|A5K7V6_PLAVS RRM domain-containing protein OX=126793 GN=PVX_082480 PE=4 SV=1 |
| 381 | SNKKVKKM(+15.99) IK | tr\|A5KE19\|A5KE19_PLAVS Merozoite capping protein 1 OX=126793 GN=PVX_111355 PE=4 SV=1 |
| 382 | SNMESDDAGDG | tr\|A5KC05\|A5KC05_PLAVS Serine/threonine-specific protein kinase OX=126793 GN=PVX_002945 PE=4 SV=1 |
| 383 | SQKLYTKVA | tr\|A5K124\|A5K124_PLAVS 40S ribosomal protein S25 OX=126793 GN=PVX_085420 PE=4 SV=1 |
| 384 | SRKGLDPKFFK | tr\|A5K3F2\|A5K3F2_PLAVS 60S ribosomal protein L29 OX=126793 GN=PVX_117440 PE=3 SV=1 |
| 385 | SSHAKGIVV | tr\|A5KB86\|A5KB86_PLAVS 40S ribosomal protein S23 OX=126793 GN=PVX_119470 PE=3 SV=1 |
| 386 | SSHAKGIVVEKV | tr\|A5KB86\|A5KB86_PLAVS 40S ribosomal protein S23 OX=126793 GN=PVX_119470 PE=3 SV=1 |
| 387 | STTTGHIIYK | tr\|A5K2H7\|A5K2H7_PLAVS Elongation factor 1-alpha OX=126793 GN=PVX_114830 PE=3 SV=1 |
| 388 | STVITDQYVS(-.98) | tr\|A5JZN7\|A5JZN7_PLAVS Alba domain-containing protein OX=126793 GN=PVX_123060 PE=4 SV=1 |
| 389 | SVINAKAKLQKTEE | tr\|A5K6B0\|A5K6B0_PLAVS 60S ribosomal protein L32 OX=126793 GN=PVX_098640 PE=4 SV=1 |
| 390 | SVKSNKKVKKM(+15 .99)IK | tr\|A5KE19\|A5KE19_PLAVS Merozoite capping protein 1 OX=126793 GN=PVX_111355 PE=4 SV=1 |
| 391 | SYLFKKIKKKVF | tr\|A5K4L3\|A5K4L3_PLAVS Uncharacterized protein OX=126793 GN=PVX_091635 PE=4 SV=1 |
| 392 | TDEDAGKKKKVKKSL | tr\|A5K858\|A5K858_PLAVS 40S ribosomal protein S6 OX=126793 GN=PVX_083000 PE=4 SV=1 |
| 393 | TDVGDSDIIKTNE | tr\|A5KCD7\|A5KCD7_PLAVS 60S ribosomal protein L30 OX=126793 GN=PVX_001835 PE=4 SV=1 |
| 394 | TEGSTPKPKQR | tr\|A5KA70\|A5KA70_PLAVS Ribosomal protein L37 OX=126793 GN=PVX_087860 PE=3 SV=1 |
| 395 | TEYPPLGRF | tr\|A5K2H7\|A5K2H7_PLAVS Elongation factor 1-alpha OX=126793 GN=PVX_114830 PE=3 SV=1 |
| 396 | TEYPPLGRFA | tr\|A5K2H7\|A5K2H7_PLAVS Elongation factor 1-alpha OX=126793 GN=PVX_114830 PE=3 SV=1 |
| 397 | TFLFNKKKKK | tr\|A5K2B4\|A5K2B4_PLAVS Ethanolaminephosphotransferase OX=126793 GN=PVX_114515 PE=3 SV=1 |
| 398 | TGKYGTRYGSSL | tr\|A5KBQ3\|A5KBQ3_PLAVS 60S ribosomal protein L37a OX=126793 GN=PVX_003955 PE=3 SV=1 |
| 399 | TGLLRGAK | tr\|A5K9J0\|A5K9J0_PLAVS 60S ribosomal protein L8 OX=126793 GN=PVX_080405 PE=4 SV=1 |
| 400 | TGLLRGAKKTKLVG | tr\|A5K9J0\|A5K9J0_PLAVS 60S ribosomal protein L8 OX=126793 GN=PVX_080405 PE=4 SV=1 |
| 401 | TGRKKGPNSKL | tr\|A5KBT5\|A5KBT5_PLAVS 40S ribosomal protein S30 OX=126793 GN=PVX_002590 PE=3 SV=1 |

Figure 3 continued

| | | |
|---|---|---|
| 402 | TKILIVHV | tr\|A5K4W2\|A5K4W2_PLAVS 60S acidic ribosomal protein P0 OX=126793 GN=PVX_092120 PE=3 SV=1 |
| 403 | TKLVGKTED | tr\|A5K9J0\|A5K9J0_PLAVS 60S ribosomal protein L8 OX=126793 GN=PVX_080405 PE=4 SV=1 |
| 404 | TKRNLKKSIK | tr\|A5K4B5\|A5K4B5_PLAVS 60S ribosomal protein L36 OX=126793 GN=PVX_091145 PE=3 SV=1 |
| 405 | TLESPDNAEIDM(+15.99)SS | tr\|A5K8G8\|A5K8G8_PLAVS Uncharacterized protein OX=126793 GN=PVX_083555 PE=4 SV=1 |
| 405 | TLESPDNAEIDMSS | tr\|A5K8G8\|A5K8G8_PLAVS Uncharacterized protein OX=126793 GN=PVX_083555 PE=4 SV=1 |
| 407 | TPGGKLTI | tr\|A5KAB1\|A5KAB1_PLAVS 60S ribosomal protein L34-A OX=126793 GN=PVX_088065 PE=4 SV=1 |
| 408 | TPIEKLHPI | tr\|A5JZN9\|A5JZN9_PLAVS 60S ribosomal protein L13 OX=126793 GN=PVX_123070 PE=3 SV=1 |
| 409 | TPIITNKPFG | tr\|A5K676\|A5K676_PLAVS Early transcribed membrane protein (ETRAMP) |
| 410 | TPIITNKPFGK | tr\|A5K676\|A5K676_PLAVS Early transcribed membrane protein (ETRAMP) OX=126793 GN=PVX_090230 PE=4 SV=1 |
| 411 | TSNSAKAGLQFPV | tr\|A5K214\|A5K214_PLAVS Histone H2A OX=126793 GN=PVX_114015 PE=3 SV=1 |
| 412 | TTKVKRVQT | tr\|A5JZP0\|A5JZP0_PLAVS 40S ribosomal protein S16 OX=126793 GN=PVX_123075 PE=3 SV=1 |
| 413 | TTKVKRVQTF | tr\|A5JZP0\|A5JZP0_PLAVS 40S ribosomal protein S16 OX=126793 GN=PVX_123075 PE=3 SV=1 |
| 414 | VAKKESKIIKKQK | tr\|A5K5N3\|A5K5N3_PLAVS 60S ribosomal protein L22 OX=126793 GN=PVX_089280 PE=4 SV=1 |
| 415 | VAKKESKIIKKQKK | tr\|A5K5N3\|A5K5N3_PLAVS 60S ribosomal protein L22 OX=126793 GN=PVX_089280 PE=4 SV=1 |
| 416 | VETEPDDIDYGK | tr\|A5K8G8\|A5K8G8_PLAVS Uncharacterized protein OX=126793 GN=PVX_083555 PE=4 SV=1 |
| 417 | VETEPDDIDYGKSD | tr\|A5K8G8\|A5K8G8_PLAVS Uncharacterized protein OX=126793 GN=PVX_083555 PE=4 SV=1 |
| 418 | VETEPDDIDYGKSDD | tr\|A5K8G8\|A5K8G8_PLAVS Uncharacterized protein OX=126793 GN=PVX_083555 PE=4 SV=1 |
| 419 | VFPYDNTLPKYKF | tr\|A5K8G8\|A5K8G8_PLAVS Uncharacterized protein OX=126793 GN=PVX_083555 PE=4 SV=1 |
| 420 | VGDSDIIKTNE | tr\|A5KCD7\|A5KCD7_PLAVS 60S ribosomal protein L30 OX=126793 GN=PVX_001835 PE=4 SV=1 |
| 421 | VGNILLGV | tr\|A5KD48\|A5KD48_PLAVS Variable surface protein Vir14 OX=126793 GN=PVX_169270 PE=4 SV=1 |
| 422 | VITDVGDSDIIKTNE | tr\|A5KCD7\|A5KCD7_PLAVS 60S ribosomal protein L30 OX=126793 GN=PVX_001835 PE=4 SV=1 |
| 423 | VKEVIKRKNVIGIIP | tr\|A5K4N4\|A5K4N4_PLAVS Uncharacterized protein OX=126793 GN=PVX_091735 PE=4 SV=1 |
| 424 | VKYAKKLRD | tr\|A5K8F1\|A5K8F1_PLAVS 60S ribosomal protein L17 OX=126793 GN=PVX_083465 PE=3 SV=1 |
| 425 | VNVPKTRKT | tr\|A5KB61\|A5KB61_PLAVS 60S Ribosomal protein L44 OX=126793 GN=PVX_119345 PE=3 SV=1 |
| 426 | VNVPKTRKTY | tr\|A5KB61\|A5KB61_PLAVS 60S Ribosomal protein L44 OX=126793 GN=PVX_119345 PE=3 SV=1 |
| 426 | VNVPKTRKTY(-.98) | tr\|A5KB61\|A5KB61_PLAVS 60S Ribosomal protein L44 OX=126793 GN=PVX_119345 PE=3 SV=1 |
| 428 | VPNGGMYL | tr\|A5KCD3\|A5KCD3_PLAVS GYF domain-containing protein OX=126793 GN=PVX_001810 PE=4 SV=1 |

Figure 3 continued

| | | |
|---|---|---|
| 429 | VRVADNSLKTNIHQY | tr\|A5K851\|A5K851_PLAVS 60S ribosomal protein L18a OX=126793 GN=PVX_082965 PE=3 SV=1 |
| 430 | VSEVTTVEKDE | tr\|A5K306\|A5K306_PLAVS 60S ribosomal protein L9 OX=126793 GN=PVX_116715 PE=4 SV=1 |
| 431 | VSKRKKLTGRAK | tr\|A5KBT5\|A5KBT5_PLAVS 40S ribosomal protein S30 OX=126793 GN=PVX_002590 PE=3 SV=1 |
| 432 | VSKRKKLTGRAKK | tr\|A5KBT5\|A5KBT5_PLAVS 40S ribosomal protein S30 OX=126793 GN=PVX_002590 PE=3 SV=1 |
| 433 | VVAPPER(+31.99)K | tr\|A5K8W3\|A5K8W3_PLAVS Actin OX=126793 GN=PVX_101200 PE=3 SV=1 |
| 434 | VVVVKGQPRKLK | tr\|A5KAS9\|A5KAS9_PLAVS Tryptophan-rich antigen (Pv-fam-a) OX=126793 GN=PVX_097575 PE=4 SV=1 |
| 435 | VYLIKILMIK | tr\|A5K3Y1\|A5K3Y1_PLAVS SEC7 domain-containing protein OX=126793 GN=PVX_118345 PE=4 SV=1 |
| 436 | WGKYQKMK | tr\|A5K285\|A5K285_PLAVS DNA polymerase 1 OX=126793 GN=PVX_114370 PE=4 SV=1 |
| 437 | WNYKAIRKIAK | tr\|A5K6T8\|A5K6T8_PLAVS Para-aminobenzoic acid synthetase OX=126793 GN=PVX_099530 PE=4 SV=1 |
| 438 | YAANWGGT | tr\|A5K4L2\|A5K4L2_PLAVS Uncharacterized protein OX=126793 GN=PVX_091630 PE=4 SV=1 |
| 439 | YESIEVSKI | tr\|A5JZN9\|A5JZN9_PLAVS 60S ribosomal protein L13 OX=126793 GN=PVX_123070 PE=3 SV=1 |
| 440 | YESIEVSKID | tr\|A5JZN9\|A5JZN9_PLAVS 60S ribosomal protein L13 OX=126793 GN=PVX_123070 PE=3 SV=1 |
| 441 | YFDLSRASF | tr\|A5KBP3\|A5KBP3_PLAVS Transmission-blocking target antigen Pfs230 OX=126793 GN=PVX_003905 PE=4 SV=1 |
| 442 | YFDLSRASFS | tr\|A5KBP3\|A5KBP3_PLAVS Transmission-blocking target antigen Pfs230 OX=126793 GN=PVX_003905 PE=4 SV=1 |
| 443 | YGPLKKDLKA | tr\|A5KE14\|A5KE14_PLAVS Ribosomal protein L3 OX=126793 GN=PVX_111330 PE=3 SV=1 |
| 444 | YGRIFKKKITKK | tr\|A5KAZ9\|A5KAZ9_PLAVS 60S ribosomal subunit protein L4/L1 OX=126793 GN=PVX_097915 PE=4 SV=1 |
| 445 | YGRIFKKKITKKN | tr\|A5KAZ9\|A5KAZ9_PLAVS 60S ribosomal subunit protein L4/L1 OX=126793 GN=PVX_097915 PE=4 SV=1 |
| 446 | YINKVYLFVYN | tr\|A5K0C5\|A5K0C5_PLAVS Dynein heavy chain OX=126793 GN=PVX_084160 PE=4 SV=1 |
| 447 | YKILIKDKLK | tr\|A5K0R6\|A5K0R6_PLAVS Uncharacterized protein OX=126793 GN=PVX_084865 PE=4 SV=1 |
| 448 | YLNDLCRN | tr\|A5JZ31\|A5JZ31_PLAVS PI3K/PI4K domain-containing protein OX=126793 GN=PVX_122030 PE=3 SV=1 |
| 449 | YRGDVVPKDVNAAVA | tr\|A5K661\|A5K661_PLAVS Tubulin alpha chain OX=126793 GN=PVX_090155 PE=3 SV=1:tr\|A5K6A8\|A5K6A8_PLAVS Tubulin alpha chain OX=126793 GN=PVX_098630 PE=3 SV=1 |
| 450 | YRGVVTEEGA | tr\|A5KA47\|A5KA47_PLAVS Uncharacterized protein OX=126793 GN=PVX_087745 PE=4 SV=1 |
| 451 | YRVKGKKK | tr\|A5K826\|A5K826_PLAVS 60S ribosomal protein L6 OX=126793 GN=PVX_082840 PE=4 SV=1 |
| 452 | YYDNGDNHN | tr\|A5K6C2\|A5K6C2_PLAVS Uncharacterized protein OX=126793 GN=PVX_098700 PE=4 SV=1 |
| 453 | YYRVKGKKKILIPV | tr\|A5K826\|A5K826_PLAVS 60S ribosomal protein L6 OX=126793 GN=PVX_082840 PE=4 SV=1 |

| Efficacy | Delay to 1% | P value |
|---|---|---|
| 3/10 (30%) | Yes | <0.0001 (****) |

| Efficacy | Delay to 1% | P value |
|---|---|---|
| 5/10 (50%) | Yes | <0.0001 (****) |

Figure 9

| SEQ ID № | Accession number | ELISPOT ID | Protein | Peptide Sequence |
|---|---|---|---|---|
| 279 | A5K3U1 | 40S S2 | 40S ribosomal protein S2 | LETYQNMKIQKQTP |
| 371 | A5K858 | 40S S6-1 | 40S ribosomal protein S6 | SKNGKNRFIKPKIQ |
| 133 | A5K858 | 40S S6-2 | 40S ribosomal protein S6 | GVKKDVAK |
| 120 | A5K858 | 40S S6- 3 | 40S ribosomal protein S6 | GPKRATKIRK |
| 351 | A5K1E3 | 40S S8- 1 | 40S ribosomal protein S8 | RLTGGKKKIHKKK |
| 130 | A5K1E3 | 40S S8- 2 | 40S ribosomal protein S8 | GSKQVHVV |
| 364 | A5K7Q0 | 40S S11 | 40S ribosomal protein S11 | SFFNSKKIKKGSKS |
| 386 | A5KB86 | 40S S23 | 40S ribosomal protein S23 | SSHAKGIVVEKV |
| 97 | A5K124 | 40S S25- 1 | 40S ribosomal protein S25 | GKGKNKEKL |
| 100 | A5K124 | 40S S25- 2 | 40S ribosomal protein S25 | GKGKNKEKLNHAVF |
| 361 | A5KBT5 | 40S S30- 1 | 40S ribosomal protein S30 | SDGTGRKKGPNSKL |
| 131 | A5KBT5 | 40S S30- 2 | 40S ribosomal protein S30 | GTGRKKGPNSKL |
| 401 | A5KBT5 | 40S S30- 3 | 40S ribosomal protein S30 | TGRKKGPNSKL |
| 82 | A5K3E2 | 50S S28e | 50S ribosomal protein S28e | GDTELSGRFL |
| 18 | A5KAZ9 | 60S L4/L1- 1 | 60S ribosomal subunit protein L4/L1 | ANKALLPTAGDD |
| 306 | A5KAZ9 | 60S L4/L1- 2 | 60S ribosomal subunit protein L4/L1 | NKALLPTAGDD |
| 444 | A5KAZ9 | 60S L4/L1- 3 | 60S ribosomal subunit protein L4/L1 | YGRIFKKKITKK |
| 430 | A5K306 | 60S L9 | 60S ribosomal protein L9 | VSEVTTVEKDE |
| 78 | A5K186 | 60S L10 | 60S ribosomal protein L10 | GAFGKPNGV |
| 293 | A5K762 | 60S 13a | 60S ribosomal protein L13a | MYKKVYVID |
| 440 | A5JZN9 | 60S L13- 1 | 60S ribosomal protein L13 | YESIEVSKID |
| 132 | A5JZN9 | 60S L13- 2 | 60S ribosomal protein L13 | GTPIEKLHPI |
| 240 | A5JZN9 | 60S L13- 3 | 60S ribosomal protein L13 | KNIKSKNGIGGIPAD |

Figure 9 continued

| | | | | |
|---|---|---|---|---|
| 325 | A5K3F2 | 60S L29 | 60S ribosomal protein L29 | PKFFKNQRY |
| 422 | A5KCD7 | 60S L30 | 60S ribosomal protein L30 | VITDVGDSDIIKTNE |
| 11 | A5KAW8 | 60S L31 | 60S ribosomal protein L31 | AKAVKKQKKTLKPV |
| 33 | A5K6B0 | 60S L32-1 | 60S ribosomal protein L32 | AVKKVGKIVKKRT |
| 31 | A5K6B0 | 60S L32-2 | 60S ribosomal protein L32 | AVKKVGKIVK |
| 230 | A5K4R0 | 60S L35 | 60S ribosomal protein L35 | KKYKNKKFKPY |
| 227 | *A5KBH5 | ETRAMP- 1 | Early transcribed membrane protein (ETRAMP) | KKVAAGYKKLTD |
| 114 | *A5KBH5 | ETRAMP- 2 | Early transcribed membrane protein (ETRAMP) | GLNQKQPTKGSNIQ |
| 289 | *A5KBH5 | ETRAMP- 3 | Early transcribed membrane protein (ETRAMP) | LNQKQPTKGSNIQ |
| 282 | *A5KBH5 | ETRAMP- 4 | Early transcribed membrane protein (ETRAMP) | LGGLNQKQPT |
| 258 | *A5K676 | ETRAMP- 5 | Early transcribed membrane protein (ETRAMP) | KSAGADSKSLKKLD |
| 409 | *A5K676 | ETRAMP- 6 | Early transcribed membrane protein (ETRAMP) | TPIITNKPFG |
| 125 | *A5K214 | Hist. H2A- 1 | Histone H2A | GRIGRYLKKGKYAK |
| 24 | *A5K214 | Hist. H2A- 2 | Histone H2A | ASGGVLPNIHNV |
| 366 | *A5K214 | Hist. H2A- 3 | Histone H2A | SGGVLPNIHNV |
| 124 | *A5K214 | Hist. H2A- 4 | Histone H2A | GRIGRYLKKGKYA |
| 273 | *A5K7L8 | Hist. H2A- 5 | Histone H2A | KVPVPPTQAKKPKKN |
| 19 | *A5K1U7 | Hist. H3 | Histone H3 | APISAGIKKPHR |
| 284 | A5K8J8 | Unch A5K8J8 | Uncharacterized protein | LILRAAIKTK |
| 50 | A5JZN7 | Unch A5JZN7.1 | Uncharacterized protein | DNNEHVVQEKTVSF |
| 51 | A5JZN7 | Unch A5JZN7.2 | Uncharacterized protein | DNNEHVVQEKTV |
| 56 | A5K8G9 | Unch A5K8G9 | Uncharacterized protein | EDYSPRKV |
| 8 | A5K2R4 | Ubqt/ribos- 1 | Ubiquitin/ribosomal | AIEPSLAQLAQK |
| 317 | A5K2R4 | Ubqt/ribos- 2 | Ubiquitin/ribosomal | NQLRPKKKLK |
| 20 | *A5K197 | Don Juan | Sperm-specific protein Don juan | AQKIKKKKKLTPA |

SEQUENCE LISTING

```
<160> NUMBER OF SEQ ID NOS: 722

<210> SEQ ID NO 1
<211> LENGTH: 12
<212> TYPE: PRT
<213> ORGANISM: Plasmodium vivax

<400> SEQUENCE: 1

Ala Thr Val Arg Pro Val Ala Asn Val Tyr Ser Thr
1               5                   10


<210> SEQ ID NO 2
<211> LENGTH: 15
<212> TYPE: PRT
<213> ORGANISM: Plasmodium vivax

<400> SEQUENCE: 2

Ala Ala Ala Ala Ala Ser Gly Arg Ser Lys Lys Lys Lys Trp Gly
1               5                   10                  15


<210> SEQ ID NO 3
<211> LENGTH: 8
<212> TYPE: PRT
<213> ORGANISM: Plasmodium vivax

<400> SEQUENCE: 3

Ala Ala Lys Arg Pro Ser Thr Tyr
1               5


<210> SEQ ID NO 4
<211> LENGTH: 13
<212> TYPE: PRT
<213> ORGANISM: Plasmodium vivax

<400> SEQUENCE: 4

Ala Ala Gln Lys Lys Pro Ala Ala Pro Glu Thr Ser Ala
1               5                   10


<210> SEQ ID NO 5
<211> LENGTH: 9
<212> TYPE: PRT
<213> ORGANISM: Plasmodium vivax

<400> SEQUENCE: 5

Ala Asp Lys Glu Lys Lys Gln Leu Tyr
1               5


<210> SEQ ID NO 6
<211> LENGTH: 13
<212> TYPE: PRT
<213> ORGANISM: Plasmodium vivax

<400> SEQUENCE: 6
```

Ala Gly Lys Glu Lys Asp Asp Lys Lys Lys Gly Lys Asp
1 5 10

<210> SEQ ID NO 7
<211> LENGTH: 12
<212> TYPE: PRT
<213> ORGANISM: Plasmodium vivax

<400> SEQUENCE: 7

Ala Gly Lys Lys Asp Gly Ala Lys Lys Glu Val Ala
1 5 10

<210> SEQ ID NO 8
<211> LENGTH: 12
<212> TYPE: PRT
<213> ORGANISM: Plasmodium vivax

<400> SEQUENCE: 8

Ala Ile Glu Pro Ser Leu Ala Gln Leu Ala Gln Lys
1 5 10

<210> SEQ ID NO 9
<211> LENGTH: 13
<212> TYPE: PRT
<213> ORGANISM: Plasmodium vivax

<400> SEQUENCE: 9

Ala Ile Glu Pro Ser Leu Ala Gln Leu Ala Gln Lys Tyr
1 5 10

<210> SEQ ID NO 10
<211> LENGTH: 14
<212> TYPE: PRT
<213> ORGANISM: Plasmodium vivax

<400> SEQUENCE: 10

Ala Ile Glu Pro Ser Leu Ala Gln Leu Ala Gln Lys Tyr Asn
1 5 10

<210> SEQ ID NO 11
<211> LENGTH: 14
<212> TYPE: PRT
<213> ORGANISM: Plasmodium vivax

<400> SEQUENCE: 11

Ala Lys Ala Val Lys Lys Gln Lys Lys Thr Leu Lys Pro Val
1 5 10

<210> SEQ ID NO 12
<211> LENGTH: 11
<212> TYPE: PRT
<213> ORGANISM: Plasmodium vivax

<400> SEQUENCE: 12

Ala Lys Asp Lys Lys Gln Leu Lys Lys Pro Ser
1 5 10

<210> SEQ ID NO 13
<211> LENGTH: 13
<212> TYPE: PRT
<213> ORGANISM: Plasmodium vivax

<400> SEQUENCE: 13

Ala Lys Lys Ala Asp Ala Lys Lys Ala Asp Ala Lys Lys
1 5 10

<210> SEQ ID NO 14
<211> LENGTH: 13
<212> TYPE: PRT
<213> ORGANISM: Plasmodium vivax

<400> SEQUENCE: 14

Ala Lys Lys Gly Glu Ala Lys Lys Gly Glu Ala Lys Lys
1 5 10

<210> SEQ ID NO 15
<211> LENGTH: 15
<212> TYPE: PRT
<213> ORGANISM: Plasmodium vivax

<400> SEQUENCE: 15

Ala Lys Ser Lys Asn His Thr Asn His Asn Gln Asn Arg Lys Ala
1 5 10 15

<210> SEQ ID NO 16
<211> LENGTH: 8
<212> TYPE: PRT
<213> ORGANISM: Plasmodium vivax

<400> SEQUENCE: 16

Ala Lys Val Val Lys Glu Val Lys
1 5

<210> SEQ ID NO 17
<211> LENGTH: 12
<212> TYPE: PRT
<213> ORGANISM: Plasmodium vivax

<400> SEQUENCE: 17

Ala Leu Phe Lys Glu Lys Lys Glu Lys Pro Arg Ser
1 5 10

<210> SEQ ID NO 18
<211> LENGTH: 12
<212> TYPE: PRT
<213> ORGANISM: Plasmodium vivax

<400> SEQUENCE: 18

Ala Asn Lys Ala Leu Leu Pro Thr Ala Gly Asp Asp
1 5 10

<210> SEQ ID NO 19
<211> LENGTH: 12
<212> TYPE: PRT
<213> ORGANISM: Plasmodium vivax

<400> SEQUENCE: 19

Ala Pro Ile Ser Ala Gly Ile Lys Lys Pro His Arg
1 5 10

<210> SEQ ID NO 20
<211> LENGTH: 13
<212> TYPE: PRT
<213> ORGANISM: Plasmodium vivax

<400> SEQUENCE: 20

Ala Gln Lys Ile Lys Lys Lys Lys Lys Leu Thr Pro Ala
1 5 10

<210> SEQ ID NO 21
<211> LENGTH: 15
<212> TYPE: PRT
<213> ORGANISM: Plasmodium vivax

<400> SEQUENCE: 21

Ala Gln Lys Ile Lys Lys Lys Lys Lys Leu Thr Pro Ala Lys Val
1 5 10 15

<210> SEQ ID NO 22
<211> LENGTH: 12
<212> TYPE: PRT
<213> ORGANISM: Plasmodium vivax

<400> SEQUENCE: 22

Ala Gln Lys Lys Pro Ala Ala Pro Glu Thr Ser Ala
1 5 10

<210> SEQ ID NO 23
<211> LENGTH: 15
<212> TYPE: PRT
<213> ORGANISM: Plasmodium vivax

<400> SEQUENCE: 23

Ala Arg Lys Lys Pro Ala Thr Pro Lys Lys Gln Ala Thr Pro Lys
1 5 10 15

<210> SEQ ID NO 24
<211> LENGTH: 12
<212> TYPE: PRT
<213> ORGANISM: Plasmodium vivax

<400> SEQUENCE: 24

Ala Ser Gly Gly Val Leu Pro Asn Ile His Asn Val
1 5 10

<210> SEQ ID NO 25
<211> LENGTH: 11
<212> TYPE: PRT
<213> ORGANISM: Plasmodium vivax

<400> SEQUENCE: 25

Ala Ser Gly Asn Asp Lys Leu Gly Lys Lys Lys
1 5 10

<210> SEQ ID NO 26
<211> LENGTH: 8
<212> TYPE: PRT
<213> ORGANISM: Plasmodium vivax

<400> SEQUENCE: 26

Ala Ser Ser Glu Ala Gln Lys Leu
1 5

<210> SEQ ID NO 27
<211> LENGTH: 10
<212> TYPE: PRT
<213> ORGANISM: Plasmodium vivax

<400> SEQUENCE: 27

Ala Thr Glu Ala Ala Thr Asn Met Asn Ala
1 5 10

<210> SEQ ID NO 28
<211> LENGTH: 12

<212> TYPE: PRT
<213> ORGANISM: Plasmodium vivax

<400> SEQUENCE: 28

Ala Thr Arg Phe Lys Lys Asn Arg Lys Lys Arg Gly
1 5 10

<210> SEQ ID NO 29
<211> LENGTH: 14
<212> TYPE: PRT
<213> ORGANISM: Plasmodium vivax

<400> SEQUENCE: 29

Ala Val Lys Lys Gln Lys Lys Thr Leu Lys Pro Val Thr Lys
1 5 10

<210> SEQ ID NO 30
<211> LENGTH: 9
<212> TYPE: PRT
<213> ORGANISM: Plasmodium vivax

<400> SEQUENCE: 30

Ala Val Lys Lys Val Gly Lys Ile Val
1 5

<210> SEQ ID NO 31
<211> LENGTH: 10
<212> TYPE: PRT
<213> ORGANISM: Plasmodium vivax

<400> SEQUENCE: 31

Ala Val Lys Lys Val Gly Lys Ile Val Lys
1 5 10

<210> SEQ ID NO 32
<211> LENGTH: 11
<212> TYPE: PRT
<213> ORGANISM: Plasmodium vivax

<400> SEQUENCE: 32

Ala Val Lys Lys Val Gly Lys Ile Val Lys Lys
1 5 10

<210> SEQ ID NO 33
<211> LENGTH: 13
<212> TYPE: PRT
<213> ORGANISM: Plasmodium vivax

<400> SEQUENCE: 33

Ala Val Lys Lys Val Gly Lys Ile Val Lys Lys Arg Thr
1 5 10

<210> SEQ ID NO 34
<211> LENGTH: 14
<212> TYPE: PRT
<213> ORGANISM: Plasmodium vivax

<400> SEQUENCE: 34

Ala Val Lys Lys Val Gly Lys Ile Val Lys Lys Arg Thr Lys
1 5 10

<210> SEQ ID NO 35
<211> LENGTH: 10
<212> TYPE: PRT
<213> ORGANISM: Plasmodium vivax

<400> SEQUENCE: 35

Ala Val Pro Ser Ser Val Ala Ser His Gly
1 5 10

<210> SEQ ID NO 36
<211> LENGTH: 10
<212> TYPE: PRT
<213> ORGANISM: Plasmodium vivax

<400> SEQUENCE: 36

Ala Val Ser Ala Lys Asn Pro Ala Lys Lys
1 5 10

<210> SEQ ID NO 37
<211> LENGTH: 10
<212> TYPE: PRT
<213> ORGANISM: Plasmodium vivax

<400> SEQUENCE: 37

Cys Pro Thr Gln Arg Tyr Asn Phe Arg Ser
1 5 10

<210> SEQ ID NO 38
<211> LENGTH: 13
<212> TYPE: PRT
<213> ORGANISM: Plasmodium vivax

<400> SEQUENCE: 38

Asp Ala Asn Lys Ala Leu Leu Pro Thr Ala Gly Asp Asp
1 5 10

<210> SEQ ID NO 39
<211> LENGTH: 8
<212> TYPE: PRT
<213> ORGANISM: Plasmodium vivax

<400> SEQUENCE: 39

Asp Glu Ile Glu Arg Val Ala Lys
1 5

<210> SEQ ID NO 40
<211> LENGTH: 9
<212> TYPE: PRT
<213> ORGANISM: Plasmodium vivax

<400> SEQUENCE: 40

Asp Gly Asp His Ser Asp Tyr Asn Thr
1 5

<210> SEQ ID NO 41
<211> LENGTH: 12
<212> TYPE: PRT
<213> ORGANISM: Plasmodium vivax

<400> SEQUENCE: 41

Asp Gly Asn Gly Lys Lys Phe Asn Lys Lys Pro Phe
1 5 10

<210> SEQ ID NO 42
<211> LENGTH: 12
<212> TYPE: PRT
<213> ORGANISM: Plasmodium vivax

<400> SEQUENCE: 42

Asp Gly Arg Phe Asn Ile Leu Ile Val Val Lys Asp
1 5 10

<210> SEQ ID NO 43
<211> LENGTH: 10
<212> TYPE: PRT
<213> ORGANISM: Plasmodium vivax

<400> SEQUENCE: 43

Asp Ile Val Tyr Ser Leu Lys Arg Gln Gly
1 5 10

<210> SEQ ID NO 44
<211> LENGTH: 8
<212> TYPE: PRT
<213> ORGANISM: Plasmodium vivax

<400> SEQUENCE: 44

Asp Lys Glu Lys Lys Gln Leu Tyr
1 5

<210> SEQ ID NO 45
<211> LENGTH: 8
<212> TYPE: PRT
<213> ORGANISM: Plasmodium vivax

<400> SEQUENCE: 45

Asp Lys Ile Arg Tyr Glu Ala Ile
1 5

<210> SEQ ID NO 46
<211> LENGTH: 14
<212> TYPE: PRT
<213> ORGANISM: Plasmodium vivax

<400> SEQUENCE: 46

Asp Lys Lys Asp Asp Lys Lys Val Lys Lys Asn Ile Leu Lys
1 5 10

<210> SEQ ID NO 47
<211> LENGTH: 10
<212> TYPE: PRT
<213> ORGANISM: Plasmodium vivax

<400> SEQUENCE: 47

Asp Lys Lys Val Lys Lys Asn Ile Leu Lys
1 5 10

<210> SEQ ID NO 48
<211> LENGTH: 11
<212> TYPE: PRT
<213> ORGANISM: Plasmodium vivax

<400> SEQUENCE: 48

Asp Lys Ser Tyr Leu Ala Tyr Lys Thr Leu Arg
1 5 10

<210> SEQ ID NO 49
<211> LENGTH: 15
<212> TYPE: PRT
<213> ORGANISM: Plasmodium vivax

<400> SEQUENCE: 49

Asp Asn Lys Lys Ala Lys Lys Val Gly Asp Lys Arg Lys Gly Arg 1 5 10 15

<210> SEQ ID NO 50
<211> LENGTH: 14
<212> TYPE: PRT
<213> ORGANISM: Plasmodium vivax

<400> SEQUENCE: 50

Asp Asn Asn Glu His Val Val Gln Glu Lys Thr Val Ser Phe
1 5 10

<210> SEQ ID NO 51
<211> LENGTH: 12
<212> TYPE: PRT
<213> ORGANISM: Plasmodium vivax

<400> SEQUENCE: 51

Asp Asn Asn Glu His Val Val Gln Glu Lys Thr Val
1 5 10

<210> SEQ ID NO 52
<211> LENGTH: 14
<212> TYPE: PRT
<213> ORGANISM: Plasmodium vivax

<400> SEQUENCE: 52

Asp Asn Asn Glu His Val Val Gln Glu Lys Thr Val Ser Phe
1 5 10

<210> SEQ ID NO 53
<211> LENGTH: 15
<212> TYPE: PRT
<213> ORGANISM: Plasmodium vivax

<400> SEQUENCE: 53

Asp Ser Glu Glu Lys Glu Glu Gln Gly Gln Lys Pro Glu Lys Val
1 5 10 15

<210> SEQ ID NO 54
<211> LENGTH: 8
<212> TYPE: PRT
<213> ORGANISM: Plasmodium vivax

<400> SEQUENCE: 54

Asp Ser Pro Gly Gly Glu Ala Asn
1 5

<210> SEQ ID NO 55
<211> LENGTH: 13
<212> TYPE: PRT
<213> ORGANISM: Plasmodium vivax

<400> SEQUENCE: 55

Asp Ser Arg Ala Asn Ala Ala Leu Asp Glu Pro Val Leu
1 5 10

<210> SEQ ID NO 56
<211> LENGTH: 8
<212> TYPE: PRT
<213> ORGANISM: Plasmodium vivax

<400> SEQUENCE: 56

Glu Asp Tyr Ser Pro Arg Lys Val
1 5

<210> SEQ ID NO 57
<211> LENGTH: 10
<212> TYPE: PRT
<213> ORGANISM: Plasmodium vivax

<400> SEQUENCE: 57

Glu Asp Tyr Ser Pro Arg Lys Val Ala Phe
1               5                   10

<210> SEQ ID NO 58
<211> LENGTH: 11
<212> TYPE: PRT
<213> ORGANISM: Plasmodium vivax

<400> SEQUENCE: 58

Glu Asp Tyr Ser Pro Arg Lys Val Ala Phe Arg
1               5                   10

<210> SEQ ID NO 59
<211> LENGTH: 10
<212> TYPE: PRT
<213> ORGANISM: Plasmodium vivax

<400> SEQUENCE: 59

Glu Glu Asp Gly Tyr Pro Glu Glu Gly Tyr
1               5                   10

<210> SEQ ID NO 60
<211> LENGTH: 15
<212> TYPE: PRT
<213> ORGANISM: Plasmodium vivax

<400> SEQUENCE: 60

Glu Glu Glu Thr Phe Glu Glu Lys Lys Ser Glu Glu Lys Lys Asp
1               5                   10                  15

<210> SEQ ID NO 61
<211> LENGTH: 15
<212> TYPE: PRT
<213> ORGANISM: Plasmodium vivax

<400> SEQUENCE: 61

Glu Glu Thr Leu Gln Glu Glu Ser Asn Leu Pro Val Lys Gly Asp
1               5                   10                  15

<210> SEQ ID NO 62
<211> LENGTH: 8
<212> TYPE: PRT
<213> ORGANISM: Plasmodium vivax

<400> SEQUENCE: 62

Glu Phe Cys Phe Thr Asp Tyr Glu
1               5

<210> SEQ ID NO 63
<211> LENGTH: 8
<212> TYPE: PRT
<213> ORGANISM: Plasmodium vivax

<400> SEQUENCE: 63

Glu Ile Lys Arg Leu Glu Glu Val
1               5

<210> SEQ ID NO 64

<211> LENGTH: 12
<212> TYPE: PRT
<213> ORGANISM: Plasmodium vivax

<400> SEQUENCE: 64

Glu Lys Phe Glu Lys Ile Lys Ile Ile Asp Phe Asn
1 5 10

<210> SEQ ID NO 65
<211> LENGTH: 9
<212> TYPE: PRT
<213> ORGANISM: Plasmodium vivax

<400> SEQUENCE: 65

Glu Lys Lys Lys Lys Lys His Thr Gln
1 5

<210> SEQ ID NO 66
<211> LENGTH: 8
<212> TYPE: PRT
<213> ORGANISM: Plasmodium vivax

<400> SEQUENCE: 66

Glu Lys Leu Asn His Ala Val Phe
1 5

<210> SEQ ID NO 67
<211> LENGTH: 9
<212> TYPE: PRT
<213> ORGANISM: Plasmodium vivax

<400> SEQUENCE: 67

Glu Val Ala Ser Ile Ser Glu Lys His
1 5

<210> SEQ ID NO 68
<211> LENGTH: 13
<212> TYPE: PRT
<213> ORGANISM: Plasmodium vivax

<400> SEQUENCE: 68

Glu Val Ser Lys Ile Asp Lys Ser Tyr Leu Ala Tyr Lys
1 5 10

<210> SEQ ID NO 69
<211> LENGTH: 13
<212> TYPE: PRT
<213> ORGANISM: Plasmodium vivax

<400> SEQUENCE: 69

Phe Ala Lys Ser Lys Gln Val Asn Met Ala Lys Thr Lys
1 5 10

<210> SEQ ID NO 70
<211> LENGTH: 13
<212> TYPE: PRT
<213> ORGANISM: Plasmodium vivax

<400> SEQUENCE: 70

Phe Ala Lys Ser Lys Gln Val Asn Met Ala Lys Thr Lys
1 5 10

<210> SEQ ID NO 71
<211> LENGTH: 10
<212> TYPE: PRT

<213> ORGANISM: Plasmodium vivax

<400> SEQUENCE: 71

Phe Glu Gly Glu Asp Glu Asp Glu Gly Glu
1 5 10

<210> SEQ ID NO 72
<211> LENGTH: 8
<212> TYPE: PRT
<213> ORGANISM: Plasmodium vivax

<400> SEQUENCE: 72

Phe Gly Gly Gln Thr Lys Pro Val
1 5

<210> SEQ ID NO 73
<211> LENGTH: 14
<212> TYPE: PRT
<213> ORGANISM: Plasmodium vivax

<400> SEQUENCE: 73

Phe Lys Lys Lys Ala Lys Thr Thr Lys Lys Ile Val Leu Lys
1 5 10

<210> SEQ ID NO 74
<211> LENGTH: 8
<212> TYPE: PRT
<213> ORGANISM: Plasmodium vivax

<400> SEQUENCE: 74

Phe Thr His Cys Thr Glu His Cys
1 5

<210> SEQ ID NO 75
<211> LENGTH: 12
<212> TYPE: PRT
<213> ORGANISM: Plasmodium vivax

<400> SEQUENCE: 75

Phe Tyr Lys Arg Lys Met Asp Lys Lys Lys Arg Asn
1 5 10

<210> SEQ ID NO 76
<211> LENGTH: 10
<212> TYPE: PRT
<213> ORGANISM: Plasmodium vivax

<400> SEQUENCE: 76

Gly Ala Asp Lys Glu Lys Lys Gln Leu Tyr
1 5 10

<210> SEQ ID NO 77
<211> LENGTH: 11
<212> TYPE: PRT
<213> ORGANISM: Plasmodium vivax

<400> SEQUENCE: 77

Gly Ala Asp Lys Lys Lys Lys Gly Ala Val Tyr
1 5 10

<210> SEQ ID NO 78
<211> LENGTH: 9
<212> TYPE: PRT
<213> ORGANISM: Plasmodium vivax

<400> SEQUENCE: 78

Gly Ala Phe Gly Lys Pro Asn Gly Val
1 5

<210> SEQ ID NO 79
<211> LENGTH: 13
<212> TYPE: PRT
<213> ORGANISM: Plasmodium vivax

<400> SEQUENCE: 79

Gly Ala Ser Cys Gly Glu Ser Ala Asp Gln Ser Gly Asp
1 5 10

<210> SEQ ID NO 80
<211> LENGTH: 13
<212> TYPE: PRT
<213> ORGANISM: Plasmodium vivax

<400> SEQUENCE: 80

Gly Asp Arg Val Arg Ile Leu Met Tyr Pro Ser Asn Ile
1 5 10

<210> SEQ ID NO 81
<211> LENGTH: 9
<212> TYPE: PRT
<213> ORGANISM: Plasmodium vivax

<400> SEQUENCE: 81

Gly Asp Thr Glu Leu Ser Gly Arg Phe
1 5

<210> SEQ ID NO 82
<211> LENGTH: 10
<212> TYPE: PRT
<213> ORGANISM: Plasmodium vivax

<400> SEQUENCE: 82

Gly Asp Thr Glu Leu Ser Gly Arg Phe Leu
1 5 10

<210> SEQ ID NO 83
<211> LENGTH: 11
<212> TYPE: PRT
<213> ORGANISM: Plasmodium vivax

<400> SEQUENCE: 83

Gly Asp Thr Glu Leu Ser Gly Arg Phe Leu Ile
1 5 10

<210> SEQ ID NO 84
<211> LENGTH: 10
<212> TYPE: PRT
<213> ORGANISM: Plasmodium vivax

<400> SEQUENCE: 84

Gly Gly Gly Met Phe Asn Pro Thr Lys Val
1 5 10

<210> SEQ ID NO 85
<211> LENGTH: 9
<212> TYPE: PRT
<213> ORGANISM: Plasmodium vivax

<400> SEQUENCE: 85

Gly Ile Leu His Leu Leu His Lys His
1 5

<210> SEQ ID NO 86
<211> LENGTH: 13
<212> TYPE: PRT
<213> ORGANISM: Plasmodium vivax

<400> SEQUENCE: 86

Gly Ile Leu Lys Lys Lys Lys Glu Leu Lys Leu Lys Gln
1 5 10

<210> SEQ ID NO 87
<211> LENGTH: 15
<212> TYPE: PRT
<213> ORGANISM: Plasmodium vivax

<400> SEQUENCE: 87

Gly Ile Leu Lys Tyr Pro Leu Thr Ser Glu Lys Ala Met Lys Lys
1 5 10 15

<210> SEQ ID NO 88
<211> LENGTH: 10
<212> TYPE: PRT
<213> ORGANISM: Plasmodium vivax

<400> SEQUENCE: 88

Gly Ile Ser Arg Asp Gly Arg His Lys Leu
1 5 10

<210> SEQ ID NO 89
<211> LENGTH: 14
<212> TYPE: PRT
<213> ORGANISM: Plasmodium vivax

<400> SEQUENCE: 89

Gly Ile Ser Arg Asp Gly Arg His Lys Leu Arg Leu Thr Gly
1 5 10

<210> SEQ ID NO 90
<211> LENGTH: 15
<212> TYPE: PRT
<213> ORGANISM: Plasmodium vivax

<400> SEQUENCE: 90

Gly Ile Ser Arg Asp Gly Arg His Lys Leu Arg Leu Thr Gly Gly
1 5 10 15

<210> SEQ ID NO 91
<211> LENGTH: 10
<212> TYPE: PRT
<213> ORGANISM: Plasmodium vivax

<400> SEQUENCE: 91

Gly Lys Ala Gly Lys Gly Thr Gly Ser Phe
1 5 10

<210> SEQ ID NO 92
<211> LENGTH: 11
<212> TYPE: PRT
<213> ORGANISM: Plasmodium vivax

<400> SEQUENCE: 92

Gly Lys Ala Gly Lys Gly Thr Gly Ser Phe Gly
1 5 10

<210> SEQ ID NO 93
<211> LENGTH: 12
<212> TYPE: PRT
<213> ORGANISM: Plasmodium vivax

<400> SEQUENCE: 93

Gly Lys Ala Gly Lys Gly Thr Gly Ser Phe Gly Lys
1 5 10

<210> SEQ ID NO 94
<211> LENGTH: 13
<212> TYPE: PRT
<213> ORGANISM: Plasmodium vivax

<400> SEQUENCE: 94

Gly Lys Ala Gly Lys Gly Thr Gly Ser Phe Gly Lys Arg
1 5 10

<210> SEQ ID NO 95
<211> LENGTH: 14
<212> TYPE: PRT
<213> ORGANISM: Plasmodium vivax

<400> SEQUENCE: 95

Gly Lys Ala Gly Lys Gly Thr Gly Ser Phe Gly Lys Arg Asn
1 5 10

<210> SEQ ID NO 96
<211> LENGTH: 15
<212> TYPE: PRT
<213> ORGANISM: Plasmodium vivax

<400> SEQUENCE: 96

Gly Lys Ala Gly Lys Gly Thr Gly Ser Phe Gly Lys Arg Asn Gly
1 5 10 15

<210> SEQ ID NO 97
<211> LENGTH: 9
<212> TYPE: PRT
<213> ORGANISM: Plasmodium vivax

<400> SEQUENCE: 97

Gly Lys Gly Lys Asn Lys Glu Lys Leu
1 5

<210> SEQ ID NO 98
<211> LENGTH: 12
<212> TYPE: PRT
<213> ORGANISM: Plasmodium vivax

<400> SEQUENCE: 98

Gly Lys Gly Lys Asn Lys Glu Lys Leu Asn His Ala
1 5 10

<210> SEQ ID NO 99
<211> LENGTH: 13
<212> TYPE: PRT
<213> ORGANISM: Plasmodium vivax

<400> SEQUENCE: 99

Gly Lys Gly Lys Asn Lys Glu Lys Leu Asn His Ala Val
1 5 10

<210> SEQ ID NO 100
<211> LENGTH: 14
<212> TYPE: PRT
<213> ORGANISM: Plasmodium vivax

<400> SEQUENCE: 100

Gly Lys Gly Lys Asn Lys Glu Lys Leu Asn His Ala Val Phe
1               5                   10

<210> SEQ ID NO 101
<211> LENGTH: 15
<212> TYPE: PRT
<213> ORGANISM: Plasmodium vivax

<400> SEQUENCE: 101

Gly Lys Gly Lys Asn Lys Glu Lys Leu Asn His Ala Val Phe Ile
1               5                   10                  15

<210> SEQ ID NO 102
<211> LENGTH: 11
<212> TYPE: PRT
<213> ORGANISM: Plasmodium vivax

<400> SEQUENCE: 102

Gly Lys Lys Lys Gly Ala Asp Lys Glu Lys Lys
1               5                   10

<210> SEQ ID NO 103
<211> LENGTH: 14
<212> TYPE: PRT
<213> ORGANISM: Plasmodium vivax

<400> SEQUENCE: 103

Gly Lys Lys Lys Gly Ala Asp Lys Glu Lys Lys Gln Leu Tyr
1               5                   10

<210> SEQ ID NO 104
<211> LENGTH: 11
<212> TYPE: PRT
<213> ORGANISM: Plasmodium vivax

<400> SEQUENCE: 104

Gly Lys Leu Leu Lys Pro Gly Lys Val Val Ile
1               5                   10

<210> SEQ ID NO 105
<211> LENGTH: 12
<212> TYPE: PRT
<213> ORGANISM: Plasmodium vivax

<400> SEQUENCE: 105

Gly Lys Asn Lys Glu Lys Leu Asn His Ala Val Phe
1               5                   10

<210> SEQ ID NO 106
<211> LENGTH: 8
<212> TYPE: PRT
<213> ORGANISM: Plasmodium vivax

<400> SEQUENCE: 106

Gly Lys Val His Gly Ser Leu Ala
1               5

<210> SEQ ID NO 107
<211> LENGTH: 9

<212> TYPE: PRT
<213> ORGANISM: Plasmodium vivax

<400> SEQUENCE: 107

Gly Lys Val His Gly Ser Leu Ala Arg
1               5

<210> SEQ ID NO 108
<211> LENGTH: 10
<212> TYPE: PRT
<213> ORGANISM: Plasmodium vivax

<400> SEQUENCE: 108

Gly Lys Val His Gly Ser Leu Ala Arg Ala
1               5                   10

<210> SEQ ID NO 109
<211> LENGTH: 11
<212> TYPE: PRT
<213> ORGANISM: Plasmodium vivax

<400> SEQUENCE: 109

Gly Lys Val His Gly Ser Leu Ala Arg Ala Gly
1               5                   10

<210> SEQ ID NO 110
<211> LENGTH: 12
<212> TYPE: PRT
<213> ORGANISM: Plasmodium vivax

<400> SEQUENCE: 110

Gly Lys Val His Gly Ser Leu Ala Arg Ala Gly Lys
1               5                   10

<210> SEQ ID NO 111
<211> LENGTH: 14
<212> TYPE: PRT
<213> ORGANISM: Plasmodium vivax

<400> SEQUENCE: 111

Gly Lys Val His Gly Ser Leu Ala Arg Ala Gly Lys Val Lys
1               5                   10

<210> SEQ ID NO 112
<211> LENGTH: 8
<212> TYPE: PRT
<213> ORGANISM: Plasmodium vivax

<400> SEQUENCE: 112

Gly Leu Asp Pro Lys Phe Phe Lys
1               5

<210> SEQ ID NO 113
<211> LENGTH: 10
<212> TYPE: PRT
<213> ORGANISM: Plasmodium vivax

<400> SEQUENCE: 113

Gly Leu Leu Arg Gly Ala Lys Lys Thr Lys
1               5                   10

<210> SEQ ID NO 114
<211> LENGTH: 14
<212> TYPE: PRT
<213> ORGANISM: Plasmodium vivax

<400> SEQUENCE: 114

Gly Leu Asn Gln Lys Gln Pro Thr Lys Gly Ser Asn Ile Gln
1 5 10

<210> SEQ ID NO 115
<211> LENGTH: 8
<212> TYPE: PRT
<213> ORGANISM: Plasmodium vivax

<400> SEQUENCE: 115

Gly Leu Arg Leu Lys Glu Lys Asp
1 5

<210> SEQ ID NO 116
<211> LENGTH: 12
<212> TYPE: PRT
<213> ORGANISM: Plasmodium vivax

<400> SEQUENCE: 116

Gly Leu Thr Val Glu Asp Ile Arg Asn Arg Lys Ala
1 5 10

<210> SEQ ID NO 117
<211> LENGTH: 13
<212> TYPE: PRT
<213> ORGANISM: Plasmodium vivax

<400> SEQUENCE: 117

Gly Asn Ala Lys Gly Lys Lys Pro Ala Lys Lys Val Ile
1 5 10

<210> SEQ ID NO 118
<211> LENGTH: 11
<212> TYPE: PRT
<213> ORGANISM: Plasmodium vivax

<400> SEQUENCE: 118

Gly Asn Gly Lys Lys Phe Asn Lys Lys Pro Phe
1 5 10

<210> SEQ ID NO 119
<211> LENGTH: 9
<212> TYPE: PRT
<213> ORGANISM: Plasmodium vivax

<400> SEQUENCE: 119

Gly Pro Lys Arg Ala Thr Lys Ile Arg
1 5

<210> SEQ ID NO 120
<211> LENGTH: 10
<212> TYPE: PRT
<213> ORGANISM: Plasmodium vivax

<400> SEQUENCE: 120

Gly Pro Lys Arg Ala Thr Lys Ile Arg Lys
1 5 10

<210> SEQ ID NO 121
<211> LENGTH: 8
<212> TYPE: PRT
<213> ORGANISM: Plasmodium vivax

<400> SEQUENCE: 121

Gly Pro Val Arg Gly Ile Ser Leu
1 5

<210> SEQ ID NO 122
<211> LENGTH: 15
<212> TYPE: PRT
<213> ORGANISM: Plasmodium vivax

<400> SEQUENCE: 122

Gly Gln Thr Lys Pro Val Phe Lys Lys Lys Ala Lys Thr Thr Lys
1 5 10 15

<210> SEQ ID NO 123
<211> LENGTH: 14
<212> TYPE: PRT
<213> ORGANISM: Plasmodium vivax

<400> SEQUENCE: 123

Gly Arg Glu Thr Pro Ala Lys Gly Gly Gly His Asn Val Ile
1 5 10

<210> SEQ ID NO 124
<211> LENGTH: 13
<212> TYPE: PRT
<213> ORGANISM: Plasmodium vivax

<400> SEQUENCE: 124

Gly Arg Ile Gly Arg Tyr Leu Lys Lys Gly Lys Tyr Ala
1 5 10

<210> SEQ ID NO 125
<211> LENGTH: 14
<212> TYPE: PRT
<213> ORGANISM: Plasmodium vivax

<400> SEQUENCE: 125

Gly Arg Ile Gly Arg Tyr Leu Lys Lys Gly Lys Tyr Ala Lys
1 5 10

<210> SEQ ID NO 126
<211> LENGTH: 9
<212> TYPE: PRT
<213> ORGANISM: Plasmodium vivax

<400> SEQUENCE: 126

Gly Arg Lys Ser Thr Ile Lys Pro Ala
1 5

<210> SEQ ID NO 127
<211> LENGTH: 14
<212> TYPE: PRT
<213> ORGANISM: Plasmodium vivax

<400> SEQUENCE: 127

Gly Arg Lys Ser Thr Ile Lys Pro Ala Thr Gly Ile Ala Val
1 5 10

<210> SEQ ID NO 128
<211> LENGTH: 8
<212> TYPE: PRT
<213> ORGANISM: Plasmodium vivax

<400> SEQUENCE: 128

Gly Ser Ala Glu Asp Asp Leu Lys 1 5

<210> SEQ ID NO 129
<211> LENGTH: 8
<212> TYPE: PRT
<213> ORGANISM: Plasmodium vivax

<400> SEQUENCE: 129

Gly Ser Gly Lys Pro Ser Gly Leu
1 5

<210> SEQ ID NO 130
<211> LENGTH: 8
<212> TYPE: PRT
<213> ORGANISM: Plasmodium vivax

<400> SEQUENCE: 130

Gly Ser Lys Gln Val His Val Val
1 5

<210> SEQ ID NO 131
<211> LENGTH: 12
<212> TYPE: PRT
<213> ORGANISM: Plasmodium vivax

<400> SEQUENCE: 131

Gly Thr Gly Arg Lys Lys Gly Pro Asn Ser Lys Leu
1 5 10

<210> SEQ ID NO 132
<211> LENGTH: 10
<212> TYPE: PRT
<213> ORGANISM: Plasmodium vivax

<400> SEQUENCE: 132

Gly Thr Pro Ile Glu Lys Leu His Pro Ile
1 5 10

<210> SEQ ID NO 133
<211> LENGTH: 8
<212> TYPE: PRT
<213> ORGANISM: Plasmodium vivax

<400> SEQUENCE: 133

Gly Val Lys Lys Asp Val Ala Lys
1 5

<210> SEQ ID NO 134
<211> LENGTH: 10
<212> TYPE: PRT
<213> ORGANISM: Plasmodium vivax

<400> SEQUENCE: 134

Gly Tyr Pro Ser Ala Lys Lys Arg Arg Phe
1 5 10

<210> SEQ ID NO 135
<211> LENGTH: 11
<212> TYPE: PRT
<213> ORGANISM: Plasmodium vivax

<400> SEQUENCE: 135

His Gly Ala Ser Arg Tyr Lys Lys Ser Arg Ala
1 5 10

<210> SEQ ID NO 136
<211> LENGTH: 9
<212> TYPE: PRT
<213> ORGANISM: Plasmodium vivax

<400> SEQUENCE: 136

His Gly Lys Pro Lys His Gln Gly Val
1               5

<210> SEQ ID NO 137
<211> LENGTH: 8
<212> TYPE: PRT
<213> ORGANISM: Plasmodium vivax

<400> SEQUENCE: 137

His His Lys Tyr Arg Val Lys Arg
1               5

<210> SEQ ID NO 138
<211> LENGTH: 15
<212> TYPE: PRT
<213> ORGANISM: Plasmodium vivax

<400> SEQUENCE: 138

His Leu Pro Thr Leu Lys Lys Glu Tyr Arg Arg Lys Tyr Ala Ala
1               5                   10                  15

<210> SEQ ID NO 139
<211> LENGTH: 9
<212> TYPE: PRT
<213> ORGANISM: Plasmodium vivax

<400> SEQUENCE: 139

His Leu Ser Ala Lys Ser Arg Pro Ser
1               5

<210> SEQ ID NO 140
<211> LENGTH: 11
<212> TYPE: PRT
<213> ORGANISM: Plasmodium vivax

<400> SEQUENCE: 140

His Leu Ser Ala Lys Ser Arg Pro Ser Ile Arg
1               5                   10

<210> SEQ ID NO 141
<211> LENGTH: 11
<212> TYPE: PRT
<213> ORGANISM: Plasmodium vivax

<400> SEQUENCE: 141

His Pro Gly His Gln Tyr Pro Asn Ala Leu Gly
1               5                   10

<210> SEQ ID NO 142
<211> LENGTH: 10
<212> TYPE: PRT
<213> ORGANISM: Plasmodium vivax

<400> SEQUENCE: 142

His Gln Leu Val Glu Asn Ala Asp Glu Val
1               5                   10

<210> SEQ ID NO 143

<211> LENGTH: 12
<212> TYPE: PRT
<213> ORGANISM: Plasmodium vivax

<400> SEQUENCE: 143

His Ser Asn Met His Cys Ser Pro Tyr Ser Gly Cys
1 5 10

<210> SEQ ID NO 144
<211> LENGTH: 8
<212> TYPE: PRT
<213> ORGANISM: Plasmodium vivax

<400> SEQUENCE: 144

Ile Asp Glu His Ala His Leu Val
1 5

<210> SEQ ID NO 145
<211> LENGTH: 14
<212> TYPE: PRT
<213> ORGANISM: Plasmodium vivax

<400> SEQUENCE: 145

Ile Glu Lys Phe Glu Lys Glu Ser Ala Glu Met Gly Lys Gly
1 5 10

<210> SEQ ID NO 146
<211> LENGTH: 10
<212> TYPE: PRT
<213> ORGANISM: Plasmodium vivax

<400> SEQUENCE: 146

Ile Gly Arg Phe Phe Ser Phe Leu Val Arg
1 5 10

<210> SEQ ID NO 147
<211> LENGTH: 11
<212> TYPE: PRT
<213> ORGANISM: Plasmodium vivax

<400> SEQUENCE: 147

Ile Gly Tyr Gly Ser Asn Lys Lys Thr Lys Phe
1 5 10

<210> SEQ ID NO 148
<211> LENGTH: 9
<212> TYPE: PRT
<213> ORGANISM: Plasmodium vivax

<400> SEQUENCE: 148

Ile His Lys Ile Lys Lys Val Val Arg
1 5

<210> SEQ ID NO 149
<211> LENGTH: 9
<212> TYPE: PRT
<213> ORGANISM: Plasmodium vivax

<400> SEQUENCE: 149

Ile Lys Lys Glu Arg Lys Lys Gly Ile
1 5

<210> SEQ ID NO 150
<211> LENGTH: 8
<212> TYPE: PRT

<213> ORGANISM: Plasmodium vivax

<400> SEQUENCE: 150

Ile Lys Ser Lys Thr His Ser Ile
1 5

<210> SEQ ID NO 151
<211> LENGTH: 10
<212> TYPE: PRT
<213> ORGANISM: Plasmodium vivax

<400> SEQUENCE: 151

Ile Leu Lys Tyr Pro Leu Thr Ser Glu Lys
1 5 10

<210> SEQ ID NO 152
<211> LENGTH: 15
<212> TYPE: PRT
<213> ORGANISM: Plasmodium vivax

<400> SEQUENCE: 152

Ile Ser Lys Gln Asn Phe Ala Lys Asn Lys Lys Lys Ala Ala Asn
1 5 10 15

<210> SEQ ID NO 153
<211> LENGTH: 8
<212> TYPE: PRT
<213> ORGANISM: Plasmodium vivax

<400> SEQUENCE: 153

Lys Ala Phe Ile Pro Cys Leu Lys
1 5

<210> SEQ ID NO 154
<211> LENGTH: 11
<212> TYPE: PRT
<213> ORGANISM: Plasmodium vivax

<400> SEQUENCE: 154

Lys Ala Lys Gly Ala Lys Asn Glu Met Val Lys
1 5 10

<210> SEQ ID NO 155
<211> LENGTH: 10
<212> TYPE: PRT
<213> ORGANISM: Plasmodium vivax

<400> SEQUENCE: 155

Lys Ala Leu Leu Pro Thr Ala Gly Asp Asp
1 5 10

<210> SEQ ID NO 156
<211> LENGTH: 9
<212> TYPE: PRT
<213> ORGANISM: Plasmodium vivax

<400> SEQUENCE: 156

Lys Ala Asn Gly Asp Ser Ala Asn Lys
1 5

<210> SEQ ID NO 157
<211> LENGTH: 14
<212> TYPE: PRT
<213> ORGANISM: Plasmodium vivax

<400> SEQUENCE: 157

Lys Ala Pro Arg Lys Gln Leu Ala Ser Lys Ala Ala Arg Lys
1 5 10

<210> SEQ ID NO 158
<211> LENGTH: 12
<212> TYPE: PRT
<213> ORGANISM: Plasmodium vivax

<400> SEQUENCE: 158

Lys Asp Ala Gly Lys Lys Asp Ala Gly Lys Lys Asp
1 5 10

<210> SEQ ID NO 159
<211> LENGTH: 9
<212> TYPE: PRT
<213> ORGANISM: Plasmodium vivax

<400> SEQUENCE: 159

Lys Asp Ala Pro Pro Pro Tyr Glu Thr
1 5

<210> SEQ ID NO 160
<211> LENGTH: 9
<212> TYPE: PRT
<213> ORGANISM: Plasmodium vivax

<400> SEQUENCE: 160

Lys Asp Phe Ala Lys Ser Lys Gln Val
1 5

<210> SEQ ID NO 161
<211> LENGTH: 12
<212> TYPE: PRT
<213> ORGANISM: Plasmodium vivax

<400> SEQUENCE: 161

Lys Asp Gly Val Lys Lys Asp Val Ala Lys Lys Asp
1 5 10

<210> SEQ ID NO 162
<211> LENGTH: 13
<212> TYPE: PRT
<213> ORGANISM: Plasmodium vivax

<400> SEQUENCE: 162

Lys Asp Ile Lys Lys Glu Arg Lys Lys Gly Ile Arg Ser
1 5 10

<210> SEQ ID NO 163
<211> LENGTH: 9
<212> TYPE: PRT
<213> ORGANISM: Plasmodium vivax

<400> SEQUENCE: 163

Lys Asp Ile Asn Thr Ile Ile Glu Ser
1 5

<210> SEQ ID NO 164
<211> LENGTH: 9
<212> TYPE: PRT
<213> ORGANISM: Plasmodium vivax

<400> SEQUENCE: 164

Lys Asp Lys Ala Gly Cys Gln Asn Lys
1 5

<210> SEQ ID NO 165
<211> LENGTH: 12
<212> TYPE: PRT
<213> ORGANISM: Plasmodium vivax

<400> SEQUENCE: 165

Lys Asp Ser Gln Lys Lys Gly Gly Lys Lys Lys Asp
1 5 10

<210> SEQ ID NO 166
<211> LENGTH: 14
<212> TYPE: PRT
<213> ORGANISM: Plasmodium vivax

<400> SEQUENCE: 166

Lys Asp Ser Gln Lys Lys Gly Gly Lys Lys Lys Asp Lys Lys
1 5 10

<210> SEQ ID NO 167
<211> LENGTH: 12
<212> TYPE: PRT
<213> ORGANISM: Plasmodium vivax

<400> SEQUENCE: 167

Lys Asp Val Ala Lys Lys Asp Ala Gly Lys Lys Asp
1 5 10

<210> SEQ ID NO 168
<211> LENGTH: 10
<212> TYPE: PRT
<213> ORGANISM: Plasmodium vivax

<400> SEQUENCE: 168

Lys Asp Tyr Ser Asp Asn Tyr Cys Glu Lys
1 5 10

<210> SEQ ID NO 169
<211> LENGTH: 11
<212> TYPE: PRT
<213> ORGANISM: Plasmodium vivax

<400> SEQUENCE: 169

Lys Glu Asp Ala Lys Gly Gly Lys Lys Lys Lys
1 5 10

<210> SEQ ID NO 170
<211> LENGTH: 12
<212> TYPE: PRT
<213> ORGANISM: Plasmodium vivax

<400> SEQUENCE: 170

Lys Glu Gly Leu Ile Leu Lys Lys Pro Gln Lys Val
1 5 10

<210> SEQ ID NO 171
<211> LENGTH: 12
<212> TYPE: PRT
<213> ORGANISM: Plasmodium vivax

<400> SEQUENCE: 171

Lys Glu Lys Lys Gln Leu Tyr Lys Gly Lys Val Lys
1 5 10

<210> SEQ ID NO 172
<211> LENGTH: 9
<212> TYPE: PRT
<213> ORGANISM: Plasmodium vivax

<400> SEQUENCE: 172

Lys Glu Lys Leu Asn His Ala Val Phe
1 5

<210> SEQ ID NO 173
<211> LENGTH: 8
<212> TYPE: PRT
<213> ORGANISM: Plasmodium vivax

<400> SEQUENCE: 173

Lys Glu Pro Ile Phe Ser Asn Thr
1 5

<210> SEQ ID NO 174
<211> LENGTH: 9
<212> TYPE: PRT
<213> ORGANISM: Plasmodium vivax

<400> SEQUENCE: 174

Lys Glu Pro Leu Leu Gly Gly Leu Asn
1 5

<210> SEQ ID NO 175
<211> LENGTH: 14
<212> TYPE: PRT
<213> ORGANISM: Plasmodium vivax

<400> SEQUENCE: 175

Lys Glu Pro Leu Leu Gly Gly Leu Asn Gln Lys Gln Pro Thr
1 5 10

<210> SEQ ID NO 176
<211> LENGTH: 15
<212> TYPE: PRT
<213> ORGANISM: Plasmodium vivax

<400> SEQUENCE: 176

Lys Glu Pro Leu Leu Gly Gly Leu Asn Gln Lys Gln Pro Thr Lys
1 5 10 15

<210> SEQ ID NO 177
<211> LENGTH: 10
<212> TYPE: PRT
<213> ORGANISM: Plasmodium vivax

<400> SEQUENCE: 177

Lys Phe Phe Arg Arg Arg Gly Glu Ala Thr
1 5 10

<210> SEQ ID NO 178
<211> LENGTH: 9
<212> TYPE: PRT
<213> ORGANISM: Plasmodium vivax

<400> SEQUENCE: 178

Lys Gly Ala Ala Pro Lys Lys Gly Ala
1 5

<210> SEQ ID NO 179
<211> LENGTH: 11
<212> TYPE: PRT
<213> ORGANISM: Plasmodium vivax

<400> SEQUENCE: 179

Lys Gly Ala Asp Lys Glu Lys Lys Gln Leu Tyr
1               5                   10

<210> SEQ ID NO 180
<211> LENGTH: 12
<212> TYPE: PRT
<213> ORGANISM: Plasmodium vivax

<400> SEQUENCE: 180

Lys Gly Ala Glu Gln Asn Gly Arg Glu Pro Asn Gly
1               5                   10

<210> SEQ ID NO 181
<211> LENGTH: 11
<212> TYPE: PRT
<213> ORGANISM: Plasmodium vivax

<400> SEQUENCE: 181

Lys Gly Gly Ser Gly Gly Gly Asn Ile Lys Lys
1               5                   10

<210> SEQ ID NO 182
<211> LENGTH: 8
<212> TYPE: PRT
<213> ORGANISM: Plasmodium vivax

<400> SEQUENCE: 182

Lys Gly Lys Asp Thr Cys Cys Cys
1               5

<210> SEQ ID NO 183
<211> LENGTH: 8
<212> TYPE: PRT
<213> ORGANISM: Plasmodium vivax

<400> SEQUENCE: 183

Lys Gly Lys Lys Asn Ala Thr Thr
1               5

<210> SEQ ID NO 184
<211> LENGTH: 10
<212> TYPE: PRT
<213> ORGANISM: Plasmodium vivax

<400> SEQUENCE: 184

Lys Gly Lys Lys Pro Ala Lys Lys Val Ile
1               5                   10

<210> SEQ ID NO 185
<211> LENGTH: 8
<212> TYPE: PRT
<213> ORGANISM: Plasmodium vivax

<400> SEQUENCE: 185

Lys Gly Lys Asn Lys Glu Lys Leu
1               5

<210> SEQ ID NO 186
<211> LENGTH: 12

<212> TYPE: PRT
<213> ORGANISM: Plasmodium vivax

<400> SEQUENCE: 186

Lys Gly Lys Asn Lys Glu Lys Leu Asn His Ala Val
1 5 10

<210> SEQ ID NO 187
<211> LENGTH: 13
<212> TYPE: PRT
<213> ORGANISM: Plasmodium vivax

<400> SEQUENCE: 187

Lys Gly Lys Asn Lys Glu Lys Leu Asn His Ala Val Phe
1 5 10

<210> SEQ ID NO 188
<211> LENGTH: 13
<212> TYPE: PRT
<213> ORGANISM: Plasmodium vivax

<400> SEQUENCE: 188

Lys Gly Lys Ser Ser Arg Ser Gly Arg Ser Ala Arg Ser
1 5 10

<210> SEQ ID NO 189
<211> LENGTH: 15
<212> TYPE: PRT
<213> ORGANISM: Plasmodium vivax

<400> SEQUENCE: 189

Lys Gly Lys Val Lys Lys Ser Leu Gly Lys Gln Val Gly Gly Lys
1 5 10 15

<210> SEQ ID NO 190
<211> LENGTH: 13
<212> TYPE: PRT
<213> ORGANISM: Plasmodium vivax

<400> SEQUENCE: 190

Lys His Glu Lys Pro Lys Lys Leu Asn Ala Lys Leu Arg
1 5 10

<210> SEQ ID NO 191
<211> LENGTH: 14
<212> TYPE: PRT
<213> ORGANISM: Plasmodium vivax

<400> SEQUENCE: 191

Lys His Glu Lys Pro Lys Lys Leu Asn Ala Lys Leu Arg Lys
1 5 10

<210> SEQ ID NO 192
<211> LENGTH: 8
<212> TYPE: PRT
<213> ORGANISM: Plasmodium vivax

<400> SEQUENCE: 192

Lys His Ile Lys Lys Thr Lys Met
1 5

<210> SEQ ID NO 193
<211> LENGTH: 10
<212> TYPE: PRT
<213> ORGANISM: Plasmodium vivax

<400> SEQUENCE: 193

Lys Ile Phe Asp Glu Ile Ile Val Asn Ala
1 5 10

<210> SEQ ID NO 194
<211> LENGTH: 13
<212> TYPE: PRT
<213> ORGANISM: Plasmodium vivax

<400> SEQUENCE: 194

Lys Ile Arg Asp Glu Ile Lys Arg Thr Phe Cys Gln Arg
1 5 10

<210> SEQ ID NO 195
<211> LENGTH: 11
<212> TYPE: PRT
<213> ORGANISM: Plasmodium vivax

<400> SEQUENCE: 195

Lys Lys Ala Ala Pro Lys Lys Val Ala Ala Pro
1 5 10

<210> SEQ ID NO 196
<211> LENGTH: 9
<212> TYPE: PRT
<213> ORGANISM: Plasmodium vivax

<400> SEQUENCE: 196

Lys Lys Gly Ala Asp Lys Glu Lys Lys
1 5

<210> SEQ ID NO 197
<211> LENGTH: 13
<212> TYPE: PRT
<213> ORGANISM: Plasmodium vivax

<400> SEQUENCE: 197

Lys Lys Ala Ala Ala Arg Lys Lys Pro Ala Thr Pro Lys
1 5 10

<210> SEQ ID NO 198
<211> LENGTH: 15
<212> TYPE: PRT
<213> ORGANISM: Plasmodium vivax

<400> SEQUENCE: 198

Lys Lys Ala Ala Gln Lys Lys Pro Ala Ala Pro Glu Thr Ser Ala
1 5 10 15

<210> SEQ ID NO 199
<211> LENGTH: 10
<212> TYPE: PRT
<213> ORGANISM: Plasmodium vivax

<400> SEQUENCE: 199

Lys Lys Ala Asp Lys Lys Asp Glu Lys Lys
1 5 10

<210> SEQ ID NO 200
<211> LENGTH: 8
<212> TYPE: PRT
<213> ORGANISM: Plasmodium vivax

<400> SEQUENCE: 200

Lys Lys Ala Pro Ala Lys Pro Gln
1 5

<210> SEQ ID NO 201
<211> LENGTH: 14
<212> TYPE: PRT
<213> ORGANISM: Plasmodium vivax

<400> SEQUENCE: 201

Lys Lys Ala Pro Asn Thr Thr Lys Pro Lys Glu Asp Thr Lys
1 5 10

<210> SEQ ID NO 202
<211> LENGTH: 13
<212> TYPE: PRT
<213> ORGANISM: Plasmodium vivax

<400> SEQUENCE: 202

Lys Lys Asp Ala Gly Lys Lys Asp Ala Gly Lys Lys Asp
1 5 10

<210> SEQ ID NO 203
<211> LENGTH: 8
<212> TYPE: PRT
<213> ORGANISM: Plasmodium vivax

<400> SEQUENCE: 203

Lys Lys Asp Asp Lys Thr Lys Lys
1 5

<210> SEQ ID NO 204
<211> LENGTH: 13
<212> TYPE: PRT
<213> ORGANISM: Plasmodium vivax

<400> SEQUENCE: 204

Lys Lys Asp Asp Lys Lys Val Lys Lys Asn Ile Leu Lys
1 5 10

<210> SEQ ID NO 205
<211> LENGTH: 14
<212> TYPE: PRT
<213> ORGANISM: Plasmodium vivax

<400> SEQUENCE: 205

Lys Lys Asp Ile Lys Lys Glu Arg Lys Lys Gly Ile Arg Ser
1 5 10

<210> SEQ ID NO 206
<211> LENGTH: 14
<212> TYPE: PRT
<213> ORGANISM: Plasmodium vivax

<400> SEQUENCE: 206

Lys Lys Glu Lys Ala Lys Ser Glu Lys Ala Val Ile Lys Lys
1 5 10

<210> SEQ ID NO 207
<211> LENGTH: 14
<212> TYPE: PRT
<213> ORGANISM: Plasmodium vivax

<400> SEQUENCE: 207

Lys Lys Glu Leu Lys Leu Lys Gln Lys Gln Glu Lys Lys Asn 1 5 10

<210> SEQ ID NO 208
<211> LENGTH: 8
<212> TYPE: PRT
<213> ORGANISM: Plasmodium vivax

<400> SEQUENCE: 208

Lys Lys Gly Ile Arg Ser Asn Pro
1 5

<210> SEQ ID NO 209
<211> LENGTH: 8
<212> TYPE: PRT
<213> ORGANISM: Plasmodium vivax

<400> SEQUENCE: 209

Lys Lys Gly Pro Asn Ser Lys Leu
1 5

<210> SEQ ID NO 210
<211> LENGTH: 13
<212> TYPE: PRT
<213> ORGANISM: Plasmodium vivax

<400> SEQUENCE: 210

Lys Lys Ile Asp Lys Lys Lys Glu Gln Leu Ser Lys Lys
1 5 10

<210> SEQ ID NO 211
<211> LENGTH: 10
<212> TYPE: PRT
<213> ORGANISM: Plasmodium vivax

<400> SEQUENCE: 211

Lys Lys Ile Gly Lys Ser Lys Gln Ile Asp
1 5 10

<210> SEQ ID NO 212
<211> LENGTH: 13
<212> TYPE: PRT
<213> ORGANISM: Plasmodium vivax

<400> SEQUENCE: 212

Lys Lys Lys Ala Lys Thr Thr Lys Lys Ile Val Leu Lys
1 5 10

<210> SEQ ID NO 213
<211> LENGTH: 15
<212> TYPE: PRT
<213> ORGANISM: Plasmodium vivax

<400> SEQUENCE: 213

Lys Lys Lys Glu Leu Lys Leu Lys Gln Lys Gln Glu Lys Lys Asn
1 5 10 15

<210> SEQ ID NO 214
<211> LENGTH: 10
<212> TYPE: PRT
<213> ORGANISM: Plasmodium vivax

<400> SEQUENCE: 214

Lys Lys Lys Gly Ala Asp Lys Glu Lys Lys
1 5 10

<210> SEQ ID NO 215
<211> LENGTH: 13
<212> TYPE: PRT
<213> ORGANISM: Plasmodium vivax

<400> SEQUENCE: 215

Lys Lys Lys Gly Ala Asp Lys Glu Lys Lys Gln Leu Tyr
1 5 10

<210> SEQ ID NO 216
<211> LENGTH: 8
<212> TYPE: PRT
<213> ORGANISM: Plasmodium vivax

<400> SEQUENCE: 216

Lys Lys Lys Lys Gly Ala Val Tyr
1 5

<210> SEQ ID NO 217
<211> LENGTH: 12
<212> TYPE: PRT
<213> ORGANISM: Plasmodium vivax

<400> SEQUENCE: 217

Lys Lys Lys Lys Trp Gly Lys Gly Lys Asn Lys Glu
1 5 10

<210> SEQ ID NO 218
<211> LENGTH: 9
<212> TYPE: PRT
<213> ORGANISM: Plasmodium vivax

<400> SEQUENCE: 218

Lys Lys Lys Leu Val Lys Arg Ser Thr
1 5

<210> SEQ ID NO 219
<211> LENGTH: 10
<212> TYPE: PRT
<213> ORGANISM: Plasmodium vivax

<400> SEQUENCE: 219

Lys Lys Lys Val Ile Lys Glu Tyr Lys Lys
1 5 10

<210> SEQ ID NO 220
<211> LENGTH: 14
<212> TYPE: PRT
<213> ORGANISM: Plasmodium vivax

<400> SEQUENCE: 220

Lys Lys Lys Val Ile Lys Glu Tyr Lys Lys Val Leu Asn Lys
1 5 10

<210> SEQ ID NO 221
<211> LENGTH: 8
<212> TYPE: PRT
<213> ORGANISM: Plasmodium vivax

<400> SEQUENCE: 221

Lys Lys Asn Leu Lys Gly Ala Lys
1 5

<210> SEQ ID NO 222

<211> LENGTH: 13
<212> TYPE: PRT
<213> ORGANISM: Plasmodium vivax

<400> SEQUENCE: 222

Lys Lys Asn Leu Lys Gly Ala Lys Ala Glu Glu Gly Lys
1 5 10

<210> SEQ ID NO 223
<211> LENGTH: 9
<212> TYPE: PRT
<213> ORGANISM: Plasmodium vivax

<400> SEQUENCE: 223

Lys Lys Asn Ser Leu His Leu Glu Lys
1 5

<210> SEQ ID NO 224
<211> LENGTH: 13
<212> TYPE: PRT
<213> ORGANISM: Plasmodium vivax

<400> SEQUENCE: 224

Lys Lys Pro Ala Thr Pro Lys Lys Gln Ala Thr Pro Lys
1 5 10

<210> SEQ ID NO 225
<211> LENGTH: 10
<212> TYPE: PRT
<213> ORGANISM: Plasmodium vivax

<400> SEQUENCE: 225

Lys Lys Ser Asp Tyr Asp Lys Leu Asp Lys
1 5 10

<210> SEQ ID NO 226
<211> LENGTH: 10
<212> TYPE: PRT
<213> ORGANISM: Plasmodium vivax

<400> SEQUENCE: 226

Lys Lys Ser Thr Ala Lys Asp Ala Lys Lys
1 5 10

<210> SEQ ID NO 227
<211> LENGTH: 12
<212> TYPE: PRT
<213> ORGANISM: Plasmodium vivax

<400> SEQUENCE: 227

Lys Lys Val Ala Ala Gly Tyr Lys Lys Leu Thr Asp
1 5 10

<210> SEQ ID NO 228
<211> LENGTH: 9
<212> TYPE: PRT
<213> ORGANISM: Plasmodium vivax

<400> SEQUENCE: 228

Lys Lys Val Lys Lys Asn Ile Leu Lys
1 5

<210> SEQ ID NO 229
<211> LENGTH: 15
<212> TYPE: PRT

<213> ORGANISM: Plasmodium vivax

<400> SEQUENCE: 229

Lys Lys Val Lys Lys Asn Ile Leu Lys Thr Gln Lys Thr Lys Lys
1 5 10 15

<210> SEQ ID NO 230
<211> LENGTH: 11
<212> TYPE: PRT
<213> ORGANISM: Plasmodium vivax

<400> SEQUENCE: 230

Lys Lys Tyr Lys Asn Lys Lys Phe Lys Pro Tyr
1 5 10

<210> SEQ ID NO 231
<211> LENGTH: 15
<212> TYPE: PRT
<213> ORGANISM: Plasmodium vivax

<400> SEQUENCE: 231

Lys Lys Tyr Lys Asn Lys Lys Phe Lys Pro Tyr Asn Leu Arg Lys
1 5 10 15

<210> SEQ ID NO 232
<211> LENGTH: 8
<212> TYPE: PRT
<213> ORGANISM: Plasmodium vivax

<400> SEQUENCE: 232

Lys Leu Leu Leu Cys Val Val Leu
1 5

<210> SEQ ID NO 233
<211> LENGTH: 9
<212> TYPE: PRT
<213> ORGANISM: Plasmodium vivax

<400> SEQUENCE: 233

Lys Leu Met His Gly Arg Asp Ile Glu
1 5

<210> SEQ ID NO 234
<211> LENGTH: 9
<212> TYPE: PRT
<213> ORGANISM: Plasmodium vivax

<400> SEQUENCE: 234

Lys Met Lys Lys Ser Ile Glu Ala Lys
1 5

<210> SEQ ID NO 235
<211> LENGTH: 11
<212> TYPE: PRT
<213> ORGANISM: Plasmodium vivax

<400> SEQUENCE: 235

Lys Met Lys Glu Phe Ser Asp Ala Phe Ser Thr
1 5 10

<210> SEQ ID NO 236
<211> LENGTH: 8
<212> TYPE: PRT
<213> ORGANISM: Plasmodium vivax

<400> SEQUENCE: 236

Lys Asn Phe Lys Lys Glu Asn Gln
1 5

<210> SEQ ID NO 237
<211> LENGTH: 12
<212> TYPE: PRT
<213> ORGANISM: Plasmodium vivax

<400> SEQUENCE: 237

Lys Asn Gly Ile Lys Lys Pro Lys Lys His Lys Phe
1 5 10

<210> SEQ ID NO 238
<211> LENGTH: 14
<212> TYPE: PRT
<213> ORGANISM: Plasmodium vivax

<400> SEQUENCE: 238

Lys Asn Gly Ile Lys Lys Pro Lys Lys His Lys Phe Met Ser
1 5 10

<210> SEQ ID NO 239
<211> LENGTH: 10
<212> TYPE: PRT
<213> ORGANISM: Plasmodium vivax

<400> SEQUENCE: 239

Lys Asn Ile Lys Ser Lys Asn Gly Ile Gly
1 5 10

<210> SEQ ID NO 240
<211> LENGTH: 15
<212> TYPE: PRT
<213> ORGANISM: Plasmodium vivax

<400> SEQUENCE: 240

Lys Asn Ile Lys Ser Lys Asn Gly Ile Gly Gly Ile Pro Ala Asp
1 5 10 15

<210> SEQ ID NO 241
<211> LENGTH: 11
<212> TYPE: PRT
<213> ORGANISM: Plasmodium vivax

<400> SEQUENCE: 241

Lys Asn Lys Glu Lys Leu Asn His Ala Val Phe
1 5 10

<210> SEQ ID NO 242
<211> LENGTH: 8
<212> TYPE: PRT
<213> ORGANISM: Plasmodium vivax

<400> SEQUENCE: 242

Lys Asn Pro Lys Cys Pro Lys Val
1 5

<210> SEQ ID NO 243
<211> LENGTH: 14
<212> TYPE: PRT
<213> ORGANISM: Plasmodium vivax

<400> SEQUENCE: 243

Lys Asn Gln Thr Pro Lys Val Pro Lys Val Ser Lys Arg Lys
1 5 10

<210> SEQ ID NO 244
<211> LENGTH: 10
<212> TYPE: PRT
<213> ORGANISM: Plasmodium vivax

<400> SEQUENCE: 244

Lys Asn Ser Leu Thr Asn Phe Ala Val Arg
1 5 10

<210> SEQ ID NO 245
<211> LENGTH: 15
<212> TYPE: PRT
<213> ORGANISM: Plasmodium vivax

<400> SEQUENCE: 245

Lys Asn Ser Val Lys Ser Asn Lys Lys Val Lys Lys Met Ile Lys
1 5 10 15

<210> SEQ ID NO 246
<211> LENGTH: 9
<212> TYPE: PRT
<213> ORGANISM: Plasmodium vivax

<400> SEQUENCE: 246

Lys Asn Ser Tyr Ser Ala Ala Ser Lys
1 5

<210> SEQ ID NO 247
<211> LENGTH: 15
<212> TYPE: PRT
<213> ORGANISM: Plasmodium vivax

<400> SEQUENCE: 247

Lys Asn Tyr Gly Leu Phe Ser Asp Asn Tyr Phe Thr Thr Ala Tyr
1 5 10 15

<210> SEQ ID NO 248
<211> LENGTH: 9
<212> TYPE: PRT
<213> ORGANISM: Plasmodium vivax

<400> SEQUENCE: 248

Lys Pro Ala Ala Pro Glu Thr Ser Ala
1 5

<210> SEQ ID NO 249
<211> LENGTH: 9
<212> TYPE: PRT
<213> ORGANISM: Plasmodium vivax

<400> SEQUENCE: 249

Lys Pro Ala Ala Pro Lys Lys Pro Ala
1 5

<210> SEQ ID NO 250
<211> LENGTH: 8
<212> TYPE: PRT
<213> ORGANISM: Plasmodium vivax

<400> SEQUENCE: 250

Lys Pro Ala His Val Thr Ser Lys
1 5

<210> SEQ ID NO 251
<211> LENGTH: 8
<212> TYPE: PRT
<213> ORGANISM: Plasmodium vivax

<400> SEQUENCE: 251

Lys Pro Leu Ile Lys Phe Gly Thr
1               5

<210> SEQ ID NO 252
<211> LENGTH: 8
<212> TYPE: PRT
<213> ORGANISM: Plasmodium vivax

<400> SEQUENCE: 252

Lys Pro Asn Arg His Ile Asn Leu
1               5

<210> SEQ ID NO 253
<211> LENGTH: 12
<212> TYPE: PRT
<213> ORGANISM: Plasmodium vivax

<400> SEQUENCE: 253

Lys Pro Gln Lys Glu Asp Ala Lys Gly Gly Lys Lys
1               5                   10

<210> SEQ ID NO 254
<211> LENGTH: 8
<212> TYPE: PRT
<213> ORGANISM: Plasmodium vivax

<400> SEQUENCE: 254

Lys Pro Ser Arg Thr Thr Ile Thr
1               5

<210> SEQ ID NO 255
<211> LENGTH: 10
<212> TYPE: PRT
<213> ORGANISM: Plasmodium vivax

<400> SEQUENCE: 255

Lys Gln Val Gly Gly Lys Asn Gln Gln Val
1               5                   10

<210> SEQ ID NO 256
<211> LENGTH: 15
<212> TYPE: PRT
<213> ORGANISM: Plasmodium vivax

<400> SEQUENCE: 256

Lys Arg Asn Leu Lys Lys Ser Ile Lys Lys Lys Pro Lys Ser Lys
1               5                   10                  15

<210> SEQ ID NO 257
<211> LENGTH: 9
<212> TYPE: PRT
<213> ORGANISM: Plasmodium vivax

<400> SEQUENCE: 257

Lys Ser Ile Glu Ile Asp Asp Glu Lys
1               5

<210> SEQ ID NO 258
<211> LENGTH: 14
<212> TYPE: PRT
<213> ORGANISM: Plasmodium vivax

<400> SEQUENCE: 258

Lys Ser Ala Gly Ala Asp Ser Lys Ser Leu Lys Lys Leu Asp
1 5 10

<210> SEQ ID NO 259
<211> LENGTH: 8
<212> TYPE: PRT
<213> ORGANISM: Plasmodium vivax

<400> SEQUENCE: 259

Lys Ser Ala Tyr Ala Ile Ser Lys
1 5

<210> SEQ ID NO 260
<211> LENGTH: 8
<212> TYPE: PRT
<213> ORGANISM: Plasmodium vivax

<400> SEQUENCE: 260

Lys Ser Asp Ser Ser Lys Ile Ala
1 5

<210> SEQ ID NO 261
<211> LENGTH: 10
<212> TYPE: PRT
<213> ORGANISM: Plasmodium vivax

<400> SEQUENCE: 261

Lys Ser Ile Glu Ala Lys Lys Asn Asn Lys
1 5 10

<210> SEQ ID NO 262
<211> LENGTH: 9
<212> TYPE: PRT
<213> ORGANISM: Plasmodium vivax

<400> SEQUENCE: 262

Lys Ser Asn Asp Arg Ser Tyr Tyr Thr
1 5

<210> SEQ ID NO 263
<211> LENGTH: 9
<212> TYPE: PRT
<213> ORGANISM: Plasmodium vivax

<400> SEQUENCE: 263

Lys Ser Asn Gly Lys Arg Asp Pro Lys
1 5

<210> SEQ ID NO 264
<211> LENGTH: 12
<212> TYPE: PRT
<213> ORGANISM: Plasmodium vivax

<400> SEQUENCE: 264

Lys Ser Asn Pro Phe Arg Gly Ser Ser His Ala Lys
1 5 10

<210> SEQ ID NO 265
<211> LENGTH: 8

<212> TYPE: PRT
<213> ORGANISM: Plasmodium vivax

<400> SEQUENCE: 265

Lys Ser Asn Ser Ile Ser Leu Ser
1 5

<210> SEQ ID NO 266
<211> LENGTH: 8
<212> TYPE: PRT
<213> ORGANISM: Plasmodium vivax

<400> SEQUENCE: 266

Lys Ser Thr Asn Ile Leu Gly Glu
1 5

<210> SEQ ID NO 267
<211> LENGTH: 11
<212> TYPE: PRT
<213> ORGANISM: Plasmodium vivax

<400> SEQUENCE: 267

Lys Ser Thr Thr Thr Gly His Ile Ile Tyr Lys
1 5 10

<210> SEQ ID NO 268
<211> LENGTH: 8
<212> TYPE: PRT
<213> ORGANISM: Plasmodium vivax

<400> SEQUENCE: 268

Lys Thr Ile Asn Lys Thr Ile Asp
1 5

<210> SEQ ID NO 269
<211> LENGTH: 14
<212> TYPE: PRT
<213> ORGANISM: Plasmodium vivax

<400> SEQUENCE: 269

Lys Thr Ile Asn Lys Thr Ile Asp Lys Gln Lys Lys Ala Pro
1 5 10

<210> SEQ ID NO 270
<211> LENGTH: 8
<212> TYPE: PRT
<213> ORGANISM: Plasmodium vivax

<400> SEQUENCE: 270

Lys Thr Ile Tyr Asn Phe Leu Ile
1 5

<210> SEQ ID NO 271
<211> LENGTH: 14
<212> TYPE: PRT
<213> ORGANISM: Plasmodium vivax

<400> SEQUENCE: 271

Lys Val Asp Lys Lys Ala Pro Ala Lys Pro Gln Lys Glu Asp
1 5 10

<210> SEQ ID NO 272
<211> LENGTH: 10
<212> TYPE: PRT
<213> ORGANISM: Plasmodium vivax

<400> SEQUENCE: 272

Lys Val Ile Asn Met Lys Lys Ala Pro Asn
1 5 10

<210> SEQ ID NO 273
<211> LENGTH: 15
<212> TYPE: PRT
<213> ORGANISM: Plasmodium vivax

<400> SEQUENCE: 273

Lys Val Pro Val Pro Pro Thr Gln Ala Lys Lys Pro Lys Lys Asn
1 5 10 15

<210> SEQ ID NO 274
<211> LENGTH: 9
<212> TYPE: PRT
<213> ORGANISM: Plasmodium vivax

<400> SEQUENCE: 274

Lys Tyr Phe Leu Gly Leu Ala Arg Glu
1 5

<210> SEQ ID NO 275
<211> LENGTH: 12
<212> TYPE: PRT
<213> ORGANISM: Plasmodium vivax

<400> SEQUENCE: 275

Lys Tyr Gln Ser Ser Thr Ala Ser Ala Leu Ile Ala
1 5 10

<210> SEQ ID NO 276
<211> LENGTH: 15
<212> TYPE: PRT
<213> ORGANISM: Plasmodium vivax

<400> SEQUENCE: 276

Lys Tyr Arg Gln Ile Arg Glu Gly Leu Ile Thr Lys Glu Asn Lys
1 5 10 15

<210> SEQ ID NO 277
<211> LENGTH: 15
<212> TYPE: PRT
<213> ORGANISM: Plasmodium vivax

<400> SEQUENCE: 277

Lys Tyr Tyr Arg Val Lys Gly Lys Lys Lys Ile Leu Ile Pro Val
1 5 10 15

<210> SEQ ID NO 278
<211> LENGTH: 11
<212> TYPE: PRT
<213> ORGANISM: Plasmodium vivax

<400> SEQUENCE: 278

Leu Glu Thr Glu Arg Glu Ala Arg Arg Leu Arg
1 5 10

<210> SEQ ID NO 279
<211> LENGTH: 14
<212> TYPE: PRT
<213> ORGANISM: Plasmodium vivax

<400> SEQUENCE: 279

Leu Glu Thr Tyr Gln Asn Met Lys Ile Gln Lys Gln Thr Pro
1 5 10

<210> SEQ ID NO 280
<211> LENGTH: 14
<212> TYPE: PRT
<213> ORGANISM: Plasmodium vivax

<400> SEQUENCE: 280

Leu Glu Thr Tyr Gln Asn Met Lys Ile Gln Lys Gln Thr Pro
1 5 10

<210> SEQ ID NO 281
<211> LENGTH: 14
<212> TYPE: PRT
<213> ORGANISM: Plasmodium vivax

<400> SEQUENCE: 281

Leu Glu Thr Tyr Gln Asn Met Lys Ile Gln Lys Gln Thr Pro
1 5 10

<210> SEQ ID NO 282
<211> LENGTH: 10
<212> TYPE: PRT
<213> ORGANISM: Plasmodium vivax

<400> SEQUENCE: 282

Leu Gly Gly Leu Asn Gln Lys Gln Pro Thr
1 5 10

<210> SEQ ID NO 283
<211> LENGTH: 9
<212> TYPE: PRT
<213> ORGANISM: Plasmodium vivax

<400> SEQUENCE: 283

Leu Gly Ser Leu Val Gly Phe Val Phe
1 5

<210> SEQ ID NO 284
<211> LENGTH: 10
<212> TYPE: PRT
<213> ORGANISM: Plasmodium vivax

<400> SEQUENCE: 284

Leu Ile Leu Arg Ala Ala Ile Lys Thr Lys
1 5 10

<210> SEQ ID NO 285
<211> LENGTH: 9
<212> TYPE: PRT
<213> ORGANISM: Plasmodium vivax

<400> SEQUENCE: 285

Leu Leu Ile Asn Val Phe Leu His His
1 5

<210> SEQ ID NO 286
<211> LENGTH: 9
<212> TYPE: PRT
<213> ORGANISM: Plasmodium vivax

<400> SEQUENCE: 286

Leu Leu Pro Lys Lys Ser Gln Leu Lys 1 5

<210> SEQ ID NO 287
<211> LENGTH: 11
<212> TYPE: PRT
<213> ORGANISM: Plasmodium vivax

<400> SEQUENCE: 287

Leu Leu Pro Lys Lys Ser Gln Leu Lys Ser Gly
1 5 10

<210> SEQ ID NO 288
<211> LENGTH: 11
<212> TYPE: PRT
<213> ORGANISM: Plasmodium vivax

<400> SEQUENCE: 288

Leu Asn Ala Leu Glu Asn Pro Pro Lys Pro Gly
1 5 10

<210> SEQ ID NO 289
<211> LENGTH: 13
<212> TYPE: PRT
<213> ORGANISM: Plasmodium vivax

<400> SEQUENCE: 289

Leu Asn Gln Lys Gln Pro Thr Lys Gly Ser Asn Ile Gln
1 5 10

<210> SEQ ID NO 290
<211> LENGTH: 8
<212> TYPE: PRT
<213> ORGANISM: Plasmodium vivax

<400> SEQUENCE: 290

Leu Arg Pro Lys Lys Lys Leu Lys
1 5

<210> SEQ ID NO 291
<211> LENGTH: 8
<212> TYPE: PRT
<213> ORGANISM: Plasmodium vivax

<400> SEQUENCE: 291

Leu Ser Ala Ala Pro Ala Gly Val
1 5

<210> SEQ ID NO 292
<211> LENGTH: 13
<212> TYPE: PRT
<213> ORGANISM: Plasmodium vivax

<400> SEQUENCE: 292

Met Lys Gln Lys Gly Phe Gly Gly Gln Thr Lys Pro Val
1 5 10

<210> SEQ ID NO 293
<211> LENGTH: 9
<212> TYPE: PRT
<213> ORGANISM: Plasmodium vivax

<400> SEQUENCE: 293

Met Tyr Lys Lys Val Tyr Val Ile Asp
1 5

<210> SEQ ID NO 294
<211> LENGTH: 9
<212> TYPE: PRT
<213> ORGANISM: Plasmodium vivax

<400> SEQUENCE: 294

Met Ser Cys Asp Thr Ser Ala Ser Ala
1 5

<210> SEQ ID NO 295
<211> LENGTH: 11
<212> TYPE: PRT
<213> ORGANISM: Plasmodium vivax

<400> SEQUENCE: 295

Met Val Ser Gly Thr Thr Gly Ser Thr Ala Asn
1 5 10

<210> SEQ ID NO 296
<211> LENGTH: 9
<212> TYPE: PRT
<213> ORGANISM: Plasmodium vivax

<400> SEQUENCE: 296

Met Tyr Lys Lys Val Tyr Val Ile Asp
1 5

<210> SEQ ID NO 297
<211> LENGTH: 12
<212> TYPE: PRT
<213> ORGANISM: Plasmodium vivax

<400> SEQUENCE: 297

Asn Ala Lys Gly Lys Lys Pro Ala Lys Lys Val Ile
1 5 10

<210> SEQ ID NO 298
<211> LENGTH: 13
<212> TYPE: PRT
<213> ORGANISM: Plasmodium vivax

<400> SEQUENCE: 298

Asn Ala Gln Leu Thr Lys Gln Lys Thr Lys Lys Val Ile
1 5 10

<210> SEQ ID NO 299
<211> LENGTH: 9
<212> TYPE: PRT
<213> ORGANISM: Plasmodium vivax

<400> SEQUENCE: 299

Asn Cys Ala Gln Gly His Cys Ser Gln
1 5

<210> SEQ ID NO 300
<211> LENGTH: 13
<212> TYPE: PRT
<213> ORGANISM: Plasmodium vivax

<400> SEQUENCE: 300

Asn Glu Gly Asp Pro Ser Lys Gly Glu Gly Ala Glu Thr
1 5 10

<210> SEQ ID NO 301

<211> LENGTH: 11
<212> TYPE: PRT
<213> ORGANISM: Plasmodium vivax

<400> SEQUENCE: 301

Asn Glu Lys Lys Glu Leu Lys Thr Glu Ala Leu
1 5 10

<210> SEQ ID NO 302
<211> LENGTH: 8
<212> TYPE: PRT
<213> ORGANISM: Plasmodium vivax

<400> SEQUENCE: 302

Asn Phe Asp Lys Tyr His Pro Gly
1 5

<210> SEQ ID NO 303
<211> LENGTH: 9
<212> TYPE: PRT
<213> ORGANISM: Plasmodium vivax

<400> SEQUENCE: 303

Asn Phe Asp Val Ala Ala Glu Arg Phe
1 5

<210> SEQ ID NO 304
<211> LENGTH: 10
<212> TYPE: PRT
<213> ORGANISM: Plasmodium vivax

<400> SEQUENCE: 304

Asn Phe Ser Lys Asn Ile Lys Lys Lys Lys
1 5 10

<210> SEQ ID NO 305
<211> LENGTH: 8
<212> TYPE: PRT
<213> ORGANISM: Plasmodium vivax

<400> SEQUENCE: 305

Asn Ile Pro Pro Lys Ala Phe Gly
1 5

<210> SEQ ID NO 306
<211> LENGTH: 11
<212> TYPE: PRT
<213> ORGANISM: Plasmodium vivax

<400> SEQUENCE: 306

Asn Lys Ala Leu Leu Pro Thr Ala Gly Asp Asp
1 5 10

<210> SEQ ID NO 307
<211> LENGTH: 9
<212> TYPE: PRT
<213> ORGANISM: Plasmodium vivax

<400> SEQUENCE: 307

Asn Lys Glu Lys Leu Asn His Ala Val
1 5

<210> SEQ ID NO 308
<211> LENGTH: 10
<212> TYPE: PRT

<213> ORGANISM: Plasmodium vivax

<400> SEQUENCE: 308

Asn Lys Glu Lys Leu Asn His Ala Val Phe
1 5 10

<210> SEQ ID NO 309
<211> LENGTH: 14
<212> TYPE: PRT
<213> ORGANISM: Plasmodium vivax

<400> SEQUENCE: 309

Asn Lys Lys Gly Thr Pro Asn Thr Lys Lys Glu Pro Leu Leu
1 5 10

<210> SEQ ID NO 310
<211> LENGTH: 10
<212> TYPE: PRT
<213> ORGANISM: Plasmodium vivax

<400> SEQUENCE: 310

Asn Lys Lys Val Tyr Lys Leu Asp Lys Glu
1 5 10

<210> SEQ ID NO 311
<211> LENGTH: 11
<212> TYPE: PRT
<213> ORGANISM: Plasmodium vivax

<400> SEQUENCE: 311

Asn Lys Asn Ser Leu Thr Asn Phe Ala Val Arg
1 5 10

<210> SEQ ID NO 312
<211> LENGTH: 15
<212> TYPE: PRT
<213> ORGANISM: Plasmodium vivax

<400> SEQUENCE: 312

Asn Lys Val Arg Pro Ile Arg Thr Pro Gly Gly Lys Leu Thr Ile
1 5 10 15

<210> SEQ ID NO 313
<211> LENGTH: 13
<212> TYPE: PRT
<213> ORGANISM: Plasmodium vivax

<400> SEQUENCE: 313

Asn Leu Lys Gly Ala Lys Ala Glu Glu Gly Lys Lys Asp
1 5 10

<210> SEQ ID NO 314
<211> LENGTH: 11
<212> TYPE: PRT
<213> ORGANISM: Plasmodium vivax

<400> SEQUENCE: 314

Asn Asn Asp Phe Gln Lys Leu Glu Ser Tyr Asp
1 5 10

<210> SEQ ID NO 315
<211> LENGTH: 9
<212> TYPE: PRT
<213> ORGANISM: Plasmodium vivax

<400> SEQUENCE: 315

Asn Pro Phe Asn Arg Tyr Pro Ala Tyr
1               5

<210> SEQ ID NO 316
<211> LENGTH: 12
<212> TYPE: PRT
<213> ORGANISM: Plasmodium vivax

<400> SEQUENCE: 316

Asn Gln Lys Gln Pro Thr Lys Gly Ser Asn Ile Gln
1               5                   10

<210> SEQ ID NO 317
<211> LENGTH: 10
<212> TYPE: PRT
<213> ORGANISM: Plasmodium vivax

<400> SEQUENCE: 317

Asn Gln Leu Arg Pro Lys Lys Lys Leu Lys
1               5                   10

<210> SEQ ID NO 318
<211> LENGTH: 9
<212> TYPE: PRT
<213> ORGANISM: Plasmodium vivax

<400> SEQUENCE: 318

Asn Ser Leu Thr Asn Phe Ala Val Arg
1               5

<210> SEQ ID NO 319
<211> LENGTH: 14
<212> TYPE: PRT
<213> ORGANISM: Plasmodium vivax

<400> SEQUENCE: 319

Asn Ser Val Lys Ser Asn Lys Lys Val Lys Lys Met Ile Lys
1               5                   10

<210> SEQ ID NO 320
<211> LENGTH: 10
<212> TYPE: PRT
<213> ORGANISM: Plasmodium vivax

<400> SEQUENCE: 320

Asn Thr Ile Ala Phe Val Ala Thr Glu Lys
1               5                   10

<210> SEQ ID NO 321
<211> LENGTH: 8
<212> TYPE: PRT
<213> ORGANISM: Plasmodium vivax

<400> SEQUENCE: 321

Asn Val Cys Tyr Arg Val Cys Cys
1               5

<210> SEQ ID NO 322
<211> LENGTH: 10
<212> TYPE: PRT
<213> ORGANISM: Plasmodium vivax

<400> SEQUENCE: 322

Asn Val Lys Gly Asn Pro Lys Ala Ala Ala
1 5 10

<210> SEQ ID NO 323
<211> LENGTH: 10
<212> TYPE: PRT
<213> ORGANISM: Plasmodium vivax

<400> SEQUENCE: 323

Pro Gly Arg Gly Ala Pro Leu Ala Lys Ile
1 5 10

<210> SEQ ID NO 324
<211> LENGTH: 8
<212> TYPE: PRT
<213> ORGANISM: Plasmodium vivax

<400> SEQUENCE: 324

Pro Lys Phe Phe Lys Asn Gln Arg
1 5

<210> SEQ ID NO 325
<211> LENGTH: 9
<212> TYPE: PRT
<213> ORGANISM: Plasmodium vivax

<400> SEQUENCE: 325

Pro Lys Phe Phe Lys Asn Gln Arg Tyr
1 5

<210> SEQ ID NO 326
<211> LENGTH: 15
<212> TYPE: PRT
<213> ORGANISM: Plasmodium vivax

<400> SEQUENCE: 326

Pro Lys Ile Glu Pro Pro Lys Lys Lys Phe Ile Pro Ser Val Leu
1 5 10 15

<210> SEQ ID NO 327
<211> LENGTH: 10
<212> TYPE: PRT
<213> ORGANISM: Plasmodium vivax

<400> SEQUENCE: 327

Pro Leu Pro Asp Arg Asn Asp Val Pro Leu
1 5 10

<210> SEQ ID NO 328
<211> LENGTH: 9
<212> TYPE: PRT
<213> ORGANISM: Plasmodium vivax

<400> SEQUENCE: 328

Pro Leu Ser Asn Lys Lys Thr Val Lys
1 5

<210> SEQ ID NO 329
<211> LENGTH: 8
<212> TYPE: PRT
<213> ORGANISM: Plasmodium vivax

<400> SEQUENCE: 329

Pro Pro Lys Asp Val Val Pro Ser
1 5

<210> SEQ ID NO 330
<211> LENGTH: 14
<212> TYPE: PRT
<213> ORGANISM: Plasmodium vivax

<400> SEQUENCE: 330

Pro Pro Lys Glu Arg Lys Thr Lys Glu Gln Ile Ala Ala Ala
1               5                   10

<210> SEQ ID NO 331
<211> LENGTH: 12
<212> TYPE: PRT
<213> ORGANISM: Plasmodium vivax

<400> SEQUENCE: 331

Pro Pro Ser Gly Gly Ser Pro Asn Arg Ser Pro Pro
1               5                   10

<210> SEQ ID NO 332
<211> LENGTH: 13
<212> TYPE: PRT
<213> ORGANISM: Plasmodium vivax

<400> SEQUENCE: 332

Pro Gln Lys Glu Asp Ala Lys Gly Gly Lys Lys Lys Lys
1               5                   10

<210> SEQ ID NO 333
<211> LENGTH: 13
<212> TYPE: PRT
<213> ORGANISM: Plasmodium vivax

<400> SEQUENCE: 333

Pro Arg Asn Pro Asn Tyr Arg Asp Gln Gln Tyr Pro Asp
1               5                   10

<210> SEQ ID NO 334
<211> LENGTH: 9
<212> TYPE: PRT
<213> ORGANISM: Plasmodium vivax

<400> SEQUENCE: 334

Gln Phe Thr Lys Gln Arg Ser Asn Ile
1               5

<210> SEQ ID NO 335
<211> LENGTH: 11
<212> TYPE: PRT
<213> ORGANISM: Plasmodium vivax

<400> SEQUENCE: 335

Gln Lys Lys Pro Ala Ala Pro Glu Thr Ser Ala
1               5                   10

<210> SEQ ID NO 336
<211> LENGTH: 11
<212> TYPE: PRT
<213> ORGANISM: Plasmodium vivax

<400> SEQUENCE: 336

Gln Lys Gln Pro Thr Lys Gly Ser Asn Ile Gln
1               5                   10

<210> SEQ ID NO 337
<211> LENGTH: 10
<212> TYPE: PRT
<213> ORGANISM: Plasmodium vivax

<400> SEQUENCE: 337

Gln Arg Ser Ala Leu Val Asn Asn Pro Leu
1 5 10

<210> SEQ ID NO 338
<211> LENGTH: 10
<212> TYPE: PRT
<213> ORGANISM: Plasmodium vivax

<400> SEQUENCE: 338

Arg Ala Ala Pro Glu Glu His Pro Val Leu
1 5 10

<210> SEQ ID NO 339
<211> LENGTH: 9
<212> TYPE: PRT
<213> ORGANISM: Plasmodium vivax

<400> SEQUENCE: 339

Arg Gly Ser Ala Glu Asp Asp Leu Lys
1 5

<210> SEQ ID NO 340
<211> LENGTH: 14
<212> TYPE: PRT
<213> ORGANISM: Plasmodium vivax

<400> SEQUENCE: 340

Arg Ala Gly Lys Val Lys Asn Gln Thr Pro Lys Val Pro Lys
1 5 10

<210> SEQ ID NO 341
<211> LENGTH: 15
<212> TYPE: PRT
<213> ORGANISM: Plasmodium vivax

<400> SEQUENCE: 341

Arg Ala Ile Ser Lys Asn Gly Lys Asn Arg Phe Ile Lys Pro Lys
1 5 10 15

<210> SEQ ID NO 342
<211> LENGTH: 15
<212> TYPE: PRT
<213> ORGANISM: Plasmodium vivax

<400> SEQUENCE: 342

Arg Gly Glu Thr Asp Val Glu Thr Arg Gln Asn Asn Ile Leu Leu
1 5 10 15

<210> SEQ ID NO 343
<211> LENGTH: 12
<212> TYPE: PRT
<213> ORGANISM: Plasmodium vivax

<400> SEQUENCE: 343

Arg Lys Ala His Lys Asn Gly Ile Lys Lys Pro Lys
1 5 10

<210> SEQ ID NO 344
<211> LENGTH: 9

<212> TYPE: PRT
<213> ORGANISM: Plasmodium vivax

<400> SEQUENCE: 344

Arg Lys Lys Gly Pro Asn Ser Lys Leu
1 5

<210> SEQ ID NO 345
<211> LENGTH: 14
<212> TYPE: PRT
<213> ORGANISM: Plasmodium vivax

<400> SEQUENCE: 345

Arg Lys Lys Pro Ala Thr Pro Lys Lys Gln Ala Thr Pro Lys
1 5 10

<210> SEQ ID NO 346
<211> LENGTH: 15
<212> TYPE: PRT
<213> ORGANISM: Plasmodium vivax

<400> SEQUENCE: 346

Arg Lys Lys Pro Ala Thr Pro Lys Lys Gln Ala Thr Pro Lys Lys
1 5 10 15

<210> SEQ ID NO 347
<211> LENGTH: 9
<212> TYPE: PRT
<213> ORGANISM: Plasmodium vivax

<400> SEQUENCE: 347

Arg Lys Tyr Lys Ile Ile Leu Ala Phe
1 5

<210> SEQ ID NO 348
<211> LENGTH: 10
<212> TYPE: PRT
<213> ORGANISM: Plasmodium vivax

<400> SEQUENCE: 348

Arg Leu Glu Leu Thr Pro Lys Gln Lys Val
1 5 10

<210> SEQ ID NO 349
<211> LENGTH: 10
<212> TYPE: PRT
<213> ORGANISM: Plasmodium vivax

<400> SEQUENCE: 349

Arg Leu Thr Gly Gly Lys Lys Lys Ile His
1 5 10

<210> SEQ ID NO 350
<211> LENGTH: 11
<212> TYPE: PRT
<213> ORGANISM: Plasmodium vivax

<400> SEQUENCE: 350

Arg Leu Thr Gly Gly Lys Lys Lys Ile His Lys
1 5 10

<210> SEQ ID NO 351
<211> LENGTH: 13
<212> TYPE: PRT
<213> ORGANISM: Plasmodium vivax

<400> SEQUENCE: 351

Arg Leu Thr Gly Gly Lys Lys Lys Ile His Lys Lys Lys
1 5 10

<210> SEQ ID NO 352
<211> LENGTH: 11
<212> TYPE: PRT
<213> ORGANISM: Plasmodium vivax

<400> SEQUENCE: 352

Arg Asn Lys Lys Ile Tyr Arg Ile Gly Leu Lys
1 5 10

<210> SEQ ID NO 353
<211> LENGTH: 13
<212> TYPE: PRT
<213> ORGANISM: Plasmodium vivax

<400> SEQUENCE: 353

Arg Asn Leu Lys Lys Ser Ile Lys Lys Lys Pro Lys Ser
1 5 10

<210> SEQ ID NO 354
<211> LENGTH: 14
<212> TYPE: PRT
<213> ORGANISM: Plasmodium vivax

<400> SEQUENCE: 354

Arg Asn Leu Lys Lys Ser Ile Lys Lys Lys Pro Lys Ser Lys
1 5 10

<210> SEQ ID NO 355
<211> LENGTH: 13
<212> TYPE: PRT
<213> ORGANISM: Plasmodium vivax

<400> SEQUENCE: 355

Arg Pro Pro Ser Asn Thr Lys Leu Gly Ser Lys Gln Val
1 5 10

<210> SEQ ID NO 356
<211> LENGTH: 14
<212> TYPE: PRT
<213> ORGANISM: Plasmodium vivax

<400> SEQUENCE: 356

Arg Ser Ser Gly Leu Thr Asn Ser Arg Gln Gln Lys Met Lys
1 5 10

<210> SEQ ID NO 357
<211> LENGTH: 8
<212> TYPE: PRT
<213> ORGANISM: Plasmodium vivax

<400> SEQUENCE: 357

Arg Ser Tyr Ser Phe Asn Ser Met
1 5

<210> SEQ ID NO 358
<211> LENGTH: 9
<212> TYPE: PRT
<213> ORGANISM: Plasmodium vivax

<400> SEQUENCE: 358

Arg Thr Pro Gly Gly Lys Leu Thr Ile
1 5

<210> SEQ ID NO 359
<211> LENGTH: 11
<212> TYPE: PRT
<213> ORGANISM: Plasmodium vivax

<400> SEQUENCE: 359

Arg Thr Val Gly Val Ser Lys Lys Lys Gly Ala
1 5 10

<210> SEQ ID NO 360
<211> LENGTH: 15
<212> TYPE: PRT
<213> ORGANISM: Plasmodium vivax

<400> SEQUENCE: 360

Ser Ala Gly Ile Lys Lys Pro His Arg Tyr Arg Pro Gly Thr Val
1 5 10 15

<210> SEQ ID NO 361
<211> LENGTH: 14
<212> TYPE: PRT
<213> ORGANISM: Plasmodium vivax

<400> SEQUENCE: 361

Ser Asp Gly Thr Gly Arg Lys Lys Gly Pro Asn Ser Lys Leu
1 5 10

<210> SEQ ID NO 362
<211> LENGTH: 8
<212> TYPE: PRT
<213> ORGANISM: Plasmodium vivax

<400> SEQUENCE: 362

Ser Asp Ile Ile Lys Thr Asn Glu
1 5

<210> SEQ ID NO 363
<211> LENGTH: 13
<212> TYPE: PRT
<213> ORGANISM: Plasmodium vivax

<400> SEQUENCE: 363

Ser Phe Phe Asn Ser Lys Lys Ile Lys Lys Gly Ser Lys
1 5 10

<210> SEQ ID NO 364
<211> LENGTH: 14
<212> TYPE: PRT
<213> ORGANISM: Plasmodium vivax

<400> SEQUENCE: 364

Ser Phe Phe Asn Ser Lys Lys Ile Lys Lys Gly Ser Lys Ser
1 5 10

<210> SEQ ID NO 365
<211> LENGTH: 11
<212> TYPE: PRT
<213> ORGANISM: Plasmodium vivax

<400> SEQUENCE: 365

Ser Gly Phe Leu Leu His Pro Ser Val Thr Phe 1 5 10

<210> SEQ ID NO 366
<211> LENGTH: 11
<212> TYPE: PRT
<213> ORGANISM: Plasmodium vivax

<400> SEQUENCE: 366

Ser Gly Gly Val Leu Pro Asn Ile His Asn Val
1 5 10

<210> SEQ ID NO 367
<211> LENGTH: 13
<212> TYPE: PRT
<213> ORGANISM: Plasmodium vivax

<400> SEQUENCE: 367

Ser Gly Lys Ser Thr Thr Thr Gly His Ile Ile Tyr Lys
1 5 10

<210> SEQ ID NO 368
<211> LENGTH: 10
<212> TYPE: PRT
<213> ORGANISM: Plasmodium vivax

<400> SEQUENCE: 368

Ser Lys Asp Gly Lys Asn Glu Ala Ala Leu
1 5 10

<210> SEQ ID NO 369
<211> LENGTH: 11
<212> TYPE: PRT
<213> ORGANISM: Plasmodium vivax

<400> SEQUENCE: 369

Ser Lys Gly Pro Asp Thr Pro Ile Ile Thr Asn
1 5 10

<210> SEQ ID NO 370
<211> LENGTH: 12
<212> TYPE: PRT
<213> ORGANISM: Plasmodium vivax

<400> SEQUENCE: 370

Ser Lys Asn Gly Lys Asn Arg Phe Ile Lys Pro Lys
1 5 10

<210> SEQ ID NO 371
<211> LENGTH: 14
<212> TYPE: PRT
<213> ORGANISM: Plasmodium vivax

<400> SEQUENCE: 371

Ser Lys Asn Gly Lys Asn Arg Phe Ile Lys Pro Lys Ile Gln
1 5 10

<210> SEQ ID NO 372
<211> LENGTH: 14
<212> TYPE: PRT
<213> ORGANISM: Plasmodium vivax

<400> SEQUENCE: 372

Ser Lys Gln Asn Phe Ala Lys Asn Lys Lys Lys Ala Ala Asn
1 5 10

<210> SEQ ID NO 373
<211> LENGTH: 10
<212> TYPE: PRT
<213> ORGANISM: Plasmodium vivax

<400> SEQUENCE: 373

Ser Leu Ala Leu Gln Lys Lys Lys Ala Ala
1               5                   10

<210> SEQ ID NO 374
<211> LENGTH: 14
<212> TYPE: PRT
<213> ORGANISM: Plasmodium vivax

<400> SEQUENCE: 374

Ser Leu Gly Lys Gln Val Gly Gly Lys Asn Gln Gln Val Lys
1               5                   10

<210> SEQ ID NO 375
<211> LENGTH: 15
<212> TYPE: PRT
<213> ORGANISM: Plasmodium vivax

<400> SEQUENCE: 375

Ser Leu Leu Ala Leu Phe Lys Glu Lys Lys Glu Lys Pro Arg Ser
1               5                   10                  15

<210> SEQ ID NO 376
<211> LENGTH: 11
<212> TYPE: PRT
<213> ORGANISM: Plasmodium vivax

<400> SEQUENCE: 376

Ser Leu Thr Thr Pro Ala Ala Val Ala Ala Lys
1               5                   10

<210> SEQ ID NO 377
<211> LENGTH: 9
<212> TYPE: PRT
<213> ORGANISM: Plasmodium vivax

<400> SEQUENCE: 377

Ser Leu Val Lys Gln Arg Ser Asn Ile
1               5

<210> SEQ ID NO 378
<211> LENGTH: 13
<212> TYPE: PRT
<213> ORGANISM: Plasmodium vivax

<400> SEQUENCE: 378

Ser Met Lys Asn Lys Lys Asp Lys Thr Pro Pro Ser Lys
1               5                   10

<210> SEQ ID NO 379
<211> LENGTH: 8
<212> TYPE: PRT
<213> ORGANISM: Plasmodium vivax

<400> SEQUENCE: 379

Ser Met Cys Glu Thr Thr Glu Thr
1               5

<210> SEQ ID NO 380

<211> LENGTH: 15
<212> TYPE: PRT
<213> ORGANISM: Plasmodium vivax

<400> SEQUENCE: 380

Ser Asn Asp Asp Gly Asn Gly Lys Lys Phe Asn Lys Lys Pro Phe
1 5 10 15

<210> SEQ ID NO 381
<211> LENGTH: 10
<212> TYPE: PRT
<213> ORGANISM: Plasmodium vivax

<400> SEQUENCE: 381

Ser Asn Lys Lys Val Lys Lys Met Ile Lys
1 5 10

<210> SEQ ID NO 382
<211> LENGTH: 11
<212> TYPE: PRT
<213> ORGANISM: Plasmodium vivax

<400> SEQUENCE: 382

Ser Asn Met Glu Ser Asp Asp Ala Gly Asp Gly
1 5 10

<210> SEQ ID NO 383
<211> LENGTH: 9
<212> TYPE: PRT
<213> ORGANISM: Plasmodium vivax

<400> SEQUENCE: 383

Ser Gln Lys Leu Tyr Thr Lys Val Ala
1 5

<210> SEQ ID NO 384
<211> LENGTH: 11
<212> TYPE: PRT
<213> ORGANISM: Plasmodium vivax

<400> SEQUENCE: 384

Ser Arg Lys Gly Leu Asp Pro Lys Phe Phe Lys
1 5 10

<210> SEQ ID NO 385
<211> LENGTH: 9
<212> TYPE: PRT
<213> ORGANISM: Plasmodium vivax

<400> SEQUENCE: 385

Ser Ser His Ala Lys Gly Ile Val Val
1 5

<210> SEQ ID NO 386
<211> LENGTH: 12
<212> TYPE: PRT
<213> ORGANISM: Plasmodium vivax

<400> SEQUENCE: 386

Ser Ser His Ala Lys Gly Ile Val Val Glu Lys Val
1 5 10

<210> SEQ ID NO 387
<211> LENGTH: 10
<212> TYPE: PRT

<213> ORGANISM: Plasmodium vivax

<400> SEQUENCE: 387

Ser Thr Thr Thr Gly His Ile Ile Tyr Lys
1 5 10

<210> SEQ ID NO 388
<211> LENGTH: 10
<212> TYPE: PRT
<213> ORGANISM: Plasmodium vivax

<400> SEQUENCE: 388

Ser Thr Val Ile Thr Asp Gln Tyr Val Ser
1 5 10

<210> SEQ ID NO 389
<211> LENGTH: 14
<212> TYPE: PRT
<213> ORGANISM: Plasmodium vivax

<400> SEQUENCE: 389

Ser Val Ile Asn Ala Lys Ala Lys Leu Gln Lys Thr Glu Glu
1 5 10

<210> SEQ ID NO 390
<211> LENGTH: 13
<212> TYPE: PRT
<213> ORGANISM: Plasmodium vivax

<400> SEQUENCE: 390

Ser Val Lys Ser Asn Lys Lys Val Lys Lys Met Ile Lys
1 5 10

<210> SEQ ID NO 391
<211> LENGTH: 12
<212> TYPE: PRT
<213> ORGANISM: Plasmodium vivax

<400> SEQUENCE: 391

Ser Tyr Leu Phe Lys Lys Ile Lys Lys Lys Val Phe
1 5 10

<210> SEQ ID NO 392
<211> LENGTH: 15
<212> TYPE: PRT
<213> ORGANISM: Plasmodium vivax

<400> SEQUENCE: 392

Thr Asp Glu Asp Ala Gly Lys Lys Lys Lys Val Lys Lys Ser Leu
1 5 10 15

<210> SEQ ID NO 393
<211> LENGTH: 15
<212> TYPE: PRT
<213> ORGANISM: Plasmodium vivax

<400> SEQUENCE: 393

Thr Asp Glu Asp Ala Gly Lys Lys Lys Lys Val Lys Lys Ser Leu
1 5 10 15

<210> SEQ ID NO 394
<211> LENGTH: 11
<212> TYPE: PRT
<213> ORGANISM: Plasmodium vivax

<400> SEQUENCE: 394

Thr Glu Gly Ser Thr Pro Lys Pro Lys Gln Arg
1 5 10

<210> SEQ ID NO 395
<211> LENGTH: 9
<212> TYPE: PRT
<213> ORGANISM: Plasmodium vivax

<400> SEQUENCE: 395

Thr Glu Tyr Pro Pro Leu Gly Arg Phe
1 5

<210> SEQ ID NO 396
<211> LENGTH: 10
<212> TYPE: PRT
<213> ORGANISM: Plasmodium vivax

<400> SEQUENCE: 396

Thr Glu Tyr Pro Pro Leu Gly Arg Phe Ala
1 5 10

<210> SEQ ID NO 397
<211> LENGTH: 10
<212> TYPE: PRT
<213> ORGANISM: Plasmodium vivax

<400> SEQUENCE: 397

Thr Phe Leu Phe Asn Lys Lys Lys Lys Lys
1 5 10

<210> SEQ ID NO 398
<211> LENGTH: 12
<212> TYPE: PRT
<213> ORGANISM: Plasmodium vivax

<400> SEQUENCE: 398

Thr Gly Lys Tyr Gly Thr Arg Tyr Gly Ser Ser Leu
1 5 10

<210> SEQ ID NO 399
<211> LENGTH: 8
<212> TYPE: PRT
<213> ORGANISM: Plasmodium vivax

<400> SEQUENCE: 399

Thr Gly Leu Leu Arg Gly Ala Lys
1 5

<210> SEQ ID NO 400
<211> LENGTH: 14
<212> TYPE: PRT
<213> ORGANISM: Plasmodium vivax

<400> SEQUENCE: 400

Thr Gly Leu Leu Arg Gly Ala Lys Lys Thr Lys Leu Val Gly
1 5 10

<210> SEQ ID NO 401
<211> LENGTH: 11
<212> TYPE: PRT
<213> ORGANISM: Plasmodium vivax

<400> SEQUENCE: 401

Thr Gly Arg Lys Lys Gly Pro Asn Ser Lys Leu
1 5 10

<210> SEQ ID NO 402
<211> LENGTH: 8
<212> TYPE: PRT
<213> ORGANISM: Plasmodium vivax

<400> SEQUENCE: 402

Thr Lys Ile Leu Ile Val His Val
1 5

<210> SEQ ID NO 403
<211> LENGTH: 9
<212> TYPE: PRT
<213> ORGANISM: Plasmodium vivax

<400> SEQUENCE: 403

Thr Lys Leu Val Gly Lys Thr Glu Asp
1 5

<210> SEQ ID NO 404
<211> LENGTH: 10
<212> TYPE: PRT
<213> ORGANISM: Plasmodium vivax

<400> SEQUENCE: 404

Thr Lys Arg Asn Leu Lys Lys Ser Ile Lys
1 5 10

<210> SEQ ID NO 405
<211> LENGTH: 14
<212> TYPE: PRT
<213> ORGANISM: Plasmodium vivax

<400> SEQUENCE: 405

Thr Leu Glu Ser Pro Asp Asn Ala Glu Ile Asp Met Ser Ser
1 5 10

<210> SEQ ID NO 406
<211> LENGTH: 14
<212> TYPE: PRT
<213> ORGANISM: Plasmodium vivax

<400> SEQUENCE: 406

Thr Leu Glu Ser Pro Asp Asn Ala Glu Ile Asp Met Ser Ser
1 5 10

<210> SEQ ID NO 407
<211> LENGTH: 8
<212> TYPE: PRT
<213> ORGANISM: Plasmodium vivax

<400> SEQUENCE: 407

Thr Pro Gly Gly Lys Leu Thr Ile
1 5

<210> SEQ ID NO 408
<211> LENGTH: 9
<212> TYPE: PRT
<213> ORGANISM: Plasmodium vivax

<400> SEQUENCE: 408

Thr Pro Ile Glu Lys Leu His Pro Ile
1 5

<210> SEQ ID NO 409
<211> LENGTH: 10
<212> TYPE: PRT
<213> ORGANISM: Plasmodium vivax

<400> SEQUENCE: 409

Thr Pro Ile Ile Thr Asn Lys Pro Phe Gly
1 5 10

<210> SEQ ID NO 410
<211> LENGTH: 11
<212> TYPE: PRT
<213> ORGANISM: Plasmodium vivax

<400> SEQUENCE: 410

Thr Pro Ile Ile Thr Asn Lys Pro Phe Gly Lys
1 5 10

<210> SEQ ID NO 411
<211> LENGTH: 13
<212> TYPE: PRT
<213> ORGANISM: Plasmodium vivax

<400> SEQUENCE: 411

Thr Ser Asn Ser Ala Lys Ala Gly Leu Gln Phe Pro Val
1 5 10

<210> SEQ ID NO 412
<211> LENGTH: 9
<212> TYPE: PRT
<213> ORGANISM: Plasmodium vivax

<400> SEQUENCE: 412

Thr Thr Lys Val Lys Arg Val Gln Thr
1 5

<210> SEQ ID NO 413
<211> LENGTH: 10
<212> TYPE: PRT
<213> ORGANISM: Plasmodium vivax

<400> SEQUENCE: 413

Thr Thr Lys Val Lys Arg Val Gln Thr Phe
1 5 10

<210> SEQ ID NO 414
<211> LENGTH: 13
<212> TYPE: PRT
<213> ORGANISM: Plasmodium vivax

<400> SEQUENCE: 414

Val Ala Lys Lys Glu Ser Lys Ile Ile Lys Lys Gln Lys
1 5 10

<210> SEQ ID NO 415
<211> LENGTH: 14
<212> TYPE: PRT
<213> ORGANISM: Plasmodium vivax

<400> SEQUENCE: 415

Val Ala Lys Lys Glu Ser Lys Ile Ile Lys Lys Gln Lys Lys
1 5 10

<210> SEQ ID NO 416
<211> LENGTH: 12
<212> TYPE: PRT
<213> ORGANISM: Plasmodium vivax

<400> SEQUENCE: 416

Val Glu Thr Glu Pro Asp Asp Ile Asp Tyr Gly Lys
1 5 10

<210> SEQ ID NO 417
<211> LENGTH: 14
<212> TYPE: PRT
<213> ORGANISM: Plasmodium vivax

<400> SEQUENCE: 417

Val Glu Thr Glu Pro Asp Asp Ile Asp Tyr Gly Lys Ser Asp
1 5 10

<210> SEQ ID NO 418
<211> LENGTH: 15
<212> TYPE: PRT
<213> ORGANISM: Plasmodium vivax

<400> SEQUENCE: 418

Val Glu Thr Glu Pro Asp Asp Ile Asp Tyr Gly Lys Ser Asp Asp
1 5 10 15

<210> SEQ ID NO 419
<211> LENGTH: 13
<212> TYPE: PRT
<213> ORGANISM: Plasmodium vivax

<400> SEQUENCE: 419

Val Phe Pro Tyr Asp Asn Thr Leu Pro Lys Tyr Lys Phe
1 5 10

<210> SEQ ID NO 420
<211> LENGTH: 11
<212> TYPE: PRT
<213> ORGANISM: Plasmodium vivax

<400> SEQUENCE: 420

Val Gly Asp Ser Asp Ile Ile Lys Thr Asn Glu
1 5 10

<210> SEQ ID NO 421
<211> LENGTH: 8
<212> TYPE: PRT
<213> ORGANISM: Plasmodium vivax

<400> SEQUENCE: 421

Val Gly Asn Ile Leu Leu Gly Val
1 5

<210> SEQ ID NO 422
<211> LENGTH: 15
<212> TYPE: PRT
<213> ORGANISM: Plasmodium vivax

<400> SEQUENCE: 422

Val Ile Thr Asp Val Gly Asp Ser Asp Ile Ile Lys Thr Asn Glu
1 5 10 15

<210> SEQ ID NO 423
<211> LENGTH: 15

<212> TYPE: PRT
<213> ORGANISM: Plasmodium vivax

<400> SEQUENCE: 423

Val Lys Glu Val Ile Lys Arg Lys Asn Val Ile Gly Ile Ile Pro
1 5 10 15

<210> SEQ ID NO 424
<211> LENGTH: 9
<212> TYPE: PRT
<213> ORGANISM: Plasmodium vivax

<400> SEQUENCE: 424

Val Lys Tyr Ala Lys Lys Leu Arg Asp
1 5

<210> SEQ ID NO 425
<211> LENGTH: 9
<212> TYPE: PRT
<213> ORGANISM: Plasmodium vivax

<400> SEQUENCE: 425

Val Asn Val Pro Lys Thr Arg Lys Thr
1 5

<210> SEQ ID NO 426
<211> LENGTH: 10
<212> TYPE: PRT
<213> ORGANISM: Plasmodium vivax

<400> SEQUENCE: 426

Val Asn Val Pro Lys Thr Arg Lys Thr Tyr
1 5 10

<210> SEQ ID NO 427
<211> LENGTH: 10
<212> TYPE: PRT
<213> ORGANISM: Plasmodium vivax

<400> SEQUENCE: 427

Val Asn Val Pro Lys Thr Arg Lys Thr Tyr
1 5 10

<210> SEQ ID NO 428
<211> LENGTH: 8
<212> TYPE: PRT
<213> ORGANISM: Plasmodium vivax

<400> SEQUENCE: 428

Val Pro Asn Gly Gly Met Tyr Leu
1 5

<210> SEQ ID NO 429
<211> LENGTH: 15
<212> TYPE: PRT
<213> ORGANISM: Plasmodium vivax

<400> SEQUENCE: 429

Val Arg Val Ala Asp Asn Ser Leu Lys Thr Asn Ile His Gln Tyr
1 5 10 15

<210> SEQ ID NO 430
<211> LENGTH: 11
<212> TYPE: PRT
<213> ORGANISM: Plasmodium vivax

<400> SEQUENCE: 430

Val Ser Glu Val Thr Thr Val Glu Lys Asp Glu
1 5 10

<210> SEQ ID NO 431
<211> LENGTH: 12
<212> TYPE: PRT
<213> ORGANISM: Plasmodium vivax

<400> SEQUENCE: 431

Val Ser Lys Arg Lys Lys Leu Thr Gly Arg Ala Lys
1 5 10

<210> SEQ ID NO 432
<211> LENGTH: 13
<212> TYPE: PRT
<213> ORGANISM: Plasmodium vivax

<400> SEQUENCE: 432

Val Ser Lys Arg Lys Lys Leu Thr Gly Arg Ala Lys Lys
1 5 10

<210> SEQ ID NO 433
<211> LENGTH: 8
<212> TYPE: PRT
<213> ORGANISM: Plasmodium vivax

<400> SEQUENCE: 433

Val Val Ala Pro Pro Glu Arg Lys
1 5

<210> SEQ ID NO 434
<211> LENGTH: 12
<212> TYPE: PRT
<213> ORGANISM: Plasmodium vivax

<400> SEQUENCE: 434

Val Val Val Val Lys Gly Gln Pro Arg Lys Leu Lys
1 5 10

<210> SEQ ID NO 435
<211> LENGTH: 10
<212> TYPE: PRT
<213> ORGANISM: Plasmodium vivax

<400> SEQUENCE: 435

Val Tyr Leu Ile Lys Ile Leu Met Ile Lys
1 5 10

<210> SEQ ID NO 436
<211> LENGTH: 8
<212> TYPE: PRT
<213> ORGANISM: Plasmodium vivax

<400> SEQUENCE: 436

Trp Gly Lys Tyr Gln Lys Met Lys
1 5

<210> SEQ ID NO 437
<211> LENGTH: 11
<212> TYPE: PRT
<213> ORGANISM: Plasmodium vivax

<400> SEQUENCE: 437

Trp Asn Tyr Lys Ala Ile Arg Lys Ile Ala Lys
1 5 10

<210> SEQ ID NO 438
<211> LENGTH: 8
<212> TYPE: PRT
<213> ORGANISM: Plasmodium vivax

<400> SEQUENCE: 438

Tyr Ala Ala Asn Trp Gly Gly Thr
1 5

<210> SEQ ID NO 439
<211> LENGTH: 9
<212> TYPE: PRT
<213> ORGANISM: Plasmodium vivax

<400> SEQUENCE: 439

Tyr Glu Ser Ile Glu Val Ser Lys Ile
1 5

<210> SEQ ID NO 440
<211> LENGTH: 10
<212> TYPE: PRT
<213> ORGANISM: Plasmodium vivax

<400> SEQUENCE: 440

Tyr Glu Ser Ile Glu Val Ser Lys Ile Asp
1 5 10

<210> SEQ ID NO 441
<211> LENGTH: 9
<212> TYPE: PRT
<213> ORGANISM: Plasmodium vivax

<400> SEQUENCE: 441

Tyr Phe Asp Leu Ser Arg Ala Ser Phe
1 5

<210> SEQ ID NO 442
<211> LENGTH: 10
<212> TYPE: PRT
<213> ORGANISM: Plasmodium vivax

<400> SEQUENCE: 442

Tyr Phe Asp Leu Ser Arg Ala Ser Phe Ser
1 5 10

<210> SEQ ID NO 443
<211> LENGTH: 10
<212> TYPE: PRT
<213> ORGANISM: Plasmodium vivax

<400> SEQUENCE: 443

Tyr Gly Pro Leu Lys Lys Asp Leu Lys Ala
1 5 10

<210> SEQ ID NO 444
<211> LENGTH: 12
<212> TYPE: PRT
<213> ORGANISM: Plasmodium vivax

<400> SEQUENCE: 444

Tyr Gly Arg Ile Phe Lys Lys Lys Ile Thr Lys Lys 1 5 10

<210> SEQ ID NO 445
<211> LENGTH: 13
<212> TYPE: PRT
<213> ORGANISM: Plasmodium vivax

<400> SEQUENCE: 445

Tyr Gly Arg Ile Phe Lys Lys Lys Ile Thr Lys Lys Asn
1 5 10

<210> SEQ ID NO 446
<211> LENGTH: 11
<212> TYPE: PRT
<213> ORGANISM: Plasmodium vivax

<400> SEQUENCE: 446

Tyr Ile Asn Lys Val Tyr Leu Phe Val Tyr Asn
1 5 10

<210> SEQ ID NO 447
<211> LENGTH: 10
<212> TYPE: PRT
<213> ORGANISM: Plasmodium vivax

<400> SEQUENCE: 447

Tyr Lys Ile Leu Ile Lys Asp Lys Leu Lys
1 5 10

<210> SEQ ID NO 448
<211> LENGTH: 8
<212> TYPE: PRT
<213> ORGANISM: Plasmodium vivax

<400> SEQUENCE: 448

Tyr Leu Asn Asp Leu Cys Arg Asn
1 5

<210> SEQ ID NO 449
<211> LENGTH: 15
<212> TYPE: PRT
<213> ORGANISM: Plasmodium vivax

<400> SEQUENCE: 449

Tyr Arg Gly Asp Val Val Pro Lys Asp Val Asn Ala Ala Val Ala
1 5 10 15

<210> SEQ ID NO 450
<211> LENGTH: 10
<212> TYPE: PRT
<213> ORGANISM: Plasmodium vivax

<400> SEQUENCE: 450

Tyr Arg Gly Val Val Thr Glu Glu Gly Ala
1 5 10

<210> SEQ ID NO 451
<211> LENGTH: 8
<212> TYPE: PRT
<213> ORGANISM: Plasmodium vivax

<400> SEQUENCE: 451

Tyr Arg Val Lys Gly Lys Lys Lys
1 5

<210> SEQ ID NO 452
<211> LENGTH: 9
<212> TYPE: PRT
<213> ORGANISM: Plasmodium vivax

<400> SEQUENCE: 452

Tyr Tyr Asp Asn Gly Asp Asn His Asn
1 5

<210> SEQ ID NO 453
<211> LENGTH: 14
<212> TYPE: PRT
<213> ORGANISM: Plasmodium vivax

<400> SEQUENCE: 453

Tyr Tyr Arg Val Lys Gly Lys Lys Lys Ile Leu Ile Pro Val
1 5 10

<210> SEQ ID NO 454
<211> LENGTH: 12
<212> TYPE: PRT
<213> ORGANISM: Plasmodium vivax

<400> SEQUENCE: 454

Thr Leu Ser Lys Lys Val Val Asn Arg Ala Pro Lys
1 5 10

<210> SEQ ID NO 455
<211> LENGTH: 14
<212> TYPE: PRT
<213> ORGANISM: Plasmodium vivax

<400> SEQUENCE: 455

Thr Thr Lys Val Lys Arg Val Gln Thr Phe Gly Lys Lys Lys
1 5 10

<210> SEQ ID NO 456
<211> LENGTH: 11
<212> TYPE: PRT
<213> ORGANISM: Plasmodium vivax

<400> SEQUENCE: 456

Lys Asp Cys Phe Ser Ser Ser Cys Gly Lys Thr
1 5 10

<210> SEQ ID NO 457
<211> LENGTH: 9
<212> TYPE: PRT
<213> ORGANISM: Plasmodium vivax

<400> SEQUENCE: 457

His Ala Val Phe Ile Asp Lys Ala Leu
1 5

<210> SEQ ID NO 458
<211> LENGTH: 15
<212> TYPE: PRT
<213> ORGANISM: Plasmodium vivax

<400> SEQUENCE: 458

Pro Pro Lys Glu Arg Lys Thr Lys Glu Gln Ile Ala Ala Ala Ala
1 5 10 15

<210> SEQ ID NO 459

<211> LENGTH: 15
<212> TYPE: PRT
<213> ORGANISM: Plasmodium vivax

<400> SEQUENCE: 459

Asn Ile Ser Val Leu Glu Pro Lys Thr Glu Thr Ile Glu Ala Leu
1 5 10 15

<210> SEQ ID NO 460
<211> LENGTH: 8
<212> TYPE: PRT
<213> ORGANISM: Plasmodium vivax

<400> SEQUENCE: 460

Lys Glu Arg Asn Thr Lys Pro Phe
1 5

<210> SEQ ID NO 461
<211> LENGTH: 12
<212> TYPE: PRT
<213> ORGANISM: Plasmodium vivax

<400> SEQUENCE: 461

Val Arg Val Ala Asp Asn Ser Leu Lys Thr Asn Ile
1 5 10

<210> SEQ ID NO 462
<211> LENGTH: 13
<212> TYPE: PRT
<213> ORGANISM: Plasmodium vivax

<400> SEQUENCE: 462

Lys Glu Lys Lys Gln Leu Tyr Lys Gly Lys Val Lys Lys
1 5 10

<210> SEQ ID NO 463
<211> LENGTH: 8
<212> TYPE: PRT
<213> ORGANISM: Plasmodium vivax

<400> SEQUENCE: 463

Lys Lys Asn Ala Lys Asn Val Lys
1 5

<210> SEQ ID NO 464
<211> LENGTH: 14
<212> TYPE: PRT
<213> ORGANISM: Plasmodium vivax

<400> SEQUENCE: 464

Glu Ala Lys Asn Lys Ser Arg Met Ala Gly Lys Glu Lys Asp
1 5 10

<210> SEQ ID NO 465
<211> LENGTH: 8
<212> TYPE: PRT
<213> ORGANISM: Plasmodium vivax

<400> SEQUENCE: 465

Lys Gly Lys Lys Pro Ala Lys Lys
1 5

<210> SEQ ID NO 466
<211> LENGTH: 10
<212> TYPE: PRT

<213> ORGANISM: Plasmodium vivax

<400> SEQUENCE: 466

Gly Phe Asn Ser Gly His Val Val Thr Lys
1 5 10

<210> SEQ ID NO 467
<211> LENGTH: 13
<212> TYPE: PRT
<213> ORGANISM: Plasmodium vivax

<400> SEQUENCE: 467

Lys Lys Ser Lys Thr Lys Lys Asn Thr Ile Ile Thr Lys
1 5 10

<210> SEQ ID NO 468
<211> LENGTH: 13
<212> TYPE: PRT
<213> ORGANISM: Plasmodium vivax

<400> SEQUENCE: 468

Glu Met Gly Ala Asp Lys Lys Lys Lys Gly Ala Val Tyr
1 5 10

<210> SEQ ID NO 469
<211> LENGTH: 13
<212> TYPE: PRT
<213> ORGANISM: Plasmodium vivax

<400> SEQUENCE: 469

Lys Lys Lys Ile Thr Lys Lys Asn Tyr Ile Leu Pro Lys
1 5 10

<210> SEQ ID NO 470
<211> LENGTH: 13
<212> TYPE: PRT
<213> ORGANISM: Plasmodium vivax

<400> SEQUENCE: 470

Gly Gly Lys Ser Lys Gly Lys Arg Ser Gly Thr Arg Tyr
1 5 10

<210> SEQ ID NO 471
<211> LENGTH: 14
<212> TYPE: PRT
<213> ORGANISM: Plasmodium vivax

<400> SEQUENCE: 471

Cys Ala Ser Cys Gly Tyr Pro Ser Ala Lys Lys Arg Arg Phe
1 5 10

<210> SEQ ID NO 472
<211> LENGTH: 14
<212> TYPE: PRT
<213> ORGANISM: Plasmodium vivax

<400> SEQUENCE: 472

Lys Glu Pro Leu Leu Gly Gly Leu Asn Gln Lys Gln Pro Thr
1 5 10

<210> SEQ ID NO 473
<211> LENGTH: 8
<212> TYPE: PRT
<213> ORGANISM: Plasmodium vivax

<400> SEQUENCE: 473

Ala Gly Ala Asp Ser Lys Ser Leu
1 5

<210> SEQ ID NO 474
<211> LENGTH: 14
<212> TYPE: PRT
<213> ORGANISM: Plasmodium vivax

<400> SEQUENCE: 474

Val Ser Leu Glu Pro Lys Lys Pro Met Val Val Glu Thr Phe
1 5 10

<210> SEQ ID NO 475
<211> LENGTH: 118
<212> TYPE: PRT
<213> ORGANISM: Plasmodium falciparum

<400> SEQUENCE: 475

Met Ser Lys Leu Met Lys Gly Ala Ile Asp Asn Glu Lys Tyr Arg Leu
1 5 10 15

Arg Arg Ile Arg Ile Ala Leu Thr Ser Lys Asn Leu Arg Ala Ile Glu
20 25 30

Lys Val Cys Ser Asp Ile Met Lys Gly Ala Lys Glu Lys Asn Leu Asn
35 40 45

Val Ser Gly Pro Val Arg Leu Pro Val Lys Thr Leu Arg Ile Thr Thr
50 55 60

Arg Lys Ser Pro Cys Gly Glu Gly Thr Asn Thr Trp Asp Arg Phe Glu
65 70 75 80

Leu Arg Ile Tyr Lys Arg Leu Ile Asp Leu Tyr Ser Gln Cys Glu Val
85 90 95

Val Thr Gln Met Thr Ser Ile Asn Ile Asp Pro Val Val Glu Val Glu
100 105 110

Val Ile Ile Thr Asp Ser
115

<210> SEQ ID NO 476
<211> LENGTH: 11
<212> TYPE: PRT
<213> ORGANISM: Plasmodium falciparum

<400> SEQUENCE: 476

Ala Ala Glu Glu Gly Ala Lys Ala Gly Ala Leu
1 5 10

<210> SEQ ID NO 477
<211> LENGTH: 11
<212> TYPE: PRT
<213> ORGANISM: Plasmodium falciparum

<400> SEQUENCE: 477

Asp Asn Asn Asn Tyr Asp Asp Asp Glu Ile Ile
1 5 10

<210> SEQ ID NO 478
<211> LENGTH: 13
<212> TYPE: PRT
<213> ORGANISM: Plasmodium falciparum

<400> SEQUENCE: 478

Glu Glu Tyr Asp Glu Ser Gly Pro Ser Ile Val His Arg 1 5 10

<210> SEQ ID NO 479
<211> LENGTH: 10
<212> TYPE: PRT
<213> ORGANISM: Plasmodium falciparum

<400> SEQUENCE: 479

Gly Gly Ala Thr Gly Ala Gly Leu Ala Leu
1 5 10

<210> SEQ ID NO 480
<211> LENGTH: 16
<212> TYPE: PRT
<213> ORGANISM: Plasmodium falciparum

<400> SEQUENCE: 480

Gly Lys Glu Lys Thr His Ile Asn Leu Val Val Ile Gly His Val Asp
1 5 10 15

<210> SEQ ID NO 481
<211> LENGTH: 10
<212> TYPE: PRT
<213> ORGANISM: Plasmodium falciparum

<400> SEQUENCE: 481

His Gly Asn Asn Met Asn Thr Cys Leu Met
1 5 10

<210> SEQ ID NO 482
<211> LENGTH: 9
<212> TYPE: PRT
<213> ORGANISM: Plasmodium falciparum

<400> SEQUENCE: 482

Lys Ile Tyr Glu Lys Lys Ile Leu Lys
1 5

<210> SEQ ID NO 483
<211> LENGTH: 8
<212> TYPE: PRT
<213> ORGANISM: Plasmodium falciparum

<400> SEQUENCE: 483

Lys Thr Ala Thr Leu Gly Val Ile
1 5

<210> SEQ ID NO 484
<211> LENGTH: 8
<212> TYPE: PRT
<213> ORGANISM: Plasmodium falciparum

<400> SEQUENCE: 484

Leu Glu Gly Lys Glu Leu Pro Gly
1 5

<210> SEQ ID NO 485
<211> LENGTH: 16
<212> TYPE: PRT
<213> ORGANISM: Plasmodium falciparum

<400> SEQUENCE: 485

Leu Val Ile Thr Asp Val Gly Asp Ser Asp Ile Ile Lys Thr Asn Glu
1 5 10 15

<210> SEQ ID NO 486
<211> LENGTH: 9
<212> TYPE: PRT
<213> ORGANISM: Plasmodium falciparum

<400> SEQUENCE: 486

Asn Glu Ala Glu Glu Phe Glu Asp Tyr
1               5

<210> SEQ ID NO 487
<211> LENGTH: 9
<212> TYPE: PRT
<213> ORGANISM: Plasmodium falciparum

<400> SEQUENCE: 487

Pro Glu Glu Val Ala Glu Glu Leu Val
1               5

<210> SEQ ID NO 488
<211> LENGTH: 8
<212> TYPE: PRT
<213> ORGANISM: Plasmodium falciparum

<400> SEQUENCE: 488

Pro Gln Asn Ile Asn Glu Tyr Phe
1               5

<210> SEQ ID NO 489
<211> LENGTH: 10
<212> TYPE: PRT
<213> ORGANISM: Plasmodium falciparum

<400> SEQUENCE: 489

Gln Gly Gly Gly Ser Pro Leu Leu Gly Thr
1               5                   10

<210> SEQ ID NO 490
<211> LENGTH: 11
<212> TYPE: PRT
<213> ORGANISM: Plasmodium falciparum

<400> SEQUENCE: 490

Gln Gly Ile Ser Asp Asp Ser Ser Ile His His
1               5                   10

<210> SEQ ID NO 491
<211> LENGTH: 9
<212> TYPE: PRT
<213> ORGANISM: Plasmodium falciparum

<400> SEQUENCE: 491

Ser Leu Gly Ser Ser Ile Leu Thr Lys
1               5

<210> SEQ ID NO 492
<211> LENGTH: 10
<212> TYPE: PRT
<213> ORGANISM: Plasmodium falciparum

<400> SEQUENCE: 492

Ser Leu Asn Asp Ala Leu Ile Val Ser Ile
1               5                   10

<210> SEQ ID NO 493

<211> LENGTH: 8
<212> TYPE: PRT
<213> ORGANISM: Plasmodium falciparum

<400> SEQUENCE: 493

Val Ala Asn Lys Ile Gly Ile Leu
1               5

<210> SEQ ID NO 494
<211> LENGTH: 15
<212> TYPE: PRT
<213> ORGANISM: Plasmodium falciparum

<400> SEQUENCE: 494

Val Ile Thr Asp Val Gly Asp Ser Asp Ile Ile Lys Thr Asn Glu
1               5                   10                  15

<210> SEQ ID NO 495
<211> LENGTH: 8
<212> TYPE: PRT
<213> ORGANISM: Plasmodium falciparum

<400> SEQUENCE: 495

Val Leu Pro Glu Leu Asn Gly Lys
1               5

<210> SEQ ID NO 496
<211> LENGTH: 136
<212> TYPE: PRT
<213> ORGANISM: Plasmodium vivax

<400> SEQUENCE: 496

Met Asp Lys Met Leu Pro His His Lys Tyr Ser Tyr Ile Pro Lys Gln
1               5                   10                  15

Asn Lys Lys Leu Ile Tyr Glu Tyr Leu Phe Lys Glu Gly Val Ile Val
            20                  25                  30

Val Glu Lys Asp Ala Lys Val Pro Arg His Pro His Leu Asn Ile Pro
        35                  40                  45

Asn Leu His Ile Met Met Thr Leu Lys Ser Leu Lys Ser Arg Asn Tyr
    50                  55                  60

Val Asp Glu Lys Tyr Asn Trp Lys His Gln Tyr Phe Ile Leu Asn Asn
65                  70                  75                  80

Glu Gly Ile Glu Tyr Leu Arg Glu Phe Leu His Leu Pro Pro Ser Ile
                85                  90                  95

Phe Pro Ala Thr Leu Ser Lys Lys Val Val Asn Arg Ala Pro Lys Met
            100                 105                 110

Glu Glu Glu Phe Ser Arg Glu Leu Arg Gln Pro Met Gly Arg Gly Arg
        115                 120                 125

Ser Tyr Asp Lys Arg Ala Phe Glu
    130                 135

<210> SEQ ID NO 497
<211> LENGTH: 161
<212> TYPE: PRT
<213> ORGANISM: Plasmodium vivax

<400> SEQUENCE: 497

Met Ala Thr Thr Leu Asp Val Gln His Glu Arg Ala Tyr Gln Lys Gln
1               5                   10                  15

Glu Gly Ala Ser Phe Phe Asn Ser Lys Lys Ile Lys Lys Gly Ser Lys
            20                  25                  30

Ser Tyr Thr Arg Tyr Trp Lys Lys Val Gly Leu Gly Phe Ala Thr Pro
35 40 45

Lys Glu Ala Lys Glu Gly Val Tyr Val Asp Lys Lys Cys Pro Phe Thr
50 55 60

Gly Asn Val Ser Ile Arg Gly Arg Ile Leu Lys Gly Met Val Ile Ser
65 70 75 80

Ser Lys Met Lys Arg Thr Ile Ile Ile Arg Arg Asn Tyr Leu His Tyr
85 90 95

Val Lys Lys Tyr Asn Arg Phe Glu Lys Arg His Lys Asn Ile Pro Cys
100 105 110

His Cys Ser Pro Cys Phe Asp Val Lys Glu Gly Asp Ile Val Thr Val
115 120 125

Gly Gln Cys Arg Pro Leu Ser Lys Thr Val Arg Phe Asn Val Leu His
130 135 140

Val Glu Lys His Gln Ile Phe Gly Ser Ala Arg Lys Gln Phe Val Leu
145 150 155 160

Phe

<210> SEQ ID NO 498
<211> LENGTH: 143
<212> TYPE: PRT
<213> ORGANISM: Plasmodium vivax

<400> SEQUENCE: 498

Met Thr Asp Val Glu Ser Val Asp Asn Asn Val Val Val Glu Glu Lys
1 5 10 15

Thr Val Phe Asp His Thr Thr Ala Ile Gln Lys Val Leu Lys Asn Ala
20 25 30

Leu Val His Asp Gly Leu Lys Ile Gly Ile Arg Glu Val Ile Lys Ser
35 40 45

Ile Glu Ser Lys Glu Ala Lys Ala Cys Phe Leu Ser Asp Val Cys Ser
50 55 60

Glu Pro Ala Tyr Lys Lys Leu Ile Thr Ala Leu Cys Thr Glu Lys Asn
65 70 75 80

Ile Pro Leu Phe Met Val Glu Asn Asp Ser Lys Asp Leu Gly Gln Trp
85 90 95

Val Gly Leu Phe Lys Leu Asp Lys Glu Gly Asn Ala Arg Lys Ile Ile
100 105 110

Gly Ala Ser Ser Val Ser Ile Ile Asp Phe Gly Glu Glu Ser Ala Glu
115 120 125

Arg Asp Tyr Leu Met Gln Gln Gln Asn Gln Pro Ala Ala Ala Ala
130 135 140

<210> SEQ ID NO 499
<211> LENGTH: 151
<212> TYPE: PRT
<213> ORGANISM: Plasmodium vivax

<400> SEQUENCE: 499

Met Gly Arg Met Tyr Gly Lys Gly Lys Gly Ile Ser Ser Ser Thr Ile
1 5 10 15

Pro Tyr Lys Arg Lys Gln Pro Ser Trp Leu Lys Gln Lys Pro Ser Glu
20 25 30

Ile Glu Asp Ala Ile Ile Lys Leu Ala Lys Lys Gly Gln Thr Pro Ser
35 40 45

Gln Ile Gly Ala Thr Leu Arg Asp Asn Tyr Gly Ile Pro Gln Val Lys
    50                  55                  60

Ala Val Thr Gly Asn Lys Ile Leu Arg Ile Leu Arg Ala His Gly Val
65                  70                  75                  80

Ala Thr Thr Ile Pro Glu Asp Leu Tyr Phe Leu Ile Lys Lys Ala Val
                85                  90                  95

Ser Met Arg Lys His Leu Glu Lys Asn Lys Lys Asp Lys Asp Cys Lys
            100                 105                 110

Phe Arg Leu Ile Leu Thr Glu Ser Lys Ile His Arg Ile Ser Arg Tyr
        115                 120                 125

Tyr Lys Arg Lys Lys Leu Leu Pro Ser Asn Trp Lys Tyr Gln Ser Ser
    130                 135                 140

Thr Ala Ser Ala Leu Ile Ala
145                 150

<210> SEQ ID NO 500
<211> LENGTH: 151
<212> TYPE: PRT
<213> ORGANISM: Plasmodium vivax

<400> SEQUENCE: 500

Met Ala Ser Lys Lys Val Lys Ala Pro Gln Pro Glu Thr Ala Ile Val
1               5                   10                  15

Ser Gly Pro Gln Pro Lys Glu Gly Glu Leu Val Phe Gly Val Ala His
            20                  25                  30

Ile Phe Ala Ser Phe Asn Asp Thr Phe Ile His Val Thr Asp Leu Ser
        35                  40                  45

Gly Arg Glu Thr Leu Val Arg Ile Thr Gly Gly Met Lys Val Lys Ala
    50                  55                  60

Asp Arg Asp Glu Ser Ser Pro Tyr Ala Ala Met Met Ala Ala Gln Asp
65                  70                  75                  80

Val Ala Ala Arg Leu Lys Glu Leu Gly Val Ser Ala Ile His Ile Lys
                85                  90                  95

Leu Arg Ala Ser Gly Gly Thr Lys Ser Lys Thr Pro Gly Pro Gly Ala
            100                 105                 110

Gln Ser Ala Leu Arg Ala Leu Ala Arg Ser Gly Leu Lys Ile Gly Arg
        115                 120                 125

Ile Glu Asp Val Thr Pro Ile Pro Thr Asp Ser Thr Arg Lys Lys Ser
    130                 135                 140

Gly Arg Arg Gly Arg Arg Leu
145                 150

<210> SEQ ID NO 501
<211> LENGTH: 145
<212> TYPE: PRT
<213> ORGANISM: Plasmodium vivax

<400> SEQUENCE: 501

Met Glu Asp Ala Asn Lys Pro Lys Lys Arg Thr Phe Arg Thr Phe His
1               5                   10                  15

Tyr Arg Gly Val Glu Leu Asp Lys Leu Leu Asp Leu Ser Gln Asp Glu
            20                  25                  30

Leu Val Lys Leu Phe Arg Ala Arg Gln Arg Arg Lys Phe Lys Arg Gly
        35                  40                  45

Ile Ser Lys Lys Glu Lys Ser Leu Leu Lys Lys Leu Arg Lys Ala Lys
    50                  55                  60

Lys Glu Cys Glu Val Gly Glu Lys Pro Arg Ala Ile Pro Thr His Leu
65 70 75 80

Arg Asn Met Thr Ile Ile Pro Glu Met Val Gly Ser Ile Val Ala Val
85 90 95

His Asn Gly Lys Gln Tyr Asn Asn Val Glu Ile Lys Pro Glu Met Ile
100 105 110

Gly Tyr Tyr Leu Gly Glu Phe Ser Ile Thr Tyr Lys His Thr Arg His
115 120 125

Gly Lys Pro Gly Ile Gly Ala Thr His Ser Ser Arg Phe Ile Pro Leu
130 135 140

Lys
145

<210> SEQ ID NO 502
<211> LENGTH: 130
<212> TYPE: PRT
<213> ORGANISM: Plasmodium vivax

<400> SEQUENCE: 502

Met Val Arg Met Ser Val Leu Ala Asp Cys Leu Lys Thr Ile Asn Asn
1 5 10 15

Ala Glu Lys Arg Gly Arg Arg Gln Val Leu Ile Arg Pro Ser Ser Lys
20 25 30

Val Val Val Lys Phe Leu Gln Tyr Met Gln Lys Lys Gly Tyr Ile Gly
35 40 45

Asn Phe Glu Ile Val Asp Asp His Arg Ser Gly Lys Ile Val Val Asn
50 55 60

Leu Leu Gly Arg Ile Asn Lys Cys Ala Val Ile Ser Pro Arg Tyr Asp
65 70 75 80

Val Lys Leu Asp Glu Ile Glu Lys Ile Ile Thr Asn Ile Leu Pro Ser
85 90 95

Arg Leu Phe Gly His Leu Ile Leu Thr Thr Pro Tyr Gly Ile Met Asp
100 105 110

His Glu Glu Ala Arg Arg Lys His Thr Gly Gly Lys Val Leu Gly Phe
115 120 125

Phe Phe
130

<210> SEQ ID NO 503
<211> LENGTH: 144
<212> TYPE: PRT
<213> ORGANISM: Plasmodium vivax

<400> SEQUENCE: 503

Met Thr Thr Lys Val Lys Arg Val Gln Thr Phe Gly Lys Lys Lys Thr
1 5 10 15

Ser Val Ala Val Ala Thr Val Thr Asn Gly Lys Gly Leu Ile Lys Leu
20 25 30

Asn Gly Lys Asn Leu Asp Leu Val Glu Pro Tyr Ile Leu Arg Thr Lys
35 40 45

Val Tyr Glu Pro Leu Trp Leu Ile Gly Ser Ala Lys Leu Lys Asn Leu
50 55 60

Asp Ile Arg Ile Arg Val Lys Gly Gly Gly Gln Thr Ala Gln Ile Tyr
65 70 75 80

Ala Ile Arg Gln Ala Ile Gly Lys Gly Val Ile Ser Tyr Tyr Gln Lys
85 90 95

```
Tyr Val Asp Glu Ser Thr Lys Lys Glu Leu Lys Asp Ala Leu Leu Arg
            100                 105                 110

Tyr Asp Arg Thr Leu Leu Val Gly Asp Thr Arg Arg Cys Glu Pro Lys
        115                 120                 125

Lys Phe Gly Gly Lys Gly Ala Arg Ala Arg Tyr Gln Lys Ser Tyr Arg
    130                 135                 140


<210> SEQ ID NO 504
<211> LENGTH: 137
<212> TYPE: PRT
<213> ORGANISM: Plasmodium vivax

<400> SEQUENCE: 504

Met Gly Arg Val Arg Thr Lys Thr Ile Lys Arg Ala Ala Arg Gln Ile
1               5                   10                  15

Val Glu Lys Tyr Tyr Ala Lys Leu Thr Leu Asp Phe Gln Ile Asn Lys
            20                  25                  30

Lys Ile Thr Glu Glu Val Ala Ile Ile Pro Ser Lys Arg Met Lys Asn
        35                  40                  45

Lys Val Ala Gly Phe Val Thr His Leu Met Lys Arg Ile Gln Lys Gly
    50                  55                  60

Pro Val Arg Gly Ile Ser Leu Lys Leu Gln Glu Glu Glu Arg Glu Arg
65                  70                  75                  80

Arg Leu Asp Phe Val Pro Glu Lys Ser Gln Ile Asp Val Asn Val Ile
                85                  90                  95

Tyr Val Glu Pro Asp Thr Val Arg Met Ile Lys Ala Leu Gly Ile Asn
            100                 105                 110

Ile Ser Asn Met Lys Val His Asn Pro Met Ile Asn Ser Asn Gln Gln
        115                 120                 125

Lys Gln Asn Arg Met Asn Thr His Tyr
    130                 135


<210> SEQ ID NO 505
<211> LENGTH: 156
<212> TYPE: PRT
<213> ORGANISM: Plasmodium vivax

<400> SEQUENCE: 505

Met Ser Leu Gln Val Met Asp Gln Asn Asp Phe Gln His Ile Leu Arg
1               5                   10                  15

Ile Leu Asn Thr Asn Val Asp Gly Lys Glu Lys Val Thr Ile Ala Leu
            20                  25                  30

Thr Ala Ile Lys Gly Ile Gly Lys Arg Met Ala Thr Val Ile Cys Lys
        35                  40                  45

Gln Ala Asn Val Asp Ser Thr Lys Arg Ala Gly Glu Leu Thr Thr Glu
    50                  55                  60

Glu Ile Asn Asn Ile Val His Ile Met Asn Ala Pro Ser Gln Phe Lys
65                  70                  75                  80

Ile Pro Asp Trp Phe Leu Asn Arg Arg Lys Asp Val Lys Glu Gly Lys
                85                  90                  95

Asn Leu His Val Ile Ala Asn Gln Leu Asp Ser Tyr Leu Arg Glu Asp
            100                 105                 110

Leu Glu Arg Met Lys Lys Ile Arg Leu His Arg Gly Leu Arg His His
        115                 120                 125

Trp Gly Leu Arg Val Arg Gly Gln His Thr Lys Thr Thr Gly Arg Arg
    130                 135                 140
```

Gly Arg Thr Val Gly Val Ser Lys Lys Lys Gly Ala
145 150 155

<210> SEQ ID NO 506
<211> LENGTH: 172
<212> TYPE: PRT
<213> ORGANISM: Plasmodium vivax

<400> SEQUENCE: 506

Met Ala Glu Glu Phe Thr Glu Asp Ile Gly Val Val Asn Lys Arg Leu
1 5 10 15

Leu Glu Pro Val Pro Phe Val Arg Thr Asn Asn Cys Ile Lys Asp Val
20 25 30

Asp Ser Glu Leu Phe Ile Lys Ala Tyr Ala Ser Tyr Leu Lys Leu His
35 40 45

Asn Lys Ile Thr Phe Pro Lys Trp Cys Asn Phe Val Lys Thr Gly Lys
50 55 60

Gly Arg Lys Leu Ala Pro Leu Asn Glu Asp Trp Tyr Phe Val Lys Ala
65 70 75 80

Ser Ser Ile Leu Arg Lys Leu Tyr Leu Ser Pro Asp Ile Gly Val Gly
85 90 95

Phe Leu Arg Arg His Tyr Ser Tyr Lys Gln Arg Arg Gly Val Ala Pro
100 105 110

Asn His Thr Ser Leu Ala Ser Gly Lys Ile Leu Arg Ser Ile Leu Gln
115 120 125

Gln Leu Glu Asn Leu Gly Tyr Val Glu Gln Asn Pro Lys Lys Lys Gly
130 135 140

Arg Arg Leu Thr Thr Lys Gly Glu Asn Ala Ile Asn Asn Phe Ala Arg
145 150 155 160

Tyr Ile Asn Lys Lys Val Tyr Lys Leu Asp Lys Glu
165 170

<210> SEQ ID NO 507
<211> LENGTH: 274
<212> TYPE: PRT
<213> ORGANISM: Plasmodium vivax

<400> SEQUENCE: 507

Met Glu Gly Asp Arg Gly Gly Phe Ser Arg Gly Phe Gly Arg Gly Met
1 5 10 15

Arg Gly Ala Arg Gly Gly Arg Gly Arg Gly Arg Gly Arg Gly Arg Gly
20 25 30

Arg Gly Ser Ala Glu Asp Asp Leu Lys Asn Trp Val Pro Val Thr Lys
35 40 45

Leu Gly Arg Leu Val Lys Glu Gly Lys Ile Val Ser Ile Glu Glu Ile
50 55 60

Tyr Leu His Ser Leu Pro Ile Lys Glu Tyr Gln Ile Ile Asp Tyr Phe
65 70 75 80

Phe Gln Pro Gly Glu Cys Ala His Pro Leu Lys Asp Asp Val Val Lys
85 90 95

Ile Met Pro Val Gln Lys Gln Thr Arg Ala Gly Gln Arg Thr Arg Phe
100 105 110

Lys Ala Phe Val Ala Ile Gly Asp Gly Asn Gly His Cys Gly Leu Gly
115 120 125

Val Lys Cys Ala Lys Glu Val Ala Thr Ala Ile Arg Gly Ala Ile Ile
130 135 140

Ala Ala Lys Leu Ser Leu Ile Pro Val Arg Arg Gly Tyr Trp Gly Asn
145 150 155 160

Lys Ile Gly Asp Pro His Thr Val Pro Met Lys Val Ser Gly Lys Cys
165 170 175

Gly Ser Val Arg Ile Arg Leu Val Pro Ala Pro Arg Gly Thr Gln Ile
180 185 190

Val Gly Ala Pro Thr Thr Lys Lys Met Leu Asn Phe Ala Gly Ile Lys
195 200 205

Asp Cys Phe Ser Ser Ser Cys Gly Lys Thr Lys Thr Arg Gly Asn Phe
210 215 220

Leu Arg Ala Ile Phe Asn Ala Leu Ser Lys Thr Tyr Gly Tyr Leu Thr
225 230 235 240

Pro Asp Leu Trp Lys Val Thr Lys Phe Asp Lys Ser Pro Tyr Glu Glu
245 250 255

Trp Ser Asp Phe Leu Glu Thr Tyr Gln Asn Met Lys Ile Gln Lys Gln
260 265 270

Thr Pro

<210> SEQ ID NO 508
<211> LENGTH: 82
<212> TYPE: PRT
<213> ORGANISM: Plasmodium vivax

<400> SEQUENCE: 508

Met Phe Asn Asp Gln Lys Val Leu Val Asp Ile Tyr Ile Pro Arg Lys
1 5 10 15

Cys Ser Ala Thr Ser Arg Leu Ile Pro Ala Lys Glu His Gly Ala Val
20 25 30

Gln Ile Asn Val Gly Met Val Asn Lys Asn Gly Val Tyr Thr Gly Glu
35 40 45

Met Glu Thr Phe Ala Ile Ala Gly His Val Arg Gln Lys Gly Glu Ser
50 55 60

Asp Ala Cys Leu Asn Arg Leu Leu His Glu Lys Thr Met Leu Ser Phe
65 70 75 80

Ser Asn

<210> SEQ ID NO 509
<211> LENGTH: 145
<212> TYPE: PRT
<213> ORGANISM: Plasmodium vivax

<400> SEQUENCE: 509

Met Gly Ser Gly Lys Pro Ser Gly Leu Arg Ala Ala Arg Lys Leu Arg
1 5 10 15

Ile Arg Arg Arg Thr Gln Arg Trp Ala Asp Lys Gly Tyr Lys Lys Ser
20 25 30

His Leu Gly Thr Arg Trp Lys Ser Asn Pro Phe Arg Gly Ser Ser His
35 40 45

Ala Lys Gly Ile Val Val Glu Lys Val Ala Ile Glu Ala Lys Gln Pro
50 55 60

Asn Ser Ala Tyr Arg Lys Cys Val Arg Val Gln Leu Ile Lys Asn Gly
65 70 75 80

Lys Lys Ile Thr Ala Phe Val Pro Gly Asp Gly Cys Leu Asn Phe Ile
85 90 95

Asp Glu Asn Asp Glu Val Leu Val Ser Gly Phe Gly Arg Ser Gly His
100 105 110

Ser Val Gly Asp Leu Pro Gly Val Lys Phe Lys Val Val Lys Val Ala
115 120 125

Arg Val Ser Leu Leu Ala Leu Phe Lys Glu Lys Lys Glu Lys Pro Arg
130 135 140

Ser
145

<210> SEQ ID NO 510
<211> LENGTH: 133
<212> TYPE: PRT
<213> ORGANISM: Plasmodium vivax

<400> SEQUENCE: 510

Met Ala Glu Gln Phe Thr Ile Arg Val Lys Lys Tyr Met Ser Asn Pro
1 5 10 15

Leu Leu Arg Arg Lys Gln Phe Ala Leu Glu Ile Leu His Pro Asn Lys
20 25 30

Gly Ser Val Ser Lys Lys Asp Val Lys Glu Arg Leu Ala Lys Met Tyr
35 40 45

Lys Leu Asn Asn Val Asn Thr Ile Val Leu Phe Gly Phe Lys Ser Leu
50 55 60

Phe Gly Gly Gly Arg Thr Lys Gly Phe Gly Leu Ile Tyr Asn Ser Val
65 70 75 80

Asp Ala Val Lys Lys Phe Glu Lys Lys Tyr Arg Gln Ile Arg Glu Gly
85 90 95

Leu Ile Thr Lys Glu Asn Lys Pro Gly Arg Arg Ala Ala Lys Glu Leu
100 105 110

Lys Asn Arg Arg Lys Lys Val Arg Gly Thr Ala Lys Thr Lys Val Ser
115 120 125

Gly Ala Lys Lys Lys
130

<210> SEQ ID NO 511
<211> LENGTH: 133
<212> TYPE: PRT
<213> ORGANISM: Plasmodium vivax

<400> SEQUENCE: 511

Met Ala Glu Gln Phe Thr Ile Arg Val Lys Lys Tyr Met Ser Asn Pro
1 5 10 15

Leu Leu Arg Arg Lys Gln Phe Ala Leu Glu Ile Leu His Pro Asn Lys
20 25 30

Gly Ser Val Ser Lys Lys Asp Val Lys Glu Arg Leu Ala Lys Met Tyr
35 40 45

Lys Leu Asn Asn Val Asn Thr Ile Val Leu Phe Gly Phe Lys Ser Leu
50 55 60

Phe Gly Gly Gly Arg Thr Lys Gly Phe Gly Leu Ile Tyr Asn Ser Val
65 70 75 80

Asp Ala Val Lys Lys Phe Glu Lys Lys Tyr Arg Gln Ile Arg Glu Gly
85 90 95

Leu Ile Thr Lys Glu Asn Lys Pro Gly Arg Arg Ala Ala Lys Glu Leu
100 105 110

Lys Asn Arg Arg Lys Lys Val Arg Gly Thr Ala Lys Thr Lys Val Ser
115 120 125

Gly Ala Lys Lys Lys
130

<210> SEQ ID NO 512
<211> LENGTH: 107
<212> TYPE: PRT
<213> ORGANISM: Plasmodium vivax

<400> SEQUENCE: 512

Met Pro Lys Lys Arg Arg Asn Gly Gly Arg Ser Lys His Asn Arg Gly
1               5                   10                  15

His Val Asn Pro Leu Arg Cys Ser Asn Cys Gly Arg Cys Val Pro Lys
            20                  25                  30

Asp Lys Ala Ile Lys Arg Phe Asn Ile Arg Asn Ile Val Asp Thr Ser
        35                  40                  45

Ala Gln Arg Asp Ile Lys Glu Ala Ser Val Tyr Ser Thr Phe Gln Leu
    50                  55                  60

Pro Lys Leu Tyr Ile Lys Gln Cys Tyr Cys Val Ser Cys Ala Ile His
65                  70                  75                  80

Ser Arg Phe Val Arg Val Arg Ser Arg Glu Gln Arg Arg Val Arg Lys
                85                  90                  95

Glu Thr Ser Lys His Val Asn Pro Ser Gln Leu
            100                 105

<210> SEQ ID NO 513
<211> LENGTH: 82
<212> TYPE: PRT
<213> ORGANISM: Plasmodium vivax

<400> SEQUENCE: 513

Met Asn Val Asp Leu Leu Asn Arg Asp Pro Ala Glu Glu Ala Lys Lys
1               5                   10                  15

His Lys Leu Lys Arg Leu Ile Pro Ser Pro Asn Ser Tyr Phe Met Asp
            20                  25                  30

Val Lys Cys Pro Gly Cys Leu Gln Ile Thr Thr Leu Phe Ser His Ala
        35                  40                  45

Gln Asn Val Val Leu Cys Gly Ser Cys Asn Ile Met Leu Cys Gln Pro
    50                  55                  60

Thr Gly Gly Lys Cys Lys Leu Thr Glu Gly Cys Ser Phe Arg Lys Lys
65                  70                  75                  80

Ile Glu

<210> SEQ ID NO 514
<211> LENGTH: 59
<212> TYPE: PRT
<213> ORGANISM: Plasmodium vivax

<400> SEQUENCE: 514

Met Gly Cys Ile Gln Asn Val His Pro Lys Lys Tyr Gly Gln Gly Ser
1               5                   10                  15

Arg Gln Cys Arg Val Cys Ser Asn Arg His Ala Ile Ile Arg Lys Tyr
            20                  25                  30

Asn Ile Asn Ile Cys Arg Gln Cys Phe Arg Glu Arg Ala Asp Ile Ile
        35                  40                  45

Gly Phe Lys Lys Val Arg Thr Tyr Leu Trp Glu
    50                  55

<210> SEQ ID NO 515
<211> LENGTH: 222
<212> TYPE: PRT

<213> ORGANISM: Plasmodium vivax

<400> SEQUENCE: 515

Met Ser Ala Pro Ile Ser Lys Lys Arg Lys Phe Ile Asn Asp Gly Val
1               5                   10                  15

Phe Gln Ala Glu Leu Asn Glu Phe Leu Ala Arg Ile Leu Ala Glu Asp
            20                  25                  30

Gly Tyr Ser Gly Val Glu Val Arg Val Thr Pro Ile Arg Thr Glu Val
        35                  40                  45

Ile Ile Arg Ala Thr Arg Thr Arg Glu Val Leu Gly Asp Lys Gly Arg
    50                  55                  60

Arg Ile Arg Glu Leu Thr Ser Leu Val Gln Lys Arg Phe Phe Asn Lys
65                  70                  75                  80

Ser Thr Asn Ser Val Glu Leu Phe Ala Glu Arg Val Glu His Arg Gly
                85                  90                  95

Leu Cys Ala Met Ala Gln Ala Glu Ser Leu Arg Tyr Lys Leu Leu Lys
            100                 105                 110

Gly Leu Ala Val Arg Arg Ala Cys Tyr Gly Val Leu Arg His Ile Met
        115                 120                 125

Glu Ser Gly Ala Lys Gly Cys Glu Val Ile Val Ser Gly Lys Leu Arg
    130                 135                 140

Ala Gln Arg Ala Lys Ser Met Lys Phe Arg Asp Gly Tyr Leu Ile Ser
145                 150                 155                 160

Thr Gly Glu Pro Ser Lys Arg Phe Val Asn Thr Ala Thr Arg Ser Ala
                165                 170                 175

Gln Leu Lys Gln Gly Val Leu Gly Ile Lys Val Lys Ile Met Leu Pro
            180                 185                 190

Thr Ala Val Asp Ser Lys Thr Gly Leu Pro Ser Ile Leu Pro Asp Asn
        195                 200                 205

Ile Ser Val Leu Glu Pro Lys Thr Glu Thr Ile Glu Ala Leu
    210                 215                 220

<210> SEQ ID NO 516
<211> LENGTH: 58
<212> TYPE: PRT
<213> ORGANISM: Plasmodium vivax

<400> SEQUENCE: 516

Met Gly Lys Val His Gly Ser Leu Ala Arg Ala Gly Lys Val Lys Asn
1               5                   10                  15

Gln Thr Pro Lys Val Pro Lys Val Ser Lys Arg Lys Lys Leu Thr Gly
            20                  25                  30

Arg Ala Lys Lys Arg Gln Leu Tyr Asn Arg Arg Phe Ser Asp Gly Thr
        35                  40                  45

Gly Arg Lys Lys Gly Pro Asn Ser Lys Leu
    50                  55

<210> SEQ ID NO 517
<211> LENGTH: 262
<212> TYPE: PRT
<213> ORGANISM: Plasmodium vivax

<400> SEQUENCE: 517

Met Ala Val Gly Lys Asn Lys Arg Thr Ser Lys Gly Lys Lys Gly Gly
1               5                   10                  15

Lys Lys Lys Val Thr Asp Val Phe Thr Lys Lys Glu Trp Tyr Asp Leu
            20                  25                  30

```
Lys Ala Pro Lys Met Phe Leu Val Arg Asn Phe Gly Lys Thr Leu Val
        35                  40                  45

Thr Lys Thr Ile Gly Lys Lys Leu Ala Thr Asp Gly Leu Lys Gly Arg
    50                  55                  60

Ile Tyr Glu Val Asn Leu Ala Asp Leu Asn Asn Asp Glu Asp Gln Ala
65                  70                  75                  80

His Lys Lys Ile Lys Leu Cys Cys Asp His Ile Ile Asn Lys Asp Cys
                85                  90                  95

Tyr Thr Asp Phe Cys Gly Leu Ser Ile Thr Arg Asp Lys Leu Cys Ser
            100                 105                 110

Leu Ile Arg Lys Gly Tyr Thr Leu Ile Glu Gly Tyr Thr Asp Val Lys
        115                 120                 125

Thr Ile Asp Asn Tyr Gln Leu Arg Met Phe Cys Ile Ala Phe Thr Lys
    130                 135                 140

Lys Arg Pro Asn Gln Thr Lys Thr Thr Cys Tyr Ala Gln Thr Ser Gln
145                 150                 155                 160

Ile Lys Lys Ile Arg Lys Lys Met Val Asp Ile Met Asn Ala Glu Ala
                165                 170                 175

Ser Lys Val Met Leu Lys Asp Leu Val Lys Lys Phe Ile Pro Glu Ser
            180                 185                 190

Ile Gly Lys Glu Val Glu Lys Gln Cys Lys Lys Ile Tyr Pro Leu Gln
        195                 200                 205

Asn Val Leu Ile Arg Lys Val Lys Ile Leu Lys Arg Pro Lys Leu Asp
    210                 215                 220

Ile Ser Lys Leu Met Glu Leu His Thr Asp Ser Lys Glu Asp Ala Gly
225                 230                 235                 240

Lys Asn Val Lys Ser Leu Pro Glu Ser Lys Glu Ala Thr Asn Ile Leu
                245                 250                 255

Ser Ala Glu Leu Lys His
            260


<210> SEQ ID NO 518
<211> LENGTH: 261
<212> TYPE: PRT
<213> ORGANISM: Plasmodium vivax

<400> SEQUENCE: 518

Met Gly Lys Gly Ile Lys Lys His Met Lys Arg Val Asn Ala Pro Ser
1               5                   10                  15

His Trp Met Leu Asn Lys Met Gly Gly Gln Tyr Ala Pro Lys Thr Ser
            20                  25                  30

Ser Gly Pro His Arg Leu Ile Glu Ser Ile Pro Leu Val Ile Leu Leu
        35                  40                  45

Arg Asn Arg Leu Lys Tyr Ala Leu Thr Phe Asp Glu Val Lys Met Ile
    50                  55                  60

Leu Ile Gln Lys Ile Val Lys Val Asp Asn Lys Ile Arg Thr Asp Cys
65                  70                  75                  80

Thr Phe Pro Val Gly Leu Met Asp Val Ile His Ile Thr Lys Ser Asn
                85                  90                  95

Glu Tyr Phe Arg Leu Leu Tyr Asp Ile Lys Gly Arg Phe Val Pro His
            100                 105                 110

Arg Ile Thr Asn Glu Glu Ser Lys Tyr Lys Leu Cys Lys Val Lys Lys
        115                 120                 125

Met Ile Leu Arg Lys Gly Arg Leu Ser Ile Ala Val Thr His Asp Gly
```

```
    130                 135                 140

Arg Ser Ile Pro Tyr Ile His Pro Asp Val Lys Val Asn Asp Thr Val
145                 150                 155                 160

Arg Leu Asp Leu Glu Thr Gly Lys Val Leu Glu His Leu Lys Phe Gln
                165                 170                 175

Ile Gly Ser Met Val Met Val Thr Ala Gly His Ser Val Gly Arg Val
            180                 185                 190

Gly Ile Ile Ser Ser Ile Asp Lys Asn Ile Gly Thr Tyr Asp Ile Ile
        195                 200                 205

His Val Lys Asp Ser Arg Gly Lys Ile Phe Ala Thr Arg Leu Ser Asn
    210                 215                 220

Val Phe Val Ile Gly Asp Asn Ser Lys Pro Tyr Ile Ser Leu Pro Arg
225                 230                 235                 240

Glu Lys Gly Ile Lys Leu Asp Ile Ile Glu Glu Arg Arg Asn Lys Leu
                245                 250                 255

Lys Ala Gln Asn Asn
            260


<210> SEQ ID NO 519
<211> LENGTH: 195
<212> TYPE: PRT
<213> ORGANISM: Plasmodium vivax

<400> SEQUENCE: 519

Met Glu Ser Thr Thr Ala Asp Ile Lys Leu Phe Lys Lys Trp Ser Tyr
1               5                   10                  15

Glu Asp Val Asn Ile Ala Asp Leu Ser Leu Val Asp Cys Ile Ala Val
            20                  25                  30

Ser Gln Lys Ala Cys Val Tyr Thr Pro His Thr Ala Gly Arg Tyr Gln
        35                  40                  45

Lys Lys Arg Phe Arg Lys Ala Leu Cys Pro Ile Val Glu Arg Leu Val
    50                  55                  60

Asn Ser Met Met Met His Gly Arg Asn Asn Gly Lys Lys Leu Lys Ala
65                  70                  75                  80

Ile Arg Ile Val Ala Tyr Ala Phe Glu Ile Ile His Leu Met Thr Gly
                85                  90                  95

Glu Asn Pro Ile Gln Val Tyr Val Asn Ala Val Gln Lys Gly Gly Pro
            100                 105                 110

Arg Glu Asp Ser Thr Arg Ile Gly Ser Ala Gly Val Val Arg Arg Gln
        115                 120                 125

Ala Val Asp Val Ser Pro Leu Arg Arg Val Asn Gln Ala Ile Tyr Leu
    130                 135                 140

Ile Cys Thr Gly Ala Arg Asn Ala Ala Phe Arg Asn Ile Lys Ser Ile
145                 150                 155                 160

Ser Glu Cys Leu Ala Glu Glu Ile Ile Asn Cys Ala Asn Glu Ser Ser
                165                 170                 175

Ser Ser Tyr Ala Ile Lys Lys Lys Asp Glu Ile Glu Arg Val Ala Lys
            180                 185                 190

Ala Asn Arg
        195


<210> SEQ ID NO 520
<211> LENGTH: 391
<212> TYPE: PRT
<213> ORGANISM: Plasmodium vivax
```

<400> SEQUENCE: 520

Met His Lys Lys Lys Lys Glu Leu Phe Tyr Phe Phe Pro Phe Arg Arg
1               5                   10                  15

Glu Ser Lys Arg Lys Leu Ile Phe Phe Phe Phe Tyr Ile Lys Ala Val
            20                  25                  30

Thr Ile Leu Ser Lys Arg Ile Gln Lys Met Lys Leu Asn Ile Ser Asn
        35                  40                  45

Pro Leu Asn Asn Val Gln Lys Ser Ile Glu Ile Asp Asp Glu Lys Lys
    50                  55                  60

Leu Leu Pro Phe Met Glu Lys Arg Ile Gly Asn Val Val Pro Gly Asp
65                  70                  75                  80

Ser Ile Gly Glu Glu Phe Leu Gly Tyr Val Phe Arg Ile Thr Gly Gly
                85                  90                  95

Asn Asp Lys Gln Gly Phe Pro Met Met Gln Gly Val Leu Thr Asn Asn
            100                 105                 110

Arg Val Arg Leu Leu Phe Lys Lys Gly Met Lys Cys Tyr Arg Pro Arg
        115                 120                 125

Lys Lys Gly Glu Lys Arg Arg Lys Ser Val Arg Gly Cys Ile Val Gly
    130                 135                 140

Gln Asp Leu Ser Ala Leu Asn Leu Thr Leu Val Lys Lys Gly Thr Asn
145                 150                 155                 160

Glu Ile Pro Gly Leu Thr Asp Lys Ala Val Gly Lys Lys Leu Gly Pro
                165                 170                 175

Lys Arg Ala Thr Lys Ile Arg Lys Leu Phe Asn Leu Asp Lys Thr Asp
            180                 185                 190

Asp Val Arg Lys Tyr Val Ile Gly Arg Ala Ile Ser Lys Asn Gly Lys
        195                 200                 205

Asn Arg Phe Ile Lys Pro Lys Ile Gln Arg Leu Val Thr Glu Lys Arg
    210                 215                 220

Leu Leu Arg Lys Arg Thr Leu Ile Ala Lys Lys Glu Lys Arg Arg Leu
225                 230                 235                 240

Glu Lys Lys Lys Val Ile Lys Glu Tyr Lys Lys Val Leu Asn Lys Tyr
                245                 250                 255

Arg Asn Glu Leu Leu Thr Lys Thr Asp Glu Asp Ala Gly Lys Lys Lys
            260                 265                 270

Lys Val Lys Lys Ser Leu Ser Lys Asp Ser Gln Lys Lys Gly Gly Lys
        275                 280                 285

Lys Lys Asp Lys Lys Asn Leu Lys Gly Ala Lys Ala Glu Glu Gly Lys
    290                 295                 300

Lys Asp Gly Val Lys Lys Asp Val Ala Lys Lys Asp Ala Gly Lys Lys
305                 310                 315                 320

Asp Ala Gly Lys Lys Asp Ala Gly Lys Lys Asp Gly Ala Lys Lys Glu
                325                 330                 335

Val Ala Lys Lys Asp Ala Gly Lys Lys Ala Ala Thr Gly Ser Ala Ala
            340                 345                 350

Ala Ser Lys Val Lys Glu Glu Lys Gln Ser Lys Gln Glu Ser Lys Ala
        355                 360                 365

Val Lys Val Asp Lys Lys Ala Pro Ala Lys Pro Gln Lys Glu Asp Ala
    370                 375                 380

Lys Gly Gly Lys Lys Lys Lys
385                 390

<210> SEQ ID NO 521

<211> LENGTH: 194
<212> TYPE: PRT
<213> ORGANISM: Plasmodium vivax

<400> SEQUENCE: 521

Met Val Ser Val Lys Thr Lys Val Leu Lys Asn Asn Pro Ser Asp Leu
1               5                   10                  15

Glu Lys Glu Ile Ala Gln Cys Leu Ile Asp Ile Glu Leu Ser Ser Ser
            20                  25                  30

Ser Asp Ile Lys Asn Asp Ala Lys Glu Ile Lys Ile Leu Ser Cys Asp
        35                  40                  45

Leu Ile Glu Val Glu Lys Ile Lys Lys Lys Thr Ile Leu Ile Tyr Ile
    50                  55                  60

Pro Tyr Lys Ile Tyr Thr Thr Tyr Val Arg Lys Ile Gln Arg Lys Leu
65                  70                  75                  80

Ile Asn Glu Leu Glu Lys Lys Thr Lys Lys Tyr Val Val Leu Val Ala
                85                  90                  95

Lys Arg Thr Ile Leu Lys Thr Lys Gln Lys Thr Lys Ser Phe Lys Ile
            100                 105                 110

Ile Pro Arg Ser Arg Thr Leu Thr Ser Val Tyr Asp Ser Ile Leu Glu
        115                 120                 125

Asp Ile Val Ala Pro Ser Glu Ile Val Gly Lys Arg Ile Ser Met Lys
    130                 135                 140

Ala Asp Gly Lys Arg Leu Phe Lys Ile Met Leu Asp Ser Lys Glu Arg
145                 150                 155                 160

Gln Arg Asp Asn Ile Glu Glu Lys Leu Ile Ser Phe Ala Ala Val Tyr
                165                 170                 175

Lys Arg Ile Thr Arg Arg Asp Thr Val Phe Thr Leu Pro Pro Thr Asn
            180                 185                 190

Glu Lys

<210> SEQ ID NO 522
<211> LENGTH: 221
<212> TYPE: PRT
<213> ORGANISM: Plasmodium vivax

<400> SEQUENCE: 522

Met Gly Ile Ser Arg Asp Gly Arg His Lys Leu Arg Leu Thr Gly Gly
1               5                   10                  15

Lys Lys Lys Ile His Lys Lys Lys Arg Lys Tyr Glu Leu Gly Arg Pro
            20                  25                  30

Pro Ser Asn Thr Lys Leu Gly Ser Lys Gln Val His Val Val Arg Gly
        35                  40                  45

Arg Gly Arg Asn Tyr Lys Tyr Arg Ala Ile Lys Leu Asp Ser Gly Ser
    50                  55                  60

Phe Ser Trp Pro Ala Phe Gly Val Ser Lys Ile Thr Arg Ile Ile Asp
65                  70                  75                  80

Val Val Tyr Asn Ala Ser Asn Asn Glu Leu Val Arg Thr Lys Thr Leu
                85                  90                  95

Val Lys Asn Cys Ile Val Leu Ile Asp Ser His Pro Phe Thr Thr Trp
            100                 105                 110

Tyr Glu Asn Thr Phe Gly Val Thr Leu Gly Lys Lys Lys Lys Gly Lys
        115                 120                 125

Thr Asp Glu Glu Asn Lys Glu Glu Asn Lys Ala Glu Gly Glu Glu Asn
    130                 135                 140

```
Glu Glu Asn Asn Glu Glu Lys Asp Glu Lys Ala Lys Ser Ser Tyr Ser
145                 150                 155                 160

Val Ile Lys Lys Ile Gly Lys Ser Lys Gln Ile Asp Pro Ala Leu Leu
                165                 170                 175

Glu Gln Phe Lys Gln Gly Arg Val Leu Ala Cys Ile Ser Ser Arg Pro
            180                 185                 190

Gly Gln Cys Gly Lys Ala Asp Gly Tyr Ile Ile Glu Gly Asp Glu Leu
        195                 200                 205

Leu Phe Tyr Lys Arg Lys Met Asp Lys Lys Lys Arg Asn
    210                 215                 220


<210> SEQ ID NO 523
<211> LENGTH: 189
<212> TYPE: PRT
<213> ORGANISM: Plasmodium vivax

<400> SEQUENCE: 523

Met Pro Lys Ser Tyr Arg Asn Tyr Ser Lys Thr Ala Arg Asn Pro Lys
1               5                   10                  15

Arg Pro Phe Glu Lys Glu Arg Leu Asp Gln Glu Leu Lys Leu Ile Gly
            20                  25                  30

Glu Tyr Gly Leu Lys Asn Lys Arg Glu Ile Trp Arg Val Gln Tyr Leu
        35                  40                  45

Leu Ala Lys Ile Arg Ser Ala Ala Arg Tyr Leu Leu Thr Leu Asp Glu
    50                  55                  60

Lys Ser Ser Lys Arg Ile Phe Gln Gly Glu Ala Leu Leu Arg Arg Met
65                  70                  75                  80

Val Arg Gln Gly Leu Leu Gly Glu Asn Glu Glu Lys Leu Asp Tyr Val
                85                  90                  95

Leu Gly Leu Thr Leu Pro Lys Leu Leu Glu Arg Arg Leu Gln Thr Lys
            100                 105                 110

Val Phe Lys Leu Gly Leu Ala Lys Ser Val His His Ala Arg Val Leu
        115                 120                 125

Ile Arg Gln Arg His Ile Arg Val Gly Lys Gln Met Val Asp Ile Pro
    130                 135                 140

Ser Phe Leu Val Arg Val Asp Ser Glu Lys His Ile Asp Phe Ser Thr
145                 150                 155                 160

Thr Ser Pro Phe Gly Gly Ser Arg Pro Gly Arg Val Lys Arg Lys Thr
                165                 170                 175

Leu Lys Asn Gln Lys Glu Lys Asn Glu Glu Glu Asn Ser
            180                 185


<210> SEQ ID NO 524
<211> LENGTH: 263
<212> TYPE: PRT
<213> ORGANISM: Plasmodium vivax

<400> SEQUENCE: 524

Met Ser Ser Lys Lys Val Gln Ser Pro Lys Glu Glu Ser Ile Ala Lys
1               5                   10                  15

Met Leu Ile Cys Lys Val His Ile Gly Thr Lys Asn Leu Glu Asn Lys
            20                  25                  30

Met Lys Arg Tyr Val Tyr Thr Arg Ala Lys Asp Gly Val His Ile Leu
        35                  40                  45

Asn Leu Ala Lys Thr Tyr Glu Lys Leu Gln Leu Ala Ala Arg Ile Ile
    50                  55                  60
```

Val Ala Ile Asn Asn Pro Ala Asp Val Val Val Val Ser Ala Arg Pro
65 70 75 80

Phe Gly Ser Arg Ala Val Leu Lys Phe Ala Gln Tyr Thr Gly Ala Gln
85 90 95

Ala Ile Ala Gly Arg Trp Thr Pro Gly Met Leu Thr Asn Gln Ile Ile
100 105 110

Gln Lys Phe Thr Glu Pro Arg Leu Leu Ile Val Thr Asp Pro Arg Thr
115 120 125

Asp Ala Gln Pro Val Lys Glu Ser Ala Tyr Ala Asn Ile Pro Val Ile
130 135 140

Ala Leu Cys Asp Ser Asp Ser Pro Leu Glu His Val Asp Ile Ala Ile
145 150 155 160

Pro Cys Asn Asn Lys Gly Lys Glu Ser Ile Ala Leu Met Tyr Trp Leu
165 170 175

Leu Ala Gln Glu Val Leu Tyr Leu Lys Gly Thr Leu Pro Arg Ser Lys
180 185 190

Pro Trp Lys Val Met Val Asp Met Phe Leu Trp Arg Asp Pro Glu Gln
195 200 205

Phe Glu Leu Lys Asn Leu Ala Ile Glu Glu Thr Ala Pro Ala Ala Pro
210 215 220

His Leu Ala Glu Asn Gln Phe Ala Thr Glu Ala Pro Tyr Glu Glu Trp
225 230 235 240

Asn Lys Lys Glu Glu Trp Asn Asp Asn Ala Asn Glu Glu Trp Lys Asn
245 250 255

Pro Ile Ala Ala Asp Glu Trp
260

<210> SEQ ID NO 525
<211> LENGTH: 359
<212> TYPE: PRT
<213> ORGANISM: Plasmodium vivax

<400> SEQUENCE: 525

Met Thr Lys Gln Asn Gly Tyr Lys Ile Leu Val Glu Phe Phe Phe Phe
1 5 10 15

Tyr Ile Ser Leu Leu Ser Ala Gly Thr Glu Ser Tyr Val Arg Ser Gly
20 25 30

Ser Gly Gly Arg Asp Ile Ser Arg Trp Ser Asn Phe Ser Gly Ile Phe
35 40 45

Thr Glu Glu Thr Ile Gln Arg Arg Arg Leu Pro Trp Ser Ala Arg Ser
50 55 60

Ser Thr Ala Pro Arg Pro Gln Leu Pro Pro Ser Gln Leu Pro Pro Pro
65 70 75 80

Gln Leu Glu Lys Ala Thr Gln Ile Ala Pro Pro Pro Pro Gly Glu Pro
85 90 95

Thr Gln Arg Val Lys Leu Lys Lys Lys Glu Lys Lys Ile Leu Lys Lys
100 105 110

Tyr Lys Asp Phe Leu Asp Ile Leu Pro Lys Arg Asp Ser Glu Tyr Ala
115 120 125

Ile Asn Glu Ala Ile Glu Lys Ile Lys Thr Leu Ala Val His Lys Phe
130 135 140

Val Glu Ser Ile Asp Ile Tyr Leu Ser Phe Asn Gln Lys Arg Ser Lys
145 150 155 160

Met Asn Lys Asn Asp Asn Leu Lys Thr Phe Ile Thr Phe Pro His Asn
165 170 175

```
Leu Lys Lys Lys Arg Glu Lys Lys Val Tyr Val Val Thr Asn Arg Asp
            180                 185                 190

Leu Gln Lys Arg Ala Thr Asp Ser Gly Lys Asn Ile Pro Ser Glu Ala
        195                 200                 205

Asn Phe Leu Glu Gly Ala Asp Val Val Gly Glu Asp Asp Leu Ile Ser
    210                 215                 220

Lys Ile Lys Glu Arg Glu Ile Arg Leu Lys Lys Lys Asn Asn Asn Phe
225                 230                 235                 240

Leu Leu Cys Thr Asn Asp Val Ile His Lys Leu Ala Arg Val Gly Lys
                245                 250                 255

Glu Val Gly Ser Lys Gly Leu Met Pro Asn Glu Lys Ser Gly Thr Leu
            260                 265                 270

Val Ser Glu Phe Leu Leu Glu Lys His Val Lys Leu Phe Lys Phe Gly
        275                 280                 285

Asn Ser Tyr Ile Phe Lys Leu Asn Lys Leu Asn Thr Leu Asn Leu Asn
    290                 295                 300

Val Gly Asp Val Tyr Met Ser Asn Asp Glu Ile Arg Glu Asn Ile Cys
305                 310                 315                 320

His Leu Phe Glu His Leu Asp Ser Leu Glu Phe Phe His Phe Asn Ser
                325                 330                 335

Lys Asn Leu Lys Ser Val Phe Leu Ser Ser Thr Met Gly Phe Pro Phe
            340                 345                 350

Lys Ile Lys Arg Asn Phe Leu
        355


<210> SEQ ID NO 526
<211> LENGTH: 296
<212> TYPE: PRT
<213> ORGANISM: Plasmodium vivax

<400> SEQUENCE: 526

Met Lys Gly Leu Lys Leu Leu Leu Ser Cys Arg His Ala Gln Ser Gly
1               5                   10                  15

Tyr Tyr Pro His Gly Gly Asp Thr Ser Pro Leu Glu Ser Thr His Gln
            20                  25                  30

Lys Glu Glu Lys Ile Asn Phe Asn Leu Ile Ile Lys Ile Asp Ile Lys
        35                  40                  45

Arg Glu Ser Leu Arg Gly Met Cys Thr Leu Thr His Ser Val Asp Arg
    50                  55                  60

Asn Lys Lys Ile Leu Val Leu Val Asp Glu Asp His Gln Ala Leu Lys
65                  70                  75                  80

Lys Ala Gly Ala Asp Tyr Val Gly Leu Glu Tyr Ile Asn Arg Ile Lys
                85                  90                  95

Asn Gly Trp Leu Asp Phe His Met Cys Leu Ser Asn Phe Lys Asn Ile
            100                 105                 110

Asn Lys Ile Leu Pro Ile Ala Lys Ile Leu Gly Pro Lys Lys Leu Met
        115                 120                 125

Pro Asn Val Lys Ser Asn Thr Leu Val His Asn Leu Val Asp Ala Ile
    130                 135                 140

Leu Ser Ile Lys Ser Gly Asn Arg Val Glu Tyr Arg Ser Glu Gln Ile
145                 150                 155                 160

Asp Ala Glu Thr Phe Asp Leu Phe His Gln Ile Tyr His Phe Lys Asn
                165                 170                 175

Val His Leu Gly Ser Val Ala Thr Leu Asn Val Ser Ile Ala Ser Thr
```

```
            180                 185                 190

Glu Met Asn Pro His Asp Thr Leu Glu Asn Met Lys Cys Phe Val Thr
        195                 200                 205

Glu Ile Leu Lys Cys Asn Val His Ser Ser His Thr Glu Lys Asp Ala
    210                 215                 220

Lys Pro Ala Phe Thr Trp Pro Pro Val Thr Cys Lys Arg Lys Arg Asn
225                 230                 235                 240

Lys Met Arg His Leu Gln Gly Gly Gly Gly Gly Ser Pro Leu Leu Phe
                245                 250                 255

Thr Gly Gly Gly Gln Pro Ser Glu Ser Phe Leu Leu Gly Ala Tyr Val
            260                 265                 270

Thr Val Pro Gly Leu Pro Lys Ile Phe Leu His Pro His Leu Leu Leu
        275                 280                 285

Pro His Ser Glu Gly Tyr Ser Val
    290                 295


<210> SEQ ID NO 527
<211> LENGTH: 178
<212> TYPE: PRT
<213> ORGANISM: Plasmodium vivax

<400> SEQUENCE: 527

Met Ser Arg Ile Gly Arg Phe Asn Leu Val Val Leu Ser Gly Ser Ala
1               5                   10                  15

Lys Pro Ser Ala Ser Ile Gly Gln Thr Leu Gly Pro Leu Gly Ile Asn
            20                  25                  30

Met Met Thr Phe Phe Lys Glu Phe Asn Glu Arg Thr Lys Asn Ile Ser
        35                  40                  45

Lys Asn Val Pro Ile Gln Val Thr Leu Glu Pro Leu Asn Asp Arg Thr
    50                  55                  60

Tyr Arg Phe Tyr Leu Arg Thr Pro Thr Val Val Trp Phe Ile Arg Arg
65                  70                  75                  80

Cys Ala Arg Val Pro Met Phe Ser Pro Thr Ala Lys His His Thr Val
                85                  90                  95

Gly Ser Ile Thr Leu Ala Glu Val Phe His Ile Ala Lys Cys Lys Arg
            100                 105                 110

Met Asp Pro Pro Leu Ile Asn Leu Thr Leu Lys Ser Ile Cys Lys Tyr
        115                 120                 125

Ile Ile Gly Thr Cys Asn Ser Met Gly Ile Lys Val Cys Arg Glu Leu
    130                 135                 140

Asp Asp Glu Gly Lys Lys Lys Tyr Phe Val Asp Val Asn Gln Leu Asp
145                 150                 155                 160

Asn Ile Lys Lys Asp Ile Arg Thr Arg Asn Lys His Gln Lys Arg Ser
                165                 170                 175

Lys Lys


<210> SEQ ID NO 528
<211> LENGTH: 212
<212> TYPE: PRT
<213> ORGANISM: Plasmodium vivax

<400> SEQUENCE: 528

Met Ile Gly Ala Ser Ala Arg Arg Leu Ala Gly Tyr Pro Lys Ala Ser
1               5                   10                  15

Phe His Glu Gln Ser Ile Asn Pro Phe Ser Asn Val Gln Trp Lys Ser
            20                  25                  30
```

Thr Pro Phe Leu Lys Lys Asn Met Pro Lys Thr Asp Pro Phe Ala Glu
35 40 45

Glu His Val Ser Arg Asn Ala Ile Ser Val Phe Asp Arg Glu Lys Gly
50 55 60

Asn Trp Phe Val Ile Asp Ala Tyr Asn Lys Ser Val Gly Ser Leu Ser
65 70 75 80

Val Cys Ile Ser Lys Leu Leu Gln Gly Lys Tyr Arg Val Asp His Asn
85 90 95

Pro Asn Arg Val Asn Gly Ser Ser Val Ile Val Val Asn Ala Ile His
100 105 110

Val Lys Phe Tyr Gly His Thr Trp Asp Thr Lys Ile Tyr Lys Phe Pro
115 120 125

Arg Lys Ser His Ser Lys Gly Pro Lys Ile Leu Thr Cys Lys Thr Val
130 135 140

Phe Ala Arg Asn Pro Ser Met Val Leu Asn Leu Ala Val Lys Arg Met
145 150 155 160

Leu Pro Asn Asn Arg Leu Arg Gln Leu Tyr Tyr Arg Lys Leu Phe Val
165 170 175

Tyr Pro Gly Ala Ile His Pro His Trp Gly Ile Pro Gln Val Ile Val
180 185 190

Pro Lys Arg Asp Val Ala Arg Ser Ala Asp Gln Pro Thr Leu Lys Ala
195 200 205

Phe Thr Val Val
210

<210> SEQ ID NO 529
<211> LENGTH: 597
<212> TYPE: PRT
<213> ORGANISM: Plasmodium vivax

<400> SEQUENCE: 529

Met Arg Cys Pro Ala Phe Leu Leu Leu Leu Cys Thr Thr Leu Gly Arg
1 5 10 15

Gly Phe Val Ile Ser Asp Arg Lys Gly Gly Pro Leu Ser Ala Thr Gln
20 25 30

Lys Ser Pro Leu Ser Glu Arg Arg His Arg Gly Val Val Pro Gly Arg
35 40 45

Lys Lys Arg His Leu Asn Leu Phe Lys Glu Glu Glu Val Glu Glu Lys
50 55 60

Tyr Asn Met Ile Asp Thr Ile Asn Ser Leu Leu Gly Lys Val Lys Arg
65 70 75 80

Gln Phe Asn Ile Asp Phe Asp Val Glu Glu Glu Lys Arg Ala Arg Asp
85 90 95

Lys Gln Gln Gly Ser Ser Ala Glu Gly Ser Pro Met Glu Glu Ile His
100 105 110

Ser Glu Val His Ser Phe Asp Ala Glu Gly Asp Pro Thr Lys Gln Gln
115 120 125

His Arg Arg Asp Gln Asn Glu Leu Arg Gly Ile Phe Gly Thr Met Met
130 135 140

Asp Gly Ser Phe Lys Ile Gly Arg Ala Asn Thr Met Phe Lys Glu Leu
145 150 155 160

Lys Glu Glu Lys Lys Leu Val Asp Lys Lys Tyr Lys Ala Leu Ile Asn
165 170 175

Arg Lys Ile Ser Leu Arg Arg Lys Gln Phe Lys Gln Leu Glu Glu Asp

```
            180                 185                 190

Ile Lys Asn Gly Val Phe Lys Ser Pro Tyr Asn Asp Glu Gln Lys Lys
        195                 200                 205

Phe Leu Gln Asn Val Val Lys Glu Gln Glu Gln Ala Ile Glu Pro Ile
    210                 215                 220

Ile Lys Glu Ile Glu Thr Val Glu Lys Asn Lys Tyr Leu Val Tyr Asp
225                 230                 235                 240

Glu Lys Asn Glu Gln Leu Val Lys Leu Arg Glu Glu Ile Gln Lys Lys
                245                 250                 255

Ile Asn Gln Val Asn Leu Lys Tyr Gln Glu Glu Ala Ile Lys Leu Gly
            260                 265                 270

Ile Lys Lys Val Met Asp Asp Leu Tyr Glu Gln Thr Lys Thr Pro Leu
        275                 280                 285

Val Trp Asp Leu Thr Gln Met Asp Trp Pro Arg Ala Ile Tyr Pro Leu
    290                 295                 300

Ile Asn Asp Met Lys Leu Lys Ala Asp Val Tyr Trp Glu Ser Thr Val
305                 310                 315                 320

Val Gly Gly Asn Arg Glu Gln Asn Glu Tyr Phe Ile Thr Pro Phe Asn
                325                 330                 335

Ile Pro Ser Met Glu Asp Lys Lys Arg Arg Arg Lys Gly Arg Gly Val
            340                 345                 350

Gly Ser Lys Arg Gly Gly Ser Ser Gly Arg Gly Met Lys Gly Gln Lys
        355                 360                 365

Ser Arg Ser Gly Gly Ser Ile Pro Leu Gly Phe Glu Gly Gly Gln Thr
    370                 375                 380

Pro Leu Tyr Arg Lys Leu Pro Lys Phe Val Ala Ala Pro Met Gly Pro
385                 390                 395                 400

Gly Tyr His Phe Asn Arg Tyr Asp Tyr Glu Leu Ile Pro Leu Asn Leu
                405                 410                 415

Ile Asn Leu Ala Tyr Thr Arg Ser Gly Gln Lys Lys His Leu Glu Ile
            420                 425                 430

Asp Trp Asn Val Ile Asp Lys Met Gly Leu Arg Ile Gly Lys Tyr Lys
        435                 440                 445

Arg Lys His Pro Ile Lys Val Val Gly Cys Asn Leu Lys Lys Tyr Lys
    450                 455                 460

Met Lys His Gly Phe Asp Phe Glu Phe Tyr Ala Lys His Val Ile Val
465                 470                 475                 480

Lys Ala His Ser Phe Thr Val Lys Ala Ala Arg Glu Ile Ile Arg Leu
                485                 490                 495

Gly Gly Arg Cys Leu Leu Leu Lys Lys Asn Thr Gln Asp Ile Val Tyr
            500                 505                 510

Ala Glu Tyr Asn Pro Asp Asp Glu Asn Leu Asn Arg Ile Pro Arg Arg
        515                 520                 525

Ile Val Phe Ser Gly Lys Pro Ser Lys Tyr Glu Arg Lys Gln His Trp
    530                 535                 540

Leu Arg Arg Val Lys Met Glu Glu Glu Glu Arg His Arg Ala Gly Glu
545                 550                 555                 560

Ala Ala Gly Glu Ala Ala Gly Glu Val Gly Glu Val Asn Glu Val Gly
                565                 570                 575

Glu Val Asp Glu Ala Gly Glu Val Gly Asp Val Asp Glu Ser Asp Glu
            580                 585                 590

Ala Asn Glu Ala Gly
        595
```

<210> SEQ ID NO 530
<211> LENGTH: 179
<212> TYPE: PRT
<213> ORGANISM: Plasmodium vivax

<400> SEQUENCE: 530

Met Pro Pro Ile Ile Tyr Lys Ala Pro Leu Pro Val Arg Leu Lys Ala
1               5                   10                  15

Pro Lys Gly Arg Ile Val Pro Leu Asn Gly Pro Asp Ile Lys Ile Gly
            20                  25                  30

Lys Ser Leu Ile Ala Ala Cys Pro Arg Arg Ile Arg Ala Glu Lys Leu
        35                  40                  45

Ala Glu Met Lys Gln Thr Ile Arg Arg Tyr Leu Gly Lys Lys Lys Glu
    50                  55                  60

Tyr Phe Leu Asp Val His Ala Thr Tyr Ser Val Thr Lys Lys Pro Asp
65                  70                  75                  80

Gly Thr Lys Met Gly Gln Gly Lys Gly Val Ile Asp Tyr Phe Val Ala
                85                  90                  95

Arg Val Pro Thr Gly Lys Thr Ile Phe His Ile Pro Ser Ile Ser Pro
            100                 105                 110

Phe Asn Ser Leu Gly Phe Glu Asp Pro Val Tyr Lys Val Leu Lys Lys
        115                 120                 125

Ala Ala Ala Lys Val Ala Ile Pro Cys Val Phe Arg Thr Gln Asn Asn
    130                 135                 140

Ile Phe Arg Ile Asn Asn Val Lys Tyr Ile Ser Gln Lys Lys Val Ala
145                 150                 155                 160

Ala Asp Gln Leu Ile Gln Phe Asn Arg Tyr Arg Ser Lys Leu Phe Gln
                165                 170                 175

Arg Gly Glu

<210> SEQ ID NO 531
<211> LENGTH: 256
<212> TYPE: PRT
<213> ORGANISM: Plasmodium vivax

<400> SEQUENCE: 531

Met Gly Tyr Thr Ser Thr Leu Lys Phe Val Asn Leu Gly Val Arg Arg
1               5                   10                  15

Arg Leu Phe Arg Arg Ala His Lys Gln Pro His His Lys Trp Asp Ser
            20                  25                  30

Ile Lys Asn Gln Leu Asn Glu Leu Leu Lys Tyr Gly Arg Ile Glu Thr
        35                  40                  45

Thr Leu Thr Lys Ala Lys Glu Leu Gln Gly Tyr Ala Glu Glu Leu Ile
    50                  55                  60

Tyr Leu Ala Lys Lys Asn Asn Ala Glu Asn Asn Leu Lys Val Glu Ser
65                  70                  75                  80

Met Leu Arg Thr Ala Gln Gly Arg Arg Lys Leu Tyr Glu Tyr Tyr Val
                85                  90                  95

Pro Leu Tyr Arg Tyr Arg Pro Phe Phe Phe Thr Arg Val Ile Asn Gln
            100                 105                 110

Trp Arg Leu Arg Leu Arg Asp Ala Ala Pro Met Ala Phe Ile Glu Phe
        115                 120                 125

Ile Asp Arg Pro Gly Glu Leu Arg Pro Ala Lys Pro Val Gly Ala Asp
    130                 135                 140

Arg Ile Lys Tyr Ile Tyr Glu Glu Met Lys Lys Asn Arg Arg Asn Phe
145 150 155 160

Lys Gln Tyr Leu His Ile Ala Arg Lys Phe Asn Leu Leu Asp Glu Asn
165 170 175

Asp Gln Leu Ile Ser Asp Val Glu Phe Asp Ser Leu Gln Glu His Ala
180 185 190

Arg Arg Asp Leu Trp Lys Arg Asp Asp Glu Glu Glu Ile Gln Val Asp
195 200 205

Pro Glu Leu Ile Lys Arg Tyr Glu Gln Phe Gly Glu Pro Met Leu Ala
210 215 220

Gly Pro Thr Lys Gly Arg Glu Pro Phe Tyr Val Asp Leu Pro Leu Pro
225 230 235 240

Ser His Val Glu Arg Ala Phe Leu Asn Tyr Arg Lys Lys Phe Lys Pro
245 250 255

<210> SEQ ID NO 532
<211> LENGTH: 202
<212> TYPE: PRT
<213> ORGANISM: Plasmodium vivax

<400> SEQUENCE: 532

Met Ala Ser Phe Leu Phe Ser Thr Asn Trp Ile Asn Val Leu Leu Ser
1 5 10 15

Leu Lys Val Leu Arg Ala Thr Phe Ser Gly Val Gly Ile Lys Ala Leu
20 25 30

Pro Gly His Ala Pro Phe Arg Pro Pro Ser Gly Arg Pro Thr Tyr Ala
35 40 45

Gln Ala Asn Glu Pro Ile Gly Ala Thr Val Arg Ile Pro Ile Gln Val
50 55 60

Asn Ala Pro Arg Gln Pro Cys Ala Ala Cys Lys Pro Pro Arg Glu Lys
65 70 75 80

Lys Gln Lys Asn Asn Lys Lys Met Ile Lys Leu Ser Gly Ile Tyr Ser
85 90 95

Tyr Trp His Tyr Lys Ala Trp Gln Arg Ala Thr Ala Gly Tyr Leu Arg
100 105 110

Thr Phe Ile Lys Asn Asn Leu Ala Asn Asn Glu Met Val Gly Tyr Val
115 120 125

Ile Asn Asp Lys His Pro Lys Ser Ile Arg Val Ala Cys Asp Arg Tyr
130 135 140

Met Tyr Val Val Arg Tyr Lys Lys Thr Phe Arg Tyr Thr Lys Lys Ile
145 150 155 160

Trp Ala His Asp Glu Lys Ser Glu Ala Lys Ile Gly Asp Ile Val Arg
165 170 175

Ile Gln Pro Leu Gly Tyr Arg Ile Gly Pro Trp Lys Asn Tyr Ile Leu
180 185 190

Val Lys Ile Leu Tyr Lys Glu Asn Lys Glu
195 200

<210> SEQ ID NO 533
<211> LENGTH: 163
<212> TYPE: PRT
<213> ORGANISM: Plasmodium vivax

<400> SEQUENCE: 533

Met Lys Ile His Ile Leu Phe Phe Phe Leu Cys Lys Asn Leu Leu Ala
1 5 10 15

```
Tyr Val Leu Lys Gln Gly Met Ser Gly Glu Gly Ile Leu Asn Arg Ser
            20                  25                  30

Ser Phe Lys Thr Val Leu His Asn Arg Ser Asn Ser Leu Leu Ala His
        35                  40                  45

Thr Asn Lys Asn Phe Arg Lys Leu Gly Arg Asp Arg Ala Gln Arg Arg
    50                  55                  60

Ala Leu Leu Arg Ala Leu Thr Thr Ser Leu Leu Arg His Gly Lys Ile
65                  70                  75                  80

Val Thr Thr Glu Ala Lys Ala Lys Glu Ala Arg Arg Lys Val Asp Arg
                85                  90                  95

Ile Ile Thr Phe Ala Lys Lys His Asp Asp Asn Arg Gln Tyr Ala Tyr
            100                 105                 110

Arg Leu Ile Ala Asn Tyr Val Tyr Asp Arg Glu Leu Ala Leu Asn Ile
        115                 120                 125

Ala Pro Val Arg Tyr Lys Glu Arg Asn Gly Gly Tyr Thr Arg Ile Lys
    130                 135                 140

Leu Leu Pro Lys Ser Arg Lys Gly Asp Ala Ala Arg Met Ala Thr Leu
145                 150                 155                 160

Glu Leu Val


<210> SEQ ID NO 534
<211> LENGTH: 215
<212> TYPE: PRT
<213> ORGANISM: Plasmodium vivax

<400> SEQUENCE: 534

Met Asn Ala Ala Ala Leu Leu Val Pro Leu Leu Leu Leu Tyr Leu Asp
1               5                   10                  15

Val Leu His Ser Phe Ala Thr Asn Arg Ala Ala Ser Pro Arg Asn Pro
            20                  25                  30

Phe Ser Leu Phe Ser Ser Pro Asn Arg Lys Lys Ala Ala Pro Glu Gln
        35                  40                  45

Leu Pro Lys Gly Lys Ala Asn Lys Leu Lys Asp Lys Lys Lys Lys Lys
    50                  55                  60

Lys Asn Ile Ala Leu Glu Arg Leu Leu Arg Gln His Ala Glu Glu Ala
65                  70                  75                  80

Glu Lys Ala Glu Glu Val Glu Lys Arg Asp Ala Pro Asp Asn Pro Arg
                85                  90                  95

Val Asp Val Asp Glu Glu Ile Leu Gln Gly Lys Arg Val Pro Arg Leu
            100                 105                 110

Arg Ile Lys Asn Thr Asn Asn His Ile Tyr Ala Thr Val Val Asp Asp
        115                 120                 125

Tyr Arg Arg His Ile Leu Cys Phe Ser Cys Ser Arg Asp Pro Asn Leu
    130                 135                 140

Ser Gly Val Leu Gly Thr Tyr Arg Asn Lys Thr Thr Asn Arg Val Val
145                 150                 155                 160

Asn Asn Gly Arg Thr Ile Lys Ser Gly Trp Glu Ile Gly Lys Asp Ile
                165                 170                 175

Ala Arg Lys Ala Leu His Lys Gly Ile Phe Lys Val Lys Phe Asp Arg
            180                 185                 190

Gly Lys Phe Lys Tyr Ala Gly Lys Val Glu Ala Leu Ala Glu Gly Ala
        195                 200                 205

Arg Ala Val Gly Leu Gln Leu
    210                 215
```

<210> SEQ ID NO 535
<211> LENGTH: 332
<212> TYPE: PRT
<213> ORGANISM: Plasmodium vivax

<400> SEQUENCE: 535

Met Ile Lys Arg Tyr Ile Arg Thr Lys Val Ile Thr Ser Leu Ser Lys
1 5 10 15

Phe Lys Cys Tyr Thr Ile Gly Asn Glu His Thr Ala Arg Ser Trp Pro
20 25 30

Asn Val Asp Cys Ile Asp Gln Glu Glu Glu Asn Val Ala Lys Lys Thr
35 40 45

Glu Glu Glu Lys Arg Arg Pro Lys Thr Ile Pro Tyr Tyr Lys Asn Tyr
50 55 60

Met His Asp Phe Phe Gly Arg Gln Leu Ile His Asn Leu His Leu Gln
65 70 75 80

Glu Met Ser Lys Met Lys Arg Leu Arg Asn Phe Lys Met Pro Lys Ile
85 90 95

His Ala Gly Asp Leu Val Glu Val Lys Tyr Glu Leu Ser Arg Ser Gln
100 105 110

Gln Thr Phe Ala Ile Phe Gln Gly Tyr Cys Val Glu Ile Arg Arg Lys
115 120 125

Arg Leu Asp Ser Ser Phe Ile Val Lys Asn Ile Phe Asp Gly Val Gly
130 135 140

Val Glu Gln Leu Ile Pro Phe Tyr Ser Pro Arg Ile Leu Tyr Val Lys
145 150 155 160

Ile Val Lys Ser Leu His Asn Met Ser Glu Glu Lys Ala Lys Arg Phe
165 170 175

Tyr Gln Ile Asn Lys Pro Ile Thr Arg Asp Tyr Arg Tyr Met Trp Gln
180 185 190

Tyr Asn Phe Arg Gly Lys Tyr Glu Arg Pro Arg Gly Gln His Lys Pro
195 200 205

Gly Ile Arg Ser Leu Glu Pro Lys Ile Arg Arg Arg Leu Ala Lys Leu
210 215 220

Lys Lys Lys Tyr Met Arg Arg Arg Ile Glu Ser Asn Leu Ser Ser Tyr
225 230 235 240

Ile Phe Gly Gly Val Tyr Ala Gln Tyr Thr Arg Lys Arg Thr Arg Leu
245 250 255

Val Arg Ala Glu Ile Tyr Arg Arg Met Leu Ile Tyr Ala Leu Asp Glu
260 265 270

Glu Asn Arg Arg Lys Gln Lys Leu Asn Arg Arg Arg Glu Arg Glu Asn
275 280 285

Trp Ser Thr Tyr Lys Ile Asn Arg Ala Arg Gly Asp Asn Ala Phe Met
290 295 300

Ala Leu Pro Ala Ser His Pro Leu Arg Gly Gly Thr Asp Gly Ile Ser
305 310 315 320

Arg Asp Gly Arg His Lys Leu Arg Leu Thr Gly Gly
325 330

<210> SEQ ID NO 536
<211> LENGTH: 313
<212> TYPE: PRT
<213> ORGANISM: Plasmodium vivax

<400> SEQUENCE: 536

Met Tyr Ser Pro Asn Val Lys Arg Asn Ile Pro Glu Tyr Ile Asp Phe
1 5 10 15

Glu Thr Phe Phe Pro Lys Lys Glu Ile Lys Pro Asp Val Leu Thr Ala
20 25 30

Phe Thr Met Ala Lys Gln Gln Arg Leu Glu Lys Leu Leu Glu Asn Asn
35 40 45

Pro Leu Val Leu Tyr Lys Gly Arg Val Met Lys Asn Leu Ser Cys Pro
50 55 60

Arg Ile Lys Asn Ser Gly Arg Asn Asn Val Gly Lys Ile Thr Thr Arg
65 70 75 80

His Arg Gly Gly Gly His Val Gln Arg Leu Arg Phe Ile Asp Phe Lys
85 90 95

Arg Ser Arg Lys Asp Ile Tyr Ser Thr Val Leu Arg Ile Glu Tyr Asp
100 105 110

Pro Ser Arg Ser Ala His Ile Ala Leu Val Gln Tyr Glu Asp Gly Val
115 120 125

Leu Ser Tyr Ile Leu Ala Pro Leu Leu Leu Arg Pro Gly Asp Lys Ile
130 135 140

Ile Ala Ser Lys Tyr Ala Asn Ile Asn Pro Gly Asn Ser Leu Pro Leu
145 150 155 160

Lys Asn Ile Pro Val Gly Ser Ile Ile His Asn Leu Glu Met Arg Pro
165 170 175

Gly Ala Gly Gly Gln Leu Ile Arg Ala Ala Gly Thr Tyr Ala Thr Val
180 185 190

Leu Ser Lys Asp Ser Gln Tyr Ala Thr Ile Lys Leu Lys Ser Thr Glu
195 200 205

Ile Arg Lys Phe Pro Leu Glu Cys Trp Ala Thr Ile Gly Gln Val Ser
210 215 220

Asn Leu Glu Arg His Met Arg Ile Leu Gly Lys Ala Gly Val Asn Arg
225 230 235 240

Trp Leu Gly Lys Arg Pro Val Val Arg Gly Val Ala Met Asn Pro Ser
245 250 255

Lys His Pro His Gly Gly Gly Thr Ser Lys Lys His Thr Lys Arg Pro
260 265 270

Lys Cys Ser Leu Trp Gly Lys Cys Arg Asp Gly Phe Lys Thr Arg Ser
275 280 285

Lys Lys Lys Pro Leu Gly Leu Ile Ile Arg Arg Asn Ile Cys Gly Arg
290 295 300

Leu Gln Lys Lys Tyr Gly Val Thr Val
305 310

<210> SEQ ID NO 537
<211> LENGTH: 121
<212> TYPE: PRT
<213> ORGANISM: Plasmodium vivax

<400> SEQUENCE: 537

Met Lys Leu Pro Arg Glu Val Val Phe Gln Val Ala Lys Gly Phe Arg
1 5 10 15

Gly Arg Ser Lys Gly Cys Phe Lys Ile Ala Arg Ser Arg Ala Met Lys
20 25 30

Ala Leu Leu His Ser Tyr Ile Met Arg Arg Gln Arg Tyr Arg Arg Leu
35 40 45

Arg Val His Trp Ile Ala Ser Ile Asn Arg Ala Cys Arg Glu Trp Asn
50 55 60

Phe Thr Tyr Ala His Phe Met Asn Ser Leu Leu Asn Asn Asn Ile Met
65 70 75 80

Leu Asn Arg Lys Ser Leu Tyr Ser Leu Cys Tyr Thr Glu Pro Ile Ser
85 90 95

Phe Lys Cys Leu Val Asp Glu Ser Lys Tyr Val Phe Phe Gln Arg Lys
100 105 110

Leu Lys Phe Arg Asp Ile Ser Gln Leu
115 120

<210> SEQ ID NO 538
<211> LENGTH: 270
<212> TYPE: PRT
<213> ORGANISM: Plasmodium vivax

<400> SEQUENCE: 538

Met Phe Leu Thr Phe Val Arg His Thr Pro Pro Lys Thr Pro Arg Asn
1 5 10 15

Val Phe Phe Pro Trp Gln Asn Phe Ser Ile His Lys Ser Gly Ser Phe
20 25 30

Leu Glu Lys Asn Arg Leu Ala Leu Arg Val Pro Ile Asn Leu Thr Lys
35 40 45

Phe Glu Ile Arg Glu Tyr Leu Arg Lys Ile Tyr Asn Ala Lys Val Ile
50 55 60

Lys Val Asn Thr Leu Ile Lys Val Pro Glu Arg Arg Arg Asn Leu Thr
65 70 75 80

Asp Phe Arg Phe Asn Tyr Tyr Arg Asn Gly Pro Arg Tyr Lys Lys Ala
85 90 95

Ile Ile Thr Leu Glu His Glu Val Pro Asp Ser Val Lys Met Ile Gln
100 105 110

Ser Cys Lys Asn Ile Gly Arg Asn Pro Tyr Ile Thr Lys Lys Asn Val
115 120 125

Ile Tyr Gly Val Arg Ser Asp Val Lys Ile Thr Pro Thr Arg Ser Gln
130 135 140

Leu Trp Gln Met Gly Glu Cys Arg Tyr Ser Trp Arg Leu Pro Leu Thr
145 150 155 160

Asn Leu Leu Ala Asp Tyr Lys Met Asn Leu Asn Pro Asp Leu Arg Ile
165 170 175

Asp Glu Asn Leu Val Gln Leu Ala Pro Asp Met Thr Lys Pro Phe Met
180 185 190

His Ser Gly Ile Ser Ser Gln Thr Phe Lys Pro Ser Ser Val Pro Glu
195 200 205

Gln Thr Phe Pro Lys Ile Asp Leu Thr Pro Trp Arg Arg Gln Val Lys
210 215 220

Lys Ile Tyr Glu Ser Gly Thr Leu Ala Pro Pro Glu Ser Phe Pro Lys
225 230 235 240

Asp Arg Lys Arg His Gln Thr Ile Glu Tyr Ala Gly Glu Asn Lys Asn
245 250 255

Phe Lys Arg Ser Ser Arg Ser Ser Gln Trp Lys Ala Pro Ser
260 265 270

<210> SEQ ID NO 539
<211> LENGTH: 244
<212> TYPE: PRT
<213> ORGANISM: Plasmodium vivax

<400> SEQUENCE: 539

```
Met Ser Arg Tyr Val Lys Tyr Phe Val Gln Ala Lys Arg Leu Asp Lys
1               5                   10                  15

Arg Lys Arg Lys Phe Gly Gln Met Asp Phe Leu Glu Leu Ser Lys Glu
            20                  25                  30

Leu Ser Ile Pro Phe Pro Leu Arg Glu Arg Asn Gln Pro Lys His Leu
        35                  40                  45

Asp Leu Ser Lys Tyr Leu Asn Ile Lys Val Gly Asp Leu Val Lys Val
    50                  55                  60

Leu Tyr Gly Pro Tyr Lys Asp Lys Glu Gly Ile Val Leu Asn Ile Asn
65                  70                  75                  80

Thr Lys Arg Asn Thr Val Ile Val Asp Gly Cys Asn Met Lys Lys Ser
                85                  90                  95

Ala Trp Asn Val Thr Lys Lys Asn Ala Gly Ser Ile Ile Thr Gln Glu
            100                 105                 110

Met Pro Ile His Ile Thr Asn Val Ala Ile Leu Asp Pro Ile Ser Lys
        115                 120                 125

Lys Ala Thr Val Val Lys Arg Arg Tyr Met Met His Gly Glu Cys Val
    130                 135                 140

Arg Ile Ser Lys Ile Ser Gly Cys Ala Met Pro Glu Pro Val Ser Val
145                 150                 155                 160

Gln Ala Leu Lys Glu Gln Asn Asn Tyr Glu Leu Phe Ile His Lys Lys
                165                 170                 175

Lys Thr Gly Pro Pro Ile Lys Asp Ile Tyr Ala Glu Arg Asp Ser Lys
            180                 185                 190

Asn Phe Asn Leu Leu Lys Lys Ile Ala Tyr Glu Ile Lys Arg Arg Arg
        195                 200                 205

Phe Tyr Glu Met Lys Asn Phe Phe Arg Asp Ala Ser Pro Gly Lys Gly
    210                 215                 220

Ser Ala Ser Pro Gly Gly Gly Ser Ala Ser Leu Gly Glu Gly Ser Ser
225                 230                 235                 240

Ser Leu Glu Gly
```

<210> SEQ ID NO 540
<211> LENGTH: 170
<212> TYPE: PRT
<213> ORGANISM: Plasmodium vivax

<400> SEQUENCE: 540

```
Met Thr Arg Thr Thr Gln Lys Arg Arg Leu His Val Asn Asp Ile Asn
1               5                   10                  15

Ala Ser Arg Lys Ser Val Val Thr Ala Ser His Phe Lys Ser Ile Pro
            20                  25                  30

Phe Ile Asn Lys Asn Tyr Ala Lys Glu Cys Phe Ile Lys Asn His Asp
        35                  40                  45

Gln Val Val Ser Ile Ala Gln Phe Arg Arg Phe Asn Lys Leu Trp Ala
    50                  55                  60

Lys Lys Lys Gly Val Gly Ser Thr Lys Asn Gly Arg Asp Ser Asn Pro
65                  70                  75                  80

Lys Asn Leu Gly Val Lys Val Leu Gly Asn Asn Phe Ala His Ala Gly
                85                  90                  95

Asn Ile Ile Val Arg Gln Arg Gly Arg Thr Phe Lys Pro Gly His Gly
            100                 105                 110

Val Lys Gln Gly Arg Asp Phe Thr Leu Ile Ala Thr Lys Pro Gly Lys
        115                 120                 125
```

```
Val His Phe Phe Asn Arg Val Val Ser Ile Val Asp Val Ser Asp Pro
    130                 135                 140

Lys Pro Met Thr Tyr Ala Asp Val Tyr Arg Glu Asp Pro Thr Ile Leu
145                 150                 155                 160

Thr Leu Ser Arg Val Trp Thr Ser Ala Lys
                165                 170


<210> SEQ ID NO 541
<211> LENGTH: 165
<212> TYPE: PRT
<213> ORGANISM: Plasmodium vivax

<400> SEQUENCE: 541

Met Asn Leu Tyr Phe Thr Pro Leu Leu Phe Leu Leu Leu Cys Lys Ala
1               5                   10                  15

Tyr Ile Ile Arg Gly Val Asn Leu Arg Arg Lys Cys Val Ser Leu Phe
            20                  25                  30

Leu Thr Tyr Asn Leu Ser Ser Ala Leu Lys Ser Ser His Gln Ser Pro
        35                  40                  45

Leu Phe Cys Tyr Lys Lys Arg Val Lys Ala Lys Glu Leu Arg Lys Leu
    50                  55                  60

Ser Thr Glu Glu Leu Glu Lys Glu Ile Ile Lys Cys Arg Leu Asp Ile
65                  70                  75                  80

Gln Lys Phe Gln His Gln Gly Phe His Asp Ile His Asn Tyr Asn Ile
                85                  90                  95

Tyr Tyr Glu Lys Asn Ala Arg Arg Lys Leu Ala Gln Leu Leu Thr Ile
            100                 105                 110

Tyr Tyr Glu Arg Tyr Leu Asp Lys Asn Val Arg Ile Lys Ser Ser Ser
        115                 120                 125

Ser Glu Gly Ala Asp Phe Asn Ser Val Pro Pro Pro Gln Gly Gly Glu
    130                 135                 140

Glu Ala Lys Glu Leu Ser Ser His Glu Glu Arg Thr Thr Asn Ser Ser
145                 150                 155                 160

Ser Glu Thr Lys Thr
                165


<210> SEQ ID NO 542
<211> LENGTH: 280
<212> TYPE: PRT
<213> ORGANISM: Plasmodium vivax

<400> SEQUENCE: 542

Met Phe Asn Leu Ser Ser Leu Leu Lys Ala Thr Lys Val Ala Lys Pro
1               5                   10                  15

Ala Ser Ala Ala Ala Pro Asp Asn Glu Asn Ala Asp Asn Asn Ala Glu
            20                  25                  30

Gly Gly Ser Ser Glu Ala Val Lys Ile Lys Ile Ile Asn Met Gln Glu
        35                  40                  45

Tyr Lys Thr Lys Lys Phe Leu Asp Glu Arg Lys Asn Val Asn Ala Trp
    50                  55                  60

Ser Ala Ala Asn Thr Ser Gly Lys Lys Pro Ala Lys Glu Pro Lys Lys
65                  70                  75                  80

Lys Pro Glu Lys Lys Lys Ala Glu Lys Lys Lys Glu Glu Pro Lys Lys
                85                  90                  95

Glu Glu Pro Gln Lys Glu Pro Gln Lys Glu Pro Gln Lys Glu Glu Leu
            100                 105                 110
```

```
Lys Gly Glu Glu Pro Lys Lys Glu Glu Pro Glu Lys Asp Glu Ala Lys
        115                 120                 125

Lys Glu Glu Ala Lys Lys Val Glu Ala Lys Lys Val Glu Pro Lys Lys
    130                 135                 140

Ala Glu Pro Lys Lys Asp Pro Lys Ile Glu Pro Pro Lys Lys Lys Phe
145                 150                 155                 160

Ile Pro Ser Val Leu Lys Gln Lys Glu Ala Ala Met Ala Lys Val Val
                165                 170                 175

Lys Glu Val Lys Thr Glu Lys Val Glu Leu Phe Pro Asp Leu Leu Gln
            180                 185                 190

Ala Lys Lys Ser Thr Lys Thr Glu Lys Glu Lys Lys Lys Asn Gln Pro
        195                 200                 205

Gln Lys Lys Asn Lys Lys Glu Lys Ala Glu Lys Lys Lys Gln Glu Glu
    210                 215                 220

Glu Glu Asn Asn Phe Pro Pro Ile Glu Glu Val Glu Lys Ile His Phe
225                 230                 235                 240

Asn Ile Phe Asp Ile Val Asp Ile Lys Lys Glu Tyr Glu Arg Ile Met
                245                 250                 255

Arg Asn Ser Glu Lys Val Met Glu Lys Tyr Lys Asn Lys Lys Lys Phe
            260                 265                 270

Asp Asp Thr Met Ile Leu Cys Asn
        275                 280


<210> SEQ ID NO 543
<211> LENGTH: 316
<212> TYPE: PRT
<213> ORGANISM: Plasmodium vivax

<400> SEQUENCE: 543

Met His Leu Phe Ile Phe Tyr Glu Val Leu Ile Leu Ser Val Phe Phe
1               5                   10                  15

Gln Cys Ile Tyr Asn Tyr Lys Phe Val Lys Asn Cys Tyr Tyr Ser Glu
            20                  25                  30

Lys Ile Pro Phe Asp Lys Asn Gly Lys Asp Val Gly Met Pro Val Gly
        35                  40                  45

Val His Lys Ser Lys Glu Val Arg Asn Lys Arg Asn Ser Gln Leu Asn
    50                  55                  60

Met Val Lys Lys Phe Ile Asn Ala Arg Asp Pro Asn Asp Pro Gln Glu
65                  70                  75                  80

Tyr Leu Lys Asp Ile Pro Tyr Lys Asp Glu Leu Asp Arg Ile Gln Ile
                85                  90                  95

Arg Gly Lys Lys Ile Glu Met Arg Ser Ile Phe Ser Pro Asn Gly Lys
            100                 105                 110

Leu Ile Pro Ala Thr Leu Ile Glu Ile Met Pro Asn Val Ile Tyr Arg
        115                 120                 125

Phe Leu Asp Phe Gly Lys Val Gly Ile Ala Tyr Gly Lys Pro Leu Glu
    130                 135                 140

Glu Ser Arg Trp Ile Leu Lys Pro Glu Ile Gly Gln Ile Ala Lys Val
145                 150                 155                 160

Gly Cys Asn Tyr Lys Asn Thr Cys Ser Leu Thr Leu Thr Pro Pro Gln
                165                 170                 175

Asn Phe Val Leu Gly Gln Ile Ile Asp Val Ser Tyr Leu Tyr Asn Tyr
            180                 185                 190

Lys Tyr Val Asn Val Arg Gly Leu Ser Lys Gly Lys Gly Phe Cys Gly
```

```
        195                 200                 205

Val Ile Lys Arg Trp Gly Phe Arg Arg Gly Pro Met Thr His Gly Ser
    210                 215                 220

Ser His His Arg Lys Pro Gly Ser Ile Gly Ala Ser Thr His Ile Gly
225                 230                 235                 240

Arg Val Leu Lys Gly Lys Lys Met Pro Gly Lys His Gly Asn Lys Tyr
                245                 250                 255

Asn Thr Met Ile Asn Leu Lys Leu Leu Gly Leu Asn Leu Glu Arg Asn
            260                 265                 270

Glu Ile Leu Val Ser Gly Cys Ile Pro Gly Asn Arg Asn Ser Tyr Val
        275                 280                 285

Thr Val Thr Ala Thr Arg Glu Asn Arg Val Asp Lys Tyr Lys Tyr Ile
    290                 295                 300

Leu Asp Leu Leu Tyr Glu Gln Glu Lys Asn Ala Gln
305                 310                 315


<210> SEQ ID NO 544
<211> LENGTH: 336
<212> TYPE: PRT
<213> ORGANISM: Plasmodium vivax

<400> SEQUENCE: 544

Met Ile Pro Ile Met Arg Val Arg Gly Arg Pro Thr Leu Ala Asp Arg
1               5                   10                  15

Ser Thr Val Cys Ala Val Ala Arg Arg Ser Phe Tyr Ala Ser Lys Trp
            20                  25                  30

Val Arg Arg Leu Gln Leu Leu Asn Glu Lys Tyr Asn Tyr Lys Ile Asn
        35                  40                  45

Ala Glu Glu Gln Ala Glu Tyr Glu Glu Lys Lys Glu Asp Asp Lys Ile
    50                  55                  60

Glu Lys Val Tyr Pro Leu Trp Asn Ser Arg Arg Thr Gly Leu Leu Ala
65                  70                  75                  80

Tyr Lys Val Gly Cys Met Ser Ile Trp Asp Val Trp Gly Val Lys His
                85                  90                  95

Ala Val Thr Val Ala Lys Ile Asn His Cys Tyr Val Leu Asn Gln Lys
            100                 105                 110

Asn Ile Thr Lys Asn Gly Tyr Glu Ala Leu Glu Ile Gly Ile Gly Asn
        115                 120                 125

Met Asn Val Val Lys Gln Ser Lys Asn Asn Ile Gly Asn Tyr Ile Lys
    130                 135                 140

Arg Lys Leu Gly Phe Ile His Lys Ile Lys Glu Phe Lys Cys Thr Ser
145                 150                 155                 160

Asp Cys Phe Leu Pro Val Gln His Lys Phe Ser Ala Arg His Phe Ser
                165                 170                 175

Pro Gly Gln Asn Leu Phe Ile Ser Ser Thr Ile Lys Ser Lys Gly Phe
            180                 185                 190

Cys Gly Ala Met Lys Lys Trp Asn Phe Ser Gly Lys Asn Ala Ser His
        195                 200                 205

Gly Thr Glu Ser Lys Ala His Arg Ser Leu Gly Ser Val Ser Met Gly
    210                 215                 220

Lys Thr Val Asn Ile Val Phe Arg Asn Lys Lys Met Asn Thr His Ile
225                 230                 235                 240

Gly Glu Lys Thr Leu Val Lys Cys Ser Asn Asn Lys Leu Phe Arg Ile
                245                 250                 255
```

Asn Ser Leu Gln Asn Leu Leu Phe Ile Lys Gly Pro Ile Gly Gly Tyr
260 265 270

Lys Asn Lys Ile Ile Lys Ile Ser Asp Ala Lys Gly Arg Ala Phe Asn
275 280 285

Lys Phe Lys Asp Lys Ile Tyr Leu Tyr Tyr Pro Thr Phe Ile Tyr Lys
290 295 300

Lys Asn Arg Lys Tyr Lys Asn Val Ile Asp Met Pro His Ser Leu Gln
305 310 315 320

Asp Pro Phe Leu Tyr Asn Glu Ile Pro Leu Tyr Glu Pro Thr Asn Lys
325 330 335

<210> SEQ ID NO 545
<211> LENGTH: 111
<212> TYPE: PRT
<213> ORGANISM: Plasmodium vivax

<400> SEQUENCE: 545

Met Lys Lys Cys Asp Ile Phe Phe Leu Tyr Leu Ile Phe Phe Val Leu
1 5 10 15

Thr Thr Ile Lys Arg Cys Gln Pro Phe Ile Ile Pro Asn Asn Thr Lys
20 25 30

Met Val Asn Gly Pro Leu Leu Lys Ser Cys Cys Arg Ser Lys Arg Val
35 40 45

Val Thr Ile Phe Gly Lys Lys Lys Lys Asn Arg Lys Val Val Val Ile
50 55 60

Glu Cys Thr Glu Ala Arg Lys Tyr Gly Lys Gln Pro Ser Arg Tyr Val
65 70 75 80

Thr Glu Lys Asn Lys Val Asn Thr Pro Lys Lys Leu Gln Leu Tyr Lys
85 90 95

Tyr Asn Lys Tyr Leu Lys Arg Arg Thr Leu His Val Glu Ile Lys
100 105 110

<210> SEQ ID NO 546
<211> LENGTH: 162
<212> TYPE: PRT
<213> ORGANISM: Plasmodium vivax

<400> SEQUENCE: 546

Met Thr Cys Cys Leu Leu Ile Phe Ile Val Leu Leu Leu Ala Leu Arg
1 5 10 15

Leu Gly His Pro Glu Lys Leu Pro His Asp Gly Arg Asn Glu Arg Pro
20 25 30

Leu Ile Gly Ser Thr Ile His Arg Asn Ser Phe Arg Lys Lys Gly Ser
35 40 45

Ala His Lys His Thr Leu Thr Asn Lys Tyr Thr His Lys Ser Val Asn
50 55 60

Lys Lys Arg Thr His Thr Glu Ala Thr Leu Phe Leu His Pro His Gly
65 70 75 80

Leu Gln Lys Ser Asn Leu Arg Leu Ser Asn Leu His Val Arg Gly Asn
85 90 95

Thr Asn Val Lys Pro Lys Thr Asn Lys Ser Ile Ala Lys Arg Phe Lys
100 105 110

Ile Thr Lys Asn Gly Lys Val Ile Arg Lys Lys Ala Gly Arg Asn His
115 120 125

Met Leu Arg Lys Lys Thr Ser Ser Asn Lys Ala Ser Leu Arg Lys Thr
130 135 140

Thr Thr Ile Ala Ser Asn Arg Ile Ala Lys Lys Tyr Lys Ser Ala Ile
145 150 155 160

His Thr

<210> SEQ ID NO 547
<211> LENGTH: 268
<212> TYPE: PRT
<213> ORGANISM: Plasmodium vivax

<400> SEQUENCE: 547

Met Lys Arg Asn Ala Leu Val Lys Asn Ala Leu Cys Arg Ala Arg Leu
1 5 10 15

His Pro Asn Gly Ala His Ala Asn Ala Ala Val Ser Ala Ala Ala Leu
20 25 30

Ser Gly Ala Ala Leu Trp Ser Asn Lys Ala Leu Gln Thr Arg Arg Gly
35 40 45

Ser Gly Gly Ser Ala Pro Asn Ser Ser Phe Asp Leu Phe Asp Lys Ile
50 55 60

Lys Asp Ile Asn Gly Ser Asn Gln Asn Glu Glu Gly Thr Glu Gln Ile
65 70 75 80

Asp Ser Lys Lys Arg Lys Pro Ser Lys Lys Val Leu Lys Leu Val Asp
85 90 95

Glu Ile Leu Asn Leu Thr Leu Ile Glu Ala Ala Asp Leu Cys Asp Leu
100 105 110

Cys Gln Glu Lys Leu Asp Gly Gln Lys Gln Phe Asn Asn Ser Ser Phe
115 120 125

Phe Asn Arg Asn Pro Phe Pro His Pro Ser Ser Phe Phe Thr Ala Gly
130 135 140

Gly Phe Ser Ser Pro Gly Val Pro Pro Pro Met Ser Ser Ser Phe Pro
145 150 155 160

Asn His Ala Asn Ala Gln Gly Val Leu Pro Pro Gly Glu Thr Pro Asn
165 170 175

Leu Gly Ser Ala Glu Lys Gly Glu Gln Ala Gly Val Lys Lys Lys Glu
180 185 190

Glu Lys Lys Ser Ser Lys Ser Thr Phe Asn Val Lys Leu Asp Ser Phe
195 200 205

Asp Val Lys Asn Lys Ile Asn Thr Ile Lys Glu Ile Arg Lys Ile Ala
210 215 220

Asn Val Gly Leu Lys Glu Ala Lys Asp Met Val Glu Ser Ala Pro Phe
225 230 235 240

Tyr Val Gln Lys Asn Val Pro Ala Glu Lys Ala Glu Glu Met Lys Lys
245 250 255

Lys Phe Glu Glu Leu Gly Ala Thr Ile Ile Leu Glu
260 265

<210> SEQ ID NO 548
<211> LENGTH: 67
<212> TYPE: PRT
<213> ORGANISM: Plasmodium vivax

<400> SEQUENCE: 548

Met Glu Lys Ser Lys Leu Ala Lys Val Glu Lys Val Leu Gly Arg Thr
1 5 10 15

Gly Ser Arg Gly Gly Val Ile Gln Val Arg Ala Gln Phe Met Gly Asp
20 25 30

Thr Glu Leu Ser Gly Arg Phe Leu Ile Arg Asn Val Lys Gly Pro Val 35 40 45

Arg Glu Gly Asp Ile Leu Ala Leu Leu Glu Thr Glu Arg Glu Ala Arg
50 55 60

Arg Leu Arg
65

<210> SEQ ID NO 549
<211> LENGTH: 193
<212> TYPE: PRT
<213> ORGANISM: Plasmodium vivax

<400> SEQUENCE: 549

Met Leu Cys His Asn Val Ala Ser Lys Val Ser Glu Leu Leu Leu Asn
1 5 10 15

Arg Met Asn Cys Pro Phe Leu Gln Asn Val Gln Val Arg Asn His Lys
20 25 30

Ile Ile Lys Pro Arg Asn Ile Ile Lys Leu Trp Lys Ile Asn Lys Gly
35 40 45

Asp Glu Val Lys Val Ile Ser Gly Lys Asp Lys Gly Lys Ile Gly Glu
50 55 60

Val Leu Ser Cys Asp Lys Phe Arg Asn Met Val Lys Val Lys Gly Cys
65 70 75 80

Asn Leu Arg Lys Ile Tyr Leu Asp Asn Lys Phe Val Tyr Ile Glu Lys
85 90 95

Lys Ile His Tyr Ser Asn Val Gln Leu Ile Asp Asp Phe Leu Lys Thr
100 105 110

Asn Thr Lys Val Cys Ile Arg Tyr Thr Asp Asp Asn Gln Val Ile Arg
115 120 125

Ile Ser Lys Lys Ser Gly Ile Val Ile Pro Trp Pro Ser Lys Thr Asn
130 135 140

Lys Glu Asp Glu Phe Asp Asp Val Glu Glu Asn Pro Leu Asp Thr Pro
145 150 155 160

Pro Gln Glu Ala Leu Lys Lys Thr Tyr Asp Tyr Lys Ala Asp Val Lys
165 170 175

Phe Met Asn Ile Leu Arg Gln Thr Val Asn Lys Tyr Asn Arg Glu Leu
180 185 190

Ser

<210> SEQ ID NO 550
<211> LENGTH: 246
<212> TYPE: PRT
<213> ORGANISM: Plasmodium vivax

<400> SEQUENCE: 550

Met Ser Ser Lys Gly Arg Thr Tyr Lys Ala Leu Asp Arg Arg Lys Ala
1 5 10 15

Lys Val Cys Glu Gly Lys Arg Thr Lys Leu Gly Asn Lys Arg Pro Gly
20 25 30

Lys Leu Ser Arg Arg Gly Phe Trp Leu Leu Cys Leu Ala Tyr Val Val
35 40 45

Ala Tyr Phe Leu Gly Gly Ile Thr Cys Leu Thr Phe Leu Lys Arg Gln
50 55 60

Ser Lys Leu Ser Tyr Phe Tyr Leu Ile Tyr Ser Glu Lys Arg Ile Gly
65 70 75 80

Asp Asn His Arg Arg Lys Asn Tyr Leu Asn Tyr Lys Asn Glu Ile Ile
85 90 95

Leu Lys Lys Asp Ala Ser Ser Gly Arg Arg Gly Phe Thr Leu Gly Ser
100 105 110

Glu Arg Val Asn Lys Ile Ile Glu Ser Leu Lys Glu Leu Thr Leu Leu
115 120 125

Glu Ala Ser Glu Leu Val Lys Gln Ile Glu Ala Thr Phe Ser Val Asp
130 135 140

Thr Arg Gln Ser Ile Gly Ala Ser Ser Thr Asp Gln Asp Ser Arg Lys
145 150 155 160

Asn Ala Ala Asp Ala Asn Ala Glu Glu Glu Glu Asp Asp Glu Asn Lys
165 170 175

Val Tyr Asp Leu Val Leu Glu Asn Ile Glu Pro Asn Lys Lys Ile Pro
180 185 190

Ile Ile Lys Ile Val Lys Glu Ile Lys Lys Asp Leu Asn Leu Lys Gln
195 200 205

Ala Lys Asp Leu Val Asp Asn Leu Pro Gln Thr Leu Phe Glu Lys Ile
210 215 220

Asn Lys Glu Thr Ala Asp Lys Trp Lys Thr Lys Leu Thr Glu Ala Gly
225 230 235 240

Gly Ile Val Lys Leu Lys
245

<210> SEQ ID NO 551
<211> LENGTH: 183
<212> TYPE: PRT
<213> ORGANISM: Plasmodium vivax

<400> SEQUENCE: 551

Met Pro Cys Leu Phe Phe Pro His Glu Cys Thr Pro Thr His Thr Pro
1 5 10 15

Leu Arg Arg Cys Thr Cys Glu Ala Ala Arg Gln Ser Glu Ile Ser Lys
20 25 30

Thr Asp Pro His Val Arg Gly Asp Thr Gly Ala Ser Thr Pro Val Cys
35 40 45

Pro Arg Thr Lys Arg Arg Thr Pro Pro Pro Arg Arg Met Gln Leu Thr
50 55 60

Gln Val Leu Ser Gly Leu Trp Arg Gln Ser Ile Val Arg Ser Ala Asp
65 70 75 80

Asn Ser Gly Val Ile Lys Ala Cys Ile Ile Gly Ile Gly Lys Asn Lys
85 90 95

Trp Gly Thr Gly Lys Ile Gly Asp Arg Ile Arg Val Ser Ile Arg Asp
100 105 110

Lys Thr Asn Asp Cys Thr Ile Gln Glu Lys Thr Pro Lys Gly Ile Ile
115 120 125

Val Arg Arg Lys Lys Glu Thr Lys Arg Lys Asp Gly Ser Tyr Ile Lys
130 135 140

Phe Asp Asp Asn Ala Phe Val Ile Ile Ser Lys Asn Lys Leu Lys Ala
145 150 155 160

Thr Lys Ile Lys Gly Pro Val Ala Met Glu Thr Arg His Asn Cys Lys
165 170 175

Asn Leu Ala Arg Tyr Ile Phe
180

<210> SEQ ID NO 552
<211> LENGTH: 162
<212> TYPE: PRT

<213> ORGANISM: Plasmodium vivax

<400> SEQUENCE: 552

Met Thr Gly Pro Ser Thr Ala Arg Arg His His Gly Leu Asp Gly Arg
1 5 10 15

Lys Arg Ile Asn Lys Val Thr Met Leu Pro His Lys Glu Ile Lys Leu
20 25 30

Pro Ala Arg Arg Cys Met Ile Leu Gly Lys Met Asp Asn Trp Asn Ala
35 40 45

Arg Lys Ile Ser Lys Ser Gly Val Lys Thr His Arg Lys Gln Arg Val
50 55 60

Asn Leu Leu Arg Lys Arg Ile Tyr Phe Glu Glu Glu Asp Arg Phe Val
65 70 75 80

Lys Leu Arg Val Ser Ala Arg Gly Leu Lys Thr Ile Lys Lys Tyr Gly
85 90 95

Leu Gly Tyr Cys Cys Lys Lys Phe Asn Leu Asp Leu Ser Lys Lys Lys
100 105 110

Tyr Asp Ala Gly Arg Ser Pro Arg Arg Lys Lys Lys Lys Thr Asp Glu
115 120 125

Phe Ala Ser Ala Gln Asn Asp Ala Phe Asn Gln Arg Ala Pro Gln Val
130 135 140

His Glu Asp Ala Asn Glu Ile Leu Lys Asn Leu Asn Leu Asp Lys Lys
145 150 155 160

Asn Lys

<210> SEQ ID NO 553
<211> LENGTH: 315
<212> TYPE: PRT
<213> ORGANISM: Plasmodium vivax

<400> SEQUENCE: 553

Met Ala Lys Leu Ser Lys Ala Gln Lys Lys Gln Ile Tyr Ile Glu Lys
1 5 10 15

Leu Ser Ser Leu Ile Gln Gln Tyr Thr Lys Ile Leu Ile Val His Val
20 25 30

Asp Asn Val Gly Ser Asn Gln Met Ala Ser Val Arg Gln Ser Leu Arg
35 40 45

Gly Lys Ala Thr Ile Leu Met Gly Lys Asn Thr Arg Ile Arg Thr Ala
50 55 60

Leu Lys Lys Asn Leu Gln Ala Val Pro Gln Ile Glu Lys Leu Leu Pro
65 70 75 80

Leu Val Lys Leu Asn Met Gly Phe Val Phe Cys Lys Glu Asp Leu Thr
85 90 95

Glu Val Arg Asn Ile Ile Leu Gln Asn Lys Ser Pro Ala Pro Ala Arg
100 105 110

Leu Gly Val Ile Ala Pro Ile Asp Val Phe Ile Pro Pro Gly Pro Thr
115 120 125

Gly Met Asp Pro Ser His Thr Ser Phe Phe Gln Ser Leu Gly Ile Ser
130 135 140

Thr Lys Ile Val Lys Gly Gln Ile Glu Ile Gln Glu His Val His Leu
145 150 155 160

Ile Lys Gln Gly Glu Lys Val Thr Ala Ser Ser Ala Thr Leu Leu Gln
165 170 175

Lys Phe Asn Met Lys Pro Phe Ser Tyr Gly Val Asp Val Arg Thr Val
180 185 190

Tyr Asp Asp Gly Val Ile Tyr Asp Ala Lys Val Leu Asp Ile Thr Asp
195 200 205

Glu Asp Ile Leu Ala Lys Phe Gly Lys Gly Val Ala Asn Ile Ala Ala
210 215 220

Leu Ser Arg Ser Ile Gly Val Leu Thr Glu Ala Ser Tyr Pro His Val
225 230 235 240

Phe Val Glu Ala Phe Lys Asn Ile Val Ala Leu Val Ile Asp Thr Asp
245 250 255

Tyr Thr Phe Pro Leu Met Lys Lys Ile Lys Asp Met Val Glu Asn Pro
260 265 270

Glu Ala Tyr Ala Ala Ala Ala Pro Val Ala Ala Ala Ala Ala Asp Ala
275 280 285

Pro Lys Lys Glu Glu Ala Lys Lys Gln Glu Glu Glu Glu Glu Glu Glu
290 295 300

Glu Asp Gly Phe Met Gly Phe Gly Met Phe Asp
305 310 315

<210> SEQ ID NO 554
<211> LENGTH: 119
<212> TYPE: PRT
<213> ORGANISM: Plasmodium vivax

<400> SEQUENCE: 554

Met Ala Ala Val Pro Val Ala Glu Leu Ala Glu Cys Glu Lys Gln Glu
1 5 10 15

Leu Leu Cys Thr Tyr Ala Ala Leu Ile Leu His Glu Glu Lys Met Ser
20 25 30

Ile Thr Ser Glu Asn Ile Val Lys Leu Ile Lys Lys Ser Asn Asn Thr
35 40 45

Val Leu Pro Tyr Leu Pro Met Leu Phe Glu Lys Ala Leu Lys Gly Lys
50 55 60

Asp Ile Glu Gly Leu Leu Ser Asn Leu Ser Val Gly Gly Gly Ala Pro
65 70 75 80

Ala Ala Ala Ala Gln Ala Ala Ala Asp Lys Pro Ser Asp Asp Lys Lys
85 90 95

Glu Ala Lys Lys Glu Glu Lys Val Glu Glu Glu Glu Glu Glu Asp Asp
100 105 110

Leu Gly Phe Ser Leu Phe Gly
115

<210> SEQ ID NO 555
<211> LENGTH: 295
<212> TYPE: PRT
<213> ORGANISM: Plasmodium vivax

<400> SEQUENCE: 555

Met Ala Tyr Val Lys Val Val Lys Asn Lys Ala Tyr Phe Lys Arg Tyr
1 5 10 15

Gln Val Lys Tyr Arg Arg Arg Arg Glu Gly Lys Thr Asp Tyr Arg Ala
20 25 30

Arg Lys Ala Leu Ile Leu Gln Asp Lys Asn Lys Tyr Asn Ala Gln Lys
35 40 45

Leu Arg Phe Val Val Arg Lys Thr Asn Cys Gln Ile Ile Cys Gln Ile
50 55 60

Ala Ser Ala His Ile Glu Gly Asp Lys Ile Leu Ala Glu Ala Lys Ser
65 70 75 80

Lys Glu Leu Ile Arg Tyr Gly Ile Pro Val Gly Leu Lys Asn Tyr Ala
85 90 95

Ala Ala Tyr Ala Thr Gly Leu Leu Cys Ala Arg Arg Phe Leu Lys Ser
100 105 110

Leu Asn Leu Asp Thr Gln Phe Leu Gly Val Glu Lys Phe Thr Asp Asp
115 120 125

Met Asn Glu Asn Gly Asp Asp Lys Glu Asp Asp Glu Glu Arg Lys Pro
130 135 140

Ile Lys Ala Phe Leu Asp Val Gly Ile Thr Arg Thr Thr Thr Gly Asn
145 150 155 160

Arg Val Phe Ala Ala Leu Lys Gly Ala Cys Asp Gly Gly Leu Asn Ile
165 170 175

Pro His Gly Thr Asn Arg Phe Pro Gly Ser Lys Asn Glu Phe Asn Pro
180 185 190

Glu Gln Leu Arg Lys Asn Ile Leu Gly Ile His Val Ala Glu Tyr Met
195 200 205

Lys Thr Leu Gln Glu Glu Asp Met Asp Lys Tyr Lys Ala His Phe Asn
210 215 220

Asp Tyr Ile Lys Asn Lys Ile Asp Ala Asn Asn Ile Glu Gln Met Tyr
225 230 235 240

Leu Ser Ala His Glu Lys Ile Lys Lys Asn Pro Glu Lys Val Gln Lys
245 250 255

Gly Lys Asp Lys Val Lys Lys Phe Val Ala Lys His Glu Lys Pro Lys
260 265 270

Lys Leu Asn Ala Lys Leu Arg Lys Lys Arg Val Lys Glu Lys Leu Ala
275 280 285

Lys Tyr Val Glu Lys Leu Gln
290 295

<210> SEQ ID NO 556
<211> LENGTH: 219
<212> TYPE: PRT
<213> ORGANISM: Plasmodium vivax

<400> SEQUENCE: 556

Met Gly Arg Arg Pro Ala Arg Cys Tyr Arg Tyr Cys Lys Asn Lys Pro
1 5 10 15

Tyr Pro Lys Ser Arg Tyr Cys Arg Gly Val Pro Asp Pro Lys Ile Arg
20 25 30

Ile Tyr Asp Met Gly Arg Lys Lys Ala Asp Val Asn Glu Phe Ser Gly
35 40 45

Val Val His Leu Val Ser Tyr Glu Tyr Glu Gln Ile Ser Ser Glu Ala
50 55 60

Leu Glu Ala Ala Arg Ile Ser Ala Asn Lys Tyr Met Ile Thr Asn Cys
65 70 75 80

Gly Lys Asp Asn Phe His Leu Arg Val Arg Val His Pro Phe His Val
85 90 95

Leu Arg Ile Asn Lys Met Leu Ser Cys Ala Gly Ala Asp Arg Leu Gln
100 105 110

Thr Gly Met Arg Gly Ala Phe Gly Lys Pro Asn Gly Val Val Ala Arg
115 120 125

Val Asp Ile Gly Gln Val Leu Leu Ser Ile Arg Thr Lys Glu Asn Phe
130 135 140

Ile Ala Lys Ala Cys Glu Ala Leu Arg Arg Ala Lys Tyr Lys Phe Pro

```
145                 150                 155                 160

Gly Arg Gln Lys Val Phe Val Ser Asn Lys Trp Gly Phe Thr Asn Phe
                165                 170                 175

Ser Lys Asp Gln Tyr Gln Glu Tyr Lys Lys Lys Gly Arg Ile Ile Ser
            180                 185                 190

Asp Gly Val Ser Cys Lys Phe Ile Arg Glu Lys Gly Pro Leu Asp Lys
        195                 200                 205

Ile Tyr Lys Asp Ile Asn Thr Ile Ile Glu Ser
    210                 215


<210> SEQ ID NO 557
<211> LENGTH: 217
<212> TYPE: PRT
<213> ORGANISM: Plasmodium vivax

<400> SEQUENCE: 557

Met Ser Lys Leu Asn Gln Asp Leu Leu Lys Lys Ala Ile Ala Asp Val
1               5                   10                  15

Phe Glu Gly Thr Lys Thr Lys Lys Arg Lys Phe Val Glu Thr Ile Glu
            20                  25                  30

Leu Gln Ile Gly Leu Lys Asp Tyr Asp Thr Gln Arg Asp Lys Arg Phe
        35                  40                  45

Ser Gly Thr Val Lys Leu Ser Asn Glu Val Arg Lys Lys Leu Lys Val
    50                  55                  60

Cys Ile Leu Gly Asp Ala Val His Val Glu Glu Ala Gln Lys Leu Glu
65                  70                  75                  80

Leu Asp Tyr Met Asp Ile Glu Ala Met Lys Lys Leu Asn Lys Asp Lys
                85                  90                  95

Thr Leu Val Lys Lys Leu Ala Lys Lys Tyr Asp Ala Phe Leu Ala Ser
            100                 105                 110

Gln Val Ile Leu Pro Gln Ile Pro Lys Leu Leu Gly Pro Gly Leu Asn
        115                 120                 125

Lys Ala Gly Lys Phe Pro Ser Leu Ile Thr His Asn Asp Lys Ile Asn
    130                 135                 140

Asp Lys Ile Leu Glu Leu Lys Ser Ser Ile Lys Phe Gln Leu Lys Lys
145                 150                 155                 160

Val Leu Cys Met Gly Val Pro Val Gly His Ala Asn Leu Lys Glu Glu
                165                 170                 175

Glu Leu Arg Ser Asn Ile Val His Ala Ile Asn Phe Leu Val Ser Leu
            180                 185                 190

Leu Lys Lys Asn Trp Gln Asn Ile Arg Thr Leu His Ile Lys Ser Thr
        195                 200                 205

Met Gly Lys Pro Gln Arg Ile Tyr Gly
    210                 215


<210> SEQ ID NO 558
<211> LENGTH: 173
<212> TYPE: PRT
<213> ORGANISM: Plasmodium vivax

<400> SEQUENCE: 558

Met Glu Lys Lys Glu Asp Asn Val Met Arg Glu Ile Lys Val Asn Lys
1               5                   10                  15

Leu Val Leu Asn Ile Cys Val Gly Glu Ser Gly Asp Arg Leu Thr Arg
            20                  25                  30

Ala Ala Arg Val Leu Glu Gln Leu Thr Glu Gln Lys Pro Ile Phe Gly
```

```
        35                  40                  45

Lys Cys Arg Phe Thr Ile Arg Ser Phe Gly Val Arg Arg Asn Glu Lys
    50                  55                  60

Ile Ser Cys Phe Val Thr Val Arg Gly Lys Lys Ala Leu Glu Ile Leu
65                  70                  75                  80

Glu Lys Gly Leu Lys Val Lys Glu Tyr Glu Leu Arg Arg Lys Asn Phe
                85                  90                  95

Ser Glu Thr Gly Asn Phe Gly Phe Gly Ile Gln Glu His Ile Asp Leu
            100                 105                 110

Gly Ile Lys Tyr Asp Pro Ser Thr Gly Ile Tyr Gly Met Asp Phe Tyr
        115                 120                 125

Val His Leu Ser Arg Pro Gly Tyr Arg Val Thr Arg Arg Arg Arg Lys
    130                 135                 140

Arg Ser Thr Ile Ser Lys Thr His Lys Val Thr Lys Asp Glu Ala Met
145                 150                 155                 160

Lys Trp Phe Gln Thr Lys Phe Asp Gly Ile Leu Leu Lys
                165                 170


<210> SEQ ID NO 559
<211> LENGTH: 165
<212> TYPE: PRT
<213> ORGANISM: Plasmodium vivax

<400> SEQUENCE: 559

Met Ala Lys Arg Pro Asp Pro Asn Glu Ile Lys Tyr Val Tyr Ile Arg
1               5                   10                  15

Gln Val Gly Gly Glu Val Gly Ala Ser Ser Val Leu Ser Pro Lys Leu
            20                  25                  30

Gly Pro Leu Gly Leu Ser Pro Lys Lys Ile Gly Asp Asp Ile Ala Lys
        35                  40                  45

Glu Thr Gln Ser Trp Lys Gly Leu Lys Ile Cys Val Lys Leu Thr Ile
    50                  55                  60

Gln Asn Arg Gln Ala Lys Ile Glu Val Val Pro Thr Ser Ala Ser Leu
65                  70                  75                  80

Val Leu Lys Glu Leu Asn Glu Ala Pro Arg Asp Arg Lys Lys Val Lys
                85                  90                  95

Asn Ile Lys His Asn Gly Asn Leu Lys Ile Asp Gln Val Tyr Ser Ile
            100                 105                 110

Ala Arg Ile Met Lys Asp Lys Ser Arg Ala Lys Glu Phe Lys Gly Thr
        115                 120                 125

Val Lys Glu Ile Leu Gly Thr Cys Asn Ser Ile Gly Cys Thr Val Asp
    130                 135                 140

Gly Lys Lys Pro Thr Thr Val Gln Glu Met Ile Asp Ser Gly Glu Ile
145                 150                 155                 160

Asp Val Pro Asp Cys
                165


<210> SEQ ID NO 560
<211> LENGTH: 215
<212> TYPE: PRT
<213> ORGANISM: Plasmodium vivax

<400> SEQUENCE: 560

Met Val Ala His Asn Asn Val Leu Pro Asn Val His Leu His Lys Trp
1               5                   10                  15

Trp Gln Arg Tyr Val Arg Val Asn Phe Ser Lys Asn Ile Lys Lys Lys
```

```
            20                  25                  30

Lys Arg Arg Leu Leu Arg Glu Lys Arg Arg Lys Ala Asn Asp Gly Thr
        35                  40                  45

Pro Ile Glu Lys Leu His Pro Ile Val Gln Cys Pro Thr Gln Arg Tyr
    50                  55                  60

Asn Phe Arg Ser Arg Leu Gly Arg Gly Phe Thr Leu Ala Glu Leu Lys
65                  70                  75                  80

Gly Ala Lys Leu Asn Pro Leu Ala Ala Gln Ser Ile Gly Ile Cys Val
                85                  90                  95

Asp Lys Arg Arg Lys Asn Arg Cys Glu Glu Thr Leu Lys Lys Asn Ile
            100                 105                 110

Glu Arg Leu Glu Lys Tyr Lys Lys Cys Leu Val Met Ile Pro Leu Lys
        115                 120                 125

Asn Ile Lys Ser Lys Asn Gly Ile Gly Gly Ile Pro Ala Asp Ser Ser
    130                 135                 140

Lys Glu Val Val Lys Glu Leu Lys Lys Lys Lys Gln Leu Arg Ser Ile
145                 150                 155                 160

Phe Lys Lys Glu Arg Asn Thr Lys Pro Phe Tyr Glu Ser Ile Glu Val
                165                 170                 175

Ser Lys Ile Asp Lys Ser Tyr Leu Ala Tyr Lys Thr Leu Arg Arg Ala
            180                 185                 190

Lys Leu Thr Glu Arg Arg Lys Asn Lys Gln Gln Gln Lys Lys Asp Leu
        195                 200                 205

Lys Arg Lys Ser Lys Asp Asn
    210                 215


<210> SEQ ID NO 561
<211> LENGTH: 202
<212> TYPE: PRT
<213> ORGANISM: Plasmodium vivax

<400> SEQUENCE: 561

Met Tyr Lys Lys Val Tyr Val Ile Asp Cys Lys Gly His Leu Leu Gly
1               5                   10                  15

Arg Leu Ala Ser Ile Ile Ala Lys Glu Leu Leu Asn Gly Gln Arg Val
            20                  25                  30

Val Ala Val Arg Cys Glu Asp Ile Asn Ile Ser Gly Ser Leu Tyr Arg
        35                  40                  45

Asn Lys Leu Lys Tyr Gln Glu Phe Leu Arg Leu Arg Thr Asn Thr Asn
    50                  55                  60

Pro Lys Lys Gly Pro Leu His Leu Arg Glu Pro Ser Lys Ile Leu Trp
65                  70                  75                  80

Arg Cys Val Arg Gly Met Leu Pro His Lys Thr Tyr Lys Gly Lys Ile
                85                  90                  95

Ala Leu Lys Lys Leu Lys Val Phe Val Gly Met Pro Tyr Pro Tyr Asp
            100                 105                 110

Lys Lys Lys Lys Tyr Val Leu Pro Ser Ala Leu Arg Ala Phe Arg Leu
        115                 120                 125

Lys Lys His Arg Arg Tyr Cys Arg Leu Gly Thr Leu Ser Ser Arg Val
    130                 135                 140

Gly Trp Asn Tyr Asp Glu Leu Val Lys Lys Asn Glu Ile Ser Arg Lys
145                 150                 155                 160

Lys Leu Ser Lys Leu Tyr Tyr Lys Lys Lys Val Ser Val Leu Asn Glu
                165                 170                 175
```

Lys Lys Glu Leu Lys Thr Glu Ala Leu Asn Met Ile Asn Pro Glu Glu
180 185 190

Arg Lys Val Leu Glu Asn Phe Gly Tyr Ala
195 200

<210> SEQ ID NO 562
<211> LENGTH: 170
<212> TYPE: PRT
<213> ORGANISM: Plasmodium vivax

<400> SEQUENCE: 562

Met Pro Arg Val Glu Leu Thr Glu Glu Glu Lys Leu Asn Ile Gln Asn
1 5 10 15

Lys Asp Leu Leu Phe Lys Arg Phe Val Glu Pro Gly Arg Leu Cys Leu
20 25 30

Ile Glu Tyr Gly Pro Tyr Ala Gly Lys Leu Cys Phe Val Val Asp Ile
35 40 45

Val Thr Leu Thr Arg Val Ile Val Asp Gly Ala Phe Ile Thr Gly Val
50 55 60

Pro Arg Met Val Ile Pro Leu Lys Arg Leu Lys Leu Leu Lys Glu Arg
65 70 75 80

Ile Lys Ile Asn Lys Asn Cys Lys Ser Gly Phe Leu Gln Lys Thr Ile
85 90 95

Lys Ser Thr Asn Ile Leu Gly Glu Phe Lys Lys Ser Asn Leu Gly Lys
100 105 110

Lys Leu Thr Ile Lys Lys Lys Arg Asp Leu Ala Thr Asp Tyr Glu Arg
115 120 125

Phe Gln Ile Tyr His Ala Lys Arg Glu Leu Lys Lys Lys Met Asn Met
130 135 140

Leu Lys Ser Lys Lys Asp Ser Ser Thr Lys Gly Asp Lys Lys Lys Lys
145 150 155 160

Ala Lys Lys Val Lys Lys Ala Val Lys Lys
165 170

<210> SEQ ID NO 563
<211> LENGTH: 199
<212> TYPE: PRT
<213> ORGANISM: Plasmodium vivax

<400> SEQUENCE: 563

Met Val Lys Tyr Ala Lys Lys Leu Arg Asp Tyr Gly Lys Cys Ala Lys
1 5 10 15

Gly Ala Gly Met Asp Leu Arg Val His Phe Lys Asn Thr Tyr Glu Thr
20 25 30

Ala Arg Ala Ile Arg Arg Met Lys Leu Leu Asp Ala Lys Lys Tyr Leu
35 40 45

Asn Asp Val Ile Glu Lys Lys Arg Cys Val Pro Phe Arg Arg Tyr Asn
50 55 60

Gly Gly Val Gly Arg Thr Asn Gln Ala Lys Glu Phe Asn His Thr Gln
65 70 75 80

Gly Arg Trp Pro Ala Lys Ser Cys Lys Phe Leu Leu Asn Val Leu Asp
85 90 95

Asn Val Gln Ala Asn Ala Glu Ala Arg Asn Leu Glu Val Ser Lys Leu
100 105 110

Arg Leu Ile His Val Met Val Asn Arg Ala Arg Ala Gly Arg Arg Arg
115 120 125

```
Thr Phe Lys Ala His Gly Arg Ile Asn Pro Phe Met Ser Ser Pro Cys
    130                 135                 140

His Ile Gln Val Ile Ala Lys Glu Ile Ser Lys Pro Ala Lys Lys Ser
145                 150                 155                 160

Leu Leu Thr Asn Ala Glu Lys Gln Lys Glu Leu Pro Phe Lys Ile Thr
                165                 170                 175

Leu Lys Lys Leu Ile Lys Leu Asn Ile Ser Lys Gln Asn Phe Ala Lys
            180                 185                 190

Asn Lys Lys Lys Ala Ala Asn
        195


<210> SEQ ID NO 564
<211> LENGTH: 187
<212> TYPE: PRT
<213> ORGANISM: Plasmodium vivax

<400> SEQUENCE: 564

Met Ala Ile Ala Leu Lys Asn Val Gly Arg Ile Lys Lys His Gly Arg
1               5                   10                  15

Lys Asn Leu Val Ser Lys Asn Pro Tyr Leu Arg Leu Leu Val Lys Leu
            20                  25                  30

Tyr Arg Phe Leu Ala Arg Arg Thr Asn Ala Asn Phe Asn Lys Ile Ile
        35                  40                  45

Ala Lys Arg Leu Ile Met Pro Lys Arg Phe Arg Pro Pro Leu Ser Leu
    50                  55                  60

Ser Lys Leu His Arg His Met Ala Ser Tyr Glu Asp Ser Val Ala Val
65                  70                  75                  80

Val Val Gly Ser Ile Thr Asp Asp Lys Arg Leu Tyr Asp Cys Lys Lys
                85                  90                  95

Leu Lys Val Cys Ala Leu Arg Phe Thr Glu Thr Ala Arg Lys Arg Ile
            100                 105                 110

Leu Asp Ala Gly Gly Glu Cys Leu Thr Phe Asp Gln Leu Ala Leu Lys
        115                 120                 125

Tyr Pro Thr Gly Gln Lys Cys Ile Leu Leu Arg Gly Pro Thr Lys Ala
    130                 135                 140

Arg Thr Ala Glu Lys His Phe Gly Lys Ala Pro Gly Arg Pro Lys Ser
145                 150                 155                 160

Lys Ala Arg Pro Tyr Val Arg Ser Lys Gly Arg Lys Phe Glu Lys Ala
                165                 170                 175

Arg Gly Arg Arg Lys Ser Arg Ala Tyr Lys Lys
            180                 185


<210> SEQ ID NO 565
<211> LENGTH: 184
<212> TYPE: PRT
<213> ORGANISM: Plasmodium vivax

<400> SEQUENCE: 565

Met Val Arg Val Ala Asp Asn Ser Leu Lys Thr Asn Ile His Gln Tyr
1               5                   10                  15

His Ile Val Gly Arg Ala Ile Pro Thr Glu Lys Asp Lys Asn Pro Asn
            20                  25                  30

Val Tyr Arg Met Cys Ile Phe Ala Lys Asn Asp Thr Asn Ala Lys Ser
        35                  40                  45

Arg Phe Trp Tyr Phe Met Lys Lys Ile Asn Lys Leu Lys Lys Ser Asn
    50                  55                  60
```

Gly Glu Leu Leu Ala Cys Glu Gln Ile Arg Glu Arg Phe Pro Leu Arg
65 70 75 80

Val Lys Asn Tyr Gly Val Leu Leu Arg Tyr Asp Ser Arg Thr Gly Thr
85 90 95

His Asn Met Tyr Lys Glu Phe Arg Asp Thr Thr Lys Glu Gly Ala Ile
100 105 110

Ala Gln Leu Tyr Ser Glu Met Ala Gly Arg His Arg Ala Arg Ala Ser
115 120 125

Ser Ile Ser Val Ile Arg Ile Ser Glu Ile Ser Ala Asn Leu Val Arg
130 135 140

Arg Pro His Ile Lys Gln Leu Leu Lys Lys Arg Leu Arg Phe Pro Ala
145 150 155 160

Leu His Leu Pro Thr Leu Lys Lys Glu Tyr Arg Arg Lys Tyr Ala Ala
165 170 175

Lys Arg Pro Ser Thr Tyr Arg Met
180

<210> SEQ ID NO 566
<211> LENGTH: 182
<212> TYPE: PRT
<213> ORGANISM: Plasmodium vivax

<400> SEQUENCE: 566

Met Ser Leu Lys Leu Gln Lys Arg Leu Ala Ala Ser Val Leu Lys Cys
1 5 10 15

Gly Lys Asn Lys Ile Trp Met Asp Pro Asn Glu Ile Ser Glu Ile Ser
20 25 30

Leu Ala Asn Ser Arg Phe Ser Ile Arg Lys Leu Tyr Lys Glu Gly Leu
35 40 45

Ile Leu Lys Lys Pro Gln Lys Val His Ser Arg Ala Arg Val Arg Leu
50 55 60

Tyr Lys Leu Ala Lys Arg Lys Gly Arg His Met Gly Ile Gly Lys Arg
65 70 75 80

Arg Gly Thr Lys Asn Ala Arg Thr Asn Gln Lys Thr Leu Trp Ile Lys
85 90 95

Arg Gln Arg Val Leu Arg Arg Leu Leu Lys Arg Leu Arg Asp Ala Lys
100 105 110

Lys Ile Asp Arg His Leu Tyr His Ser Phe Tyr Leu Lys Cys Lys Gly
115 120 125

Asn Gln Phe Lys Asn Lys Arg Thr Leu Ile Glu Ala Ile Gln Arg Glu
130 135 140

Lys Thr Glu Thr Leu Lys Lys Lys Ser Ile Ala Asp Gln Leu Glu Ala
145 150 155 160

Lys Arg Leu Lys Ala Gln Val Leu Arg Asn Lys Arg Lys Leu Lys Lys
165 170 175

Asp Lys Glu Ala Leu Ser
180

<210> SEQ ID NO 567
<211> LENGTH: 136
<212> TYPE: PRT
<213> ORGANISM: Plasmodium vivax

<400> SEQUENCE: 567

Met Val Ala Lys Lys Glu Ser Lys Ile Ile Lys Lys Gln Lys Lys Lys
1 5 10 15

Asn Gly Lys Lys Ser Lys Val Ala Val Lys Lys Pro Lys Thr Met Lys
            20                  25                  30

Ser Thr Lys Gly Val Lys Tyr Ile Leu Asp Cys Thr Lys Pro Val Lys
        35                  40                  45

Asp Thr Ile Leu Asp Ile Ser Gly Leu Glu Gln Phe Phe Lys Asp Lys
    50                  55                  60

Ile Lys Val Asp Lys Lys Thr Asn Asn Leu Lys Asn Lys Ile Val Val
65                  70                  75                  80

Thr Ser Asp Asp Cys Lys Ile Tyr Ile Thr Val His Ile Pro Phe Ser
                85                  90                  95

Lys Arg Tyr Ile Lys Tyr Leu Ala Lys Lys Tyr Leu Lys Met His Gln
            100                 105                 110

Ile Arg Asp Phe Leu Arg Val Ile Ala Lys Gly Lys Leu Ala Tyr Glu
        115                 120                 125

Phe Lys Tyr Phe Gln Leu Asn Asn
    130                 135

<210> SEQ ID NO 568
<211> LENGTH: 139
<212> TYPE: PRT
<213> ORGANISM: Plasmodium vivax

<400> SEQUENCE: 568

Met Lys Arg Gly Arg Ala Gly Thr Leu Lys Asn Lys Met Arg Ile Thr
1               5                   10                  15

Leu Ser Leu Pro Val Gly Ala Leu Ile Asn Cys Cys Asp Asn Ser Gly
            20                  25                  30

Gly Lys Asn Leu Tyr Ile Ile Ala Val Gln Gly Phe Gly Ser Cys Leu
        35                  40                  45

Asn Arg Leu Pro Ala Ala Ser Leu Gly Asp Met Val Leu Ala Thr Val
    50                  55                  60

Lys Lys Gly Lys Pro Asp Leu Arg Lys Lys Val Leu Asn Ala Ile Ile
65                  70                  75                  80

Thr Arg Gln Ser Lys Ala Trp Arg Arg His Glu Gly Tyr Phe Ile Tyr
                85                  90                  95

Phe Glu Asp Asn Ala Gly Val Ile Val Asn Pro Lys Gly Glu Met Lys
            100                 105                 110

Gly Ser Ala Ile Thr Gly Pro Val Ala Arg Glu Cys Ala Glu Leu Trp
        115                 120                 125

Pro Lys Leu Ser Ser Ala Ala Ser Ala Ile Val
    130                 135

<210> SEQ ID NO 569
<211> LENGTH: 195
<212> TYPE: PRT
<213> ORGANISM: Plasmodium vivax

<400> SEQUENCE: 569

Met Asp Lys Lys Lys Gln Asp Ser Lys Asn Lys Lys Asn Ala Lys Asn
1               5                   10                  15

Val Lys Gly Asn Pro Lys Ala Ala Ala Ser Gly Asn Asp Lys Leu Gly
            20                  25                  30

Lys Lys Lys Gly Ala Asp Lys Glu Lys Lys Gln Leu Tyr Lys Gly Lys
        35                  40                  45

Val Lys Lys Ser Leu Gly Lys Gln Val Gly Gly Lys Asn Gln Gln Val
    50                  55                  60

Lys Lys Ala Ala Ala Glu Glu Ser Lys Lys Lys Lys Lys Ile Thr Thr
65 70 75 80

Ser Ile Lys Phe Lys Arg Pro Lys Thr Leu Lys Leu Pro Lys Asn Pro
85 90 95

Lys Cys Pro Lys Val Ile Lys Ser Cys Tyr Lys Lys Thr Leu Asp Lys
100 105 110

Tyr Gly Ile Leu Lys Tyr Pro Leu Thr Ser Glu Lys Ala Met Lys Lys
115 120 125

Ile Glu Glu Ile Asn Thr Leu Val Phe Ile Cys Asp Lys Arg Ala Asp
130 135 140

Lys Lys Lys Ile Thr Lys Ser Val Lys Asn Leu Phe Gly Ile Ser Cys
145 150 155 160

Glu Lys Val Asn Val Leu Asn Arg Leu Asn Gly Asp Lys Lys Ala Tyr
165 170 175

Val Arg Leu Ser Lys Asp His Asp Ala Leu Glu Val Ala Asn Lys Ile
180 185 190

Gly Ile Leu
195

<210> SEQ ID NO 570
<211> LENGTH: 162
<212> TYPE: PRT
<213> ORGANISM: Plasmodium vivax

<400> SEQUENCE: 570

Met Ser Ser Ile Lys Thr Thr Val Lys Thr Glu Ala Cys Ser Phe Ser
1 5 10 15

Glu Tyr Arg Ile Tyr Pro Gly Arg Gly Gln Lys Phe Ile Ala Arg Asp
20 25 30

Gly Lys Val Tyr Phe Tyr Leu Ser Ser Lys Phe Ala Ser Leu Ala Leu
35 40 45

Gln Lys Lys Lys Ala Ala Lys Leu Arg Trp Thr Gln Thr Trp Arg Arg
50 55 60

Asn Asn Lys Lys Thr Lys Ile Glu Thr Thr Gln Arg Arg Arg Tyr Lys
65 70 75 80

Lys Thr Ile Lys Val Gln Lys Ala Val Cys Gly Leu Thr Val Glu Asp
85 90 95

Ile Arg Asn Arg Lys Ala Tyr Val Gln Ser Ile Glu Ala Lys Asn Lys
100 105 110

Ser Arg Met Ala Gly Lys Glu Lys Asp Asp Lys Lys Lys Gly Lys Asp
115 120 125

Asp Lys Lys Lys Asn Ala Ala His Phe Gln Gln Lys Lys Asp Phe Ala
130 135 140

Lys Ser Lys Gln Val Asn Met Ala Lys Thr Lys Met His Lys Met Met
145 150 155 160

Lys Lys

<210> SEQ ID NO 571
<211> LENGTH: 162
<212> TYPE: PRT
<213> ORGANISM: Plasmodium vivax

<400> SEQUENCE: 571

Met Ser Ser Ile Lys Thr Thr Val Lys Thr Glu Ala Cys Ser Phe Ser
1 5 10 15

Glu Tyr Arg Ile Tyr Pro Gly Arg Gly Gln Lys Phe Ile Ala Arg Asp

```
        20                  25                  30

Gly Lys Val Tyr Phe Tyr Leu Ser Ser Lys Phe Ala Ser Leu Ala Leu
        35                  40                  45

Gln Lys Lys Lys Ala Ala Lys Leu Arg Trp Thr Gln Thr Trp Arg Arg
    50                  55                  60

Asn Asn Lys Lys Thr Lys Ile Glu Thr Thr Gln Arg Arg Arg Tyr Lys
65                  70                  75                  80

Lys Thr Ile Lys Val Gln Lys Ala Val Cys Gly Leu Thr Val Glu Asp
                85                  90                  95

Ile Arg Asn Arg Lys Ala Tyr Val Gln Ser Ile Glu Ala Lys Asn Lys
            100                 105                 110

Ser Arg Met Ala Gly Lys Glu Lys Asp Asp Lys Lys Lys Gly Lys Asp
        115                 120                 125

Asp Lys Lys Lys Asn Ala Ala His Phe Gln Gln Lys Lys Asp Phe Ala
    130                 135                 140

Lys Ser Lys Gln Val Asn Met Ala Lys Thr Lys Met His Lys Met Met
145                 150                 155                 160

Lys Lys
```

<210> SEQ ID NO 572
<211> LENGTH: 146
<212> TYPE: PRT
<213> ORGANISM: Plasmodium vivax

<400> SEQUENCE: 572

```
Met Gly Lys Leu Leu Lys Pro Gly Lys Val Val Ile Met Leu Asn Gly
1               5                   10                  15

Arg Arg Ala Gly Lys Lys Ala Ile Ile Ile Asn Thr Tyr Glu Ser Gln
            20                  25                  30

Thr Arg Glu Arg Pro Tyr Ser Tyr Cys Leu Val Ala Gly Ile Glu Lys
        35                  40                  45

His Pro Leu Lys Val Thr Lys Lys Met Ser Lys Arg Lys Ile Met Lys
    50                  55                  60

Arg Ser Lys Val Lys Ala Phe Val Lys Tyr Ile Asn Val Asn His Ile
65                  70                  75                  80

Leu Pro Thr Arg Tyr Gln Val Ala Asn Asp Phe Asp Ile Lys Ser Leu
                85                  90                  95

Ala Ser Asp Asp Val Leu Arg Ser Lys Asn Lys Lys Lys Glu Val Lys
            100                 105                 110

Lys Leu Gly Lys Met Phe Arg Asp Lys Phe Leu Asp Pro Ile Asn Lys
        115                 120                 125

Lys Thr Gly Glu Val Ser Lys Asp Ile Ser Phe Leu His Lys Lys Leu
    130                 135                 140

Tyr Phe
145
```

<210> SEQ ID NO 573
<211> LENGTH: 148
<212> TYPE: PRT
<213> ORGANISM: Plasmodium vivax

<400> SEQUENCE: 573

```
Met Ala Thr Arg Phe Lys Lys Asn Arg Lys Lys Arg Gly His Val Ser
1               5                   10                  15

Ala Gly His Gly Arg Ile Gly Lys His Arg Lys His Pro Gly Gly Arg
            20                  25                  30
```

Gly Lys Ala Gly Gly Met His His Met Arg Ile Asn Phe Asp Lys Tyr
35 40 45

His Pro Gly Tyr Phe Gly Lys Val Gly Met Arg His Phe Asn Leu Leu
50 55 60

Lys Asn Arg Lys Phe Cys Pro Thr Ile Asn Val Asp Lys Leu Trp Gly
65 70 75 80

Leu Leu Pro Glu Glu Lys Lys Lys Glu Phe Phe Glu Asn Lys Asn Ile
85 90 95

Ala Pro Val Ile Asp Val Thr Arg Lys Gly Phe Phe Lys Val Leu Gly
100 105 110

Asn Gly Lys Leu Lys His Ala Gln Pro Ile Val Val Lys Ala Arg Tyr
115 120 125

Phe Ser Ser Val Ala Glu Lys Lys Ile Lys Ala Val Gly Gly Gln Cys
130 135 140

Ile Leu Val Ala
145

<210> SEQ ID NO 574
<211> LENGTH: 127
<212> TYPE: PRT
<213> ORGANISM: Plasmodium vivax

<400> SEQUENCE: 574

Met Ser Asn Val Ser Asn Ala Leu Ile Trp Glu Leu Thr Lys Lys Asn
1 5 10 15

Asn Cys Phe Leu Lys Lys Asn Lys Ser Gly Arg Lys Gly Asn Phe Leu
20 25 30

Cys Asp Ser Tyr Asn Ile Ser Cys Lys Asn Thr Pro Ser Ser Ser Gly
35 40 45

Leu Val Lys Gln Asn Gly Val Asn Leu Arg Leu Gln Lys Gly Lys Val
50 55 60

Val Leu Cys Val Lys Ser Thr Asp Glu Asn Thr Thr Thr Asn Lys Val
65 70 75 80

Tyr Lys Thr Lys Asn Lys Gly Thr Ala Met Lys Leu Ile Asp Glu His
85 90 95

Ala His Leu Val Ser Gly Lys Asn Lys Lys Gln Leu Ile Lys Lys Tyr
100 105 110

Lys Arg Met Ser Lys Leu Tyr Asn Cys Asn Asn Lys Gly Asn Lys
115 120 125

<210> SEQ ID NO 575
<211> LENGTH: 67
<212> TYPE: PRT
<213> ORGANISM: Plasmodium vivax

<400> SEQUENCE: 575

Met Ala Lys Ser Lys Asn His Thr Asn His Asn Gln Asn Arg Lys Ala
1 5 10 15

His Lys Asn Gly Ile Lys Lys Pro Lys Lys His Lys Phe Met Ser Arg
20 25 30

Lys Gly Leu Asp Pro Lys Phe Phe Lys Asn Gln Arg Tyr Cys Leu Lys
35 40 45

Gly Ile Leu Lys Lys Lys Lys Glu Leu Lys Leu Lys Gln Lys Gln Glu
50 55 60

Lys Lys Asn
65

<210> SEQ ID NO 576
<211> LENGTH: 108
<212> TYPE: PRT
<213> ORGANISM: Plasmodium vivax

<400> SEQUENCE: 576

Met Ala Lys Lys Ser Lys Lys Ser Ala Gly Asp Asn Ile Asn Ala Lys
1 5 10 15

Leu Gln Leu Val Met Lys Ser Gly Lys Tyr Gln Phe Gly Arg Lys Ser
20 25 30

Cys Leu Lys Ala Leu Arg Thr Gly Lys Gly Lys Leu Val Ile Val Ser
35 40 45

Ser Asn Cys Pro Pro Ile Gln Arg Ser Val Ile Glu Tyr Tyr Ala Met
50 55 60

Leu Ser Lys Cys Gly Val His Asp Tyr His Gly Asp Asn Asn Asp Leu
65 70 75 80

Gly Thr Ala Cys Gly Lys Leu Phe Arg Ile Ser Cys Leu Val Ile Thr
85 90 95

Asp Val Gly Asp Ser Asp Ile Ile Lys Thr Asn Glu
100 105

<210> SEQ ID NO 577
<211> LENGTH: 119
<212> TYPE: PRT
<213> ORGANISM: Plasmodium vivax

<400> SEQUENCE: 577

Met Ala Lys Ala Val Lys Lys Gln Lys Lys Thr Leu Lys Pro Val Thr
1 5 10 15

Lys Val Ile Thr Ile Asn Leu Ser Lys Leu Thr His Asp Val Cys Tyr
20 25 30

Lys Lys Lys Ala Pro Arg Ala Ile Lys Glu Ile Arg Asn Ile Ala Gly
35 40 45

Lys Leu Met His Thr Lys Asp Val Arg Leu Asp Val Lys Leu Asn Lys
50 55 60

Phe Ile Trp Ser Lys Gly Ile Arg Asn Pro Pro Asn Arg Val Arg Val
65 70 75 80

Lys Ile Glu Arg Lys Arg Asn Glu Asp Glu Asp Ser Lys Glu Lys Met
85 90 95

Tyr Thr Ile Val Gln His Val Met Val Asp Thr Tyr Lys Gly Leu Leu
100 105 110

Asn Glu Cys Glu Val Asn Glu
115

<210> SEQ ID NO 578
<211> LENGTH: 131
<212> TYPE: PRT
<213> ORGANISM: Plasmodium vivax

<400> SEQUENCE: 578

Met Ala Val Lys Lys Val Gly Lys Ile Val Lys Lys Arg Thr Lys Lys
1 5 10 15

Phe Thr Arg Phe Gln Ser Asn Arg Phe Met Arg Val Lys Pro Ala Trp
20 25 30

Arg Lys Pro Arg Gly Ile Asp Cys Arg Val Arg Arg Arg Tyr Lys Gly
35 40 45

Thr Asn Leu Met Pro Ser Ile Gly Tyr Gly Ser Asn Lys Lys Thr Lys
50 55 60

Phe Leu Leu Pro Asn Asn Lys Tyr Lys Tyr Ile Val Arg Asn Val Arg
65 70 75 80

Glu Met Glu Pro Leu Ile Met Asn Asn Thr Lys Tyr Cys Val Gln Ile
85 90 95

Ala His Asn Val Ser Ser Lys Lys Arg Arg Glu Ile Ile Glu Arg Ala
100 105 110

Lys Gln Met Asn Val Ser Val Ile Asn Ala Lys Ala Lys Leu Gln Lys
115 120 125

Thr Glu Glu
130

<210> SEQ ID NO 579
<211> LENGTH: 146
<212> TYPE: PRT
<213> ORGANISM: Plasmodium vivax

<400> SEQUENCE: 579

Met Asp Lys Thr Lys Ser Lys Lys Gln Ile Gly Asn Ala Lys Gly Lys
1 5 10 15

Lys Pro Ala Lys Lys Val Ile Lys Lys Val Val Lys Lys Val Leu Gly
20 25 30

Lys Lys Lys Lys Thr Val Lys Lys Leu Lys Ala Val Arg Leu Tyr Glu
35 40 45

Lys Gly Val Ile Leu Gly Tyr Lys Arg Ser Gln Arg Asn Gln Asp Pro
50 55 60

Asn Phe Thr Leu Ile Ser Ile Arg Asn Val His Thr Lys Lys His Ala
65 70 75 80

Gln Phe Tyr Val Gly Lys Lys Ile Ala Tyr Val Tyr Arg Thr Asn Lys
85 90 95

His His Asp Gly Val Lys Ile Lys Cys Ile Trp Gly Lys Val Cys Arg
100 105 110

Thr His Gly Asn Ser Gly Val Ile Arg Ala Arg Phe Arg Thr Asn Ile
115 120 125

Pro Pro Lys Ala Phe Gly Asp Arg Val Arg Ile Leu Met Tyr Pro Ser
130 135 140

Asn Ile
145

<210> SEQ ID NO 580
<211> LENGTH: 150
<212> TYPE: PRT
<213> ORGANISM: Plasmodium vivax

<400> SEQUENCE: 580

Met Thr Gln Arg Val His Tyr Arg Lys His Asn His Tyr Asn Thr Lys
1 5 10 15

Ser Asn Lys Val Arg Pro Ile Arg Thr Pro Gly Gly Lys Leu Thr Ile
20 25 30

His Val Val Lys Lys Lys Ala Gly Lys Pro Lys Cys Ala Asp Cys Lys
35 40 45

Thr Ala Ile Gln Gly Val Lys Ala Leu Arg Pro Ala Asp Asn Arg Arg
50 55 60

Ala Arg Lys Lys Asp Arg Lys Val Ser Arg Ala Tyr Gly Gly Ser Ile
65 70 75 80

```
Cys Ala Lys Cys Ile Arg Glu Arg Ile Met Arg Ala Phe Leu Phe Glu
            85                  90                  95

Glu Gln Lys Cys Val Arg Gln Val Leu Lys Glu Lys Lys Lys Gln Glu
            100                 105                 110

Lys Lys Val Lys Lys Val Lys Lys Glu Lys Lys Lys Ser Thr Ala Lys
        115                 120                 125

Asp Ala Lys Lys Thr Ala Thr Asp Asn Lys Lys Ala Lys Lys Val Gly
    130                 135                 140

Asp Lys Arg Lys Gly Arg
145                 150


<210> SEQ ID NO 581
<211> LENGTH: 124
<212> TYPE: PRT
<213> ORGANISM: Plasmodium vivax

<400> SEQUENCE: 581

Met Ser Asn Val Lys Ala Phe Gln Leu Arg Pro Leu Lys Lys Gln Glu
1               5                   10                  15

Leu Leu Asp Lys Leu Glu Asp Tyr Lys Lys Glu Leu Ser Gly Leu Arg
            20                  25                  30

Ile Ser Lys Ala Ile Gly Asn Ser Ala Lys Asn Ser Lys Ile Cys Ser
        35                  40                  45

Val Arg Lys Asn Ile Ala Arg Val Leu Thr Val Tyr Asn Gln Arg Arg
    50                  55                  60

Lys Met Glu Leu Arg Lys Lys Tyr Lys Asn Lys Lys Phe Lys Pro Tyr
65                  70                  75                  80

Asn Leu Arg Lys Lys Leu Thr Lys Ala Lys Arg Leu Glu Leu Thr Pro
                85                  90                  95

Lys Gln Lys Val Ala Met Thr Leu Lys Met Lys Lys Lys Val Glu Asn
            100                 105                 110

Phe Pro Lys Arg Lys Tyr Leu Leu Val His Lys Ala
        115                 120


<210> SEQ ID NO 582
<211> LENGTH: 113
<212> TYPE: PRT
<213> ORGANISM: Plasmodium vivax

<400> SEQUENCE: 582

Met Gly Arg Lys Ser Thr Ile Lys Pro Ala Thr Gly Ile Ala Val Gly
1               5                   10                  15

Phe Asn Ser Gly His Val Val Thr Lys Arg Asn Leu Lys Lys Ser Ile
            20                  25                  30

Lys Lys Lys Pro Lys Ser Lys Lys Lys Glu Leu Ile Asn Asp Val Val
        35                  40                  45

Arg Glu Ile Thr Gly Phe Ser Pro Tyr Glu Lys Arg Leu Ile Glu Leu
    50                  55                  60

Ile Lys Ile Gly Thr Ser Ala Ala Thr Lys Arg Ser Leu Lys Tyr Ala
65                  70                  75                  80

Lys Lys Lys Leu Gly Thr His Lys Arg Gly Lys Ala Lys Arg Glu Glu
                85                  90                  95

Ile Gln Lys Ile Val Ile Met Gln Arg Arg Lys Ala Ala Thr Glu Lys
            100                 105                 110

His
```

<210> SEQ ID NO 583
<211> LENGTH: 96
<212> TYPE: PRT
<213> ORGANISM: Plasmodium vivax

<400> SEQUENCE: 583

Met Ser Arg Arg Thr Lys Lys Val Gly Leu Thr Gly Lys Tyr Gly Thr
1 5 10 15

Arg Tyr Gly Ser Ser Leu Arg Lys Gln Ile Lys Lys Ile Glu Leu Met
20 25 30

Gln His Ala Lys Tyr Met Cys Ser Phe Cys Gly Lys Thr Ala Thr Lys
35 40 45

Arg Thr Cys Val Gly Ile Trp Gln Cys Lys Lys Cys Lys Arg Lys Val
50 55 60

Cys Gly Gly Ala Trp Ser Leu Thr Thr Pro Ala Ala Val Ala Ala Lys
65 70 75 80

Ser Thr Ile Ile Arg Leu Arg Lys Gln Lys Glu Glu Ala Gln Lys Ser
85 90 95

<210> SEQ ID NO 584
<211> LENGTH: 93
<212> TYPE: PRT
<213> ORGANISM: Plasmodium vivax

<400> SEQUENCE: 584

Met Pro Lys Gln Ile Thr Asp Ile Arg Lys Phe Leu Lys Ile Ser Arg
1 5 10 15

Lys Pro Asp Thr Thr Ala Val Ile Ile Met Lys Lys Lys Ser Lys Thr
20 25 30

Lys Lys Asn Thr Ile Ile Thr Lys Leu Lys Leu Arg Thr Lys Lys Tyr
35 40 45

Leu Tyr Thr Met Val Phe Ala Asp Lys Lys Lys Ala Glu Arg Ile Glu
50 55 60

Asn Ser Leu Leu Pro Ser Leu Lys Arg Ile Tyr Tyr Pro Gln Lys Lys
65 70 75 80

Val Val Gln Pro Val Lys Lys Met Lys Tyr Ser Lys Gly
85 90

<210> SEQ ID NO 585
<211> LENGTH: 39
<212> TYPE: PRT
<213> ORGANISM: Plasmodium vivax

<400> SEQUENCE: 585

Met Ala His Gly Ala Ser Arg Tyr Lys Lys Ser Arg Ala Lys Met Arg
1 5 10 15

Trp Lys Trp Lys Lys Lys Arg Thr Arg Arg Leu Gln Lys Lys Arg Arg
20 25 30

Lys Met Arg Gln Arg Ser Arg
35

<210> SEQ ID NO 586
<211> LENGTH: 103
<212> TYPE: PRT
<213> ORGANISM: Plasmodium vivax

<400> SEQUENCE: 586

Met Val Asn Val Pro Lys Thr Arg Lys Thr Tyr Cys Ser Asn Lys Cys
1 5 10 15

Lys Lys His Thr Met His Lys Val Ser Gln Tyr Lys Lys Gly Lys Glu
20 25 30

Arg Leu Ser Ala Leu Gly Arg Arg Arg Tyr Asp Met Lys Gln Lys Gly
35 40 45

Phe Gly Gly Gln Thr Lys Pro Val Phe Lys Lys Lys Ala Lys Thr Thr
50 55 60

Lys Lys Ile Val Leu Lys Leu Glu Cys Thr Lys Cys Lys Lys Lys Arg
65 70 75 80

Phe Gln Thr Leu Lys Arg Cys Lys Thr Phe Glu Met Gly Ala Asp Lys
85 90 95

Lys Lys Lys Gly Ala Val Tyr
100

<210> SEQ ID NO 587
<211> LENGTH: 231
<212> TYPE: PRT
<213> ORGANISM: Plasmodium vivax

<400> SEQUENCE: 587

Met Ala Lys Asp Asn Lys Gly Lys Val Lys Lys Ala Ala Gly Glu Glu
1 5 10 15

Thr Val Lys Tyr Tyr Arg Val Lys Gly Lys Lys Lys Ile Leu Ile Pro
20 25 30

Val Lys Ala Lys Lys Thr Ile Ala Lys Lys Tyr Tyr Gly Arg Lys Leu
35 40 45

Ala Ser Lys Lys Lys Tyr Ile Val Gln Gly Lys Met Arg Lys Ser Ile
50 55 60

Glu Val Gly Lys Val Ala Ile Ile Leu Ser Gly Lys His Met Gly Lys
65 70 75 80

Arg Cys Ile Ile Thr Lys Val Leu Thr Ser Gly Leu Leu Ala Val Val
85 90 95

Gly Pro Tyr Glu Val Asn Gly Val Pro Leu Lys Arg Val Asn Pro Arg
100 105 110

Tyr Val Val Val Thr Ser Thr Asn Ile Phe Lys Phe Glu Asn Met Ala
115 120 125

Gly Leu Lys Asp Glu Phe Val Lys Leu Ala Glu Gln Ile Glu Asp Asn
130 135 140

Ser Phe Val Lys Ser Leu Glu Ile Lys Lys Lys Gln Lys Lys Leu Leu
145 150 155 160

Ser Lys Lys Asn Glu Gly Leu Phe Met Asn Asp Val Ile Thr Lys Ile
165 170 175

Lys Glu Leu Met Lys Glu Asp Pro Lys Met Gln Gln Leu Gln Lys Ile
180 185 190

Gln Lys Glu Ile Gly Thr Leu Leu Lys Asp Glu Ile Ala Lys Asn Lys
195 200 205

Ile Phe Ala Glu Tyr Leu Lys Ser Lys Phe Thr Leu Arg Asn Asp Met
210 215 220

Ala Leu His Lys Met Lys Phe
225 230

<210> SEQ ID NO 588
<211> LENGTH: 256
<212> TYPE: PRT
<213> ORGANISM: Plasmodium vivax

<400> SEQUENCE: 588

```
Met Ser Asn Lys Arg Ala Lys Asn Lys Gln Leu Lys Arg Lys Asn Asp
1               5                   10                  15

Ala Gly Ala Arg Lys Gln Lys Phe Val Lys Phe Arg Arg Ile Lys Lys
            20                  25                  30

Ile Lys Phe Lys Asp Glu Lys Lys Val Phe Leu Pro Asn Glu Asp Lys
        35                  40                  45

Glu Thr Lys Val Lys Thr Pro Ser Lys Arg Lys Leu Arg Thr Leu Tyr
    50                  55                  60

Lys Lys Lys Glu Phe Lys Lys Lys Arg Asp Asn Gln Thr Asn Glu Tyr
65                  70                  75                  80

Leu Thr Leu Lys Lys Glu Leu Thr Ala Gln Thr Phe Asp Glu Gln Arg
                85                  90                  95

Arg Cys Leu Phe Ala Ile Arg Asn Asn Val Glu Cys Ile Ser Ser Ser
            100                 105                 110

Pro Ser Glu Val Leu Gln Lys Leu Lys Leu Thr Glu Lys Tyr His Gly
        115                 120                 125

Val Leu Leu Ile Asn Thr Lys Ala Asn Met Lys Lys Leu Phe Leu Val
    130                 135                 140

Lys Gln Tyr Val Cys Tyr Gly Tyr Ile Gln Lys Tyr Thr Leu Tyr Ser
145                 150                 155                 160

Leu Met Glu Lys Lys Leu Phe Leu Lys Asp Gly Asn Glu Ile Lys Arg
                165                 170                 175

Cys Asp Ser Asn Lys Ile Val Glu Lys Leu Phe Ser Lys Asn Gly Ile
            180                 185                 190

Tyr Ser Phe Pro Ser Phe Cys Glu Tyr Ile Phe Glu Cys Lys Ser Asn
        195                 200                 205

Ala Asp Gln Met Met Lys Glu Gln Ile Val Pro Phe Asn Phe Ser Tyr
    210                 215                 220

Leu Ile Ser Glu Met Thr Phe Asp Phe Leu Gln Phe Lys Asn Glu Leu
225                 230                 235                 240

Ala Gly Phe Val Lys Glu Gly Ile Asn Glu Ile Leu Glu Lys Ile Ile
                245                 250                 255
```

<210> SEQ ID NO 589
<211> LENGTH: 256
<212> TYPE: PRT
<213> ORGANISM: Plasmodium vivax

<400> SEQUENCE: 589

```
Met Ala Asp Arg Tyr Glu Glu Glu Lys Lys Asp Ala Gly Lys Asn Met
1               5                   10                  15

Met Ser Leu Arg Lys Lys Lys Gln Thr Lys Tyr Leu Gln Leu Lys Glu
            20                  25                  30

Lys Thr Gln Lys Lys Met Lys Ala Gln Lys Leu Ile Asn Lys Lys Lys
        35                  40                  45

Arg Thr Glu Leu Arg Leu Arg Thr Leu Arg Tyr Glu Lys Glu Tyr Glu
    50                  55                  60

Glu Glu Arg Lys Lys Ile Val Gln Leu Lys Arg Glu Ala Arg Lys Asn
65                  70                  75                  80

Asn Cys Phe Tyr Lys Glu Ala Glu Lys Lys Val Val Phe Val Ile Arg
                85                  90                  95

Leu Lys Gly Val Asn Lys Leu Ser Pro Lys Val Arg Ser Val Phe Arg
            100                 105                 110

Leu Leu Arg Leu Leu Gln Ile His Asn Gly Val Phe Val Lys Val Asn
        115                 120                 125
```

```
Lys Ala Thr Lys Glu Met Leu Lys Ile Val Glu Pro Phe Val Thr Tyr
    130                 135                 140

Gly Tyr Pro Thr Ile Ser Thr Ile Arg Lys Leu Val Tyr Lys Arg Gly
145                 150                 155                 160

Tyr Val Lys Val Gly Lys Val Arg Arg Tyr Ala Arg Lys Lys Ile Gln
                165                 170                 175

Asp Asn His Glu Ile Ser Lys His Leu Gly Lys Tyr Asn Val His Gly
            180                 185                 190

Val Glu Asp Met Ile His Gln Leu Tyr Thr Cys Gly Pro Ala Phe Lys
        195                 200                 205

Lys Val Asn Asn Phe Leu Trp Ala Phe Lys Leu Lys Pro Pro Lys Lys
    210                 215                 220

Gly Phe Lys Ala Lys Arg His Ala Phe Asn Glu Pro Arg Pro Gly Asp
225                 230                 235                 240

Trp Gly Asn Arg Glu Ser His Ile Asn Glu Leu Ile Lys Arg Met Ile
                245                 250                 255


<210> SEQ ID NO 590
<211> LENGTH: 260
<212> TYPE: PRT
<213> ORGANISM: Plasmodium vivax

<400> SEQUENCE: 590

Met Gly Arg Val Ile Arg Gly Gln Arg Lys Gly Arg Gly Ser Ile Phe
1               5                   10                  15

Lys Ser His Asn His His Arg Lys Gly Ala Ala Lys Leu Arg His Leu
            20                  25                  30

Asp Phe Cys Glu Lys Lys Gly Tyr Ile Lys Gly Leu Ile Lys Asp Ile
        35                  40                  45

Ile His Asp Pro Gly Arg Gly Ala Pro Leu Ala Lys Ile Val Phe Lys
    50                  55                  60

Lys Thr Glu Lys Tyr Gly Lys Lys Glu Glu Leu Met Val Ala Thr Glu
65                  70                  75                  80

Gly Met Phe Thr Gly Gln Tyr Ile Ser Cys Gly Ile Lys Ala Pro Leu
                85                  90                  95

Ser Val Gly Asn Ile Leu Pro Ile Gly Lys Met Pro Glu Gly Thr Leu
            100                 105                 110

Ile Cys Asn Leu Glu His Arg Thr Gly Asn Arg Gly Thr Leu Val Lys
        115                 120                 125

Ala Ser Gly Cys Tyr Ala Thr Val Val Gly Gln Ser Glu Asp Gly Lys
    130                 135                 140

Lys Thr Lys Val Arg Leu Pro Ser Gly Ala Lys Lys Thr Ile Asp Ala
145                 150                 155                 160

Arg Ala Arg Ala Met Val Gly Val Val Gly Ala Gly Gly Arg Ile Asp
                165                 170                 175

Lys Pro Ile Leu Lys Ala Gly Val Ala His His Lys Tyr Arg Val Lys
            180                 185                 190

Arg Asn Cys Trp Pro Lys Val Arg Gly Val Ala Met Asn Pro Val Asp
        195                 200                 205

His Pro His Gly Gly Gly Asn His Gln His Ile Gly His Pro Ser Thr
    210                 215                 220

Val Ser Arg Ser Ala Pro Ala Gly Gln Lys Val Gly Leu Ile Ala Ala
225                 230                 235                 240

Arg Arg Thr Gly Leu Leu Arg Gly Ala Lys Lys Thr Lys Leu Val Gly
```

```
            245                 250                 255

Lys Thr Glu Asp
            260


<210> SEQ ID NO 591
<211> LENGTH: 190
<212> TYPE: PRT
<213> ORGANISM: Plasmodium vivax

<400> SEQUENCE: 591

Met Lys Thr Ile Val Ser Ser Gln Lys Val Ile Ile Pro Glu Gly Val
1               5                   10                  15

Gln Val Ala Ile Asn Ser Arg Lys Val Thr Val Thr Gly Lys Tyr Gly
            20                  25                  30

Thr Leu Lys Arg Ser Phe Arg His Leu Pro Ile Asp Val Arg Leu Asn
        35                  40                  45

Lys Leu Lys Lys Tyr Ile Lys Val Val Met Trp Phe Gly Val Pro Asp
    50                  55                  60

Arg Leu Ala Cys Ile Arg Thr Val Cys Thr His Leu Lys Asn Met Phe
65                  70                  75                  80

Thr Gly Val Thr Lys Lys Phe Leu Tyr Lys Met Arg Leu Val His Ala
                85                  90                  95

His Phe Pro Ile Asn Ser Asn Ile Val Asp Asn Asn Lys Ser Ile Glu
            100                 105                 110

Ile Arg Asn Tyr Leu Gly Glu Lys Arg Val Arg Phe Val Lys Ala Leu
        115                 120                 125

Pro Gly Val Leu Ile Glu Lys Ser Pro Asn Val Lys Asp Glu Ile Tyr
    130                 135                 140

Val Ser Gly Ala Asp Ile Glu Asn Val Ser Leu Thr Ala Ala Leu Ile
145                 150                 155                 160

His Gln Ser Val Leu Cys Arg Asn Lys Asp Ile Arg Lys Phe Leu Asp
                165                 170                 175

Gly Ile Tyr Val Ser Glu Val Thr Thr Val Glu Lys Asp Glu
            180                 185                 190


<210> SEQ ID NO 592
<211> LENGTH: 109
<212> TYPE: PRT
<213> ORGANISM: Plasmodium vivax

<400> SEQUENCE: 592

Met Asn Ala Leu Ile Lys Phe Met Tyr Thr Pro Lys Ala His Phe Asn
1               5                   10                  15

Ile Tyr Asn Glu Tyr Leu Asn Ala Tyr Arg Lys Lys Ile Asn Arg Ile
            20                  25                  30

Pro Phe Tyr Ile Arg Arg Thr Ala Ser Asp Asn Leu Pro Val Phe Leu
        35                  40                  45

Lys Tyr Lys Asn Asn Lys Asn Leu Val Val Thr Val Ile Arg Lys Ile
    50                  55                  60

Lys Gly Asn Lys Glu Ile Leu Lys Arg Glu Ile Glu Ser Ile Cys Asn
65                  70                  75                  80

Ser Asn Val Ile Glu Lys Thr Asp Cys Trp Leu Ile Lys Gly Asn His
                85                  90                  95

Lys Lys Lys Ile Lys Asp Tyr Phe Lys Tyr Ile Gly Tyr
            100                 105
```

<210> SEQ ID NO 593
<211> LENGTH: 206
<212> TYPE: PRT
<213> ORGANISM: Plasmodium vivax

<400> SEQUENCE: 593

Met Arg Ile Glu Lys Cys Trp Tyr Cys Ser Gly Asn Ile Tyr Pro Gly
1 5 10 15

His Gly Ile Phe Phe Ile Arg Asn Asp Ala Asn Ile Phe Arg Phe Cys
20 25 30

Arg Ser Lys Cys His Lys His Phe Lys Ala Lys His Asn Pro Arg Lys
35 40 45

Val Lys Trp Thr Lys Val Tyr Arg Lys Glu Arg Asn Lys Glu Leu Ser
50 55 60

Ala Asp Lys Thr Phe Glu Phe Glu Arg Ile Arg Ser Glu Pro Val Lys
65 70 75 80

Tyr Asp Arg Asp Leu Tyr Ile Lys Thr Ile Asn Ala Ile Lys Gln Ile
85 90 95

Asp Arg Ile Lys Glu Ala Arg Lys Met Arg Phe Tyr Lys Asn Arg Ile
100 105 110

Lys Glu Ile Ser Glu Lys Lys Ile Asn Leu Ser Leu Asn Tyr Ile Lys
115 120 125

Lys Asn Pro Ala Leu Leu Lys Asn Thr Gln Phe Glu Gly Val Leu Gly
130 135 140

Glu Leu Met Asn Glu Gln Gln Arg Glu Gly Ala Asp Phe Ser Leu Val
145 150 155 160

Lys Gly Thr Phe Asp Gln Glu Glu Leu Ile Arg Thr Asp Ala Ala Asp
165 170 175

Met Ala Gln Lys Phe Ser Ala Asp Val Thr Ser Ile Arg Asp Thr Gln
180 185 190

Gly Val Gln His Gln Lys Glu Asp Gln Asn Phe Glu Leu Ala
195 200 205

<210> SEQ ID NO 594
<211> LENGTH: 411
<212> TYPE: PRT
<213> ORGANISM: Plasmodium vivax

<400> SEQUENCE: 594

Met Ala Thr Val Arg Pro Val Ala Asn Val Tyr Ser Thr Ser Asn Lys
1 5 10 15

Gln Val Val Gly Glu Val Glu Ile Pro Val Val Phe Gln Thr Pro Ile
20 25 30

Arg Ser Asp Leu Val Gln Glu Val Phe Lys Asn Val Ser Lys Asn Arg
35 40 45

Arg His Pro Tyr Ala Val Lys Leu Gly Ala Gly Tyr Glu Thr Ser Ala
50 55 60

Glu Ser Trp Gly Thr Gly Arg Ala Val Ala Arg Ile Pro Arg Val Pro
65 70 75 80

Gly Gly Gly Thr His Arg Ala Gly Gln Gly Ala Phe Gly Asn Met Cys
85 90 95

Arg Gly Gly Gly Met Phe Asn Pro Thr Lys Val Trp Arg Arg Trp Gly
100 105 110

Arg Lys Val Asn Leu Lys Glu Lys Arg Tyr Ala Val Cys Ser Ser Ile
115 120 125

Ala Ala Ser Gly Val Thr Ser Leu Val Leu Ala Arg Gly His Arg Ile

```
    130                 135                 140

Ser Asn Met Lys Glu Val Pro Leu Val Val Ser Asn Asp Val Glu Ser
145                 150                 155                 160

Ile Ser Lys Thr Lys Glu Ala Leu Lys Phe Leu Ile Thr Leu Gly Leu
                165                 170                 175

Lys Glu Glu Val Asn Arg Leu Ile Lys Ser Lys Lys Ile Arg Ala Gly
            180                 185                 190

Lys Gly Lys Met Arg Asn Arg Lys Tyr Arg Met Arg Asn Gly Pro Leu
        195                 200                 205

Ile Ile Tyr Ser Lys Asp Cys Gly Val Lys Lys Ala Phe Arg Asn Ile
    210                 215                 220

Pro Gly Val Asp Leu Cys Lys Val Thr Lys Leu Asn Leu Met Lys Leu
225                 230                 235                 240

Ala Pro Gly Gly Ser Ile Gly Arg Leu Cys Ile Trp Ser Glu Ser Ala
                245                 250                 255

Phe Lys Lys Leu Asp Val Ile Tyr Gly Arg Ile Phe Lys Lys Lys Ile
            260                 265                 270

Thr Lys Lys Asn Tyr Ile Leu Pro Lys Ser Leu Met Ala Asn Ser Asp
        275                 280                 285

Ile Tyr Arg Ile Ile Ser Ser Glu Gln Val Gln Ala Thr Leu Leu Ala
    290                 295                 300

Arg Lys Arg Pro Cys Lys Lys Arg Leu Gln Asn Lys Asn Ser Leu Thr
305                 310                 315                 320

Asn Phe Ala Val Arg Cys Arg Leu Asn Pro Ala Tyr Lys Leu Leu Arg
                325                 330                 335

Ser Ile Ala Ile Arg Lys Met Lys Lys Ser Ile Glu Ala Lys Lys Asn
            340                 345                 350

Asn Lys Lys Glu Leu Arg Val Lys Lys Lys Ile Gln Lys Lys Glu Leu
        355                 360                 365

Gln Lys Val Asn His Ala Tyr Tyr Thr Ser Ile Ala Ser Ser Val Lys
    370                 375                 380

Arg Lys Lys Lys Lys Glu Glu Lys Lys Ala Lys Ser Lys Lys Asp Ala
385                 390                 395                 400

Asn Lys Ala Leu Leu Pro Thr Ala Gly Asp Asp
                405                 410


<210> SEQ ID NO 595
<211> LENGTH: 186
<212> TYPE: PRT
<213> ORGANISM: Plasmodium vivax

<400> SEQUENCE: 595

Met Glu Trp Gln Ser Val Gly Ile Val Tyr Ile Gln Thr Tyr Asn His
1               5                   10                  15

Phe Phe His Tyr Cys His Phe Cys Ser Val Gly Asn Asn Leu Leu Ser
            20                  25                  30

Met Leu Ser Tyr Asn Asn Glu Glu Tyr Val Leu Arg Leu His Arg Ser
        35                  40                  45

Ser Val Tyr Phe Val Arg Ala Glu Leu Ala Lys Gln Ala Glu Ala Ile
    50                  55                  60

Ile Asn Lys Asn Ser Leu Ile Ser Leu Gly Ile Cys Leu Gly Lys Phe
65                  70                  75                  80

Thr Lys Ala Asn Asn Phe Phe Ile Lys Ile Thr Ser Leu Ser Phe Leu
                85                  90                  95
```

```
Asn Glu Phe Cys Ile His Lys Ile Trp Leu Lys Glu Ser Gly Glu Lys
            100                 105                 110

Asn Phe Leu Phe Gly Asn Asn Val Leu Lys Ser His Leu Leu Lys Val
        115                 120                 125

Ser Asp Asn Ile Lys Lys Gly Asp Gly Ile Ile Val Leu Ser Met Asn
    130                 135                 140

Asp Ser Pro Ile Gly Phe Gly Ile Ser Ile Arg Asn Thr Gln Asp Ile
145                 150                 155                 160

Lys Ile Leu Asn Val Thr Asp Ile Val Leu Ile His Gln Gly Asp Val
                165                 170                 175

Gly Glu Tyr Leu Arg Ser Glu Ala Thr Ile
            180                 185


<210> SEQ ID NO 596
<211> LENGTH: 247
<212> TYPE: PRT
<213> ORGANISM: Plasmodium vivax

<400> SEQUENCE: 596

Met Ala Ile Arg Val Gln Phe Glu Asn Ser Asn Glu Val Gly Val Phe
1               5                   10                  15

Ser Arg Leu Thr Asn Ser Tyr Ala Leu Ile Ala Met Gly Gly Ser Glu
            20                  25                  30

Asn Phe Ser Ser Val Phe Glu Ser Glu Leu Ser Gln His Ile Pro Leu
        35                  40                  45

Val Tyr Thr Thr Ile Gly Gly Thr Lys Val Ile Gly Arg Val Cys Val
    50                  55                  60

Gly Asn Arg Lys Gly Leu Leu Val Ser Ser Ile Cys Thr Asp Gln Glu
65                  70                  75                  80

Leu Leu His Leu Arg Asn Ala Leu Pro Glu Asn Val Lys Ile Lys Arg
                85                  90                  95

Ile Glu Glu Arg Leu Ser Ala Leu Gly Asn Cys Ile Thr Ala Asn Asp
            100                 105                 110

Tyr Val Gly Leu Ile His Thr Asp Ile Asp Arg Glu Thr Glu Glu Ile
        115                 120                 125

Val Gln Asp Val Leu Asp Ile Glu Val Phe Arg Thr Ser Ile Ala Gly
    130                 135                 140

Asn Leu Leu Val Gly Thr Tyr Ser Tyr Phe Thr Asn Asn Gly Gly Leu
145                 150                 155                 160

Leu His Ala Met Thr Ser Ser Gln Glu Ile Glu Glu Leu Ser Glu Leu
                165                 170                 175

Leu Gln Ile Pro Leu Ile Thr Gly Thr Val Asn Arg Gly Ser Asp Leu
            180                 185                 190

Ile Gly Ala Gly Leu Val Ala Asn Asp Trp Ser Ala Phe Cys Gly Met
        195                 200                 205

Asp Thr Thr Ala Ile Glu Leu Ser Ile Ile Glu Lys Val Phe Lys Leu
    210                 215                 220

Asn Ser Ile Glu Asp Ala Asn Ile Glu Asp Asn Phe Lys Tyr Lys Ser
225                 230                 235                 240

Ser Ile Ile Gln Thr Met Ile
                245


<210> SEQ ID NO 597
<211> LENGTH: 301
<212> TYPE: PRT
<213> ORGANISM: Plasmodium vivax
```

<400> SEQUENCE: 597

Met Ala Thr Glu Glu Ala Pro Pro Arg Ala Ser Ser Gly Gly Asn Arg
1 5 10 15

Lys Tyr Arg Lys Glu Lys Pro Trp Asp Asn Glu Asn Ile Asp His Trp
20 25 30

Lys Val Glu Lys Phe Thr Arg Glu Asp Asn Lys His His Phe Leu Glu
35 40 45

Glu Ser Ser Phe Lys Val Leu Phe Pro Lys Tyr Arg Glu Lys Tyr Leu
50 55 60

Gln Gln Phe Ser Thr Asp Ile Lys Asn Val Leu Asn Asn His Phe Ile
65 70 75 80

Lys Phe Glu Met Asn Leu Ile Glu Gly Tyr Met Cys Val Lys Thr Thr
85 90 95

Lys Lys Thr Phe Asp Pro Tyr Ile Ile Ile Lys Ala Arg Asp Met Ile
100 105 110

Ser Leu Leu Ser Arg Ser Val Pro Phe Thr His Ala Lys Arg Val Leu
115 120 125

Glu Asp Glu Thr Phe Cys Asp Ile Ile Lys Ile Ser Thr Tyr Val Arg
130 135 140

Asn Arg Asn Lys Phe Ile Lys Arg Arg Gln Arg Leu Leu Gly Ser Asn
145 150 155 160

Gly Thr Thr Leu Lys Ala Leu Glu Ile Leu Thr Ser Cys Tyr Ile Cys
165 170 175

Val His Gly Lys Thr Val Ser Val Ile Gly Phe Phe Lys Ala Leu Lys
180 185 190

Val Val Arg Arg Ile Ile Ile Asp Cys Met Lys Asn Ile His Pro Val
195 200 205

Tyr His Ile Lys Glu Leu Ile Ala Lys Arg Glu Leu Gln Lys Asn Glu
210 215 220

Glu Phe Lys Asn Glu Asn Trp Glu Lys Tyr Leu Pro Asn Phe Lys Lys
225 230 235 240

Arg Asn Ala Gln Arg Arg Lys Ile Lys Gln Lys Leu Glu Lys Lys Lys
245 250 255

Gly Ala Lys Lys Glu Glu Lys Ser Val Phe Pro Pro Asp Gln Leu Pro
260 265 270

Arg Lys Ile Asp Ile Gln Met Glu Thr Gly Glu Tyr Phe Met Arg Arg
275 280 285

Ser Ser Gly Gly Val Lys Gly Lys Glu Val Ala Gly Glu
290 295 300

<210> SEQ ID NO 598
<211> LENGTH: 518
<212> TYPE: PRT
<213> ORGANISM: Plasmodium vivax

<400> SEQUENCE: 598

Met Ile Lys Lys Gly Ser Leu Lys Leu Lys Ser Leu Lys Ile Gly Arg
1 5 10 15

Ser Ser Val Gly Asn Val Lys Val Glu Gly Lys Ser Ile Cys Lys Asp
20 25 30

Glu Ala Lys Arg Lys Asn Asp Glu Lys Gln Lys Arg Leu Lys Met Tyr
35 40 45

Arg Thr Lys Ala Asn Leu Lys Lys Met Asn Ala Lys Ile Asn Glu Val
50 55 60

-continued

Arg Arg Ile Glu Pro Asn Ile Lys Trp Phe Asn Asn Thr Arg Thr Ile
65 70 75 80

Ser Gln Ser Lys Leu Ala Ile Phe Arg Asp Lys Leu Glu Glu Ala Thr
85 90 95

His Asp Pro Phe Ser Val Ile Ile Lys Arg Ser Lys Ile Pro Val Glu
100 105 110

Leu Leu Arg Gly Ser Ala Gly Glu Ser Val Pro Ala Ala Phe Ala Pro
115 120 125

Gln Phe Glu Lys Lys Lys Gln Gln Ser Glu Asn Leu Leu Arg Met Glu
130 135 140

His Phe Gln Asp Val Tyr Gly Lys Lys Lys Lys Arg Lys Arg Pro Lys
145 150 155 160

Leu Asn Val Ser Ser Leu Glu Glu Leu Ala Asn Asp Ala Asp Arg Lys
165 170 175

Leu Thr Asn Tyr Glu Val Glu Arg Asp Asn Ser Leu Ile Glu Ser Arg
180 185 190

Asn Arg Glu Val Glu Lys Lys Phe Ser Lys Asp His Leu Leu Arg Ile
195 200 205

Gly Gln Ser Lys Arg Ile Trp Thr Glu Leu Tyr Lys Val Ile Asp Ser
210 215 220

Ser Asp Ile Ile Leu Glu Val Leu Asp Ala Arg Asp Pro Ile Gly Thr
225 230 235 240

Arg Cys Arg Arg Leu Glu Glu Asn Leu Lys Lys Asp Arg Pro Asn Lys
245 250 255

His Ile Ile Leu Ile Val Asn Lys Val Asp Leu Val Pro Thr Ser Val
260 265 270

Ala Gln Lys Trp Ile Lys Ile Leu Ser Lys Glu Tyr Pro Thr Ile Ala
275 280 285

Tyr His Ala Ser Ile Ser Asn Pro Phe Gly Lys Asn Asp Leu Phe Asn
290 295 300

Val Ile Arg Gln Tyr Thr Gln Phe Phe Gln Asp Gln Arg Lys Lys His
305 310 315 320

Ile His Ile Gly Leu Ile Gly Tyr Pro Asn Val Gly Lys Ser Ala Ile
325 330 335

Ile Asn Ser Leu Lys Lys Lys Val Val Cys Ile Ser Ala Cys Leu Pro
340 345 350

Gly Gln Thr Lys Tyr Trp Gln Phe Ile Lys Leu Thr Ser Lys Ile Tyr
355 360 365

Leu Ile Asp Cys Pro Gly Ile Val Pro Tyr Asp Ile Glu Asp Ser Asp
370 375 380

Lys Ile Leu Arg Cys Thr Met Arg Leu Glu Lys Ile Thr Asn Pro His
385 390 395 400

Phe Tyr Ile Asp Asp Val Phe Lys Met Val Asn Arg Glu His Leu Leu
405 410 415

Arg Ile Tyr Lys Leu Pro Ala Asp Leu Gln Phe Gly Asn Thr Glu Glu
420 425 430

Phe Leu Glu Ile Leu Ala Arg Lys Met Gly Lys Leu Leu Lys Gly Gly
435 440 445

Glu Pro Asp Ile Thr Ser Val Ser Lys Ile Ile Leu Asn Asp Trp Ile
450 455 460

Lys Gly Lys Ile Pro Tyr Tyr Val Asp Pro Asp Ala Ala Gln Ser Thr
465 470 475 480

```
Gly Ala Ala Asp Ala Ala Ala Ser Gly Glu Glu Glu Glu Leu Ala Ala
                485                 490                 495

Glu Gly Val Gly Ala Asp Gly Leu Glu Glu Glu Glu Leu Ala Ala Asp
            500                 505                 510

Gly Val Ala Ala Gln Glu
        515


<210> SEQ ID NO 599
<211> LENGTH: 323
<212> TYPE: PRT
<213> ORGANISM: Plasmodium vivax

<400> SEQUENCE: 599

Met Leu Phe Leu Gly Leu Cys Ala Ile Phe Phe Val Phe Ser Pro Gln
1               5                   10                  15

Gly Gly Gly Ala Ala Lys Val Val Ala His Cys Ser Ser Ala Ala Lys
            20                  25                  30

Val Val Ala Pro Arg Ser Ser Thr Ser Val Val Ser Pro Pro Arg Gly
        35                  40                  45

Cys Leu Thr Phe Val Pro Ser Met Asn Gly Trp Arg Pro Lys Arg Cys
    50                  55                  60

Arg Arg Ser Lys Val Asn Val Leu Ile Asn Ser Pro Ala Gln Ile Lys
65                  70                  75                  80

Leu Ser Glu Ile Glu Asp Asp Arg Asp Arg Ser Gly Lys Phe Cys Val
                85                  90                  95

Ile Glu Ile Cys Gly Lys Ala Arg Trp Val Glu Glu Gly Arg Tyr Tyr
            100                 105                 110

Asp Val Phe Arg Ile Lys Gln Glu Glu Asn Lys Ser Ile Tyr Leu Asn
        115                 120                 125

Arg Val Phe Phe Tyr Ser Thr Met Glu Gly Lys Leu Leu Phe Gly Thr
    130                 135                 140

Pro Phe Leu Asp Asn Val Arg Ile Lys Ala Thr Val Met Lys His Phe
145                 150                 155                 160

Arg Gly Asn Lys Ile Tyr Arg Leu Lys Phe Lys Pro Lys Lys Asn Tyr
                165                 170                 175

Lys Arg Phe Tyr Gly His Arg Gln Glu Met Ser Arg Ile Tyr Ile Asn
            180                 185                 190

Arg Phe Glu Val Asn Asn Asn Leu Val Asp Arg Glu Arg Arg Lys Tyr
        195                 200                 205

Asn Phe Phe Arg Asp Asp Ser Ile Tyr Tyr Val Leu Asn Arg Ile His
    210                 215                 220

Asn Met Ile Arg Pro Ser Leu Glu Leu Lys His Leu Lys Arg His Phe
225                 230                 235                 240

Thr Asp Tyr Leu Asn Arg Phe Cys Ser Leu Lys Phe Glu Thr Phe Tyr
                245                 250                 255

Lys His Arg Gly Asn Tyr Lys Arg Glu Asn Met Leu Arg Asn Ile Leu
            260                 265                 270

Lys Thr Lys Lys Leu Ser Lys Arg Pro Glu Val Gln Glu Glu Val Arg
        275                 280                 285

Arg Ile Glu Glu Glu Lys Glu Ser Arg Arg Leu Asn Lys Tyr Asp Pro
    290                 295                 300

Leu Ala Asp Phe Asp Pro Val Ala Asn Glu Cys Phe Ile Arg Glu His
305                 310                 315                 320

Phe Tyr Val
```

<210> SEQ ID NO 600
<211> LENGTH: 221
<212> TYPE: PRT
<213> ORGANISM: Plasmodium vivax

<400> SEQUENCE: 600

Met Pro Lys Ser Lys Arg Asn Ile Thr Ile Ser Leu Thr Lys Val Lys
1 5 10 15

Lys Lys Leu Asn Lys Lys Glu Leu Lys Asp Gln Lys Leu Ser Asp Leu
20 25 30

Lys Lys Ile Ile Gln Val Pro Asn Ile Tyr Ile Tyr Ile Leu Asp Val
35 40 45

Arg Thr Tyr Ser Asn Asn Asn Leu Lys Gln Ala Ile Glu Tyr Phe Lys
50 55 60

Pro Asn Gly Arg Phe Phe Ile Gly Lys Asn Lys Leu Met Lys Leu Ala
65 70 75 80

Leu Gly Thr Ser Glu Lys Asp Glu Ala Lys Pro Asn Val Cys Lys Val
85 90 95

Ala Glu Leu Leu Val Gly Asn Arg Ile Leu Leu Ile Thr Lys Asp Pro
100 105 110

Pro Leu Lys Val Ile Lys Phe Phe Asn Glu Phe Gln Pro Glu Glu Tyr
115 120 125

Ile Lys Pro Gly Asn Ile Cys Thr Gln Asn Val Thr Leu Lys Phe Gly
130 135 140

Asp Val Leu Asn Val Pro Val Ser Met Gln Lys Asp Leu Gln Lys Arg
145 150 155 160

Lys Val Thr Phe Asp Ile Val Asp Gln Lys Ile Val Ile Arg Lys Asp
165 170 175

Lys Val Leu Ala Glu Lys Asp Lys Leu Val Ser Ala Glu Asn Ala Lys
180 185 190

Leu Leu Arg Met Leu Asn Met Lys Ile Ala Asn Phe Asp Ile Thr Val
195 200 205

Leu Gly Tyr Trp Asn Val Asn Lys Phe Val Ser Leu Met
210 215 220

<210> SEQ ID NO 601
<211> LENGTH: 155
<212> TYPE: PRT
<213> ORGANISM: Plasmodium vivax

<400> SEQUENCE: 601

Met Pro Lys Asn Lys Gly Lys Gly Gly Lys Asn Arg Arg Arg Gly Lys
1 5 10 15

Asn Asp Asn Glu Gly Glu Lys Arg Glu Leu Leu Tyr Lys Glu Glu Asp
20 25 30

Gln Glu Tyr Ala Gln Val Leu Arg Met Leu Gly Asn Gly Arg Leu Glu
35 40 45

Ala His Cys Phe Asp Gly Val Lys Arg Leu Cys His Ile Arg Gly Lys
50 55 60

Met Arg Lys Arg Val Trp Ile Asn Ser Gly Asp Ile Ile Leu Val Ser
65 70 75 80

Leu Arg Asp Tyr Gln Asp Ser Lys Ala Asp Val Ile Ala Lys Tyr Thr
85 90 95

Pro Asp Glu Ala Arg Ser Leu Lys Thr His Gly Glu Leu Pro Glu Thr
100 105 110

```
Ala Lys Ile Asn Glu Thr Asp Ile Phe Asp Asp Asp Gly Gln Asn Gly
        115                 120                 125

Val Glu Phe Leu Asp Asp Glu Ser Asp Glu Glu Ala Gln Glu Glu Met
    130                 135                 140

Asn Asn Ala Arg Lys Leu Glu Ile Glu Asp Ile
145                 150                 155


<210> SEQ ID NO 602
<211> LENGTH: 118
<212> TYPE: PRT
<213> ORGANISM: Plasmodium vivax

<400> SEQUENCE: 602

Met Ser Lys Leu Met Lys Gly Ala Ile Asp Asn Glu Lys Tyr Arg Leu
1               5                   10                  15

Arg Arg Ile Arg Ile Ala Leu Thr Ser Lys Asn Leu Arg Ala Ile Glu
            20                  25                  30

Lys Val Cys Ser Asp Ile Met Lys Gly Ala Lys Glu Lys Asn Leu Asn
        35                  40                  45

Val Ser Gly Pro Val Arg Leu Pro Val Lys Thr Leu Arg Ile Thr Thr
    50                  55                  60

Arg Lys Ser Pro Cys Gly Glu Gly Thr Asn Thr Trp Asp Arg Phe Glu
65                  70                  75                  80

Leu Arg Ile Tyr Lys Arg Leu Ile Asp Leu Tyr Ser Gln Cys Glu Val
                85                  90                  95

Val Thr Gln Met Thr Ser Ile Asn Ile Asp Pro Val Val Glu Val Glu
            100                 105                 110

Val Ile Ile Thr Asp Ser
        115


<210> SEQ ID NO 603
<211> LENGTH: 137
<212> TYPE: PRT
<213> ORGANISM: Plasmodium vivax

<400> SEQUENCE: 603

Met Asp Lys Gln Thr Leu Pro His His Lys Tyr Ser Tyr Ile Pro Lys
1               5                   10                  15

Gln Asn Lys Lys Leu Ile Tyr Glu Tyr Leu Phe Lys Glu Gly Val Ile
            20                  25                  30

Val Val Glu Lys Asp Ala Lys Ile Pro Arg His Pro His Leu Asn Val
        35                  40                  45

Pro Asn Leu His Ile Met Met Thr Leu Lys Ser Leu Lys Ser Arg Asn
    50                  55                  60

Tyr Val Glu Glu Lys Tyr Asn Trp Lys His Gln Tyr Phe Ile Leu Asn
65                  70                  75                  80

Asn Glu Gly Ile Glu Tyr Leu Arg Glu Phe Leu His Leu Pro Pro Ser
                85                  90                  95

Ile Phe Pro Ala Thr Leu Ser Lys Lys Thr Val Asn Arg Ala Pro Lys
            100                 105                 110

Met Asp Glu Asp Ile Ser Arg Asp Val Arg Gln Pro Met Gly Arg Gly
        115                 120                 125

Arg Ala Phe Asp Arg Arg Pro Phe Glu
    130                 135


<210> SEQ ID NO 604
<211> LENGTH: 161
```

<212> TYPE: PRT
<213> ORGANISM: Plasmodium vivax

<400> SEQUENCE: 604

Met Ala Thr Thr Leu Asp Val Gln His Glu Arg Ala Tyr Gln Lys Gln
1               5                   10                  15

Glu Gly Ala Ser Phe Phe Asn Ser Lys Lys Ile Lys Lys Gly Ser Lys
            20                  25                  30

Ser Tyr Ile Arg Tyr Trp Lys Lys Val Gly Leu Gly Phe Ala Thr Pro
        35                  40                  45

Lys Glu Ala Lys Glu Gly Val Tyr Val Asp Lys Lys Cys Pro Phe Thr
    50                  55                  60

Gly Asn Val Ser Ile Arg Gly Arg Ile Leu Lys Gly Met Val Ile Ser
65                  70                  75                  80

Asn Lys Met Lys Arg Thr Ile Ile Ile Arg Arg Asn Tyr Leu His Tyr
                85                  90                  95

Val Lys Lys Tyr Asn Arg Phe Glu Lys Arg His Lys Asn Ile Pro Cys
            100                 105                 110

His Cys Ser Pro Cys Phe Asp Val Lys Glu Gly Asp Ile Val Thr Val
        115                 120                 125

Gly Gln Cys Arg Pro Leu Ser Lys Thr Val Arg Phe Asn Val Leu His
    130                 135                 140

Val Glu Lys His Gln Ile Phe Gly Ser Ala Arg Lys Gln Phe Val Leu
145                 150                 155                 160

Phe

<210> SEQ ID NO 605
<211> LENGTH: 141
<212> TYPE: PRT
<213> ORGANISM: Plasmodium vivax

<400> SEQUENCE: 605

Met Ser Asp Val Glu Ser Ala Asp Asn Asn Val Val Val Glu Glu Lys
1               5                   10                  15

Ala Val Phe Asp Asn Val Thr Ala Ile Gln Lys Val Ile Lys Asn Ala
            20                  25                  30

His Val His Asp Gly Leu Lys Ile Gly Ile Arg Glu Val Ile Lys Ser
        35                  40                  45

Ile Glu Ser Gln Glu Ala Lys Val Cys Phe Leu Ser Asp Val Cys Ser
    50                  55                  60

Glu Pro Ala Tyr Lys Lys Leu Ile Thr Thr Leu Cys Ala Glu Lys Asn
65                  70                  75                  80

Ile Pro Leu Phe Met Val Gln Asn Asp Ser Lys Asp Leu Gly His Trp
                85                  90                  95

Ala Gly Leu Phe Lys Leu Asp Asn Glu Gly Asn Ala Arg Lys Ile Ile
            100                 105                 110

Gly Ala Ser Ser Val Ala Val Val Asp Phe Gly Glu Asp Ser Ala Glu
        115                 120                 125

Lys Asp Phe Leu Leu Ser Gln Asn Gln Thr Val Thr Ala
    130                 135                 140

<210> SEQ ID NO 606

<400> SEQUENCE: 606

000

<210> SEQ ID NO 607
<211> LENGTH: 151
<212> TYPE: PRT
<213> ORGANISM: Plasmodium vivax

<400> SEQUENCE: 607

Met Gly Arg Met Tyr Gly Lys Gly Lys Gly Ile Ser Ser Ser Thr Leu
1 5 10 15

Pro Tyr Lys Arg Lys Gln Pro Ser Trp Leu Lys Gln Lys Pro Ser Glu
20 25 30

Ile Glu Asp Ala Ile Ile Lys Leu Ala Lys Lys Gly Gln Thr Pro Ser
35 40 45

Gln Ile Gly Ala Thr Leu Arg Asp Asn Tyr Gly Ile Pro Gln Val Lys
50 55 60

Ser Val Thr Gly Asn Lys Ile Leu Arg Ile Leu Arg Ala Gln Gly Ile
65 70 75 80

Ala Thr Thr Ile Pro Glu Asp Leu Tyr Phe Leu Ile Lys Lys Ala Val
85 90 95

Ser Met Arg Lys His Leu Glu Lys Asn Lys Lys Asp Lys Asp Cys Lys
100 105 110

Phe Arg Leu Ile Leu Thr Glu Ser Lys Ile His Arg Ile Ser Arg Tyr
115 120 125

Tyr Lys Arg Lys Lys Leu Leu Pro Ser Asn Trp Lys Tyr Gln Ser Ser
130 135 140

Thr Ala Ser Ala Leu Ile Ala
145 150

<210> SEQ ID NO 608
<211> LENGTH: 130
<212> TYPE: PRT
<213> ORGANISM: Plasmodium vivax

<400> SEQUENCE: 608

Met Val Arg Met Ser Val Leu Ala Asp Cys Leu Lys Thr Ile Asn Asn
1 5 10 15

Ala Glu Lys Arg Gly Arg Arg Gln Val Leu Ile Arg Pro Ser Ser Lys
20 25 30

Val Val Ile Lys Phe Leu Gln Tyr Met Gln Lys Lys Gly Tyr Ile Gly
35 40 45

Ser Phe Glu Ile Val Asp Asp His Arg Ser Gly Lys Ile Val Val Asn
50 55 60

Leu Leu Gly Arg Ile Asn Lys Cys Ala Val Ile Ser Pro Arg Tyr Asp
65 70 75 80

Val Lys Leu Asp Glu Ile Glu Lys Ile Ile Thr Ser Ile Leu Pro Ser
85 90 95

Arg Leu Phe Gly His Leu Ile Leu Thr Thr Pro Tyr Gly Ile Met Asp
100 105 110

His Glu Glu Ala Arg Arg Lys His Thr Gly Gly Lys Val Leu Gly Phe
115 120 125

Phe Phe
130

<210> SEQ ID NO 609
<211> LENGTH: 144
<212> TYPE: PRT
<213> ORGANISM: Plasmodium vivax

<400> SEQUENCE: 609

Met Thr Thr Lys Val Lys Arg Val Gln Thr Phe Gly Lys Lys Lys Thr
1 5 10 15

Ala Val Ala Val Ala Thr Val Thr Asn Gly Lys Gly Leu Ile Lys Leu
20 25 30

Asn Gly Lys Asn Leu Asp Leu Val Glu Pro Tyr Ile Leu Lys Thr Lys
35 40 45

Val Tyr Glu Pro Leu Trp Leu Ile Gly Ser Gly Lys Leu Lys Asn Leu
50 55 60

Asp Ile Arg Ile Arg Val Lys Gly Gly Gly Gln Thr Ser Gln Ile Tyr
65 70 75 80

Ala Ile Arg Gln Ala Ile Gly Lys Gly Ile Ile Ser Tyr Tyr Gln Lys
85 90 95

Tyr Val Asp Glu Ser Thr Lys Lys Glu Leu Lys Asp Val Leu Leu Arg
100 105 110

Tyr Asp Arg Ser Leu Leu Val Gly Asp Thr Arg Arg Cys Glu Pro Lys
115 120 125

Lys Phe Gly Gly Lys Gly Ala Arg Ala Arg Tyr Gln Lys Ser Tyr Arg
130 135 140

<210> SEQ ID NO 610
<211> LENGTH: 137
<212> TYPE: PRT
<213> ORGANISM: Plasmodium vivax

<400> SEQUENCE: 610

Met Gly Arg Val Arg Thr Lys Thr Ile Lys Arg Ala Ala Arg Gln Ile
1 5 10 15

Val Glu Lys Tyr Tyr Ala Lys Leu Thr Leu Asp Phe Gln Ile Asn Lys
20 25 30

Lys Ile Thr Glu Glu Val Ala Ile Ile Pro Ser Lys Arg Met Lys Asn
35 40 45

Lys Val Ala Gly Phe Val Thr His Leu Met Lys Arg Ile Gln Lys Gly
50 55 60

Pro Val Arg Gly Ile Ser Leu Lys Leu Gln Glu Glu Glu Arg Glu Arg
65 70 75 80

Arg Leu Asp Phe Val Pro Glu Lys Ser Gln Ile Asp Val Ser Val Ile
85 90 95

Tyr Val Glu Pro Asp Thr Leu Arg Met Ile Lys Ser Leu Gly Ile Asn
100 105 110

Ile Ser Asn Met Lys Val His Asn Pro Met Ile Asn Thr Asn Gln Gln
115 120 125

Lys Gln Asn Arg Met Asn Asn Gln Phe
130 135

<210> SEQ ID NO 611
<211> LENGTH: 156
<212> TYPE: PRT
<213> ORGANISM: Plasmodium vivax

<400> SEQUENCE: 611

Met Ser Leu Gln Val Ile Asp Asn Asn Asp Phe Gln His Ile Leu Arg
1 5 10 15

Ile Leu Asn Thr Asn Val Asp Gly Lys Glu Lys Val Ile Ile Ala Leu
20 25 30

Thr Ala Ile Lys Gly Ile Gly Lys Arg Met Ala Thr Val Ile Cys Lys 35 40 45

Gln Ala Asn Val Asp Pro Thr Lys Arg Ala Gly Glu Leu Thr Thr Glu
50 55 60

Glu Ile Asp Asn Ile Val His Ile Met Ser Thr Pro Thr Gln Phe Lys
65 70 75 80

Ile Pro Asp Trp Phe Leu Asn Arg Arg Lys Asp Leu Lys Glu Gly Lys
85 90 95

Asn Ile His Val Ile Ala Asn Gln Leu Asp Ser Tyr Leu Arg Glu Asp
100 105 110

Leu Glu Arg Met Lys Lys Ile Arg Leu His Arg Gly Leu Arg His His
115 120 125

Trp Gly Leu Arg Val Arg Gly Gln His Thr Lys Thr Thr Gly Arg Arg
130 135 140

Gly Arg Thr Val Gly Val Ala Lys Lys Lys Gly Ala
145 150 155

<210> SEQ ID NO 612
<211> LENGTH: 145
<212> TYPE: PRT
<213> ORGANISM: Plasmodium vivax

<400> SEQUENCE: 612

Met Glu Asp Ala Asn Lys Pro Lys Lys Arg Thr Phe Arg Thr Phe Gln
1 5 10 15

Tyr Arg Gly Val Asp Leu Asp Lys Leu Leu Asp Leu Ser Gln Asp Glu
20 25 30

Leu Ile Lys Leu Phe Lys Ala Arg Gln Arg Arg Lys Phe Gln Arg Gly
35 40 45

Ile Ser Lys Lys Ala Lys Ser Leu Leu Lys Lys Ile Arg Lys Ser Lys
50 55 60

Lys Asn Cys Glu Pro Gly Glu Lys Pro Asn Pro Val Pro Thr His Leu
65 70 75 80

Arg Asn Met Thr Ile Ile Pro Glu Met Val Gly Ser Ile Val Ala Val
85 90 95

His Asn Gly Lys Gln Tyr Thr Asn Val Glu Ile Lys Pro Glu Met Ile
100 105 110

Gly Tyr Tyr Leu Gly Glu Phe Ser Ile Thr Tyr Lys His Thr Arg His
115 120 125

Gly Lys Pro Gly Ile Gly Ala Thr His Ser Ser Arg Phe Ile Pro Leu
130 135 140

Lys
145

<210> SEQ ID NO 613
<211> LENGTH: 170
<212> TYPE: PRT
<213> ORGANISM: Plasmodium vivax

<400> SEQUENCE: 613

Met Ala Glu Gln Phe Thr Glu Asp Ile Gly Val Val Asn Lys Arg Leu
1 5 10 15

Leu Glu Pro Val Pro Phe Val Lys Thr Asn Asn Cys Ile Lys Asp Val
20 25 30

Asp Ala Asp Leu Phe Ile Arg Ser Tyr Ala Thr His Leu Lys Leu His
35 40 45

Asn Lys Ile Thr Tyr Pro Lys Trp Cys Thr Phe Val Lys Thr Gly Lys

```
    50                  55                  60

Gly Arg Lys Leu Ala Pro Leu Asn Glu Asp Trp Tyr Phe Ile Arg Ala
65                  70                  75                  80

Ser Ser Ile Leu Arg Arg Leu Tyr Leu His Pro Asp Ile Gly Val Gly
                85                  90                  95

Phe Leu Arg Arg Gln Phe Ser Ser Lys Gln Arg Arg Gly Val Ala Pro
            100                 105                 110

Asn His Thr Ser Leu Ala Ser Gly Lys Ile Leu Arg Ser Ile Leu Gln
        115                 120                 125

Gln Leu Glu Asn Leu Gly Tyr Val Glu Gln Asn Pro Lys Lys Lys Gly
    130                 135                 140

Arg Arg Leu Thr Thr Lys Gly Glu Asn Ala Ile Asn Asn Phe Ala Arg
145                 150                 155                 160

Tyr Ile Asn Lys Lys Val Tyr Asn Lys Glu
                165                 170


<210> SEQ ID NO 614
<211> LENGTH: 82
<212> TYPE: PRT
<213> ORGANISM: Plasmodium vivax

<400> SEQUENCE: 614

Met Phe Asn Asp Gln Lys Val Leu Val Asp Ile Tyr Ile Pro Arg Lys
1               5                   10                  15

Cys Ser Ala Thr Ser Arg Leu Ile Pro Ala Lys Glu His Gly Ala Val
            20                  25                  30

Gln Ile Asn Val Gly Met Val Asp Ala Asn Gly Val Tyr Asn Gly Lys
        35                  40                  45

Thr Glu Thr Phe Ala Ile Ser Gly His Val Arg Gln Asn Gly Glu Ser
    50                  55                  60

Asp Ala Cys Leu Asn Arg Leu Met Tyr Glu Lys Lys Leu Leu Ser Phe
65                  70                  75                  80

Gln Asn


<210> SEQ ID NO 615
<211> LENGTH: 145
<212> TYPE: PRT
<213> ORGANISM: Plasmodium vivax

<400> SEQUENCE: 615

Met Gly Ser Gly Lys Pro Ser Gly Leu Arg Ala Ala Arg Lys Leu Arg
1               5                   10                  15

Ile Arg Arg Arg Thr Gln Arg Trp Ala Asp Lys Ser Tyr Lys Lys Ser
            20                  25                  30

His Leu Gly Thr Arg Trp Lys Ser Asn Pro Phe Arg Gly Ser Ser His
        35                  40                  45

Ala Lys Gly Ile Val Val Glu Lys Val Ala Ile Glu Ala Lys Gln Pro
    50                  55                  60

Asn Ser Ala Tyr Arg Lys Cys Val Arg Val Gln Leu Ile Lys Asn Gly
65                  70                  75                  80

Lys Lys Ile Thr Ala Phe Val Pro Gly Asp Gly Cys Leu Asn Phe Ile
                85                  90                  95

Asp Glu Asn Asp Glu Val Leu Val Ser Gly Phe Gly Arg Ser Gly His
            100                 105                 110

Ser Val Gly Asp Leu Pro Gly Val Lys Phe Lys Val Val Lys Val Ala
        115                 120                 125
```

```
Arg Val Ser Leu Leu Ala Leu Phe Lys Glu Lys Lys Glu Lys Pro Arg
    130                 135                 140

Ser
145


<210> SEQ ID NO 616
<211> LENGTH: 133
<212> TYPE: PRT
<213> ORGANISM: Plasmodium vivax

<400> SEQUENCE: 616

Met Thr Asp Gln Phe Thr Ile Arg Val Lys Lys Tyr Met Ser Asn Pro
1               5                   10                  15

Leu Leu Arg Arg Lys Gln Phe Ala Leu Glu Ile Leu His Pro Asn Lys
            20                  25                  30

Gly Ser Val Ala Lys Lys Glu Val Lys Glu Arg Leu Ala Lys Met Tyr
        35                  40                  45

Lys Leu Asn Asn Val Asn Thr Ile Val Leu Phe Gly Phe Lys Thr Leu
    50                  55                  60

Phe Gly Gly Gly Arg Thr Lys Gly Phe Gly Leu Ile Tyr Lys Asn Val
65                  70                  75                  80

Asp Ala Val Lys Lys Phe Glu Lys Lys Tyr Arg Leu Val Arg Glu Gly
                85                  90                  95

Leu Ile Asp Lys Glu Thr Lys Ala Gly Arg Arg Ala Ser Lys Glu Leu
            100                 105                 110

Lys Asn Arg Arg Lys Lys Val Arg Gly Thr Glu Lys Thr Lys Val Ser
        115                 120                 125

Gly Ala Lys Lys Lys
    130


<210> SEQ ID NO 617
<211> LENGTH: 105
<212> TYPE: PRT
<213> ORGANISM: Plasmodium vivax

<400> SEQUENCE: 617

Met Pro Pro Lys Glu Arg Lys Thr Lys Glu Gln Ile Ala Ala Ala Ala
1               5                   10                  15

Ala Ala Ser Gly Arg Thr Lys Lys Lys Lys Trp Gly Lys Gly Lys Asn
            20                  25                  30

Lys Glu Lys Leu Asn His Ala Val Phe Ile Asp Lys Ser Leu His Ser
        35                  40                  45

Lys Ile Leu Glu Cys Lys Asn Met Lys Val Ile Thr Pro Ser Ala Ile
    50                  55                  60

Ala Glu Lys Tyr Lys Val Asn Leu Ser Val Ala Arg Ala Val Ile Asn
65                  70                  75                  80

His Leu Ala Asp Lys Lys Leu Ile Ala Glu Val Cys Val Gln Ser His
                85                  90                  95

Ser Gln Lys Leu Tyr Thr Lys Val Ala
            100                 105


<210> SEQ ID NO 618
<211> LENGTH: 107
<212> TYPE: PRT
<213> ORGANISM: Plasmodium vivax

<400> SEQUENCE: 618
```

Met Pro Lys Lys Arg Arg Asn Gly Gly Arg Ser Lys His Asn Arg Gly
1 5 10 15

His Val Asn Pro Leu Arg Cys Ser Asn Cys Gly Arg Cys Val Pro Lys
20 25 30

Asp Lys Ala Ile Lys Arg Phe Asn Ile Arg Asn Ile Val Asp Thr Ser
35 40 45

Ala Gln Arg Asp Ile Lys Glu Ala Ser Val Tyr Ser Thr Phe Gln Leu
50 55 60

Pro Lys Leu Tyr Ile Lys Gln Cys Tyr Cys Val Ser Cys Ala Ile His
65 70 75 80

Ser Arg Phe Val Arg Val Arg Ser Arg Glu Gln Arg Arg Val Arg Lys
85 90 95

Glu Thr Ala Lys His Val Asn Pro Ser Gln Leu
100 105

<210> SEQ ID NO 619
<211> LENGTH: 82
<212> TYPE: PRT
<213> ORGANISM: Plasmodium vivax

<400> SEQUENCE: 619

Met Asn Val Asp Leu Leu Asn Pro Asp Pro Val Glu Glu Ser Lys Lys
1 5 10 15

His Lys Leu Lys Arg Leu Ile Pro Thr Pro Asn Ser Tyr Phe Met Asp
20 25 30

Val Lys Cys Pro Gly Cys Leu Gln Ile Thr Thr Leu Phe Ser His Ala
35 40 45

Gln Asn Val Val Leu Cys Gly Ser Cys Asn Ile Met Leu Cys Gln Pro
50 55 60

Thr Gly Gly Lys Cys Lys Leu Thr Glu Gly Cys Ser Phe Arg Lys Lys
65 70 75 80

Ile Glu

<210> SEQ ID NO 620
<211> LENGTH: 67
<212> TYPE: PRT
<213> ORGANISM: Plasmodium vivax

<400> SEQUENCE: 620

Met Glu Lys Ser Lys Leu Ala Lys Val Glu Lys Val Leu Gly Arg Thr
1 5 10 15

Gly Ser Arg Gly Gly Val Ile Gln Val Arg Ala Gln Phe Met Gly Asp
20 25 30

Ser Glu Leu Ala Gly Arg Phe Leu Ile Arg Asn Val Lys Gly Pro Val
35 40 45

Arg Glu Gly Asp Ile Leu Ala Leu Leu Glu Thr Glu Arg Glu Ala Arg
50 55 60

Arg Leu Arg
65

<210> SEQ ID NO 621
<211> LENGTH: 54
<212> TYPE: PRT
<213> ORGANISM: Plasmodium vivax

<400> SEQUENCE: 621

Met Gly Cys Ile Leu Asn Val His Pro Lys Lys Tyr Gly Gln Gly Ser
1 5 10 15

Arg Gln Cys Arg Val Cys Ser Asn Lys His Ala Ile Ile Arg Lys Tyr
20 25 30

Asn Ile Asn Ile Cys Arg Gln Cys Phe Arg Glu Arg Ala Asp Ile Ile
35 40 45

Gly Phe Lys Lys Tyr Arg
50

<210> SEQ ID NO 622
<211> LENGTH: 221
<212> TYPE: PRT
<213> ORGANISM: Plasmodium vivax

<400> SEQUENCE: 622

Met Ser Ala Pro Ile Ser Lys Lys Arg Lys Phe Ile Asn Asp Gly Val
1 5 10 15

Phe Gln Ala Glu Leu Asn Glu Phe Leu Ala Arg Ile Leu Ala Glu Asp
20 25 30

Gly Tyr Ser Gly Val Glu Val Arg Val Thr Pro Ile Arg Thr Glu Val
35 40 45

Ile Ile Arg Ala Thr Arg Thr Arg Glu Val Leu Gly Asp Lys Gly Arg
50 55 60

Arg Ile Arg Glu Leu Thr Ser Leu Val Gln Lys Arg Phe Phe Asn Lys
65 70 75 80

Ser Thr Asn Ser Val Glu Leu Phe Ala Glu Arg Val Glu His Arg Gly
85 90 95

Leu Cys Ala Met Ala Gln Ala Glu Ser Leu Arg Tyr Lys Leu Leu Lys
100 105 110

Gly Leu Ala Val Arg Arg Ala Cys Tyr Gly Val Leu Arg His Ile Met
115 120 125

Glu Ser Gly Ala Lys Gly Cys Glu Val Ile Val Ser Gly Lys Leu Arg
130 135 140

Ala Gln Arg Ala Lys Ser Met Lys Phe Arg Asp Gly Tyr Leu Ile Ser
145 150 155 160

Thr Gly Glu Pro Ser Lys Arg Phe Val Asn Thr Ala Thr Arg Ser Ala
165 170 175

Gln Leu Lys Gln Gly Val Leu Gly Ile Lys Val Lys Ile Met Leu Pro
180 185 190

Thr Ala Ile Asp Thr Arg Thr Gly Leu Thr Ser Ile Leu Pro Asp Asn
195 200 205

Ile Ser Val Leu Glu Pro Lys Thr Asp Thr Val Asp Leu
210 215 220

<210> SEQ ID NO 623
<211> LENGTH: 58
<212> TYPE: PRT
<213> ORGANISM: Plasmodium vivax

<400> SEQUENCE: 623

Met Gly Lys Val His Gly Ser Leu Ala Arg Ala Gly Lys Val Lys Asn
1 5 10 15

Gln Thr Pro Lys Val Pro Lys Leu Asp Lys Lys Lys Arg Leu Thr Gly
20 25 30

Arg Ala Lys Lys Arg Gln Leu Tyr Asn Arg Arg Phe Ser Asp Asn Gly
35 40 45

Gly Arg Lys Lys Gly Pro Asn Ser Lys Ala
50 55

<210> SEQ ID NO 624
<211> LENGTH: 58
<212> TYPE: PRT
<213> ORGANISM: Plasmodium vivax

<400> SEQUENCE: 624

```
Met Gly Lys Val His Gly Ser Leu Ala Arg Ala Gly Lys Val Lys Asn
1               5                   10                  15

Gln Thr Pro Lys Val Pro Lys Leu Asp Lys Lys Lys Arg Leu Thr Gly
            20                  25                  30

Arg Ala Lys Lys Arg Gln Leu Tyr Asn Arg Arg Phe Ser Asp Asn Gly
        35                  40                  45

Gly Arg Lys Lys Gly Pro Asn Ser Lys Ala
    50                  55
```

<210> SEQ ID NO 625
<211> LENGTH: 262
<212> TYPE: PRT
<213> ORGANISM: Plasmodium vivax

<400> SEQUENCE: 625

```
Met Ala Val Gly Lys Asn Lys Arg Thr Ser Lys Gly Lys Lys Gly Gly
1               5                   10                  15

Lys Lys Lys Val Thr Asp Val Phe Thr Lys Lys Glu Trp Tyr Asp Leu
            20                  25                  30

Lys Ala Pro Lys Met Phe Leu Val Arg Asn Phe Gly Lys Thr Leu Val
        35                  40                  45

Thr Lys Thr Ile Gly Lys Lys Leu Ala Thr Asp Ser Leu Lys Gly Arg
    50                  55                  60

Ile Tyr Glu Val Asn Leu Ala Asp Leu Asn Asn Asp Glu Asp Gln Ala
65                  70                  75                  80

His Lys Lys Ile Lys Leu Ser Cys Asp His Ile Ile Asn Arg Asp Cys
                85                  90                  95

Tyr Thr Asp Phe Cys Gly Leu Ser Ile Thr Arg Asp Lys Leu Cys Ser
            100                 105                 110

Leu Ile Arg Lys Gly Tyr Thr Leu Ile Glu Gly His Thr Asp Val Lys
        115                 120                 125

Thr Leu Asp Asn Tyr His Leu Arg Met Phe Cys Ile Ala Phe Thr Lys
    130                 135                 140

Lys Arg Gln Asn Gln Thr Lys Ser Thr Cys Tyr Ala Gln Thr Ser Gln
145                 150                 155                 160

Ile Lys Lys Ile Arg Lys Lys Met Val Asp Ile Met Thr Ala Glu Ala
                165                 170                 175

Ser Lys Val Leu Leu Lys Asp Leu Val Lys Lys Phe Ile Pro Glu Ser
            180                 185                 190

Ile Gly Lys Glu Ile Glu Lys Gln Cys Lys Lys Ile Tyr Pro Leu Gln
        195                 200                 205

Asn Val Leu Ile Arg Lys Val Lys Ile Leu Lys Arg Pro Lys Leu Asp
    210                 215                 220

Ile Ser Lys Leu Met Glu Leu His Thr Asp Pro Lys Glu Glu Ser Gly
225                 230                 235                 240

Lys Asn Val Asn Ala Leu Pro Glu Ser Lys Glu Ala Thr Asn Ile Leu
                245                 250                 255

Thr Ala Glu Leu Lys His
            260
```

<210> SEQ ID NO 626
<211> LENGTH: 261
<212> TYPE: PRT
<213> ORGANISM: Plasmodium vivax

<400> SEQUENCE: 626

Met Gly Lys Gly Ile Lys Lys His Leu Lys Arg Val Asn Ala Pro Ser
1               5                   10                  15

His Trp Met Leu Asn Lys Met Gly Gly Gln Tyr Ala Pro Lys Thr Ser
            20                  25                  30

Ser Gly Pro His Lys Leu Leu Glu Ser Ile Pro Leu Val Ile Leu Leu
        35                  40                  45

Arg Asn Arg Leu Lys Tyr Ala Leu Thr Phe Asp Glu Val Lys Met Ile
    50                  55                  60

Leu Ile Gln Lys Ile Val Lys Val Asp Asn Lys Val Arg Thr Asp Cys
65                  70                  75                  80

Thr Phe Pro Val Gly Leu Met Asp Val Ile His Ile Thr Lys Ser Asn
                85                  90                  95

Glu Tyr Phe Arg Leu Leu Tyr Asp Ile Lys Gly Arg Phe Val Pro His
            100                 105                 110

Arg Ile Thr Asn Glu Glu Ser Lys Tyr Lys Leu Cys Lys Val Lys Lys
        115                 120                 125

Ile Leu Leu Arg Lys Gly Arg Leu Ser Ile Ala Val Thr His Asp Gly
    130                 135                 140

Arg Ser Ile Pro Tyr Ile His Pro Asp Val Lys Val Asn Asp Thr Val
145                 150                 155                 160

Arg Leu Asp Leu Glu Thr Gly Lys Val Leu Glu His Leu Lys Phe Gln
                165                 170                 175

Val Gly Ser Leu Val Met Val Thr Ala Gly His Ser Val Gly Arg Val
            180                 185                 190

Gly Val Ile Ser Ser Ile Asp Lys Asn Met Gly Thr Tyr Asp Ile Ile
        195                 200                 205

His Val Lys Asp Ser Arg Asn Lys Val Phe Ala Thr Arg Leu Ser Asn
    210                 215                 220

Val Phe Val Ile Gly Asp Asn Thr Lys Pro Tyr Ile Ser Leu Pro Arg
225                 230                 235                 240

Glu Lys Gly Ile Lys Leu Asp Ile Ile Glu Glu Arg Arg Asn Arg Leu
                245                 250                 255

Lys Ala Leu Asn Asn
            260

<210> SEQ ID NO 627
<211> LENGTH: 272
<212> TYPE: PRT
<213> ORGANISM: Plasmodium vivax

<400> SEQUENCE: 627

Met Glu Asp Arg Gly Gly Phe Ser Arg Gly Phe Gly Arg Gly Val Arg
1               5                   10                  15

Gly Thr Arg Gly Arg Gly Gly Arg Gly Ala Arg Gly Arg Gly Arg Gly
            20                  25                  30

Ser Ala Glu Asp Asp Leu Lys Asn Trp Val Pro Val Thr Lys Leu Gly
        35                  40                  45

Arg Leu Val Lys Glu Gly Lys Ile Val Ser Ile Glu Glu Ile Tyr Leu
    50                  55                  60

His Ser Leu Pro Ile Lys Glu Tyr Gln Ile Ile Asp Tyr Phe Phe Gln
65 70 75 80

Pro Asn Glu Cys Ser His Pro Leu Lys Asp Asp Val Val Lys Ile Met
85 90 95

Pro Val Gln Lys Gln Thr Arg Ala Gly Gln Arg Thr Arg Phe Lys Ala
100 105 110

Phe Val Ala Ile Gly Asp Gly Asn Gly His Cys Gly Leu Gly Val Lys
115 120 125

Cys Ala Lys Glu Val Ala Thr Ala Ile Arg Gly Ala Ile Ile Ser Ala
130 135 140

Lys Leu Ser Leu Ile Pro Val Arg Arg Gly Tyr Trp Gly Asn Lys Ile
145 150 155 160

Gly Asp Pro His Thr Val Pro Met Lys Val Ser Gly Lys Cys Gly Ser
165 170 175

Val Arg Ile Arg Leu Val Pro Ala Pro Arg Gly Thr Gln Ile Val Gly
180 185 190

Ala Pro Thr Thr Lys Lys Met Leu Asn Phe Ala Gly Ile Lys Asp Cys
195 200 205

Phe Ser Ser Ser Cys Gly Lys Thr Lys Thr Lys Gly Asn Phe Leu Arg
210 215 220

Ala Ile Phe Asn Ala Leu Ser Lys Thr Tyr Gly Tyr Leu Thr Pro Asp
225 230 235 240

Leu Trp Lys Val Thr Asn Phe Asp Lys Ser Pro Tyr Glu Glu Trp Ser
245 250 255

Asp Phe Leu Glu Thr Tyr Gln Asn Leu Lys Gly Ile Lys Gly Thr Val
260 265 270

<210> SEQ ID NO 628
<211> LENGTH: 195
<212> TYPE: PRT
<213> ORGANISM: Plasmodium vivax

<400> SEQUENCE: 628

Met Glu Thr Thr Thr Ala Asp Ile Lys Leu Phe Lys Lys Trp Ser Tyr
1 5 10 15

Glu Glu Ile Asn Ile Ala Asp Leu Ser Leu Val Asp Cys Ile Ala Val
20 25 30

Ser Gln Lys Ala Cys Val Tyr Thr Pro His Thr Ala Gly Arg Tyr Gln
35 40 45

Lys Lys Arg Phe Arg Lys Ala Leu Cys Pro Ile Val Glu Arg Leu Val
50 55 60

Asn Ser Met Met Met His Gly Arg Asn Asn Gly Lys Lys Leu Lys Ala
65 70 75 80

Ile Arg Ile Val Ala Tyr Ala Phe Glu Ile Ile His Leu Met Thr Gly
85 90 95

Glu Asn Pro Leu Gln Val Phe Val Asn Ala Val Gln Lys Gly Gly Pro
100 105 110

Arg Glu Asp Ser Thr Arg Ile Gly Ser Ala Gly Val Val Arg Arg Gln
115 120 125

Ala Val Asp Val Ser Pro Leu Arg Arg Val Asn Gln Ala Ile Tyr Leu
130 135 140

Ile Cys Thr Gly Ala Arg Asn Ala Ala Phe Arg Asn Ile Lys Ser Ile
145 150 155 160

Ser Glu Cys Leu Ala Glu Glu Ile Ile Asn Cys Ala Asn Glu Ser Ser

```
                165                 170                 175

Ser Ser Tyr Ala Ile Lys Lys Lys Asp Glu Ile Glu Arg Val Ala Lys
            180                 185                 190

Ala Asn Arg
        195


<210> SEQ ID NO 629
<211> LENGTH: 306
<212> TYPE: PRT
<213> ORGANISM: Plasmodium vivax

<400> SEQUENCE: 629

Met Lys Leu Asn Ile Ser Asn Pro Leu Asn Asn Val Gln Lys Ser Ile
1               5                   10                  15

Glu Ile Asp Asp Glu Lys Lys Leu Leu Pro Phe Met Glu Lys Arg Ile
            20                  25                  30

Gly Asn Ala Val Pro Gly Asp Ser Ile Gly Glu Glu Phe Thr Gly Tyr
        35                  40                  45

Val Phe Arg Ile Thr Gly Gly Asn Asp Lys Gln Gly Phe Pro Met Ile
    50                  55                  60

Gln Gly Val Leu Thr Asn Asn Arg Val Arg Leu Leu Phe Lys Lys Gly
65                  70                  75                  80

Met Lys Cys Tyr Arg Pro Arg Lys Lys Gly Glu Arg Lys Arg Lys Ser
                85                  90                  95

Val Arg Gly Cys Ile Val Gly Gln Asp Leu Ser Ala Leu Asn Leu Thr
            100                 105                 110

Leu Val Lys Lys Gly Val Asn Glu Ile Pro Gly Leu Thr Asp Lys Ala
        115                 120                 125

Val Gly Lys Lys Leu Gly Pro Lys Arg Ala Ser Lys Ile Arg Lys Leu
    130                 135                 140

Phe Asn Leu Asp Lys Ser Asp Asp Val Arg Lys Tyr Val Ile Gly Arg
145                 150                 155                 160

Ala Ile Thr Lys Asn Gly Lys Thr Lys Phe Ile Lys Pro Lys Ile Gln
                165                 170                 175

Arg Leu Val Thr Glu Lys Arg Leu Leu Arg Lys Arg Asn Leu Leu Gln
            180                 185                 190

Ala Lys Glu Lys Arg Arg Leu Glu Lys Lys Gln Gln Leu Lys Glu Tyr
        195                 200                 205

Lys Gln Leu Leu Asn Lys Tyr Arg Ser Glu Leu Asn Gln Gln His Asp
    210                 215                 220

Val Glu Thr Thr Lys Lys Lys Lys Val Lys Lys Ser Leu Ser Lys Thr
225                 230                 235                 240

Asn Lys Thr Ala Ser Lys Ser Lys Leu Asn Thr Lys Gln Glu Gln Lys
                245                 250                 255

Asp Lys Thr Glu Lys Lys Gln Asn Lys Thr Asn Asn Ile Lys Asn Asp
            260                 265                 270

Lys Ser Glu Lys Lys Glu Gln Ala Lys Lys Lys Thr Lys Thr Asn Glu
        275                 280                 285

Asn Thr Gln Gln Thr Lys Gln Asn Lys Pro Asp Lys Lys Asn Lys Ala
    290                 295                 300

Lys Lys
305


<210> SEQ ID NO 630
<211> LENGTH: 194
```

<212> TYPE: PRT
<213> ORGANISM: Plasmodium vivax

<400> SEQUENCE: 630

Met Asp Ala Val Gln Lys Arg Val Leu Lys Ser Asn Pro Ser Asp Leu
1               5                   10                  15

Glu Lys Glu Ile Ala Gln Cys Leu Leu Asp Ile Glu Leu Ser Ser Ser
            20                  25                  30

Ser Asp Ile Lys Thr Asp Ala Lys Glu Ile Lys Leu Leu Ser Cys Asp
        35                  40                  45

Leu Ile Glu Val Glu Lys Leu Lys Lys Lys Thr Ile Leu Ile Tyr Ile
    50                  55                  60

Pro Tyr Lys Ile Tyr Thr Thr Tyr Val Arg Lys Ile Gln Arg Lys Leu
65                  70                  75                  80

Ile Asn Glu Leu Glu Lys Lys Thr Lys Lys Tyr Val Val Leu Val Ala
                85                  90                  95

Lys Arg Thr Ile Leu Lys Gly Lys Gln Lys Asn Lys Ser Phe Lys Ile
            100                 105                 110

Ile Pro Arg Ser Arg Thr Leu Thr Ser Val Tyr Asp Ser Ile Leu Glu
        115                 120                 125

Asp Ile Val Ser Pro Ser Glu Ile Ile Gly Lys Arg Ile Ser Met Lys
    130                 135                 140

Ala Asp Gly Lys Arg Val Phe Lys Ile Met Leu Asp Ser Lys Glu Arg
145                 150                 155                 160

Gln Arg Asp Asn Ile Glu Glu Lys Leu Ile Ser Phe Ala Ala Val Tyr
                165                 170                 175

Lys Lys Ile Thr Arg Arg Asp Ala Val Phe Ser Leu Pro Pro Thr Asn
            180                 185                 190

Glu Lys

<210> SEQ ID NO 631
<211> LENGTH: 218
<212> TYPE: PRT
<213> ORGANISM: Plasmodium vivax

<400> SEQUENCE: 631

Met Gly Ile Ser Arg Asp Gly Arg His Lys Leu Arg Leu Thr Gly Gly
1               5                   10                  15

Lys Lys Lys Ile His Lys Lys Lys Arg Lys Tyr Glu Leu Gly Arg Pro
            20                  25                  30

Pro Ser Asn Thr Lys Leu Gly Ser Arg Gln Val His Val Val Arg Gly
        35                  40                  45

Arg Gly Arg Asn Tyr Lys Tyr Arg Ala Ile Lys Leu Asp Ser Gly Ser
    50                  55                  60

Phe Ser Trp Pro Thr Phe Gly Ile Ser Lys Asn Thr Arg Ile Ile Asp
65                  70                  75                  80

Val Val Tyr Asn Ala Ser Asn Asn Glu Leu Val Arg Thr Lys Thr Leu
                85                  90                  95

Val Lys Asn Cys Ile Val Val Ile Asp Ser His Pro Phe Thr Thr Trp
            100                 105                 110

Tyr Glu Asn Thr Phe Gly Thr Thr Leu Gly Lys Lys Lys Lys Glu Lys
        115                 120                 125

Lys Glu Glu Asp Asn Lys Glu Glu Asn Lys Gln Glu Val Glu Asn Asn
    130                 135                 140

Glu Glu Ala Ala Lys Asp Glu Thr Thr Lys Thr Tyr Gly Val Ile Lys 145 150 155 160

Lys Ile Gly Lys Ser Lys Asn Ile Asp Pro Leu Leu Leu Glu Gln Phe
165 170 175

Lys Gln Gly Arg Val Leu Ala Cys Ile Ser Ser Arg Pro Gly Gln Cys
180 185 190

Gly Lys Ala Asp Gly Tyr Ile Ile Glu Gly Asp Glu Leu Leu Phe Tyr
195 200 205

Lys Arg Lys Met Asp Lys Lys Lys Arg Asn
210 215

<210> SEQ ID NO 632
<211> LENGTH: 189
<212> TYPE: PRT
<213> ORGANISM: Plasmodium vivax

<400> SEQUENCE: 632

Met Pro Lys Ser Tyr Arg Asn Tyr Ser Lys Thr Ala Arg Asn Pro Lys
1 5 10 15

Arg Pro Phe Glu Lys Glu Arg Leu Asp Gln Glu Leu Lys Leu Ile Gly
20 25 30

Glu Tyr Gly Leu Lys Asn Lys Arg Glu Ile Trp Arg Val Gln Tyr Leu
35 40 45

Leu Ala Lys Ile Arg Ser Ala Ala Arg Tyr Leu Leu Thr Leu Asp Glu
50 55 60

Lys Ser Ser Lys Arg Ile Phe Gln Gly Glu Ala Leu Leu Arg Arg Met
65 70 75 80

Val Arg Gln Gly Leu Leu Gly Glu Asn Glu Glu Lys Leu Asp Tyr Val
85 90 95

Leu Gly Leu Thr Leu Pro Lys Leu Leu Glu Arg Arg Leu Gln Thr Lys
100 105 110

Val Phe Lys Leu Gly Leu Ala Lys Ser Val His His Ala Arg Val Leu
115 120 125

Ile Arg Gln Arg His Ile Arg Val Gly Lys Gln Met Val Asp Ile Pro
130 135 140

Ser Phe Leu Val Arg Val Asp Ser Glu Lys His Ile Asp Phe Ala Thr
145 150 155 160

Thr Ser Pro Phe Gly Gly Ala Arg Pro Gly Arg Val Lys Arg Lys Ser
165 170 175

Leu Lys Lys Gln Lys Glu Lys Thr Glu Ala Glu Ala Glu
180 185

<210> SEQ ID NO 633
<211> LENGTH: 263
<212> TYPE: PRT
<213> ORGANISM: Plasmodium vivax

<400> SEQUENCE: 633

Met Ser Asn Lys Lys Gly Gln Ser Pro Lys Glu Glu Ser Ile Ala Lys
1 5 10 15

Met Leu Ile Cys Lys Val His Ile Gly Thr Lys Asn Leu Glu Asn Lys
20 25 30

Met Lys Arg Tyr Val Tyr Thr Arg Ala Lys Asp Gly Val His Ile Ile
35 40 45

Asn Leu Ala Lys Thr Tyr Glu Lys Leu Gln Leu Ala Ala Arg Ile Ile
50 55 60

Val Ala Ile Ser Asn Pro Ala Asp Val Val Val Val Ser Ala Arg Pro

```
65                  70                  75                  80

Phe Gly Ser Arg Ala Val Leu Lys Phe Ala Gln Tyr Thr Gly Ala Gln
                85                  90                  95

Ala Ile Ala Gly Arg Trp Thr Pro Gly Met Leu Thr Asn Gln Ile Ile
            100                 105                 110

Gln Lys Phe Thr Glu Pro Arg Leu Leu Ile Val Thr Asp Pro Arg Thr
        115                 120                 125

Asp Ala Gln Ser Val Lys Glu Ser Ala Tyr Ala Asn Ile Pro Val Ile
    130                 135                 140

Ala Leu Cys Asp Ser Asp Ser Pro Leu Glu His Val Asp Ile Ala Ile
145                 150                 155                 160

Pro Cys Asn Asn Lys Gly Lys Glu Ser Ile Ala Leu Met Tyr Trp Leu
                165                 170                 175

Leu Ala Gln Glu Val Leu Tyr Leu Lys Gly Val Ile Pro Arg Ser Glu
            180                 185                 190

Pro Trp Asn Val Met Val Asp Met Phe Leu Trp Arg Asp Pro Glu Gln
        195                 200                 205

Phe Glu Leu Lys Asn Leu Ala Asn Glu Glu Asn Thr Pro Thr Ala Pro
    210                 215                 220

His Leu Ile Glu Asn Gln Tyr Ala Ala Glu Ala Pro Tyr Asp Glu Trp
225                 230                 235                 240

Thr Lys Lys Glu Glu Trp Asn Asp Asn Thr Asn Glu Asp Trp Lys Asn
                245                 250                 255

Pro Ile Ala Ala Glu Glu Trp
            260


<210> SEQ ID NO 634
<211> LENGTH: 263
<212> TYPE: PRT
<213> ORGANISM: Plasmodium vivax

<400> SEQUENCE: 634

Met Ser Asn Lys Lys Gly Gln Ser Pro Lys Glu Glu Ser Ile Ala Lys
1               5                   10                  15

Met Leu Ile Cys Lys Val His Ile Gly Thr Lys Asn Leu Glu Asn Lys
            20                  25                  30

Met Lys Arg Tyr Val Tyr Thr Arg Ala Lys Asp Gly Val His Ile Ile
        35                  40                  45

Asn Leu Ala Lys Thr Tyr Glu Lys Leu Gln Leu Ala Ala Arg Ile Ile
    50                  55                  60

Val Ala Ile Ser Asn Pro Ala Asp Val Val Val Val Ser Ala Arg Pro
65                  70                  75                  80

Phe Gly Ser Arg Ala Val Leu Lys Phe Ala Gln Tyr Thr Gly Ala Gln
                85                  90                  95

Ala Ile Ala Gly Arg Trp Thr Pro Gly Met Leu Thr Asn Gln Ile Ile
            100                 105                 110

Gln Lys Phe Thr Glu Pro Arg Leu Leu Ile Val Thr Asp Pro Arg Thr
        115                 120                 125

Asp Ala Gln Ser Val Lys Glu Ser Ala Tyr Ala Asn Ile Pro Val Ile
    130                 135                 140

Ala Leu Cys Asp Ser Asp Ser Pro Leu Glu His Val Asp Ile Ala Ile
145                 150                 155                 160

Pro Cys Asn Asn Lys Gly Lys Glu Ser Ile Ala Leu Met Tyr Trp Leu
                165                 170                 175
```

Leu Ala Gln Glu Val Leu Tyr Leu Lys Gly Val Ile Pro Arg Ser Glu
180 185 190

Pro Trp Asn Val Met Val Asp Met Phe Leu Trp Arg Asp Pro Glu Gln
195 200 205

Phe Glu Leu Lys Asn Leu Ala Asn Glu Glu Asn Thr Pro Thr Ala Pro
210 215 220

His Leu Ile Glu Asn Gln Tyr Ala Ala Glu Ala Pro Tyr Asp Glu Trp
225 230 235 240

Thr Lys Lys Glu Glu Trp Asn Asp Asn Thr Asn Glu Asp Trp Lys Asn
245 250 255

Pro Ile Ala Ala Glu Glu Trp
260

<210> SEQ ID NO 635
<211> LENGTH: 339
<212> TYPE: PRT
<213> ORGANISM: Plasmodium vivax

<400> SEQUENCE: 635

Met Thr Leu Lys Asn Gly Tyr Arg Lys Ile Ile Lys Ile Leu Phe Ile
1 5 10 15

Phe Ile His Ile Phe His Ile Thr Ile Glu Ser Phe Val Thr Asn Tyr
20 25 30

Leu Cys Thr Ile Asn Glu Ala Thr His Tyr Asn Asn Val Phe Tyr Lys
35 40 45

Asn Lys Asn Arg Thr Ile Leu Lys Asp Lys Lys Tyr Leu Leu Glu Lys
50 55 60

Lys Lys Lys Asn Leu Phe Asn Val Gln Pro Ser Thr Val Ile Thr Pro
65 70 75 80

Asp Asn Glu Thr Ser Asn Glu Ile Ile Lys Lys Val Lys Leu Lys Lys
85 90 95

Lys Asp Lys Lys Ile Phe Lys Lys Tyr Lys Asp Phe Leu Asp Ile Leu
100 105 110

Pro Lys Lys Thr Asn Glu Tyr Thr Leu Met Glu Ala Ile Glu Lys Ile
115 120 125

Lys Thr Leu Ala Ile His Lys Phe Val Glu Ser Ile Asp Ile Tyr Leu
130 135 140

Ser Phe Asn Pro Lys Lys Ser Lys Met Thr Lys Asn Asp Asn Ile Lys
145 150 155 160

Thr Phe Ile Thr Phe Pro His Asn Leu Lys Lys Lys Arg Glu Lys Lys
165 170 175

Val Tyr Val Val Thr Asn Ala Lys Leu Gln Lys Ile Ala Ser Gln Ser
180 185 190

Gly Ala Asp Val Val Gly Glu Asp Asp Leu Ile Asn Lys Ile Lys Glu
195 200 205

Arg Glu Ile Arg Leu Gln Lys Arg Asn Asn Asn Phe Leu Ile Cys Thr
210 215 220

Asn Asp Cys Ile His Lys Leu Thr Arg Val Gly Lys Glu Ile Gly Arg
225 230 235 240

Lys Gly Leu Met Pro Asn Glu Lys Cys Gly Thr Leu Val Ser Glu Phe
245 250 255

Leu Leu Pro Lys His Val Lys Leu Phe Lys Ser Glu Asn Thr Tyr Ile
260 265 270

Phe Lys Leu Asn Lys Leu Asn Thr Leu Asn Ile Asn Ile Gly Asp Val
275 280 285

```
Tyr Met Ser Asn Asp Glu Ile Arg Glu Asn Ile Asn His Leu Phe Glu
    290                 295                 300

His Leu Glu Asn Leu Glu Phe Phe His Phe Asn Phe Lys His Val Lys
305                 310                 315                 320

Thr Ile Tyr Leu Ser Ser Thr Met Gly Phe Pro Phe Lys Ile Lys Lys
                325                 330                 335

Asn Ser Leu


<210> SEQ ID NO 636
<211> LENGTH: 399
<212> TYPE: PRT
<213> ORGANISM: Plasmodium vivax

<400> SEQUENCE: 636

Met Met Arg Asn Phe Phe Ser Ser Leu Thr Gly Met Ser Phe Leu Lys
1               5                   10                  15

Ser Asn Ser Lys His Asn Asn Asn Lys Val Phe Trp Leu Ile Gln Lys
            20                  25                  30

Arg Gly Arg Lys Tyr Ile Pro Phe Tyr Asp Ile Asn Lys Lys Lys Gln
        35                  40                  45

Lys Lys Lys Gly Phe Asn Lys Val His Glu Lys Lys Lys Glu Asp Asp
    50                  55                  60

Asp Asn Glu Ile Asn Thr Glu Lys Arg Val Glu Arg Asp Val Asp Asn
65                  70                  75                  80

Ile Glu Ser Glu Lys Leu Thr Gln Gly Asp Asn Ile Gln Phe Val Asn
                85                  90                  95

Arg Lys Lys Asp Tyr Val Ser Ser Thr Tyr Ser Leu Arg Ser Asn Leu
            100                 105                 110

Leu Pro Ala Leu Ser Pro Met Lys Gly Leu Lys Leu Leu Leu Ser Leu
        115                 120                 125

Asn Asp Ser Asn Tyr Phe Asn Met Leu Lys Asn Asp Asp Ser Lys Ile
    130                 135                 140

Asn Phe Asn Leu Ile Ile Lys Ile Asp Ile Lys Arg Glu Ser Leu Arg
145                 150                 155                 160

Gly Met Cys Asn Leu Val His Ser Val Asp Lys Asn Lys Lys Ile Leu
                165                 170                 175

Val Leu Val Asp Glu Glu His Gln Asn Leu Lys Lys Tyr Gly Ala Asp
            180                 185                 190

Tyr Val Gly Leu Glu Tyr Ile Asn Lys Ile Lys Asn Gly Trp Leu Asp
        195                 200                 205

Phe Asn Ile Cys Ile Thr Asn Phe Lys Asn Ile Asn Lys Ile Leu Cys
    210                 215                 220

Ile Ala Lys Ile Leu Gly Pro Lys Lys Leu Met Pro Asn Ile Lys Ser
225                 230                 235                 240

Asp Thr Leu Val Asp Asn Leu Glu Glu Thr Ile Lys Lys Ile Lys Ser
                245                 250                 255

Gly Asn Thr Ile Glu Tyr Arg Ser Glu Pro Ile Asp Leu Tyr Thr Phe
            260                 265                 270

Gln Leu Tyr Asn Glu Ile Tyr Asn Phe Gln Gln Ile Asp Leu Asn Ser
        275                 280                 285

Ile Ala His Ile Asn Val Gln Ile Ala Pro Ile Asp Met Asn Phe Tyr
    290                 295                 300

His Ile Leu Glu Asn Met Lys Cys Phe Thr Ser Glu Ile Ile Lys Asn
305                 310                 315                 320
```

```
Asn Ile His Ser Thr His Thr Gln Lys Glu Asn Lys Thr Thr Ala Phe
                325                 330                 335

Thr Trp Pro Pro Ile Thr Ala Lys His Lys Lys Gln Lys Ile Asn Ile
            340                 345                 350

Glu Glu Lys Ile Asn Leu Phe His Lys Asn Asp Asp Ser Ser Gln Ser
        355                 360                 365

Phe Ile Leu Gly Gly Tyr Ile Thr Tyr Gly Asn Tyr Pro Lys Ile Phe
    370                 375                 380

Leu Arg Ser Asn Leu Leu His Pro His Ser Asp Gly Tyr Ser Asn
385                 390                 395


<210> SEQ ID NO 637
<211> LENGTH: 280
<212> TYPE: PRT
<213> ORGANISM: Plasmodium vivax

<400> SEQUENCE: 637

Met Phe Ile Lys Lys Ile Asn Ile Lys Tyr Leu Ser Phe Ser Leu Leu
1               5                   10                  15

Val Tyr Phe Ile Tyr Asn Ala Tyr Val Tyr Asn Thr Ile Lys Leu Gln
            20                  25                  30

Lys Cys Phe Asn Tyr Glu His Lys Lys Gly Asn Phe Leu Val Ser Ser
        35                  40                  45

Leu Val Leu Asp Gly Lys Asp Ile Lys Gly Arg Arg Asn Lys Gly Ile
    50                  55                  60

Ile Asn Phe Ile Arg Ser Asn Ile Ile Thr Thr Asn Lys Phe Lys Leu
65                  70                  75                  80

Ile Lys Lys Lys Asn Val His Lys His Lys Asn Phe Leu Leu Lys Ser
                85                  90                  95

Arg Lys Cys Asp Gly Tyr Arg Asn Thr Lys Glu Gly Lys Glu Glu Thr
            100                 105                 110

Ile Arg Lys Ile Lys Arg Ile Leu Lys Val Thr Lys Leu Leu Ile Gln
        115                 120                 125

Leu Asn Ser Phe Lys Leu Ser Pro Asn Leu Arg Met Asp Leu Leu Ile
    130                 135                 140

Asn Met Pro Arg Pro His Val Arg Met His Met Val Lys Asn Thr Leu
145                 150                 155                 160

Met Lys Leu Ser Val Lys Asn Thr Pro Phe Glu Ala Ile Thr Pro Tyr
                165                 170                 175

Leu Lys Glu Ser Asn Val Tyr Leu Phe Ile Met Asn Glu Asn Tyr Ile
            180                 185                 190

Ser Phe Thr Leu Tyr Arg Asn Lys Met Phe Ser Ser Leu Tyr Lys Asp
        195                 200                 205

Tyr Lys Leu Asn Asn Phe Ile Lys Val Ser Val Tyr Glu Asn Thr Ile
    210                 215                 220

Leu Asp Lys Lys Glu Thr Glu Asp Leu Ile Asn Leu Lys Ser His Lys
225                 230                 235                 240

Val Tyr Phe Gly His Val Val Asn Lys Ile Asn Asn Ile Ile Thr Ser
                245                 250                 255

Ile Pro Asn Ser Ile Leu Gln Ile Pro Ser Ser Ile Ala Arg Gly Ile
            260                 265                 270

Tyr Leu Asn Thr Gln Lys Asn Gln
        275                 280
```

<210> SEQ ID NO 638
<211> LENGTH: 257
<212> TYPE: PRT
<213> ORGANISM: Plasmodium vivax

<400> SEQUENCE: 638

Met Lys Ser Val Gly Ser Lys Val Thr Lys Leu Ile Gly Lys Ile Leu
1 5 10 15

Cys Lys Asn Glu Lys Lys Asn Arg Arg Arg Lys Asn Asn Lys Thr Lys
20 25 30

Asp Cys Ser Leu Phe Phe Ile Ile Lys Lys Gln Ser Cys Pro Leu Leu
35 40 45

Tyr Ile Ile Leu Ser Ile Leu Tyr Ile Thr Tyr Cys Met Glu Cys Ile
50 55 60

Val Cys Met Lys Leu Ser Lys Asn Asp Asn Cys Leu Asn Arg Asn Lys
65 70 75 80

Tyr Phe Phe Leu Glu Tyr Lys Leu Asn Asn Asp Tyr Tyr Gly Lys Lys
85 90 95

Ser Tyr Val Asn Asn Ile Arg Lys His Ile Ser Lys Lys Asp Asn Val
100 105 110

Ile Asn Asn His Lys Asn Phe Lys Leu Lys Ser Ser Lys Val Asp Glu
115 120 125

Ile Ile Glu Ser Leu Lys Asn Leu Thr Leu Leu Glu Ala Ser Glu Leu
130 135 140

Val Lys Lys Ile Glu Leu Thr Phe Ser Val Asp Thr Lys Gln Asn Leu
145 150 155 160

Asn Ala Ser Asn Ser Ser Gly Gln Glu Asn Lys Gln Asn Glu Ser Asp
165 170 175

Gly Lys Glu Asn Glu Glu Asp Glu Glu Asn Lys Val Tyr Asp Leu Ile
180 185 190

Leu Glu Asn Ile Glu Pro Asn Lys Lys Ile Pro Ile Ile Lys Ile Val
195 200 205

Lys Glu Ile Lys Lys Asp Leu Asn Leu Lys Gln Ala Lys Asp Leu Val
210 215 220

Asp Asn Leu Pro Gln Thr Leu Phe Glu Lys Val Asn Lys Glu Thr Ala
225 230 235 240

Asp Lys Trp Lys Thr Lys Leu Thr Glu Ala Gly Gly Ile Val Lys Leu
245 250 255

Lys

<210> SEQ ID NO 639
<211> LENGTH: 166
<212> TYPE: PRT
<213> ORGANISM: Plasmodium vivax

<400> SEQUENCE: 639

Met Lys Ile Trp Ile Leu Phe Phe Leu Phe Cys Lys Ser Val Leu Asn
1 5 10 15

Phe Lys Leu Lys Gln Asn Val Ser Asn Ile Tyr Ile Met Asn Arg Glu
20 25 30

Pro Leu Lys Tyr Ile Ser Asn Lys Arg Asn Thr Ser Leu Leu Ala His
35 40 45

Thr Asn Lys Asn Phe Arg Lys Leu Gly Arg Asp Arg Ala Gln Arg Arg
50 55 60

Ala Leu Leu Arg Ala Leu Thr Thr Ser Leu Leu Arg Tyr Gly Lys Ile
65 70 75 80

Val Thr Thr Glu Ala Lys Ala Lys Glu Thr Arg Arg Lys Val Asp Arg
85 90 95

Ile Ile Thr Tyr Ala Lys Lys His Asp Asn Asn Arg Gln Tyr Ala Tyr
100 105 110

Arg Leu Ile Ala Asn Tyr Val Tyr Asp Arg Glu Leu Ala Leu Asn Val
115 120 125

Val Lys Gln Ala Pro Val Arg Tyr Lys Glu Arg His Gly Gly Tyr Thr
130 135 140

Lys Ile Lys Leu Leu Pro Lys Ser Arg Lys Gly Asp Ala Ser Arg Met
145 150 155 160

Ala Met Leu Glu Leu Leu
165

<210> SEQ ID NO 640
<211> LENGTH: 294
<212> TYPE: PRT
<213> ORGANISM: Plasmodium vivax

<400> SEQUENCE: 640

Met Ile Arg Lys Ile Lys Leu Ile Ile Ile Met Leu Ile Phe Gln Val
1 5 10 15

Leu Leu Asp Glu Ile Ile Leu Val Tyr Asn Leu Ser Phe Ser Asp Lys
20 25 30

Lys Lys Tyr Asp Leu Ala Phe Ile Lys Gly Asp Ser Asn Lys Ile Met
35 40 45

Ile Arg Asn Asn Ser Leu Arg Asn Asn Thr Ile Ile Lys Lys Thr Cys
50 55 60

Glu Lys Asp Lys Phe Val Leu Asn Asn Ile Cys Gln Thr Lys Glu Glu
65 70 75 80

Asn Lys Leu Val Asp Thr Ile Ser Ser Asn Asp Asn Val Thr Met Asp
85 90 95

Ser Asn Asn Leu Leu Tyr Asp Asp Met Asp Leu Phe Glu Asn Asp Gly
100 105 110

Leu Gln Leu Lys Gln Trp Tyr Phe Pro Glu Lys Val Lys Glu Lys Trp
115 120 125

Lys Glu Lys His Ile Glu Asn Val Arg Asp Asn Tyr Lys Lys Val Leu
130 135 140

Leu Asn Asn Lys Tyr Asn Glu Leu Phe Asn Met Tyr Arg Asn Ile Lys
145 150 155 160

Lys Asn Asn Ile Glu Asn Tyr Lys Lys Arg Val Lys Thr Asn Arg Ile
165 170 175

Asn Pro Val Ile Tyr Val Lys Lys Arg Leu Val Ser Ala Thr Ala Lys
180 185 190

Tyr Ile Lys Met Ser Phe Met Lys Thr Arg Lys Ile Leu Trp Lys Ile
195 200 205

Arg Tyr Met Pro Ile Ile Lys Ala Phe Ala Phe Leu Tyr Tyr Tyr Gly
210 215 220

Thr Asn Lys Tyr Thr Val Asn Ile Tyr Lys Cys Ile Lys Ser Cys Leu
225 230 235 240

His Asn Ala Ile Asn Lys Tyr Gly Arg Asn Asn Ile Lys Pro Val Phe
245 250 255

His Thr Leu Gln Ala Asn Met Gly Gly Tyr Thr Lys Lys Ile Asn Ile
260 265 270

Arg Ala Arg Gly Lys Thr Asp Ile Ile Arg Glu Pro His Thr His Ile 275 280 285

Arg Val Val Leu Glu Val
290

<210> SEQ ID NO 641
<211> LENGTH: 299
<212> TYPE: PRT
<213> ORGANISM: Plasmodium vivax

<400> SEQUENCE: 641

Met Met Asn Lys Ser Cys Phe Ser Lys Tyr Ile Ile Gly Thr Arg Cys
1 5 10 15

Glu Lys Asn Val Cys Ile Tyr Gln Ser Tyr Ile Asn Lys Arg Leu Ile
20 25 30

Asn Thr Asn Val Gln Leu Arg Asn Pro Tyr Tyr Arg Lys Lys Gly Phe
35 40 45

Trp Glu Trp Arg Arg Arg Ile Ile His Arg Tyr Asn Glu Lys Arg Tyr
50 55 60

Ile Lys Lys Gly Ile Lys Pro Lys Phe Val Asn Asn Asn Lys Lys Glu
65 70 75 80

Glu Asn Pro Ile Lys Asn Lys Asn Asp Asp Val Tyr Trp Thr Phe Lys
85 90 95

Val Tyr Gln Leu Lys Ile Ser Leu Arg Asn Leu His Asn Leu Gly Arg
100 105 110

Leu Ile Lys Gly Leu His Leu Glu Asp Ala Ile Val Phe Leu Glu Ser
115 120 125

Ile Pro Gln Ile Arg Ile Asn Asn Ile Leu Asn Ser Leu Leu Thr Cys
130 135 140

Lys Glu Arg Ile Ile Asn Asn Leu Asn Gly Asp Ile Ser Arg Leu Tyr
145 150 155 160

Ile Asp Asn Val Gln Ile His Tyr Asn Thr Pro Met Lys Tyr Ile Lys
165 170 175

Tyr His Ala Met Gly His Phe Gly Leu Val Lys Ser Tyr Arg Asn Ile
180 185 190

Phe Thr Tyr Thr Ile Lys Gln Met Asn Ile Glu Glu Phe Tyr His Lys
195 200 205

Leu Phe Ile Arg Gly Asn Val Pro Arg Thr Leu Ser His Phe Met Arg
210 215 220

Leu Tyr Leu Lys Gln Lys Arg Ile Asn Thr Asn Asn Leu Ile Glu Trp
225 230 235 240

Tyr Pro Tyr Ile Cys Ala Asn Ser Arg Tyr Phe Phe Arg Gln Lys Leu
245 250 255

Asn Tyr Leu Asn Asn Ile Tyr Gln Phe Asn Tyr Tyr Lys Ser Arg His
260 265 270

Ile Trp Ile Gln Asn Tyr Phe Asn Asn Ile Glu Arg Arg Asn Arg Glu
275 280 285

Leu Gln Gln Gln Arg Gly Ile Ile Thr Glu Tyr
290 295

<210> SEQ ID NO 642
<211> LENGTH: 194
<212> TYPE: PRT
<213> ORGANISM: Plasmodium vivax

<400> SEQUENCE: 642

Met Phe Trp Ser Ser Phe Ile Gly Lys Ile Asn Gln Leu Pro Val Leu 1 5 10 15

Ser Gln Leu Asn Asn Ser Phe Leu Lys His Val Ser Val Arg Asn His
20 25 30

Lys Ile Ile Lys Pro Arg Asn Ile Ile Lys Met Trp Lys Ile Arg Lys
35 40 45

Gly Asp Glu Val Lys Val Ile Ser Gly Lys Asp Lys Gly Lys Ile Gly
50 55 60

Glu Val Leu Ser Cys Asp Lys Phe Arg Asn Met Val Lys Val Lys Gly
65 70 75 80

Cys Asn Met Arg Lys Leu Phe Val Asp Asn Lys Phe Val Tyr Ile Glu
85 90 95

Lys Lys Ile His Tyr Ser Asn Val Gln Leu Ile Asp Asn Phe Leu Lys
100 105 110

Thr Asn Thr Lys Val Ala Leu Arg Tyr Thr Asp Asp Asn Gln Val Ile
115 120 125

Arg Ile Ser Lys Lys Ser Gly Thr Val Ile Pro Trp Pro Ser Glu Lys
130 135 140

Thr Lys Glu Glu Asp Tyr Asp Gln Ile Glu Glu Asn Pro Leu Asp Thr
145 150 155 160

Leu Pro Gln Glu Ala Leu Lys Lys Thr Tyr Asp Tyr Lys Thr Asp Val
165 170 175

Lys Phe Met Asn Ile Leu Arg Gln Thr Val Asn Lys Tyr Asn Arg Glu
180 185 190

Leu Ser

<210> SEQ ID NO 643
<211> LENGTH: 227
<212> TYPE: PRT
<213> ORGANISM: Plasmodium vivax

<400> SEQUENCE: 643

Met Ser Arg Tyr Val Lys Tyr Phe Val Gln Ala Lys Arg Leu Asp Lys
1 5 10 15

Arg Lys Arg Lys Tyr Tyr Lys Leu Asp Phe Leu Glu Leu Asn Lys Glu
20 25 30

Leu Ser Ile Pro His Pro Leu Arg Glu Gln Asn Gln Pro Lys Arg Leu
35 40 45

Asp Leu Ser Lys Tyr Leu Asn Ile Glu Val Gly Asp Leu Val Lys Val
50 55 60

Leu Tyr Gly Pro Asp Lys Asp Lys Glu Gly Leu Val Leu Ser Ile Asn
65 70 75 80

Pro Lys Arg Asn Thr Val Thr Val Asp Gly Cys Asn Met Lys Lys Ser
85 90 95

Ala Trp Asn Val Thr Asp Asn Lys Lys Gly Ser Ile Ile Thr Gln Glu
100 105 110

Met Pro Ile His Ile Thr Asn Val Ser Leu Leu Asp Pro Ile Ser Lys
115 120 125

Lys Pro Thr Val Val Lys Arg Arg Tyr Met Met Asn Gly Glu Cys Val
130 135 140

Arg Ile Ser Lys Ile Ser Gly Cys Ala Met Pro Glu Pro Val His Lys
145 150 155 160

Asn Ile Leu Lys Glu Gln Asn Asn Tyr Glu Arg Phe Met His Lys Lys
165 170 175

Lys Ile Gly Pro Pro Ile Lys Asp Ile Tyr Ala Glu Lys Asp Tyr Lys

```
            180                 185                 190

Asn Phe Asn Leu Leu Lys Lys Ile Ala Tyr Glu Ile Lys Lys Lys Arg
        195                 200                 205

Phe Tyr Asp Met Lys Asn Phe Phe Lys Lys Asp Asp Lys Val Glu Asn
    210                 215                 220

Ala Thr Asp
225


<210> SEQ ID NO 644
<211> LENGTH: 262
<212> TYPE: PRT
<213> ORGANISM: Plasmodium vivax

<400> SEQUENCE: 644

Met Gln Ile Thr Asn Lys Ile Tyr Lys Leu Ile Lys Tyr Val Tyr Ile
1               5                   10                  15

Leu Tyr Ile Ile Ile His Ser Asn Phe Ile Phe Pro Lys Val Ile Leu
            20                  25                  30

Thr Gln Ile Asn Lys Asn Lys Thr Asn Asn Ile Leu Lys Tyr Pro Asn
        35                  40                  45

Tyr Phe Tyr Val Ile Ser Leu Tyr Arg Lys Asn Val Arg Phe Lys Asn
    50                  55                  60

Asn Asn Val Leu Asn Lys Ser Val Thr Lys Phe Ala Leu Asn Thr Lys
65                  70                  75                  80

Lys Arg His Lys Glu Ala Leu Ala Ile Arg Lys Tyr Arg Met Thr Gly
                85                  90                  95

Pro Ser Ser Ile Lys Lys His Tyr Gly Phe Gly Ala His Lys Arg Ile
            100                 105                 110

Asn Lys Val Thr Met Leu Pro His Lys Glu Ile Lys Leu Pro Ile Arg
        115                 120                 125

Arg Cys Ala Ile Leu Gly Lys Met Asp Asn Trp Asn Ala Arg Lys Ile
    130                 135                 140

Ser Lys Ser Gly Val Arg Thr His Arg Ile Gln Arg Leu Asn Leu Ile
145                 150                 155                 160

Asn Lys Arg Ile Phe Phe Glu Glu Glu Asn Arg Phe Ile Lys Met Lys
                165                 170                 175

Val Ser Ala Lys Gly Leu Lys Thr Ile Lys Lys Tyr Gly Leu Ala Tyr
            180                 185                 190

Cys Ile Lys Lys Phe Asn Leu Asp Phe Ser Lys Lys Lys Tyr Asp Ala
        195                 200                 205

Gly Tyr Ser Ser Arg Arg Arg Lys Lys Lys Thr Gln Glu Leu Asn Gln
    210                 215                 220

Thr Asn Ser Glu Arg Thr Asn Val Thr Asn Glu Asn Thr Gln Gln Ser
225                 230                 235                 240

Val Glu Glu Val Asp Lys Ile Met Asp Lys Leu Asn Leu Asp Asp Lys
                245                 250                 255

Lys Ile His Lys Asp Leu
            260


<210> SEQ ID NO 645
<211> LENGTH: 317
<212> TYPE: PRT
<213> ORGANISM: Plasmodium vivax

<400> SEQUENCE: 645

Met Pro Leu Phe Phe Leu Tyr Ser Phe Leu Ile Tyr Leu Ile Leu Phe
```

1 5 10 15

Gln Cys Ile Arg Asn Tyr Lys His Leu Ser Thr Leu Gln Leu Ser Asn
20 25 30

Arg Gly Leu Val Gly Asn His Val Gly Ser Asn Leu Ser Tyr Ala Cys
35 40 45

Trp Leu Gly Lys Leu Lys Asn Ile Asn Asn Arg Lys Thr Phe Glu Ile
50 55 60

Asn Met Ile Lys Lys Phe Ile Asn Ala Arg Asp Pro Phe Glu Pro Gln
65 70 75 80

Asp His Leu Lys Asp Ile Pro Tyr Lys Asp Glu Leu Asp Lys Ile Gln
85 90 95

Ile Arg Gly Arg Lys Ile Glu Met Lys Ser Ile Phe Ser Pro Gln Gly
100 105 110

Asp Leu Ile Pro Ala Thr Leu Ile Glu Ile Met Pro Asn Val Ile Tyr
115 120 125

Arg Phe Leu Asp Phe Gly Lys Val Gly Ile Ala Tyr Gly Lys Pro Leu
130 135 140

Asp Glu Ser Arg Trp Ile Leu Lys Pro Glu Ile Gly Gln Ile Ala Lys
145 150 155 160

Val Gly Cys Asn Leu Lys Asn Thr Cys Ser Leu Thr Leu Thr Pro Pro
165 170 175

Gln Asn Phe Val Leu Gly Gln Ile Ile Asp Val Ser Tyr Leu Tyr Asn
180 185 190

Tyr Lys Tyr Val Asn Val Arg Gly Leu Ser Lys Gly Lys Gly Phe Cys
195 200 205

Gly Val Ile Lys Arg Trp Gly Phe Lys Arg Gly Pro Met Ser His Gly
210 215 220

Ser Ser His His Arg Lys Pro Gly Ser Ile Gly Ala Ser Thr His Ile
225 230 235 240

Gly Arg Val Leu Lys Gly Lys Lys Met Pro Gly Lys His Gly Asn Lys
245 250 255

Tyr Arg Thr Met Ile Asn Leu Lys Leu Leu Gly Leu Asn Leu Glu Arg
260 265 270

Asn Glu Ile Leu Val Ser Gly Cys Ile Pro Gly Asn Arg Asn Ser Tyr
275 280 285

Val Thr Val Thr Ala Thr Arg Asp Asn Lys Val Asn Lys Tyr Lys Tyr
290 295 300

Ile Leu Asp Met Leu Tyr Lys Gln Glu Lys Asn Val Lys
305 310 315

<210> SEQ ID NO 646
<211> LENGTH: 119
<212> TYPE: PRT
<213> ORGANISM: Plasmodium vivax

<400> SEQUENCE: 646

Met Leu Phe Leu Ser Asn Val Leu Phe Arg Cys Lys Ser Lys Arg Val
1 5 10 15

His Ile Asn Leu Ile Ser Ser Cys Ala Ser Asn Tyr Ile Tyr Ser Thr
20 25 30

Tyr Ile Ser Pro Ser Lys Ser Lys Tyr Arg Leu Ser Leu Arg Lys His
35 40 45

Asp Pro Val Val Asn Arg His Val Met Phe Tyr Gln Lys His Ile Lys
50 55 60

Ala Arg Ser Lys Lys Lys Leu Thr Leu His Gly Ile Asn Tyr Ala Arg
65 70 75 80

Phe Thr Gly Lys Asn Lys Asn Leu Arg Pro Leu Leu Lys Arg Val Glu
85 90 95

Lys Ser Tyr Leu Tyr Gly Lys Phe Asn Lys Leu Ile Asp Asn Thr Tyr
100 105 110

Arg Ser Leu Pro Arg Met Ser
115

<210> SEQ ID NO 647
<211> LENGTH: 191
<212> TYPE: PRT
<213> ORGANISM: Plasmodium vivax

<400> SEQUENCE: 647

Met Lys Cys Leu Leu Val Lys Leu Phe Met Leu Ile Phe Ile Arg Ser
1 5 10 15

Tyr Thr Tyr Ala Ile Lys Tyr Lys Ile Asn Lys Ala Ala Cys Met Asn
20 25 30

Lys Val Gly Gly Ile Asp Ile Tyr Ala Asn Ile Lys Tyr Asn Met Lys
35 40 45

Lys Lys Glu Lys Lys Asn Ile Asn Lys Lys Met Asn Ile Tyr Asn Asn
50 55 60

Met Ile Arg Lys Thr Asn Ser Leu His Lys Asn Phe Ile Pro Glu Gln
65 70 75 80

Leu Val Leu Phe Pro Arg Asn Lys Leu Leu Asn Glu Ile Lys Tyr Phe
85 90 95

Tyr Ile Ser Phe Thr Tyr His Ile Leu Lys Arg Glu Lys Lys Thr Lys
100 105 110

Ile His Lys Ser Asp Phe Ile Leu His Val Arg Gly Cys Thr Asn Ile
115 120 125

Lys Pro Lys Thr Asn Lys Ser Ile Ala Lys Arg Phe Lys Leu Thr Lys
130 135 140

Asn Gly Lys Leu Ile Arg Lys Lys Pro Gly Arg Asn His Phe Leu Arg
145 150 155 160

Lys Lys Thr Ser Ser Asn Lys Ala Ser Leu Arg Lys Thr Thr Thr Ile
165 170 175

Asp Ser Gly Arg Ile Gln Lys Lys Tyr Lys Ser Val Ile Phe Lys
180 185 190

<210> SEQ ID NO 648
<211> LENGTH: 197
<212> TYPE: PRT
<213> ORGANISM: Plasmodium vivax

<400> SEQUENCE: 648

Met His Tyr Ala Phe Phe Phe Leu Ile Tyr Ile Phe Tyr Ile Ile Phe
1 5 10 15

Leu Pro Ser Tyr Ser Arg Gly Phe Ile Thr Pro His Ile Lys Arg Pro
20 25 30

Ser Cys Val Leu Tyr Ala Val Lys Arg Lys Lys Lys Lys Asn Pro Lys
35 40 45

Leu Ile His Ile Thr Val Ser Ser Asp Asn Glu Ile Gly Lys Lys Gly
50 55 60

Glu Val Lys Gln Val Lys Leu Ser His Ala Phe Asn Tyr Ile Ile Pro
65 70 75 80

```
Gln Arg Leu Gly Tyr Arg Ser Thr Thr Asp Glu Leu Val Glu Lys Glu
                85                  90                  95

Lys Glu Asp Asn Thr Leu Lys Tyr Ile Asp Asp Ile Arg Thr Ser Phe
            100                 105                 110

Ile Trp Ala Tyr Lys Lys Lys Leu Asn Asp Leu Asn Ile Leu Phe His
        115                 120                 125

Phe Lys Lys Asp Gln Lys Phe Ala Val Thr Gln Asp Asp Leu Ile Asn
    130                 135                 140

Tyr Leu Leu Thr Arg Gly Leu Ile Arg Glu Asn Asp Asp Val Tyr Glu
145                 150                 155                 160

Lys Ile Glu Ser Lys Lys Ile Lys Leu Thr Asp Phe Gly Thr Tyr Pro
                165                 170                 175

Ile Lys Tyr Thr Phe Ile Asn Asn Ile Ser Ile Asn Met Ser Ile His
            180                 185                 190

Ile Ile Lys Thr Gly
        195


<210> SEQ ID NO 649
<211> LENGTH: 316
<212> TYPE: PRT
<213> ORGANISM: Plasmodium vivax

<400> SEQUENCE: 649

Met Ala Lys Leu Ser Lys Gln Gln Lys Lys Gln Met Tyr Ile Glu Lys
1               5                   10                  15

Leu Ser Ser Leu Ile Gln Gln Tyr Ser Lys Ile Leu Ile Val His Val
            20                  25                  30

Asp Asn Val Gly Ser Asn Gln Met Ala Ser Val Arg Lys Ser Leu Arg
        35                  40                  45

Gly Lys Ala Thr Ile Leu Met Gly Lys Asn Thr Arg Ile Arg Thr Ala
    50                  55                  60

Leu Lys Lys Asn Leu Gln Ala Val Pro Gln Ile Glu Lys Leu Leu Pro
65                  70                  75                  80

Leu Val Lys Leu Asn Met Gly Phe Val Phe Cys Lys Asp Asp Leu Ser
                85                  90                  95

Glu Ile Arg Asn Ile Ile Leu Asp Asn Lys Ser Pro Ala Pro Ala Arg
            100                 105                 110

Leu Gly Val Ile Ala Pro Ile Asp Val Phe Ile Pro Pro Gly Pro Thr
        115                 120                 125

Gly Met Asp Pro Ser His Thr Ser Phe Phe Gln Ser Leu Gly Ile Ser
    130                 135                 140

Thr Lys Ile Val Lys Gly Gln Ile Glu Ile Gln Glu His Val His Leu
145                 150                 155                 160

Ile Lys Gln Gly Glu Lys Val Thr Ala Ser Ser Ala Thr Leu Leu Gln
                165                 170                 175

Lys Phe Asn Met Lys Pro Phe Ser Tyr Gly Val Asp Val Arg Thr Val
            180                 185                 190

Tyr Asp Asp Gly Val Ile Tyr Asp Ala Lys Val Leu Asp Ile Thr Asp
        195                 200                 205

Glu Asp Ile Leu Glu Lys Phe Ser Lys Gly Val Ser Asn Val Ala Ala
    210                 215                 220

Leu Ser Arg Ala Thr Gly Val Ile Thr Glu Ala Ser Tyr Pro His Val
225                 230                 235                 240

Phe Val Glu Ala Phe Lys Asn Ile Val Ala Leu Ile Ile Asp Ser Asp
                245                 250                 255
```

Tyr Thr Phe Pro Leu Met Glu Asn Ile Lys Lys Met Val Glu Asn Pro
260 265 270

Glu Ala Phe Ala Ala Val Ala Ala Pro Ala Ser Ala Ala Lys Ala Asp
275 280 285

Glu Pro Lys Lys Glu Glu Ala Lys Lys Val Glu Glu Glu Glu Glu Glu
290 295 300

Glu Glu Asp Gly Phe Met Gly Phe Gly Met Phe Asp
305 310 315

<210> SEQ ID NO 650
<211> LENGTH: 118
<212> TYPE: PRT
<213> ORGANISM: Plasmodium vivax

<400> SEQUENCE: 650

Met Ala Ser Ile Pro Ala Ser Glu Leu Pro Glu Cys Glu Lys Gln Glu
1 5 10 15

Leu Leu Cys Thr Tyr Ala Ala Leu Ile Leu His Glu Glu Lys Met Ser
20 25 30

Ile Thr Ser Asp Asn Ile Leu Lys Leu Ile Lys Asn Ser Asn Asn Thr
35 40 45

Val Leu Pro Tyr Leu Pro Met Leu Phe Glu Arg Ala Leu Lys Gly Lys
50 55 60

Asp Ile Gln Ser Leu Leu Ser Asn Leu Ser Val Gly Ser Ala Pro Ala
65 70 75 80

Ala Ala Ala Gln Val Thr Thr Glu Lys Pro Ser Glu Asp Lys Lys Glu
85 90 95

Ala Lys Lys Glu Glu Lys Val Glu Glu Glu Glu Glu Glu Asp Asp Leu
100 105 110

Gly Phe Ser Leu Phe Gly
115

<210> SEQ ID NO 651
<211> LENGTH: 112
<212> TYPE: PRT
<213> ORGANISM: Plasmodium vivax

<400> SEQUENCE: 651

Met Ala Met Lys Tyr Val Ala Ala Tyr Leu Met Cys Val Leu Gly Gly
1 5 10 15

Asn Glu Asn Pro Ser Thr Lys Glu Val Lys Asn Val Leu Gly Ala Val
20 25 30

Asn Ala Asp Val Glu Asp Glu Val Leu Asn Asn Phe Ile Asp Ser Leu
35 40 45

Lys Gly Lys Ser Cys His Glu Leu Ile Thr Asp Gly Leu Lys Lys Leu
50 55 60

Gln Asn Ile Gly Gly Gly Val Ala Ala Ala Pro Ala Gly Ala Ala Ala
65 70 75 80

Val Glu Thr Ala Glu Ala Lys Lys Glu Asp Lys Lys Glu Glu Lys Lys
85 90 95

Glu Glu Glu Glu Glu Glu Glu Asp Asp Leu Gly Phe Ser Leu Phe Gly
100 105 110

<210> SEQ ID NO 652
<211> LENGTH: 888
<212> TYPE: PRT
<213> ORGANISM: Plasmodium vivax

<400> SEQUENCE: 652

Met Asn Gly Lys Lys Asp Asp Glu Leu Ile Ile Glu Gly Glu His Asn
1               5                   10                  15

Asp Lys Met Lys Ser Pro Gly Lys Ser Leu Ile Pro Cys Ile Lys Glu
            20                  25                  30

Lys Phe Asn Glu Thr Asn Leu Lys Met Lys Ile Val Lys Lys Val Thr
        35                  40                  45

Phe Ile Asp Glu His Glu Asp Tyr Ile Lys Asn Lys Lys Glu Ile Glu
    50                  55                  60

Cys Glu Ser Glu Ser Asn Ser Tyr Cys Lys Lys Glu Asp Glu Asn Asp
65                  70                  75                  80

Ile Lys Lys Lys Glu Asp Ile Asp Glu Lys Glu Ser Ile Leu Glu Gln
                85                  90                  95

Leu Asn Gly Asn Ile Ser Asn Glu Lys Asn Gly Tyr His Thr Tyr Glu
            100                 105                 110

Ser Lys Asn Cys Asp Phe Asn Phe Lys Tyr Asp Asp Thr Asp Asn Ile
        115                 120                 125

Asn Met Tyr Glu Glu Asn Ile Glu Asn Asp Ile His Leu Asn Lys Asn
    130                 135                 140

Asn Tyr Tyr His Tyr Asn Lys Tyr Met Asn Leu Asp Tyr Lys Asp Asn
145                 150                 155                 160

Ile Thr Asn Glu Lys Val Ile Tyr Glu Lys Tyr Asp Lys Arg Glu Tyr
                165                 170                 175

Ser Glu Asn His Ile His Pro Ser Thr Ile Met Asn Gly Phe Ser Ser
            180                 185                 190

Leu Lys Asn Gln Glu Glu Asn Tyr Ser Thr Tyr Glu Asn Asn Asn Ile
        195                 200                 205

Ile Asp Asn Ile Asn Glu Asn Leu Asn Ile Ser Tyr Tyr Asn Gln Met
    210                 215                 220

Asn Gly Asn Asn Asp Leu Ser Thr Asn Lys Glu Ile Asn Glu Tyr Ile
225                 230                 235                 240

Asn Glu Lys Asp Glu Glu Lys Arg Lys Gly Ile Leu Lys Asn Glu Ser
                245                 250                 255

Pro Asp Phe Asn Lys Ser Tyr Asn Asp Ser Leu Asn Asn Tyr Leu Ser
            260                 265                 270

Ser Ser Phe Val Asp Ile Leu Asn Thr Leu Lys Asp Val Lys Asn Glu
        275                 280                 285

Asn Asn Asp Gly Ser Tyr Ile Asn Ser Asn Gly Ser Tyr Ile Asn Asn
    290                 295                 300

Pro Glu Asn Ser Asn Ser Asn Asn Asn Asp Asp Thr Asn Leu Arg Tyr
305                 310                 315                 320

Ile Ser Cys Ile Leu Cys Gly Asp Ser Ile Lys Ala Asn Thr Ser Lys
                325                 330                 335

Met Cys His Asn Cys Ile Leu Gln Asn Ile Glu Ser Asn Ser Ile Asn
            340                 345                 350

Ile Asn Lys Asp Thr Tyr Leu Ile Tyr Tyr Cys Arg Glu Cys Lys Arg
        355                 360                 365

Tyr Leu His Asn Arg Trp Val Tyr Cys Glu Leu Glu Ser Lys Glu Leu
    370                 375                 380

Leu Ala Leu Cys Leu Lys Lys Val Asn Lys Leu Lys Lys Leu Lys Ile
385                 390                 395                 400

Leu Asp Ala Lys Phe Leu Tyr Thr Glu Pro His Ser Lys Arg Leu Lys

```
                405                 410                 415

Val His Val Ser Val Gln Glu Glu Leu Ile Asn Asn Phe Ile Ser Glu
            420                 425                 430

Met Glu Ile Ile Ile His Tyr Val Ile Lys Tyr Thr Gln Cys Asp Asp
        435                 440                 445

Cys Lys Lys Lys Tyr Thr Pro Tyr Thr Tyr Asn Thr Cys Val Ser Val
    450                 455                 460

Arg Gln Lys Val Glu His Lys Lys Thr Leu Leu Phe Leu Glu Asn Leu
465                 470                 475                 480

Leu Leu Lys Cys Asn Met Asn Glu Asn Ile Ile Asn Ile Val Ser Asn
                485                 490                 495

Pro Asp Gly Leu Asp Phe His Phe Leu Ser Arg Thr Asp Ala Leu Lys
            500                 505                 510

Phe Cys Asp Phe Ile Leu Ser Lys Thr Met Ser Lys Cys Lys Asn Ser
        515                 520                 525

Lys His Leu Ile Asn His Asp Ala Asn Asn Asn Thr Tyr Asn Tyr Leu
    530                 535                 540

Tyr Thr Phe Ser Ile Asp Ile Cys Pro Ile Cys Lys Tyr Asp Leu Ile
545                 550                 555                 560

Phe Phe Pro Lys Gly Leu Ala Asn Lys Tyr Gly Ile Lys Asn Val Phe
                565                 570                 575

Tyr Leu Cys Ile His Val Ser Ile Phe Ile Ile Leu Ile Asn Pro Phe
            580                 585                 590

Ser Ser Ala Asn His Val Tyr Val Ser Pro Glu Arg Tyr Asn Lys Asn
        595                 600                 605

Pro Phe Leu Pro Leu Leu Ser Lys Ala Asp Ala Lys Val Phe Leu Ile
    610                 615                 620

Leu Asn Ile Glu Tyr Ile Asn Asp Asp Val Asn Thr Asn Asn His Lys
625                 630                 635                 640

Asn Asn Asn Met Asn Pro Ser Ile Ser Asn Asn Asp Asn Ile Asn Leu
                645                 650                 655

Asn Gly His Thr Asn Ile Cys Lys Lys Lys Asn Lys Lys Arg Lys Asn
            660                 665                 670

Lys Arg Lys Lys Gly Ile Asn Thr Lys Asp Asp Asp Ser Asp Ser Ile
        675                 680                 685

Glu Glu Asp Asn His Leu Leu Ser Asn Asp Val Asn Asn Asn His Tyr
    690                 695                 700

Asn Tyr Ser Thr Asn Lys Asn Asn Leu Lys Arg Lys Lys Lys Asp Ser
705                 710                 715                 720

Asn Asn Leu Glu Asp Ile Asn Lys Asn Ser Phe Val Phe Ser Ser Ser
                725                 730                 735

Asp Asn Glu Glu Glu Asn Leu His Lys Pro Asn Asp Phe Asp Lys Asn
            740                 745                 750

Ser Asp Ile Tyr Thr Asp Gly Lys Ser Ala Lys Ser Ser Ser Arg Lys
        755                 760                 765

Val Lys Leu Asp Lys Leu Val Tyr Ala Phe Val Glu Leu Tyr Asp Glu
    770                 775                 780

Ser Asn Gly Thr Thr Ile Leu Thr Lys Thr Cys Asn Ala Lys His Leu
785                 790                 795                 800

Arg Pro Gly Asp Tyr Val Asn Ala Tyr Asp Leu Arg Lys His Ser Phe
                805                 810                 815

Asp Asn Glu Ile Asn Leu Phe Leu Glu Lys Asn Asp Asn Tyr Asn Ile
            820                 825                 830
```

Ile Ile Ile Asp Lys Val Lys Thr Lys Glu Lys Glu Lys Ile Glu Asn
835 840 845

Tyr Leu Gln Val Gln Asn Asn Asn Ile Glu Thr Leu Lys Arg Thr Asn
850 855 860

Glu Gln Asp Ile Phe Asn Arg Ile Leu Leu Asn Asn Cys Lys Ala Leu
865 870 875 880

Glu Asn Met Ala Ile Thr Ser Thr
885

<210> SEQ ID NO 653
<211> LENGTH: 217
<212> TYPE: PRT
<213> ORGANISM: Plasmodium vivax

<400> SEQUENCE: 653

Met Ser Lys Leu Asn Gln Asp Leu Leu Lys Lys Ala Ile Ser Asp Val
1 5 10 15

Phe Glu Gly Thr Lys Gln Lys Lys Arg Lys Phe Val Glu Thr Ile Glu
20 25 30

Leu Gln Ile Gly Leu Lys Asp Tyr Asp Thr Gln Arg Asp Lys Arg Phe
35 40 45

Ser Gly Thr Val Arg Leu Ser Asn Glu Val Arg Lys Lys Leu Lys Val
50 55 60

Cys Ile Leu Gly Asp Ala Val His Val Glu Glu Ala Gln Lys Leu Glu
65 70 75 80

Leu Asp Tyr Met Asp Ile Glu Ala Met Lys Lys Leu Asn Lys Asp Lys
85 90 95

Thr Leu Val Lys Lys Leu Ala Lys Lys Tyr Asp Ala Phe Leu Ala Ser
100 105 110

Gln Val Ile Leu Pro Gln Ile Pro Lys Leu Leu Gly Pro Gly Leu Asn
115 120 125

Lys Ala Gly Lys Phe Pro Ser Leu Ile Thr His Asn Asp Lys Ile Asn
130 135 140

Asp Lys Ile Leu Glu Leu Lys Ser Ser Ile Lys Phe Gln Leu Lys Lys
145 150 155 160

Val Leu Cys Met Gly Val Pro Val Gly His Ala Asn Leu Lys Glu Glu
165 170 175

Glu Leu Arg Ser Asn Ile Val His Ala Ile Asn Phe Leu Val Ser Leu
180 185 190

Leu Lys Lys Asn Trp Gln Asn Ile Arg Thr Leu His Ile Lys Ser Thr
195 200 205

Met Gly Lys Pro Gln Arg Ile Tyr Gly
210 215

<210> SEQ ID NO 654
<211> LENGTH: 219
<212> TYPE: PRT
<213> ORGANISM: Plasmodium vivax

<400> SEQUENCE: 654

Met Gly Arg Arg Pro Ala Arg Cys Tyr Arg Tyr Cys Lys Asn Lys Pro
1 5 10 15

Tyr Pro Lys Ser Arg Tyr Cys Arg Gly Val Pro Asp Pro Lys Ile Arg
20 25 30

Ile Tyr Asp Met Gly Arg Lys Lys Ala Asp Val Asn Glu Phe Ser Gly
35 40 45

```
Val Val His Leu Val Ser Tyr Glu Tyr Glu Gln Ile Ser Ser Glu Ala
    50                  55                  60

Leu Glu Ala Ala Arg Ile Ser Ala Asn Lys Tyr Met Ile Thr Asn Cys
65                  70                  75                  80

Gly Lys Asp Asn Phe His Leu Arg Val Arg Ile His Pro Phe His Val
                85                  90                  95

Leu Arg Ile Asn Lys Met Leu Ser Cys Ala Gly Ala Asp Arg Leu Gln
            100                 105                 110

Thr Gly Met Arg Gly Ala Phe Gly Lys Pro Asn Gly Val Val Ala Arg
        115                 120                 125

Val Asp Ile Gly Gln Val Leu Leu Ser Ile Arg Thr Lys Glu Asn Phe
    130                 135                 140

Val Ser Lys Ala Cys Glu Ala Leu Arg Arg Ala Lys Tyr Lys Phe Pro
145                 150                 155                 160

Gly Arg Gln Lys Val Phe Val Ser Asn Lys Trp Gly Phe Thr Pro Phe
                165                 170                 175

Ser Lys Asp Glu Tyr Gln Gln Tyr Lys Lys Lys Gly Arg Ile Ile Ser
            180                 185                 190

Asp Gly Val Ser Cys Lys Phe Ile Arg Glu Lys Gly Pro Leu Asp Lys
        195                 200                 205

Ile Tyr Lys Asp Ile Asn Thr Val Leu Glu Ser
    210                 215
```

<210> SEQ ID NO 655
<211> LENGTH: 173
<212> TYPE: PRT
<213> ORGANISM: Plasmodium vivax

<400> SEQUENCE: 655

```
Met Glu Asn Lys Glu Gln Asn Val Met Arg Glu Ile Lys Val Asn Lys
1               5                   10                  15

Leu Val Leu Asn Ile Cys Val Gly Glu Ser Gly Asp Arg Leu Thr Arg
            20                  25                  30

Ala Ala Arg Val Leu Glu Gln Leu Thr Glu Gln Lys Pro Ile Phe Gly
        35                  40                  45

Lys Cys Arg Phe Thr Ile Arg Ser Phe Gly Val Arg Arg Asn Glu Lys
    50                  55                  60

Ile Ser Cys Phe Val Thr Val Arg Gly Lys Lys Ala Leu Glu Ile Leu
65                  70                  75                  80

Glu Lys Gly Leu Lys Val Lys Glu Tyr Glu Leu Arg Arg Lys Asn Phe
                85                  90                  95

Ser Asp Thr Gly Asn Phe Gly Phe Gly Ile Gln Glu His Ile Asp Leu
            100                 105                 110

Gly Ile Lys Tyr Asp Pro Ser Thr Gly Ile Tyr Gly Met Asp Phe Tyr
        115                 120                 125

Val His Leu Ser Arg Ser Gly Tyr Arg Val Thr Arg Arg Thr Arg Arg
    130                 135                 140

Arg Ser Lys Ile Ser Lys Thr His Lys Val Thr Lys Glu Asp Ala Met
145                 150                 155                 160

Lys Trp Phe Gln Thr Lys Phe Asp Gly Ile Leu Leu Lys
                165                 170
```

<210> SEQ ID NO 656
<211> LENGTH: 165
<212> TYPE: PRT

<213> ORGANISM: Plasmodium vivax

<400> SEQUENCE: 656

Met Ala Lys Lys Pro Asp Pro Asn Glu Ile Lys Tyr Val Phe Ile Arg
1               5                   10                  15

Gln Val Gly Gly Glu Val Gly Ala Ser Ser Val Leu Ser Pro Lys Leu
            20                  25                  30

Gly Pro Leu Gly Leu Ser Pro Lys Lys Val Gly Asp Asp Ile Ala Lys
        35                  40                  45

Glu Thr Gln Ser Trp Lys Gly Leu Lys Ile Cys Val Lys Leu Thr Ile
    50                  55                  60

Gln Asn Arg Gln Ala Lys Val Glu Val Val Pro Thr Ser Ala Ala Leu
65                  70                  75                  80

Ile Leu Lys Glu Leu Asn Glu Ala Pro Arg Asp Arg Lys Lys Val Lys
                85                  90                  95

Asn Ile Lys His Asn Gly Asn Leu Lys Leu Glu Gln Val Tyr Ser Ile
            100                 105                 110

Ala Arg Val Met Lys Glu Lys Ser Arg Ala Lys Glu Phe Lys Gly Thr
        115                 120                 125

Val Lys Glu Met Leu Gly Thr Cys Asn Ser Ile Gly Cys Thr Val Asp
    130                 135                 140

Gly Lys Lys Pro Thr Thr Ile Gln Glu Met Ile Asp Ser Gly Glu Ile
145                 150                 155                 160

Asp Val Pro Leu Glu
                165

<210> SEQ ID NO 657
<211> LENGTH: 215
<212> TYPE: PRT
<213> ORGANISM: Plasmodium vivax

<400> SEQUENCE: 657

Met Val Ala His Asn Asn Val Leu Pro Asn Val His Leu His Lys Trp
1               5                   10                  15

Trp Gln Arg His Val Arg Val Asn Phe Ser Lys Asn Ile Lys Lys Lys
            20                  25                  30

Lys Arg Arg Leu Leu Arg Glu Lys Arg Arg Lys Ala Asn Gly Gly Thr
        35                  40                  45

Pro Ile Glu Lys Leu His Pro Ile Val His Cys Pro Thr Gln Arg Tyr
    50                  55                  60

Asn Phe Arg Thr Arg Leu Gly Lys Gly Phe Thr Phe Glu Glu Leu Lys
65                  70                  75                  80

Gly Ala Gly Leu Thr Pro Arg Ala Ala Gln Thr Ile Gly Ile Cys Tyr
                85                  90                  95

Asp Lys Arg Arg Lys Asn Arg Ser Glu Glu Ser Leu Thr Lys Asn Val
            100                 105                 110

Glu Arg Leu Leu Lys Tyr Lys Asn Ser Leu Val Met Ile Pro Leu Lys
        115                 120                 125

Lys Asn Lys Ala Lys Lys Gly Ile Gly Gly Ile Pro Ala Asp Ala Asp
    130                 135                 140

Lys Asn Thr Ile Lys Glu Phe Arg Asn Lys Lys Pro Leu Leu Ser Ile
145                 150                 155                 160

Phe Lys Lys Glu Lys Asn Thr Lys Pro Phe Tyr Glu Thr Ile Glu Val
                165                 170                 175

Ser Lys Ile Asp Lys Glu Phe Leu Ala Tyr Lys Thr Leu Arg Arg Ala 180 185 190

Lys Leu Ala Glu Arg Arg Lys Asn Arg Arg Gln Gln Lys Lys Asp Ile
195 200 205

Lys Phe Lys Ser Lys Asp Asn
210 215

<210> SEQ ID NO 658
<211> LENGTH: 202
<212> TYPE: PRT
<213> ORGANISM: Plasmodium vivax

<400> SEQUENCE: 658

Met Tyr Lys Lys Glu Tyr Val Ile Asp Cys Lys Gly His Leu Leu Gly
1 5 10 15

Arg Leu Ala Ser Leu Ile Ala Lys Glu Leu Leu Asn Gly Gln Arg Ile
20 25 30

Val Ala Val Arg Cys Glu Asp Ile Asn Ile Ser Gly Ser Leu Tyr Arg
35 40 45

Asn Lys Leu Lys Tyr Gln Glu Phe Leu Arg Leu Arg Thr Asn Thr Asn
50 55 60

Pro Lys Lys Gly Pro Leu His Leu Arg Glu Pro Ser Lys Ile Leu Trp
65 70 75 80

Arg Cys Val Arg Gly Met Leu Pro His Lys Thr Tyr Lys Gly Gln Leu
85 90 95

Ala Leu Lys Lys Leu Lys Val Cys Val Gly Met Pro Tyr Pro Tyr Asp
100 105 110

Lys Lys Lys Lys Tyr Val Leu Pro Ser Ala Leu Arg Ala Phe Arg Leu
115 120 125

Lys Lys His Arg Arg Tyr Cys Arg Leu Gly Thr Leu Ser Ser Arg Val
130 135 140

Gly Trp Asn Tyr Asp Thr Leu Val Lys Lys Asn Glu Val Leu Arg Lys
145 150 155 160

Gln Val Ser Lys Ala Tyr Tyr Lys Lys Lys Val Asn Asn Leu Asn Glu
165 170 175

Lys Lys Glu Ile Lys Thr Glu Ala Leu Asn Leu Ile Asn Pro Glu Gln
180 185 190

Arg Gln Val Leu Glu Asn Phe Gly Tyr Ala
195 200

<210> SEQ ID NO 659
<211> LENGTH: 165
<212> TYPE: PRT
<213> ORGANISM: Plasmodium vivax

<400> SEQUENCE: 659

Met Pro Arg Val Glu Leu Thr Glu Glu Glu Lys Leu Tyr Ile Ser Lys
1 5 10 15

Lys Asn Leu Leu Phe Lys Arg Phe Val Glu Pro Gly Arg Leu Cys Leu
20 25 30

Ile Glu Tyr Gly Pro Tyr Ala Gly Lys Leu Cys Phe Ile Val Asp Ile
35 40 45

Val Thr Ile Thr Arg Val Ile Val Asp Gly Ala Phe Ile Thr Gly Val
50 55 60

Pro Arg Met Val Ile Pro Leu Lys Arg Leu Lys Leu Leu Lys Glu Arg
65 70 75 80

Ile Lys Ile Asn Lys Asn Cys Lys Ser Gly Phe Leu Arg Lys Thr Val

```
                85                  90                  95

Asn Ser Thr Lys Val Leu Glu Glu Phe Asn Asn Ser Lys Leu Gly Lys
            100                 105                 110

Lys Met Ile Ile Lys Lys Lys Arg Asp Glu Ala Thr Asp Phe Glu Arg
        115                 120                 125

Phe Gln Val Tyr Phe Ala Lys Arg Glu Leu Lys Lys Lys Met Thr Thr
    130                 135                 140

Ile Lys Asn Lys Lys Asn Gly Glu Asn Lys Lys Val Lys Lys Asn Val
145                 150                 155                 160

Gln Lys Val Lys Ala
                165


<210> SEQ ID NO 660
<211> LENGTH: 203
<212> TYPE: PRT
<213> ORGANISM: Plasmodium vivax

<400> SEQUENCE: 660

Met Val Lys Tyr Ala Lys Lys Ile Arg Asn Leu Gly Lys Cys Ala Lys
1               5                   10                  15

Gly Ala Gly Val Asp Leu Arg Val His Phe Lys Asn Thr Tyr Glu Ala
            20                  25                  30

Ala Arg Ala Ile Arg Arg Met Lys Leu Leu Glu Ala Lys Lys Tyr Leu
        35                  40                  45

Asn Asp Val Ile Glu Lys Lys Arg Cys Val Pro Phe Arg Lys Tyr Asn
    50                  55                  60

Gly Gly Val Gly Arg Thr Asn Gln Ala Lys Glu Phe Asn His Thr Gln
65                  70                  75                  80

Gly Arg Trp Pro Ala Lys Ser Cys Lys Phe Leu Leu Asn Ile Leu Asp
                85                  90                  95

Asn Val Gln Ala Asn Ala Glu Ser Arg Asn Leu Asp Val Ser Lys Leu
            100                 105                 110

Arg Leu Ile His Val Met Val Asn Lys Ala Arg Pro Gly Arg Arg Arg
        115                 120                 125

Thr Tyr Lys Ala His Gly Arg Ile Asn Pro Phe Met Ser Ser Pro Cys
    130                 135                 140

His Ile Gln Ile Ile Ala Arg Glu Ile Asn Lys Pro Ala Lys Lys Ser
145                 150                 155                 160

Leu Leu Ser Asn Ala Glu Lys Gln Lys Lys Leu Pro Phe Lys Val Thr
                165                 170                 175

Leu Lys Lys Leu Ile Lys Leu Asn Ile Ser Asn Gln Asn Arg Leu Lys
            180                 185                 190

Asn Lys Ser Val Lys Lys Gln Gln Thr Val Gln
        195                 200


<210> SEQ ID NO 661
<211> LENGTH: 187
<212> TYPE: PRT
<213> ORGANISM: Plasmodium vivax

<400> SEQUENCE: 661

Met Gly Ile Ala Leu Lys Asn Val Gly Arg Ile Lys Lys His Gly Arg
1               5                   10                  15

Lys His Leu Val Ser Lys Asn Pro Tyr Leu Arg Leu Leu Val Lys Leu
            20                  25                  30

Tyr Asn Phe Leu Ala Arg Arg Thr Asn Ala Asn Phe Asn Lys Ile Ile
```

```
        35                  40                  45

Ala Lys Arg Leu Ile Met Pro Lys Arg Tyr Arg Pro Pro Leu Ser Leu
    50                  55                  60

Ser Lys Leu Gln Tyr His Met Ala Asn His Pro Asn Asp Ile Ala Val
65                  70                  75                  80

Val Val Gly Ser Ile Thr Asp Asp Lys Arg Leu Phe Ser Leu Lys Gln
                85                  90                  95

Leu Lys Val Cys Ala Leu Arg Phe Thr Glu Thr Ala Arg Lys Arg Ile
            100                 105                 110

Glu Asp Ala Gly Gly Glu Cys Leu Thr Phe Asp Gln Leu Ala Leu Lys
        115                 120                 125

Tyr Pro Thr Gly Lys Lys Cys Val Leu Leu Arg Gly Pro Thr Lys Ala
    130                 135                 140

Arg Thr Ala Glu Lys His Phe Gly Lys Ala Pro Gly Lys Pro Lys Ser
145                 150                 155                 160

Lys Ala Arg Pro Tyr Val Arg Ser Lys Gly Arg Lys Phe Glu Lys Ala
                165                 170                 175

Arg Gly Arg Arg Lys Ser Arg Ala Tyr Lys Lys
            180                 185


<210> SEQ ID NO 662
<211> LENGTH: 184
<212> TYPE: PRT
<213> ORGANISM: Plasmodium vivax

<400> SEQUENCE: 662

Met Val Lys Lys Ile Asp Asn Ser Leu Asn Thr Asn Ile His Gln Tyr
1               5                   10                  15

His Ile Val Gly Arg Ala Ile Pro Thr Ala Lys Asp Lys Asn Pro Asn
            20                  25                  30

Val Tyr Arg Met Cys Ile Phe Ala Lys Asn Asp Thr Asn Ala Lys Ser
        35                  40                  45

Arg Phe Trp Tyr Phe Met Lys Lys Ile Asn Lys Leu Lys Lys Ser Asn
    50                  55                  60

Gly Glu Leu Leu Ala Cys Glu Gln Ile Lys Glu Arg Phe Pro Leu Arg
65                  70                  75                  80

Val Lys Asn Tyr Gly Val Leu Leu Arg Tyr Asp Ser Arg Thr Gly Thr
                85                  90                  95

His Asn Met Tyr Lys Glu Phe Arg Asp Thr Thr Lys Glu Gly Ala Ile
            100                 105                 110

Ala Gln Leu Tyr Ser Glu Met Ala Gly Arg His Arg Ala Arg Ala Ser
        115                 120                 125

Ser Ile Asn Ile Ile Arg Ile Ser Glu Ile Ser Ser Ser Leu Val Arg
    130                 135                 140

Arg Pro His Ile Lys Gln Leu Leu Lys Arg Arg Leu Arg Phe Pro Ala
145                 150                 155                 160

Leu His Leu Pro Thr Leu Gln Lys Glu Tyr Arg Lys Lys Phe Ala Ser
                165                 170                 175

Lys Arg Pro Ser Thr Tyr Arg Met
            180


<210> SEQ ID NO 663
<211> LENGTH: 182
<212> TYPE: PRT
<213> ORGANISM: Plasmodium vivax
```

<400> SEQUENCE: 663

Met Ser Leu Thr Leu Gln Lys Arg Leu Ala Ala Ser Val Leu Lys Cys
1               5                   10                  15

Gly Lys Asn Lys Ile Trp Met Asp Pro Asn Glu Ile Ser Glu Ile Ser
            20                  25                  30

Leu Ala Asn Ser Arg Phe Ser Ile Arg Lys Leu Tyr Lys Glu Gly Leu
        35                  40                  45

Ile Leu Lys Lys Pro Gln Lys Val His Ser Arg Ala Arg Val Arg Leu
    50                  55                  60

Tyr Lys Leu Ala Lys Arg Lys Gly Arg His Met Gly Ile Gly Lys Arg
65                  70                  75                  80

Lys Gly Thr Lys Asn Ala Arg Thr Asn Gln Lys Thr Leu Trp Ile Lys
                85                  90                  95

Arg Gln Arg Val Leu Arg Arg Leu Leu Lys Arg Leu Arg Asp Ser Lys
            100                 105                 110

Lys Val Asp Arg His Leu Tyr His Ser Phe Tyr Leu Lys Cys Lys Gly
        115                 120                 125

Asn Gln Phe Lys Asn Lys Arg Thr Leu Ile Glu Ala Ile Gln Arg Glu
    130                 135                 140

Lys Asn Glu Thr Leu Lys Lys Lys Ala Ile Ala Asp Gln Leu Glu Ala
145                 150                 155                 160

Lys Arg Leu Lys Ala Gln Val Leu Arg Asn Lys Arg Lys Leu Lys Lys
                165                 170                 175

Asp Lys Glu Val Val Ala
            180

<210> SEQ ID NO 664
<211> LENGTH: 260
<212> TYPE: PRT
<213> ORGANISM: Plasmodium vivax

<400> SEQUENCE: 664

Met Gly Arg Val Ile Arg Gly Gln Arg Lys Gly Arg Gly Ser Ile Phe
1               5                   10                  15

Lys Ser His Asn His His Arg Lys Gly Ala Ala Lys Leu Arg His Leu
            20                  25                  30

Asp Tyr Cys Glu Lys Lys Gly Tyr Ile Lys Gly Leu Val Lys Asp Ile
        35                  40                  45

Ile His Asp Pro Gly Arg Gly Ala Pro Leu Ala Lys Val Ile Phe Lys
    50                  55                  60

Arg Thr Glu Lys Tyr Gly Lys Lys Glu Glu Leu Ile Ile Ala Ser Glu
65                  70                  75                  80

Gly Met Phe Thr Gly Gln Tyr Ile Ser Cys Gly Thr Lys Ala Pro Leu
                85                  90                  95

Ser Val Gly Asn Ile Leu Pro Ile Gly Lys Met Pro Glu Gly Thr Leu
            100                 105                 110

Ile Cys Asn Leu Glu His Arg Thr Gly Asn Arg Gly Thr Leu Val Lys
        115                 120                 125

Ala Ser Gly Cys Tyr Ala Thr Val Val Gly Gln Ser Glu Asp Gly Lys
    130                 135                 140

Lys Thr Lys Val Arg Leu Pro Ser Gly Ala Lys Lys Thr Ile Asp Ala
145                 150                 155                 160

Lys Ala Arg Ala Met Val Gly Val Val Gly Ala Gly Gly Arg Ile Asp
                165                 170                 175

```
Lys Pro Ile Leu Lys Ala Gly Val Ala His His Lys Tyr Arg Val Lys
            180                 185                 190

Arg Asn Cys Trp Pro Lys Val Arg Gly Val Ala Met Asn Pro Val Glu
        195                 200                 205

His Pro His Gly Gly Gly Asn His Gln His Ile Gly His Pro Ser Thr
    210                 215                 220

Val Ser Arg Ser Ala Pro Ala Gly Gln Lys Val Gly Leu Ile Ala Ala
225                 230                 235                 240

Arg Arg Thr Gly Leu Leu Arg Gly Ala Lys Lys Thr Lys Leu Val Gly
                245                 250                 255

Lys Ser Glu Glu
            260
```

<210> SEQ ID NO 665
<211> LENGTH: 161
<212> TYPE: PRT
<213> ORGANISM: Plasmodium vivax

<400> SEQUENCE: 665

```
Met Gly Gly Lys Ser Arg Gly Lys Arg Ser Gly Thr Arg Tyr Lys Phe
1               5                   10                  15

Ser Lys Lys Phe Arg Lys His Gly Glu Cys Thr Ala Asn Lys Tyr Leu
            20                  25                  30

Glu Lys Leu Asn Tyr Gly Asp Tyr Val Asp Ile Val Cys Asp Ser Thr
        35                  40                  45

Gln Gln Lys Gly Met Pro Phe Asn Tyr Tyr His Gly Lys Thr Gly Lys
    50                  55                  60

Ile Phe His Ile Thr Lys Arg Gly Val Gly Val Leu Val Asn Lys Arg
65                  70                  75                  80

Val Lys His Arg Ile Glu Gln Lys Lys Val Cys Val Arg Ile Glu His
                85                  90                  95

Val Arg Lys Ser Arg Cys Asn Glu Asp Phe Leu Leu Arg Lys Ile Lys
            100                 105                 110

Asn Ala Glu Leu Ile Lys Glu Ala Lys Leu Lys Asn Glu His Ile Asn
        115                 120                 125

Ile Lys Arg Lys Thr Glu Gly Pro Lys Pro Ala Ala Met Ile Lys Val
    130                 135                 140

Pro Pro Ser Lys Ile Ile Thr Ile Glu Pro Leu Pro Phe Tyr Glu Glu
145                 150                 155                 160

Tyr
```

<210> SEQ ID NO 666
<211> LENGTH: 139
<212> TYPE: PRT
<213> ORGANISM: Plasmodium vivax

<400> SEQUENCE: 666

```
Met Val Ala Lys Lys Asp Ser Thr Lys Val Ser Lys Lys Leu Lys Lys
1               5                   10                  15

Lys Val Val Lys Lys Thr Lys Ile Val Lys Gly Leu Lys Lys Gln Lys
            20                  25                  30

Met Asn Lys Ser Thr Lys Gly Ile Lys Tyr Val Leu Asp Cys Thr Lys
        35                  40                  45

Pro Val Lys Asp Thr Ile Leu Asp Ile Ser Gly Leu Glu Gln Phe Phe
    50                  55                  60

Lys Asp Lys Ile Lys Val Asp Lys Lys Thr Asn Asn Leu Lys Asn Lys
```

```
65                  70                  75                  80

Val Val Val Thr Ser Asp Glu Tyr Lys Ile Tyr Ile Thr Val His Ile
                85                  90                  95

Pro Phe Ser Lys Arg Tyr Ile Lys Tyr Leu Ala Lys Lys Tyr Ile Lys
            100                 105                 110

Met His Gln Ile Arg Asp Phe Leu Arg Val Ile Ala Lys Gly Lys Leu
        115                 120                 125

Ala Tyr Glu Phe Lys Tyr Phe Gln Leu Asn Asn
    130                 135


<210> SEQ ID NO 667
<211> LENGTH: 190
<212> TYPE: PRT
<213> ORGANISM: Plasmodium vivax

<400> SEQUENCE: 667

Met Thr Gln Val Glu Lys Lys Lys Lys Asn Val Lys Asn Val Asn Lys
1               5                   10                  15

His Lys Ile Ile His Lys Arg Val Ile Lys Lys Gly Asn Arg Lys Tyr
            20                  25                  30

Thr Asn Gly Asn Thr Lys Val Lys Tyr Arg Lys Gln Val Val Lys Lys
        35                  40                  45

Thr Ile Asn Lys Asn Val Ser Lys Lys Lys Leu Leu Lys Glu Asn Val
    50                  55                  60

Asp Lys Asp Glu Lys Lys Lys Lys Met Lys Ile Ser Ile Arg Phe Lys
65                  70                  75                  80

Lys Pro Lys Thr Leu Ile Tyr Ala Arg Asn Pro Lys Cys Pro Arg Ile
                85                  90                  95

Val Lys Ser Cys His Ser Lys Thr Leu Asp Lys Tyr Gly Leu Ile Lys
            100                 105                 110

Tyr Pro Leu Thr Ser Glu Lys Ala Met Lys Lys Ile Glu Glu Ile Asn
        115                 120                 125

Thr Leu Val Phe Met Cys Asp Lys Arg Ala Asn Lys Lys Asn Ile Lys
    130                 135                 140

Lys Ser Val Lys Asn Leu Phe Gly Ile Glu Cys Asp Lys Val Asn Val
145                 150                 155                 160

Leu Asn Thr Leu Asn Gly Asp Lys Lys Ala Tyr Val Arg Leu Ser Gly
                165                 170                 175

Glu His Asp Ala Leu Glu Val Ala Asn Lys Ile Gly Ile Leu
            180                 185                 190


<210> SEQ ID NO 668
<211> LENGTH: 139
<212> TYPE: PRT
<213> ORGANISM: Plasmodium vivax

<400> SEQUENCE: 668

Met Lys Arg Gly Arg Ala Gly Thr Leu Lys Asn Lys Met Arg Ile Thr
1               5                   10                  15

Leu Ser Leu Pro Val Gly Ala Leu Ile Asn Cys Cys Asp Asn Ser Gly
            20                  25                  30

Gly Lys Asn Leu Tyr Ile Ile Ala Val Gln Gly Phe Gly Ser Cys Leu
        35                  40                  45

Asn Arg Leu Pro Ala Ala Ser Leu Gly Asp Met Val Leu Ala Thr Val
    50                  55                  60

Lys Lys Gly Lys Pro Asp Leu Arg Lys Lys Val Leu Asn Ala Ile Ile
```

65 70 75 80

Cys Arg Gln Ser Lys Ala Trp Arg Arg His Glu Gly Tyr Tyr Ile Tyr
85 90 95

Phe Glu Asp Asn Ala Gly Val Ile Val Asn Pro Lys Gly Glu Met Lys
100 105 110

Gly Ser Ala Ile Thr Gly Pro Val Ala Arg Glu Cys Ala Glu Leu Trp
115 120 125

Pro Lys Leu Ser Ser Ala Ala Ser Ala Ile Val
130 135

<210> SEQ ID NO 669
<211> LENGTH: 162
<212> TYPE: PRT
<213> ORGANISM: Plasmodium vivax

<400> SEQUENCE: 669

Met Ser Gln Ile Lys Thr Thr Val Lys Thr Glu Ala Cys Ser Phe Ser
1 5 10 15

Glu Tyr Arg Ile Tyr Pro Gly Arg Gly Gln Lys Tyr Ile Ala Arg Asp
20 25 30

Gly Lys Val Tyr Phe Tyr Leu Ser Ser Lys Phe Ala Ser Leu Ala Leu
35 40 45

Gln Lys Lys Lys Ala Ala Lys Leu Arg Trp Thr Gln Thr Trp Arg Arg
50 55 60

Asn Asn Lys Lys Thr Lys Ile Glu Thr Thr Gln Arg Arg Arg Tyr Lys
65 70 75 80

Lys Thr Ile Lys Val Gln Lys Ala Val Cys Gly Leu Thr Val Glu Asp
85 90 95

Ile Arg Asn Arg Lys Ala Tyr Val Gln Ser Ile Glu Ala Lys Asn Lys
100 105 110

Ala Lys Phe Gly Thr Lys Glu Lys Glu Asp Lys Lys Lys Thr Lys Asp
115 120 125

Asp Lys Lys Lys Asn Leu Val His Phe Gln Gln Lys Lys Asp Phe Thr
130 135 140

Lys Ser Lys Met Leu Asn Met Ala Lys Ser Lys Met His Lys Met Met
145 150 155 160

Lys Lys

<210> SEQ ID NO 670
<211> LENGTH: 126
<212> TYPE: PRT
<213> ORGANISM: Plasmodium vivax

<400> SEQUENCE: 670

Met Lys Phe Asn Lys Gln Lys Ser Ser Ser Arg Arg Lys Met Arg Lys
1 5 10 15

Ala His Phe Thr Ala Pro Ala Gly Leu Arg Arg Lys Ile Met Ser Ser
20 25 30

Lys Leu Ser Lys Glu Leu Arg Leu Lys Tyr Lys Thr Arg Ser Leu Pro
35 40 45

Val Arg Lys Asp Asp Glu Val Leu Ile Cys Arg Gly His Asn His Gly
50 55 60

Arg Glu Gly Lys Val Val Lys Ile Asn Arg Lys Arg Tyr Lys Ile Tyr
65 70 75 80

Val Glu Arg Val Thr Arg Glu Lys Val Asn Gly Glu Ser Thr Phe Ile
85 90 95

```
Gly Ile His Pro Ser Asn Val Val Leu Thr Lys Leu Lys Val Asp Lys
            100                 105                 110

Asn Arg Lys Lys Ile Leu Asp Arg Lys Ala Ala Lys Glu Asn
        115                 120                 125


<210> SEQ ID NO 671
<211> LENGTH: 146
<212> TYPE: PRT
<213> ORGANISM: Plasmodium vivax

<400> SEQUENCE: 671

Met Gly Lys Leu Leu Lys Pro Gly Lys Val Ile Ile Ile Leu Asn Gly
1               5                   10                  15

Arg Arg Ala Gly Lys Lys Ala Val Ile Val Asn Thr Tyr Glu Gly Gln
            20                  25                  30

Thr Arg Glu Arg Pro Tyr Ser Tyr Cys Leu Val Ala Gly Ile Glu Lys
        35                  40                  45

His Pro Leu Lys Val Asn Lys Ser Met Thr Lys Lys Lys Ile Val Lys
    50                  55                  60

Arg Ser Lys Val Lys Ala Phe Ile Lys Cys Ile Asn Val Asn His Ile
65                  70                  75                  80

Leu Pro Thr Arg Tyr Gln Val Ala Asn Asp Phe Asp Ile Lys Ser Leu
                85                  90                  95

Ala Ser Asp Asp Val Leu Lys Ser Lys Asn Lys Lys Lys Glu Val Lys
            100                 105                 110

Lys Leu Gly Lys Ile Phe Arg Asp Lys Phe Leu Glu Pro Val Asn Lys
        115                 120                 125

Lys Thr Gly Glu Val Ser Lys Asp Ile Ser Phe Leu His Lys Lys Leu
    130                 135                 140

Tyr Phe
145


<210> SEQ ID NO 672
<211> LENGTH: 148
<212> TYPE: PRT
<213> ORGANISM: Plasmodium vivax

<400> SEQUENCE: 672

Met Ala Thr Arg Phe Lys Lys Asn Arg Lys Lys Arg Gly His Val Ser
1               5                   10                  15

Ala Gly His Gly Arg Val Gly Lys His Arg Lys His Pro Gly Gly Arg
            20                  25                  30

Gly Lys Ala Gly Gly Leu His His Met Arg Ile Asn Phe Asp Lys Tyr
        35                  40                  45

His Pro Gly Tyr Phe Gly Lys Val Gly Met Arg His Leu Asn Leu Leu
    50                  55                  60

Lys Asn Arg Thr Tyr Cys Pro Thr Ile Asn Val Asp Lys Leu Trp Gly
65                  70                  75                  80

Leu Leu Pro Glu Glu Lys Lys Lys Glu Phe Ser Glu Asn Lys Asp Ile
                85                  90                  95

Ala Pro Val Ile Asp Val Thr Arg Lys Gly Tyr Phe Lys Val Leu Gly
            100                 105                 110

Asn Gly Lys Leu Lys His Asn Gln Pro Ile Val Val Lys Ala Arg Tyr
        115                 120                 125

Phe Ser Ser Val Ala Glu Lys Lys Ile Lys Ala Val Gly Gly Gln Cys
    130                 135                 140
```

Ile Leu Val Ala
145

<210> SEQ ID NO 673
<211> LENGTH: 127
<212> TYPE: PRT
<213> ORGANISM: Plasmodium vivax

<400> SEQUENCE: 673

Met Ser Asn Val Ser Asn Ala Leu Val Trp Glu Leu Thr Arg Lys Ser
1 5 10 15

Asn Cys Phe Ile Lys Lys Asn Lys Ala Gly Lys Lys Gly Val Phe Leu
20 25 30

Cys Asp Pro Leu Asn Val Asn Tyr Lys Asn Thr Pro Ser Ser Ser Gly
35 40 45

Leu Val Lys Ser Asn Ser Thr Asn Val Thr Leu Lys Asp Gly Lys Val
50 55 60

Val Phe Ser Val Lys Thr Ser Lys Glu Ser Asn Val Val Asn Gln His
65 70 75 80

Phe Lys Ala Lys Asn Met Lys Asn Val Glu Lys Leu Leu Gln Gln His
85 90 95

Gly Ser Phe Glu Lys Ala Lys Asn Lys Glu Lys Leu Leu Lys Lys Tyr
100 105 110

Lys Arg Leu Ser Lys Leu Tyr Glu Thr Ser His Lys Lys Thr Asn
115 120 125

<210> SEQ ID NO 674
<211> LENGTH: 67
<212> TYPE: PRT
<213> ORGANISM: Plasmodium vivax

<400> SEQUENCE: 674

Met Ala Lys Ser Lys Asn His Thr Asn His Asn Gln Asn Arg Lys Ala
1 5 10 15

His Lys Asn Gly Ile Lys Lys Pro Lys Lys His Lys Phe Met Ser Arg
20 25 30

Lys Gly Leu Asp Pro Asn Phe Phe Arg Asn Gln Lys Tyr Cys Leu Lys
35 40 45

Gly Ile Gln Lys Lys Lys Lys Glu Leu Lys Leu Lys Ala Lys Gln Glu
50 55 60

Lys Asn Asn
65

<210> SEQ ID NO 675
<211> LENGTH: 386
<212> TYPE: PRT
<213> ORGANISM: Plasmodium vivax

<400> SEQUENCE: 675

Met Ser His Arg Lys Phe Glu Arg Pro Arg His Gly Ser Leu Gly Phe
1 5 10 15

Leu Pro Arg Lys Arg Cys Lys Arg Leu Arg Gly Lys Ile Arg Ser Phe
20 25 30

Pro Lys Asp Asp Lys Glu Lys Pro Pro His Phe Thr Ala Phe Met Gly
35 40 45

Tyr Lys Ala Gly Met Thr His Ile Val Arg Glu Val Asp Lys Pro Gly
50 55 60

Ser Lys Leu His Lys Lys Glu Ile Val Glu Ala Cys Thr Ile Ile Glu
65 70 75 80

Cys Ala Pro Met Val Val Val Gly Ile Val Gly Tyr Arg Glu Thr Pro
85 90 95

Lys Gly Leu Arg Ile Leu Ser Thr Val Trp Ala Asn His Val Ser Asp
100 105 110

Glu Phe Arg Arg Arg Tyr Tyr Lys Asn Trp Tyr Lys Ser Glu Lys Lys
115 120 125

Ala Phe Thr Lys Ser Leu Asn Val Pro Glu Ala Thr Lys Asn Cys Leu
130 135 140

Leu Lys Arg Ile Glu Lys Tyr Cys Thr Val Leu Arg Ala Ile Cys His
145 150 155 160

Thr Gln Pro Ser Lys Thr Pro Leu Arg Met Lys Lys Ala His Ile Met
165 170 175

Glu Val Gln Ile Asn Gly Gly Ser Met Lys Glu Lys Leu Glu Phe Val
180 185 190

Lys Glu Met Leu Glu Lys Asn Leu Pro Val Ser Thr Val Phe Asn Pro
195 200 205

Asn Glu Met Ile Asp Val Ile Ser Val Thr Lys Gly His Gly Thr Lys
210 215 220

Gly Val Val Ser Arg Tyr Gly Val Lys Arg Leu Pro Arg Lys Thr His
225 230 235 240

Arg Gly Leu Arg Lys Val Ala Cys Ile Gly Ala Trp His Pro Ala Arg
245 250 255

Val Gln Phe Gln Ile Pro Arg His Gly Gln Lys Gly Tyr Phe His Arg
260 265 270

Thr Glu Arg Asn Lys Lys Ile Tyr Arg Ile Gly Leu Lys Thr Asp Lys
275 280 285

Asn Ser Ala Ser Thr Asp Ala Asp Ile Thr Glu Lys Lys Ile Thr Pro
290 295 300

Met Gly Gly Phe Pro His Tyr Gly Val Val Asn Glu Asp Phe Leu Leu
305 310 315 320

Leu Lys Gly Cys Val Ala Gly Thr Lys Lys Arg Pro Ile Thr Leu Arg
325 330 335

Lys Asn Ile Val Pro Gln Val Ser Arg Asp Ala Leu Ala Gln Val Ser
340 345 350

Leu Lys Phe Ile Asp Thr Ser Ser Lys Ile Gly His Gly Arg Phe Gln
355 360 365

Thr Ser Glu Glu Lys Val Lys Tyr Tyr Gly Pro Leu Lys Lys Asp Leu
370 375 380

Lys Ala
385

<210> SEQ ID NO 676
<211> LENGTH: 108
<212> TYPE: PRT
<213> ORGANISM: Plasmodium vivax

<400> SEQUENCE: 676

Met Ala Lys Lys Ser Lys Lys Ser Ala Gly Asp Asn Ile Asn Ala Lys
1 5 10 15

Leu Gln Leu Val Met Lys Ser Gly Lys Tyr Gln Phe Gly Arg Lys Ser
20 25 30

Cys Leu Lys Ala Leu Arg Thr Gly Lys Gly Lys Leu Val Ile Val Ser
35 40 45

Ser Asn Cys Pro Ser Ile Gln Arg Ser Val Ile Glu Tyr Tyr Ala Met
    50                  55                  60

Leu Ser Lys Cys Gly Val His Asp Tyr His Gly Asp Asn Asn Asp Leu
65                  70                  75                  80

Gly Thr Ala Cys Gly Lys Leu Phe Arg Ile Ser Cys Leu Val Ile Thr
                85                  90                  95

Asp Val Gly Asp Ser Asp Ile Ile Lys Thr Asn Glu
            100                 105

<210> SEQ ID NO 677
<211> LENGTH: 120
<212> TYPE: PRT
<213> ORGANISM: Plasmodium vivax

<400> SEQUENCE: 677

Met Val Lys Gly Thr Val Lys Lys Gln Lys Lys Thr Leu Lys Pro Val
1               5                   10                  15

Thr Lys Phe Ile Thr Ile Asn Leu Ser Lys Leu Thr His Lys Val Cys
            20                  25                  30

Tyr Lys Arg Lys Ala Pro Arg Ala Ile Lys Glu Ile Arg Ser Ile Ala
        35                  40                  45

Gly Lys Leu Met His Thr Lys Asp Val Arg Leu Asp Val Lys Leu Asn
    50                  55                  60

Lys Phe Ile Trp Ser Lys Gly Val Arg Asn Pro Pro Lys Arg Val Arg
65                  70                  75                  80

Val Lys Leu Glu Arg Lys Arg Asn Glu Asp Glu Asp Ser Lys Glu Lys
                85                  90                  95

Met Tyr Thr Ile Val Glu His Val Met Val Asp Ser Tyr Lys Gly Leu
            100                 105                 110

Val Asn Glu Cys Glu Ala Asn Glu
        115                 120

<210> SEQ ID NO 678
<211> LENGTH: 131
<212> TYPE: PRT
<213> ORGANISM: Plasmodium vivax

<400> SEQUENCE: 678

Met Ala Val Lys Lys Val Gly Lys Ile Ile Lys Lys Arg Thr Lys Lys
1               5                   10                  15

Phe Thr Arg Phe Gln Ser Asn Arg Phe Met Arg Val Lys Pro Ala Trp
            20                  25                  30

Arg Lys Pro Arg Gly Ile Asp Cys Arg Val Arg Arg Arg Tyr Lys Gly
        35                  40                  45

Thr Asn Leu Met Pro Ser Ile Gly Tyr Gly Ser Asn Lys Lys Thr Lys
    50                  55                  60

Phe Leu Leu Pro Asn Asn Lys Tyr Lys Tyr Val Val Lys Asn Val Lys
65                  70                  75                  80

Glu Met Glu Pro Leu Ile Met Asn His Thr Lys Tyr Cys Val Gln Ile
                85                  90                  95

Ala His Asn Val Ser Ser Lys Lys Arg Lys Gln Ile Ile Glu Arg Ala
            100                 105                 110

Lys Gln Met Asn Val Ser Val Ile Asn Ala Lys Ala Arg Leu Gln Lys
        115                 120                 125

Thr Glu Glu
    130

<210> SEQ ID NO 679
<211> LENGTH: 150
<212> TYPE: PRT
<213> ORGANISM: Plasmodium vivax

<400> SEQUENCE: 679

Met Ala Gln Arg Val His Tyr Arg Arg His Asn His Tyr Asn Thr Lys
1 5 10 15

Ser Asn Lys Val Arg Pro Val Arg Thr Pro Gly Gly Lys Leu Thr Ile
20 25 30

His Val Val Lys Lys Lys Ala Gly Lys Pro Lys Cys Ala Asp Cys Lys
35 40 45

Thr Ala Ile Gln Gly Val Lys Ala Leu Arg Pro Ala Asp Asn Tyr Arg
50 55 60

Ala Arg Arg Lys Asn Arg Thr Val Ala Arg Ala Tyr Gly Gly Ser Ile
65 70 75 80

Cys Ala Arg Cys Ile Arg Glu Arg Ile Met Arg Ala Phe Leu Phe Glu
85 90 95

Glu Gln Lys Cys Val Arg Gln Val Leu Lys Glu Lys Lys Lys Gln Glu
100 105 110

Lys Lys Val Lys Lys Val Lys Lys Glu Lys Lys Lys Val Asn Ala Lys
115 120 125

Glu Val Lys Lys Thr Ala Thr Asp Asn Lys Lys Ala Lys Lys Val Ala
130 135 140

Asp Lys Lys Lys Gly Lys
145 150

<210> SEQ ID NO 680
<211> LENGTH: 124
<212> TYPE: PRT
<213> ORGANISM: Plasmodium vivax

<400> SEQUENCE: 680

Met Ser Asn Val Lys Ala Tyr Glu Leu Arg Thr Leu Lys Lys Lys Glu
1 5 10 15

Leu Leu Asp Lys Leu Asp Glu Leu Lys Lys Glu Leu Ser Gly Leu Arg
20 25 30

Ile Ser Lys Ala Leu Gly Asn Ser Ala Lys Asn Ser Lys Ile His Gly
35 40 45

Val Arg Lys Asn Val Ala Arg Val Leu Thr Val Tyr Asn Gln Lys Arg
50 55 60

Lys Met Glu Leu Arg Gln Leu Tyr Lys Asn Lys Lys Phe Lys Pro Tyr
65 70 75 80

Asn Leu Arg Lys Lys Leu Thr Lys Asn Lys Arg Leu Gln Leu Ser Pro
85 90 95

Lys Gln Lys Ala Ala Met Thr Leu Arg Gln Lys Lys Lys Val Gln Asn
100 105 110

Phe Pro Gln Arg Lys Tyr Leu Val Val His Lys Glu
115 120

<210> SEQ ID NO 681
<211> LENGTH: 140
<212> TYPE: PRT
<213> ORGANISM: Plasmodium vivax

<400> SEQUENCE: 681

```
Met Glu Asn Val Lys Val Lys Lys Glu Gln Thr Glu Val Ser Gln Lys
1               5                   10                  15

Lys Lys Val Val Lys Lys Val Leu Lys Lys Asn Lys Lys Thr Ser Asn
            20                  25                  30

Lys Lys Leu Gln Ala Val Arg Leu Tyr Glu Lys Gly Val Ile Leu Gly
        35                  40                  45

Tyr Lys Arg Ser Gln Arg Asn Gln Asp Pro Asn Phe Thr Leu Ile Ser
    50                  55                  60

Ile Lys Asn Val Asn Thr Lys Lys His Ala Gln Phe Tyr Val Gly Lys
65                  70                  75                  80

Arg Val Ala Tyr Val Tyr Arg Thr Thr Lys His His Asp Gly Val Lys
                85                  90                  95

Ile Lys Cys Ile Trp Gly Lys Val Cys Arg Thr His Gly Asn Ser Gly
            100                 105                 110

Val Ile Arg Ala Lys Phe Lys Thr His Ile Pro Pro Lys Ala Phe Gly
        115                 120                 125

Asp Arg Val Arg Ile Leu Met Tyr Pro Ser Asn Ile
    130                 135                 140


<210> SEQ ID NO 682
<211> LENGTH: 112
<212> TYPE: PRT
<213> ORGANISM: Plasmodium vivax

<400> SEQUENCE: 682

Met Gly Arg Lys Ser Thr Ile Lys Pro Ala Thr Gly Ile Ala Val Gly
1               5                   10                  15

Phe Asn Ser Gly His Val Val Thr Lys Arg Asn Leu Lys Leu His Lys
            20                  25                  30

Lys Lys Lys Pro Phe Ser Lys Arg Lys Glu Leu Ile Lys Asp Val Val
        35                  40                  45

Arg Glu Ile Thr Gly Phe Ser Pro Tyr Glu Lys Arg Ile Ile Glu Leu
    50                  55                  60

Ile Lys Ile Gly Thr Ser Ala Ser Thr Lys Arg Ser Leu Lys Tyr Ala
65                  70                  75                  80

Lys Lys Lys Leu Gly Thr His Lys Arg Gly Lys Ala Lys Arg Glu Glu
                85                  90                  95

Ile Gln Lys Val Val Ile Leu Gln Arg Arg Lys Ala Ala Glu Lys His
            100                 105                 110


<210> SEQ ID NO 683
<211> LENGTH: 96
<212> TYPE: PRT
<213> ORGANISM: Plasmodium vivax

<400> SEQUENCE: 683

Met Ser Arg Arg Thr Lys Lys Val Gly Leu Thr Gly Lys Tyr Gly Thr
1               5                   10                  15

Arg Tyr Gly Ser Ser Leu Arg Lys Gln Ile Lys Lys Ile Glu Leu Met
            20                  25                  30

Gln His Ala Lys Tyr Leu Cys Thr Phe Cys Gly Lys Thr Ala Thr Lys
        35                  40                  45

Arg Thr Cys Val Gly Ile Trp Lys Cys Lys Lys Cys Lys Arg Lys Val
    50                  55                  60

Cys Gly Gly Ala Trp Ser Leu Thr Thr Pro Ala Ala Val Ala Ala Lys
65                  70                  75                  80
```

Ser Thr Ile Ile Arg Leu Arg Lys Gln Lys Glu Glu Ala Gln Lys Ser
85 90 95

<210> SEQ ID NO 684
<211> LENGTH: 96
<212> TYPE: PRT
<213> ORGANISM: Plasmodium vivax

<400> SEQUENCE: 684

Met Ser Arg Arg Thr Lys Lys Val Gly Leu Thr Gly Lys Tyr Gly Thr
1 5 10 15

Arg Tyr Gly Ser Ser Leu Arg Lys Gln Ile Lys Lys Ile Glu Leu Met
20 25 30

Gln His Ala Lys Tyr Leu Cys Thr Phe Cys Gly Lys Thr Ala Thr Lys
35 40 45

Arg Thr Cys Val Gly Ile Trp Lys Cys Lys Lys Cys Lys Arg Lys Val
50 55 60

Cys Gly Gly Ala Trp Ser Leu Thr Thr Pro Ala Ala Val Ala Ala Lys
65 70 75 80

Ser Thr Ile Ile Arg Leu Arg Lys Gln Lys Glu Glu Ala Gln Lys Ser
85 90 95

<210> SEQ ID NO 685
<211> LENGTH: 87
<212> TYPE: PRT
<213> ORGANISM: Plasmodium vivax

<400> SEQUENCE: 685

Met Pro Lys Gln Ile Thr Asp Ile Arg Lys Phe Leu Lys Ile Ser Arg
1 5 10 15

Lys Pro Asp Thr Thr Ala Val Ile Ile Met Lys Lys Lys Ser Lys Thr
20 25 30

Lys Lys Asn Thr Val Ile Thr Lys Leu Lys Leu Arg Thr Lys Lys Tyr
35 40 45

Leu Tyr Thr Met Val Phe Ala Asp Arg Lys Lys Ala Glu Arg Ile Glu
50 55 60

Asn Ser Leu Leu Pro Ser Leu Lys Arg Ile Tyr Tyr Pro Gln Lys Lys
65 70 75 80

Val Gly Lys Thr Val Lys Lys
85

<210> SEQ ID NO 686
<211> LENGTH: 51
<212> TYPE: PRT
<213> ORGANISM: Plasmodium vivax

<400> SEQUENCE: 686

Met Gly Ser Ile Lys Arg Phe Arg Leu Lys Gln Arg Leu Gly Lys Cys
1 5 10 15

Arg Arg Gln Asn Arg Pro Val Pro His Trp Tyr Arg Leu Lys Lys Asp
20 25 30

Thr Lys Ile Arg Tyr Asn Thr Lys Arg Arg His Trp Arg Arg Thr Lys
35 40 45

Leu Gly Leu
50

<210> SEQ ID NO 687
<211> LENGTH: 411
<212> TYPE: PRT

<213> ORGANISM: Plasmodium vivax

<400> SEQUENCE: 687

Met Ala Thr Ile Arg Pro Val Ala Asn Val Tyr Ser Thr Asn Gly Lys
1 5 10 15

Asn Val Val Gly Glu Val Glu Ile Pro Val Val Phe Gln Thr Pro Ile
20 25 30

Arg Asn Asp Leu Ile Gln Ser Val Tyr Thr Asn Met Ser Lys Asn Arg
35 40 45

Arg His Pro Tyr Ala Val Lys Leu Gly Ala Gly Tyr Glu Thr Ser Ala
50 55 60

Glu Ser Trp Gly Thr Gly Arg Ala Val Ala Arg Ile Pro Arg Val Pro
65 70 75 80

Gly Gly Gly Thr His Arg Ala Gly Gln Gly Ala Phe Gly Asn Met Cys
85 90 95

Arg Gly Gly Gly Met Phe Asn Pro Thr Lys Ile Trp Arg Arg Trp Gly
100 105 110

Arg Lys Val Asn Leu Lys Glu Lys Arg Tyr Ala Val Cys Ser Ser Ile
115 120 125

Ala Ala Ser Gly Val Thr Ser Leu Val Leu Ala Arg Gly His Arg Ile
130 135 140

Ser His Leu Lys Glu Val Pro Leu Val Val Ser Asn Asp Ile Glu Ser
145 150 155 160

Leu Ser Lys Thr Lys Glu Ala Val Asn Phe Leu Val Ser Leu Gly Leu
165 170 175

Lys Asp Glu Val Asn Arg Leu Val Lys Ser Lys Lys Ile Arg Ala Gly
180 185 190

Lys Gly Lys Met Arg Asn Arg Lys Tyr Lys Ile Arg Asn Gly Pro Leu
195 200 205

Ile Ile Tyr Glu Asn Asp Asn Gly Val Lys Lys Ala Phe Arg Asn Ile
210 215 220

Pro Gly Val Asp Leu Cys Lys Val Thr Lys Leu Asn Leu Leu Lys Leu
225 230 235 240

Ala Pro Gly Gly Ser Ile Gly Arg Leu Cys Ile Trp Ser Glu Ser Ala
245 250 255

Phe Lys Lys Leu Asp Val Ile Tyr Gly Lys Ile His Glu Lys Lys Val
260 265 270

Thr Lys Lys Asn Tyr Ile Leu Pro Lys Ser Ile Val His Asn Pro Asp
275 280 285

Ile Tyr Arg Ile Ile His Ser Asp Lys Val Gln Ala Ser Leu Leu Ala
290 295 300

Lys Lys Lys Pro Cys Lys Lys Arg Leu Gln Asn Lys Asn Ser Leu Thr
305 310 315 320

Asn Phe Ala Val Arg Cys Arg Leu Asn Pro Ala Tyr Lys Leu Leu Arg
325 330 335

Ser Leu Ala Val Leu Arg Met Arg Lys Ser Ile Leu Glu Lys Ser Lys
340 345 350

Asn Lys Lys Glu Lys Arg Val Gln Lys Gln Ile Gln Lys Lys Glu Leu
355 360 365

Gln Lys Ile Asn His Asp Tyr Tyr Lys Gly Val Ala Lys Ala Val Lys
370 375 380

Lys Lys Lys Lys Arg Glu Glu Lys Lys Ala Lys Ser Lys Lys Thr Ala
385 390 395 400

Asn Gln Ala Val Ile Asn Val Ala Ala Glu Glu
405 410

<210> SEQ ID NO 688
<211> LENGTH: 39
<212> TYPE: PRT
<213> ORGANISM: Plasmodium vivax

<400> SEQUENCE: 688

Met Ala His Gly Ala Ser Arg Tyr Lys Lys Ser Arg Ala Lys Met Arg
1 5 10 15

Trp Lys Trp Lys Lys Lys Arg Thr Arg Arg Leu Gln Lys Lys Arg Arg
20 25 30

Lys Met Arg Gln Arg Ser Arg
35

<210> SEQ ID NO 689
<211> LENGTH: 104
<212> TYPE: PRT
<213> ORGANISM: Plasmodium vivax

<400> SEQUENCE: 689

Met Val Asn Val Pro Lys Thr Arg Lys Thr Tyr Cys Ser Asn Lys Cys
1 5 10 15

Lys Lys His Thr Met His Lys Val Ser Gln Tyr Lys Lys Gly Lys Glu
20 25 30

Arg Leu Ser Ser Leu Gly Arg Arg Arg Tyr Asp Met Lys Gln Lys Gly
35 40 45

Phe Gly Gly Gln Thr Lys Pro Val Phe Lys Lys Lys Ala Lys Thr Thr
50 55 60

Lys Lys Ile Val Leu Lys Leu Glu Cys Thr Lys Cys Lys Lys Lys Arg
65 70 75 80

Phe Gln Thr Met Lys Arg Cys Lys Thr Phe Glu Met Gly Ala Asp Lys
85 90 95

Lys Lys Lys Gly Gly Ala Val Tyr
100

<210> SEQ ID NO 690
<211> LENGTH: 294
<212> TYPE: PRT
<213> ORGANISM: Plasmodium vivax

<400> SEQUENCE: 690

Met Ala Tyr Val Lys Val Val Lys Asn Lys Ala Tyr Phe Lys Arg Tyr
1 5 10 15

Gln Val Lys Tyr Arg Arg Arg Arg Glu Gly Lys Thr Asp Tyr Arg Ala
20 25 30

Arg Lys Ala Leu Ile Leu Gln Asp Lys Asn Lys Tyr Asn Ala Gln Lys
35 40 45

Leu Arg Phe Val Val Arg Lys Thr Asn Ser Gln Val Ile Cys Gln Ile
50 55 60

Ala Cys Ala His Ile Glu Gly Asp Lys Ile Leu Ala Glu Ala Lys Ser
65 70 75 80

Lys Glu Leu Ile Arg Tyr Gly Ile Pro Val Gly Leu Lys Asn Tyr Ala
85 90 95

Ala Ala Tyr Ala Thr Gly Leu Leu Cys Ala Arg Arg Phe Leu Lys Ser
100 105 110

Leu Asn Leu Asp Thr Gln Phe Leu Gly Val Glu Lys Val Thr Gly Glu

```
        115                 120                 125

Ile Glu Asn Asn Glu Asp Lys Glu Asp Glu Glu Gly Arg Lys Pro Ile
    130                 135                 140

Lys Ala Phe Leu Asp Val Gly Ile Thr Arg Thr Thr Thr Gly Asn Arg
145                 150                 155                 160

Val Phe Ala Ala Leu Lys Gly Ala Cys Asp Gly Gly Leu Asn Ile Pro
                165                 170                 175

His Gly Asn Asn Arg Phe Pro Gly Ser Lys Asn Glu Phe Asn Pro Glu
            180                 185                 190

Gln Leu Arg Lys Asn Ile Leu Gly Ile His Val Ala Glu Tyr Met Lys
        195                 200                 205

Thr Leu Gln Glu Glu Asp Asn Asp Lys Tyr Lys Thr His Phe Asn Asp
    210                 215                 220

Tyr Leu Lys Asn Asn Ile Gly Ala Asp Asp Ile Glu Gln Met Tyr Leu
225                 230                 235                 240

Asn Ala His Glu Lys Ile Arg Gln Asn Pro Glu Lys Glu Ser Lys Asp
                245                 250                 255

Thr Lys Asn Val Lys Lys Phe Val Ser Lys His Glu Lys Pro Lys Lys
            260                 265                 270

Leu Asn Ala Lys Leu Arg Lys Lys Arg Val Lys Glu Lys Leu Ala Leu
        275                 280                 285

Tyr Val Glu Lys Leu Gln
    290


<210> SEQ ID NO 691
<211> LENGTH: 190
<212> TYPE: PRT
<213> ORGANISM: Plasmodium vivax

<400> SEQUENCE: 691

Met Lys Thr Ile Val Ser Thr Gln Lys Val Leu Ile Pro Glu Gly Val
1               5                   10                  15

Lys Val Ala Ile Asn Ala Arg Lys Val Thr Val Ser Gly Lys Tyr Gly
            20                  25                  30

Thr Leu Arg Arg Ser Phe Arg His Leu Pro Ile Asp Ile Arg Leu Asn
        35                  40                  45

Lys Leu Lys Lys Tyr Ile Lys Val Val Met Trp Phe Gly Val Pro Asp
    50                  55                  60

Ser Leu Ala Cys Ile Arg Thr Val Cys Thr His Leu Lys Asn Met Phe
65                  70                  75                  80

Thr Gly Val Thr Lys Lys Phe Leu Tyr Lys Met Arg Leu Val His Ala
                85                  90                  95

His Phe Pro Ile Asn Ser Asn Ile Val Asp Asn Asn Thr Arg Ile Glu
            100                 105                 110

Ile Arg Asn Tyr Leu Gly Glu Lys Ser Val Arg Phe Val Lys Ala Leu
        115                 120                 125

Pro Gly Val Val Ile Glu Lys Ser Pro Asn Val Lys Asp Glu Ile Tyr
    130                 135                 140

Val Ser Gly Ala Asp Ile Glu Asn Val Ser Leu Thr Ala Ala Leu Ile
145                 150                 155                 160

His Gln Ser Val Leu Cys Arg Asn Lys Asp Ile Arg Lys Phe Leu Asp
                165                 170                 175

Gly Ile Tyr Val Ser Glu Val Thr Thr Val Glu Lys Asp Glu
            180                 185                 190
```

<210> SEQ ID NO 692
<211> LENGTH: 257
<212> TYPE: PRT
<213> ORGANISM: Plasmodium vivax

<400> SEQUENCE: 692

Met Ala Asp Arg Tyr Glu Asn Gln Val Glu Asn Glu Leu Gly Lys Ser
1 5 10 15

Met Thr Ser Leu Arg Ala Lys Lys Val Asn Lys Asn Lys Glu Leu Lys
20 25 30

Gln Ala Ala Ala Lys Lys Ile Lys Thr Leu Lys Leu Ile Asn Lys Lys
35 40 45

Lys Arg Asn Asp Leu Arg Gln Arg Thr Leu Arg Tyr Glu Glu Glu Tyr
50 55 60

Glu Ser Glu Arg Lys Lys Ile Ile Glu Leu Lys Arg Glu Ala Arg Lys
65 70 75 80

Asn Asn Cys Phe Tyr Arg Glu Ala Glu Lys Lys Val Val Phe Val Ile
85 90 95

Arg Leu Lys Gly Val Asn Lys Leu Pro Pro Lys Val Arg Ser Val Phe
100 105 110

Arg Leu Leu Arg Leu Leu Gln Val His Asn Gly Val Phe Val Lys Val
115 120 125

Asn Lys Ala Thr Lys Glu Met Leu Lys Ile Val Glu Pro Tyr Val Thr
130 135 140

Tyr Gly Tyr Pro Thr Leu Ser Thr Val Arg Lys Leu Leu Tyr Lys Arg
145 150 155 160

Gly Tyr Val Arg Val Gly Lys Val Arg Arg Tyr Ala Arg Lys Lys Ile
165 170 175

Gln Asp Asn Ala Asp Ile Ser Lys His Leu Gly Lys Tyr Asn Val His
180 185 190

Gly Ile Glu Asp Met Val Tyr Gln Leu Tyr Thr Cys Gly Pro Val Phe
195 200 205

Lys Lys Val Asn Asn Phe Leu Trp Ala Phe Lys Leu Lys Pro Pro Arg
210 215 220

Lys Gly Phe Lys Ala Lys Arg His Ala Phe Asn Glu Pro Arg Pro Gly
225 230 235 240

Asp Trp Gly Asn Arg Glu Ala His Ile Asn Glu Leu Ile Asn Arg Met
245 250 255

Ile

<210> SEQ ID NO 693
<211> LENGTH: 252
<212> TYPE: PRT
<213> ORGANISM: Plasmodium vivax

<400> SEQUENCE: 693

Met Asp Lys Lys Lys Ser Lys Lys Glu Pro Ile Lys Lys Lys Glu Tyr
1 5 10 15

Asn Lys Val Lys His Val Lys Phe Arg Arg Ile Lys Lys Ile Asn Phe
20 25 30

Lys Glu Glu Lys Ile Arg Thr Asp Lys Arg Lys Ile Asn Ile Glu Lys
35 40 45

Ile Arg Lys Arg Gln Lys Lys Phe Asp Thr Leu Tyr Lys Lys Lys Glu
50 55 60

Tyr Thr Lys Lys Leu Asn Gly Gln Lys Asn Glu Tyr Met Asn Leu Lys

```
65                  70                  75                  80

Asn Glu Leu Val Asn Glu Lys Phe Asp Thr Glu Arg Gln Cys Val Phe
                85                  90                  95

Ile Ile Arg Asn Asp Val Asp Cys Ile His Asn Glu Ser Lys Leu Leu
            100                 105                 110

Leu Lys Glu Leu Lys Leu Ile Asn Lys Tyr Asp Gly Ile Ile Leu Ile
        115                 120                 125

Asn Thr Glu Glu Asn Met Lys Lys Leu Tyr Val Ile Lys Pro Tyr Ile
    130                 135                 140

Cys Tyr Gly Tyr Ile Lys Lys Tyr Asn Phe Tyr Asn Leu Met Glu Lys
145                 150                 155                 160

Arg Leu Tyr Ile Arg Asp Gln Asp Gln Ile Lys Arg Cys Asp Ser Asn
                165                 170                 175

Lys Met Ile Glu Gln Ile Phe Ser Lys Glu Gly Ile Tyr Ser Phe Arg
            180                 185                 190

Ser Phe Cys Asp Tyr Ile Phe Glu Cys Lys Asp Asn Ala Asp Ile Ile
        195                 200                 205

Thr Lys Asn Tyr Ile Tyr Pro Phe Asp Phe Ser Phe Leu Asn Thr Lys
    210                 215                 220

Ile Thr Phe Asp Phe Leu Gln Phe Lys Gln Asp Phe Lys Gly Phe Leu
225                 230                 235                 240

Lys Asn Glu Ile Asn Glu Ile Leu Glu Lys Ile Ile
                245                 250


<210> SEQ ID NO 694
<211> LENGTH: 283
<212> TYPE: PRT
<213> ORGANISM: Plasmodium vivax

<400> SEQUENCE: 694

Met Ala Lys Asp Lys Lys Gln Gln Lys Lys Pro Ser Lys Lys Thr Pro
1               5                   10                  15

Ala Pro Cys Pro Leu Ser Thr Lys Val Thr Val Lys Lys Glu Ile Lys
            20                  25                  30

Lys Glu Lys Lys Thr Gly Ile Lys Asp Asn Pro Leu Ile Phe Glu Lys
        35                  40                  45

Lys Lys Arg Ser Asn Ile Ile Gly Val Gly Val Arg Pro Lys Lys Asp
    50                  55                  60

Leu Ser Lys Tyr Val Lys Trp Pro Arg Tyr Ile Arg Ile Gln Arg Lys
65                  70                  75                  80

Lys Lys Ile Leu Leu Gln Arg Leu Lys Val Pro Pro Ser Ile Asn Gln
                85                  90                  95

Phe Asn His Thr Leu Pro Lys Ser Gln Thr Gln Asp Leu Leu Asn Phe
            100                 105                 110

Leu Lys Ala Tyr Lys Pro Glu Ser Lys Thr Asp Lys Lys Gln Arg Leu
        115                 120                 125

Leu Asn Lys Ala Lys Glu Ala Leu Asn Lys Asn Ile Thr Lys Asp Lys
    130                 135                 140

Lys Pro Leu Phe Leu Lys Tyr Gly Ile Asn His Ile Thr Lys Leu Val
145                 150                 155                 160

Glu Asn Lys Lys Ala Asn Leu Val Val Ile Ala Asn Asp Val Ser Pro
                165                 170                 175

Ile Glu Leu Val Leu Phe Leu Pro Ala Leu Cys Arg Leu Lys Glu Val
            180                 185                 190
```

```
Pro Tyr Cys Ile Val Lys Asp Lys Ala Thr Leu Gly Lys Leu Val His
        195                 200                 205

Lys Lys Thr Ala Thr Ala Val Cys Leu Glu Ser Val Lys Lys Glu Asp
    210                 215                 220

Gln Glu Lys Leu Asp Tyr Phe Ala Lys Val Cys Lys Glu Asn Phe Asn
225                 230                 235                 240

Asp Asn Val Asp Leu Arg Arg Lys Trp Gly Gly Gln Lys Met Ser Ala
                245                 250                 255

Lys Ser Met Leu Leu Lys Lys Met Lys Asp Lys Ala Arg Lys Ile Glu
            260                 265                 270

Glu Ala Lys Lys Lys Glu Ile Ser Ala Lys Leu
        275                 280


<210> SEQ ID NO 695
<211> LENGTH: 236
<212> TYPE: PRT
<213> ORGANISM: Plasmodium vivax

<400> SEQUENCE: 695

Met Arg Glu Asp Ile Asn Lys Leu Lys Lys Asn Asn Asn Asp Ser Asn
1               5                   10                  15

Leu Ser Asn Asp Glu Glu Glu His Ser Val Asp Asp Glu Gly Ser Ile
            20                  25                  30

Asn Asn Asp Asn Asp Asn Asn Asp Asn Asn Asp Asn Lys Lys Glu Lys
        35                  40                  45

Lys Lys Gly Tyr Glu Lys Ile Ile Glu Asp Ile Lys Glu Glu Asn Lys
    50                  55                  60

Asn Ser Tyr Val Ser Lys Ile Ser Glu Pro Met Leu Lys Lys Lys Tyr
65                  70                  75                  80

Leu Lys Asn Val Leu Lys Ile Leu Asp Tyr Val Tyr Tyr Ala Lys Leu
                85                  90                  95

Asn Ser Ser Gln Ile Leu Lys Thr Asn Asn Ser Leu Asp Glu Glu Lys
            100                 105                 110

Gln Lys Leu Leu Lys Lys Lys Leu Ile Val Ile Gly Leu Thr Gln Val
        115                 120                 125

Ile Lys Cys Ile Arg Lys Gly Tyr Ser Gly Ile Val Leu Ile Ala Ile
    130                 135                 140

Asp Val Phe Pro Ile Asn Ile Ile Cys His Leu Pro Ser Phe Cys Glu
145                 150                 155                 160

Gln Tyr Lys Ile Pro Tyr Thr Phe Val Thr Thr Lys Asn Lys Leu Ala
                165                 170                 175

His Leu Cys Lys Leu Lys Arg Ser Ile Thr Cys Leu Phe Ile Leu Lys
            180                 185                 190

Pro Asp Ile His Ile Leu Thr Phe Glu Gln Thr Ile Asn Gln His Ser
        195                 200                 205

Pro Lys Lys Lys Ile His Asn Tyr Gln Lys Leu Tyr Asp Lys Leu Ile
    210                 215                 220

Ser Gly Val Lys Lys Asn His Pro Phe Phe Gln Ser
225                 230                 235


<210> SEQ ID NO 696
<211> LENGTH: 204
<212> TYPE: PRT
<213> ORGANISM: Plasmodium vivax

<400> SEQUENCE: 696
```

Met Arg Ile Glu Lys Cys Trp Tyr Cys Ser Gly Asn Ile Tyr Pro Gly
1 5 10 15

His Gly Ile Phe Phe Ile Arg Asn Asp Cys Asn Val Phe Lys Phe Cys
20 25 30

Arg Ser Lys Cys His Lys His Phe Lys Ala Lys His Asn Pro Arg Lys
35 40 45

Val Lys Trp Thr Lys Ile Tyr Arg Lys Glu Arg Asn Lys Glu Leu Ser
50 55 60

Tyr Asp Lys Thr Phe Glu Phe Glu Lys Ile Arg Asn Glu Pro Ile Lys
65 70 75 80

Tyr Asp Arg Asp Ile Tyr Ile Lys Thr Ile Asn Ala Ile Lys Lys Ile
85 90 95

Asp Thr Ile Lys Glu Lys Arg Lys Met Arg Phe Tyr Lys Asn Arg Ile
100 105 110

Ile Glu Thr Ser Asp Lys Asn Ile Asn Leu Ser Leu Asn Tyr Ile Lys
115 120 125

Lys Asn Pro Leu Leu Leu Lys Asn Thr Glu Tyr Glu Asn Val Ile Gln
130 135 140

Glu Leu Thr Leu Asn Lys Gln Glu Arg Asp Asp Thr Leu Ile Ile Lys
145 150 155 160

Asn Thr Phe Glu Asp Asp His Ile Ile Phe Thr Lys Asn Asp Gln Asp
165 170 175

Ile Lys Tyr Lys Ala Asp Ile Ser Thr Ile Ser Asp Lys Gln Lys Phe
180 185 190

Asn Val Glu Lys Asn Asn Lys Asn Leu Ile Leu Glu
195 200

<210> SEQ ID NO 697
<211> LENGTH: 179
<212> TYPE: PRT
<213> ORGANISM: Plasmodium vivax

<400> SEQUENCE: 697

Met Arg Pro Leu Asn Asp Gln Glu Thr Met Ile Val Phe Lys Lys Leu
1 5 10 15

Ser Lys Phe Val Gly Asn Asn Leu Leu Thr Met Leu Ser Tyr Ser Asn
20 25 30

Glu Glu Tyr Ile Leu Arg Leu His Arg Ser Asn Val Tyr Phe Val Arg
35 40 45

Ala Asp Val Ala Lys Gln Ala Glu Ser Leu Asn Lys Asn Ser Leu Ile
50 55 60

Ser Met Gly Ile Cys Leu Gly Lys Phe Thr Lys Thr Asn Asn Phe Phe
65 70 75 80

Ile Lys Ile Thr Ala Ile Ser Phe Leu Asn Gln Phe Cys Ile His Lys
85 90 95

Ile Trp Leu Lys Glu Ser Gly Glu Lys Asn Phe Leu Phe Gly Asn Asn
100 105 110

Val Leu Lys Ser His Leu Leu Lys Ile Ser Asp Asn Ile Lys Lys Gly
115 120 125

Asp Gly Ile Met Val Leu Ser Met Asn Asp Asn Pro Ile Gly Phe Gly
130 135 140

Ile Ser Val Arg Asn Thr Gln Asp Ile Lys Ile Leu Asn Val Thr Asp
145 150 155 160

Thr Val Leu Ile His Gln Ser Asp Ile Gly Glu Tyr Leu Arg Cys Glu
165 170 175

Thr Ala Ile

<210> SEQ ID NO 698
<211> LENGTH: 661
<212> TYPE: PRT
<213> ORGANISM: Plasmodium vivax

<400> SEQUENCE: 698

Met Ile Pro Asp Asn Asn Glu Asn Asn Asn Asn Leu Tyr Phe Leu Ala
1               5                   10                  15

Phe Ser Lys Asn Lys Val Thr Ile Tyr Glu Tyr Asp Val Asp Leu Ser
            20                  25                  30

Lys Asn Ile Val Asp Asp Ile Asn Asp Glu Ile Lys Arg Cys Glu Glu
        35                  40                  45

Glu Asp Glu Lys Asn Lys Ile Asn Glu Asn Thr Val Pro Met Thr Asn
    50                  55                  60

Asp Glu Lys Lys Val Asp Met Asn His Ile Arg Asn Asn Asn Ile Ile
65                  70                  75                  80

Asn Asn Asn Thr Asn Asn Thr Asn Gln Ile Lys Lys Ser Thr Asn Lys
                85                  90                  95

Phe Asn Asn Asp Phe Val Leu Asn Arg Gly Ile Lys Ile Tyr Lys Glu
            100                 105                 110

Tyr Asp Asp Val Glu Leu Ala Thr Cys Thr Asn Asp Tyr Lys Lys Ile
        115                 120                 125

Ile Leu Val Arg Lys Ser Asp Leu Asn Val Ala Glu Ile Ile Asp Ile
    130                 135                 140

Lys Ser Glu Asn Lys Asn Val Thr Cys Ile Lys Thr Lys Thr Gln Ile
145                 150                 155                 160

Lys Arg Ile Ile Thr Ser Pro Arg Asp Asn Tyr Ile Val Leu His Cys
                165                 170                 175

Gln Tyr Lys Pro Asp Ile Thr Asn Thr Asn Leu Tyr Val Tyr Lys Leu
            180                 185                 190

Asn Val Lys Ser Ser Lys Lys Lys Lys Lys Lys Asp Lys Lys Asn Ser
        195                 200                 205

Glu Cys Glu Asn Ile Lys Gly Glu Glu Asn Ser Val Gly Lys Glu Asn
    210                 215                 220

Asp Asn Tyr Glu Glu Glu Lys Lys Asn Ile Asn Met Asn Asn Asn Asn
225                 230                 235                 240

Val Pro Ile His Asn Asn Asn Asn Asn Ser Asp Asn Asn Glu Ser Thr
                245                 250                 255

Asn Asp Asn Ile Ile Tyr Asn Glu Asn Leu Ile Ile Glu Leu Thr Leu
            260                 265                 270

Lys Ser Tyr Ser Asn Lys Asn Trp Pro Phe Phe Lys Trp Ser Asp Ser
        275                 280                 285

Glu Ser Ile Cys Thr Cys Leu Ile Asn Asn Gln Val Tyr Ile Tyr Lys
    290                 295                 300

Asp Asn Asn Phe Asn Thr Thr Val Asn Lys Leu Lys Leu Asp Asn Ile
305                 310                 315                 320

Glu Phe Phe Asp Ile Ser Pro Glu Leu Asn Asn Lys Lys Gly Ile Leu
                325                 330                 335

Ile Ala Thr Tyr Glu Gln Gly Ser Lys Gly Asn Pro Ser Ile Phe Lys
            340                 345                 350

Ile Phe His Ile Asp Asn Leu Asn Lys His Ile Tyr Ser Lys Asn Phe
        355                 360                 365

Phe Asn Ser Asp Glu Ile Lys Leu Lys Trp Asn Lys Asn Gly Ser Ser
370 375 380

Leu Leu Leu Gln Ile His Thr Gln Val Asp Lys Glu Lys Gln Ser Tyr
385 390 395 400

Tyr Gly Ser Ser Asn Leu Tyr Phe Ile Asp Thr Val Thr Leu Lys Asp
405 410 415

Val Asn Val Met Thr Asn Lys Gly Leu Ile Tyr Asp Thr Ile Trp Ser
420 425 430

Asn Asn Gln Asn Lys Phe Tyr Val Cys Lys Gly Glu Ile Pro Ala Glu
435 440 445

Ile Val Leu His Asp Lys Asn Gly Asn Val Ser His Ser Tyr Gly Arg
450 455 460

His Lys Phe Asn Thr Leu Lys Leu Asn Tyr Asn Glu Lys Leu Leu Leu
465 470 475 480

Thr Gly Gly Phe Gly Asn Leu Ser Gly Asp Ile Ser Ile Trp Asn Thr
485 490 495

Ser Thr Lys Lys Glu Ile Thr Lys Thr Lys Ser Ser Cys Ala Val Ile
500 505 510

Cys Glu Phe Phe Asn Asp Gly Lys His Phe Leu Thr Ala Thr Thr His
515 520 525

Pro Arg Leu Arg Val Asp Asn Asn Leu Lys Ile Phe Lys Tyr Asn Gly
530 535 540

Leu Ile Val Ser Arg Ile Asn Phe Glu Glu Leu Tyr Asn Val Ile Ile
545 550 555 560

Leu Pro Phe Asn Lys Ile Lys Phe Gln Gln Thr Glu Glu Pro Val Asp
565 570 575

Ile Asn Leu Glu His Thr Thr Leu Gln Pro Tyr Ile Asn Lys Gln Leu
580 585 590

Gly Ile Asp Ser Lys Lys Thr Gly Ile Tyr Arg Ala Pro Arg Ser Thr
595 600 605

Gly Leu Val Asn Leu Asn Gly Tyr Leu Ser Ser Lys Leu Pro Asp Arg
610 615 620

Glu Lys Ser Ser Leu Pro Pro Gly Cys Asn Phe Val Asn Glu Asn Lys
625 630 635 640

Asn Tyr Asn Lys Lys Lys Lys Lys Lys Arg Ser Ser Lys Ser Lys Gln
645 650 655

Lys Arg Glu Thr Phe
660

<210> SEQ ID NO 699
<211> LENGTH: 1377
<212> TYPE: PRT
<213> ORGANISM: Plasmodium vivax

<400> SEQUENCE: 699

Met Gln Thr Phe Gln Lys Pro Glu Asn Ala Leu Lys Arg Ala Glu Glu
1 5 10 15

Leu Gln Phe Ile Gly Gln Asn Glu Asp Ala Leu Gln Ile Leu His Ser
20 25 30

Ala Ile Gly His Arg Thr Phe Arg Leu Gln Gly Trp His Ile Leu Gln
35 40 45

Glu Gln Ile Met Leu Arg Tyr Ile Glu Phe Cys Leu Tyr Leu Glu Lys
50 55 60

Leu Ser Leu Val Lys Asp Gly Leu His Gln Tyr Arg Ile Ile Cys Gln

-continued

```
65                  70                  75                  80

His Gly Asn Ile Ala Ser Leu Gly Lys Val Ile Thr Asp Phe Arg Asp
                85                  90                  95

Lys Ala Glu Glu Lys Val Arg Leu Ala Lys Glu Asn Val Val Leu Asn
            100                 105                 110

Lys Glu Lys Ile Glu Gln Glu Glu Ser Asn Val Asp Val Thr Glu Lys
        115                 120                 125

Ile Leu Met Ala Ser Leu Asp Ile Glu Ile Thr Gly Lys His Glu Arg
    130                 135                 140

Lys Leu Gln Asn Ala Tyr Arg Ile Cys Met Glu Thr Tyr Lys Met Ile
145                 150                 155                 160

Leu Glu Ile Leu Arg Ala Thr Pro Lys Leu Glu Lys Ala Tyr His Glu
                165                 170                 175

Thr Ala Lys Lys Ala Ile Leu Phe Cys Lys Glu Asn Lys Arg Val Thr
            180                 185                 190

Glu Phe Lys Lys Leu Ser Asp Leu Leu Arg Asn His Tyr Asn Leu Ile
        195                 200                 205

Leu Arg Gly Lys His Lys Pro Glu Tyr Gln Ser Leu Leu Lys Ile Glu
    210                 215                 220

Tyr His Leu Glu Thr Lys Ile Ile Gln Leu Glu Ala Ala Cys Glu Leu
225                 230                 235                 240

Ala Met Trp Lys Glu Ala Ser Asn Ile Ala Glu Asp Ile Tyr Asn Leu
                245                 250                 255

Asn Met His Asp Tyr Phe Tyr Lys Ser Leu Lys Ser Asn Ile Met Met
            260                 265                 270

Glu Pro Glu Leu Val Ser Val Ile Asp Thr Val Lys Ser Gly Asp Lys
        275                 280                 285

Asn Glu Glu Glu Lys Asn Lys Val Asn Asp Val Asp Ala Asp Ala Lys
    290                 295                 300

Ala Lys Glu Asp Ile Leu Lys Gly Val Glu Gln Gln Asp Asn Asn Val
305                 310                 315                 320

Glu Asn Asn Asn Asn Asn Asn Asn Asn Asn Asn Asp Asn Asn Asn Asn
                325                 330                 335

Asn Asn Asn Asn Asn Asn Asn Asn Asn Asn Asn Asn Lys Glu Asp Glu
            340                 345                 350

Glu Asp Gly Lys Ile Gln Ser Gly Asp Thr Ile Thr Lys Thr Thr Asp
        355                 360                 365

Gly Asn Val Gly Thr Gly His Asn Thr Ser His Ser Leu Asn Gln Ser
    370                 375                 380

Lys Glu Lys Leu Arg Asn Trp Ile Ala Ile Phe Tyr Glu Lys Met Ala
385                 390                 395                 400

Asp Ile Leu Phe Val Tyr Glu Ser Glu Leu Phe His Gly Leu Ala Trp
                405                 410                 415

Leu Lys Tyr Cys Phe His Ile Leu Asn Phe Lys Arg Asn Met Thr Glu
            420                 425                 430

Lys Glu Lys Thr Tyr Ile Cys Asn Lys Ala Val Leu Ala Val Leu Ser
        435                 440                 445

Ile Pro Val Ile Gly Asn Lys Lys Lys Ser Glu Asp Phe Thr Lys Gln
    450                 455                 460

Phe Glu Ala His Lys Lys Met Ser Gln Leu Leu Gly His Thr Ser Val
465                 470                 475                 480

Pro Val Lys Glu Ser Leu Lys Asn Ala Leu Arg Ile Arg Asn Ile Leu
                485                 490                 495
```

```
Asn Tyr Ala Asp Glu Asn Ile Gln Lys Leu Tyr Ser Leu Leu Glu Asn
            500                 505                 510

Gln Phe Thr Pro Leu Ser Leu Cys Leu Glu Cys Glu Val Leu Leu Lys
        515                 520                 525

Glu Leu Glu Asn Thr Glu Tyr Ala Ile Tyr Thr Lys Lys Ile Lys Glu
    530                 535                 540

Val Ile Phe His Lys Leu Ile Leu Gln Leu Ser Arg Val Tyr Ser Tyr
545                 550                 555                 560

Ile Ser Ile Asp Tyr Phe Ile Glu Asn Ile Cys Pro Asp His Phe Met
                565                 570                 575

Ser Trp Asn Glu Ala Glu Lys Met Leu Val Asp Leu Val Tyr Gln Arg
            580                 585                 590

Glu Leu Glu Met Lys Ile Asp Leu Thr Met Arg Ala Ile His Phe Gly
        595                 600                 605

Asp Lys Gln Val Leu Asn Ser Ser Val Met Ile Lys Asp Ser Leu Ile
    610                 615                 620

Asn Met Tyr Asn Asp Leu Gln Asn Gly Leu Lys Met Ile Asn Glu Thr
625                 630                 635                 640

Ile Ala Ile Glu Asn Glu Val Glu Asn Leu Thr Met Ser Thr Leu Thr
                645                 650                 655

Tyr Glu Glu Glu Phe Ala Tyr Leu Asp Lys Ser Asn Lys Asn Ile Asn
            660                 665                 670

Tyr Asn Thr Ala Thr Leu Glu Asp Ile Ile Glu Asn Glu Val Phe Glu
        675                 680                 685

Glu Lys Pro Ile Glu Asn Glu Lys Leu Leu Lys Lys Ile Tyr Glu Lys
    690                 695                 700

Ile Asp Glu Glu His His Lys Ile Gln Leu Leu Ser Glu Glu His Asn
705                 710                 715                 720

Lys Lys Arg Lys Glu Leu Leu Lys Lys Gln Lys Glu Leu Glu Gln Ala
                725                 730                 735

Gln Leu Lys Leu Lys Met Glu Lys Lys Leu Leu Glu Glu Lys Leu Glu
            740                 745                 750

Lys Glu Lys Lys Glu Glu Leu Ala Arg Lys Gly Glu Lys Leu Arg Ile
        755                 760                 765

Lys Glu Glu Lys His Lys Lys Lys Thr Glu Ala Ala Glu Gln Met Leu
    770                 775                 780

Lys Glu Ile Lys Lys Leu Cys Ser Thr Asn Thr Thr Lys Ile Leu Met
785                 790                 795                 800

Lys Gly Lys Tyr Met Asp Glu Ile Thr Ile Asp Asp Ile Leu Asn Gly
                805                 810                 815

Tyr Val Asp Phe Asp Asp Ile Glu Glu Ala Gln Glu Lys Leu Arg Leu
            820                 825                 830

Asn Glu Arg Asn Glu Ile Ile Lys Val Arg Lys Met Glu Ala Lys Lys
        835                 840                 845

Val Asp His Tyr Phe Arg Ala Val Arg Gln Val Glu Leu Ser His Met
    850                 855                 860

Asn Arg Trp Ile Ala Leu Val Phe Gln Glu Asp Thr Glu Ile Leu Leu
865                 870                 875                 880

Gln Glu Gln Lys Ala Ala Glu Glu Glu Gln Lys Ala Asp Phe Glu Ala
                885                 890                 895

Ala Leu Lys Glu Lys Glu Glu Tyr Val Lys Phe Ser Ile Asp Ile Glu
            900                 905                 910
```

```
Glu Phe Thr Lys Asn Glu Met Lys Leu Arg Val Glu Glu Phe Glu Lys
        915                 920                 925

Asn Leu Lys Ala Gln Lys Glu Arg Leu Tyr Asn Ile Leu Lys Glu Glu
    930                 935                 940

Lys Ile Gln Arg Ala Lys Glu Arg Arg Asp Gln His Ile Arg Lys Leu
945                 950                 955                 960

Lys Ala Glu Glu Glu Arg Lys Arg Arg Glu Glu Glu Glu Glu Arg Leu
                965                 970                 975

Leu Lys Glu Glu Met Glu Arg Lys Lys Lys Glu Glu Ala Arg Lys Lys
            980                 985                 990

Leu Glu Glu Ile Ser Lys Ala Gln  Arg Glu Arg Asp Leu  Glu Met Asp
        995                 1000                 1005

Leu Gln  Met Lys Arg Lys Lys  Glu Glu Ser Arg Arg  Ser Glu Arg
    1010                 1015                 1020

Ser His  Arg Lys Ser Ser Ile  Asp Asp Asp Leu Thr  Trp Arg Arg
    1025                 1030                 1035

Gly Asp  Lys Gly Gly Ser Gln  Asn Gly Asp Asp Ser  Tyr Arg Arg
    1040                 1045                 1050

His Asp  Asp His His Asp Gly  Thr His Arg Asp Arg  Ser Glu Met
    1055                 1060                 1065

Arg Asp  Arg Arg Asp Trp Ser  Gly Arg Asp Arg Asp  Arg Asp Arg
    1070                 1075                 1080

Glu Arg  Asp Arg Asp Arg Asp  Arg Asp Arg Glu His  Arg Arg Asp
    1085                 1090                 1095

Arg Asp  Arg Asp Arg Glu Arg  Asp Arg Asp Arg Asp  Arg Glu Arg
    1100                 1105                 1110

Asp Arg  Asp Arg Asp Arg Glu  Arg Asp Arg Asp Arg  Asp Arg Glu
    1115                 1120                 1125

His Arg  Arg Asp Arg Asp Arg  Asp Arg Glu Arg Asp  Arg Asp Arg
    1130                 1135                 1140

Asp Arg  Glu Arg Asp Arg Asp  Arg Asp Arg Glu Arg  Asp Arg Asp
    1145                 1150                 1155

Arg Asp  Arg Glu His Arg Arg  Asp Arg Asp Arg Asp  Arg Glu Arg
    1160                 1165                 1170

Asp Arg  Asp Arg Asp Arg Glu  Arg Asp Arg Asp Arg  Asp Arg Glu
    1175                 1180                 1185

Arg Asp  Arg Asp Arg Asp Arg  Glu Arg Asp Arg Asp  Arg Asp Arg
    1190                 1195                 1200

Glu Arg  Glu Arg Asp Arg Asp  Arg Asp Arg Asp Arg  Asp Ile Lys
    1205                 1210                 1215

Arg Ser  Asp Arg Asp His Lys  Lys Asp Arg Asp Asp  Lys Leu Asp
    1220                 1225                 1230

Arg Asp  Ser Arg Arg Arg Glu  Arg Ser Gly Lys Pro  Glu Asn Glu
    1235                 1240                 1245

Lys Lys  Arg Glu Asn Asp Ile  Ser Lys Arg Asn Gly  Thr Thr Glu
    1250                 1255                 1260

Glu Arg  Thr Lys Asn Ala Trp  Asn Leu Lys Glu Asp  Asp Asp Ser
    1265                 1270                 1275

Lys Ala  Lys His Glu Thr Ser  Glu Glu Asn Thr Lys  Ser Trp Arg
    1280                 1285                 1290

Asn Asn  Asn Lys Val Ile Asp  Asn Glu Ile Glu Lys  Ala Glu Lys
    1295                 1300                 1305

Tyr Lys  Asp Gly Glu Lys Lys  Asp Gly Glu Lys Asn  Lys Asp Glu
```

```
    1310                1315                1320

Asn Ser  Ser Lys Asn Lys Glu  Asn Asp Glu Leu Ala  Asn Gly Asn
    1325                1330                1335

Glu Glu  Asn Glu Asn Asp Glu  Val Lys Lys Asn Asp  Asp Glu Glu
    1340                1345                1350

Ala Ser  Asp Gly Gly Asp Phe  Thr Val Phe Lys Lys  Lys Lys Arg
    1355                1360                1365

Asn Ile  Leu Arg Phe Phe Met  Lys Ala
    1370                1375


<210> SEQ ID NO 700
<211> LENGTH: 716
<212> TYPE: PRT
<213> ORGANISM: Plasmodium vivax

<400> SEQUENCE: 700

Met Val Arg Val Ser Asp Asn Glu Leu Ser Asp Lys Glu Leu Val Asp
1               5                   10                  15

Phe Leu Ser Glu Asp Ser Asp Asn Gly Asp Glu Asn Leu Leu Asn Lys
            20                  25                  30

Lys Tyr Ser Asp Lys Glu Ala Leu Ile Thr Leu Glu Val Asp Phe Pro
        35                  40                  45

Lys Ile Val Thr Ile Leu Gly Ile Pro Lys Val Glu Ser Glu Lys His
    50                  55                  60

Gly Arg Leu Ala Glu Val Leu Lys Lys Leu Phe Ile Arg His Leu Ser
65                  70                  75                  80

Ala Lys Ile Ser Asp Ser Ser Leu Leu Asn Met Lys Ile His Met Pro
                85                  90                  95

Thr Asp Glu Glu Asn Lys Thr Lys Gly Ile Cys Phe Val Thr Phe Asn
            100                 105                 110

Asp Ser Phe Gln Ala Asn Glu Ala Val Lys Ile Leu Asn Lys Leu Lys
        115                 120                 125

Leu Asp Ala Lys His Ile Leu Thr Thr Ser Lys Met Asp Asp Ile Glu
    130                 135                 140

Asn Ile Ile Asn Arg Asp Glu Lys Ala Met Pro Ile Asn Val Val Gly
145                 150                 155                 160

Phe Thr Arg Glu Lys Ile Arg Trp Trp Leu Tyr Asp Glu Lys Cys Arg
                165                 170                 175

Glu Gln Phe Ile Val Arg Tyr Asp Ser His Phe Glu Val His Trp Phe
            180                 185                 190

Asp Pro Leu Glu Lys Glu Pro Gln Leu Ile Tyr Thr Thr Phe Lys Lys
        195                 200                 205

Asn Ala Pro Phe Ser Ser Val Gln Trp Ser Asn Gln Gly Ser Tyr Leu
    210                 215                 220

Val Ser Phe His Asn Pro Gly Ile Ala Leu Trp Gly Gly Asp Ser Phe
225                 230                 235                 240

Glu Lys Leu Ile Arg Leu Gln His Lys Ser Val Lys Glu Ile Met Phe
                245                 250                 255

Ser Pro Asn Glu Asn Tyr Val Leu Thr Trp Asp Gly Thr Pro Tyr Ser
            260                 265                 270

Leu Arg Asn Glu Lys Ser Ile Cys Ile Trp Arg Val Ile Thr Gly Lys
        275                 280                 285

Leu Leu Arg Ser Phe Ile Thr Pro Glu Tyr Ser Pro Lys Glu Lys Met
    290                 295                 300
```

```
Phe Pro His Phe Leu Trp Ser Pro Asp Asp Lys Tyr Ile Ala Cys Ile
305                 310                 315                 320

Gly Lys Gln Lys Glu Val Tyr Val Tyr Glu Leu Pro Ser Met Leu Leu
                325                 330                 335

Ile Glu Asp Gln Glu Lys Lys Arg Thr Pro Leu Lys Tyr Ser Gly Val
            340                 345                 350

Lys Glu Phe Asp Trp Ser Pro Val Asp Asn Ile Leu Ala Ile Trp Ile
        355                 360                 365

Pro Gln Thr Asn Asp Thr Pro Gly Thr Leu Ile Leu Val Asp Val Pro
    370                 375                 380

Ser Arg Lys Glu Leu Val Ser Arg Lys Ile Tyr Asp Val Ser Val Ala
385                 390                 395                 400

Ser Ile His Trp His Asn Lys Gly Asp Tyr Leu Cys Leu Lys Thr Thr
                405                 410                 415

Ile Gln Lys Lys Ser Gly Lys Lys Ile Lys Lys Glu Tyr Thr Gln Leu
            420                 425                 430

Glu Ile Phe Arg Met Arg Glu Lys Asn Ile Pro Val Asp Asn Val Gln
        435                 440                 445

Ile Glu Ala Val Lys Thr Lys Gln Phe His Trp Glu Glu Ser Asn Ser
    450                 455                 460

Asn Arg Phe Ala Leu Ile Leu Arg Glu Glu Thr Thr Asn Lys Gln Gln
465                 470                 475                 480

Ile Arg Phe Tyr Lys Ile Ser Asn Lys Gly Thr Ala Arg Asp Ala Lys
                485                 490                 495

Trp Ser Ser Thr Phe Asp Ile Asn Asn Gln Met Asn Phe Met Lys Trp
            500                 505                 510

Ser Pro Gln Gly Thr Tyr Phe Ile Leu Ala Ser Leu Ala Ser Glu Gly
        515                 520                 525

Thr Leu Tyr Phe Cys Cys Leu Asn Asn Asn Asp Glu Val Asp Val Ile
    530                 535                 540

His Lys Asp Glu His Leu Leu Val Asn Ser Ile Ser Trp Ser Arg Cys
545                 550                 555                 560

Gly Arg Phe Leu Val Ser Ala Val Ser Asn Asn Pro Asn Ala Phe Asn
                565                 570                 575

Thr Gly Tyr Arg Glu Glu Asn Ser Glu Ala Gly Phe His Ile Trp Thr
            580                 585                 590

Phe Gln Gly Lys Cys Leu Met Arg Ile Lys Lys Pro Ser Phe Ile Gln
        595                 600                 605

Phe Leu Phe Arg Pro His Pro Lys Ser Leu Phe Asn Asp Lys Leu Lys
    610                 615                 620

Leu Asp Ile Lys Asn Asn Leu Asn Asn Tyr Ser Lys Lys Phe Asp Asn
625                 630                 635                 640

Ile Asp Glu Lys Met Lys Thr Ala Lys Lys Asn Ala Leu Leu Thr Glu
                645                 650                 655

Arg Lys Asn Val Glu Asn Ser Phe Asn Gln Lys Phe Gln Glu Ile Thr
            660                 665                 670

Ala Leu Phe Gln Ser Tyr Gln Glu Tyr Glu Gln Leu Lys Lys Asn Trp
        675                 680                 685

Glu Thr Phe Glu Asn Gln Phe Glu Trp Glu Glu Lys Thr Ile Val Ile
    690                 695                 700

Glu His Val Leu Ser Val Lys Glu Glu Ile Phe Ala
705                 710                 715
```

<210> SEQ ID NO 701
<211> LENGTH: 984
<212> TYPE: PRT
<213> ORGANISM: Plasmodium vivax

<400> SEQUENCE: 701

Met Gln Ser Lys Phe Trp Ala Lys Ala Ile Asp Glu Asp Ser Gly Asp
1 5 10 15

Asn Val Thr Glu Ser Ser Glu Ser Glu Val Glu Glu Lys Lys Pro Ile
20 25 30

Val Ser Ala Gln Ala Glu Arg Trp Ala Ala Ile Asp Ser Ser Ser Ser
35 40 45

Glu Glu Glu Glu Arg Val Ile Lys Thr Tyr Glu Gly Lys Arg Leu His
50 55 60

Phe Tyr Glu Thr Thr Gly Asn Ser Leu Asn Glu Asn Met Tyr Asn Asn
65 70 75 80

Asp Phe Asn Leu Leu Leu Lys Asp Tyr Glu Asn Leu Tyr Lys Phe Met
85 90 95

Ile Lys Glu Ser Ala Asp Cys Ile Pro Asn Phe Ala Ile Ile Tyr Leu
100 105 110

Asp Lys Leu Ser Lys Tyr Val Glu Lys Thr Phe Gln Asn Asn Val Glu
115 120 125

Lys Lys Asn Leu Ser Lys Asn Lys Ala Gln Thr Leu Asn Lys Leu Arg
130 135 140

Ala Lys Ile Arg Lys Cys Ser Glu Phe Tyr Gln Glu Lys Leu Asn Leu
145 150 155 160

Tyr Asn Glu Asn Pro Asp Asp Phe Lys Asp Asp Arg Lys Lys Asp Met
165 170 175

Asp Asp Asp Glu Asp Asp Glu Asp Asn Glu Glu Asp Asp Glu Glu Glu
180 185 190

Glu Glu Asp Glu Glu Glu Gln Glu Asp Gln Asp Asp Asp Asn Glu Asp
195 200 205

Glu Lys Asp Gln Asp Asp Asp Glu Asp Gly Lys Gly Lys Lys Lys Leu
210 215 220

Ser Ser Lys Thr Lys Ser Lys Lys Gly Lys Glu Lys Lys Glu Glu Lys
225 230 235 240

Glu Asp Tyr Asp Asp Asp Asn Asp Glu Glu Lys Glu Asp Glu Ala Asp
245 250 255

Asp Asp Asn Asp Asp Asp Asp Asp Asp Ser Asp Asp Trp Ser Tyr Ser
260 265 270

Glu Asp Asp Asn Tyr Ala Ser Asp Glu Glu Asp Asp Lys Thr Lys Asn
275 280 285

Ala Met Ser Lys Trp Gly Leu Lys Thr Ser Thr Lys Val Glu Lys Lys
290 295 300

Lys Thr Val Lys Gln Lys Lys Val Lys Lys Glu Ser Thr Lys Lys Glu
305 310 315 320

Glu Lys Ala Asn Arg Val Val Glu Asp Ser Gln Ser Ala Lys Asn Lys
325 330 335

Gly Tyr Ala Glu Leu Leu Ser Thr Lys Asn Leu Thr Glu Asp Val Ile
340 345 350

Arg Glu Arg Val Lys Leu Val Ile Glu Lys Arg Gly Arg Lys Gly Leu
355 360 365

Asp Lys His Glu His Ile Asn Ile Leu Ser Lys Leu Cys Glu Ile Ala
370 375 380

Lys Thr Ile Ser Thr Gln Ser Tyr Ile Glu Val Leu Glu His Leu Ile
385 390 395 400

Asn Leu Glu Phe Asp Val Val Ser Ser Val Tyr Thr Tyr Met Ser Phe
405 410 415

Asn Ile Trp Asn Lys Val Phe Lys Tyr Val Glu Leu Ile Leu Asp Ile
420 425 430

Leu Ile Gln Asn Glu Asn Phe Tyr Leu Val Ser Ile Asn Ile Ala Glu
435 440 445

Glu Ile Thr Glu Glu Thr Thr Asn Glu Lys Glu Lys Ile Ile Lys Ser
450 455 460

Cys Lys Thr Leu Ile Ser Phe Leu Ala Lys Leu Asp Asp Glu Leu Leu
465 470 475 480

Lys Ala Leu Leu Tyr Ile Asp Val Gln Thr Glu Glu Tyr Arg Lys Arg
485 490 495

Leu Gly Lys Thr Ile His Met Ile Gly Leu Leu Lys Lys Gly Tyr Asn
500 505 510

Tyr Val Lys Cys Leu Lys Asn Met Pro Asp Leu Ala Ile His Ile Ser
515 520 525

Ser Arg Ile Leu Glu His Met Tyr Tyr Lys Pro Glu Met Leu Phe Lys
530 535 540

Gln Ile Trp Thr Tyr Leu Met Asn Gly Lys Glu Met Leu Ser Asp Ser
545 550 555 560

Leu Asn Asn Ser Asn Asn Ile Ala Ser Lys Glu Asp Gly Gln Gly Lys
565 570 575

Lys Lys Lys Arg Ile Asp Asn Asp Leu Phe Asp Glu Lys Leu Ile Asn
580 585 590

Asn Asp Ser Ile Asn Pro Pro Lys Ile Ile Glu Glu Tyr Val Tyr Glu
595 600 605

Ile Phe Glu Phe Gly Thr Lys Gln Gln Lys Val Lys Ala Leu Leu Gln
610 615 620

Leu Ser Tyr Asn Lys Ser Leu Tyr Asp Glu Tyr Leu Glu Ala Lys Glu
625 630 635 640

Leu Leu Asn Val Ala Asn Val His Glu Leu Ala Met Asn Ser Asp Ile
645 650 655

Gln Thr Gln Ile Leu Tyr Asn Arg Asn Leu Ile Gln Leu Gly Leu Cys
660 665 670

Ala Phe Arg His Gly Lys Ile Tyr Glu Ala His Cys Cys Leu Met Glu
675 680 685

Ile Cys Ser Gln Asn Lys His Lys Glu Leu Ile Ala Gln Gly Ile Ser
690 695 700

Asn Leu Lys Asn Gln Glu Lys Thr Leu Glu Gln Glu Arg Ala Glu Lys
705 710 715 720

Arg Arg Leu Leu Ser Tyr His Met His Ile Ser Ile Glu Leu Ile Glu
725 730 735

Cys Val Asn Asn Ile Cys Ala Met Leu Leu Glu Val Pro Asn Leu Ala
740 745 750

Lys Asn Thr Tyr Glu Ser Lys Lys Asp Ile Ile Ser Arg Gln Phe Arg
755 760 765

Arg Phe Leu Asp Ile Tyr Asp Lys Gln Ile Phe Asn Asn Pro Pro Glu
770 775 780

Asn Asn Lys Glu Ile Ile Ile Leu Ala Thr Lys His Leu Gln Lys Gly
785 790 795 800

Asn Trp Lys Leu Cys Cys Glu Lys Ile Phe Ser Leu Ser Ile Trp Pro

```
                805                 810                 815

Lys Phe Pro Asp Lys Glu Lys Val Gln Asn Ile Leu Lys Glu Lys Ile
            820                 825                 830

Lys Gln Glu Ala Met Arg Thr Tyr Ile Phe Arg Tyr Ile Ser Ile Tyr
        835                 840                 845

Glu Ser Phe Ser Ile Asp Gln Leu Cys Val Met Phe Asp Leu Asn Gln
    850                 855                 860

Asn Val Val His Ser Ile Leu Ser Lys Met Met Ile Asn Gln Glu Ile
865                 870                 875                 880

Pro Ala Phe Trp Asn Glu Ser Ser Lys Phe Ile Leu Ile Ser Lys Val
                885                 890                 895

Asn Pro Thr Thr Leu Gln Asn Leu Ala Leu Lys Leu Ala Glu Asn Val
            900                 905                 910

Asn Glu Val Met Glu Gln Asn Glu Leu Ala Leu Asn Met Lys Asn Pro
        915                 920                 925

Lys Phe Met Phe Met Gln Glu Arg Arg Thr Gln Met Lys Glu Glu Lys
    930                 935                 940

Ser Asn Trp Thr Gln Lys Lys Gly Asp Gln Lys Tyr Gln Lys Asn Tyr
945                 950                 955                 960

Asn Gln Lys Lys Asn Ala His Tyr Lys Lys Asn Tyr Lys Asp Asn Asn
                965                 970                 975

Ala Asn Lys Asn Tyr Lys Lys Asn
            980


<210> SEQ ID NO 702
<211> LENGTH: 543
<212> TYPE: PRT
<213> ORGANISM: Plasmodium vivax

<400> SEQUENCE: 702

Met Ser Ser Phe Asn Leu Val Gly Val Ile Asn Asn Arg Thr Trp Gly
1               5                   10                  15

Pro Asp Ser Lys Asn Glu Glu Leu Val Asn Tyr Cys Met Pro Asp Ile
            20                  25                  30

Lys Lys Tyr Gln Phe Glu Pro Ser Met Lys Phe Glu Arg Ile Gly Lys
        35                  40                  45

Val Cys Asp Phe Thr Met Asn Ser Tyr Gln Lys Asn Thr Lys Asp Ile
    50                  55                  60

Asn Lys Asn Ser Asn Asp Val Asn Ala Phe Glu Glu Glu Leu Gln Phe
65                  70                  75                  80

Gln Thr Val Asp Leu Arg Thr Gly Gln Lys Gln Lys Gly Ser Ile Phe
                85                  90                  95

Asn Lys Lys Lys Ile His Asn Lys Gln Asn Thr Thr Gln Ala Phe Thr
            100                 105                 110

Gln Lys Gln Gln Glu Glu Asp Asn Leu Tyr Ser Ser Arg Ile Lys Thr
        115                 120                 125

Ala Glu Gln Lys Lys Gln Lys Leu Leu Gln Gln Ala Lys Thr Ala Arg
    130                 135                 140

Ile Asn Ala Arg His Arg Ile Phe Thr Glu Trp Ser Ile Glu Pro Thr
145                 150                 155                 160

Pro Leu Trp Thr Val Glu Cys Glu Ile Met Phe Asn Glu Leu Pro Lys
                165                 170                 175

Lys Ile Ile Lys Ile Asp Asn Leu Lys Val Glu Asp Leu Phe Phe Lys
            180                 185                 190
```

```
Gly Lys Ser Leu Phe Tyr Asp Lys Lys Ile Glu Asn Ile Asn Val Lys
        195                 200                 205

Asn Pro Pro Leu Leu Phe His His Thr Lys Glu Gly Ile Asn Leu Ile
    210                 215                 220

Pro Lys Thr Lys Glu Asp His Asn Leu Ile Asn Ile Leu Asn Asn Glu
225                 230                 235                 240

Asn Lys Asn Lys Ile Ile Ser Asn Glu Glu Asp Pro Asn Asn Ile Asn
                245                 250                 255

Asn Ile Ile Val Ile Ser Thr Asp Gln Ile Leu Ser Cys Leu Met Ser
            260                 265                 270

Cys Val Gln Ser Lys Tyr Ser Trp His Leu Leu Ile Lys Lys Lys Gly
        275                 280                 285

Asn Gln Ile Ile Ile Asp Lys Asp Asp Asp Ser Ile Ile Asp Leu Leu
    290                 295                 300

Thr Val Asn Glu Asn Ser Ile Asp Ala Pro Thr Gln Asp Asn Glu Asn
305                 310                 315                 320

Lys Ile Asn Ser Leu Gln Ala Leu Gly Ile Glu Ala Val Lys Ile Asn
                325                 330                 335

Gln Arg Phe Arg Lys Gln Val Ile Leu Lys Asn Asp Ile Ala Glu Glu
            340                 345                 350

Phe Glu Pro Gly Asn Phe Asn Ile Lys Asn Ile Lys Ile Asn Asp Ile
        355                 360                 365

Leu Tyr Arg Tyr Arg Lys Phe Gln Ile Pro Pro Leu Val Gln Ser Asn
    370                 375                 380

Asn Lys Lys Thr Tyr Thr Leu Ile Thr Arg Gly Glu Ile His Ser Gln
385                 390                 395                 400

Ile Lys Gly Leu Asn Lys Ser Tyr Val Tyr Val Cys Ala Leu Asn Glu
                405                 410                 415

Tyr Asp Ile Lys Ser His Lys Asn Trp Arg Ser Gln Ile Glu Asn Gln
            420                 425                 430

Lys Gly Ala Leu Leu Ala Asn Glu Ile Arg Asn Asn Thr Ser Lys Leu
        435                 440                 445

Gln Lys Phe Ile Ser Gln Ala Leu Leu Ser Gly Cys Asp Asp Val Lys
    450                 455                 460

Leu Gly Phe Ile Ser Arg Lys Asn Ala Asn Asp Pro Asp Asn His His
465                 470                 475                 480

Ile Leu Ser Ile Gln Ser His Lys Thr Lys Asp Leu Ser Thr Gln Ile
                485                 490                 495

Gly Leu Lys Tyr Asp Asn Met Trp Gly Ile Phe Arg Phe Val Ile Asp
            500                 505                 510

Asn Leu Ala Asp Lys Pro Asn Gly Asn Tyr Val Ile Leu Lys Asp Pro
        515                 520                 525

Leu Lys Pro Leu Leu Arg Leu Tyr Cys Thr His Glu Asp Ser Asn
    530                 535                 540
```

<210> SEQ ID NO 703
<211> LENGTH: 517
<212> TYPE: PRT
<213> ORGANISM: Plasmodium vivax

<400> SEQUENCE: 703

```
Met Glu Glu Asn Asn Asn Asn Asp Leu Thr Gly Lys Ile Cys Ser Tyr
1               5                   10                  15

Leu Asp Pro His Met Val Gln Ile Ile Leu Thr Trp Leu Lys Glu Asn
            20                  25                  30
```

```
Lys Val Gly Asp Val Asn Asp Leu Glu Lys Asn Leu Glu Leu Leu Asn
        35                  40                  45

Glu Gly Cys Asp Lys Glu Ile Ala Leu Ile Glu Asn Glu Cys Thr Asn
    50                  55                  60

Gly Asn Arg Gly Val Ile Asn Asn Tyr Leu Glu Ser Val Glu Leu Glu
65                  70                  75                  80

Ile Asp Glu Phe Gln Glu Ala Met Asn Glu Tyr Lys Ile Asp Gln Met
                85                  90                  95

Asn Arg Ile Gly Ser Asn Leu Glu Lys Lys Ser Ile Val Gly Leu Arg
            100                 105                 110

Asp Trp Cys Asn Thr Tyr Leu Leu Asp Lys Asn Lys Met Tyr Thr Phe
        115                 120                 125

Ser Asp Asn Ile Asp Asp Lys Ile Leu Lys Leu Ser Arg Tyr Tyr Tyr
    130                 135                 140

Gln Lys Lys Asp Tyr Val Lys Ser Lys Gln Tyr Leu Leu Leu Tyr Ile
145                 150                 155                 160

Leu Asn Ile Ser Glu Met Ile Ile Asn Ile Ser Glu Ser Ser Lys Met
                165                 170                 175

Lys Thr Cys Tyr Trp Gly Ile Ile Ser Asn Ile Ile Asn Ser Phe Phe
            180                 185                 190

Met Asn Ile Asn Asn Asp Asp Tyr Leu Phe Ser Lys Asn Glu Asp Gly
        195                 200                 205

Lys Ile Ile Val Lys Glu Asp Ile Ile Asn Glu Met Asn Val Cys Ile
    210                 215                 220

Glu Ser Ile Val Lys Leu Ser Gln Leu Leu Asn Lys Glu Lys Val Ser
225                 230                 235                 240

Lys Asn Glu Ile Ile Leu Gln Arg Ser Trp Leu Ile His Trp Ser Leu
                245                 250                 255

Ile Ile Ile Phe His Phe Phe Met Tyr Val Ile Tyr Val Lys Asn Thr
            260                 265                 270

Tyr Pro Lys Asn Asn Ser Phe Ser Met Leu Gln Asp Trp Phe Ile Asp
        275                 280                 285

Glu Lys Asn Leu Ser Ile Leu Asn Leu Ile Cys Pro His Ile Ile Arg
    290                 295                 300

Tyr Tyr Cys Val Tyr Ala Ile Phe Tyr Arg Asn Arg Lys Asp His Phe
305                 310                 315                 320

Glu Leu Ile Leu Asn Thr Leu Asn Phe Ile Lys Ser Lys Tyr Asn Asp
                325                 330                 335

Ser Phe Thr Ser Leu Leu Ile Ser Ile Phe Thr Asp Tyr Asp Phe Asn
            340                 345                 350

Met Ala Gln Thr Cys Ile Ala Thr Ile Gly Thr Leu Cys Glu Arg Asp
        355                 360                 365

Val Phe Leu Tyr Lys Leu Lys Pro Tyr Ile Glu Glu His Cys Arg Phe
    370                 375                 380

Ile Ile Phe Glu Thr Tyr Cys Arg Ile His Lys Ser Ile Asn Ile Asp
385                 390                 395                 400

Met Ile Ser Ser Lys Val Asn Leu Thr Arg Glu Gln Ala Glu Lys Trp
                405                 410                 415

Ile Val Asn Leu Ile Arg Asn Ala Lys Leu Asp Ala Lys Ile Asn Ser
            420                 425                 430

Glu Lys Asn Cys Ile Glu Ile Ser Thr Pro Pro Pro Asn Leu Tyr Gln
        435                 440                 445
```

Gln Val Ile Asp Lys Thr Gln Asn Leu Ile Met Arg Ser Asn Phe Ile
    450                 455                 460

Val Gln Val Leu Asn Arg Ser Ser Asn Asp Asp Gln Gln Gln Ile Gln
465                 470                 475                 480

Lys Asn Leu Arg Phe Lys Asn Lys Asn Glu Lys Asn Leu Lys Asn Asn
                485                 490                 495

Lys Arg Asn Lys Asn Phe Asn His Met Tyr His Ile Asn Asn Lys Ile
            500                 505                 510

Val Ala Pro Asp Thr
        515

<210> SEQ ID NO 704
<211> LENGTH: 320
<212> TYPE: PRT
<213> ORGANISM: Plasmodium vivax

<400> SEQUENCE: 704

Met Ser Ile Asn Arg Tyr Asn Tyr Lys Thr Met Asn Ser Leu Leu Lys
1               5                   10                  15

Asp Lys Ile Pro Gln His Phe Asp Ile Leu Pro His Thr Thr Ile Lys
            20                  25                  30

Cys Ile Ile His Pro Ser Val Ile Phe Thr Ile Leu Asp Ala Tyr Leu
        35                  40                  45

Arg Arg Asp Glu Asp Gln Thr His Val Ile Gly Thr Leu Met Gly Ser
    50                  55                  60

Val Ile Asp Thr Asn Leu Val Glu Ile Ser Asp Cys Phe Val Asp Lys
65                  70                  75                  80

His Ser Leu Asn Glu Gly Gly Phe Leu Gln Ile Ile Lys Asp His His
                85                  90                  95

Glu Thr Met Tyr Glu Leu Lys Gln Lys Ile Arg Pro Arg Asp Gln Val
            100                 105                 110

Val Gly Trp Phe Cys Ser Gly Ser Glu Leu Ser Glu Leu Ser Cys Ala
        115                 120                 125

Val His Gly Trp Phe Lys Glu His Asn Ser Ile Ser Lys Phe Tyr Pro
    130                 135                 140

His Thr Pro Leu Asn Glu Pro Ile His Leu Leu Val Asp Ala Ser Leu
145                 150                 155                 160

Glu Ser Gly Phe Leu Asn Ile Lys Ala Tyr Val Gln Leu Pro Ile Ser
                165                 170                 175

Leu Val Lys Asp Tyr Phe Val His Phe His Glu Ile Gln Thr Glu Leu
            180                 185                 190

Leu Pro Cys Asn Val Glu Arg Ala Asp Val Ser Leu Val Lys Gly Asn
        195                 200                 205

Ile His Ala His Lys Asp Asn His Thr Asn Asn Leu Glu His Asn His
    210                 215                 220

Asn Asn Asn Gln Ile Asp Met Asn Glu Leu Ser Leu Lys Lys Leu Leu
225                 230                 235                 240

Ile Met Leu Lys Gln Cys Lys Ser Tyr Val Gln Asp Val Ile Asp Gln
                245                 250                 255

Lys Lys Lys Gly Asn Ile Ser Val Gly Arg Tyr Leu His Lys Val Leu
            260                 265                 270

Ser Asn Asp Thr Phe Leu Thr Leu Glu Lys Phe Asp Ser Ile Asn Glu
        275                 280                 285

Ser Val Leu Gln Asp Asn Leu Met Ile Ser Tyr Leu Ser Asn Leu Ala
    290                 295                 300

Asn Leu Gln Phe Leu Ile Ala Glu Lys Leu Asn Ser Ser Ser Leu Gln
305 310 315 320

<210> SEQ ID NO 705
<211> LENGTH: 268
<212> TYPE: PRT
<213> ORGANISM: Plasmodium vivax

<400> SEQUENCE: 705

Met Ile Gln Thr Glu Lys Lys Trp Ala Asp Ile Asp Val Asp Asp Asp
1 5 10 15

Glu Ser Ile Asn Asp Asn Glu Ile Lys Lys Lys Trp Glu Asp Ile Asp
20 25 30

Ala Asp Asp Asp Leu Glu Ala Asn Lys Lys Leu Ser Tyr Phe Thr Asn
35 40 45

Tyr Glu Asn Gly Ile Lys Val Val Thr Lys Tyr Ser Glu Asn Leu Lys
50 55 60

Lys Gln Thr Val Lys Val Thr Lys Lys Ile Gln Glu Val Val Ile Lys
65 70 75 80

Lys Lys Leu Asn Lys Glu Ile Asn Asn Arg Leu Asn Leu Lys Asn Phe
85 90 95

Asn Ile Asp Ile His Ser Ser Val Thr Val Glu Pro Thr Asp Val Val
100 105 110

Asn Ile Glu Val Pro Lys Asn Asn Pro Leu Asp Phe Leu Lys Asp Thr
115 120 125

Glu Tyr Asp Tyr Leu Phe Ala Glu Gln Thr Asn Lys Thr Ala Lys Asp
130 135 140

Leu Lys Asn Arg Phe Lys Ile Leu Lys Asp Glu Glu Thr Glu Asp Val
145 150 155 160

Lys Ala Glu Asp Pro Ser Lys Ala Ala Gly Arg Arg Glu Gly Leu Tyr
165 170 175

Tyr Arg Pro His Asp Thr Gln Asn Lys Glu Cys Thr Val Arg Val Thr
180 185 190

Asn Leu Ser Glu Asp Val Asn Glu Asn Glu Leu Ser Asn Leu Phe Gly
195 200 205

Lys Val Gly Asn Ile Val Arg Met Phe Leu Ala Lys His Lys Glu Thr
210 215 220

Gln Asn Ser Lys Gly Phe Ala Phe Ile Thr Tyr Ser Lys Arg Glu Glu
225 230 235 240

Ala Lys Arg Ala Ile Glu Lys Leu Asn Arg His Gly Phe Glu Asn Leu
245 250 255

Leu Leu Ser Val Glu Trp Ala Lys Pro Ser Asn Arg
260 265

<210> SEQ ID NO 706
<211> LENGTH: 327
<212> TYPE: PRT
<213> ORGANISM: Plasmodium vivax

<400> SEQUENCE: 706

Met Lys Arg Lys Tyr Leu Ser Gly His Asn Arg Pro Leu Thr His Val
1 5 10 15

Asn Thr Asn Tyr Asp Gly Asp Leu Leu Phe Thr Thr Gly Arg Asp Lys
20 25 30

Lys Phe Ile Leu Trp Arg Val Ser Asp Gly Thr Gln Ile Gly Leu Tyr
35 40 45

Glu Cys Ser Gly Ala Val Tyr Asn Ser Asp Val Thr Tyr Asp Ser Lys
    50                  55                  60

Arg Ile Val Cys Ser Ser Ala Ala Asn Lys Val Tyr Leu Phe Asp Val
65                  70                  75                  80

Tyr Thr Gly Glu Pro Leu Lys Ile Ile Glu Glu Asn Gly Pro Val Arg
                85                  90                  95

Phe Val Glu Phe Asn Lys Asp Pro Leu Asn Gln Asp Lys Ile Val Val
            100                 105                 110

Ala His Asp Arg Leu Lys Ser Asp His Lys Arg Ser Ile Lys Leu Tyr
        115                 120                 125

Asp Leu Lys Ser Asp Asn Leu Ile Trp Lys Gln Asp His Glu Ser Arg
    130                 135                 140

Cys Ile Gln Val Arg Trp Cys Phe Phe Asp Lys Leu Ile Leu Ser Ala
145                 150                 155                 160

His Glu Asn Gly Glu Ile Val Val Trp Asn Ala Glu Asp Gly His Leu
                165                 170                 175

Ile Arg Lys Phe Gln Ala His Ser Lys Glu Val Thr Asn Leu Ser Phe
            180                 185                 190

Asp Lys Asp Arg Met Leu Met Leu Ser Ser Ser Leu Asp Gly Thr Ala
        195                 200                 205

Lys Leu Arg Asp Gly Val Asn Phe Glu Ile Ile Asn Glu Tyr Lys Thr
    210                 215                 220

Asp Arg Pro Leu Asn Thr Cys Asp Ile Ser Pro Leu Phe Lys Asn Glu
225                 230                 235                 240

Asn Asn Pro Lys Asn His Ile Ile Leu Ala Gly Gly Gln Ala Ala Glu
                245                 250                 255

His Val Thr Thr Thr Ala Ser Gly Glu Gly Lys Phe Gln Thr Leu Leu
            260                 265                 270

Tyr Asp Ile Ile His Ser Asn Glu Leu Gly Ser Ile Lys Gly His Phe
        275                 280                 285

Gly Pro Val His Ser Ile Lys Phe Leu Pro His Gly Asp Gly Phe Val
    290                 295                 300

Ser Gly Gly Glu Asp Gly Phe Ala Arg Ile Tyr His Phe Asp Asn Asp
305                 310                 315                 320

Tyr Phe Ile Gly Lys Tyr Asp
                325

<210> SEQ ID NO 707
<211> LENGTH: 656
<212> TYPE: PRT
<213> ORGANISM: Plasmodium vivax

<400> SEQUENCE: 707

Met Ala Glu Val Ser Pro Val Glu Glu Asn Val Ile Glu Glu Ile Val
1               5                   10                  15

Ser Phe Glu Glu Glu Val Glu Thr Phe Leu Ile Asn Leu His Asp Phe
            20                  25                  30

Val Tyr His Arg Asn Ala Glu Ala Ile Lys Lys Leu Phe Asp Thr Asp
        35                  40                  45

Phe Tyr Thr Ile Ser Glu Ile Tyr Phe Lys Asn Ile Arg Trp Pro Ser
    50                  55                  60

Ile Lys Leu Val Asp Ile Phe Tyr Lys Gln Lys Asn Arg Phe His Asn
65                  70                  75                  80

Leu Ile His Ser Leu Tyr Glu Glu Leu Tyr Tyr Arg His Val Phe Ile

```
                85                  90                  95

Ile Lys Asp Ile Thr Leu Glu Asp Arg Lys Asn Ser Trp Asp Asn Tyr
            100                 105                 110

Lys Cys Leu Leu Asn Phe Ile Thr Thr Ile Cys Thr Asp Leu Ser Gly
        115                 120                 125

Asp Ser Asn Asp Asn Val Leu Val Met Pro Asn Val Trp Ile Tyr Asp
    130                 135                 140

Phe Leu Ser Glu Tyr Ile Tyr Gln Tyr Gln Ser Met Cys His Tyr Arg
145                 150                 155                 160

Leu Gln Leu Leu Lys Asp Leu Glu Lys Asn Glu Glu Gly Ile Leu Phe
                165                 170                 175

Val Thr Arg Asn Thr Glu Val Phe Glu Ser Ser Ile Val Phe Glu Val
            180                 185                 190

Leu His Asn Leu Leu Leu Lys Gly Glu Phe Ser Thr Leu Pro Leu Glu
        195                 200                 205

Glu Lys Ser Thr Phe Val Asn Asn Ile Tyr Asn Ile Asn Asn Glu Glu
    210                 215                 220

Ile Asn Ser Lys Tyr Gln Phe Ala Tyr Phe Ala Cys Cys Ile Leu Leu
225                 230                 235                 240

Asn Leu Tyr Val Leu Ile Gly Asp Tyr Tyr Thr Ala Leu Lys Ile Ile
                245                 250                 255

Ser Asn Ile Glu Leu Asn His Lys Ala Leu Tyr Trp Lys Val Thr Leu
            260                 265                 270

Cys His Leu Ser Ile Phe Tyr Asn Ile Ala Phe Ser Tyr Met Met Leu
        275                 280                 285

Lys Arg Tyr Asn Asp Ser Ile Lys Val Leu Ser Gln Ile Leu Ile Tyr
    290                 295                 300

Leu Ser Lys Gln Lys Ile His Val Ser Asn Gln Gln Lys Tyr Gln Gln
305                 310                 315                 320

Asn Leu Ile His Lys Leu Ile Asp Lys Met Tyr Leu Ile Ile Ile Ile
                325                 330                 335

Cys His Ser Leu Thr Asn Thr Arg Leu Asp Glu Thr Ile Leu Gln Asn
            340                 345                 350

Ile Lys Glu Asn Tyr Ser Gly Lys Phe Tyr Ala Leu Gln Ser Ala Asn
        355                 360                 365

Glu Gln Thr Tyr Ala Glu Leu Phe Ile Arg Val Ala Pro Lys Phe Ile
    370                 375                 380

Asp Pro Leu Ser Asn Ile Ser Phe Gln Ile Leu Ser Asn Phe Gln Asn
385                 390                 395                 400

Ile Gln Asn Gln Thr Tyr Ser Ser Asp Pro Thr Asn Arg Gln Leu Ala
                405                 410                 415

Ile Phe Leu Lys Asp Val Ser Tyr Gln Lys Lys Ala Phe Tyr Phe Ile
            420                 425                 430

Ser Tyr Ala Lys Leu Tyr His Asn Ile Gln Leu Lys Lys Leu Ala Asn
        435                 440                 445

Leu Met Asn Tyr Asn Glu Leu Ile Asn Asn Asp Asp Glu His Glu Gln
    450                 455                 460

Glu Gln Asn Val Ser Ser Asp Ile Met Cys Val Lys Asn Cys Ser Lys
465                 470                 475                 480

Gln Leu Ile Trp Lys Glu Gly Pro Leu Tyr Thr Gly Asp Ile Ile Asn
                485                 490                 495

Ser Ile Phe Gly Asn Ser Phe Asp Phe Phe Ile Asp Leu Asp Ile Val
            500                 505                 510
```

```
Asn Ile Lys Thr Arg Ala His Gln Lys Ile Phe Ile Asp Tyr Phe Val
        515                 520                 525

His Gln Ile Asn Met Ser Lys Asn Leu Met Asn Asn Leu Leu Gly Ala
    530                 535                 540

Ala Ser Thr His Met Tyr Lys Thr Lys Tyr Asp Asn Phe Arg Lys Lys
545                 550                 555                 560

Leu Lys Asn Lys Thr Arg Asn Lys His Asn Asn Asn Asn Asn Asn Asn
                565                 570                 575

Asn Asn Asn Asn Asn Asn Asn Asn Asn Asn Asn Asn Asn Asn Asn Asn
            580                 585                 590

Asn Asn Asn Asn Asn Asn Asn Asn Asn Tyr Tyr Tyr Tyr His Lys Asn
        595                 600                 605

Lys Gln Asn Lys Gln Asp Lys Gln Asp Lys Gln Asn Lys Leu Asn Arg
    610                 615                 620

Gln Asn Lys Gln Asn Lys Gln Asn His Leu Asn Arg His Asn Asn Gln
625                 630                 635                 640

Asn Lys Pro Asn His Gln Asn Asn Met His Ala Gln Val Ala Ala Ser
                645                 650                 655


<210> SEQ ID NO 708
<211> LENGTH: 429
<212> TYPE: PRT
<213> ORGANISM: Plasmodium vivax

<400> SEQUENCE: 708

Met Ser Ile Tyr Ile Gln Leu Thr His Asp Leu Ser Gly Thr Val Thr
1               5                   10                  15

Ala Val Thr Ile Gly Asp Trp Ile Leu Gly Ile Leu Lys Glu Lys Asn
            20                  25                  30

Ile Gln Glu Tyr Glu Val Phe Phe Lys Lys Phe Leu His Ile Tyr Gln
        35                  40                  45

Lys Gln Asp Lys Asp Ser Glu Cys Asn Asn Arg Ser Glu Ile Phe Ser
    50                  55                  60

Leu Leu Leu Ser Ala Ser Asp Phe Val Phe Glu Thr Leu Val Glu Thr
65                  70                  75                  80

Lys Lys Asn Asn Lys Ile Lys Val Ile Ile Asp Asn Lys Glu Ser Val
                85                  90                  95

Lys Ser Tyr Asn Glu Phe Tyr Lys Glu Val Glu Glu Tyr Phe Val Ile
            100                 105                 110

Leu Ile Ser Ile Leu Gln Leu Glu Phe Lys Ser Val Glu Glu Leu Asn
        115                 120                 125

Asn Ala Thr Asn Asn Phe Ile Lys Ala Ile Lys Asn Tyr Asn Glu Phe
    130                 135                 140

Pro Glu Leu Arg Leu Lys Ile Leu Gln Leu Leu Tyr Asn Ser Phe Asn
145                 150                 155                 160

Val Asn Phe Ser Phe Arg Phe Pro Thr Phe Ile Ala Ile Leu Gln Phe
                165                 170                 175

Cys Ser Gln Asn Asn Ile Phe His Asn Met Leu Pro Tyr Ile Lys Tyr
            180                 185                 190

Ile Asp Asp Trp Ile Lys Glu Trp Asn Ile Ser Thr Arg Glu Lys Arg
        195                 200                 205

His Ile Tyr Leu Ile Ile Ser Gln Glu Leu Lys Lys Leu Lys Lys Tyr
    210                 215                 220

Glu Glu Ser Tyr Glu His Leu Lys Lys His Ile Tyr Tyr Tyr Asp Asn
```

```
225                 230                 235                 240

Glu His Lys Asp Ile Leu Asn His Pro Asn Ser Ile Asn Ala Ser Ile
                245                 250                 255

Glu Leu Ile Val Asp Ala Ile Asn Ile Asn Asn Asn Ile Tyr Phe His
            260                 265                 270

Glu Ile Ile Asn Leu His Ala Ile Gln Asn Leu Gln Phe Ile Pro Gln
        275                 280                 285

His Gln Pro Leu Phe Asp Leu Leu Leu Ile Phe Tyr Lys Tyr Thr Ile
    290                 295                 300

Asn Glu Phe Leu Val Phe Lys Asn Lys His Gly Ser Asp Phe Phe Asn
305                 310                 315                 320

Lys Tyr Asn Ile Asp Ile Gln Thr Cys Glu Ser Lys Ile Tyr Leu Leu
                325                 330                 335

Ser Ile Ile Ser Leu Phe Asn Asp His Lys Val Gln Asn Ile Gln Phe
            340                 345                 350

Ile Ser Lys Gln Leu Asn Ile Ser Val Val Gln Ile Glu Asn Ile Leu
        355                 360                 365

Val Ala Ala Ile Gly Ser Gly Val Ile Asp Ala Lys Ile Asp Gln Ile
    370                 375                 380

Asn Gln Thr Val His Met Lys Thr Thr Ile Leu Arg Asn Phe Asp Asp
385                 390                 395                 400

Glu Asn Trp Lys Gln Leu Asn Asn Gln Ile Thr Lys Tyr Ile Asn Asn
                405                 410                 415

Val Gln Lys Ile Leu Glu Leu Thr Lys His Ala Asn Lys
            420                 425


<210> SEQ ID NO 709
<211> LENGTH: 247
<212> TYPE: PRT
<213> ORGANISM: Plasmodium vivax

<400> SEQUENCE: 709

Met Ala Ile Arg Val Gln Phe Glu Asn Ser Asn Glu Val Gly Val Phe
1               5                   10                  15

Ser Arg Leu Thr Asn Ser Tyr Ala Leu Val Ala Leu Gly Gly Ser Glu
            20                  25                  30

Asn Phe Ser Ser Val Phe Glu Ser Glu Leu Ser Gln His Ile Pro Leu
        35                  40                  45

Val Tyr Thr Thr Ile Gly Gly Thr Arg Val Ile Gly Arg Val Cys Val
    50                  55                  60

Gly Asn Arg Lys Gly Leu Leu Val Ser Ser Ile Cys Thr Asp Gln Glu
65                  70                  75                  80

Leu Leu His Leu Arg Asn Cys Leu Pro Glu Asn Val Lys Ile Lys Arg
                85                  90                  95

Ile Glu Glu Arg Leu Ser Ala Leu Gly Asn Cys Ile Thr Thr Asn Asp
            100                 105                 110

Tyr Val Gly Leu Ile His Thr Asp Ile Asp Lys Glu Thr Glu Glu Ile
        115                 120                 125

Ile Gln Asp Val Leu Asp Ile Glu Val Phe Arg Thr Ser Ile Ala Gly
    130                 135                 140

Asn Leu Leu Val Gly Thr Tyr Ser Tyr Phe Thr Asn Asn Gly Gly Leu
145                 150                 155                 160

Leu His Ala Met Thr Ser Ser Gln Glu Ile Glu Glu Leu Ser Glu Leu
                165                 170                 175
```

Leu Gln Ile Pro Leu Ile Thr Gly Thr Ile Asn Arg Gly Ser Asp Leu
180 185 190

Ile Gly Ser Gly Leu Val Ala Asn Asp Trp Ser Ala Phe Cys Gly Met
195 200 205

Asp Thr Thr Ala Ile Glu Leu Ser Ile Ile Glu Lys Val Phe Lys Leu
210 215 220

Asn Asn Ile Thr Asp Asn Asn Met Glu Asp Thr Phe Lys Tyr Lys Ser
225 230 235 240

Ser Ile Ile Gln Thr Met Ile
245

<210> SEQ ID NO 710
<211> LENGTH: 300
<212> TYPE: PRT
<213> ORGANISM: Plasmodium vivax

<400> SEQUENCE: 710

Met Ser Asn Ala Glu Glu Glu Thr Val Lys Lys Lys Lys Lys Tyr Arg
1 5 10 15

Lys Asp Lys Pro Trp Asp Asn Glu Asn Ile Asp His Trp Lys Val Glu
20 25 30

Lys Phe Thr Gln Glu Asp Asn Lys His His Phe Leu Glu Glu Ser Ser
35 40 45

Phe Lys Val Leu Phe Pro Lys Tyr Arg Glu Lys Tyr Leu Gln Gln Phe
50 55 60

Ser Ser Asp Ile Lys Asn Val Leu Asn Lys His Phe Ile Lys Phe Glu
65 70 75 80

Ile Asp Leu Ile Glu Gly Tyr Met Cys Val Lys Thr Thr Lys Lys Thr
85 90 95

Phe Asp Pro Tyr Ile Ile Ile Lys Ser Arg Asp Met Ile Ser Leu Leu
100 105 110

Ser Arg Ser Val Pro Phe Val His Ala Lys Arg Val Leu Glu Asp Glu
115 120 125

Thr Tyr Cys Asp Ile Ile Lys Ile Ser Gly Tyr Val Arg Asn Lys Asn
130 135 140

Lys Phe Ile Lys Arg Arg Gln Arg Leu Leu Gly Ser Asn Ala Thr Thr
145 150 155 160

Leu Lys Ala Leu Glu Ile Leu Thr Asn Cys Tyr Ile Cys Ile His Gly
165 170 175

Lys Thr Val Ser Val Ile Gly His Phe Lys Ser Leu Lys Val Val Arg
180 185 190

Arg Ile Ile Ile Asp Cys Met Lys Asn Ile His Pro Val Tyr His Ile
195 200 205

Lys Glu Leu Ile Ala Lys Arg Glu Leu Glu Lys Asn Glu Glu Phe Lys
210 215 220

Asn Glu Asn Trp Glu Lys Phe Leu Pro Asn Phe Lys Lys Arg Asn Val
225 230 235 240

Gln Arg Lys Lys Ile Lys Glu Lys Leu Asp Lys Lys Lys Lys Lys Asn
245 250 255

Lys Ser Val Phe Pro Pro Asp Gln Leu Pro Arg Lys Ile Asp Ile Gln
260 265 270

Met Glu Thr Gly Glu Tyr Phe Leu Asn Asn Gln Lys Asn Lys Lys Lys
275 280 285

Asp Lys Thr Gln Asp Lys Gln Gln Lys Gly Asn Asp
290 295 300

<210> SEQ ID NO 711
<211> LENGTH: 686
<212> TYPE: PRT
<213> ORGANISM: Plasmodium vivax

<400> SEQUENCE: 711

```
Met Lys Glu Ser Asn Leu Tyr Arg Phe Lys Asp Ile Lys Pro Val Val
1               5                   10                  15

Ser Ala Lys Glu Leu Val Asp Val Val Leu Ser Lys Thr Gln Arg Lys
            20                  25                  30

Thr Pro Thr Glu Ile His Lys Gly Phe Lys Ile Thr Arg Ile Arg Asn
        35                  40                  45

Phe Tyr Met Arg Lys Val Lys Ile Cys Gln Glu Leu Phe Arg Glu Lys
    50                  55                  60

Leu Gln Asn Ile Ile Asn Asp Phe Pro Lys Leu Asp Asp Ile His Pro
65                  70                  75                  80

Phe Tyr Ser Asp Leu Ala Asn Ile Leu Tyr Asp Arg Asp His Tyr Lys
                85                  90                  95

Leu Ser Leu Gly Gln Cys Ser Tyr Val Ser Lys Ser Leu Ile Arg Ile
            100                 105                 110

Cys His Asp Tyr Ile Lys Leu Leu Lys Phe Ser Ser Ser Leu Tyr Lys
        115                 120                 125

Cys Lys Met Leu Lys Ile Ser Ala Leu Gly Arg Met Cys Lys Leu Val
    130                 135                 140

Lys Lys Leu Gln Pro Ser Leu Leu Tyr Leu Glu Glu Val Arg Gln Asn
145                 150                 155                 160

Leu Ser Arg Leu Pro Ser Ile Asn Pro His Lys Lys Thr Ile Ile Leu
                165                 170                 175

Ser Gly Ala Pro Asn Val Gly Lys Ser Ser Phe Met Asn Ile Val Ser
            180                 185                 190

Arg Ala Asn Val Asp Val Gln Ser Tyr Ser Phe Thr Thr Lys Asn Leu
        195                 200                 205

Tyr Val Gly His Phe Asp His Lys Leu Asn Lys Tyr Gln Ile Ile Asp
    210                 215                 220

Thr Pro Gly Leu Leu Asp Arg Ala Phe Glu Asn Arg Asn Thr Ile Glu
225                 230                 235                 240

Met Thr Thr Ile Thr Ala Leu Ala His Ile Asn Gly Val Ile Leu Phe
                245                 250                 255

Ile Ile Asp Ile Ser Glu Gln Cys Gly Leu Thr Ile Lys Glu Gln Ile
            260                 265                 270

Asn Leu Phe Tyr Ser Ile Lys Ser Val Phe Ser Asn Lys Ser Ile Val
        275                 280                 285

Ile Gly Phe Asn Lys Ile Asp Lys Cys Asn Met Asp Ser Leu Ser Ile
    290                 295                 300

Asp Asn Lys Leu Leu Ile Lys Gln Ile Leu Asp Asn Val Lys Asn Pro
305                 310                 315                 320

Ile Lys Phe Ser Ser Phe Ser Thr Leu Thr Gly Val Gly Val Glu Gln
                325                 330                 335

Ala Lys Ile Thr Ala Cys Glu Leu Leu Lys Asn Asp Gln Ala Glu Ser
            340                 345                 350

Ile Leu Leu Asp Gln Glu Gln Leu Leu Asn Thr Lys Leu Gly Glu Thr
        355                 360                 365

Lys Asn His Leu Asn Arg Thr Pro Phe Ile Pro Glu Ser Val Ile Arg
```

```
    370                 375                 380

Glu Arg Lys Leu Arg Gln Glu Lys Ala Gln Ser Thr Asn Asn Met Phe
385                 390                 395                 400

Asp Ser Thr Asn Ala Asp Ser Ile Thr Ser Pro Cys Asp Pro Thr Asn
                405                 410                 415

Ala Thr Glu Gly Asp Pro Asn Lys Gln Tyr Thr Met Arg Glu Leu Lys
            420                 425                 430

Leu Lys Lys Lys Asn Lys Ser Arg Gln Ser Tyr Leu Ser Asn Arg Thr
        435                 440                 445

Asp Asp Lys Val Leu Gln Ile Asp Leu Gln Asn Glu Asn Gly Gly Ala
    450                 455                 460

Gly Val Tyr Ser Val Asp Ile Arg Asn Asn Tyr Asp Ile Lys Glu Glu
465                 470                 475                 480

Tyr Lys Tyr Asp Val Ile Pro Glu Ile Tyr Asn Gly Lys Asn Ile Ser
                485                 490                 495

Asp Phe Ile Asp Met Asp Ile Glu Lys Lys Leu Leu Glu Leu Glu Lys
            500                 505                 510

Glu Glu Glu Glu Leu Tyr Asp Lys Asp Ala Asn Ile Asp Pro Leu Trp
        515                 520                 525

Phe Lys Thr Gln Lys Ile Leu Glu Lys Met Lys Leu Arg Leu Lys Ser
    530                 535                 540

Val Arg Leu Asp Ala Lys Leu Lys Asp Gln Asn Val Gln Ile Tyr Asn
545                 550                 555                 560

Lys Arg Lys Lys Asn Ile Glu Glu Ile Glu Lys Lys Leu Leu Asp Leu
                565                 570                 575

Lys Leu Asp Lys Glu Lys Val Ile Lys Ser Met Thr Glu Lys Ala Arg
            580                 585                 590

Asn Lys Asn Lys Gln Pro Val Val Lys Lys Gln Lys Val Lys Lys Asp
        595                 600                 605

Ile Ser Lys Lys Lys Gln Ile Lys Asp Asn Ile Tyr Asn Asp Glu Asn
    610                 615                 620

Lys Leu Ser Lys Ile Phe Leu Ser Thr Ser Thr Glu Leu Gln Arg Lys
625                 630                 635                 640

Lys Ala Tyr Lys Leu Asn Lys Met Ala Tyr Lys Lys Ile Thr Lys Gly
                645                 650                 655

Thr Lys Gly Glu Ala Asp Arg Ser Ile Pro Ser Leu Lys Pro Arg His
            660                 665                 670

Leu Phe Ser Gly Lys Arg Ser Ile Gly Lys Thr Ser Arg Arg
        675                 680                 685


<210> SEQ ID NO 712
<211> LENGTH: 487
<212> TYPE: PRT
<213> ORGANISM: Plasmodium vivax

<400> SEQUENCE: 712

Met Ile Lys Lys Gly Ser Leu Lys Ile Lys Asn Leu Ser Val Ala Lys
1               5                   10                  15

Asn Arg Val Asn Asn Val Lys Glu Asn Gly Arg Leu Ile Asn Lys Gly
            20                  25                  30

Asn Gly Gln Glu Lys Lys Glu Ala Glu Lys Leu Lys Arg Leu Lys Met
        35                  40                  45

Tyr Arg Thr Lys Ala Asn Leu Lys Lys Met Asn Gln Lys Ile Asn Glu
    50                  55                  60
```

Val Arg Arg Ile Glu Pro Ser Ile Lys Trp Phe Asn Asn Thr Arg Thr
65 70 75 80

Ile Ser Gln Asn Lys Leu Glu Ile Phe Arg Asn Lys Leu Glu Glu Thr
85 90 95

Thr His Asp Pro Phe Ser Ile Val Ile Lys Arg Ser Lys Ile Pro Val
100 105 110

Glu Leu Leu Lys Asp Glu Lys Asn Val Val Thr Lys Lys Tyr Lys Asn
115 120 125

Glu Asn Phe Leu Arg Ile Glu Lys Tyr His Asp Ile Tyr Ser Lys Lys
130 135 140

Lys Lys Arg Lys Lys Pro Lys Leu Asn Val Gly Thr Leu Glu Glu Tyr
145 150 155 160

Ala Lys Arg Ala Glu Gln Asn Leu Ser Thr Tyr Glu Thr Lys Asn Asp
165 170 175

Asn Ser Leu Ile Glu Lys Arg Asn Glu Ile Glu Lys Lys Phe Ser Lys
180 185 190

Asp Gln Leu Leu Lys Ile Gly Gln Ser Lys Arg Ile Trp Ala Glu Leu
195 200 205

Tyr Lys Val Ile Asp Ser Ser Asp Ile Leu Leu Gln Val Leu Asp Ala
210 215 220

Arg Asp Pro Ile Gly Thr Arg Cys Lys Lys Leu Glu Glu Thr Leu Lys
225 230 235 240

Lys Asp Arg Pro Asn Lys His Met Ile Leu Ile Leu Asn Lys Ile Asp
245 250 255

Leu Ile Pro Val Ser Val Ala Glu Lys Trp Ile Lys Ile Leu Ser Lys
260 265 270

Asp Tyr Pro Thr Ile Ala Tyr His Ala Asn Ile Asn Lys Pro Phe Gly
275 280 285

Lys Ser Asp Leu Phe Asn Ile Ile Arg Gln Tyr Thr Asp Phe Phe Lys
290 295 300

Ser Gln Lys Lys Lys His Ile His Ile Gly Leu Ile Gly Tyr Pro Asn
305 310 315 320

Val Gly Lys Ser Ala Ile Ile Asn Ser Leu Lys Lys Lys Val Val Cys
325 330 335

Ile Ser Ala Cys Ile Pro Gly Gln Thr Lys Tyr Trp Gln Phe Ile Lys
340 345 350

Leu Thr Asn Lys Ile Tyr Leu Ile Asp Cys Pro Gly Ile Val Pro Tyr
355 360 365

Asp Ile Glu Asp Ser Glu Lys Ile Leu Arg Cys Thr Met Arg Leu Glu
370 375 380

Lys Ile Thr Asn Pro His Phe Tyr Ile Asp Asp Ile Phe Lys Met Val
385 390 395 400

Asn Leu Ser Tyr Ile Leu Lys Ile Tyr Lys Leu Pro Glu Asp Leu Thr
405 410 415

Phe Lys Asn Ser Glu Glu Phe Leu Glu Ile Leu Ala Lys Lys Met Gly
420 425 430

Lys Leu Leu Lys Gly Gly Glu Pro Asp Ile Thr Ser Val Ser Lys Val
435 440 445

Ile Ile Asn Asp Trp Ile Lys Gly Lys Ile Pro Tyr Phe Val Asn Pro
450 455 460

Asp Lys Tyr Leu Thr Glu Gln Asp Lys Thr Gln Lys Asp Glu Lys Glu
465 470 475 480

Asp Lys Asn Glu Thr Asp Lys

485

<210> SEQ ID NO 713
<211> LENGTH: 213
<212> TYPE: PRT
<213> ORGANISM: Plasmodium vivax

<400> SEQUENCE: 713

Met Tyr Ile Ser Phe Ile Leu Phe Ser Ile Ile Phe Ile Phe Leu Gly
1 5 10 15

Val Ile Glu Asn Phe Ile Ile Asn Lys Arg Val Leu Tyr Lys Pro Asn
20 25 30

Phe Leu Leu Tyr Ser Glu Lys Lys Asn Lys Lys Lys Ser Thr Pro Glu
35 40 45

Gln Val Thr Thr Arg Val Asn Lys Asp Leu Lys Glu Lys Lys Arg Lys
50 55 60

Arg Pro Arg Ser Lys Ile Leu Glu Cys Leu Leu Lys Glu Lys Val Glu
65 70 75 80

Lys Val Glu Lys Val Glu Lys Asn Ser Asp Glu Asn Gln Cys Ser Asn
85 90 95

Val Asp Lys Glu Ile Arg Glu Gly Lys Arg Val Pro Arg Leu Arg Val
100 105 110

Arg Asn Thr Asn Asn His Ile Tyr Ala Ser Ile Ile Asp Asp Tyr Lys
115 120 125

Lys Tyr Val Leu Cys Ser Thr Cys Ser Arg Asp Ala Thr Leu Ser Lys
130 135 140

Ile Leu Gly Thr Tyr Arg Arg Lys Ala Thr Asn Arg Val Ile Asn Asn
145 150 155 160

Gly Arg Thr Ile Lys Ser Ala Trp Glu Ile Gly Lys Ile Ile Gly Lys
165 170 175

Lys Ala Leu Ser Lys Gly Ile Phe Lys Val Arg Phe Asp Arg Ala Arg
180 185 190

His Pro Tyr Ala Gly Lys Val Glu Ala Leu Ala Glu Gly Ala Arg Ala
195 200 205

Val Gly Leu Leu Leu
210

<210> SEQ ID NO 714
<211> LENGTH: 205
<212> TYPE: PRT
<213> ORGANISM: Plasmodium vivax

<400> SEQUENCE: 714

Met Gly Ala Tyr Lys Tyr Ile Gln Glu Ile Trp Lys Lys Lys Gln Ser
1 5 10 15

Asp Ala Met His Phe Leu Leu Arg Val Arg Thr Trp Glu Tyr Arg Gln
20 25 30

Leu Pro Val Val His Arg Val Ser Lys Pro Ser Arg Pro Asp Lys Ala
35 40 45

Arg Arg Leu Gly Tyr Lys Ala Ile Gln Gly Phe Val Ile Tyr Arg Val
50 55 60

Arg Val Arg Arg Gly Asp Arg Lys Lys Arg Val Lys Lys Gly Ile Val
65 70 75 80

His Gly Lys Pro Lys His Gln Gly Val His Lys Gln Lys Ser Thr Arg
85 90 95

Asn Leu Lys Ser Val Ala Glu Gly Lys Val Gly Lys Ser Ile Cys Gly

```
            100                 105                 110

Asn Leu Arg Val Leu Asn Ser Tyr Trp Val Gly Gln Asp Ala Val Tyr
        115                 120                 125

Lys Tyr Tyr Glu Val Ile Leu Val Asp Pro Asn His Asn Ala Val Arg
    130                 135                 140

Asn Asn Pro Lys Ile Asn Trp Ile Cys Asn Pro Val His Lys His Arg
145                 150                 155                 160

Glu Leu Arg Gly Leu Thr Ser Ala Gly Lys Lys Tyr Arg Gly Leu Arg
                165                 170                 175

Val Lys Gly His Leu Ser Ala Lys Ser Arg Pro Ser Ile Arg Ala Asn
            180                 185                 190

Trp Lys Arg Arg Gln Leu Ile Lys Leu Arg Lys Cys Arg
        195                 200                 205


<210> SEQ ID NO 715
<211> LENGTH: 92
<212> TYPE: PRT
<213> ORGANISM: Plasmodium vivax

<400> SEQUENCE: 715

Met Gly Lys Ala Gly Lys Gly Thr Gly Ser Phe Gly Lys Arg Asn Gly
1               5                   10                  15

Lys Thr His Phe Leu Cys Leu Arg Cys Gly Lys Arg Ser Tyr His Leu
            20                  25                  30

Gln Lys Lys Lys Cys Ala Ser Cys Gly Tyr Pro Ser Ala Lys Lys Arg
        35                  40                  45

Arg Phe Asn Trp Ser Val Lys Ala Lys Arg Arg Asn Thr Thr Gly Thr
    50                  55                  60

Gly Arg Cys Arg Tyr Ile Lys Thr Leu Arg Arg Lys Leu Lys Asn Lys
65                  70                  75                  80

Phe Thr Glu Gly Ser Thr Pro Lys Pro Lys Gln Arg
                85                  90


<210> SEQ ID NO 716
<211> LENGTH: 155
<212> TYPE: PRT
<213> ORGANISM: Plasmodium vivax

<400> SEQUENCE: 716

Met Pro Lys Asn Lys Gly Lys Gly Gly Lys Asn Arg Arg Arg Gly Lys
1               5                   10                  15

Asn Asp Asn Glu Gly Glu Lys Arg Glu Leu Leu Tyr Lys Glu Glu Asp
            20                  25                  30

Gln Glu Tyr Ala Gln Val Leu Arg Met Leu Gly Asn Gly Arg Leu Glu
        35                  40                  45

Ala His Cys Phe Asp Gly Val Lys Arg Leu Cys His Ile Arg Gly Lys
    50                  55                  60

Met Arg Lys Arg Val Trp Ile Asn Ser Gly Asp Ile Ile Leu Val Ser
65                  70                  75                  80

Leu Arg Asp Tyr Gln Asp Ser Lys Ala Asp Val Ile Ala Lys Tyr Thr
                85                  90                  95

Pro Asp Glu Ala Arg Ser Leu Lys Ala His Gly Glu Leu Pro Glu Thr
            100                 105                 110

Ala Lys Ile Asn Glu Thr Asp Ile Phe Asp Asp Asp Gly Gln Asn Gly
        115                 120                 125

Val Glu Phe Leu Asp Asp Glu Ser Asp Glu Glu Ala Gln Glu Glu Met
```

```
    130                 135                 140

Asn Asn Ala Arg Arg Leu Asp Ile Glu Asp Ile
145                 150                 155


<210> SEQ ID NO 717
<211> LENGTH: 149
<212> TYPE: PRT
<213> ORGANISM: Plasmodium vivax

<400> SEQUENCE: 717

Met Lys Ile Leu Ile Asn Ile Pro Tyr Asp Glu Ser Leu Cys Leu Glu
1               5                   10                  15

Ser Ser Asn Ile Asn Asn Ile Lys Asn Val Lys Glu Gln Ile Phe Glu
            20                  25                  30

Leu Lys Gly Ile Pro Tyr Glu Leu Gln Lys Leu Tyr Lys Asn Gly Arg
        35                  40                  45

His Leu Glu Asp Glu Glu Leu Leu Glu Ile Asp Lys Ser Asp Tyr Ala
    50                  55                  60

Tyr Thr Leu Asn Leu Asn Phe Gly Leu Leu Gly Gly Ala Lys Lys Lys
65                  70                  75                  80

Lys Lys Lys Val Tyr Lys Lys Pro Lys Lys Glu Lys His Lys Lys Lys
                85                  90                  95

Lys Val Lys Leu Ala Val Leu Lys Phe Tyr Lys Val Gly Asp Asp Gly
            100                 105                 110

Lys Val Phe Arg Leu Lys Arg Gln Cys Asp Asn Cys Ala Pro Gly Thr
        115                 120                 125

Leu Met Ala Ser His Phe Asp Arg Asp Tyr Cys Gly Arg Cys His Leu
    130                 135                 140

Thr Ile Met Lys Lys
145


<210> SEQ ID NO 718
<211> LENGTH: 128
<212> TYPE: PRT
<213> ORGANISM: Plasmodium vivax

<400> SEQUENCE: 718

Met Gln Ile Phe Val Lys Thr Leu Thr Gly Lys Thr Ile Thr Leu Asp
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Ala Ile Glu Pro
65                  70                  75                  80

Ser Leu Ala Gln Leu Ala Gln Lys Tyr Asn Cys Gln Lys Leu Ile Cys
                85                  90                  95

Arg Lys Cys Tyr Ala Arg Leu His Pro Arg Ala Thr Asn Cys Arg Asn
            100                 105                 110

Lys Lys Cys Gly Arg Thr Asn Gln Leu Arg Pro Lys Lys Lys Leu Lys
        115                 120                 125


<210> SEQ ID NO 719
<211> LENGTH: 103
<212> TYPE: PRT
```

<213> ORGANISM: Plasmodium vivax

<400> SEQUENCE: 719

Met Ser Gly Arg Gly Lys Gly Gly Lys Gly Leu Gly Lys Gly Gly Ala
1 5 10 15

Lys Arg His Arg Lys Ile Leu Arg Asp Asn Ile Gln Gly Ile Thr Lys
20 25 30

Pro Ala Ile Arg Arg Leu Ala Arg Arg Gly Gly Val Lys Arg Ile Ser
35 40 45

Gly Leu Ile Tyr Glu Glu Ile Arg Gly Val Leu Lys Val Phe Leu Glu
50 55 60

Asn Val Ile Lys Asp Ser Ile Met Tyr Thr Glu His Ala Lys Arg Lys
65 70 75 80

Thr Val Thr Ala Met Asp Ile Val Tyr Ser Leu Lys Arg Gln Gly Arg
85 90 95

Thr Leu Tyr Gly Phe Gly Gly
100

<210> SEQ ID NO 720
<211> LENGTH: 136
<212> TYPE: PRT
<213> ORGANISM: Plasmodium vivax

<400> SEQUENCE: 720

Met Ala Arg Thr Lys Gln Thr Ala Arg Lys Ser Thr Ala Gly Lys Ala
1 5 10 15

Pro Arg Lys Gln Leu Ala Ser Lys Ala Ala Arg Lys Ser Ala Pro Ile
20 25 30

Ser Ala Gly Ile Lys Lys Pro His Arg Tyr Arg Pro Gly Thr Val Ala
35 40 45

Leu Arg Glu Ile Arg Arg Tyr Gln Lys Ser Thr Asp Leu Leu Ile Arg
50 55 60

Lys Leu Pro Phe Gln Arg Leu Val Arg Glu Ile Ala Gln Asp Tyr Lys
65 70 75 80

Thr Asp Leu Arg Phe Gln Ser Ser Ala Val Met Ala Leu Gln Glu Ala
85 90 95

Ala Glu Ala Tyr Leu Val Gly Leu Phe Glu Asp Thr Asn Leu Cys Ala
100 105 110

Ile His Ala Lys Arg Val Thr Ile Met Pro Lys Asp Ile Gln Leu Ala
115 120 125

Arg Arg Ile Arg Gly Glu Arg Ser
130 135

<210> SEQ ID NO 721
<211> LENGTH: 133
<212> TYPE: PRT
<213> ORGANISM: Plasmodium vivax

<400> SEQUENCE: 721

Met Ser Ala Lys Gly Lys Thr Gly Arg Lys Lys Ala Val Lys Gly Thr
1 5 10 15

Ser Asn Ser Ala Lys Ala Gly Leu Gln Phe Pro Val Gly Arg Ile Gly
20 25 30

Arg Tyr Leu Lys Lys Gly Lys Tyr Ala Lys Arg Val Gly Ala Gly Ala
35 40 45

Pro Val Tyr Leu Ala Ala Val Leu Glu Tyr Leu Cys Ala Glu Ile Leu
50 55 60

```
Glu Leu Ala Gly Asn Ala Ala Arg Asp Asn Lys Lys Ser Arg Ile Thr
65                  70                  75                  80

Pro Arg His Ile Gln Leu Ala Val Arg Asn Asp Glu Glu Leu Asn Lys
                85                  90                  95

Phe Leu Ala Gly Val Thr Phe Ala Ser Gly Gly Val Leu Pro Asn Ile
            100                 105                 110

His Asn Val Leu Leu Pro Lys Lys Ser Gln Leu Lys Ser Gly Ala Thr
        115                 120                 125

Ala Asn Gln Asp Tyr
    130


<210> SEQ ID NO 722
<211> LENGTH: 158
<212> TYPE: PRT
<213> ORGANISM: Plasmodium vivax

<400> SEQUENCE: 722

Met Glu Val Pro Gly Lys Val Ile Gly Gly Lys Val Gly Gly Lys Val
1               5                   10                  15

Gly Gly Lys Val Leu Gly Leu Gly Lys Gly Gly Lys Gly Lys Thr Gly
            20                  25                  30

Ser Gly Lys Thr Lys Lys Ala Pro Leu Ser Arg Ala Ser Arg Ala Gly
        35                  40                  45

Leu Gln Phe Pro Val Gly Arg Val His Arg Met Leu Lys Thr Arg Ile
    50                  55                  60

Ser Ser Asp Gly Arg Val Gly Ser Thr Ala Ala Val Tyr Ala Ala Ala
65                  70                  75                  80

Ile Leu Glu Tyr Leu Thr Ala Glu Val Leu Glu Leu Ala Gly Asn Ala
                85                  90                  95

Thr Lys Asp Leu Lys Val Lys Arg Ile Thr Pro Arg His Leu Gln Leu
            100                 105                 110

Ala Ile Arg Gly Asp Glu Glu Leu Asp Thr Leu Ile Lys Ala Thr Ile
        115                 120                 125

Ala Gly Gly Gly Val Ile Pro His Ile His Lys Ala Leu Met Asn Lys
    130                 135                 140

Val Pro Val Pro Pro Thr Gln Ala Lys Lys Pro Lys Lys Asn
145                 150                 155
```

VACCINE IMMUNOGENS

The material contained in the Sequence Listing provided herewith in ASCII compliant format in the text file entitled "220553_23 ST25_06182025.txt created on Jun. 18, 2025 and containing 518,559 bytes, is hereby incorporated by reference herein.

The invention relates to immunogenic proteins or fragments thereof derived from *Plasmodium falciparum* and/or *Plasmodium vivax* for use in the treatment or prevention of malaria.

Malaria is a serious and life-threatening mosquito-borne infectious disease caused by parasitic protozoans of the genus *Plasmodium*. In 2018, there were approximately 500,000 deaths from malaria mainly caused by *Plasmodium falciparum*. Whilst preventive small molecule based medicines exist to prevent malaria, such as chloroquine, they can be associated with significant side-effects, they are unsuitable for long-term use, and drug resistance is increasingly problematic. Vaccination programs have proven to be effective in the reduction and eradication of various diseases worldwide. The aim is to develop an effective malaria vaccine, which is urgently needed. However, current single-component vaccines lack sufficient efficacy for deployment in the field. The two leading malaria vaccine candidates, RTS,S and ChAd63-MVA ME-TRAP, are both sub-unit vaccines targeting the pre-erythrocytic phase of malaria. Whilst neither vaccine currently provides optimal protective efficacy for deployment in endemic countries, they both demonstrate the strength of targeting the pre-erythrocytic phase, as no blood-stage vaccine has progressed as far as in clinical development.

The most advanced vaccine in clinical development, RTS,S/AS01, has completed a phase III trial in African infants and children, where efficacy in young infants was <20% and in 5-17 month olds was 35%. This vaccine is based on a platform in which RTS,S has four molecules of unfused HBsAg (Hepatitis B surface antigen) for each fusion protein containing HBsAg fused to the C-terminal half of the circumsporozoite protein (CSP). The vaccine works by inducing production of a high titre of antibodies against the central four amino acid conserved repeat of the circumsporozoite protein (CSP) of the malaria sporozoites. But as antibody titres fall over time, protection is reduced and then lost. There have also been suggestions of possible safety issues in the phase III trial and also uncertainty about logistic deployability which has led to a delay in WHO prequalification, licensure and deployment of this vaccine.

Vaccination with irradiated sporozoites delivered by mosquito bite has been considered the 'gold-standard' of malaria vaccines, as whilst it is impractical for deployment, this regimen has repeatedly shown sterile protection in vaccinated volunteers. The increased efficacy of irradiated sporozoite immunization over sub-unit vaccines is likely because immune responses are induced to a broad range of antigenic targets. However, perhaps not only multiple targets are needed to create an efficacious sub-unit vaccine, but also better targets than those traditionally focused on (e.g. CSP and TRAP). Over 5000 different proteins are expressed throughout the *Plasmodium* life-cycle, leading to a high probability that alternative target antigens other than CSP or TRAP may exist, or a target antigen to be used alongside CSP or TRAP in a multicomponent vaccination strategy.

Several approaches are being utilised to try and produce an improved or alternative vaccine. One such approach may be to target the pre-erythrocytic, liver stage of the life cycle of the parasite. This type of malaria vaccine, unlike those described above, targets not the sporozoites themselves but the liver-stage parasite that grows in hepatocytes for approximately seven days after sporozoites successfully infect the liver.

The second part of the pre-erythrocytic stage (the liver-stage) ends with the emergence of large numbers of merozoites from each hepatocyte seven days after infection of the hepatocyte. Typically about 20,000 parasites emerge from each hepatocyte and rapidly invade erythrocytes, to start the blood-stage of infection. If the blood-stage is not controlled rapidly, the infected individual develops malaria and may die from the disease. Clearly, pre-erythrocytic vaccines have the potential advantage of stopping the malaria infection before any blood-stage infection occurs and when the number of potentially infected host cells is small.

A particularly promising approach to malaria liver-stage vaccine development has been to use recombinant non-replication-competent viral vectors such as adenoviral vectors or attenuated vaccine vectors, for example simian or human adenoviruses and modified vaccinia Ankara (MVA). Plasma DNA vectors and RNA-based vectors have also been tested but have yet to show clear clinical efficacy when used alone, but may usefully be used in heterologous prime boost regimens with viral vectors. Viral vectors appear to be particularly effective against the liver-stage because of their ability in inducing a cellular immune response, specifically malaria-specific CD8+ T cells that can target and kill malaria-infected hepatocytes.

CD8+ T cells recognise peptide antigens that are displayed on the surface of major histocompatibility complex (MHC) class I molecules, also known as HLA class I molecules in humans, on the surface of infected cells. CD8+ T cells, which are highly cytolytic, are strongly implicated in anti-malaria immunity at the liver stage. In some vaccine trials, the number of vaccine-induced malaria-specific CD8+ T cells has been shown to correlate with liver stage vaccine efficacy in humans, consistent with many experimental animal vaccine studies which have demonstrated this protective mechanism.

Because of this correlation, a so-called heterologous prime-boost vaccination regime is frequently used. This involves sequential immunisation with two different viral vectors encoding the same malaria antigen(s) or epitope(s). The vectors may be replication competent but preferentially are non-replication competent. This generates higher numbers of circulating CD8+ T cells compared to use of a single vector alone or with repeated administrations and leads to much higher vaccine efficacy in many clinical trials. A recent further development of liver-stage immunisation approaches has been to use a so-called prime-target immunisation regime. This involves administering the last dose of viral vector by an intravenous route (or other route that leads to antigen deposition in the liver) and has been found to increase the number of malaria-specific CD8+ T cells amongst the resident memory T cell population in the liver. Importantly, this generally leads to substantially greater vaccine efficacy (see WO2017/178809).

However, a challenge in developing effective liver-stage vaccines against malaria has been in identifying suitable target antigens to induce strong protective effects.

Murine malaria models exist but these are not helpful for studying *P. falciparum* infection in humans, and many antigens in *P. falciparum* have no homologues in the rodent parasites. Furthermore, hundreds or perhaps thousands of the 5000 or so genes in the *P. falciparum* genome are likely expressed in the liver and there has been no way of finding out which of these is a good vaccine immunogen. However, it is likely that only a small number or minority of the many genes expressed in the liver by *P. falciparum* produce proteins that end up as peptides presented by MHC class 1 molecules on the infected liver cell surface. These are the potential targets of vaccine-induced T cells whereas antigens that do not reach the surface in MHC molecules cannot be protective when using a liver stage vaccine. Because parasite antigens in the liver are inside a parasitophorous vacuole, which is surrounded by a parasitophorous vacuole (PV) membrane, most parasite antigens will be unable to reach the liver cell cytoplasm where they can be degraded, loaded on the MHC molecules and transported to the hepatocyte surface. Due to various technical difficulties limiting the ability of identification of the MHC-peptide complexes on the liver-cell surface directly, it has not been possible to determine which *P. falciparum* antigens/immunogens would be suitable liver-stage vaccine antigens/immunogens. These difficulties include:

- in vitro only a small number of liver cells can be infected by *P. falciparum* and the excess of self-peptides from non-infected and also infected cells makes identification of parasite peptides very difficult, even using state of the art mass spectrometry techniques to sequence eluted peptides;
- direct analysis of infected human livers (where only a tiny proportion of cells is infected) with ongoing malaria liver-stage infection is not practicable;
- separation of parasitized liver cells from non-infected ones has proven difficult in the absence of suitable labelled parasites for use as tools; and
- many hundreds of thousands, millions, or even billions of infected cells are required to allow a reasonable number of infected hepatocytes to be studied.

Further, as it has been possible to achieve higher efficacy in humans by immunizing with whole irradiated sporozoites, it is widely believed that there may well be other, more protective, immunogens yet to be identified that are expressed by the *Plasmodium* parasite inside liver cells, which when used as vaccines would be more suitable and effective.

Therefore, it would be desirable to provide alternative immunogens, and improved delivery and vaccination methods for eliciting a protective immune response against malaria.

The inventors have identified proteins and peptides which are presented on HLA class I molecules of *Plasmodium* infected cells. Surprisingly, a large proportion (approx. 57%) are derived from ribosomal proteins or ribosomal associated proteins of the parasite, many of which are highly conserved between *Plasmodium* species. The peptides have been shown to be effective immunogens capable of producing a protective cellular response against the *Plasmodium* parasite, and provide a new class of immunogens useful in vaccines, in particular against malaria.

The present invention provides novel immunogens which may be used in vaccine compositions; in particular the invention provides novel immunogens which may be used in vaccine compositions for use against malaria, preferably wherein the vaccine targets the CD8+ T cell immunological response, both at liver and blood stage.

According to a first aspect of the invention, there is provided one or more *Plasmodium*-derived proteins or immunogenic fragments thereof for use in eliciting an immune response in a subject. The one or more *Plasmodium*-derived protein or immunogenic fragment thereof may be, or may be derived from, a ribosomal protein or ribosomal associated protein. The one or more *Plasmodium*-derived protein or immunogenic fragment thereof may be, or may be derived from, a malarial early transcribed membrane protein (ETRAMP) or a histone. The one or more *Plasmodium*-derived protein or immunogenic fragment thereof may be, or may be derived from, a protein recited in FIG. 1, or a protein or a peptide recited in FIG. 2 or FIG. 3.

The one or more *Plasmodium*-derived protein or immunogenic fragment thereof may be derived from *Plasmodium falciparum* and/or from *Plasmodium vivax*.

The invention may provide one or more *Plasmodium falciparum* or *Plasmodium vivax* proteins or immunogenic fragments thereof for use in raising an immune response in a subject. The one or more *Plasmodium*-derived protein or immunogenic fragment thereof may be, or may be derived from, a ribosomal protein or ribosome associated protein. The one or more *Plasmodium*-derived protein or immunogenic fragment thereof may be, or may be derived from, a malarial early transcribed membrane protein (ETRAMP) or a histone. The one or more *Plasmodium*-derived protein or immunogenic fragment thereof may be, or may be derived from, a protein recited in FIG. 1, or a protein or a peptide recited in FIG. 2 or FIG. 3. The immune response elicited may be to prevent or treat malaria.

In a further aspect, the invention provides an immunogenic composition comprising:

a) one or more *Plasmodium*-derived protein or immunogenic fragment thereof; and/or
b) a polynucleotide encoding one or more *Plasmodium*-derived protein or immunogenic fragment thereof. The one or more *Plasmodium*-derived protein or immunogenic fragment thereof may be, or may be derived from, a ribosomal protein or ribosomal associated protein. The one or more *Plasmodium*-derived protein or immunogenic fragment thereof may be, or may be derived from, an ETRAMP or a histone. The one or more *Plasmodium*-derived protein or immunogenic fragment thereof may be, or may be derived from, a protein recited in FIG. 1, or a protein or a peptide recited in FIG. 2 or FIG. 3.

The immunogenic composition may further comprise a pharmaceutically acceptable excipient or carrier. The one or more *Plasmodium*-derived protein or immunogenic fragment thereof may be derived from *Plasmodium falciparum* and/or from *Plasmodium vivax*. The immunogenic composition may be used as a vaccine to treat or prevent malaria.

In another aspect the invention provides a method of eliciting an immune response in a subject, the method comprising the step of administering an immunogenic composition according to the invention to the subject. Preferably the immune response elicited is sufficient to treat or prevent malaria.

In a further aspect of the invention, there is provided an immunogenic composition according to the invention for use in treating or preventing malaria.

In a further aspect of the invention, there is provided an immunogenic composition according to the invention for use in the preparation of a medicament for treating or preventing malaria.

The immune response elicited in a subject by a composition according to the invention may be against malaria. Suitably, the immune response elicited may be sufficient to treat or prevent malaria caused by infection with *Plasmodium falciparum* and/or *Plasmodium vivax*. The malaria may comprise liver-stage malaria. The malaria may comprise pre-erythrocytic-stage malaria. The malaria may comprise erythrocytic-stage malaria.

The immune response elicited by a composition of the invention may be a protective immune response. Suitably, the protective immune response induces the activation of CD8+ T-cells. Where the immunogen is or is derived from a ribosomal protein or a ribosomal associated protein, or an ETRAMP, or a histone, or a protein recited in FIG. 1, or a protein or a peptide recited in FIG. 2 or FIG. 3, or a fragment thereof derived from *Plasmodium falciparum* and/or from *Plasmodium vivax*, the protective immune response elicited may treat or prevent malaria, in particular the immune response may activate CD8+ T-cells which may induce cytotoxicity of *Plasmodium falciparum* and/or *Plasmodium vivax* infected hepatocytes and infected reticulocytes.

The term "protective immune response" used herein, may be understood to be a host immune response that can sterilise the *Plasmodium* infection in a subject or reduce the number of parasites emerging from the liver (so that they are more readily cleared by blood-stage immunity). The protective immune response may sterilise the *Plasmodium* infection in at least 20% of subjects treated. The protective immune response may sterilise the *Plasmodium* infection in at least 35% of subjects treated. The protective immune response may sterilise the *Plasmodium* infection in at least 40% of subjects treated. The protective immune response may sterilise the *Plasmodium* infection in at least 50% of subjects treated. The protective immune response may sterilise the *Plasmodium* infection in at least 60% of subjects treated.

The protective immune response may provide clinical benefit in a subject by preventing the development of clinical malaria of a chronic parasitaemia. A protective immune response may comprise at least 0.1% of CD8+ T cells being antigen/immunogen-specific as determined, for example, by flow cytometry staining, and/or at least 500 spot forming cells (SFU) per million peripheral blood mononuclear cells (PBMC). Spot forming cells (SFU) may be determined by an ELISpot assay (enzyme-linked immunosorbent spot assay (For example the ELISpot assay provided by Mabtech AB, Sweden, see: http://www.mabtech.com/Main/Page.asp?PageId=16).

A protective immune response may comprise at least 0.2% of CD8+ T cells being antigen/immunogen-specific. A protective immune response may comprise at least 0.4% of CD8+ T cells being antigen/immunogen-specific. A protective immune response may comprise at least 0.8% of CD8+ T cells being antigen/immunogen-specific. A protective immune response may comprise at least 1% of CD8+ T cells being antigen/immunogen-specific.

A protective immune response may comprise at least 100 spot forming cells (SFU) per million peripheral blood mononuclear cells (PBMC). A protective immune response may comprise at least 300 spot forming cells (SFU) per million peripheral blood mononuclear cells (PBMC). A protective immune response may comprise at least 1000 spot forming cells (SFU) per million peripheral blood mononuclear cells (PBMC). A protective immune response may comprise at least 2000 spot forming cells (SFU) per million peripheral blood mononuclear cells (PBMC).

The *Plasmodium*-derived protein or immunogenic fragment thereof may have a sequence which is 80%, 85%, 90%, 95%, 98%, 99% or 100% identical to a protein or a fragment of a protein recited in FIG. 1, or a peptide recited in FIG. 2 or FIG. 3.

The *Plasmodium*-derived protein or immunogenic fragment thereof may have a sequence which is 80%, 85%, 90%, 95%, 98%, 99% or 100% identical to a protein or a fragment of a protein recited in FIG. 2 or FIG. 3.

The *Plasmodium*-derived protein or immunogenic fragment thereof may have a sequence which is 80%, 85%, 90%, 95%, 98%, 99% or 100% identical to a 40S ribosomal protein, preferably the 40S ribosomal protein S20e or a fragment of the 40S ribosomal protein S20e. The 40S ribosomal protein S20e may be derived from *P. falciparum* (Accession Q8IK02) or *P. vivax* (Accession A5K757). Preferably, the 40S ribosomal protein S20e is derived from *P. falciparum* (Accession Q8IK02).

The *Plasmodium*-derived protein or immunogenic fragment thereof may have a sequence which is 80%, 85%, 90%, 95%, 98%, 99% or 100% identical to an ETRAMP or a fragment of an ETRAMP. The ETRAMP may be derived from *P. falciparum* or P. *Vivax*. Preferably, the ETRAMP is derived from *P. vivax* (Accession A5KBH5 and A5K676).

The *Plasmodium*-derived protein or immunogenic fragment thereof may have a sequence which is 80%, 85%, 90%, 95%, 98%, 99% or 100% identical to a protein or a fragment of a protein selected from:

the 40S ribosomal protein S20e (Accession A5K757)
60S ribosomal subunit protein L4/L1, putative (Accession A5K AZ9)
40S ribosomal protein S25, putative (Accession A5K124)
Early transcribed membrane protein (ETRAMP) (Accession A5K676)
Early transcribed membrane protein (ETRAMP) (Accession A5KBH5)
40S ribosomal protein S2, putative (Accession A5K3U1)
60S ribosomal protein L9, putative (Accession A5K306)
60S ribosomal protein L30, putative (Accession A5KCD7)
40S ribosomal protein S23, putative (Accession A5KB86)
40S ribosomal protein S30 (Accession A5KBT5)
60S ribosomal protein L29 (Accession A5K3F2)
40S ribosomal protein S6, putative (Accession A5K858)
40S ribosomal protein S8 (Accession A5K1E3)
60S ribosomal protein L13, putative (Accession A5JZN9)
60S ribosomal protein L23a, putative (Accession A5K303)
Ribosomal protein L37 (Accession A5KA70)
40S ribosomal protein S11, putative (Accession A5K7Q0)
Histone H2A (Accession A5K214)
Histone H3 (Accession A5K1U7).

Accession numbers, where given, relate to those identifiable using UniProt (Universal Protein Resource), a comprehensive catalogue of information on proteins ('UniProt: a hub for protein information' Nucleic Acids Res. 43: D204-D212 (2015)).

Due to a high level of sequence conservation across the *Plasmodium* species, a high level of sequence homology exists between many *Plasmodium*-derived proteins, including ribosomal proteins and ribosomal associated proteins, of *Plasmodium falciparum* and *Plasmodium vivax*. A *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof, derived from either *Plasmodium falciparum* or *Plasmodium vivax* may therefore be cross-reactive in raising an immune response in a subject. Suitably, a *Plasmodium*-derived protein or immunogenic fragment thereof, such as a ribosomal protein or ribosomal associated protein or an ETRAMP, or a hi stone, or a protein or peptide of FIG. 1, FIG. 2 or FIG. 3, or an immunogenic fragment thereof derived from *Plasmodium falciparum* may be suitable for use in eliciting an immune response to treat or prevent malaria in a subject infected with either *Plasmodium falciparum* or *Plasmodium*

*vivax*. Suitably, a *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof derived from *Plasmodium vivax* may be suitable for use in eliciting an immune response to treat or prevent malaria in a subject infected with either *Plasmodium falciparum* or *Plasmodium vivax.*

The term "fragment" encompasses immunogenic and/or antigenic fragments of a *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3. Preferably the fragments elicit an immune response when administered to a subject sufficient to generate a protective immune response. The fragment may be derived from a ribosomal protein or ribosomal associated protein, or an ETRAMP, or histone, or a protein or peptide of FIG. 1, FIG. 2 or FIG. 3, from *Plasmodium falciparum* and/or from *Plasmodium vivax*, and the protective immune response elicited may be sufficient to treat or prevent malaria. The fragment is preferably from about 5 to about 20 amino acids long, preferably from about 7 to about 15 amino acids long. The fragment may have a sequence which is 80%, 85%, 90%, 95%, 98%, 99% or 100% identical to a peptide recited in FIG. 2 or FIG. 3.

Percentage sequence identity is defined as the percentage of amino acids in a sequence that are identical with the amino acids in a provided sequence after aligning the sequences and introducing gaps if necessary to achieve the maximum percent sequence identity. Alignment for the purpose of determining percent sequence identity can be achieved in many ways that are well known to the man skilled in the art, and include, for example, using BLAST (National Center for Biotechnology Information Basic Local Alignment Search Tool).

Variations in percent identity may be due, for example, to amino acid substitutions, insertions or deletions.

The *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof may include one or more conservative amino acid substitutions—the term "conservative substitution" embracing the act of replacing one or more amino acids of a protein or peptide with an alternate amino acid with similar properties and which does not substantially alter the physiochemical properties and/or structure or function of the native (or wild type) protein, for example the substitution of leucine with isoleucine is a conservative substitution. Other conservative substitutions include: Ala→Gly, Ser, Val; Arg→Lys; Asn→Gln, His; Asp→Glu; Cys→Ser; Gln→Asn; Glu→Asp; Gly→Ala; His→Arg, Asn, Gln; Ile→Leu, Val; Leu→Ile, Val; Lys→Arg, Gln, Glu; Met→Leu, Tyr, He; Phe→Met, Leu, Tyr; Ser→Thr; Thr→Ser; Trp→Tyr; Tyr→Trp, Phe; Val→He, Leu. Other substitutions are also permissible and can be determined empirically or in accord with other known conservative or non-conservative substitutions.

The skilled person will be readily able to determine the polynucleotide sequence that would be needed to encode the immunogen. Of course, one of skill will appreciate that the degeneracy of the genetic code permits substitution of one or more bases in a codon without changing the primary amino acid sequence encoded. The skilled person will also appreciate the existence of codon bias and may tailor any polynucleotide sequence to the organism in which it will be expressed, preferably a human.

A polynucleotide encoding the *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof may be codon optimised. The codon optimisation may be for optimal translation in a mammalian host cell, such as a human host cell.

The polynucleotide in the immunogenic composition may be provided in a vector. The vector may be a viral vector. Alternatively the polynucleotide may be provided in a plasmid DNA vector or as an RNA vector-based immunogen.

The polynucleotide may be expressed as a protein in a variety of cells that are known in the field (*Pichia*, human cell lines, simian cell lines, insect cell lines, bacterial host etc.). The expressed protein encoded by the polynucleotide may be delivered as a vaccine, typically in combination with an adjuvant. Adjuvants and adjuvant formulations are well known, such as alum, AS01, matrix-M, MF59, GLA, Hiltonol and others.

In an aspect, the invention may provide a vector comprising a polynucleotide encoding one or more *Plasmodium*-derived protein or immunogenic fragment thereof, such as a ribosomal protein or ribosomal associated protein, or an ETRAMP, or a histone or a protein or peptide of FIG. 1, FIG. 2 or FIG. 3, or an immunogenic fragment thereof as defined herein. The vector may be a live vector, such as a viral vector or a eukaryotic vector. The vector may be a viral vector, a DNA vector or an RNA vector.

In a further aspect the invention may provide an immunogenic composition comprising a vector of the invention, and optionally a pharmaceutically acceptable carrier or excipient. The vector may be a viral vector.

In a yet further aspect the invention may provide an immunogenic composition comprising a vector according to the invention and a pharmaceutically acceptable carrier for use as a vaccine.

The vector may be a virus (viral vector) or a protozoa parasite capable of delivering a polynucleotide encoding one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof into a host cell, such as a mammalian host cell, for example a liver cell such as a hepatocyte. The genetic material may be heterologous nucleic acid, which is not naturally encoded by the vector and/or the host cell. The vector may be modified by mutation to reduce its pathogenicity. The vector may be modified to encode an immunogenic protein or fragment thereof, in particular one or more ribosomal protein or ribosomal associated protein, or an ETRAMP, or a histone, or a protein or peptide of FIG. 1, FIG. 2 or FIG. 3, or an immunogenic fragment thereof according to the invention. The vector may be a viral vector and may comprise an adenovirus. Suitably, the vector is configured to express one or more immunogens, for example one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof according to the invention.

The viral vector may comprise a Modified Vaccinia Ankara (MVA) virus. The viral vector may be selected from any of the group comprising, a poxvirus, such as Modified Vaccinia Ankara (MVA) virus, or an adenovirus. The adenovirus may comprise a simian or human adenovirus. The adenovirus may comprise a Group E adenovirus. The adenovirus may comprise ChAd63 or ChAd3 or ChAdOx1 or ChAdOx2 or gorilla-derived adenoviruses. The adenovirus may comprise ChAdOx1. The adenovirus may comprise a group A, B, C, D or E adenovirus. The adenovirus may comprise Ad35, Ad5, Ad6, Ad26, or Ad28. The adenovirus may be of simian (e.g. chimpanzee, gorilla or bonobo) origin. The adenovirus may comprise any of ChAd63, ChAdOx1, ChAdOx2, C6, C7, C9, PanAd3, or ChAd3. The protozoa vector may comprise a *Trypanosoma cruzi*. The viral vector may be selected from any of the group comprising, a Trypanosomatidae, such as *Trypanosoma cruzi*, or *Leishmania*. The *Trypanosoma cruzi* may comprise *Trypanosoma cruzi* CL-14. The composition may comprise two or more different vectors. One or more of the vectors may be live vectors. One or more of the vectors may be viral vectors.

The *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof may be administered to a subject as a vaccine in a single dose vaccination regime or as a multi-dose regimen, for example a prime-boost vaccination regime, or a prime-target vaccination regime.

In a single dose vaccination regime the *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof, may be administered as a protein/peptide or via a polynucleotide which enables the one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof to be expressed in a host subject after administration. Where the one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof is administered as a polynucleotide for expression, the polynucleotide may be provided in a vector as described herein. The vector may be a live vector. The vector may be a viral vector. The administration may be a single dose vaccination regime using just the adenoviral vector, or the MVA vector, or a mixture of both. The administration may be a single dose vaccination regime using just *Trypanosoma cruzi*.

The administration may be part of a prime-boost vaccination regime in a subject, where a first/prime administration of the immunogenic composition of the invention is followed by a second/boost administration of the immunogenic composition of the invention.

The administration may be part of a prime-target vaccination regime in a subject, where a first/prime administration of the immunogenic composition of the invention is followed by a second/boost administration of the immunogenic composition of the invention, wherein the boost dose is administered by an intravenous route or other route that leads to antigen deposition in the liver.

Additional boost vaccinations may be provided. Alternatively only one of the prime and boosts may comprise a composition of the invention. Alternatively, only a single dose of the vaccine may be required to induce protective immunity.

Where the immunogenic composition is intended for a multiple administration regime, such as a prime-boost regime or prime-target regime, the different administration may comprise identical or different immunogenic compositions or vaccines or pharmaceutical compositions. Where the immunogenic composition is intended for a prime-boost or prime-target administration regime, the prime composition may comprise the same or different viral vector as the boost composition. The same immunogenic composition may be used for both prime and boost administrations. A different immunogenic composition or vaccine may be used for the prime and boost administrations.

The viral vector of the first/prime administration may comprise adenovirus. The viral vector of the second/boost administration may comprise poxvirus, such as MVA, or adenovirus.

The second/boost administration may be between about 1 day and about 30 days after the first/prime administration. The second/boost administration may be about 14 days after the first/prime administration.

Additional administrations of the immunogenic composition of the invention may be provided.

Suitable doses of adenoviral vectors for immunising humans are about $1\times10^8$ to about $1\times10^{11}$ viral particles. Suitable doses of MVA for immunising humans are about $1\times10^7$ pfu to about $1\times10^9$ pfu. These vectors may be given by a range of immunisation routes, typically intramuscular and intravenous, but also for example subcutaneous, intradermal, intranasal and aerosol.

According to a yet further aspect, the invention provides a host cell comprising a vector, preferably a viral vector, according to the invention. The host cell may be in vitro. The host cell may be infected with the viral vector of the invention, or may comprise and express a polynucleotide of the invention.

Suitable vectors can be chosen or constructed, containing appropriate regulatory sequences, including promoter sequences, terminator sequences, polyadenylation sequences, enhancer sequences, invariant chain sequences, marker genes and other sequences as appropriate. For further details see, for example, (Sambrook, J., E. F. Fritsch, and T. Maniatis. (1989), Molecular cloning: a laboratory manual, 2nd ed. Cold Spring Harbor Laboratory, Cold Spring Harbor, New York). Many known techniques and protocols for manipulation of nucleic acid, for example in preparation of nucleic acid constructs, mutagenesis, sequencing, introduction of DNA into cells and gene expression, and analysis of proteins, are described in detail in (Ausubel et al., Current protocols in molecular biology. New York: Greene Publishing Association; Wiley-Interscience, 1992). A polynucleotide of the invention may be expressed using any suitable expression system, for example in a suitable host cell infected with a viral vector encoding a polynucleotide of the invention.

A composition of the invention can be formulated using established methods of preparation (Gennaro, A. L. and Gennaro, A. R. (2000) Remington: The Science and Practice of Pharmacy, 20th Ed., Lippincott Williams & Wilkins, Philadelphia, PA).

A composition of the invention may be administered via any parenteral or non-parenteral (enteral) route that is therapeutically effective. Parenteral application methods include, for example, intracutaneous, subcutaneous, intramuscular, intratracheal, intranasal, intravitreal or intravenous injection and infusion techniques, e.g. in the form of injection solutions, infusion solutions or mixtures, as well as aerosol installation and inhalation, e.g. in the form of aerosol mixtures, sprays or powders. In a preferred embodiment, a composition of the invention is administered intramuscularly or intravenously. A composition can be administered systemically in a formulation containing conventional non-toxic pharmaceutically acceptable excipients or carriers, additives and vehicles as desired. The composition may be an aqueous solution, an oil-in water emulsion or a water-in-oil emulsion.

To prepare the compositions, pharmaceutically inert inorganic or organic excipients can be used. To prepare for example pills, powders, gelatin capsules or suppositories, lactose, talc, stearic acid and its salts, fats, waxes, solid or liquid polyols, natural and hardened oils are examples of pharmaceutically acceptable excipients which can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

For intravenous injection, the active ingredient will be in the form of a parenterally acceptable aqueous solution which is pyrogen-free and has suitable pH, isotonicity and stability. Those of relevant skill in the art are well able to prepare suitable solutions using for example, isotonic vehicles such as Sodium Chloride Injection, Ringer's Injection, Lactated Ringer's Injection. Preservatives, stabilisers, buffers, antioxidants and/or other additives may be included, as required.

The compositions are preferably administered to an individual in a "therapeutically effective amount", this being sufficient to show benefit to the individual. The optimal dosage will depend on, for example, the biodistribution of the active agent which induces immunogenicity, and the mode of administration.

The composition may also contain additives, such as, for example, fillers, binders, wetting agents, glidants, stabilizers, preservatives, emulsifiers, and furthermore solvents or solubilizers.

A pharmaceutically acceptable carrier can contain physiologically acceptable agents that act, for example, to stabilize, increase solubility or to increase the absorption of a composition. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The compositions can be a self-emulsifying drug delivery system or a selfmicroemulsifying drug delivery system. The compositions can also be a liposome or other polymer matrix, which can have incorporated therein, for example, the compositions of the invention. Liposomes, for example, which comprise phospholipids or other lipids, are nontoxic, physiologically acceptable and metabolisable carriers that are relatively simple to make and administer.

The phrase "pharmaceutically acceptable" is employed herein to refer to those compounds, materials, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A composition of the invention may further comprise, or be intended to be administered simultaneously, sequentially, or separately with an adjuvant. The adjuvant may comprise an oil emulsion. The adjuvant may be selected from any of the group comprising PEI; Alum; AS01 or AS02 (GlaxoSmithKline); inorganic compounds, such as aluminium hydroxide, aluminium phosphate, calcium phosphate hydroxide, or beryllium; mineral oil, such as paraffin oil; emulsions, such as MF59; bacterial products, such as killed bacteria *Bordetella pertussis*, or *Mycobacterium bovis*; toxoids; non-bacterial organics, such as squalene or thimerosal; the saponin adjuvant matrix M (Isconova/Novavax) or other ISCOM-type adjuvants; detergents, such as Quil A; cytokines, such as IL-1, IL-2, or IL-12; Freund's complete adjuvant; and Freund's incomplete adjuvant; or combinations thereof.

In another aspect, there is provided a method of treatment or prevention of malaria, said method comprising administering to a subject at risk of or suffering from malaria one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof of the invention; one or more a polynucleotides encoding one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof according to the invention; one or more vectors according to the invention; or one or more immunogenic compositions of the invention.

In another aspect, there is provided one or more *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof, vectors, or immunogenic compositions of the invention for use in the manufacture of a medicament for the treatment or prevention of malaria.

Thus, in another aspect of the invention, there is provided a method of prevention or treatment of malaria in a subject, comprising:

- a first administration of an immunogenic composition of the invention; and
- a second administration of an immunogenic composition of the invention.

In another aspect, there is provided a kit for a vaccination regime against malaria in a subject, comprising:

- a prime composition comprising a viral vector comprising nucleic acid encoding a *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof; and
- a boost composition comprising the same or a different viral vector comprising nucleic acid encoding the same or a different *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof.

The kit may further comprise directions to administer the prime composition prior to the boost composition in a subject. The nucleic acid of the viral vector of the kit may further encode one or more other *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof. The one or more other *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof may comprise *Plasmodium* immunogens capable of eliciting an immune response in a subject.

The kit, prime, and/or boost composition may further comprise an adjuvant.

According to another aspect of the invention, there is provided a method of manufacturing a viral vector of the invention, comprising:

- culturing host cells capable of facilitating viral replication;
- infecting the host cells with a viral vector of the invention, or transfecting host cells with DNA encoding a *Plasmodium*-derived protein or immunogenic fragment thereof, such as a ribosomal protein or ribosomal associated protein, or an ETRAMP, or a histone, or a protein or peptide of FIG. 1, FIG. 2 or FIG. 3, or an immunogenic fragment thereof, or viral vector, of the invention;
- incubating the host cells to allow the production of viral progeny; and
- harvesting and purifying the viral progeny to produce the immunogenic composition.

Suitable cell lines for production of adenoviral vectors include HEK293 cells and Per.C6 cells. Suitable cells for production of MVA include chicken embryo fibroblast, DF1 cells, AGE1.CR.pIX and EB66.

The skilled person will understand that optional features of one embodiment or aspect of the invention may be applicable, where appropriate, to other embodiments or aspects of the invention.

There now follows by way of example only a detailed description of the present invention with reference to the accompanying drawings, in which;

FIG. 1—is a table of *Plasmodium*-derived proteins, including ribosomal proteins or ribosomal associated proteins, and ETRAMPs, and histones, and other non-ribosomal associated proteins which are marked with an asterix (*) derived from *P. falciparum* and *P. vivax*.

FIG. 2 is a table of plasmodium-derived ribosomal proteins, Early Transcribed Membrane Proteins (ETRAMPs), histones and peptides thereof. Of all the peptides identified the majority come from plasmodial ribosomal proteins. Non-ribosomal associated proteins are marked with an asterix (*).

FIG. 3—is a table of all the fragments of *Plasmodium*-derived identified after elution from HLA class I molecules of *P. vivax*-infected reticulocytes and immunopeptidomic mass spectrometry sequence analysis. Of all the peptides identified the majority come from plasmodial ribosomal proteins.

FIG. 4—demonstrates the protective efficacy of Ad-MVA encoding PfS20e ribosomal protein in immunized mice after challenge with PfS20e-expressing sporozoites transgenic for this gene, expressed using the Pbuis4 promoter. Kaplan-Meier analysis of the survival curves showed a highly significant protective effect with 2/8 mice sterilely protected with a P value of P=0.0001.

Figure 5:
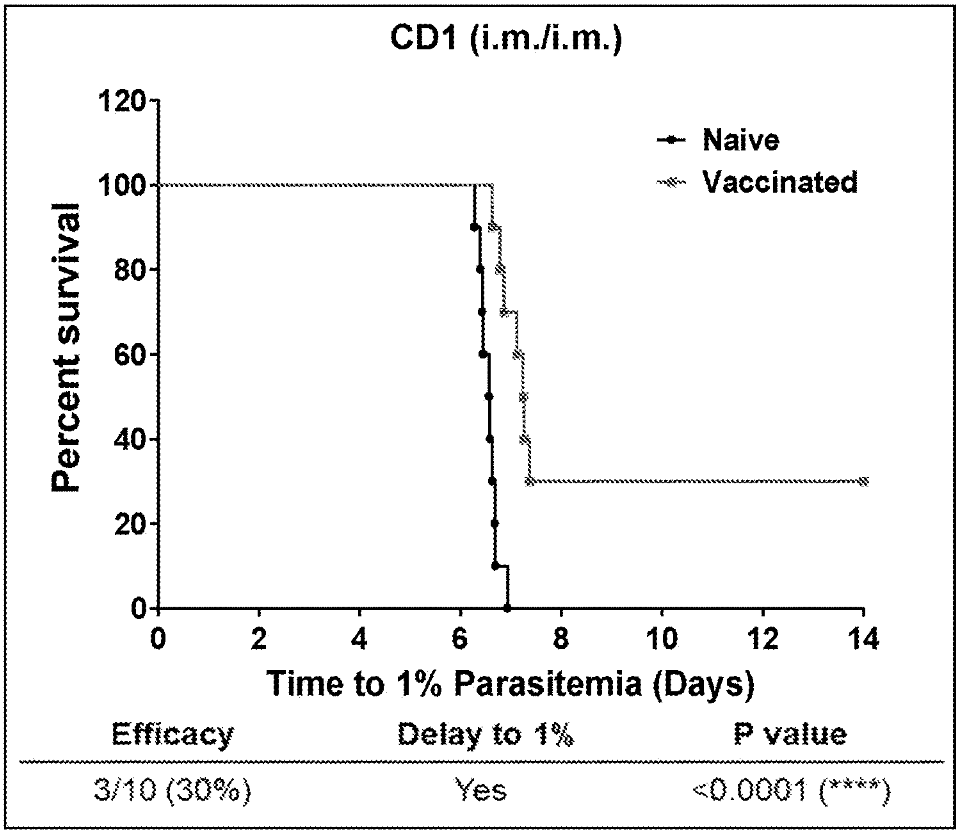

FIG. 5—demonstrates the protective efficacy of the ChAdOx1-MVA *P. falciparum* S20e vaccine in CD-1 outbred mice (n=10 vaccinated and 10 naive). The mice were vaccinated i.m. with 108 ifu of PfS20e-ChAdOx1 as a prime vaccination, followed eight weeks later by 107 pfu of PfS20e-MVA as a boost vaccination (by i.m. route). Mice were challenged with 1000 chimeric sporozoites i.v. The Kaplan-Meier curves illustrate the time to 1% parasitaemia, whilst statistical significance between the survival curves was assessed using the Log-Rank (Mantel-Cox) Test: $p<0.0001$.

Figure 6:
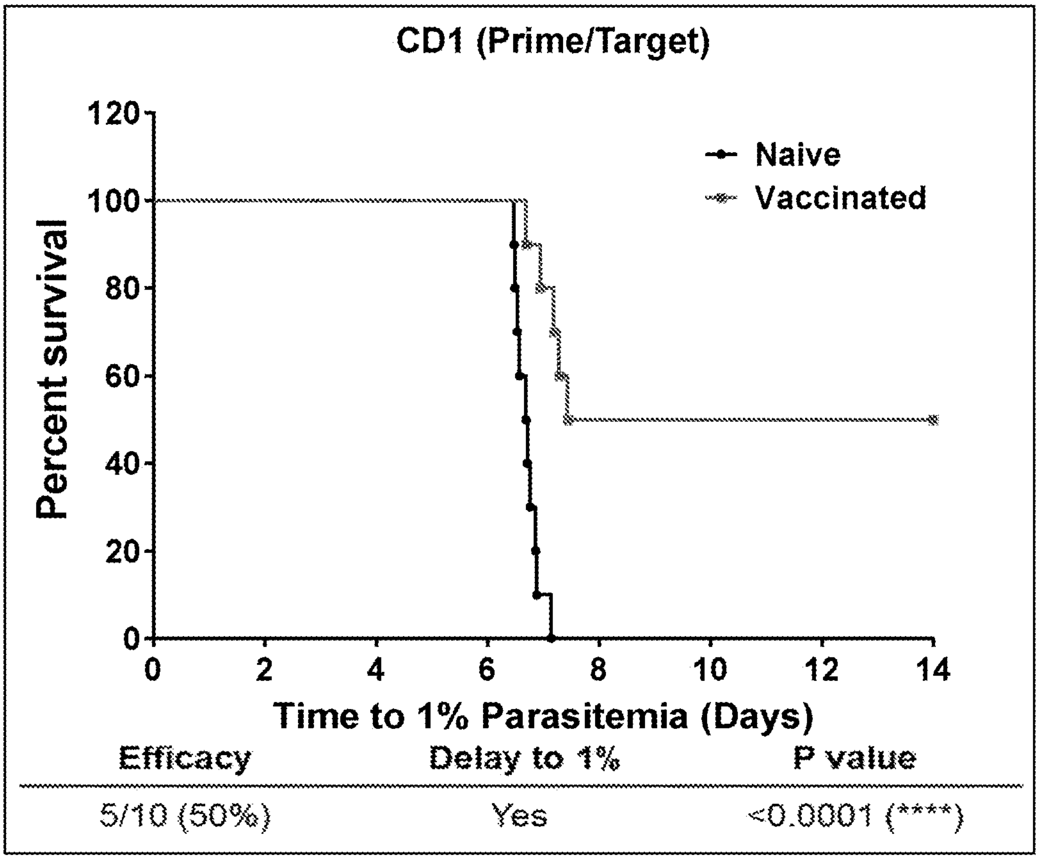

FIG. 6—shows the protective efficacy of the ChAdOx1-MVA *P. falciparum* S20e vaccine in CD-1 inbred mice (n=10 vaccinated and 10 naive). The mice were vaccinated i.m. with $10^8$ ifu of PfS20e-ChAdOx1 as prime followed three weeks later by $10^7$ pfu of PfS20e-MVA as a target-boost vaccination (by i.v. route). Mice were challenged with 1000 chimeric sporozoites i.v. The Kaplan-Meier curves illustrate the time to 1% parasitaemia, whilst statistical significance between the survival curves was assessed using the Log-Rank (Mantel-Cox) Test: $p<0.0001$.

Figure 7:
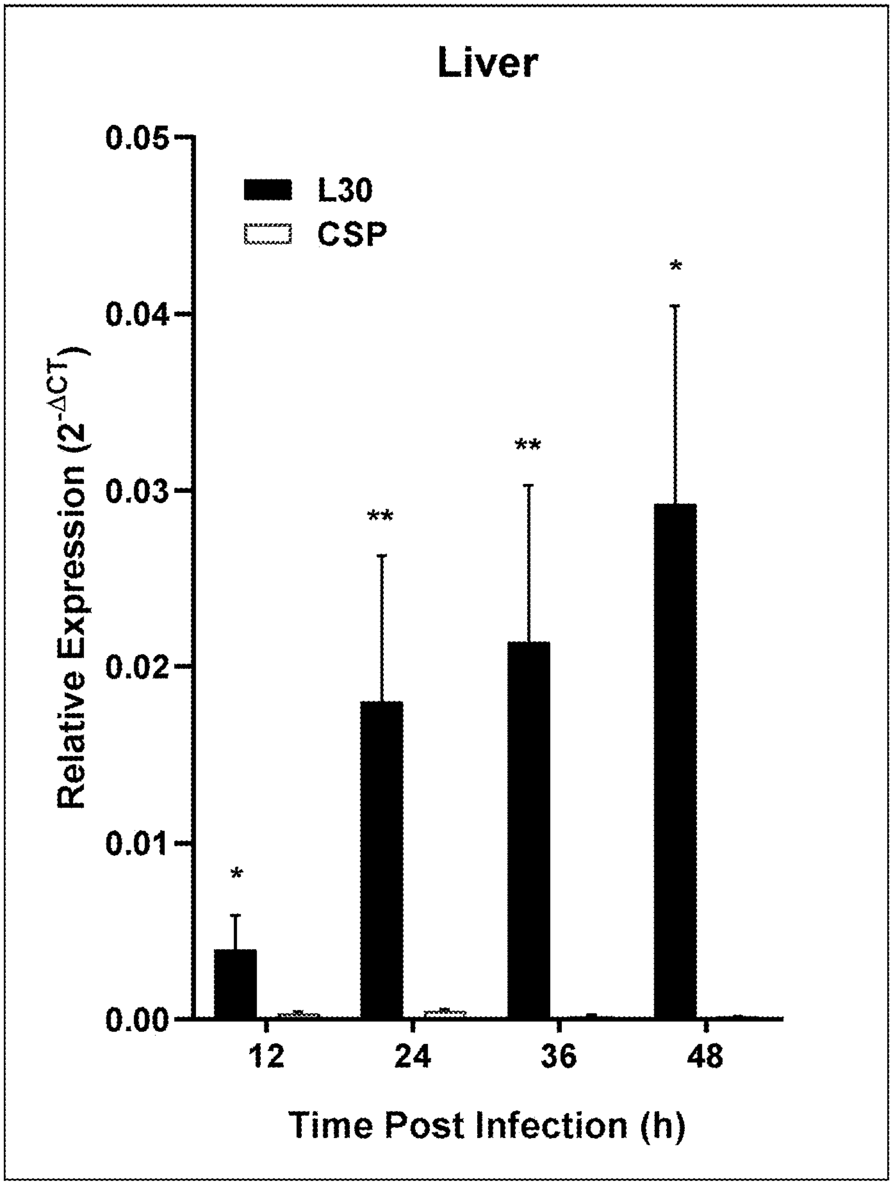

FIG. 7—demonstrates relative expression of the 60S ribosomal protein L30 *P. berghei* homologue compared to CSP in *P. berghei*-infected hepatocytes at 12, 24, 36 and 48 hours post infection by RT-qPCR normalised to levels of 18SrRNA. Average 2-ΔCT was calculated from two biological replicates, which had three technical replicates each. Error bars show the standard deviation for each sample. Kruskal Wallis Multiple Comparison Dunn's test compared to the relative expression of CSP. *$P<0.05$, **$P<0.01$.

FIG. 8—demonstrates peptide validation by ex vivo ELIspot assay. Selected peptides (see FIG. 9) were tested using PBMC isolated from patients infected with *P. vivax* (n=24), *P. falciparum* (n=7) and healthy donors from endemic (n=15) and non-endemic (n=6) regions for malaria. Cells were stimulated with 40S ribosomal peptides (a), 60S ribosomal peptides (b), ETRAMP peptides (c), histone peptides (d) and other peptides (e). Each symbol represents one individual. The circles in the top graphs in FIG. 7*a, b, c, d* and *e* represent *P. vivax* patients, the circles in the middle graphs in FIG. 7*a, b, c, d* and *e* represent *P. falciparum* patients, the triangles in the bottom graphs in FIG. 7*a, b, c, d* and *e* represent endemic healthy donors and the squares in the bottom graph in FIG. 7*a, b, c, d* and *e* represent non-endemic healthy donors. IFN-γ production was measured by spot counting and the results are expressed as spot-forming cells (SFC) by $1\times10^6$ PBMCs. Positive peptides were considered as responses that induced ≥30 spots in each patient—above the dashed horizontal line. Percentage of positive individuals for each tested peptide in each infected or healthy group are depicted by colour intensity with the legend indicated at the right of the figure (f). Red, yellow, and green represent the high, middle, or poor levels of responders in the ELIspot assay.

FIG. 9—this table details the peptides used in the ELIspot assays in FIG. 8. Non-ribosomal associated proteins are marked with an asterix (*)

MATERIALS AND METHODS

1. Humanised Mice Infected with *P. falciparum*

TK-NOG mice were transplanted/engrafted with human primary hepatocytes, which repopulate the damaged liver (repopulation (60-80%) as described in Soulard, V. et al. Nat *Commun* 6 (2015). This model allows the complete hepatic development of *P. falciparum* and the transition to erythrocytic stages, including the appearance of mature gametocytes. This mouse model closely mimics the physiological complexity and specificity of an in vivo infection in the human environment and is also a source of fresh human hepatocytes. Every mouse received hepatocytes from the same donor. The donor HLA alleles were HLA-A*03:01, HLA-A*11:01, HLA-B*40:01, HLA-B*50:01, HLA-C*03:02 and HLA-C*06:02. Thirteen TK-NOG mice were used in three independent experiments and infected with *P. falciparum* sporozoites in the tail vein as described in the Table 1.

Mice were infected sporozoites from *P. falciparum*, NF54 or NF135 strains, in the tail vein, and livers were harvested at discreet time points post-infection as described in Table 1 below.

TABLE 1

Experimental details of humanised mice infected with *P. falciparum*

| Sample number | Experiment number | *P. falciparum* strain | Number of *P. falciparum* sporozoites (10^6) | Liver Harvest (days post-infection) |
|---|---|---|---|---|
| 1 | 1 | NF54 | None | Non-Infected |
| 2 | | | 3 | 3 |
| 3 | | | 3 | 5 |
| 4 | 2 | NF54 | None | Non-Infected |
| 5 | | | 3 | 3 |
| 6 | | | 3 | 4 |
| 7 | | | 3 | 5 |
| 8, 9, 10, 11 | 3 | NF135 | None | Non-Infected |
| 12 | | | 10 | 3 |
| 13 | | | 10 | 5 |

50 μm thick liver sections were obtained and histology was performed to determine the rate of infection. The rate of infection was determined by staining the parasites with an anti-HSP70 antibody and by calculating the average of schizonts counted, divided by the total number of human hepatocytes in each liver. The total number of human hepatocytes infected (rate of infection multiplied by the total number of human hepatocytes) was also calculated. The rate of infection in these mice varied from 30,000 to 60,000 per liver.

Starting from 200 mg of liver material, cells were lysed and total proteins were collected for mass spectrometry (MS) analysis. See section 3 for details.

2. Human Reticulocytes Infected with *P. vivax*

Human reticulocytes from patients infected with *P. vivax* were purified as described in Junqueira, C. et al. Nature medicine 24, 1330-1336 (2018). Seven samples containing >99% *P. vivax*-infected reticulocytes varying from $4.3\times10^7$ to $7\times10^8$ cells (Table 2), were lysed and total proteins were collected for mass spectrometry analysis. See section 3 for details.

| Sample ID | No retics | Parasitaemia |
|---|---|---|
| 24 | $5\times10^7$ | Pv +++ |
| 26 | $1.1\times10^8$ | Pv +++ |
| 28 | $7\times10^8$ | Pv +++ |
| 30 | $4.3\times10^7$ | Pv ++ |
| 31 | $7.2\times10^7$ | Pv ++ |
| 34 | $6.2\times10^7$ | Pv +++ |
| 35 | $6.2\times10^7$ | Pv ++ |

Parasitemia was determined at the site of sample collection following local clinical protocols.

| Sample | HLA class I Allele | | | | | |
|---|---|---|---|---|---|---|
| ID | A | A | B | B | C | C |
| 24 | 11:01 | 23:01 | 35:01 | 81:01 | 04:01 | 18:01 |
| 26 | 01:04 | 02:01 | 51:04 | 57:01 | 07:01 | 15:02 |
| 28 | 02:01 | 02:22 | 15:20 | 27:02 | 02:02 | 04:01 |
| 30 | 02:01 | 24:02 | 18:01 | 35:04 | 04:01 | 07:01 |
| 31 | 03:01 | 33:03 | 35:01 | 51:01 | 07:05 | 15:02 |
| 34 | 24:02 | 24:02 | 08:01 | 51:01 | 07:01 | 15:02 |
| 35 | 02:01 | 02:01 | 35:01 | 40:02 | 03:04 | 04:01 |

3. Peptide Identification by Immunopeptidomics 3.1 Mass Spectrometry

Cells were lysed in 1 ml lysis buffer (0.5% Igepal, 150 mM NaCl, 50 mM Tris, pH 8.0, supplemented with Complete™ protease inhibitor cocktail (Roche)). HLA complexes were immunoprecipitated using 1 mg monoclonal antibody W6/32 against HLA-ABC complexes (GE healthcare) cross-linked to Protein A Sepharose beads using dimethyl pimelimidate (DMP, Sigma). Lysates were incubated overnight. Beads were subsequently washed with 10 column volumes of 2×150 mM NaCl in 50 mM Tris, 1×450 mM NaCl in 50 mM Tris and 50 mM Tris buffer without salt. Peptides bound to the HLA groove are released after mild acid elution with 5 mL 10% acetic acid to denaturate of the alpha-chains and beta-2-microglobulin. The HLA-bound peptides were further purified from beta-2-microglobulin and alpha-chains by HPLC (Ultimate 3000) on a ProSwift RP-IS 4.6×50 mm column (Thermo Scientific) by applying a linear gradient of 2-35% (v/v) acetonitrile in 0.1% (v/v) formic acid in water over 10 min. Alternating fractions that did not contain beta-2-microglobulin or alpha-chains were pooled into two final fractions, concentrated and kept at −80° C. prior to MS analysis.

Peptides were suspended in 20 μL buffer A (1% acetonitrile, 0.1% TFA in water) and analyzed by nUPLC-MS/MS using an Ultimate 3000 RSLCnano System coupled with an Orbitrap Fusion Lumos Tribrid mass spectrometer (Thermo Scientific). 9 μl of each sampled was injected and trapped onto a 3 μm particle size 0.075 mm×150 mm Acclaim PepMap RSLC column at 8 μl/min flowrate. Peptide separation was performed at 40° C. by applying a 1 h linear gradient of 3-25% (v/v) acetonitrile in 0.1% (v/v) formic acid, 5% DMSO in water at a flow rate of 250 μl/min on a 2 μm particle size, 75 μm×50 cm Acclaim PepMap RSLC column. For HLA class II samples, a linear gradient of 5-30% (v/v) acetonitrile was applied. Peptides were introduced to a Fusion Lumos mass spectrometer (Thermo Scientific) via an Easy-Spray source at 2000 V. The ion transfer tube temperature was set to 305° C. Measurement of precursor peptides was performed with a resolution of 120,000 for full MS (300-1500 m/z scan range) at an AGC target of 400,000. Precursor ion selection and fragmentation by high-energy collisional dissociation (HCD at 28% collision energy for charge state 2-4, 35% for charge state 1) was performed in TopSpeed mode at an isolation window of 1.2 Da for singly to quarterly charged ions at a resolution of 30,000 and an AGC target of 300,000 in the Orbitrap for a cycle duration of 2 s. Singly charged ions were acquired with lower priority.

3.2 Peptide Identification

MS data was analyzed with Peaks 8 (Bioinformatics Solutions and Tran, N. H. et al. Nature methods 16, 63-66 (2019)) for identification of peptide sequences. Spectra were matched to all reviewed human proteins combined with *Plasmodium falciparum* (isolate 3D7) or *Plasmodium vivax* (Salvador I), produced based on UniProt proteomes (Uni- Prot, C. UniProt: a worldwide hub of protein knowledge. Nucleic acids research 47, (2019)). The results were filtered using a score cut-off of −1g10P=15. The searches were performed with the following parameters: no enzyme specificity, no static and variable modifications, peptide tolerance: ±5 ppm and fragment tolerance: ±0.03 Da.

Human sequences were disregarded from the analysis. The peptide spectrum matches (PSMs) of plasmodial origin obtained were analysed following a pipeline consisting of: 1) Size exclusion: MHC-I peptides longer than 15 amino were excluded. Peptides smaller than 8 amino acid long were excluded; 2) A Peaks score cut-off of 15 was applied to all samples; 3) False positive peptides, that is, peptides with incorrect identification were removed from the samples; 4) A stringent blast analysis was performed in every peptides sequence using the DeBosT script (see section 3.3). Peptides with two or more amino acid different from human sequences were considered non-human and therefore identified as plasmodial peptides. Peptides with higher netMHC rank were prioritized. The amino acids leucine (L) and isoleucine (I) are isomers, which are indistinguishable from each other through the mass spectrometry protocol. All peptides were blasted for all possible combinations of I and L, and when a combination matched a human peptide, the sequence was excluded. Applying these four-step data analysis criteria, a list of *Plasmodium* peptides were identified, see FIG. 2 and FIG. 3.

3.3 DeBosT Script

Blast searches (National Library of Medicine, https.//blast.ncbi.nlm.nih.gov) of putative plasmodial sequences were performed using a batch script. Sequences that have less than two amino acid differences compared to human sequences were excluded from downstream analysis (Bettencourt, P. et al. Identification of antigens presented by MHC for vaccines against tuberculosis. npj Vaccines 5, 2 (2020)).

3.4 Peptide Validation

Malaria infected patients and healthy donors. *P. vivax* infected patients were recruited in the Tropical Medicine Research Center (Porto Velho-Brazil) along with healthy donors from the same endemic region and from a non-endemic region (Belo Horizonte-Brazil). All participants provided written informed consent for participation in the study, which has a protocol approved by the Institutional Review Boards of the Oswaldo Cruz Foundation and National Ethical Council (CAAE: 59902816.7.0000.5091). Samples were collected at three different times. Firstly, 7 samples from *P. vivax* infected patients were obtained for the mass spec experiments. Twenty two samples from *P. vivax* infected patients, eighteen healthy donors from the endemic region and 6 from a non-endemic region posteriorly were collected for the Elispot assay.

PBMC and *P. vivax* infected reticulocytes obtention. 100 mL of blood was collected from infected individuals and controls. First, mononuclear cells were separated from peripheral blood (PBMCs). For this, the blood was diluted in a 1:1 ratio, was gently added to a tube containing 15 mL of Ficoll (GE Healthcare, USA). Red blood cell pellet resulting from PBMC purification was resuspended in RPMI culture medium in a 1:4 ratio. Diluted blood was added carefully into a 50 mL tube containing Percoll 45% (GE Healthcare, USA), 5× the volume of the red blood cell pellet. Samples were centrifuged for 15 minutes at 2000 rpm. After centrifugation, the reticulocyte interface was collected. Reticulocyte purified samples had 99% purity.

ELISPOT assay. The ex vivo IFN-γ ELISpot assays were performed using $5\times10^5$ fresh PBMCs from *P. vivax* infected patients, endemic and non-endemic healthy donors. Cells were plated in duplicates into 96-well ELISpot plates (Merck Millipore) precoated with 4 μg/ml anti-human-IFN-γ (clone 1-D1K; Mabtech). Peptides of Table 3 (FIG. 9) were tested with stimulation of 10 μg/ml and stimulated for 18-20 hour at 37° C. under 5% $CO_2$. Anti-CD3/anti-CD28 antibodies were used as positive control and medium alone as negative control (subtracted from all conditions). After cell removal, plates were developed for 2 hours in the same temperature condition of the stimulus in the presence of 0.2 μg/ml IFN-γ, 7-B6-Biotin (Mabtech). Spot detection was performed following incubation for 30 min in the dark with BCIP/NBT Alkaline Phosphatase Substrate (Sigma). Spot-forming cells (SFC) were counted using the ImmunoSpot automated Elispot counter.

TABLE 3 peptides used for ELISpot assay.

| Accession No. | ELISPOT ID | Protein | Peptide Sequence | SEQ ID NO: |
|---|---|---|---|---|
| A5K3U1 | 40S S2 | 40S ribosomal protein S2 | LETYQNMKIQKQTP | 279 |
| A5K858 | 40S S6-1 | 40S ribosomal protein S6 | SKNGKNRFIKPKIQ | 341 |
| A5K858 | 40S S6-2 | 40S ribosomal protein S6 | GVKKDVAK | 133 |
| A5K858 | 40S S6-3 | 40S ribosomal protein S6 | GPKRATKIRK | 120 |
| A5K1E3 | 40S S8-1 | 40S ribosomal protein S8 | RLTGGKKKIHKKK | 351 |
| A5K1E3 | 40S S8-2 | 40S ribosomal protein S8 | GSKQVHV | 130 |
| A5K7Q0 | 40S S11 | 40S ribosomal protein S11 | SFFNSKKIKKGSKS | 364 |
| A5KB86 | 40S S23 | 40S ribosomal protein S23 | SSHAKGIVVEKV | 386 |
| A5K124 | 40S S25-1 | 40S ribosomal protein S25 | GKGKNKEKL | 97 |
| A5K124 | 40S S25-2 | 40S ribosomal protein S25 | GKGKNKEKLNHAVF | 100 |
| A5KBT5 | 40S S30-1 | 40S ribosomal protein S30 | SDGTGRKKGPNSKL | 361 |
| A5KBT5 | 40S S30-2 | 40S ribosomal protein S30 | GTGRKKGPNSKL | 131 |

TABLE 3-continued peptides used for ELISpot assay.

| Accession No. | ELISPOT ID | Protein | Peptide Sequence | SEQ ID NO: |
|---|---|---|---|---|
| A5KBT5 | 40S S30-3 | 40S ribosomal protein S30 | TGRKKGPNSKL | 401 |
| A5K3E2 | 50S S28e | 50S ribosomal protein S28e | GDTELSGRFL | 82 |
| A5KAZ9 | 60S L4/L1-1 | 60S ribosomal subunit protein L4/L1 | ANKALLPTAGDD | 18 |
| A5KAZ9 | 60S L4/L1-2 | 60S ribosomal subunit protein L4/L1 | NKALLPTAGDD | 306 |
| A5KAZ9 | 60S L4/L1-3 | 60S ribosomal subunit protein L4/L1 | YGRIFKKKITKK | 444 |
| A5K306 | 60S L9 | 60S ribosomal protein L9 | VSEVTTVEKDE | 430 |
| A5K186 | 60S L10 | 60S ribosomal protein L10 | GAFGKPNGV | 78 |
| A5K762 | 60S 13a | 60S ribosomal protein L13a | MYKKVYVID | 293 |
| A5JZN9 | 60S L13-1 | 60S ribosomal protein L13 | YESIEVSKID | 440 |
| A5JZN9 | 60S L13-2 | 60S ribosomal protein L13 | GTPIEKLHPI | 132 |
| A5JZN9 | 60S L13-3 | 60S ribosomal protein L13 | KNIKSKNGIGGIPAD | 240 |
| A5K3F2 | 60S L29 | 60S ribosomal protein L29 | PKFFKNQRY | 325 |
| A5KCD7 | 60S L30 | 60S ribosomal protein L30 | VITDVGDSDIIKTNE | 422 |
| A5KAW8 | 60S L31 | 60S ribosomal protein L31 | AKAVKKQKKTLKPV | 11 |
| A5K6B0 | 60S L32-1 | 60S ribosomal protein L32 | AVKKVGKIVKKRT | 33 |
| A5K6B0 | 60S L32-2 | 60S ribosomal protein L32 | AVKKVGKIVK | 31 |
| A5K4R0 | 60S L35 | 60S ribosomal protein L35 | KKYKNKKFKPY | 230 |
| A5KBH5 | ETRAMP-1 | Early transcribed membrane protein (ETRAMP) | KKVAAGYKKLTD | 227 |
| A5KBH5 | ETRAMP-2 | Early transcribed membrane protein (ETRAMP) | GLNQKQPTKGSNIQ | 114 |
| A5KBH5 | ETRAMP-3 | Early transcribed membrane protein (ETRAMP) | LNQKQPTKGSNIQ | 289 |
| A5KBH5 | ETRAMP-4 | Early transcribed membrane protein (ETRAMP) | LGGLNQKQPT | 175 |
| A5K676 | ETRAMP-5 | Early transcribed membrane protein (ETRAMP) | KSAGADSKSLKKLD | 258 |
| A5K676 | ETRAMP-6 | Early transcribed membrane protein (ETRAMP) | TPIITNKPFG | 409 |
| A5K214 | Hist. H2A-1 | Histone H2A | GRIGRYLKKGKYAK | 125 |
| A5K214 | Hist. H2A-2 | Histone H2A | ASGGVLPNIHNV | 24 |
| A5K214 | Hist. H2A-3 | Histone H2A | SGGVLPNIHNV | 366 |
| A5K214 | Hist. H2A-4 | Histone H2A | GRIGRYLKKGKYA | 124 |
| A5K7L8 | Hist. H2A-5 | Histone H2A | KVPVPPTQAKKPKKN | 273 |
| A5K1U7 | Hist. H3 | Histone H3 | APISAGIKKPHR | 19 |
| A5K8J8 | Unch A5K8J8 | Uncharacterized protein | LILRAAIKTK | 284 |
| A5JZN7 | Unch A5JZN7.1 | Uncharacterized protein | DNNEHVVQEKTVSF | 50 |
| A5JZN7 | Unch A5JZN7.2 | Uncharacterized protein | DNNEHVVQEKTV | 51 |
| A5K8G9 | Unch A5K8G9 | Uncharacterized protein | EDYSPRKV | 56 |
| A5K2R4 | Ubqt/ribos-1 | Ubiquitin/ribosomal | AIEPSLAQLAQK | 8 |
| A5K2R4 | Ubqt/ribos-2 | Ubiquitin/ribosomal | NQLRPKKKLK | 317 |
| A5K197 | Don Juan | Sperm-specific protein Don juan | AQKIKKKKKLTPA | 20 |

3.5 Spectral Match Validation

To further confirm the identity of the peptide sequences identified, a spectral match validation experiment will be performed. Synthetic peptides will be produced and compared to a selection of PSMs obtained from the experiments (the biological peptides). Synthetic peptides will be run in the same experimental conditions as biological peptides. The mass over charge [m/z] for each peptide, the charge state, the intensity and distribution of each peak within each peptide sequences, as well as the peptide specific retention time (RT) on the Liquid Chromatography will be compared between synthetic and biological peptides.

3.6 CD8+ T-Cell Response

The CD8+ T-cell responses from healthy patients from endemic and non-endemic areas for malaria, and those of *P. falciparum* and *P. vivax*-infected patients were analysed against peptides identified by immunopeptidomics (Table 3), using IFN-gamma ELISpot. Several peptides, including ribosomal protein peptides were shown to be recognised in ex vivo ELISPOT assays. This demonstrated that peptides displayed on MHC-1 molecules on reticulocytes, including those derived from ribosomal proteins, are naturally immunogenic in human infections and thus are good immunogens for vaccination.

3.7 Efficacy and Immunogenicity of New Vaccine Candidates

The immunogens described here may be cloned into viral vectors for use as vaccines. The platform of subunit vaccines has proved to be very safe and is very powerful in inducing CD8+ T-cell responses against the antigen that is being expressed. Generation of ChAdOx1, AdHu5 and/or MVA expressing each antigen may be cloned using GeneArt Technology (ThermoFisher Scientific, UK). Subunit vaccines expressing liver stage antigens may be produced. Immunogens may be mammalian codon-optimized flanked by a Kozak consensus sequence, a tPA leader sequence and a GS linker at the 5'-end and at the 3' end, cloned into a GeneArt entry vector and then recombined into an ChAdOx1, AdHu5 and/or MVA destination plasmid as previously described in Dicks, M. D. et al. PloS one 7 (2012) and McConkey, S. J. et al. Nature medicine 9, 729-735 (2003). Efficacy and immunogenicity of the viral vectors will be evaluated in a malaria challenge mouse model.

EXAMPLES

Example 1

*Plasmodium vivax* is the most widespread cause of human malaria and the second most lethal after *P. falciparum*. Unusually, *P. vivax* preferentially infects reticulocytes and recently it has been demonstrated that *P. vivax*-infected patients have circulating CD8+ T cells that recognize and form immunological synapses with *P. vivax*-infected reticulocytes in an HLA-dependent manner, releasing their cytotoxic granules to kill both host cell and intracellular parasite, preventing reinvasion. 50 and 700 million reticulocytes per subject were obtained from seven Brazilian subjects infected with *P. vivax*, as described in section of the materials and methods.

453 unique peptides were identified by tandem mass spectrometry sequencing and these were from 176 distinct *P. vivax* antigens. There was significant overlap in immunogens identified in the six subjects, with peptides from 29 antigens found in at least 50% of the subjects and peptides from two antigens found in all six subjects, with high quality data. A most striking and unexpected finding was that over half of the peptides (57%) came from a single class of proteins, plasmodial ribosomal or ribosome associated proteins. A list of peptides identified and the protein they are derived from is provided in FIG. 2 and FIG. 3.

Ribosomal proteins are species-specific and between humans and Plasmodia, most ribosomal proteins share approximately 60% sequence identity on average. This divergence provides adequate differences for regions on non-identify between human/mammalian ribosomal and parasite ribosomal sequences to avoid self-tolerance and be suitably immunogenic. However, proteins with less homology to humans are preferred so as to potentially maximise immunogenicity. Furthermore proteins with identify or greater similarity between *P. falciparum* and *P. vivax* are preferred because they are more likely to provide a cross-species protective effect.

Further, ribosomes are required for protein production and their structure and mechanism of polypeptide generation are well understood. Cells and microbes that are rapidly dividing or very metabolically active may need a lot of ribosomes and ribosomal proteins to engage in the required protein synthesis. This is likely to be true of parasitized reticulocytes in which *P. vivax* grows very rapidly. Similarly, within hepatocytes, malaria parasites generally grow very rapidly. For example, in the case of *P. falciparum*, one sporozoite infects a liver cell and seven days later 20,000 parasites with a largely different antigenic composition, malaria merozoites, emerge from the same liver cell. Therefore, the findings of the mass spectrometry analysis support the fact the parasite will need to generate a lot of ribosomal proteins intracellularly, which are capable of ending up on the HLA class I molecules in parasitized cells.

In addition to the vast majority of ribosomal proteins identified in the mass spectrometry analysis of peptides eluted from HLA-I expressed on infected reticulocytes, two Pv ETRAMPs peptides that are expressed both in hepatocyte and reticulocyte stages were also identified. The ETRAMPs compose a family of polymorphic, small, highly-charged transmembrane proteins unique to malaria parasites, they localize in the parasitophorous vacuole membrane (PVM) with the C-terminal region exposed to the RBC cytosol and are also exported to the host cell cytoplasm. Therefore, the ETRAMPs are accessible to the protein machinery that processes and presents endogenous antigens. Furthermore, they are expressed in the first hours of invasion and, thus, the infected reticulocytes may become targets to CTLs at the early stages of infection. In addition, the ETRAMPs are recognized by antibodies from *Plasmodium falciparum* and *Plasmodium vivax* malaria patients and CD4+ T cells from *P. berghei*-infected mice. In conclusion, the HLA-I binding and biology of ETRAMPs suggest that they could be key targets for protective CD8+ T cell-mediated immunity against malaria. Like ribosomal proteins, ETRAMPs have not been employed or evaluated for CD8+ T cell mediated immunity.

Example 2

As a proof of concept, one plasmodial ribosomal protein gene was selected and expressed to test the concept that plasmodial ribosomal proteins could be suitable immunogens for developing immunogenic, protective malaria vaccines.

The *P. falciparum* 40S ribosomal protein S20e was selected, which is 118 amino acids in length (sequence: MSKLMKGAIDNEKYRLRRIRIALTSKNL-RAIEKVCSDIMKG AKEKNLNVSGPVRLPVKTL- RITTRKSPCGEGTNTWDRFELRIYKRLIDLYSQCE VVTQMTSINIDPVVEVEVIITDS, Uniprot accession: PF3D7_1003500.1; SEQ ID NO 475). The protein was expressed in both a simian adenoviral vector ChAdOxl and in MVA. BALB/c Mice were immunised with a single shot of 1×10[8] infectious units of the ChAd recombinant and boosted with the MVA three weeks later with a dose of 1×10[8] pfu and challenged intravenously three weeks later with 1000 *P. berghei* sporozoites transgenic for *P. falciparum* 40S ribosomal protein S20e (expressed under a Pbuis4 promoter). There was highly significant protective efficacy with 2 of 8 mice sterilely protected and the remaining six delayed in time to parasitaemia reflecting a substantial reduction of liver parasite load, P=0.0001 (FIG. 5).

CD-1 mice were immunised with a single shot of 1×10[8] infectious units of the ChAd recombinant and boosted with the MVA eight weeks later with a dose of 1×10[8] pfu and challenged intravenously three weeks later with 1000 *P. berghei* sporozoites transgenic for *P. falciparum* 40S ribosomal protein S20e (expressed under a Pbuis4 promoter). There was highly significant protective efficacy with 3 of 10 mice sterilely protected and the remaining six delayed in time to parasitaemia reflecting a substantial reduction of liver parasite load, P=0.0001 (FIG. 6).

Using prime-target vaccination regime in CD-1 mice, there was highly significant protective efficacy with 5 of 10 mice sterilely protected and the remaining 5 delayed in time to parasitaemia reflecting a substantial reduction of liver parasite load, P=0.0001 (FIG. 7).

This efficacy with a *Plasmodium falciparum* ribosomal protein immunogen demonstrates that ribosomal protein immunogens are a new class of antigens for malaria vaccination, especially to target the liver-stage of infection.

Example 3

To allow analysis of larger numbers of *P. falciparum*-infected human hepatocytes, a recently described mouse strain (TK-NOG) in which most of the mouse liver has been replaced by human hepatocytes was utilised (which unlike mouse hepatocytes will support invasion and growth of *P. falciparum*).

The TK-NOG mice (Soulard et al Nature Communications 2015) express the HSVtk transgene under the albumin promoter onto the NOD SCID IL2Rg/background. In this mouse strain, the loss of endogenous hepatocytes is inducible by a brief exposure to a non-toxic dose of ganciclovir, a method that is rapid and temporally restricted, and routinely leads to substantial repopulation (60-80%) with human hepatocytes. The human herpes simplex virus thymidine kinase type 1 gene (HSVtk) acts as a conditional lethal marker in mammalian cells. The HSVtk-encoded enzyme is able to phosphorylate certain nucleoside analogs (e.g. ganciclovir, an antiherpetic drug), thus converting them to toxic DNA replication inhibitors. The utility of HSVtk is a conditional negative-selection marker.

These TK-NOG mice were infected with 1×10[7] *P. falciparum* sporozoites of a rapidly growing strain (e.g. *P. falciparum* NF135) and livers were removed at 3-5 days post-infection. After applying the immunopeptidomics pipeline to identify peptides bound to MHC molecules, Table 4 was obtained. Remarkably, the peptide sequence VITDVGDSDIIKTNE (SEQ ID NO: 422) that is part of the protein W4IGCO form *P. falciparum* NF135 (Ribosomal_7Ae domain-containing protein) (FIGS. 2 and 3), was also found amongst the peptides eluted from *P. vivax* infected reticulocytes, here designated as protein A5KCD7 (60S ribosomal protein L30) (Table 4). Moreover, another peptide from the protein W4ID94 form *P. falciparum* NF135 (Ribosomal L23eN domain-containing protein) was identified in this example (Table 4). Peptides from the corresponding homologous protein in *P. vivax* were also identified amongst the peptides eluted from *P. vivax* infected reticulocytes, here designated as protein A5K303 (60S ribosomal protein L23a) (FIGS. 2 and 3).

Finding two antigens in a short list of few confirmed eluted peptides from this type of experiment using human hepatocytes, provides clear evidence that ribosomal protein peptides can be presented on the HLA class I molecules of *P. falciparum*-infected liver cells. This further supports the concept that vaccines based on ribosomal proteins would be effective malaria vaccines.

TABLE 4

Peptides identified by immunopeptidomics in humanized mice infected with *P. falciparum* NF135.

| Peptide | SEQ ID NO | Identifier |
|---|---|---|
| AAEEGAKAGAL | 476 | tr\|W4I970\|W4I970_PLAFA Uncharacterized protein OS = *Plasmodium falciparum* NF135/5.C10 OX = 1036726 GN = PFNF135_05454 PE = 4 SV = 1 |
| DNNNYDDDEII | 477 | tr\|W4IEZ4\|W4IEZ4_PLAFA Uncharacterized protein OS = *Plasmodium falciparum* NF135/5.C10 OX = 1036726 GN = PFNF135_03293 PE = 4 SV = 1 |
| E(-18.01) EYDESGPSIVHR | 478 | tr\|W4IC91\|W4IC91_PLAFA Actin-1 OS = *Plasmodium falciparum* NF135/5.C10 OX = 1036726 GN = PFNF135_04291 PE = 3 SV = 1 |
| GGATGAGLAL | 479 | tr\|W4IN72\|W4IN72_PLAFA Glycerol-3-phosphate dehydrogenase OS = *Plasmodium falciparum* NF135/5.C10 OX = 1036726 GN = PFNF135_00472 PE = 3 SV = 1 |
| GK(+42.05) EKTHINLVVIGHVD | 480 | tr\|W4IAJ3\|W4IAJ3_PLAFA Elongation factor 1-alpha OS = *Plasmodium falciparum* NF135/5.C10 OX = 1036726 GN = PFNF135_05027 PE = 3 SV = 1 |
| HGNNMNTCLM | 481 | tr\|W4IGK7\|W4IGK7_PLAFA Uncharacterized protein OS = *Plasmodium falciparum* NF135/5.C10 OX = 1036726 GN = PFNF135_03672 PE = 4 SV = 1 |

TABLE 4-continued

Peptides identified by immunopeptidomics in humanized mice infected with *P. falciparum* NF135.

| Peptide | SEQ ID NO | Identifier |
|---|---|---|
| KIYEKKILK | 482 | tr\|W4IH49\|W4IH49_PLAFADNA polymerase OS = *Plasmodium falciparum* NF135/5.C10 OX = 1036726 GN = PFNF135_03009 PE = 3 SV = 1 |
| KTATLGVI | 483 | tr\|W4IGU9\|W4IGU9_PLAFA Uncharacterized protein OS = *Plasmodium falciparum* NF135/5.C10 OX = 1036726 GN = PFNF135_02418 PE = 4 SV = 1:tr\|W4IGJ3\|W4IGJ3_PLAFA Uncharacterized protein OS = *Plasmodium falciparum* NF135/5.C10 OX = 1036726 GN = PFNF135_02842 PE = 4 SV = 1 |
| LEGKELPG | 484 | tr\|W4IHK5\|W4IHK5_PLAFA Phosphoglycerate kinase OS = *Plasmodium falciparum* NF135/5.C10 OX = 1036726 GN = PFNF135_02647 PE = 3 SV = 1 |
| LVTDVGDSDIIKTNE | 485 | tr\|W4IGC0\|W4IGC0_PLAFA Uncharacterized protein OS = *Plasmodium falciparum* NF135/5.C10 OX = 1036726 GN = PFNF135_03035 PE = 4 SV = 1 |
| NEAEEFEDY | 486 | tr\|W4IKH7\|W4IKH7_PLAFA Uncharacterized protein OS = *Plasmodium falciparum* NF135/5.C10 OX = 1036726 GN = PFNF135_01561 PE = 4 SV = 1 |
| PEEVAEELV | 487 | tr\|W4IFR1\|W4IFR1_PLAFA Uncharacterized protein OS = *Plasmodium falciparum* NF135/5.C10 OX = 1036726 GN = PFNF135_03212 PE = 4 SV = 1 |
| PQNINEYF | 488 | tr\|W4ICP6\| W4ICP6_PLAFA Uncharacterized protein OS = *Plasmodium falciparum* NF135/5.C10 OX-1036726 GN = PFNF135_05101 PE = 4 SV = 1 |
| QGGGSPLLGT | 489 | tr\|W4IM59\|W4IM59_PLAFA Uncharacterized protein OS = *Plasmodium falciparum* NF135/5.C10 OX = 1036726 GN = PFNF135_00968 PE = 4 SV = 1 |
| QGISDDSSIHH | 490 | tr\|W4IBP5\|W4IBP5_PLAFA Uncharacterized protein OS = *Plasmodium falciparum* NF135/5.C10 OX = 1036726 GN = PFNF135_05175 PE = 4 SV = 1 |
| SLGSSILTK | 491 | tr\|W4IB92\|W4IB92_PLAFA Uncharacterized protein OS = Plasmodium *falciparum* NF135/5.C10 OX = 1036726 GN = PFNF135_05237 PE = 4 SV = 1 |
| SLNDALIVSI | 492 | tr\|W4IAD7\|W4IAD7_PLAFA Uncharacterized protein OS = *Plasmodium falciparum* NF135/5.C10 OX = 1036726 GN = PFNF135_06050 PE = 4 SV = 1 |
| VANKIGIL | 493 | tr\|W4ID94\|W4ID94_PLAFA Uncharacterized protein OS = *Plasmodium falciparum* NF135/5.C10 OX = 1036726 GN = PFNF135_04649 PE = 3 SV = 1 |
| VITDVGDSDIIKTNE | 422 | tr\|W4IGC0\|W4IGC0_PLAFA Uncharacterized protein OS = *Plasmodium falciparum* NF135/5.C10 OX = 1036726 GN = PFNF135_03035 PE = 4 SV = 1 |
| VLPELNGK | 495 | tr\|W4I9B4\|W4I9B4_PLAFA Glyceraldehyde-3-phospliate dehydrogenase OS = *Plasmodium falciparum* NF135/5.C10 OX = 1036726 GN = PFNF135_05644 PE = 3 SV = 1 |

Example 4

Peptide Validation by ELIspot Assay 48 peptides were tested by ex vivo IFN-γ ELIspot assay. The peptides are detailed in FIG. 9. All peptides were tested in *P. vivax, P. falciparum* and Endemic and Non-endemic healthy donors. The peptides were divided into ribosomal peptides, ETRAMP peptides, hi stone peptides and other peptides.

Figure 8A:
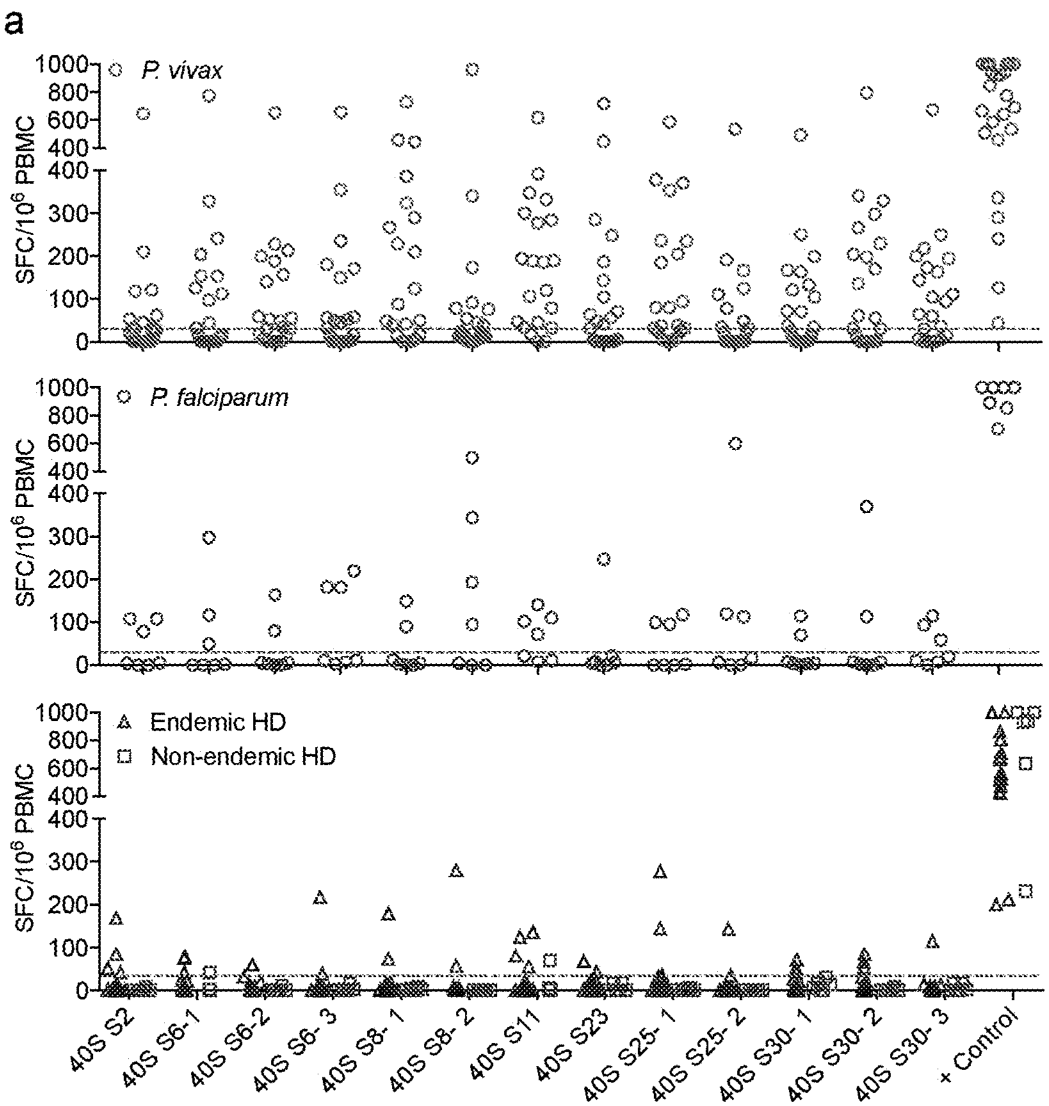
Figure 8B:
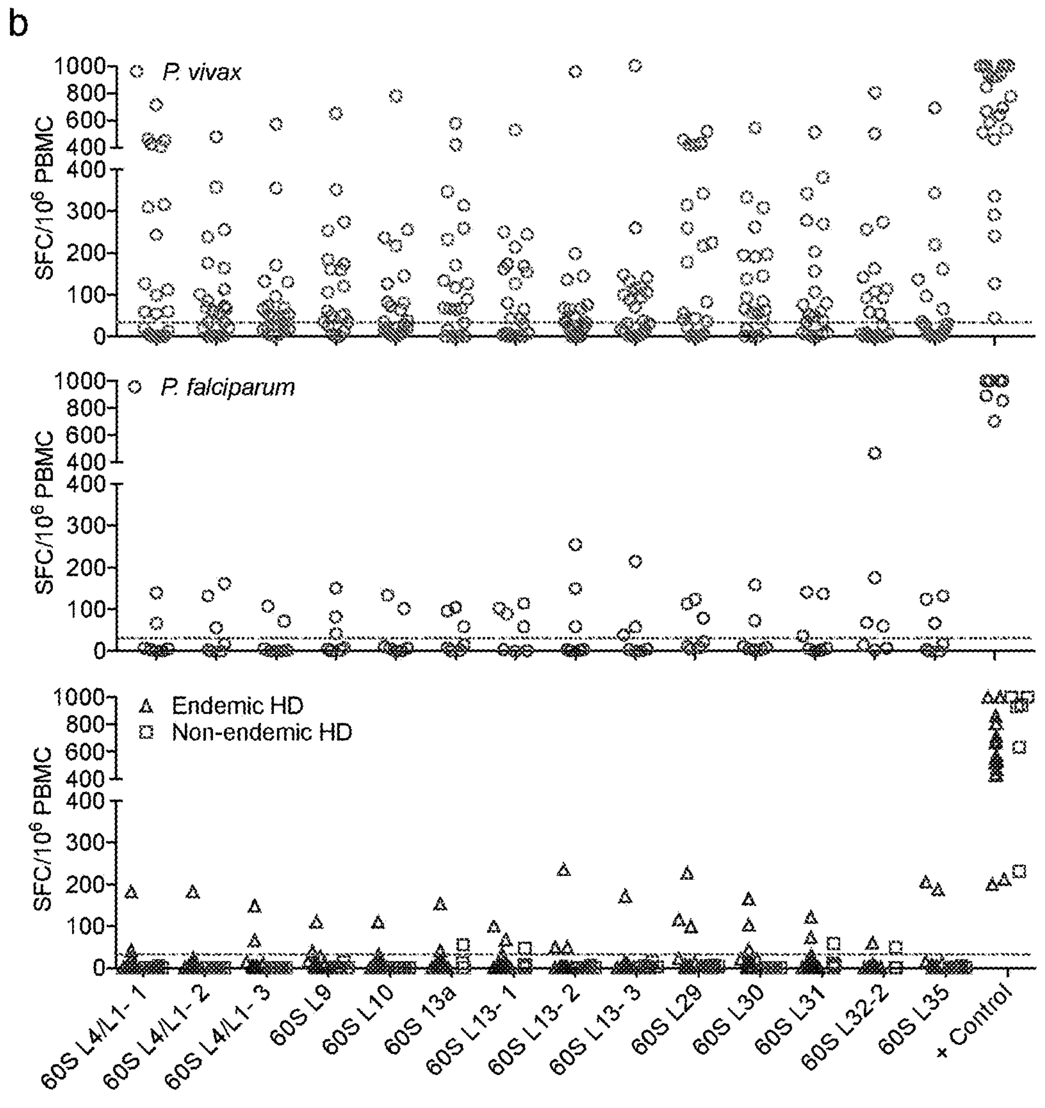

All ribosomal peptides were immunogenic in the *P. vivax* tested samples and twelve were positive in at least 70% of the patients (FIG. 8*a*). Peptide 40S S11 for example, was immunogenic in 86% of *P. vivax* samples, and 60S L4/L1-2, 60S L9, 60S L13-a, 60S L13-3 and 60S L29 were positive in 72%. *P. falciparum* samples were positive for nine ribosomal peptides. Among these peptides, three were immunogenic in more than half of *P. falciparum* samples, the 40S S8, 40S S11, 60S L13-1 and the 60S L32-2. Only one healthy donor individual from a non-endemic area showed a positive response to seven ribosomal peptides, whereas in healthy donors from an endemic malaria region, only 26% of the individuals showed a positive response after stimulation with ribosomal peptides.

Figure 8C:
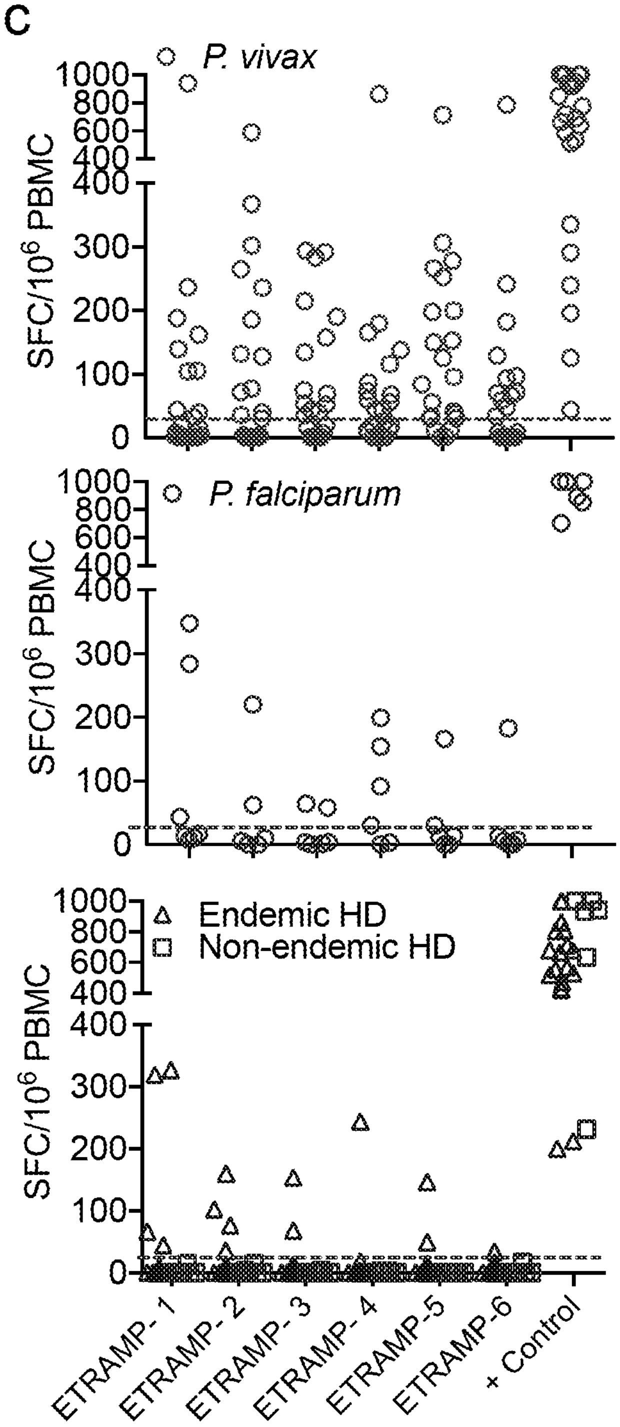
Figure 8D:
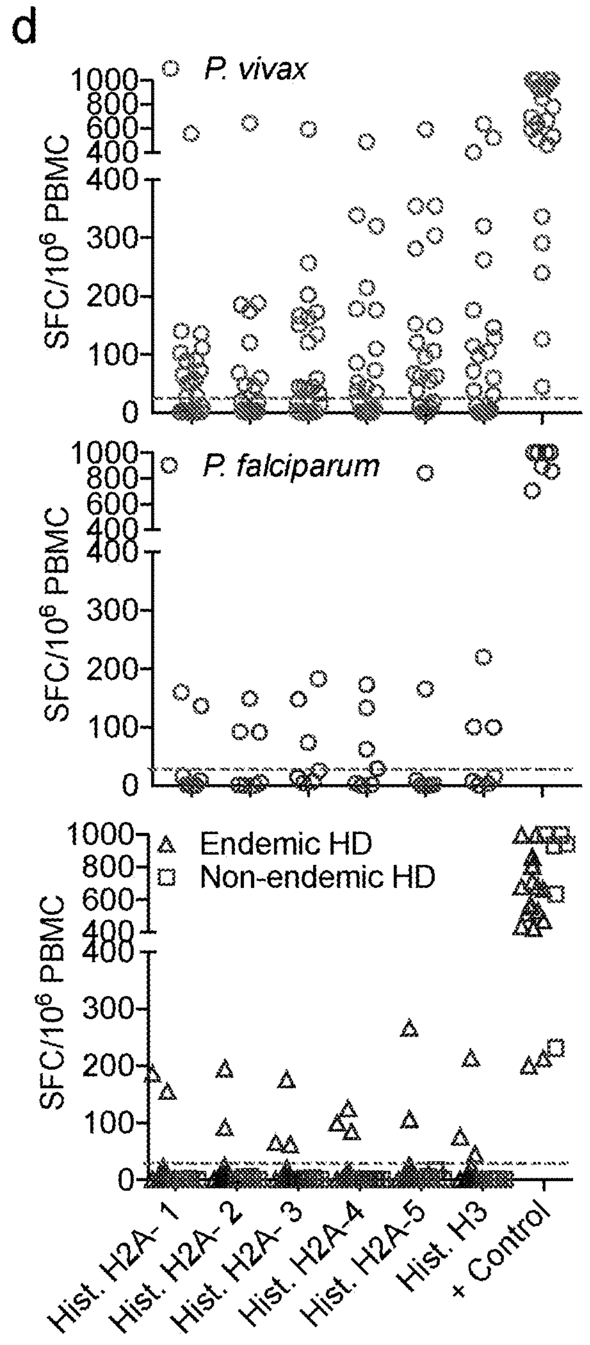

All the ETRAMP peptides tested were immunogenic in the *P. vivax* samples, ranging from 47.8 to 82.6% positivity in the tested patients (FIG. 8*c*). Regarding *P. falciparum*, from six ETRAMP peptides tested, three showed a positive response for at least half of the patients. The higher positivity in healthy donors from an endemic area was 26%, while healthy donors from a non-endemic area did not show a positive response to any peptide.

All the histone peptides tested were immunogenic in all *P. vivax* and all *P. falciparum* tested samples. In *P. vivax* the rate of responder patients ranged between 40% and 71.4% (FIG. 8*d*) and *P. falciparum* at least two in seven patients obtained a positive response to these peptides. No healthy individual from a non-endemic area showed a positive response, whereas the rate of positivity in healthy individuals from an endemic area was only 13.33%.

Figure 8E:
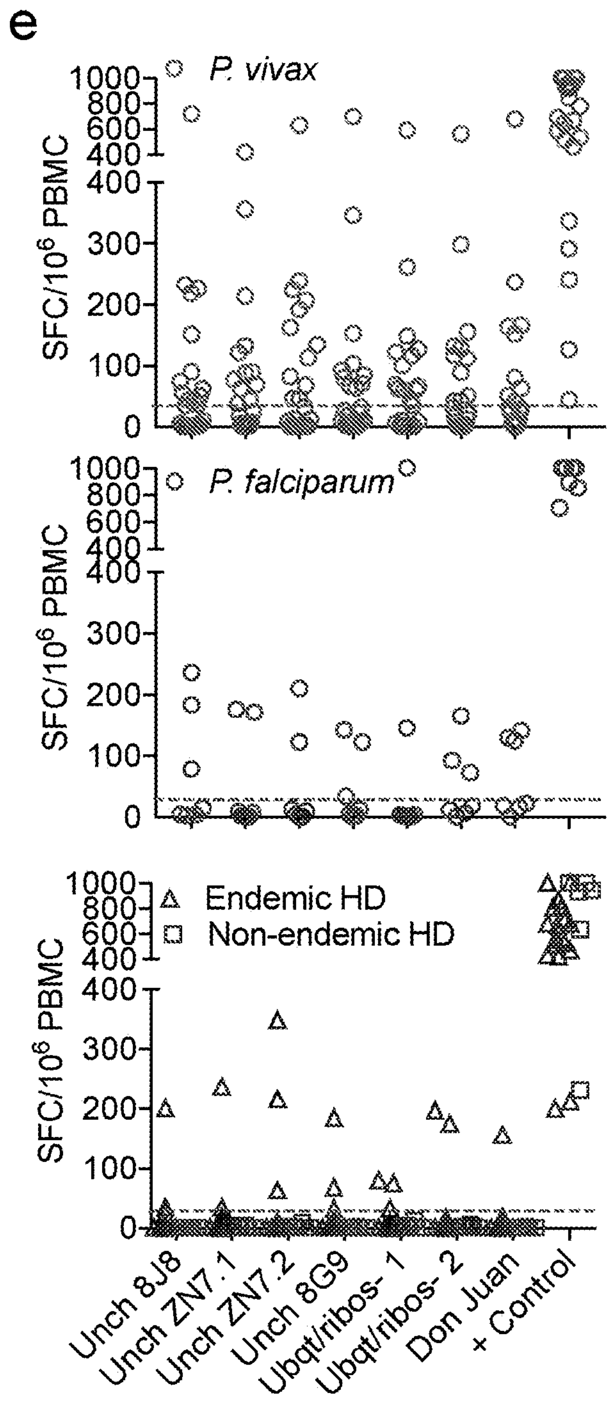
Figure 8F:
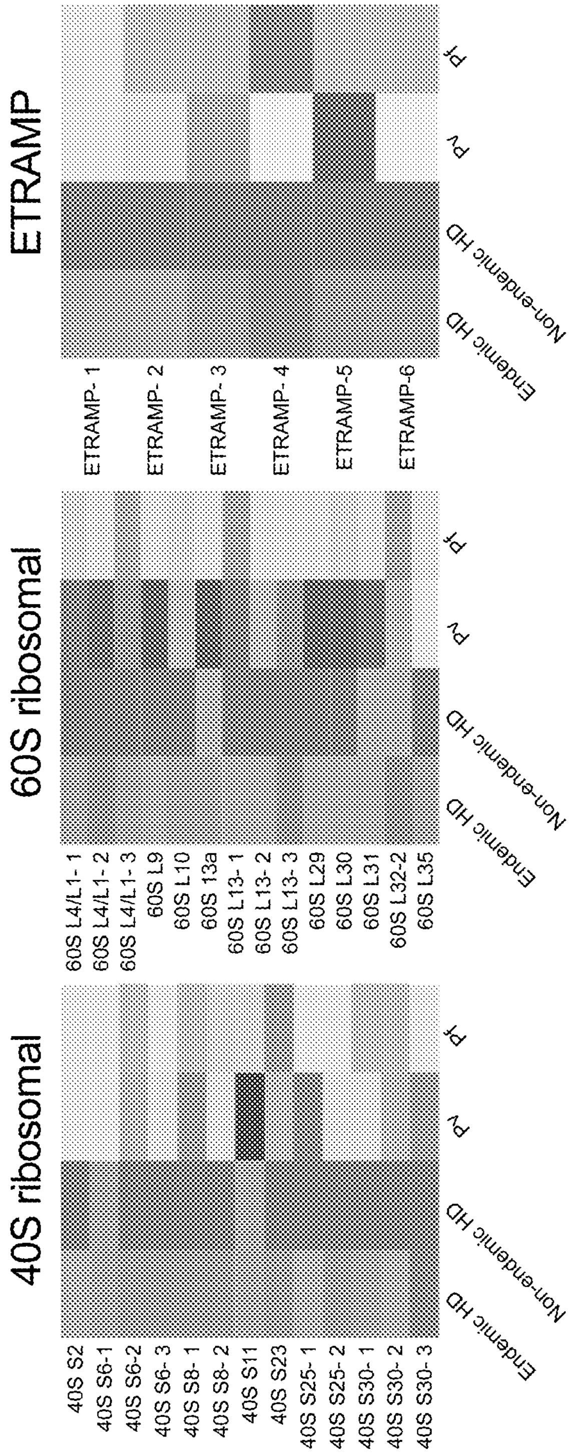
Figure 8F:
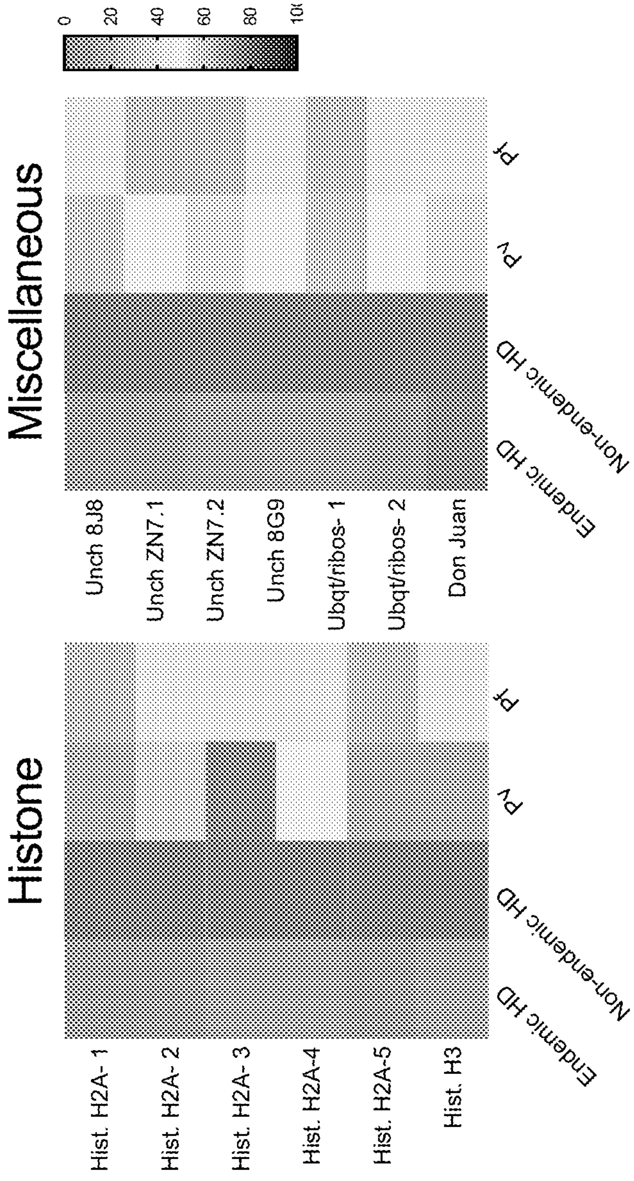

The Uncharacterized proteins or Don Juan peptides showed a rate of patients with positive responses between 45 and 63.6% (FIG. 8*e*). From the groups of patients infected with *P. falciparum* or from healthy donors in an endemic malaria region, a positive response was observed in one individual for all the peptides tested. No individual from a non-endemic area showed a positive response to these peptides.

The invention claimed is:

1. An immunogenic composition comprising:

one or more *plasmodium*-derived ribosomal or ribosomal associated protein, peptide or immunogenic fragment thereof which consists of SEQ ID NO: 576 or SEQ ID NO: 422.

2. The immunogenic composition of claim 1, wherein the immune response elicited is a protective immune response.

3. The immunogenic composition of claim 1, wherein the immune response elicited is a CD8+ T-cell response.

4. The immunogenic composition of claim 1, further comprising a pharmaceutically acceptable excipient or carrier.

5. A method of raising an immune response against malaria in a subject comprising administering to a subject an immunogenic composition comprising SEQ ID NO: 576 or SEQ ID NO: 422.

6. The method of claim 5, wherein the immune response in a subject is effective to treat or prevent malaria.

* * * * *